(12) United States Patent
Rabuka et al.

(10) Patent No.: US 9,493,413 B2
(45) Date of Patent: Nov. 15, 2016

(54) HYDRAZINYL-PYRROLO COMPOUNDS AND METHODS FOR PRODUCING A CONJUGATE

(71) Applicant: Redwood Bioscience, Inc., Emeryville, CA (US)

(72) Inventors: David Rabuka, Kensington, CA (US); Aaron Edward Albers, San Francisco, CA (US); Romas Alvydas Kudirka, Berkeley, CA (US); Albert W. Garofalo, South San Francisco, CA (US)

(73) Assignee: Redwood Bioscience, Inc., Emeryville, CA (US)

( * ) Notice: Subject to any disclaimer, the term of this patent is extended or adjusted under 35 U.S.C. 154(b) by 0 days.

(21) Appl. No.: 14/555,283

(22) Filed: Nov. 26, 2014

(65) Prior Publication Data

US 2015/0157736 A1 Jun. 11, 2015

Related U.S. Application Data

(60) Provisional application No. 61/909,897, filed on Nov. 27, 2013.

(51) Int. Cl.
| | |
|---|---|
| C07D 405/12 | (2006.01) |
| C07D 498/18 | (2006.01) |
| A61K 47/48 | (2006.01) |
| A61K 31/5386 | (2006.01) |
| C07D 209/14 | (2006.01) |

(52) U.S. Cl.
CPC ......... *C07D 209/14* (2013.01); *A61K 31/5386* (2013.01); *A61K 47/48061* (2013.01); *A61K 47/48215* (2013.01); *A61K 47/48376* (2013.01); *C07D 405/12* (2013.01); *C07D 498/18* (2013.01)

(58) Field of Classification Search
CPC .................. A61K 31/5386; A61K 47/48061; A61K 47/48215; A61K 47/48376; A61K 47/48384; C07D 209/14; C07D 405/12; C07D 498/18; C07H 5/04; C07K 7/02
USPC .................. 544/235, 238, 314, 333
See application file for complete search history.

(56) References Cited

U.S. PATENT DOCUMENTS

| | | | |
|---|---|---|---|
| 4,816,567 A | 3/1989 | Cabilly et al. | |
| 4,935,496 A | 6/1990 | Kudo et al. | |
| 5,225,539 A | 7/1993 | Winter | |
| 5,502,167 A | 3/1996 | Waldmann et al. | |
| 5,530,101 A | 6/1996 | Queen et al. | |
| 5,558,864 A | 9/1996 | Bendig et al. | |
| 5,565,332 A | 10/1996 | Hoogenboom et al. | |
| 5,585,089 A | 12/1996 | Queen et al. | |
| 5,693,493 A | 12/1997 | Robinson et al. | |
| 5,698,417 A | 12/1997 | Robinson et al. | |
| 5,705,154 A | 1/1998 | Dalie et al. | |
| 5,750,078 A | 5/1998 | Shitara et al. | |
| 5,770,403 A | 6/1998 | Dalie et al. | |
| 6,570,040 B2 | 5/2003 | Saxon et al. | |
| 7,049,311 B1 | 5/2006 | Thurston et al. | |
| 7,067,511 B2 | 6/2006 | Thurston et al. | |
| 7,517,903 B2 | 4/2009 | Chen et al. | |
| 7,754,884 B2 * | 7/2010 | Bornhop et al. | 546/146 |
| 7,985,783 B2 | 7/2011 | Carrico et al. | |
| 8,343,928 B2 | 1/2013 | Doronina et al. | |
| 2003/0069430 A1 | 4/2003 | Davis et al. | |
| 2004/0086979 A1 | 5/2004 | Zhang et al. | |
| 2005/0033031 A1 | 2/2005 | Couto | |
| 2006/0116417 A1 | 6/2006 | Chen et al. | |
| 2007/0275962 A1 | 11/2007 | Koul et al. | |
| 2011/0117621 A1 | 5/2011 | Rush et al. | |
| 2014/0141025 A1 * | 5/2014 | Kudirka et al. | 424/181.1 |

FOREIGN PATENT DOCUMENTS

| | | |
|---|---|---|
| EP | 239400 | 9/1987 |
| EP | 519596 | 12/1992 |
| EP | 592106 | 4/1994 |
| WO | 9109967 | 7/1991 |
| WO | 9845331 | 10/1998 |
| WO | 9845332 | 10/1998 |
| WO | 2011099718 | 8/2011 |

OTHER PUBLICATIONS

Agarwal et al. "Hydrazino-Pictet-Spengler Ligation as a Biocompatible Method for the Generation of Stable Protein Conjugates" Bioconj. Chem. 2013, 24, 846-851.*
Agarwal et al. "Hydrazino-Pictet-Spengler Ligation as a Biocompatible Method for the Generation of Stable Protein Conjugates," Bioconjugate Chemistry 24(6): 846-851 (2013).
Padlan, "A Possible Procedure for Reducing the Immunogenicity of Antibody Variable Domains While Preserving Their Ligand-Binding Properties," Molecular Immunology 28(4/5):489-498 (1991).
Riechmann et al., "Reshaping human antibodies for therapy," Nature 332(6162): 323-327 (1988).
Roguska. et al., "Humanization of murine monoclonal antibodies through variable domain resurfacing," PNAS 91(3): 969-973 (1994).
Studnicka et al., "Human-engineered monoclonal antibodies retain full specific bindibg activity by preserving non-CDR complementarity-modulating residues," Protein Engineering 7(6):805-814 (1994).

* cited by examiner

*Primary Examiner* — Nyeemah A Grazier
*Assistant Examiner* — Amanda L Aguirre
(74) *Attorney, Agent, or Firm* — Rudy J. Ng; Glenn J. Foulds; Bozicevic, Field & Francis LLP

(57) ABSTRACT

The present disclosure provides conjugate structures and hydrazinyl-pyrrolo compound structures used to produce these conjugates. The disclosure also encompasses methods of production of such conjugates, as well as methods of using the same.

17 Claims, 99 Drawing Sheets

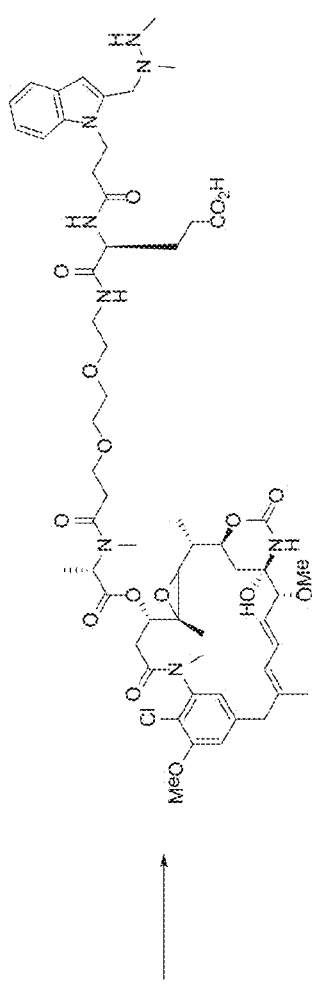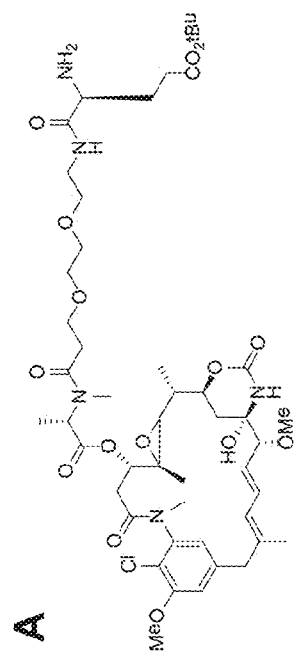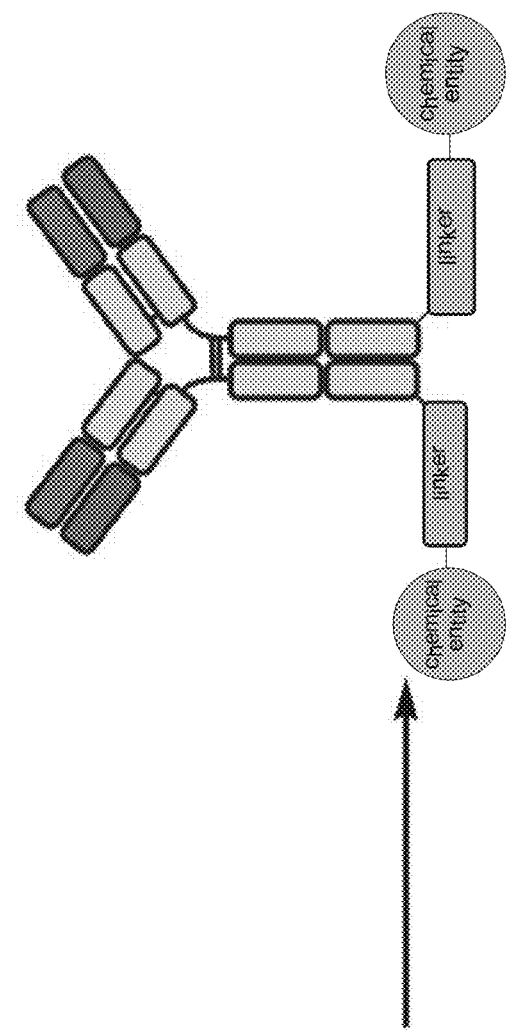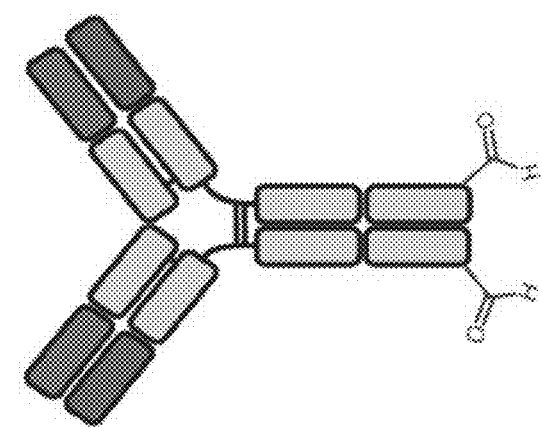
FIG. 2

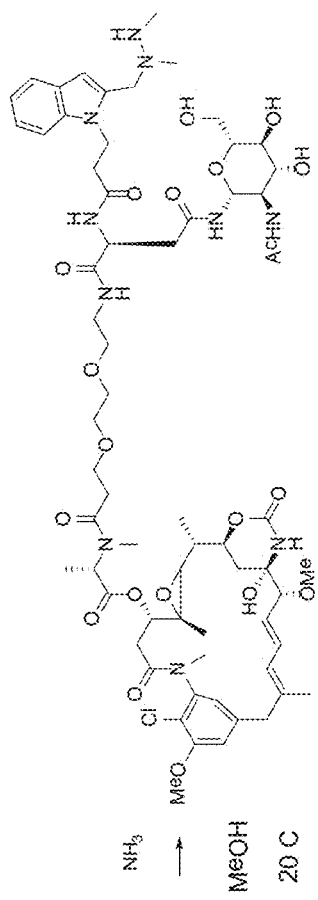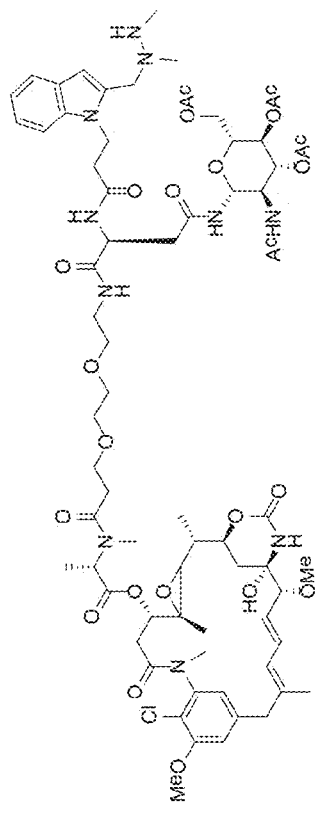
FIG. 23

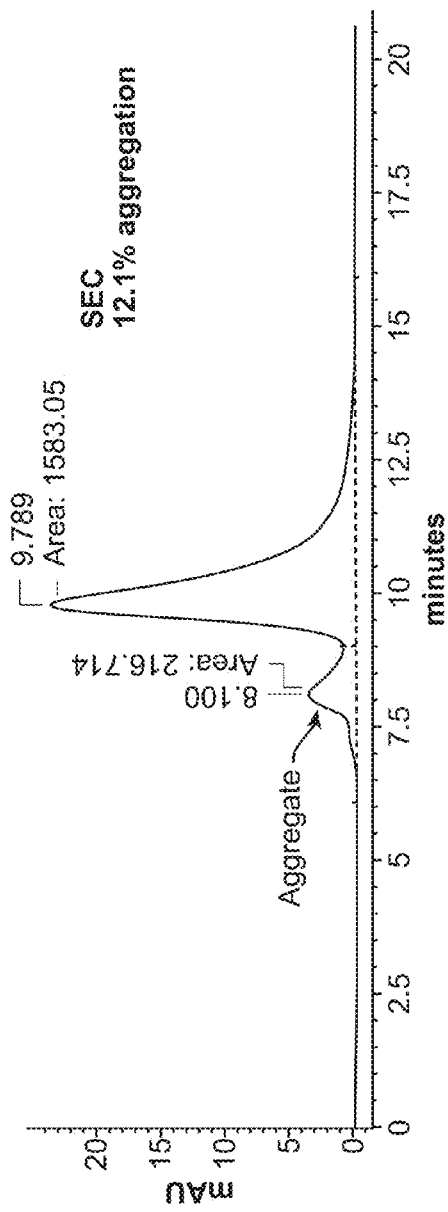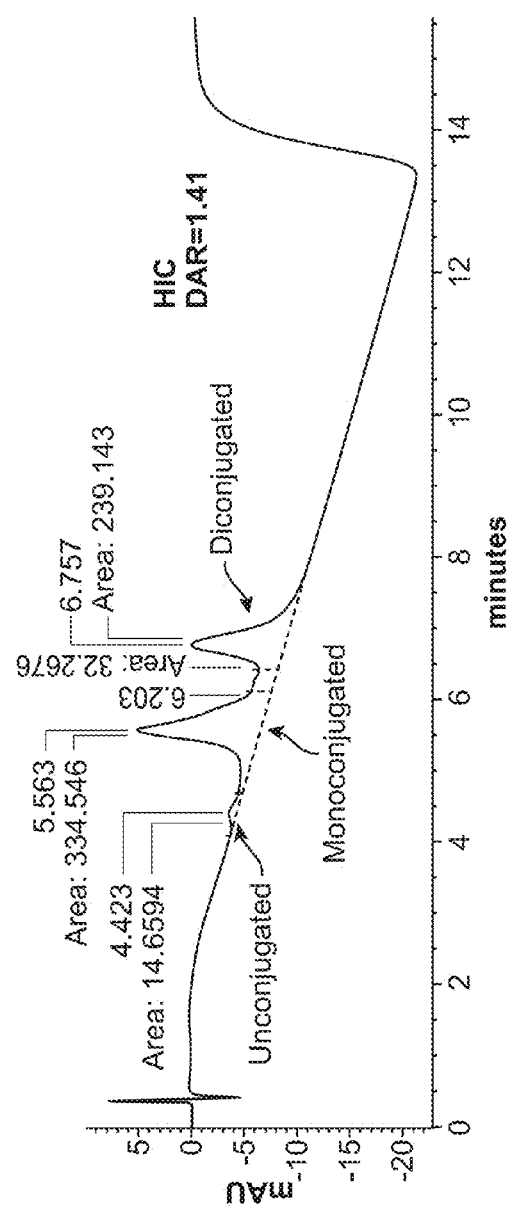

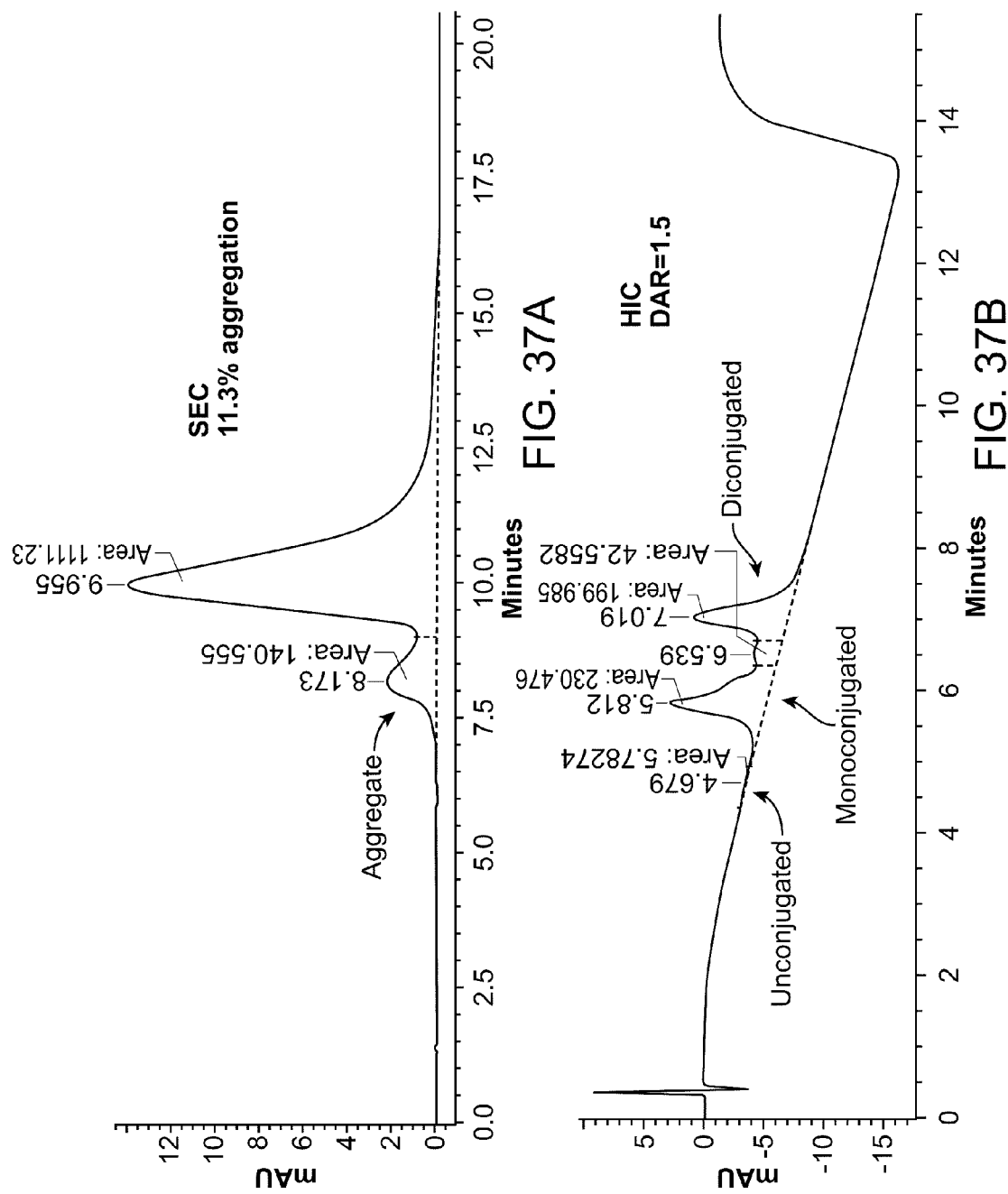

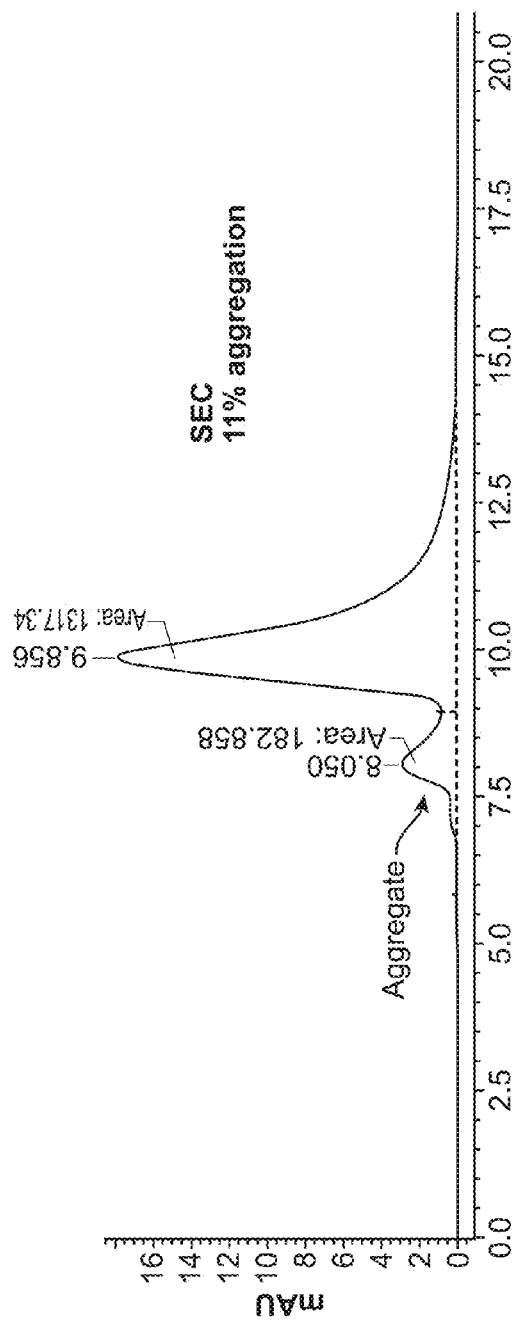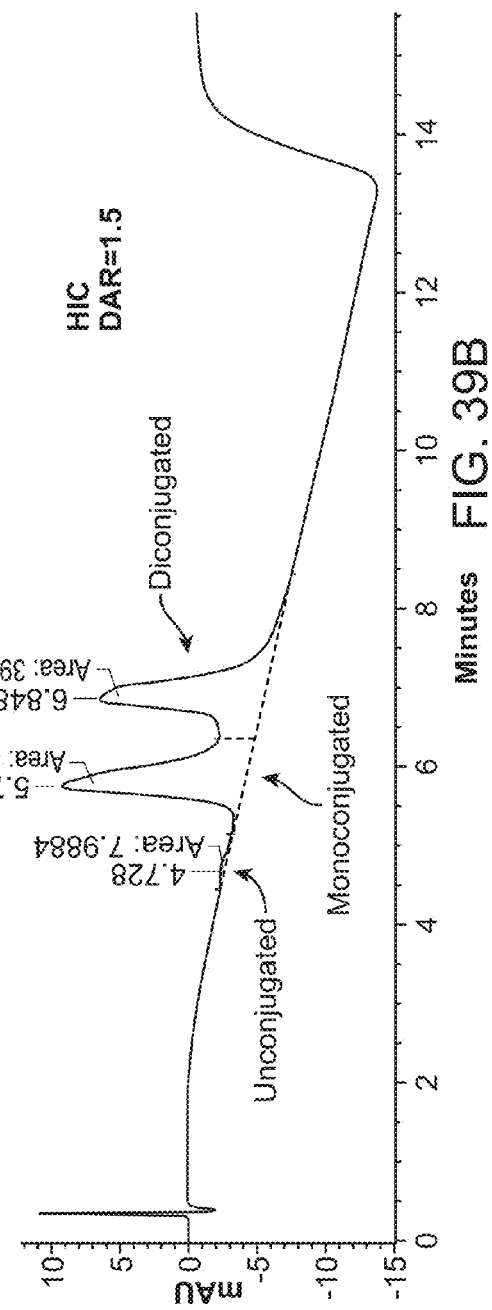

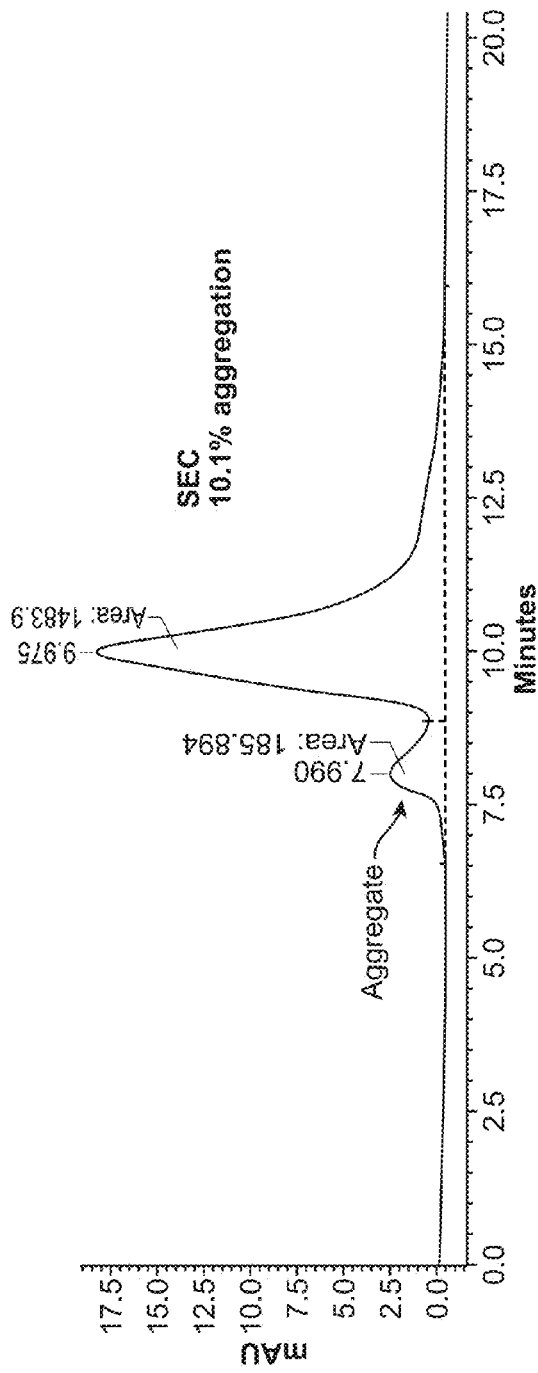
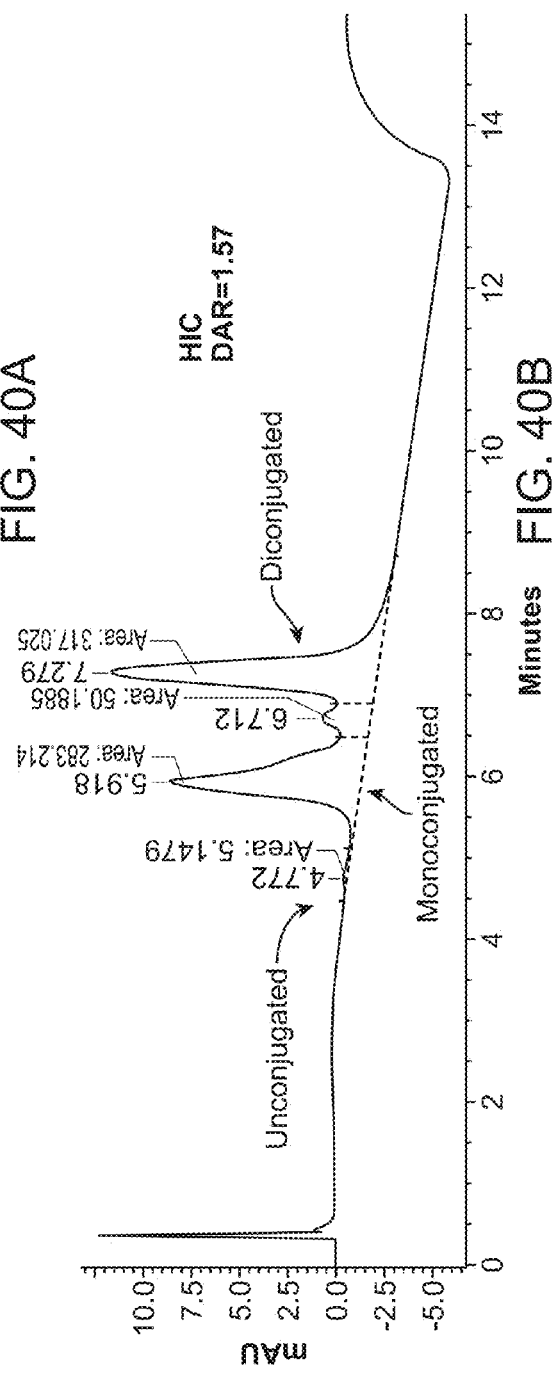

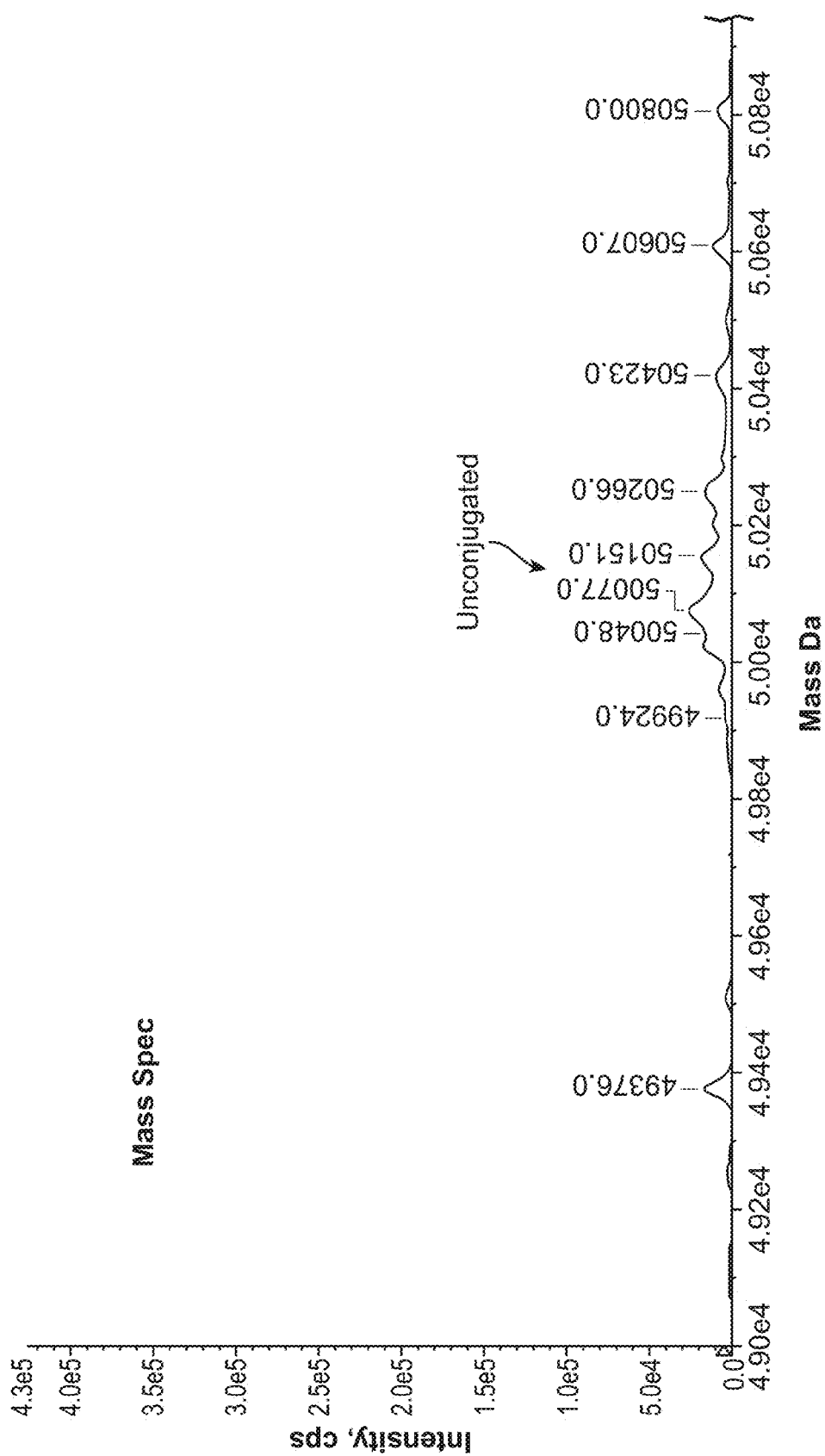

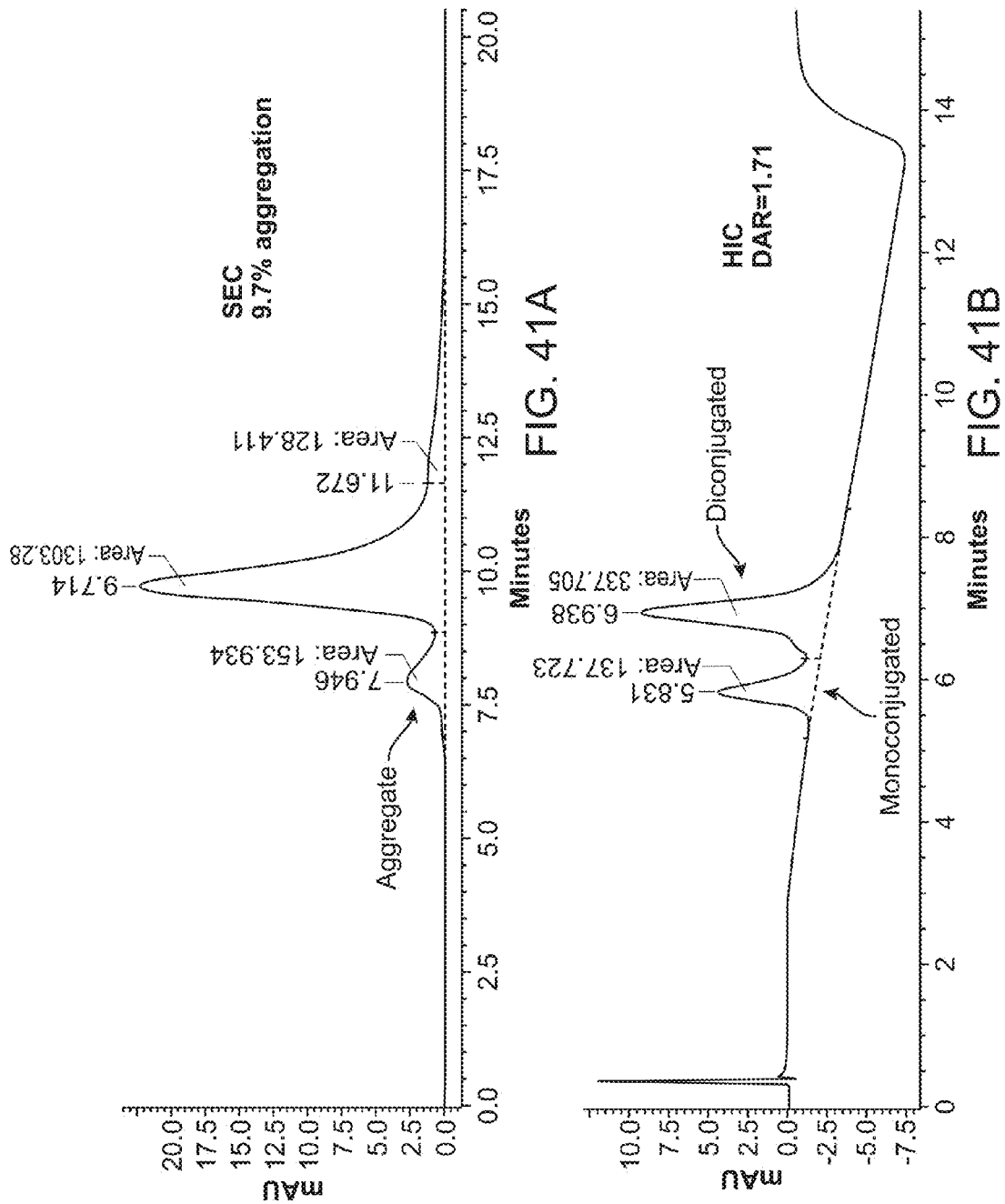

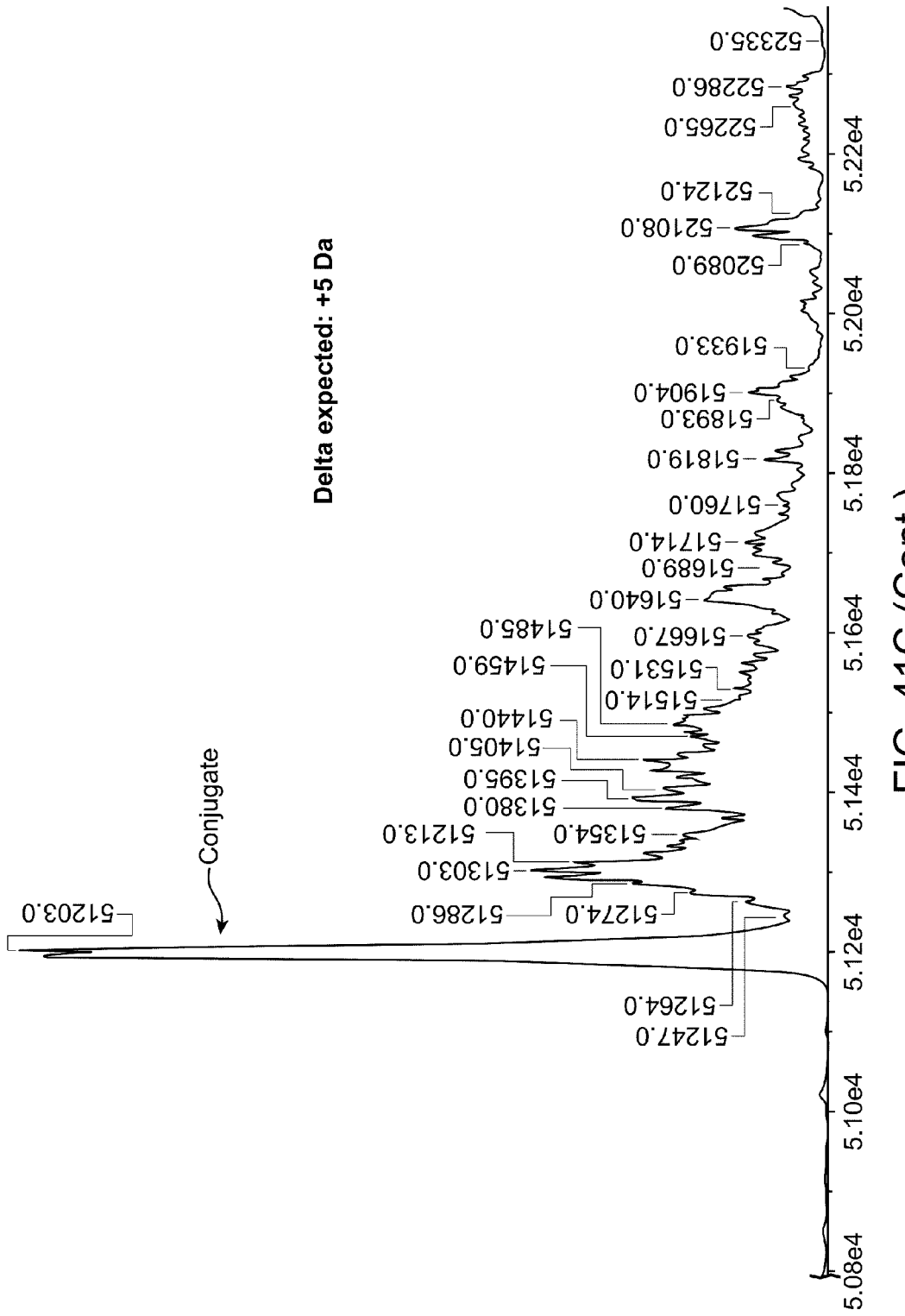

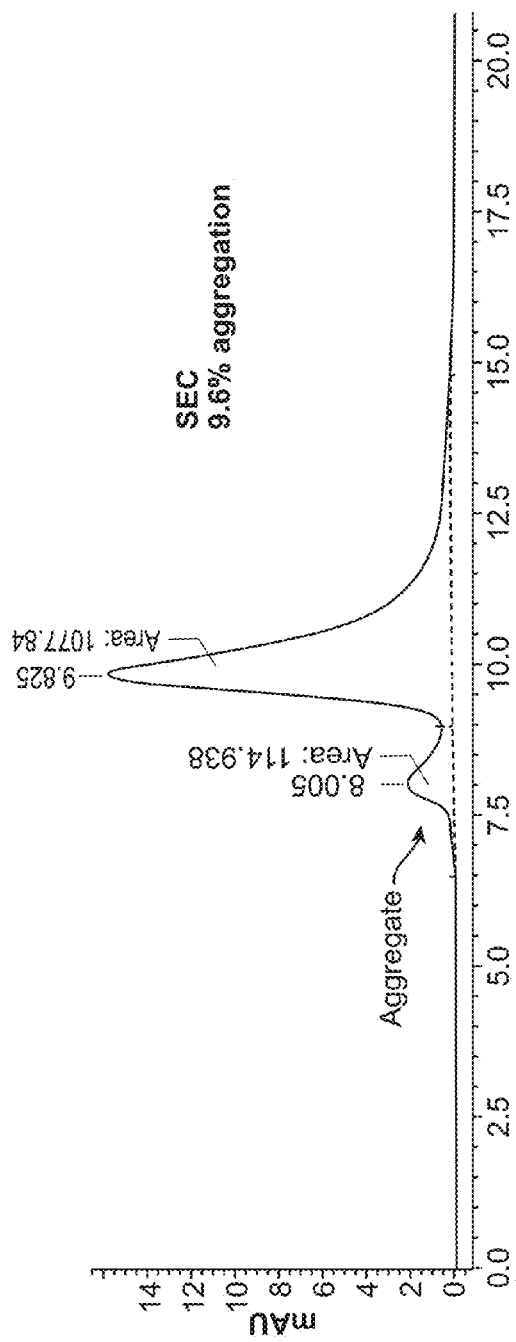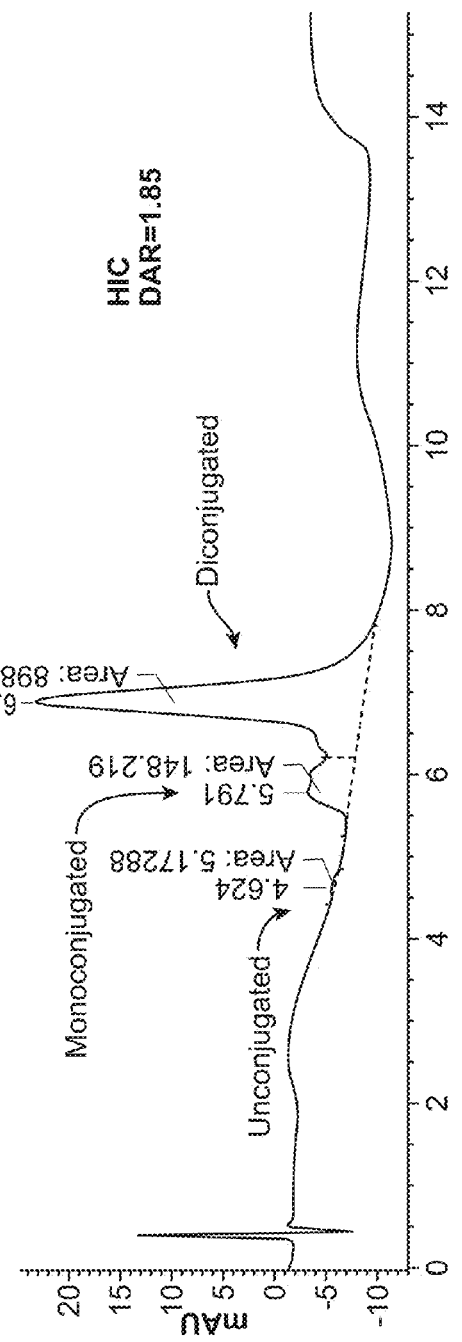

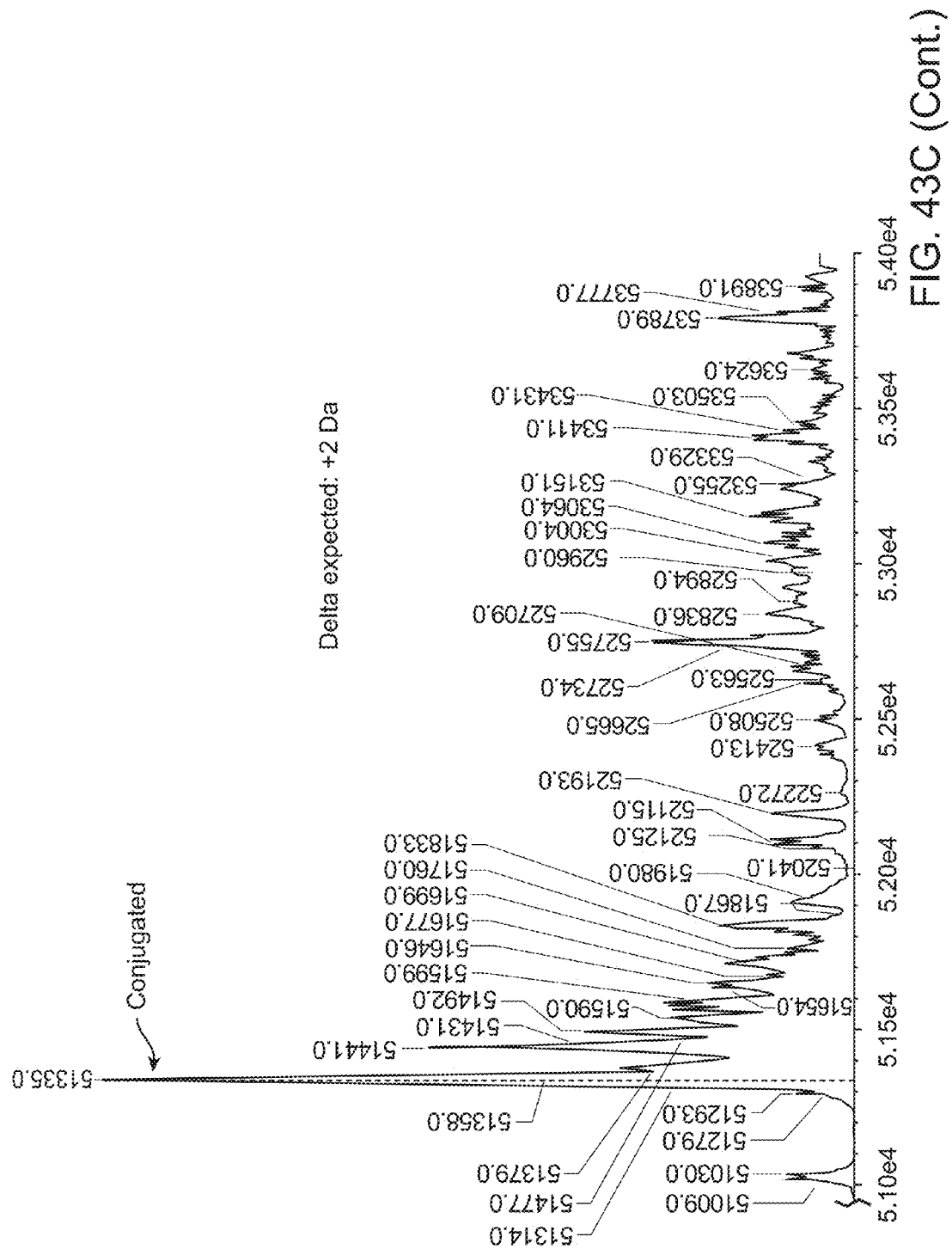

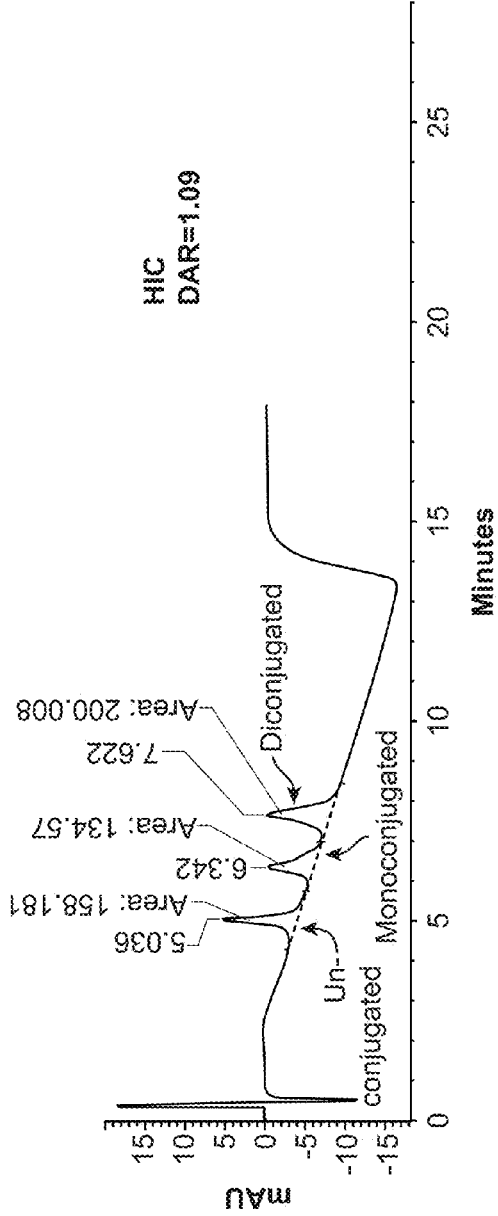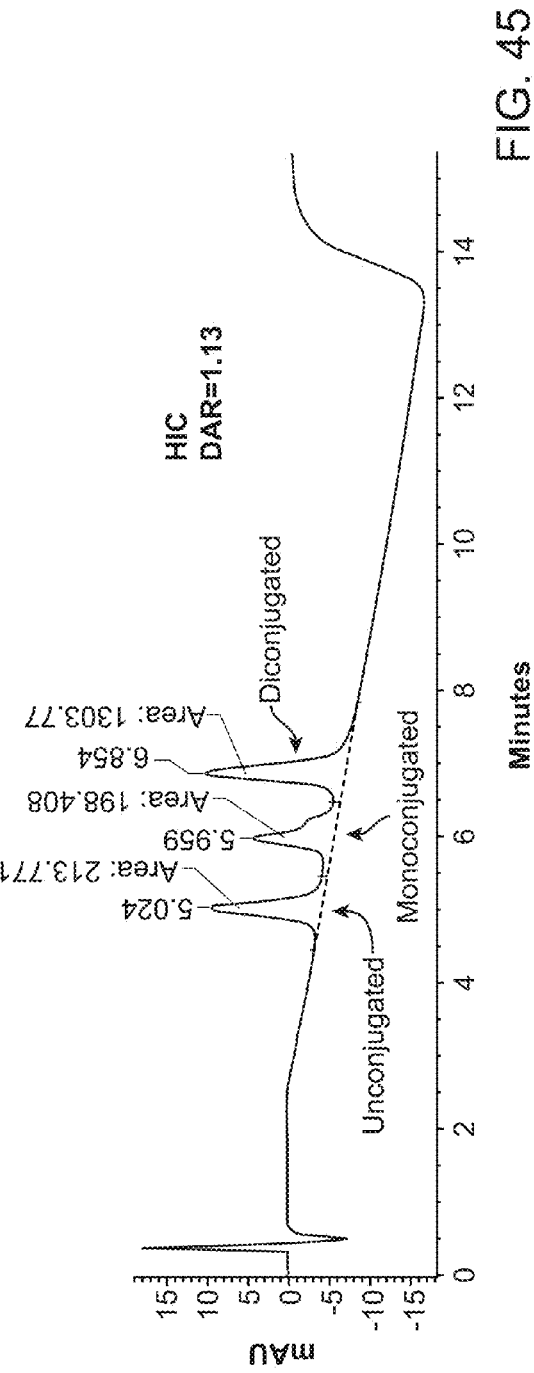

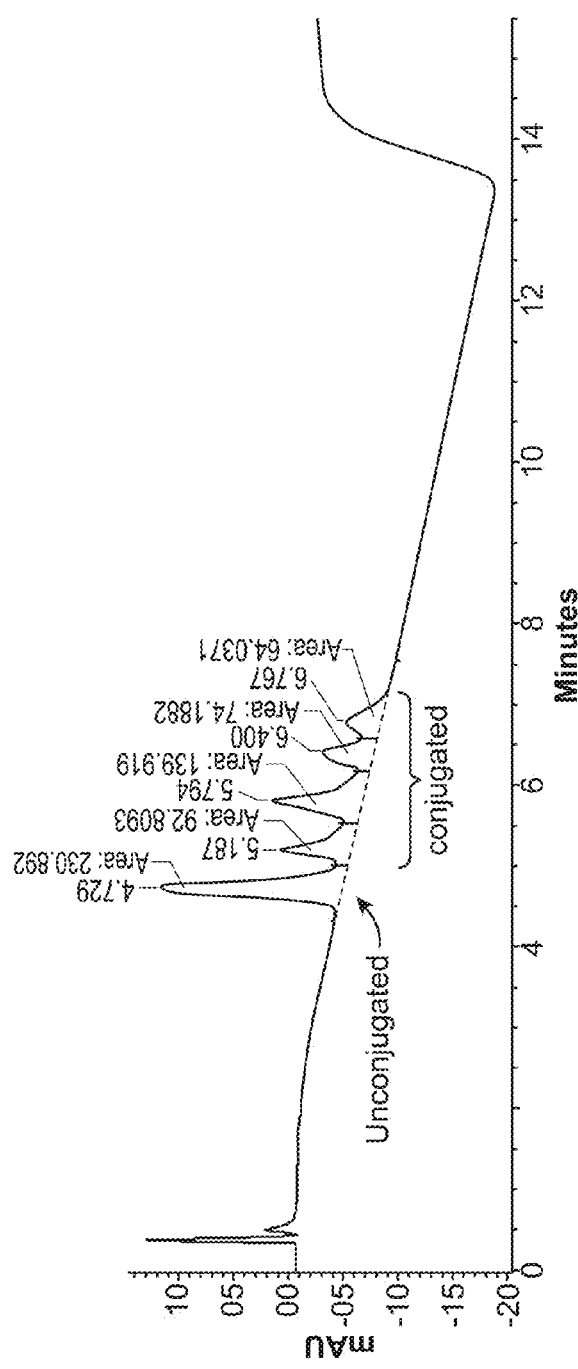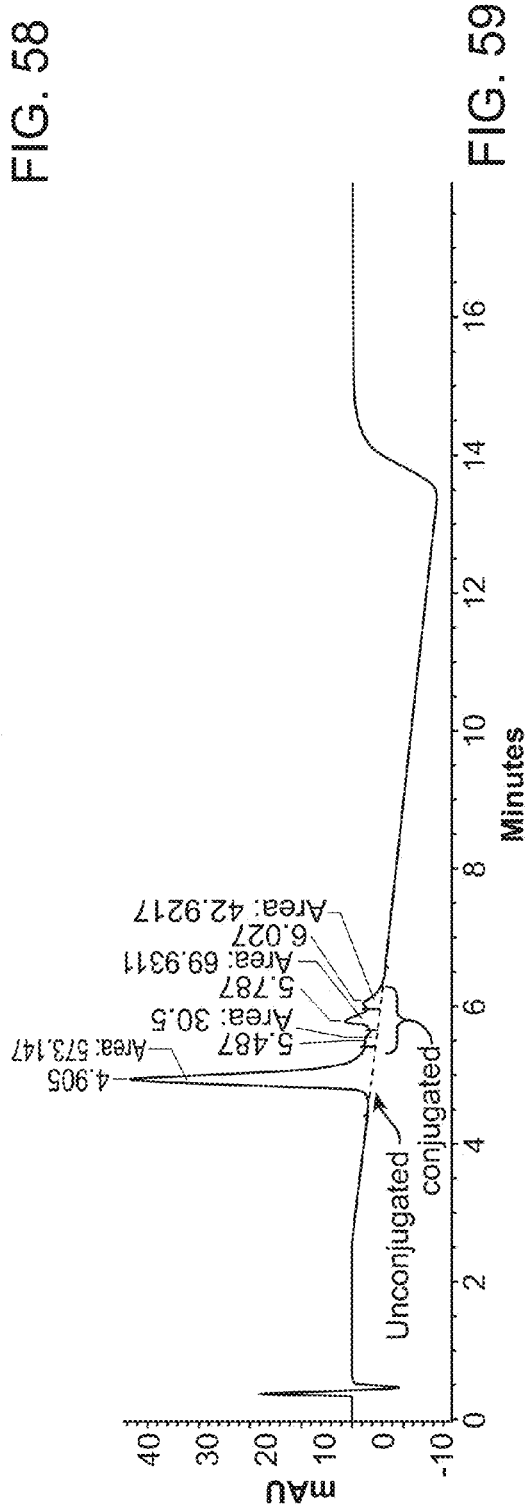

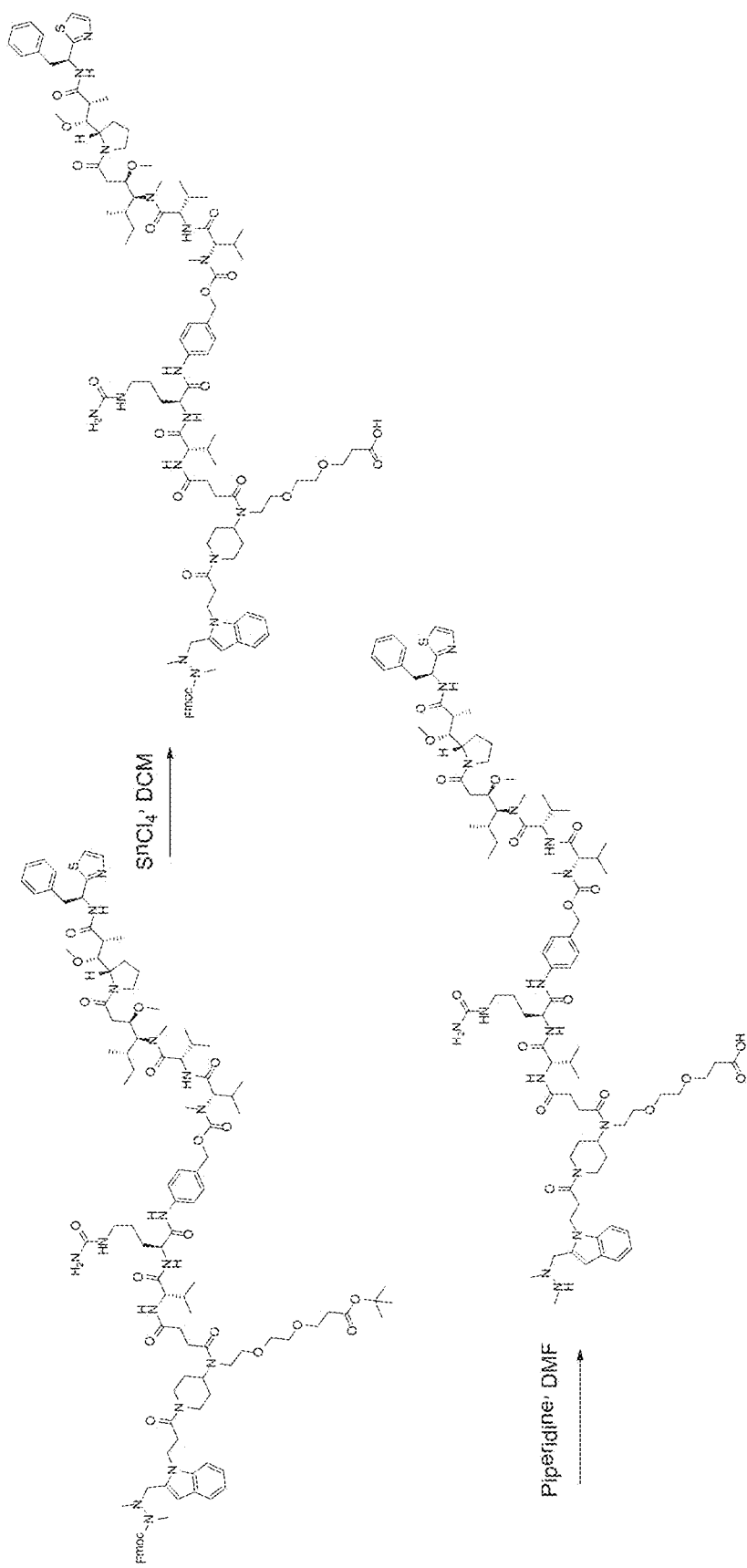
FIG. 64, continued

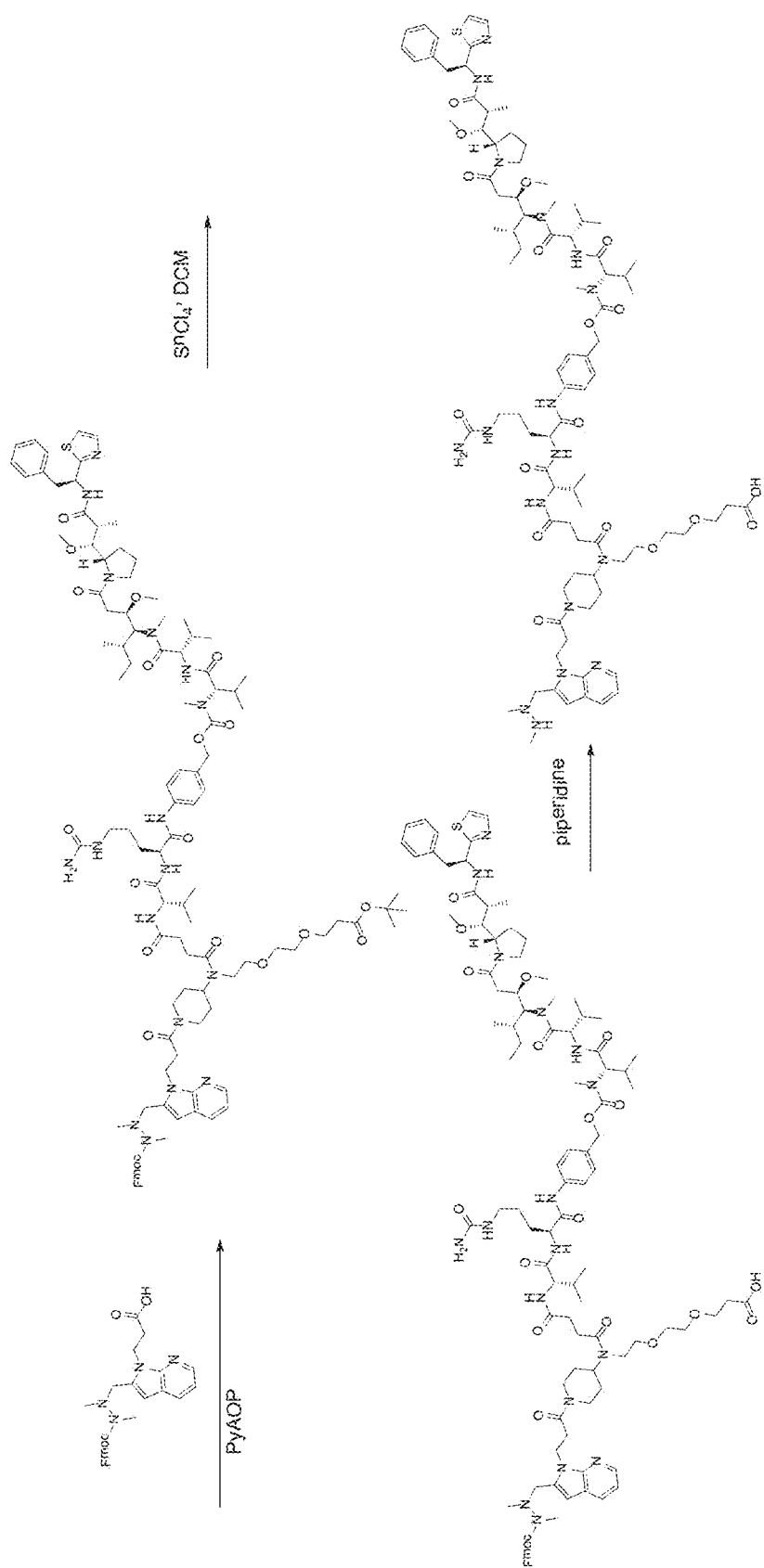
FIG. 65, continued

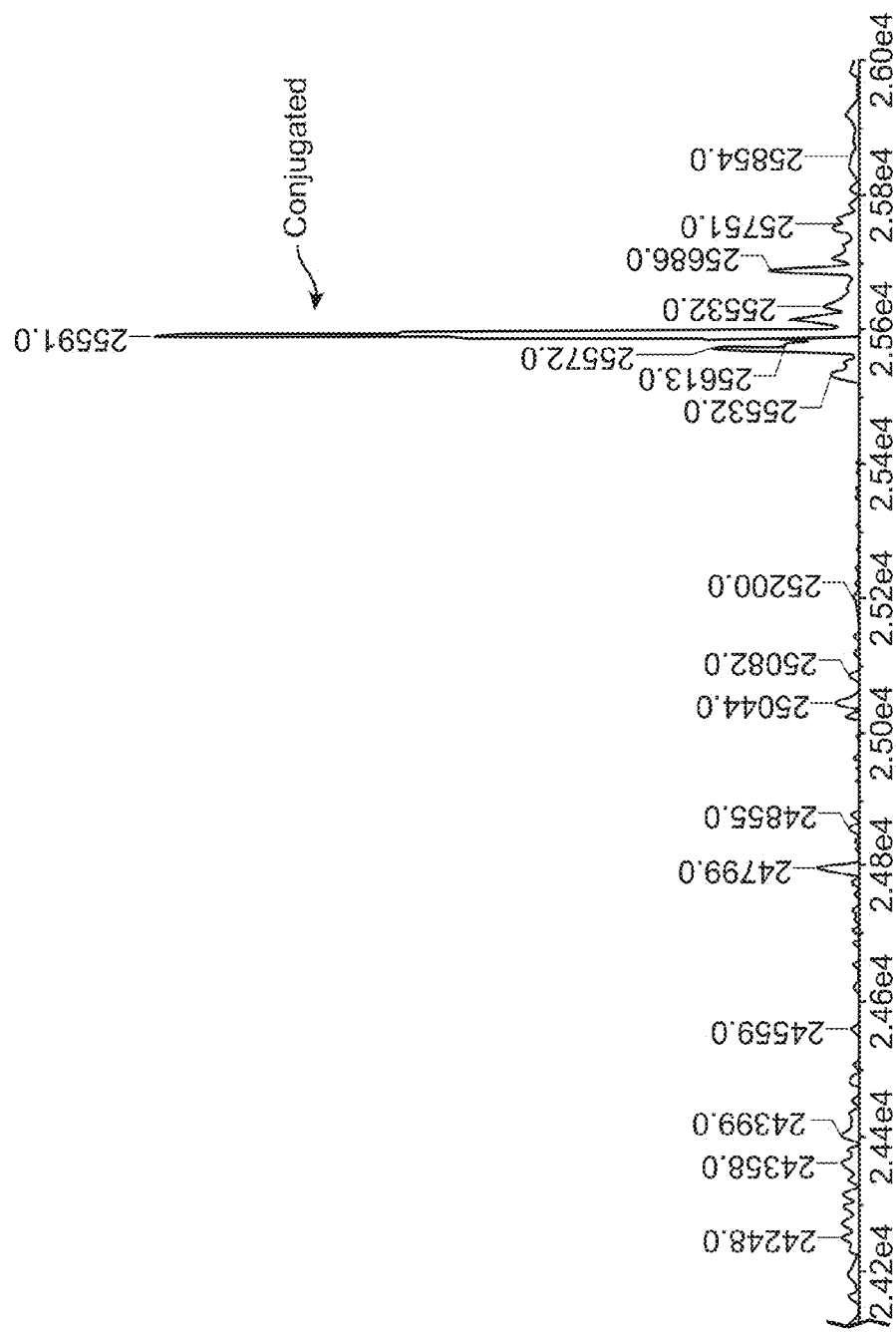

HYDRAZINYL-PYRROLO COMPOUNDS AND METHODS FOR PRODUCING A CONJUGATE

CROSS-REFERENCE TO RELATED APPLICATIONS

Pursuant to 35 U.S.C. §119(e), this application claims priority benefit of U.S. Provisional Application Ser. No. 61/909,897, filed Nov. 27, 2013, which application is incorporated herein by reference in its entirety.

INTRODUCTION

The field of protein-small molecule therapeutic conjugates has advanced greatly, providing a number of clinically beneficial drugs with the promise of providing more in the years to come. Protein-conjugate therapeutics can provide several advantages, due to, for example, specificity, multiplicity of functions and relatively low off-target activity, resulting in fewer side effects. Chemical modification of proteins may extend these advantages by rendering them more potent, stable, or multimodal.

A number of standard chemical transformations are commonly used to create and manipulate post-translational modifications on proteins. There are a number of methods where one is able to modify the side chains of certain amino acids selectively. For example, carboxylic acid side chains (aspartate and glutamate) may be targeted by initial activation with a water-soluble carbodiimide reagent and subsequent reaction with an amine. Similarly, lysine can be targeted through the use of activated esters or isothiocyanates, and cysteine thiols can be targeted with maleimides and α-halo-carbonyls.

One significant obstacle to the creation of a chemically altered protein therapeutic or reagent is the production of the protein in a biologically active, homogenous form. Conjugation of a drug or detectable label to a polypeptide can be difficult to control, resulting in a heterogeneous mixture of conjugates that differ in the number of drug molecules attached and in the position of chemical conjugation. In some instances, it may be desirable to control the site of conjugation and/or the drug or detectable label conjugated to the polypeptide using the tools of synthetic organic chemistry to direct the precise and selective formation of chemical bonds on a polypeptide.

SUMMARY

The present disclosure provides conjugate structures and hydrazinyl-pyrrolo compound structures used to produce these conjugates. The disclosure also encompasses methods of production of such conjugates, as well as methods of using the same.

Aspects of the present disclosure include a conjugate comprising at least one modified amino acid residue of formula (I):

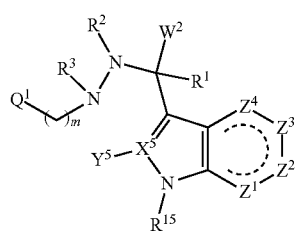

(I)

wherein
m is 0 or 1;
$R^1$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;
$R^2$ and $R^3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, or $R^2$ and $R^3$ are optionally cyclically linked to form a 5 or 6-membered heterocyclyl;
$Z^1$, $Z^2$, $Z^3$ and $Z^4$ are each independently selected from $CR^{11}$, $NR^{12}$, O and S, wherein one of $Z^1$, $Z^2$, $Z^3$ and $Z^4$ is optional;
$X^5$ is C;
$Y^5$, $R^{11}$ and $R^{12}$ are each independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;
$Q^1$ is a bond to either $Z^4$ or $X^5$, wherein if $Q^1$ is a bond to $Z^4$, then $Z^4$ is $CR^{11}$ or $NR^{12}$ and $R^{11}$ or $R^{12}$ is absent, or if $Q^1$ is a bond to $X^5$, then $Y^5$ is absent;
$R^{15}$ is -L-$W^1$ or -L-$W^1$ is attached to one of $Z^1$, $Z^2$, $Z^3$ or $Z^4$, wherein if -L-$W^1$ is attached to one of $Z^1$, $Z^2$, $Z^3$ or $Z^4$, then $R^{15}$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;
L is a linker comprising -$(T^1-V^1)_a$-$(T^2-V^2)_b$-$(T^3-V^3)_c$-$(T^4-V^4)_d$-$(T^5-V^5)$, wherein a, b, c, d and e are each independently 0 or 1, where the sum of a, b, c, d and e is 1 to 5;
$T^1$, $T^2$, $T^3$, $T^4$ and $T^5$ are each independently selected from $(C_1-C_{12})$alkyl, substituted $(C_1-C_{12})$alkyl, $(EDA)_w$, $(PEG)_n$, $(AA)_p$, —$(CR^{13}OH)_h$—, piperidin-4-amino (P4A), para-amino-benzyloxycarbonyl (PABC), meta-amino-benzyloxycarbonyl (MABC), para-amino-benzyloxy (PABO), meta-amino-benzyloxy (MABO), para-aminobenzyl, an acetal group, a disulfide, a hydrazine, a protease-cleavable moiety, a glucuronidase cleavable moiety, a beta-lactamase cleavable moiety, and an ester, wherein EDA is an ethylene diamine moiety, PEG is a polyethylene glycol or a modified polyethylene glycol, and AA is an amino acid residue;
w is an integer from 1 to 20;
n is an integer from 1 to 30;
p is an integer from 1 to 20;
h is an integer from 1 to 12; and
$V^1$, $V^2$, $V^3$, $V^4$ and $V^5$ are each independently selected from the group consisting of a covalent bond, —CO—, —$NR^{11}$—, —$CONR^{11}$—, —$NR^{11}CO$—, —C(O)O—, —OC(O)—, —O—, —S—, —S(O)—, —$SO_2$—, —$SO_2NR^{11}$—, —$NR^{11}SO_2$— and —P(O)OH—,
wherein one of $W^1$ and $W^2$ is a polypeptide and the other is a chemical entity, and wherein when the sum of a, b, c, d and e is 2 and one of T$^1$-V$^1$, T$^2$-V$^2$, T$^3$-V$^3$, T$^4$-V$^4$ or T$^5$-V$^5$ is (PEG)$_n$-CO, then n is not 6.

In some embodiments, the conjugate includes at least one modified amino acid residue of formula (II):

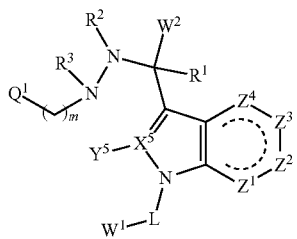

(II)

wherein m, R$^1$, R$^2$, R$^{3'}$ X$^5$, L, Q$^1$, W$^1$, W$^2$, Y$^5$, Z$^1$, Z$^2$, Z$^3$ and Z$^4$ are as defined in formula (I).

In some embodiments, the conjugate includes at least one modified amino acid residue of formula (III):

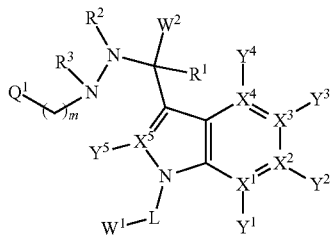

(III)

wherein m, R$^1$, R$^2$, R$^{3'}$ X$^5$, L, W$^1$ and W$^2$ are as defined in formula (I);

X$^1$, X$^2$, X$^3$ and X$^4$ are each independently selected from C, N, O and S;

Y$^1$, Y$^2$, Y$^3$, Y$^4$ and Y$^5$, if present, are each independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, wherein Y$^1$ and Y$^2$, Y$^2$ and Y$^3$, or Y$^3$ and Y$^4$ are optionally cyclically linked; and Q$^1$ is a bond to either X$^4$ or X$^5$, wherein if Q$^1$ is a bond to X$^4$, then Y$^4$ is absent, or if Q$^1$ is a bond to X$^5$, then Y$^5$ is absent.

In some embodiments, Y$^1$ and Y$^2$, Y$^2$ and Y$^3$, or Y$^3$ and Y$^4$ are cyclically linked to form a fused benzo ring.

In some embodiments, the conjugate includes at least one modified amino acid residue of formula (IVa) or (IVb):

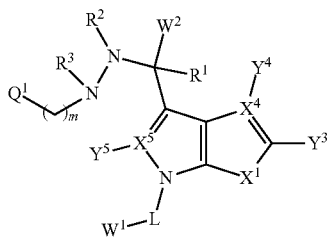

(IVa)

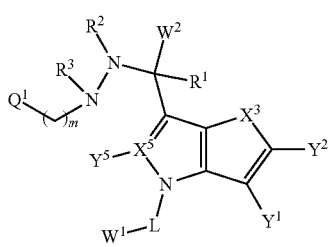

(IVb)

wherein:

m, R$^1$, R$^2$, R$^{3'}$ R$^{12'}$ X$^5$, Y$^{5'}$ L, W$^1$ and W$^2$ are as defined in formula (I); X$^1$ and X$^3$ are each independently O, S or NR$^{12}$;

Y$^1$, Y$^2$, Y$^3$ and Y$^4$, if present, are each independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, wherein Y$^1$ and Y$^2$ or Y$^3$ and Y$^4$ are optionally cyclically linked;

Q$^1$ is a bond to either X$^4$ or X$^5$, wherein if Q$^1$ is a bond to X$^4$, then X$^4$ is C and Y$^4$ is absent, or if Q$^1$ is a bond to X$^5$, then Y$^5$ is absent; and Q$^2$ is a bond to either X$^3$ or X$^5$, wherein if Q$^2$ is a bond to X$^3$, then X$^3$ is NR$^{12}$ and R$^{12}$ is absent, or if Q$^2$ is a bond to X$^5$, then Y$^5$ is absent.

In some embodiments, Y$^1$ and Y$^2$ or Y$^3$ and Y$^4$ are cyclically linked to form a fused benzo ring.

In some embodiments,

T$^1$ is selected from a (C$_1$-C$_{12}$)alkyl and a substituted (C$_1$-C$_{12}$)alkyl; T$^2$, T$^3$, T$^4$ and T$^5$ are each independently selected from (EDA)$_w$, (PEG)$_n$, (C$_1$-C$_{12}$)alkyl, substituted (C$_1$-C$_{12}$)alkyl, (AA)$_p$, —(CR$^{13}$OH)$_h$—, piperidin-4-amino, MABC, MABO, PABO, PABC, para-aminobenzyl, an acetal group, a disulfide, a hydrazine, a protease-cleavable moiety, a glucuronidase cleavable moiety, a beta-lactamase cleavable moiety, an ester, (AA)$_p$-MABC-(AA)$_p$, (AA)$_p$-MABO-(AA)$_p$, (AA)$_p$-PABO-(AA)$_p$ and (AA)$_p$-PABC-(AA)$_p$; and V$^1$, V$^2$, V$^3$, V$^4$ and V$^5$ are each independently selected from the group consisting of: a covalent bond, —CO—, —NR$^{11}$—, —CONR$^{11}$—, —NR$^{11}$CO—, —C(O)O—, —OC(O)—, —O—, —S—, —S(O)—, —SO$_2$—, —SO$_2$NR$^{11}$—, —NR$^{11}$SO$_2$—, and —P(O)OH—;

wherein:

(PEG)$_n$ is

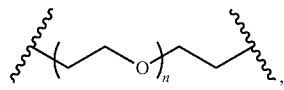

where n is an integer from 1 to 30;

EDA is an ethylene diamine moiety having the following structure:

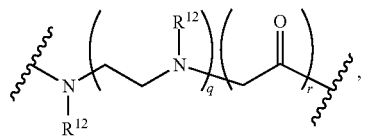

where q is an integer from 1 to 6 and r is 0 or 1;

piperidin-4-amino is

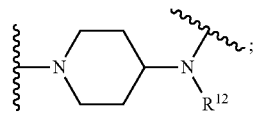

each $R^{11}$ and $R^{12}$ is independently selected from hydrogen, an alkyl, a substituted alkyl, a PEG, an aryl and a substituted aryl, wherein any two adjacent $R^{12}$ groups may be cyclically linked to form a piperazinyl ring; and $R^{13}$ is selected from hydrogen, an alkyl, a substituted alkyl, an aryl, and a substituted aryl.

In some embodiments, a, b, c and d are each 1; and e is 0.

In some embodiments, a, b and c are each 1; and d and e are each 0.

In some embodiments, a and b are each 1; and c, d and e are each 0.

In some embodiments, $T^1$, $T^2$, $T^3$, $T^4$ and $T^5$ and $V^1$, $V^2$, $V^3$, $V^4$ and $V^5$ are selected from the following table:

| $T^1$ | $V^1$ | $T^2$ | $V^2$ | $T^3$ | $V^3$ | $T^4$ | $V^4$ | $T^5$ | $V^5$ |
|---|---|---|---|---|---|---|---|---|---|
| (C$_1$-C$_{12}$)alkyl | —CONR$^{11}$— | (PEG)$_n$ | —CO— | — | — | — | — | — | — |
| (C$_1$-C$_{12}$)alkyl | —CO— | (AA)$_p$ | —NR$^{11}$— | (PEG)$_n$ | —CO— | — | — | — | — |
| (C$_1$-C$_{12}$)alkyl | —CO— | (AA)$_p$ | — | — | — | — | — | — | — |
| (C$_1$-C$_{12}$)alkyl | —CONR$^{11}$— | (PEG)$_n$ | NR$^{11}$— | — | — | — | — | — | — |
| (C$_1$-C$_{12}$)alkyl | —CO— | (AA)$_p$ | NR$^{11}$— | (PEG)$_n$ | —NR$^{11}$— | — | — | — | — |
| (C$_1$-C$_{12}$)alkyl | —CO— | (EDA)$_w$ | —CO— | — | — | — | — | — | — |
| (C$_1$-C$_{12}$)alkyl | —CONR$^{11}$— | (C$_1$-C$_{12}$)alkyl | —NR$^{11}$— | — | — | — | — | — | — |
| (C$_1$-C$_{12}$)alkyl | —CONR$^{11}$— | (PEG)$_n$ | —CO— | (EDA)$_w$ | — | — | — | — | — |
| (C$_1$-C$_{12}$)alkyl | —CO— | (EDA)$_w$ | —CO— | (CR$^{13}$OH)$_h$ | —CONR$^{11}$— | (C$_1$-C$_{12}$)alkyl | —CO— | — | — |
| (C$_1$-C$_{12}$)alkyl | —CO— | (AA)$_p$ | —NR$^{11}$— | (C$_1$-C$_{12}$)alkyl | —CO— | — | — | — | — |
| (C$_1$-C$_{12}$)alkyl | —CONR$^{11}$— | (PEG)$_n$ | —CO— | (AA)$_p$ | — | — | — | — | — |
| (C$_1$-C$_{12}$)alkyl | —CONR$^{11}$— | (PEG)$_n$ | —CO— | (AA)$_p$ | — | MABO | — | — | — |
| (C$_1$-C$_{12}$)alkyl | —CONR$^{11}$— | (PEG)$_n$ | —CO— | (AA)$_p$ | — | PABO | — | — | — |
| (C$_1$-C$_{12}$)alkyl | —CONR$^{11}$— | (PEG)$_n$ | —CO— | (AA)$_p$ | — | PABC | — | — | — |
| (C$_1$-C$_{12}$)alkyl | —CO— | (EDA)$_w$ | —CO— | (CR$^{13}$OH)$_h$ | —CO— | (AA)$_p$ | — | — | — |
| (C$_1$-C$_{12}$)alkyl | —CO— | (AA)$_p$ | —NR$^{11}$— | (C$_1$-C$_{12}$)alkyl | —CO— | (AA)$_p$ | — | — | — |
| (C$_1$-C$_{12}$)alkyl | —CO— | (AA)$_p$ | —NR$^{11}$— | (PEG)$_n$ | —CO— | (AA)$_p$ | — | — | — |
| (C$_1$-C$_{12}$)alkyl | —CO— | (AA)$_p$ | —NR$^{11}$— | (C$_1$-C$_{12}$)alkyl | —CO— | (AA)$_p$ | — | — | — |
| (C$_1$-C$_{12}$)alkyl | —CO— | (AA)$_p$ | —NR$^{11}$— | (PEG)$_n$ | —CO— | (AA)$_p$-PABC-(AA)$_p$ | — | — | — |
| (C$_1$-C$_{12}$)alkyl | —CO— | (AA)$_p$ | —NR$^{11}$— | (PEG)$_n$ | —CO— | (AA)$_p$- | — | PABC-(AA)$_p$ | — |
| (C$_1$-C$_{12}$)alkyl | —CO— | (AA)$_p$ | —NR$^{11}$— | (PEG)$_n$ | —CO— | (AA)$_p$-PABO | — | — | — |
| (C$_1$-C$_{12}$)alkyl | —CO— | (AA)$_p$ | —NR$^{11}$— | (PEG)$_n$ | —CO— | (AA)$_p$ | — | PABO | — |
| (C$_1$-C$_{12}$)alkyl | —CO— | (AA)$_p$ | —NR$^{11}$— | (PEG)$_n$ | —SO$_2$— | (AA)$_p$ | — | — | — |
| (C$_1$-C$_{12}$)alkyl | —CONR$^{11}$— | (PEG)$_n$ | —CO— | (AA)$_p$ | — | PABC-(AA)$_p$ | — | — | — |
| (C$_1$-C$_{12}$)alkyl | —CONR$^{11}$— | (PEG)$_n$ | —CO— | (AA)$_p$ | — | PABC | — | (AA)$_p$ | — |
| (C$_1$-C$_{12}$)alkyl | —CO— | (EDA)$_w$ | —CO— | (CR$^{13}$OH)$_h$ | —CONR$^{11}$— | (PEG)$_n$ | —CO— | — | — |
| (C$_1$-C$_{12}$)alkyl | —CO— | (AA)$_p$ | —NR$^{11}$— | (PEG)$_n$ | —CO— | MABC-(AA)$_p$- | — | — | — |
| (C$_1$-C$_{12}$)alkyl | —CO— | (AA)$_p$ | —NR$^{11}$— | (PEG)$_n$ | —CO— | MABC | — | (AA)$_p$ | — |
| (C$_1$-C$_{12}$)alkyl | —CONR$^{11}$— | (PEG)$_n$ | —CO— | MABO | — | — | — | — | — |
| (C$_1$-C$_{12}$)alkyl | —CO— | (AA)$_p$ | —NR$^{11}$— | (PEG)$_n$ | —CO— | MABO | — | — | — |
| (C$_1$-C$_{12}$)alkyl | —CO— | (AA)$_p$ | —NR$^{11}$— | (PEG)$_n$ | —CO— | PABO | — | — | — |
| (C$_1$-C$_{12}$)alkyl | —CO— | (AA)$_p$ | —NR$^{11}$— | (PEG)$_n$ | —CO— | PABC | — | — | — |
| (C$_1$-C$_{12}$)alkyl | —CONR$^{11}$— | (PEG)$_n$ | —CO— | MABC | — | (AA)$_p$ | — | — | — |
| (C$_1$-C$_{12}$)alkyl | —CO— | (CR$^{13}$OH)$_h$ | —CO— | — | — | — | — | — | — |
| (C$_1$-C$_{12}$)alkyl | —CONR$^{11}$— | substituted (C$_1$-C$_{12}$)alkyl | —NR$^{11}$— | (PEG)$_n$ | —CO— | — | — | — | — |
| (C$_1$-C$_{12}$)alkyl | —SO$_2$— | (C$_1$-C$_{12}$)alkyl | —CO— | — | — | — | — | — | — |
| (C$_1$-C$_{12}$)alkyl | —CONR$^{11}$— | (PEG)$_n$ | —CO— | (AA)$_p$ | — | PABC | —NR$^{11}$— | — | — |
| (C$_1$-C$_{12}$)alkyl | —CONR$^{11}$— | (C$_1$-C$_{12}$)alkyl | — | (CR$^{13}$OH)$_h$ | —CONR$^{11}$— | — | — | — | — |
| (C$_1$-C$_{12}$)alkyl | —CO— | P4A | —CO— | (C$_1$-C$_{12}$)alkyl | —CO— | (AA)$_p$ | — | PABO | —CO— |
| (C$_1$-C$_{12}$)alkyl | —CO— | P4A | —CO— | (C$_1$-C$_{12}$)alkyl | —CO— | (AA)$_p$ | — | PABO | — |
| (C$_1$-C$_{12}$)alkyl | —CO— | P4A | —CO— | (C$_1$-C$_{12}$)alkyl | —CO— | (AA)$_p$ | — | PABC-(AA)$_p$ | — |
| (C$_1$-C$_{12}$)alkyl | —CO— | P4A | —CO— | (C$_1$-C$_{12}$)alkyl | —CO— | (AA)$_p$ | — | — | — |

In some embodiments, L is described by one of the following structures:
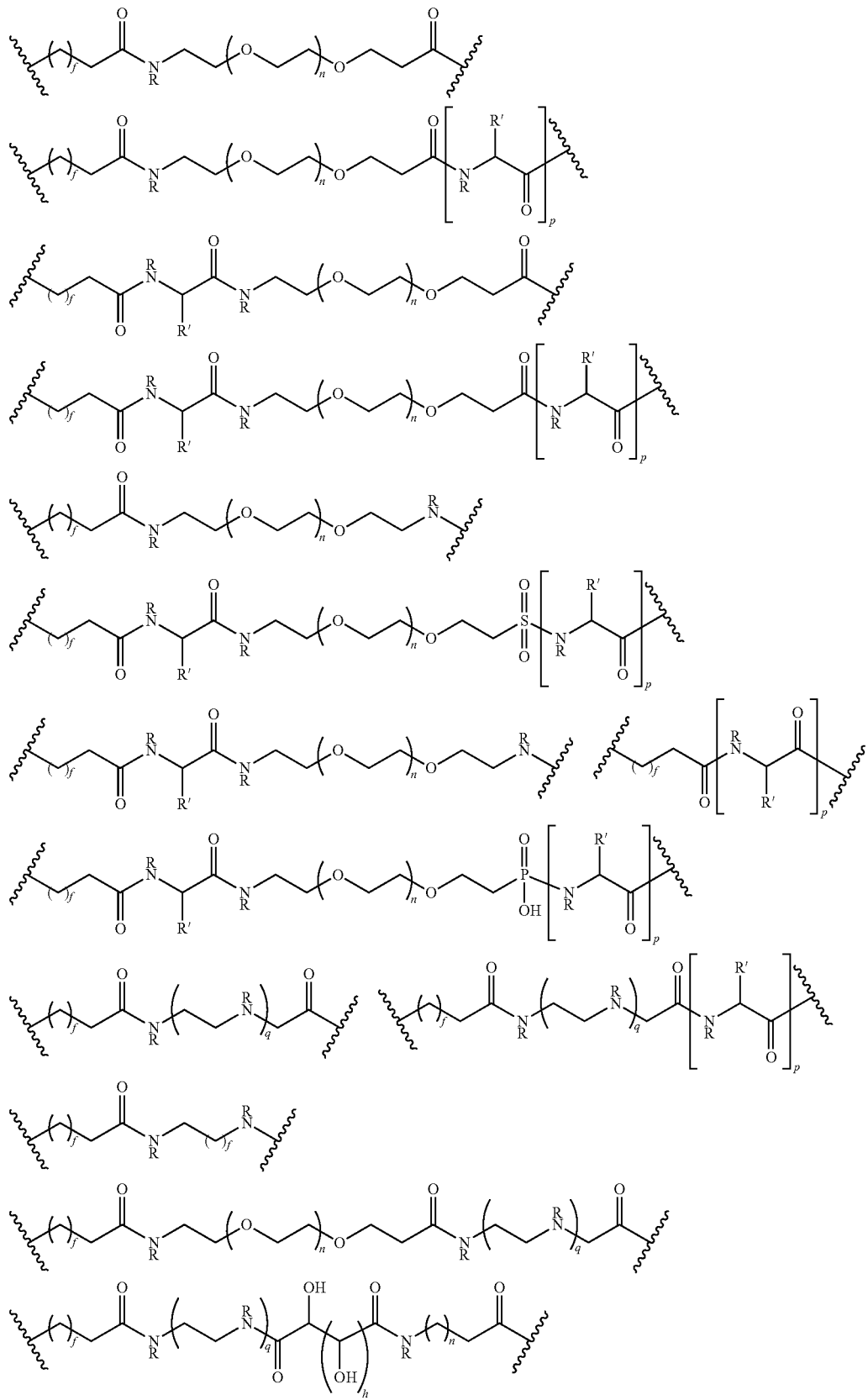

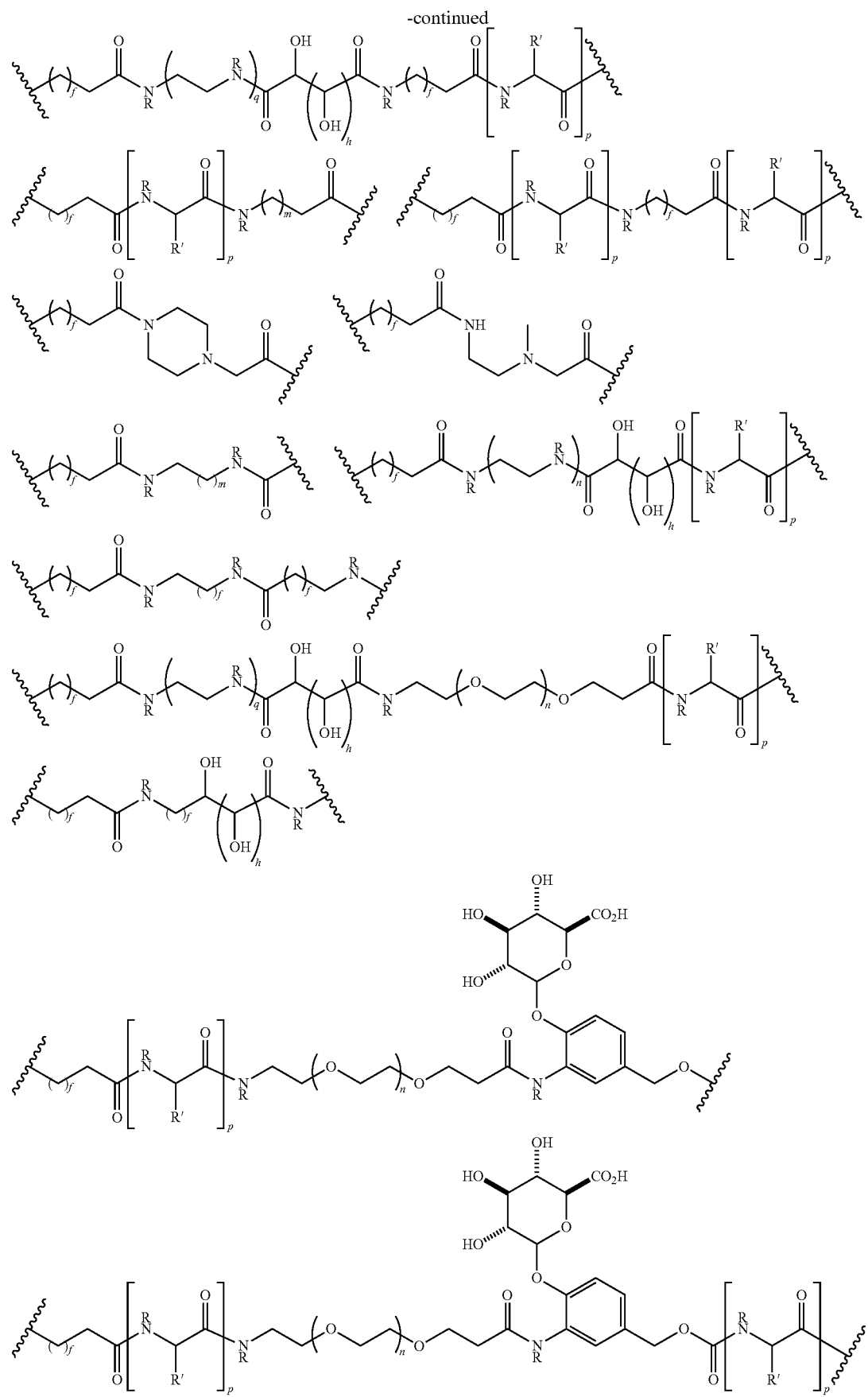

-continued
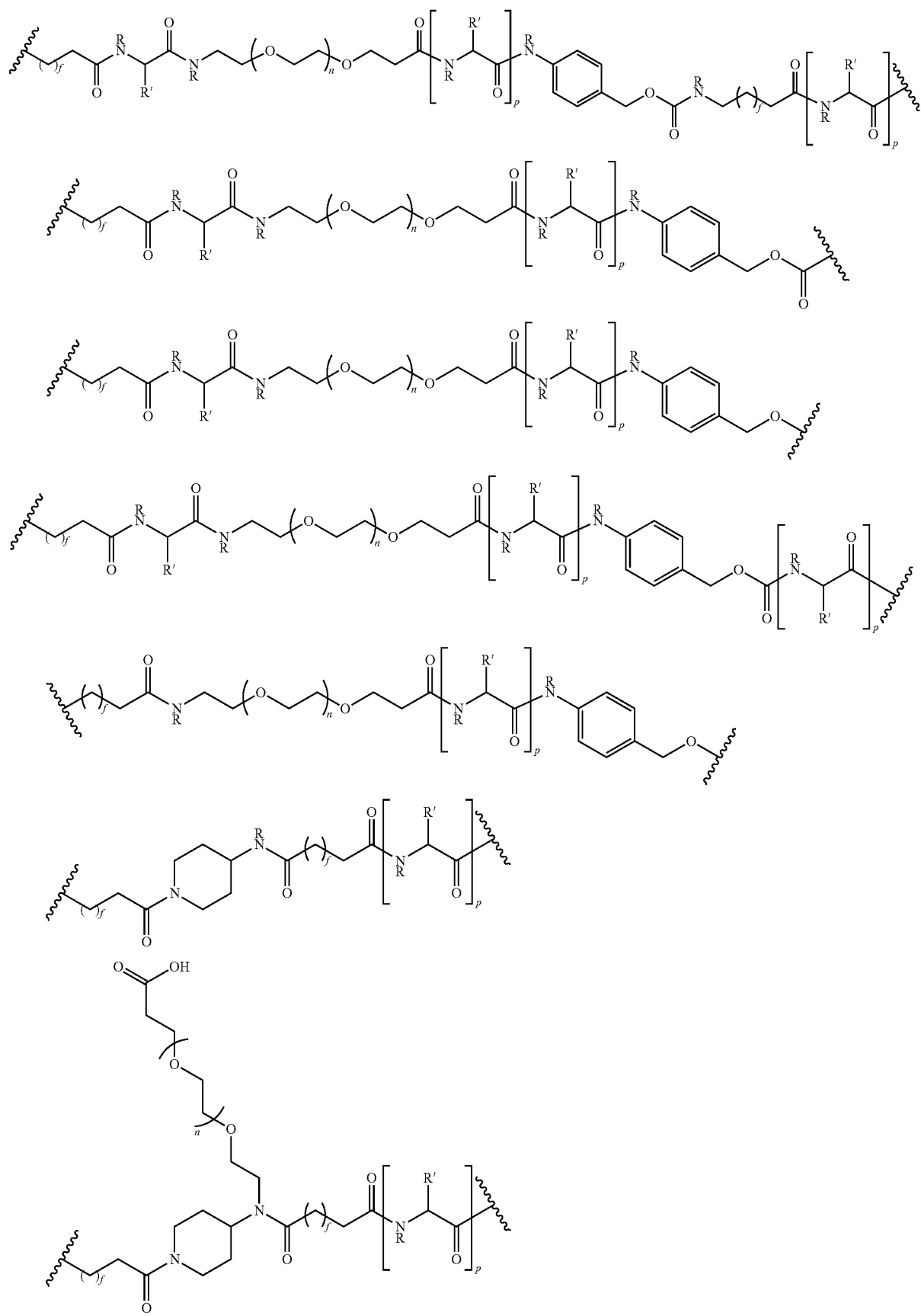

-continued

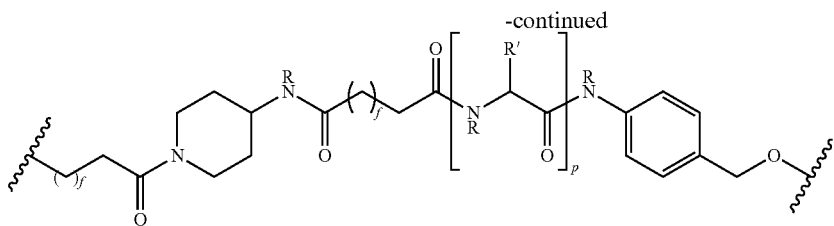

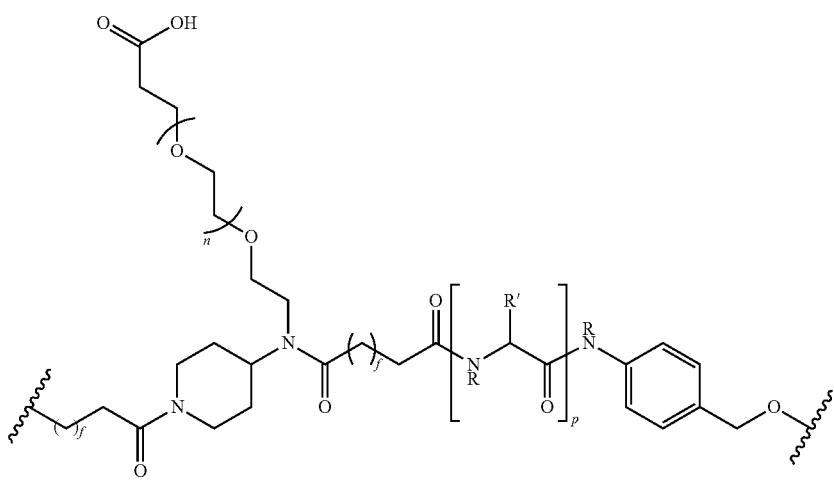

wherein:
  each f is independently 0 or an integer from 1 to 12;
  each w is independently 0 or an integer from 1 to 20;
  each n is independently 0 or an integer from 1 to 30;
  each p is independently 0 or an integer from 1 to 20;
  each h is independently 0 or an integer from 1 to 12;
  each R is independently hydrogen, alkyl, substituted alkyl, a polyethylene glycol moiety, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl; and
  each R' is independently H, a sidechain group of an amino acid, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl.
  In some embodiments, $Q^1$ is a bond to $X^4$ and $Y^4$ is absent.
  In some embodiments, $Q^1$ is a bond to $X^5$ and $Y^5$ is absent.
  In some embodiments, m is 1.
  In some embodiments, $R^2$ and $R^3$ are each independently selected from alkyl and substituted alkyl.
  In some embodiments, $R^2$ and $R^3$ are each methyl.
  In some embodiments, $X^1$, $X^2$, $X^3$ and $X^4$ are each C.

In some embodiments, $Y^1$, $Y^2$ and $Y^3$ are each H, and one of either $Y^4$ or $Y^5$ is H.
  In some embodiments, the conjugate includes at least one modified amino acid residue of formula (IIIa):

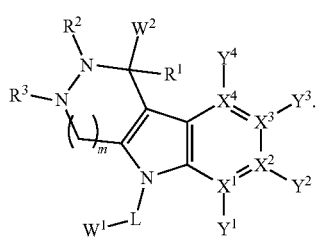

(IIIa)

In some embodiments, the conjugate includes at least one modified amino acid residue of formula (IIIb):

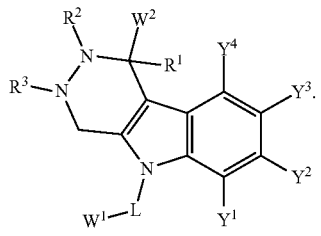

(IIIb)

In some embodiments, the conjugate includes at least one modified amino acid residue of formula (IIId):

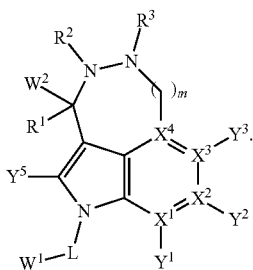

(IIId)

In some embodiments, the conjugate comprises at least one modified amino acid residue of formula (IIIe):

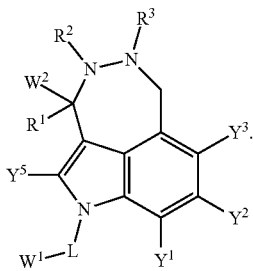

(IIIe)

In some embodiments, the chemical entity is a drug or a detectable label.

In some embodiments, $W^1$ is the chemical entity, and $W^2$ is the polypeptide.

In some embodiments, $W^1$ is the polypeptide, and $W^2$ is the chemical entity.

Aspects of the present disclosure includes a compound of formula (V):

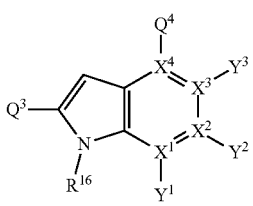

(V)

wherein
one of $Q^3$ and $Q^4$ is —$(CH_2)_m NR^3 NHR^2$ and the other is $Y^4$;

m is 0 or 1;

$R^2$ and $R^3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocycyl, or $R^2$ and $R^3$ are optionally cyclically linked to form a 5 or 6-membered heterocyclyl 1;

$X^1$, $X^2$, $X^3$ and $X^4$ are each independently selected from C, N, O and S, wherein one of $X^1$, $X^2$, $X^3$ and $X^4$ is optional;

$Y^1$, $Y^2$, $Y^3$ and $Y^4$ are each independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, wherein $Y^1$ and $Y^2$ or $Y^2$ and $Y^3$ are optionally cyclically linked, and wherein when $Q^4$ is $Y^4$, then $Y^3$ and $Y^4$ are optionally cyclically linked;

one of $R^{16}$, $Y^1$, $Y^2$, $Y^3$ or $Q^4$ is -L-$W^1$, wherein if $Q^4$ is -L-$W^1$, then $Q^3$ is —$(CH_2)_m NR^3 NHR^2$ and $Y^4$ is absent; and wherein if one of $Y^1$, $Y^2$, $Y^3$ or $Q^4$ is -L-$W^1$, then $R^{16}$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;

L is a linker comprising -$(T^1-V^1)_a$-$(T^2-V^2)_b$-$(T^3-V^3)_c$-$(T^4-V^4)_d$-$(T^5-V^5)_e$—, wherein a, b, c, d and e are each independently 0 or 1, where the sum of a, b, c, d and e is 1 to 5;

$T^1$, $T^2$, $T^3$, $T^4$ and $T^5$ are each independently selected from $(C_1-C_{12})$alkyl, substituted $(C_1-C_{12})$alkyl, $(EDA)_w$, $(PEG)_n$, $(AA)_p$, —$(CR^{13}OH)_h$—, piperidin-4-amino (P4A), para-amino-benzyloxycarbonyl (PABC), a meta-amino-benzyloxycarbonyl (MABC), a para-amino-benzyloxy (PABO), a meta-amino-benzyloxy (MABO), para-aminobenzyl, an acetal group, a disulfide, a hydrazine, a protease-cleavable moiety, a glucuronidase cleavable moiety, a beta-lactamase cleavable moiety, and an ester, wherein EDA is an ethylene diamine moiety, PEG is a polyethylene glycol or a modified polyethylene glycol, and AA is an amino acid residue;

w is an integer from 1 to 20;

n is an integer from 1 to 30;

p is an integer from 1 to 20;

h is an integer from 1 to 12;

$V^1$, $V^2$, $V^3$, $V^4$ and $V^5$ are each independently selected from the group consisting of a covalent bond, —CO—, —$NR^{11}$—, —$CONR^{11}$—, —$NR^{11}CO$—, —C(O)O—, —OC(O)—, —O—, —S—, —S(O)—, —$SO_2$—, —$SO_2NR^{11}$—, —$NR^{11}SO_2$— and —P(O)OH—; and $W^1$ is selected from a polypeptide and a chemical entity, and wherein when the sum of a, b, c, d and e is 2 and one of $T^1-V^1$, $T^2-V^2$, $T^3-V^3$, $T^4-V^4$ or $T^5-V^5$ is $(PEG)_n$-CO, then n is not 6.

In some embodiments, the compound is a compound of formula (VI):

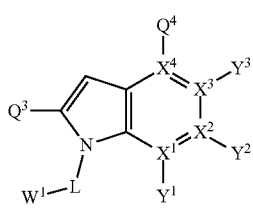

(VI)

wherein
$Q^3$, $Q^4$, $X^1$, $X^2$, $X^3$, $X^4$, L, $W^1$, $Y^1$, $Y^2$, and $Y^3$ are as defined in formula (V).

In some embodiments, the compound is a compound of formula (VIIa) or (VIIb):

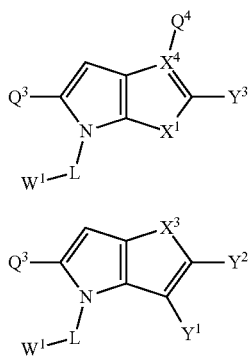

(VIIa)

(VIIb)

wherein:
X$^1$ and X$^3$ are each independently O, S or NR$^{12}$;
in formula (VIIa), one of Q$^3$ and Q$^4$ is —(CH$_2$)$_m$NR$^3$NHR$^2$ and the other is Y$^4$;
in formula (VIIb), one of Q$^3$ and R$^{12}$, if present, is —(CH$_2$)$_m$NR$^3$NHR$^2$ and the other is Y$^3$;
Y$^1$, Y$^2$, Y$^3$ and Y$^4$, if present, are each independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, wherein Y$^1$ and Y$^2$ are optionally cyclically linked, and wherein when Q$^4$ is Y$^4$, then Y$^3$ and Y$^4$ are optionally cyclically linked; and
m, R$^2$ and R$^3$ are as defined in formula (V).

In some embodiments, Y$^1$ and Y$^2$ or Y$^3$ and Y$^4$ are cyclically linked to form a fused benzo ring.

In some embodiments,
T$^1$ is selected from a (C$_1$-C$_{12}$)alkyl and a substituted (C$_1$-C$_{12}$)alkyl;
T$^2$, T$^3$, T$^4$ and T$^5$ are each independently selected from (EDA)$_w$, (PEG)$_n$, (C$_1$-C$_{12}$)alkyl, substituted (C$_1$-C$_{12}$)alkyl, (AA)$_p$, —(CR$^{13}$OH)$_h$—, piperidin-4-amino, MABC, MABO, PABO, PABC, para-aminobenzyl, an acetal group, a disulfide, a hydrazine, a protease-cleavable moiety, a glucuronidase cleavable moiety, a beta-lactamase cleavable moiety, an ester, (AA)$_p$-MABC-(AA)$_p$, (AA)$_p$-MABO-(AA)$_p$, (AA)$_p$-PABO-(AA)$_p$ and (AA)$_p$-PABC-(AA)$_p$; and
V$^1$, V$^2$, V$^3$, V$^4$ and V$^5$ are each independently selected from the group consisting of: a covalent bond, —CO—, —NR$^{11}$—, —CONR$^{11}$—, —NR$^{11}$CO—, —C(O)O—, —OC(O)—, —O—, —S—, —S(O)—, —SO$_2$—, —SO$_2$NR$^{11}$—, —NR$^{11}$SO$_2$—, and —P(O)OH—;
wherein:
(PEG)$_n$ is

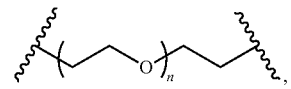

where n is an integer from 1 to 30;
EDA is an ethylene diamine moiety having the following structure:

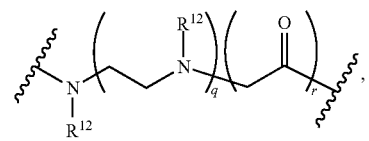

where q is an integer from 1 to 6 and r is 0 or 1;
piperidin-4-amino is

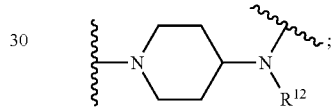

each R$^{11}$ and R$^{12}$ is independently selected from hydrogen, an alkyl, a substituted alkyl, a polyethylene glycol moiety, an aryl and a substituted aryl, wherein any two adjacent R$^{12}$ groups may be cyclically linked to form a piperazinyl ring; and R$^{13}$ is selected from hydrogen, an alkyl, a substituted alkyl, an aryl, and a substituted aryl.

In some embodiments, a, b, c and d are each 1; and e is 0.

In some embodiments, a, b and c are each 1; and d and e are 0.

In some embodiments, a and b are each 1; and c, d and e are 0.

In some embodiments, T$^1$, T$^2$, T$^3$, T$^4$ and T$^5$ and V$^1$, V$^2$, V$^3$, V$^4$ and V$^5$ are selected from the following table:

| T$^1$ | V$^1$ | T$^2$ | V$^2$ | T$^3$ | V$^3$ | T$^4$ | V$^4$ | T$^5$ | V$^5$ |
|---|---|---|---|---|---|---|---|---|---|
| (C$_1$-C$_{12}$)alkyl | —CONR$^{11}$— | (PEG)$_n$ | —CO— | — | — | — | — | — | — |
| (C$_1$-C$_{12}$)alkyl | —CO— | (AA)$_p$ | —NR$^{11}$— | (PEG)$_n$ | —CO— | — | — | — | — |
| (C$_1$-C$_{12}$)alkyl | —CO— | (AA)$_p$ | — | — | — | — | — | — | — |
| (C$_1$-C$_{12}$)alkyl | —CONR$^{11}$— | (PEG)$_n$ | —NR$^{11}$— | — | — | — | — | — | — |
| (C$_1$-C$_{12}$)alkyl | —CO— | (AA)$_p$ | —NR$^{11}$— | (PEG)$_n$ | —NR$^{11}$— | — | — | — | — |
| (C$_1$-C$_{12}$)alkyl | —CO— | (EDA)$_w$ | —CO— | — | — | — | — | — | — |
| (C$_1$-C$_{12}$)alkyl | —CONR$^{11}$— | (C$_1$-C$_{12}$)alkyl | —NR$^{11}$— | — | — | — | — | — | — |
| (C$_1$-C$_{12}$)alkyl | —CONR$^{11}$— | (PEG)$_n$ | —CO— | (EDA)$_w$ | — | — | — | — | — |
| (C$_1$-C$_{12}$)alkyl | —CO— | (EDA)$_w$ | — | — | — | — | — | — | — |
| (C$_1$-C$_{12}$)alkyl | —CO— | (EDA)$_w$ | —CO— | (CR$^{13}$OH)$_h$ | —CONR$^{11}$— | (C$_1$-C$_{12}$)alkyl | —CO— | — | — |
| (C$_1$-C$_{12}$)alkyl | —CO— | (AA)$_p$ | —NR$^{11}$— | (C$_1$-C$_{12}$)alkyl | —CO— | — | — | — | — |
| (C$_1$-C$_{12}$)alkyl | —CONR$^{11}$— | (PEG)$_n$ | —CO— | (AA)$_p$ | — | — | — | — | — |
| (C$_1$-C$_{12}$)alkyl | —CONR$^{11}$— | (PEG)$_n$ | —CO— | (AA)$_p$ | — | MABO | — | — | — |
| (C$_1$-C$_{12}$)alkyl | —CONR$^{11}$— | (PEG)$_n$ | —CO— | (AA)$_p$ | — | PABO | — | — | — |
| (C$_1$-C$_{12}$)alkyl | —CONR$^{11}$— | (PEG)$_n$ | —CO— | (AA)$_p$ | — | PABC | — | — | — |
| (C$_1$-C$_{12}$)alkyl | —CO— | (EDA)$_w$ | —CO— | (CR$^{13}$OH)$_h$ | —CO— | (AA)$_p$ | — | — | — |

| T¹ | V¹ | T² | V² | T³ | V³ | T⁴ | V⁴ | T⁵ | V⁵ |
|---|---|---|---|---|---|---|---|---|---|
| $(C_1-C_{12})$alkyl | —CO— | $(AA)_p$ | —NR¹¹— | $(C_1-C_{12})$alkyl | —CO— | $(AA)_p$ | — | — | — |
| $(C_1-C_{12})$alkyl | —CO— | $(AA)_p$ | —NR¹¹— | $(PEG)_n$ | —CO— | $(AA)_p$ | — | — | — |
| $(C_1-C_{12})$alkyl | —CO— | $(AA)_p$ | —NR¹¹— | $(C_1-C_{12})$alkyl | —CO— | $(AA)_p$ | — | — | — |
| $(C_1-C_{12})$alkyl | —CO— | $(AA)_p$ | —NR¹¹— | $(PEG)_n$ | —CO— | $(AA)_p$-PABC-$(AA)_p$ | — | — | — |
| $(C_1-C_{12})$alkyl | —CO— | $(AA)_p$ | —NR¹¹— | $(PEG)_n$ | —CO— | $(AA)_p$- | — | PABC-$(AA)_p$ | — |
| $(C_1-C_{12})$alkyl | —CO— | $(AA)_p$ | —NR¹¹— | $(PEG)_n$ | —CO— | $(AA)_p$-PABO | — | — | — |
| $(C_1-C_{12})$alkyl | —CO— | $(AA)_p$ | —NR¹¹— | $(PEG)_n$ | —CO— | $(AA)_p$ | — | PABO | — |
| $(C_1-C_{12})$alkyl | —CO— | $(AA)_p$ | —NR¹¹— | $(PEG)_n$ | —SO₂— | $(AA)_p$ | — | — | — |
| $(C_1-C_{12})$alkyl | —CONR¹¹— | $(PEG)_n$ | —CO— | $(AA)_p$ | — | PABC-$(AA)_p$ | — | — | — |
| $(C_1-C_{12})$alkyl | —CONR¹¹— | $(PEG)_n$ | —CO— | $(AA)_p$ | — | PABC | — | $(AA)_p$ | — |
| $(C_1-C_{12})$alkyl | —CO— | $(EDA)_w$ | —CO— | $(CR^{13}OH)_h$ | —CONR¹¹— | $(PEG)_n$ | —CO— | — | — |
| $(C_1-C_{12})$alkyl | —CO— | $(AA)_p$ | —NR¹¹— | $(PEG)_n$ | —CO— | MABC-$(AA)_p$- | — | — | — |
| $(C_1-C_{12})$alkyl | —CO— | $(AA)_p$ | —NR¹¹— | $(PEG)_n$ | —CO— | MABC | — | $(AA)_p$ | — |
| $(C_1-C_{12})$alkyl | —CONR¹¹— | $(PEG)_n$ | —CO— | MABO | — | — | — | — | — |
| $(C_1-C_{12})$alkyl | —CO— | $(AA)_p$ | —NR¹¹— | $(PEG)_n$ | —CO— | MABO | — | — | — |
| $(C_1-C_{12})$alkyl | —CO— | $(AA)_p$ | —NR¹¹— | $(PEG)_n$ | —CO— | PABO | — | — | — |
| $(C_1-C_{12})$alkyl | —CO— | $(AA)_p$ | —NR¹¹— | $(PEG)_n$ | —CO— | PABC | — | — | — |
| $(C_1-C_{12})$alkyl | —CONR¹¹— | $(PEG)_n$ | —CO— | MABC | — | $(AA)_p$ | — | — | — |
| $(C_1-C_{12})$alkyl | —CO— | $(CR^{13}OH)_h$ | —CO— | — | — | — | — | — | — |
| $(C_1-C_{12})$alkyl | —CONR¹¹— | substituted $(C_1-C_{12})$alkyl | —NR¹¹— | $(PEG)_n$ | —CO— | — | — | — | — |
| $(C_1-C_{12})$alkyl | —SO₂— | $(C_1-C_{12})$alkyl | —CO— | — | — | — | — | — | — |
| $(C_1-C_{12})$alkyl | —CONR¹¹— | $(PEG)_n$ | —CO— | $(AA)_p$ | — | PABC | —NR¹¹— | — | — |
| $(C_1-C_{12})$alkyl | —CONR¹¹— | $(C_1-C_{12})$alkyl | — | $(CR^{13}OH)_h$ | —CONR¹¹— | — | — | — | — |
| $(C_1-C_{12})$alkyl | —CO— | P4A | —CO— | $(C_1-C_{12})$alkyl | —CO— | $(AA)_p$ | — | PABO | —CO— |
| $(C_1-C_{12})$alkyl | —CO— | P4A | —CO— | $(C_1-C_{12})$alkyl | —CO— | $(AA)_p$ | — | PABO | — |
| $(C_1-C_{12})$alkyl | —CO— | P4A | —CO— | $(C_1-C_{12})$alkyl | —CO— | $(AA)_p$ | — | PABC-$(AA)_p$ | — |
| $(C_1-C_{12})$alkyl | —CO— | P4A | —CO— | $(C_1-C_{12})$alkyl | —CO— | $(AA)_p$ | — | — | — |

In some embodiments, L is described by one of the following structures:

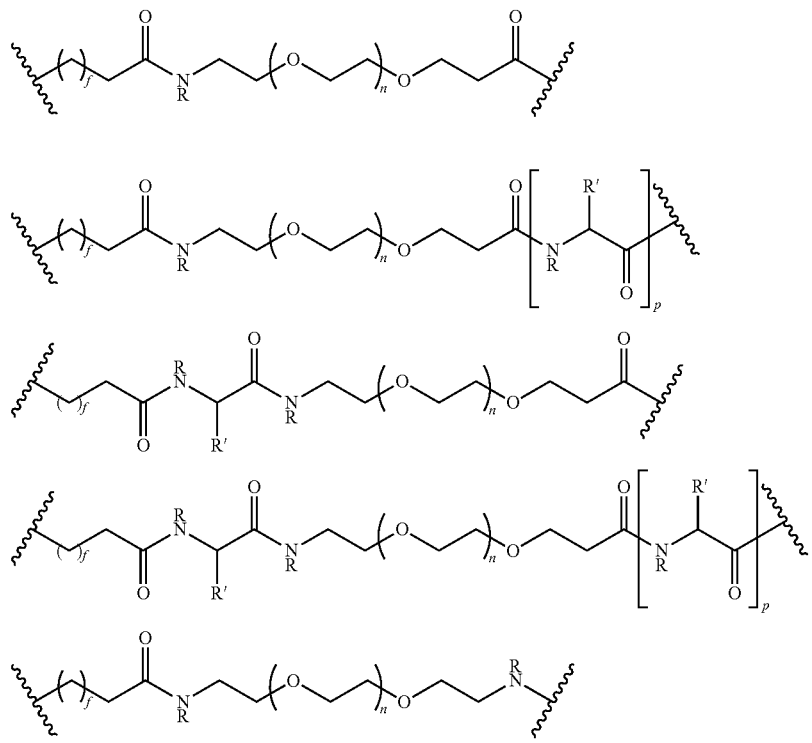

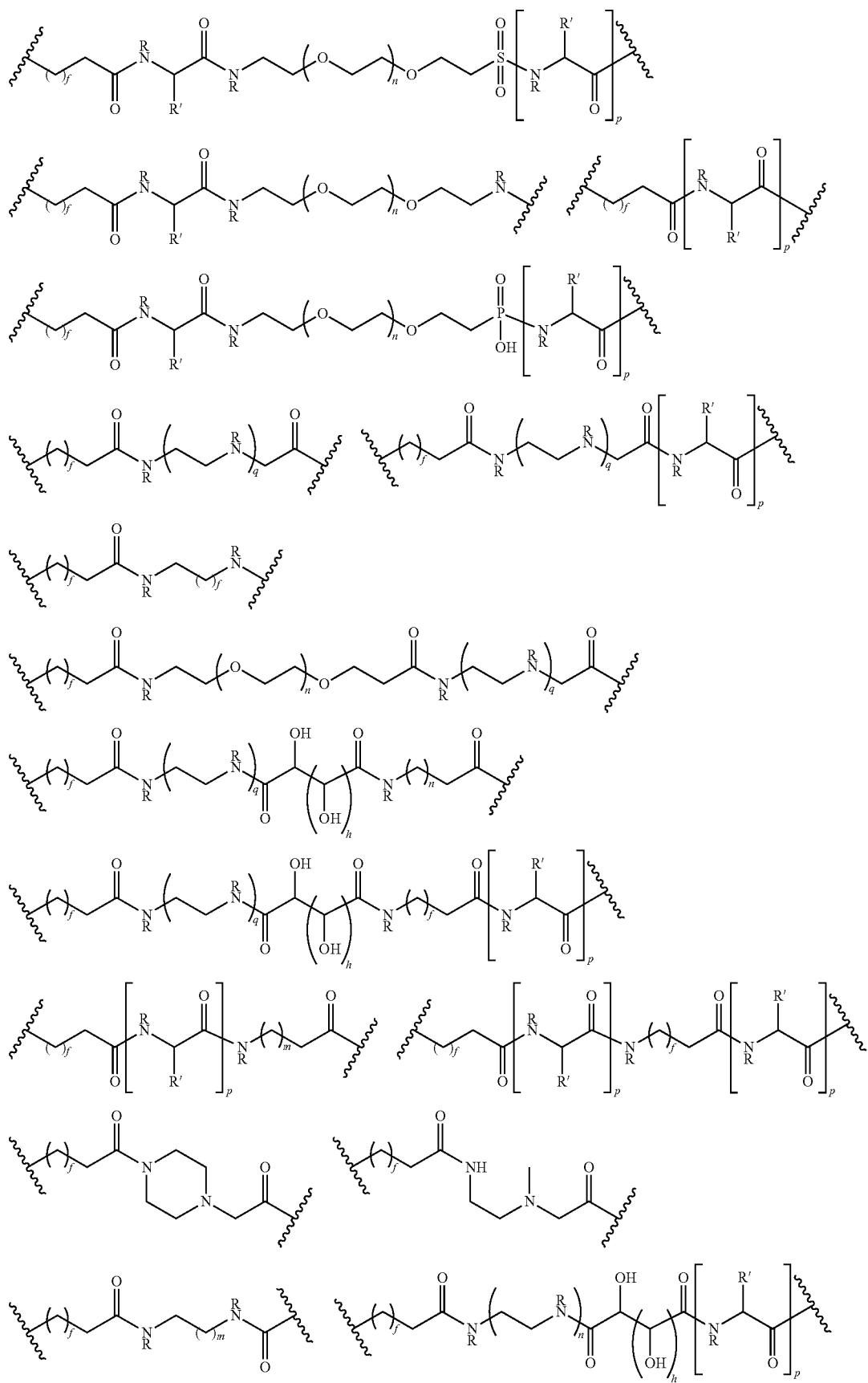

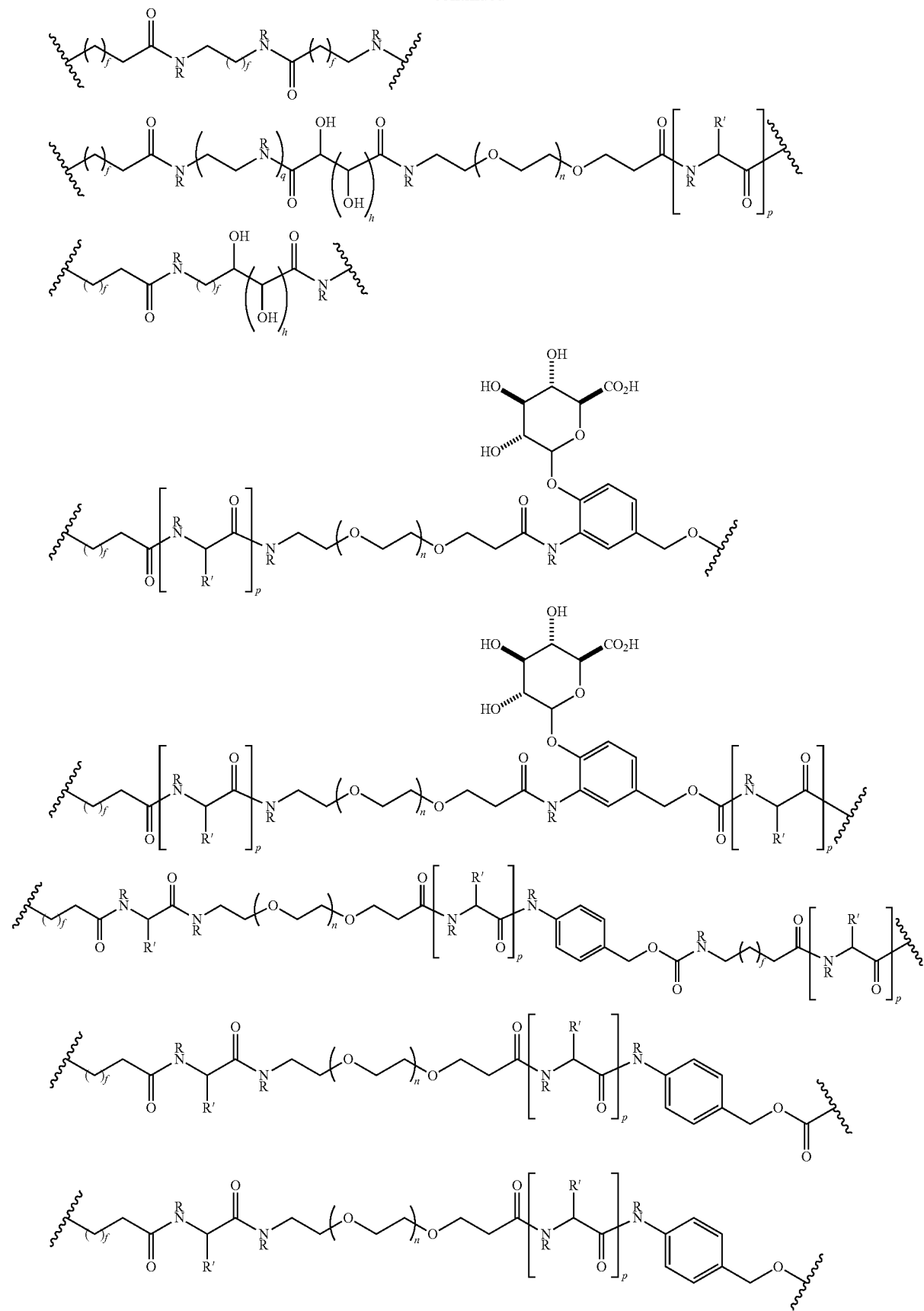

-continued
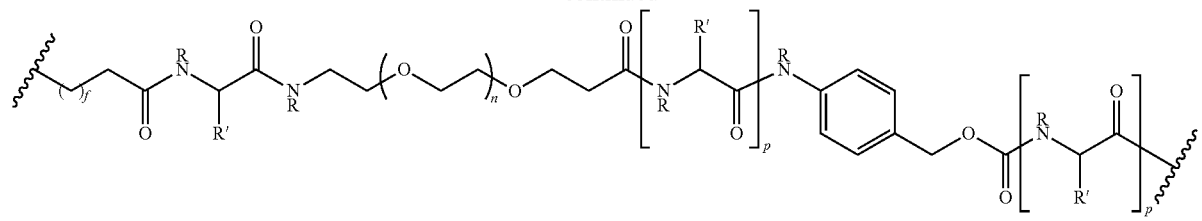
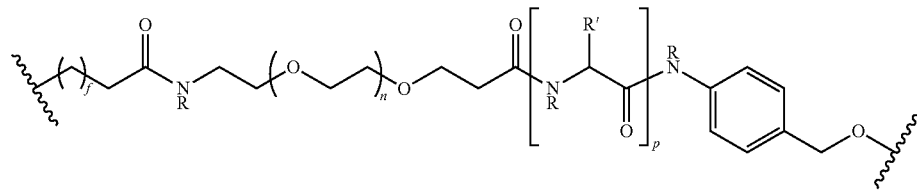
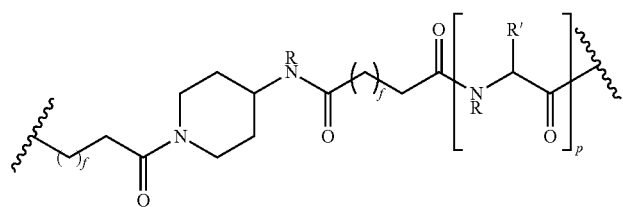
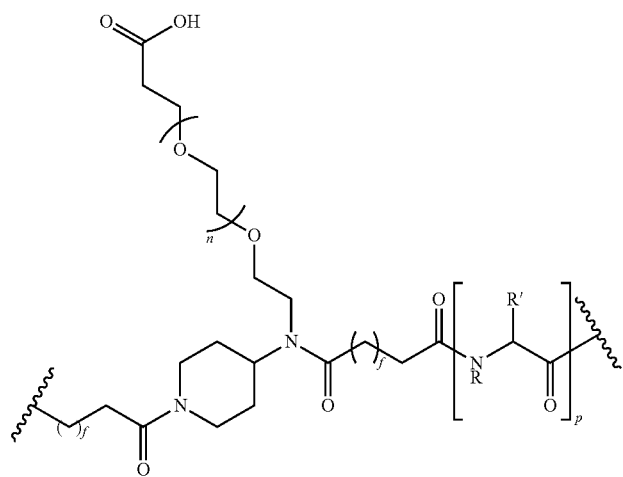
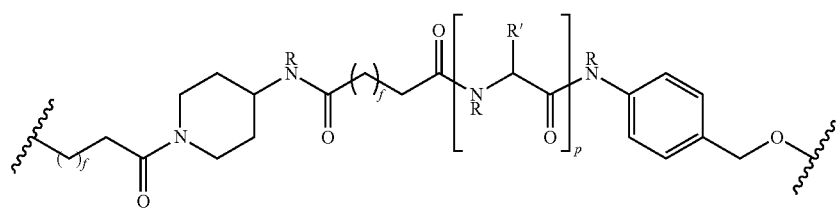

-continued

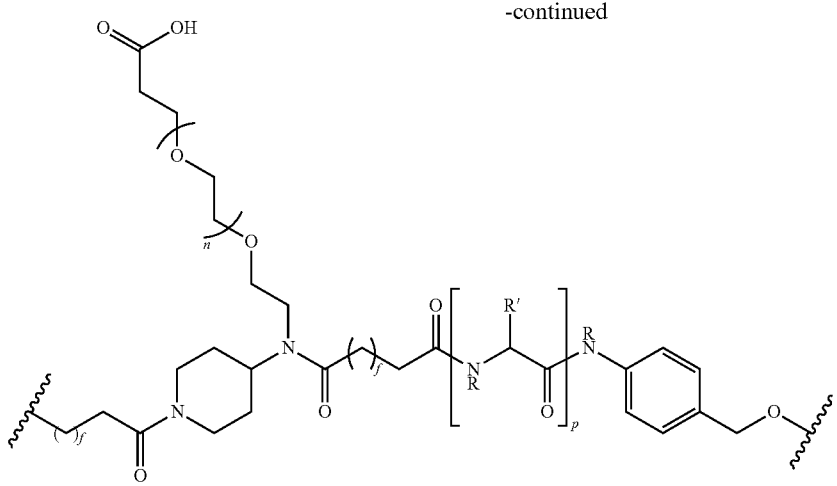

wherein:

each f is independently 0 or an integer from 1 to 12;
each w is independently 0 or an integer from 1 to 20;
each n is independently 0 or an integer from 1 to 30;
each p is independently 0 or an integer from 1 to 20;
each h is independently 0 or an integer from 1 to 12;

each R is independently hydrogen, alkyl, substituted alkyl, a polyethylene glycol moiety, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl; and each R' is independently H, a sidechain group of an amino acid, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl.

In some embodiments, $Q^3$ is $-(CH_2)_m NR^3 NHR^2$ and $Q^4$ is $Y^4$.

In some embodiments, $Q^4$ is $-(CH_2)_m NR^3 NHR^2$ and $Q^3$ is $Y^4$.

In some embodiments, m is 1.

In some embodiments, $R^2$ and $R^3$ are each independently selected from alkyl and substituted alkyl.

In some embodiments, $R^2$ and $R^3$ are each methyl.

In some embodiments, $X^1$, $X^2$, $X^3$ and $X^4$ are each C.

In some embodiments, $Y^1$, $Y^2$, $Y^3$ and $Y^4$ are each H.

In some embodiments, $X^1$ and $X^3$ are each S and $X^4$ is C.

In some embodiments, $X^1$ and $X^3$ are each O and $X^4$ is C.

In some embodiments, $X^1$ and $X^3$ are each $NR^{12}$ and $X^4$ is C.

In some embodiments, the compound is a compound of formula (VIII):

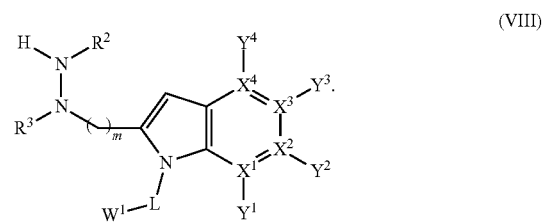

In some embodiments, the compound is a compound of formula (VIIIa):

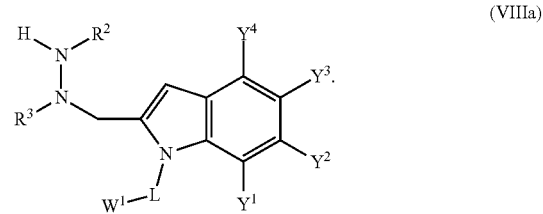

In some embodiments, the compound is a compound of formula (IX):

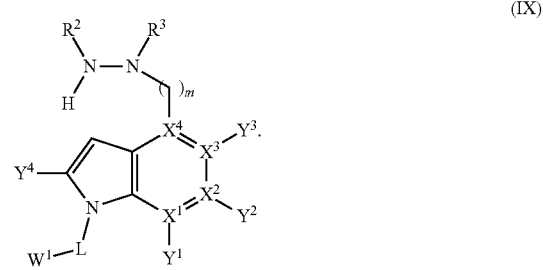

In some embodiments, the compound is a compound of formula (IXa):

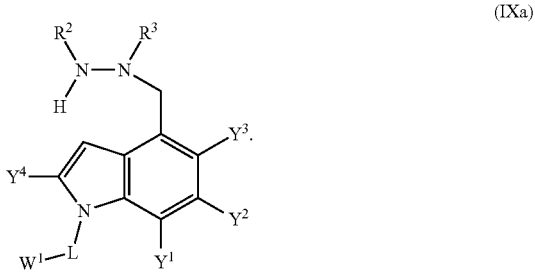

(IXa)

In some embodiments, $W^1$ is a drug or a detectable label.

In some embodiments, the detectable label comprises a fluorophore.

Aspects of the present disclosure include a method of producing a polypeptide conjugate. The method includes combining in a reaction mixture: a compound as described herein and a second compound comprising a reactive aldehyde group or a reactive ketone group, where the combining is under reaction conditions suitable to promote reaction between the compound and the reactive aldehyde group or reactive ketone group of the second compound to form the conjugate, and isolating the conjugate from the reaction mixture.

In some embodiments, $W^1$ is the chemical entity, and the second compound comprises the polypeptide.

In some embodiments, $W^1$ is the polypeptide, and the second compound comprises the chemical entity.

In some embodiments, the reaction mixture has a pH of 7.

In some embodiments, the reaction conditions are at a temperature of 37° C.

Aspects of the present disclosure include a pharmaceutical composition. The pharmaceutical composition includes a conjugate as described herein and a pharmaceutically acceptable excipient.

Aspects of the present disclosure include a method of delivering a conjugate to a subject. The method includes administering to the subject an effective amount of a conjugate as described herein.

Aspects of the present disclosure include a method of treating a condition in a subject. The method includes administering to the subject having the condition a therapeutically effective amount of a pharmaceutical composition comprising a conjugate as described herein, where the administering is effective to treat the condition in the subject.

BRIEF DESCRIPTION OF THE DRAWINGS

FIG. 2 (panel A) shows a reaction scheme for the synthesis of a functionalized detectable label, according to embodiments of the present disclosure. FIG. 2 (panel B) shows a schematic of a conjugation reaction of the functionalized detectable label to an antibody, according to embodiments of the present disclosure.

FIG. 23 shows a reaction scheme for the synthesis of compound HIPS Indole N (($OH)_3AcNH$-β-Glc) $PEG_2$ Maytansine according to embodiments of the present disclosure, see e.g., Example 10.

FIGS. 35A-35C show a size exclusion chromatography (SEC) trace (FIG. 35A), a hydrophobic interaction column (HIC) trace (FIG. 35B), and a mass spectrometer (MS) trace (FIG. 35C) of an aldehyde-tagged antibody conjugated to HIPS Cysteic Acid $PEG_2$ Maytansine, according to embodiments of the present disclosure.

FIGS. 37A-37B show a size exclusion chromatography (SEC) trace (FIG. 37A) and a hydrophobic interaction column (HIC) trace (FIG. 37B) of an aldehyde-tagged antibody conjugated to HIPS Asparagine $PEG_2$ Maytansine, according to embodiments of the present disclosure.

FIGS. 39A-39C show a size exclusion chromatography (SEC) trace (FIG. 39A), a hydrophobic interaction column (HIC) trace (FIG. 39B), and a mass spectrometer (MS) trace (FIG. 39C) of an aldehyde-tagged antibody conjugated to AzaHIPS Glutamic Acid $PEG_2$ Maytansine, according to embodiments of the present disclosure.

FIGS. 40A-40C show a size exclusion chromatography (SEC) trace (FIG. 40A), a hydrophobic interaction column (HIC) trace (FIG. 40B), and a mass spectrometer (MS) trace (FIG. 40C) of an aldehyde-tagged antibody conjugated to HIPS Tartaric Acid Maytansine, according to embodiments of the present disclosure.

FIGS. 41A-41C show a size exclusion chromatography (SEC) trace (FIG. 41A), a hydrophobic interaction column (HIC) trace (FIG. 41B), and a mass spectrometer (MS) trace (FIG. 41C) of an aldehyde-tagged antibody conjugated to HIPS Dihydroxy Maytansine, according to embodiments of the present disclosure.

FIGS. 42A-42C show a size exclusion chromatography (SEC) trace (FIG. 42A), a hydrophobic interaction column (HIC) trace (FIG. 42B), and a mass spectrometer (MS) trace (FIG. 42C) of an aldehyde-tagged antibody conjugated to HIPS Glutamic Acid $C_3$ Maytansine, according to embodiments of the present disclosure.

FIG. 44 shows a hydrophobic interaction column (HIC) trace of an aldehyde-tagged antibody conjugated to HIPS Glc NAc $PEG_2$ $Ac_3$ Maytansine, according to embodiments of the present disclosure.

FIG. 45 shows a hydrophobic interaction column (HIC) trace of an aldehyde-tagged antibody conjugated to HIPS Glc NAc $PEG_2$ Maytansine, according to embodiments of the present disclosure.

FIG. 58 shows a hydrophobic interaction column (HIC) trace of an aldehyde-tagged antibody conjugated to HIPS Trihydroxy Maytansine, according to embodiments of the present disclosure.

FIG. 59 shows a hydrophobic interaction column (HIC) trace of an aldehyde-tagged antibody conjugated to HIPS Lysine $PEG_2$ Maytansine, according to embodiments of the present disclosure.

DEFINITIONS

Figure 1:
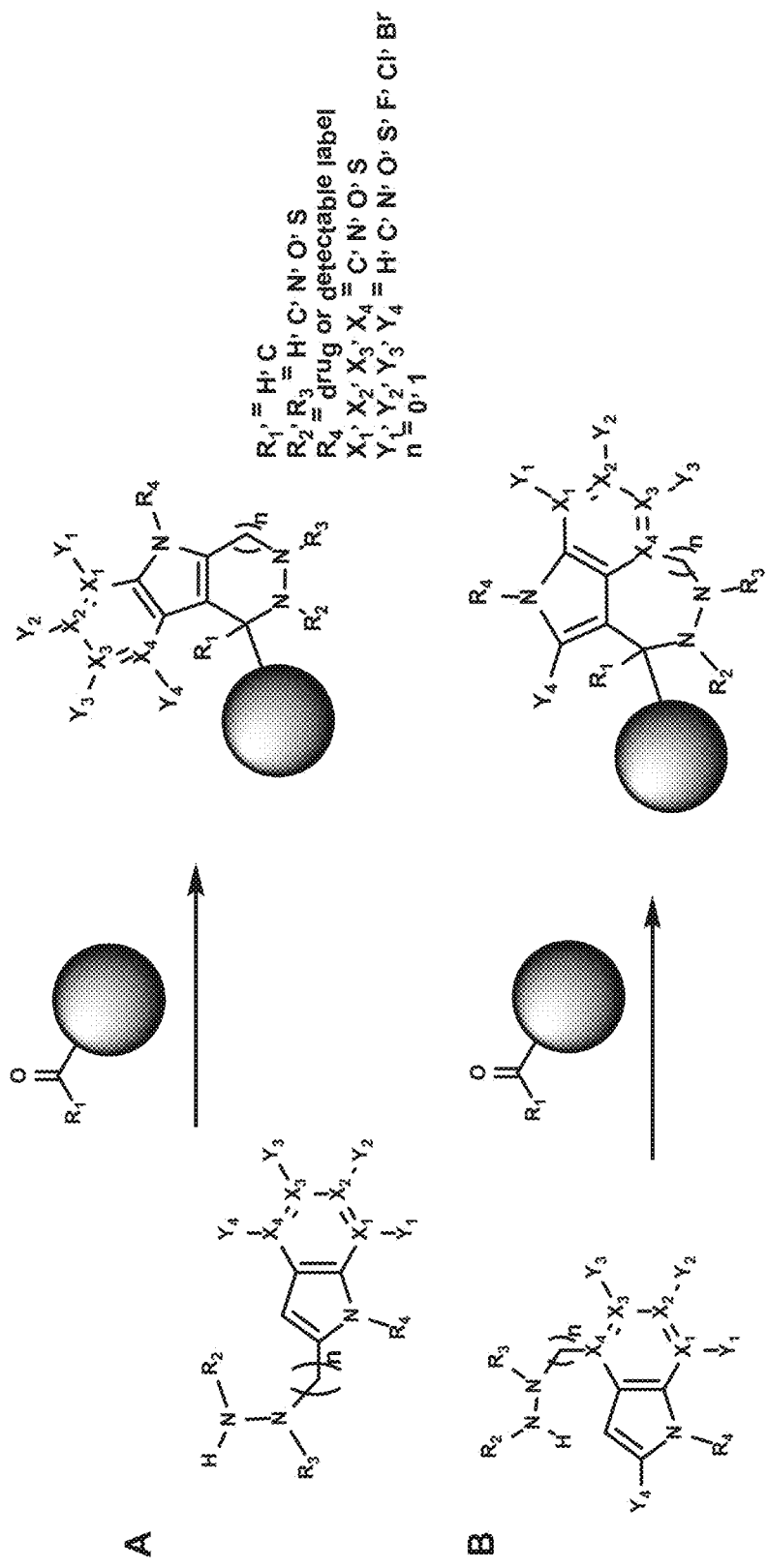
FIG. 1 (panels A and B) show a reaction schemes for the production of a polypeptide conjugate that includes a hydrazinyl-pyrrolo coupling moiety, according to embodiments of the present disclosure.

The following terms have the following meanings unless otherwise indicated. Any undefined terms have their art recognized meanings.

"Alkyl" refers to monovalent saturated aliphatic hydrocarbyl groups having from 1 to 10 carbon atoms and such as 1 to 6 carbon atoms, or 1 to 5, or 1 to 4, or 1 to 3 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$— alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C (O)—, —C(O)NR$^{10}$— and the like. This term includes, by way of example, methylene (—CH$_2$—), ethylene (—CH$_2$CH$_2$—), n-propylene (—CH$_2$CH$_2$CH$_2$—), iso-propylene (—CH$_2$CH(CH$_3$)—), (—C(CH$_3$)$_2$CH$_2$CH$_2$—), (—C(CH$_3$)$_2$CH$_2$C(O)—), (—C(CH$_3$)$_2$CH$_2$C(O)NH—), (—CH(CH$_3$)CH$_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

The term "alkylaminoalkyl", "alkylaminoalkenyl" and "alkylaminoalkynyl" refers to the groups R'NHR"— where R' is alkyl group as defined herein and R" is alkylene, alkenylene or alkynylene group as defined herein.

The term "alkaryl" or "aralkyl" refers to the groups -alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group —NH-alkoxy, wherein alkoxy is defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups -alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO—substituted alkyl, —SO-aryl, —SO-heteroaryl, —SO$_2$-alkyl, —SO$_2$-substituted alkyl, —SO$_2$-aryl and —SO$_2$-heteroaryl.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—CH$_2$C≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO—substituted alkyl, —SO-aryl, —SO-heteroaryl, —SO$_2$-alkyl, —SO$_2$-substituted alkyl, —SO$_2$-aryl, and —SO$_2$-heteroaryl.

"Alkynyloxy" refers to the group —O-alkynyl, wherein alkynyl is as defined herein. Alkynyloxy includes, by way of example, ethynyloxy, propynyloxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group CH$_3$C(O)—

"Acylamino" refers to the groups —NR$^{20}$C(O)alkyl, —NR$^{20}$C(O)substituted alkyl, NR$^{20}$C(O)cycloalkyl, —NR$^{20}$C(O)substituted cycloalkyl, —NR$^{20}$C(O)cycloalkenyl, —NR$^{20}$C(O)substituted cycloalkenyl, —NR$^{20}$C(O)alkenyl, —NR$^{20}$C(O)substituted alkenyl, —NR$^{20}$C(O)alkynyl, —NR$^{20}$C(O)substituted alkynyl, —NR$^{20}$C(O)aryl, —NR$^{20}$C(O)substituted aryl, —NR$^{20}$C(O)heteroaryl, —NR$^{20}$C(O)substituted heteroaryl, —NR$^{20}$C(O)heterocyclic, and —NR$^{20}$C(O)substituted heterocyclic, wherein R$^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{21}$C(O)NR$^{22}$R$^{23}$ where R$^{21}$, R$^{22}$, and R$^{23}$ are independently selected from hydrogen, alkyl, aryl or cycloalkyl, or where two R groups are joined to form a heterocyclyl group.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group —SO$_2$NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where R$^{21}$ and R$^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —NR$^{21}$SO$_2$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

"Aryloxy" refers to the group —O-aryl, wherein aryl is as defined herein, including, by way of example, phenoxy, naphthoxy, and the like, including optionally substituted aryl groups as also defined herein.

"Amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —N$_3$.

"Carboxyl," "carboxy" or "carboxylate" refers to —CO$_2$H or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O— alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O— substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkenyl" refers to non-aromatic cyclic alkyl groups of from 3 to 10 carbon atoms having single or multiple rings and having at least one double bond and preferably from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

The term "heteroaralkyl" refers to the groups -alkylene-heteroaryl where alkylene and heteroaryl are defined herein. This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Heterocyclyloxy" refers to the group —O-heterocyclyl.

The term "heterocyclylthio" refers to the group heterocyclic-S—.

The term "heterocyclene" refers to the diradical group formed from a heterocycle, as defined herein.

The term "hydroxyamino" refers to the group —NHOH.

"Nitro" refers to the group —NO$_2$.

"Oxo" refers to the atom (=O).

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cycloalkyl, SO$_2$-cycloalkenyl, SO$_2$-substituted cylcoalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

"Sulfonyloxy" refers to the group —OSO$_2$-alkyl, OSO$_2$-substituted alkyl, OSO$_2$-alkenyl, OSO$_2$-substituted alkenyl, OSO$_2$-cycloalkyl, OSO$_2$-substituted cycloalkyl, OSO$_2$-cycloalkenyl, OSO$_2$-substituted cylcoalkenyl, OSO$_2$-aryl, OSO$_2$-substituted aryl, OSO$_2$-heteroaryl, OSO$_2$-substituted heteroaryl, OSO$_2$-heterocyclic, and OSO$_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioxo" or the term "thioketo" refers to the atom (=S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocyclooxy" refers to the group heterocyclyl-S— wherein the heterocyclyl group is as defined herein including optionally substituted heterocyclyl groups as also defined herein.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —NR$^{80}$R$^{80}$, trihalomethyl, —CF$_3$, —CN, —OCN, —SCN, —NO, —NO$_2$, —N$_3$, —SO$_2$R$^{70}$, —SO$_3^-$M$^+$, —SO$_3$R$^{70}$, —OSO$_2$R$^{70}$, —OSO$_3^-$M$^+$, —OSO$_3$R$^{70}$, —PO$_3^{-2}$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2^-$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined, provided that in case of substituted alkene or alkyne, the substituents are not —O$^-$M$^+$, —OR$^{70}$, —SR$^{70}$, or —S$^-$M$^+$.

In addition to the groups disclosed with respect to the individual terms herein, substituent groups for hydrogens on nitrogen atoms in "substituted" heteroalkyl and cycloheteroalkyl groups are, unless otherwise specified, —R$^{60}$, —OR$^{70}$, —SR$^{70}$, —NR$^{80}$R$^{80}$, trihalomethyl, —CF$_3$, —CN, —NO, —NO$_2$, —S(O)$_2$R$^{70}$, —S(O)$_2$O$^-$M$^+$, —S(O)$_2$OR$^{70}$, —OS(O)$_2$R$^{70}$, —OS(O)$_2$O$^-$M$^+$, —OS(O)$_2$OR$^{70}$, —P(O)(O)$_2$(M$^+$)$_2$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

"Pharmaceutically effective amount" and "therapeutically effective amount" refer to an amount of a compound sufficient to treat a specified disorder or disease or one or more of its symptoms and/or to prevent the occurrence of the disease or disorder. In reference to tumorigenic proliferative disorders, a pharmaceutically or therapeutically effective amount comprises an amount sufficient to, among other things, cause the tumor to shrink or decrease the growth rate of the tumor.

"Patient" refers to human and non-human subjects, especially mammalian subjects.

The term "treating" or "treatment" as used herein means the treating or treatment of a disease or medical condition in a patient, such as a mammal (particularly a human) that includes: (a) preventing the disease or medical condition from occurring, such as, prophylactic treatment of a subject; (b) ameliorating the disease or medical condition, such as, eliminating or causing regression of the disease or medical condition in a patient; (c) suppressing the disease or medical condition, for example by, slowing or arresting the development of the disease or medical condition in a patient; or (d) alleviating a symptom of the disease or medical condition in a patient.

The terms "polypeptide," "peptide," and "protein" are used interchangeably herein to refer to a polymeric form of amino acids of any length. Unless specifically indicated otherwise, "polypeptide," "peptide," and "protein" can include genetically coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, proteins which contain at least one N-terminal methionine residue (e.g., to facilitate production in a recombinant bacterial host cell); immunologically tagged proteins; and the like.

"Native amino acid sequence" or "parent amino acid sequence" are used interchangeably herein to refer to the amino acid sequence of a polypeptide prior to modification to include a modified amino acid residue.

The terms "amino acid analog," "unnatural amino acid," and the like may be used interchangeably, and include amino acid-like compounds that are similar in structure and/or overall shape to one or more amino acids commonly found in naturally occurring proteins (e.g., Ala or A, Cys or C, Asp or D, Glu or E, Phe or F, Gly or G, His or H, Ile or I, Lys or K, Leu or L, Met or M, Asn or N, Pro or P, Gln or Q, Arg or R, Ser or S, Thr or T, Val or V, Trp or W, Tyr or Y). Amino acid analogs also include natural amino acids with modified side chains or backbones. Amino acid analogs also include amino acid analogs with the same stereochemistry as in the naturally occurring D-form, as well as the L-form of amino acid analogs. In some instances, the amino acid analogs share backbone structures, and/or the side chain structures of one or more natural amino acids, with difference(s) being one or more modified groups in the molecule. Such modification may include, but is not limited to, substitution of an atom (such as N) for a related atom (such as S), addition of a group (such as methyl, or hydroxyl, etc.) or an atom (such as Cl or Br, etc.), deletion of a group, substitution of a covalent bond (single bond for double bond, etc.), or combinations thereof. For example, amino acid analogs may include α-hydroxy acids, and α-amino acids, and the like.

The term "carbohydrate" and the like may be used to refer to monomers units and/or polymers of monosaccharides, disaccharides, oligosaccharides, and polysaccharides. The term sugar may be used to refer to the smaller carbohydrates, such as monosaccharides, disaccharides. The term "carbohydrate derivative" includes compounds where one or more functional groups of a carbohydrate of interest are substituted (replaced by any convenient substituent), modified (converted to another group using any convenient chemistry) or absent (e.g., eliminated or replaced by H). A variety of carbohydrates and carbohydrate derivatives are available and may be adapted for use in the subject compounds and conjugates.

The term "antibody" is used in the broadest sense and includes monoclonal antibodies (including full length monoclonal antibodies), polyclonal antibodies, and multispecific antibodies (e.g., bispecific antibodies), humanized antibodies, single-chain antibodies, chimeric antibodies, antibody fragments (e.g., Fab fragments), and the like. An antibody is capable of binding a target antigen. (Janeway, C., Travers, P., Walport, M., Shlomchik (2001) Immuno Biology, 5th Ed., Garland Publishing, New York). A target antigen can have one or more binding sites, also called epitopes, recognized by complementarity determining regions (CDRs) formed by one or more variable regions of an antibody.

The term "natural antibody" refers to an antibody in which the heavy and light chains of the antibody have been made and paired by the immune system of a multi-cellular organism. Spleen, lymph nodes, bone marrow and serum are examples of tissues that produce natural antibodies. For example, the antibodies produced by the antibody producing cells isolated from a first animal immunized with an antigen are natural antibodies.

The term "humanized antibody" or "humanized immunoglobulin" refers to a non-human (e.g., mouse or rabbit) antibody containing one or more amino acids (in a framework region, a constant region or a CDR, for example) that have been substituted with a correspondingly positioned amino acid from a human antibody. In general, humanized antibodies produce a reduced immune response in a human host, as compared to a non-humanized version of the same antibody. Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332). In certain embodiments, framework substitutions are identified by modeling of the interactions of the CDR and framework residues to identify framework residues important for antigen binding and sequence comparison to identify unusual framework residues at particular positions (see, e.g., U.S. Pat. No. 5,585,089; Riechmann et al., Nature 332:323 (1988)). Additional methods for humanizing antibodies contemplated for use in the present invention are described in U.S. Pat. Nos. 5,750,078; 5,502,167; 5,705,154; 5,770,403; 5,698,417; 5,693,493; 5,558,864; 4,935,496; and 4,816,567, and PCT publications WO 98/45331 and WO 98/45332. In particular embodiments, a subject rabbit antibody may be humanized according to the methods set forth in US20040086979 and US20050033031. Accordingly, the antibodies described above may be humanized using methods that are well known in the art.

The term "chimeric antibodies" refer to antibodies whose light and heavy chain genes have been constructed, typically by genetic engineering, from antibody variable and constant region genes belonging to different species. For example, the variable segments of the genes from a mouse monoclonal antibody may be joined to human constant segments, such as gamma 1 and gamma 3. An example of a therapeutic chimeric antibody is a hybrid protein composed of the variable or antigen-binding domain from a mouse antibody and the constant or effector domain from a human antibody, although domains from other mammalian species may be used.

By "genetically-encodable" as used in reference to an amino acid sequence of polypeptide, peptide or protein means that the amino acid sequence is composed of amino acid residues that are capable of production by transcription and translation of a nucleic acid encoding the amino acid sequence, where transcription and/or translation may occur in a cell or in a cell-free in vitro transcription/translation system.

The term "control sequences" refers to DNA sequences that facilitate expression of an operably linked coding sequence in a particular expression system, e.g. mammalian cell, bacterial cell, cell-free synthesis, etc. The control sequences that are suitable for prokaryote systems, for example, include a promoter, optionally an operator sequence, and a ribosome binding site. Eukaryotic cell systems may utilize promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate the initiation of translation. Generally, "operably linked" means that the DNA sequences being linked are contiguous, and, in the case of a secretory leader, contiguous and in reading frame. Linking is accomplished by ligation or through amplification reactions. Synthetic oligonucleotide adaptors or linkers may be used for linking sequences in accordance with conventional practice.

The term "expression cassette" as used herein refers to a segment of nucleic acid, usually DNA, that can be inserted into a nucleic acid (e.g., by use of restriction sites compatible with ligation into a construct of interest or by homologous recombination into a construct of interest or into a host cell genome). In general, the nucleic acid segment comprises a polynucleotide that encodes a polypeptide of interest, and the cassette and restriction sites are designed to facilitate insertion of the cassette in the proper reading frame for transcription and translation. Expression cassettes can also comprise elements that facilitate expression of a polynucleotide encoding a polypeptide of interest in a host cell. These elements may include, but are not limited to: a promoter, a minimal promoter, an enhancer, a response element, a terminator sequence, a polyadenylation sequence, and the like.

As used herein the term "isolated" is meant to describe a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound that is removed from its natural environment and is at least 60% free, at least 75% free, at least 80% free, at least 85% free, at least 90% free, at least 95% free, at least 98% free, or more than 98% free, from other components with which it is naturally associated.

The term "physiological conditions" is meant to encompass those conditions compatible with living cells, e.g., predominantly aqueous conditions of a temperature, pH, salinity, etc. that are compatible with living cells.

By "reactive partner" is meant a molecule or molecular moiety that specifically reacts with another reactive partner to produce a reaction product. Exemplary reactive partners include a cysteine or serine of a sulfatase motif and Formylglycine Generating Enzyme (FGE), which react to form a reaction product of a converted aldehyde tag containing a formylglycine (fGly) in lieu of cysteine or serine in the motif. Other exemplary reactive partners include an aldehyde of an fGly residue of a converted aldehyde tag (e.g., a reactive aldehyde group) and an "aldehyde-reactive reactive partner", which comprises an aldehyde-reactive group and a moiety of interest, and which reacts to form a reaction product of a modified aldehyde tagged polypeptide having the moiety of interest conjugated to the modified polypeptide through a modified fGly residue.

"N-terminus" refers to the terminal amino acid residue of a polypeptide having a free amine group, which amine group in non-N-terminus amino acid residues normally forms part of the covalent backbone of the polypeptide.

"C-terminus" refers to the terminal amino acid residue of a polypeptide having a free carboxyl group, which carboxyl group in non-C-terminus amino acid residues normally forms part of the covalent backbone of the polypeptide.

By "internal site" as used in referenced to a polypeptide or an amino acid sequence of a polypeptide means a region of the polypeptide that is not at the N-terminus or at the C-terminus.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed, to the extent that such combinations embrace subject matter that are, for example, compounds that are stable compounds (i.e., compounds that can be made, isolated, characterized, and tested for biological activity). In addition, all sub-combinations of the various embodiments and elements thereof (e.g., elements of the chemical groups listed in the embodiments describing such variables) are also specifically embraced by the present invention and are disclosed herein just as if each and every such sub-combination was individually and explicitly disclosed herein.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides conjugates (e.g., polypeptide conjugates), hydrazinyl-pyrrolo compounds for producing the conjugates and methods of making and using the same. Embodiments of each are described in more detail in the sections below.

Conjugates

The present disclosure provides conjugates. By "conjugate" is meant a first moiety that is stably associated with a second moiety. By "stably associated" is meant that a moiety is bound to another moiety or structure under standard conditions. In certain embodiments, the first and second moieties are bound to each other through one or more covalent bonds.

In certain embodiments, the conjugate is a polypeptide conjugate, which includes a polypeptide conjugated to a second moiety. As described in more detail below, the moiety conjugated to the polypeptide can be any of a variety of moieties such as, but not limited to, a detectable label, a drug, a water-soluble polymer, or a moiety for immobilization of the polypeptide to a membrane or a surface. The moiety of interest can be conjugated to the polypeptide at any desired site of the polypeptide. Thus, the present disclosure provides, for example, a modified polypeptide having a moiety conjugated at a site at or near the C-terminus of the polypeptide. Other examples include a modified polypeptide having a moiety conjugated at a position at or near the N-terminus of the polypeptide. Examples also include a modified polypeptide having a moiety conjugated at a position between the C-terminus and the N-terminus of the polypeptide (e.g., at an internal site of the polypeptide). Combinations of the above are also possible where the modified polypeptide is conjugated to two or more moieties.

Embodiments of the present disclosure include conjugates where a polypeptide is conjugated to one or more moieties, such as 2 moieties, 3 moieties, 4 moieties, 5 moieties, 6 moieties, 7 moieties, 8 moieties, 9 moieties, or 10 or more moieties. The moieties may be conjugated to the polypeptide at one or more sites in the polypeptide. For example, one or more moieties may be conjugated to a single amino acid residue of the polypeptide. In some cases, one moiety is conjugated to an amino acid residue of the polypeptide. In other embodiments, two moieties may be conjugated to the same amino acid residue of the polypeptide. In other embodiments, a first moiety is conjugated to a first amino acid residue of the polypeptide and a second moiety is conjugated to a second amino acid residue of the polypeptide. Combinations of the above are also possible, for example where a polypeptide is conjugated to a first moiety at a first amino acid residue and conjugated to two other moieties at a second amino acid residue. Other combinations are also possible, such as, but not limited to, a polypeptide conjugated to first and second moieties at a first amino acid residue and conjugated to third and fourth moieties at a second amino acid residue, etc.

The one or more amino acid residues that are conjugated to the one or more moieties may be naturally occurring amino acids, unnatural amino acids, or combinations thereof. For instance, the conjugate may include a moiety conjugated to a naturally occurring amino acid residue of the polypeptide. In other instances, the conjugate may include a moiety conjugated to an unnatural amino acid residue of the polypeptide. One or more moieties may be conjugated to the polypeptide at a single natural or unnatural amino acid residue as described above. One or more natural or unnatural amino acid residues in the polypeptide may be conjugated to the moiety or moieties as described herein. For example, two (or more) amino acid residues (e.g., natural or unnatural amino acid residues) in the polypeptide may each be conjugated to one or two moieties, such that multiple sites in the polypeptide are modified.

Although described herein in terms of a polypeptide conjugated to one or more moieties (e.g., a chemical entity, a polypeptide, etc.), embodiments of the present disclosure also include conjugates where a moiety (e.g., a chemical entity, such as a drug or a detectable label) is conjugated to one or more other moieties (e.g., a chemical entity, a polypeptide, etc.). For example, a drug may be conjugated to one or more other moieties (e.g., a chemical entity, a polypeptide, etc.), or in other embodiments, a detectable label may be conjugated to one or more other moieties (e.g., a chemical entity, a polypeptide, etc.). Thus, for instance, embodiments of the present disclosure include, but are not limited to, the following: a conjugate of a polypeptide and a drug; a conjugate of a polypeptide and a detectable label; a conjugate of two or more polypeptides; a conjugate of two or more drugs; a conjugate of two of more detectable labels; a conjugate of a drug and a detectable label; a conjugate of a polypeptide, a drug and a detectable label; a conjugate of a polypeptide and two or more drugs; a conjugate of a polypeptide and two or more detectable labels; a conjugate of a drug and two or more polypeptides; a conjugate of a detectable label and two or more polypeptides; and the like.

In certain embodiments, the polypeptide and the moiety of interest are conjugated through a coupling moiety. For example, the polypeptide and the moiety of interest may each be bound (e.g., covalently bonded) to the coupling moiety, thus indirectly binding the polypeptide and the moiety of interest together through the coupling moiety. In some cases, the coupling moiety includes a hydrazinyl-pyrrolo compound or a derivative of a hydrazinyl-pyrrolo compound. For instance, a general scheme for coupling a moiety of interest to a polypeptide through a hydrazinyl-pyrrolo coupling moiety is shown in the general reaction scheme below.

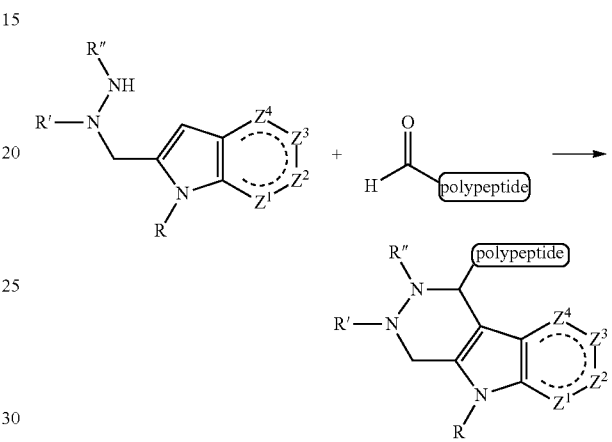

In the reaction scheme above, R may be the moiety of interest conjugated to the polypeptide. As described herein, the moiety can be any of a variety of moieties such as, but not limited to, chemical entity, such as a detectable label, a drug, a water-soluble polymer, or a moiety for immobilization of the polypeptide to a membrane or a surface of a substrate. R' and R" may each independently be any desired substituent, such as, but not limited to, hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. $Z^1$, $Z^2$, $Z^3$ and $Z^4$ may be $CR^{11}$, $NR^{12}$, N, O or S, wherein one of $Z^1$, $Z^2$, and $Z^4$ is optional and $R^{11}$ and $R^{12}$ may be any desired substituent.

Other hydrazinyl-pyrrolo coupling moieties are also possible. For example, another general scheme for coupling a moiety of interest to a polypeptide through a hydrazinyl-pyrrolo coupling moiety is shown in the general reaction scheme below.

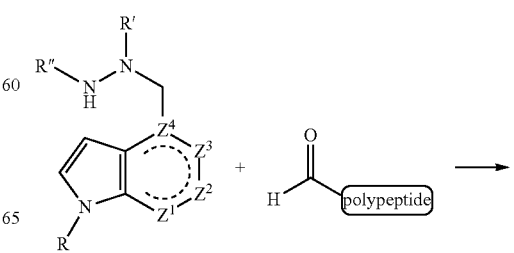

-continued

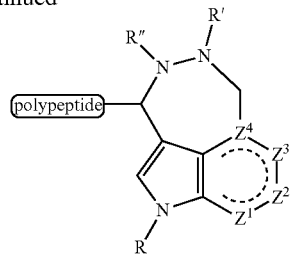

In the reaction scheme above, R may be the moiety of interest conjugated to the polypeptide. As described above, the moiety can be any of a variety of moieties such as, but not limited to, a chemical entity, such as a detectable label, a drug, a water-soluble polymer, or a moiety for immobilization of the polypeptide to a membrane or a surface of a substrate. R' and R" may each independently be any desired substituent, such as, but not limited to, hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. $Z^1$, $Z^2$, $Z^3$ and $Z^4$ may be $CR^{11}$, $NR^{12}$, N, O, C or S, wherein one of $Z^1$, $Z^2$, and $Z^4$ is optional and $R^{11}$ and $R^{12}$ may be any desired substituent. Other coupling moieties are also possible, as shown in the conjugates and compounds described in more detail below.

In certain embodiments, the conjugate includes at least one modified amino acid residue of the formula (I):

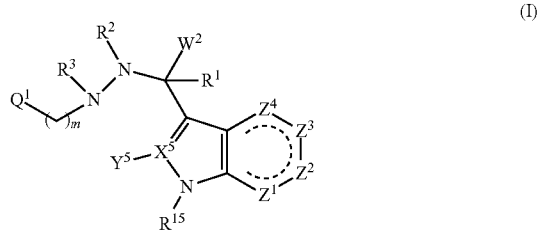

(I)

wherein
m is 0 or 1;
$R^1$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;
$R^2$ and $R^3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, or $R^2$ and $R^3$ are optionally cyclically linked to form a 5 or 6-membered heterocyclyl;
$Z^1$, $Z^2$, $Z^3$ and $Z^4$ are each independently selected from $CR^{11}$, $NR^{12}$, O, N and S, wherein one of $Z^1$, $Z^2$, $Z^3$ and $Z^4$ is optional;
$X^5$ is C;
$Y^5$, $R^{11}$ and $R^{12}$ are each independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;
$Q^1$ is a bond to either $Z^4$ or $X^5$, wherein if $Q^1$ is a bond to $Z^4$, then $Z^4$ is $CR^{11}$ or $NR^{12}$ and $R^{11}$ or $R^{12}$ is absent, or if $Q^1$ is a bond to $X^5$, then $Y^5$ is absent;
$R^{15}$ is -L-$W^1$ or -L-$W^1$ is attached to one of $Z^1$, $Z^2$, $Z^3$ or $Z^4$, wherein if -L-$W^1$ is attached to one of $Z^1$, $Z^2$, $Z^3$ or $Z^4$, then $R^{15}$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;
L is a linker (e.g., a linker as described herein), and
one of $W^1$ and $W^2$ is a polypeptide and the other is a chemical entity.

In certain embodiments, m is 0 or 1. In certain embodiments, m is 0. In certain embodiments, m is 1.

In certain embodiments, $R^1$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl. In certain embodiments, $R^1$ is hydrogen. In certain embodiments, $R^1$ is alkyl or substituted alkyl. In certain embodiments, $R^1$ is alkenyl or substituted alkenyl. In certain embodiments, $R^1$ is alkynyl or substituted alkynyl. In certain embodiments, $R^1$ is aryl or substituted aryl. In certain embodiments, $R^1$ is heteroaryl or substituted heteroaryl. In certain embodiments, $R^1$ is cycloalkyl or substituted cycloalkyl. In certain embodiments, $R^1$ is heterocyclyl or substituted heterocyclyl.

In certain embodiments, $R^2$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R^2$ is hydrogen. In certain embodiments, $R^2$ is alkyl or substituted alkyl. In certain embodiments, $R^2$ is alkenyl or substituted alkenyl. In certain embodiments, $R^2$ is alkynyl or substituted alkynyl. In certain embodiments, $R^2$ is alkoxy or substituted alkoxy. In certain embodiments, $R^2$ is amino or substituted amino. In certain embodiments, $R^2$ is carboxyl or carboxyl ester. In certain embodiments, $R^2$ is acyl or acyloxy. In certain embodiments, $R^2$ is acyl amino or amino acyl. In certain embodiments, $R^2$ is alkylamide or substituted alkylamide. In certain embodiments, $R^2$ is sulfonyl. In certain embodiments, $R^2$ is thioalkoxy or substituted thioalkoxy. In certain embodiments, $R^2$ is aryl or substituted aryl. In certain embodiments, $R^2$ is heteroaryl or substituted heteroaryl. In certain embodiments, $R^2$ is cycloalkyl or substituted cycloalkyl. In certain embodiments, $R^2$ is heterocyclyl or substituted heterocyclyl.

In certain embodiments, $R^2$ is alkyl or substituted alkyl. For example, $R^2$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R^2$ is methyl, ethyl, n-propyl, iso-propyl, n-butyl, sec-butyl, isobutyl, t-butyl, or the like. In certain cases, $R^2$ is methyl.

In certain embodiments, $R^3$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R^3$ is hydrogen. In certain embodiments, $R^3$ is alkyl or substituted alkyl. In certain embodiments, $R^3$ is alkenyl or substituted alkenyl. In certain embodiments, $R^3$ is alkynyl or substituted alkynyl. In certain embodiments, $R^3$ is alkoxy or substituted alkoxy. In certain embodiments, $R^3$ is amino or substituted amino. In certain embodiments, $R^3$ is carboxyl or carboxyl ester. In certain embodiments, $R^3$ is acyl or acyloxy. In certain embodiments, $R^3$ is acyl amino or amino acyl. In certain embodiments, $R^3$ is alkylamide or substituted alkylamide. In certain embodiments, $R^3$ is sulfonyl. In certain embodiments, $R^3$ is thioalkoxy or substituted thioalkoxy. In certain embodiments, $R^3$ is aryl or substituted aryl. In certain embodiments, $R^3$ is heteroaryl or substituted heteroaryl. In certain embodiments, $R^3$ is cycloalkyl or substituted cycloalkyl. In certain embodiments, $R^3$ is heterocyclyl or substituted heterocyclyl.

In certain embodiments, $R^3$ is alkyl or substituted alkyl. For example, $R^3$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R^3$ is methyl, ethyl, n-propyl, iso-propyl, n-butyl, sec-butyl, isobutyl, t-butyl, or the like. In certain cases, $R^3$ is methyl.

In certain embodiments, $R^2$ and $R^3$ are each independently selected from alkyl and substituted alkyl. For example, $R^2$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl), and $R^3$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R^2$ and $R^3$ are each independently selected from methyl, ethyl, n-propyl, iso-propyl, n-butyl, sec-butyl, isobutyl, t-butyl, or the like. In certain cases, $R^2$ and $R^3$ are each methyl.

In certain embodiments, $R^2$ and $R^3$ are optionally cyclically linked to form a 5 or 6-membered heterocyclyl. In some instances, $R^2$ and $R^3$ (together with the atoms to which they are attached) may be cyclically linked to form a 5-membered heterocyclyl. In some instances, $R^2$ and $R^3$ (together with the atoms to which they are attached) may be cyclically linked to form a 6-membered heterocyclyl. For example, $R^2$ and $R^3$ may each independently be an alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl), where $R^2$ and $R^3$ are optionally cyclically linked to form a 5 or 6-membered heterocyclyl, as described above. In some instances, one or more carbon atoms in $R^2$ and/or $R^3$ may be replaced with a heteroatom, such as N, O, or S.

In certain embodiments, $Z^1$ is selected from $CR^{11}$, $NR^{12}$, O, N and S. In certain embodiments, $Z^1$ is $CR^{11}$. In certain embodiments, $Z^1$ is $NR^{12}$. In certain embodiments, $Z^1$ is N. In certain embodiments, $Z^1$ is O. In certain embodiments, $Z^1$ is S.

In certain embodiments, $Z^2$ is selected from $CR^{11}$, $NR^{12}$, O, N and S. In certain embodiments, $Z^2$ is $CR^{11}$. In certain embodiments, $Z^2$ is $NR^{12}$. In certain embodiments, $Z^2$ is N. In certain embodiments, $Z^2$ is O. In certain embodiments, $Z^2$ is S.

In certain embodiments, $Z^3$ is selected from $CR^{11}$, $NR^{12}$, O, N and S. In certain embodiments, $Z^3$ is $CR^{11}$. In certain embodiments, $Z^3$ is $NR^{12}$. In certain embodiments, $Z^3$ is N. In certain embodiments, $Z^3$ is O. In certain embodiments, $Z^3$ is S.

In certain embodiments, $Z^4$ is selected from $CR^{11}$, $NR^{12}$, O, N and S. In certain embodiments, $Z^4$ is $CR^{11}$. In certain embodiments, $Z^4$ is $NR^{12}$. In certain embodiments, $Z^4$ is N. In certain embodiments, $Z^4$ is O. In certain embodiments, $Z^4$ is S.

Various combinations of $Z^1$, $Z^2$, $Z^3$ and $Z^4$ are possible. For example, in certain embodiments, each of $Z^1$, $Z^2$, $Z^3$ and $Z^4$ is $CR^{11}$. In other instances, three of $Z^1$, $Z^2$, $Z^3$ and $Z^4$ are $CR^{11}$ and one of $Z^1$, $Z^2$, $Z^3$ and $Z^4$ is N. In other embodiments, two of $Z^1$, $Z^2$, $Z^3$ and $Z^4$ are $CR^{11}$ and two of $Z^1$, $Z^2$, $Z^3$ and $Z^4$ are N. In other instances, one of $Z^1$, $Z^2$, $Z^3$ and $Z^4$ is $CR^{11}$ and three of $Z^1$, $Z^2$, $Z^3$ and $Z^4$ are N. In other embodiments, one of $Z^1$, $Z^2$, $Z^3$ and $Z^4$ is absent, two of $Z^1$, $Z^2$, $Z^3$ and $Z^4$ are $CR^{11}$ and one of $Z^1$, $Z^2$, $Z^3$ and $Z^4$ is $NR^{12}$. In other embodiments, one of $Z^1$, $Z^2$, $Z^3$ and $Z^4$ is absent, two of $Z^1$, $Z^2$, $Z^3$ and $Z^4$ are $CR^{11}$ and one of $Z^1$, $Z^2$, $Z^3$ and $Z^4$ is S. In other embodiments, one of $Z^1$, $Z^2$, $Z^3$ and $Z^4$ is absent, two of $Z^1$, $Z^2$, $Z^3$ and $Z^4$ are $CR^{11}$ and one of $Z^1$, $Z^2$, $Z^3$ and $Z^4$ is O. Other combinations of $CR^{11}$, N, O and S are possible for $Z^1$, $Z^2$, $Z^3$ and $Z^4$ as desired.

In certain embodiments, $X^5$ is C.

In certain embodiments, each $R^{11}$ (if present) is independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R^{11}$ is hydrogen. In certain embodiments, $R^{11}$ is halogen, such as F, Cl, Br or I. In certain embodiments, $R^{11}$ is F. In certain embodiments, $R^{11}$ is Cl. In certain embodiments, $R^{11}$ is Br. In certain embodiments, $R^{11}$ is I. In certain embodiments, $R^{11}$ is alkyl or substituted alkyl. In certain embodiments, $R^{11}$ is alkenyl or substituted alkenyl. In certain embodiments, $R^{11}$ is alkynyl or substituted alkynyl. In certain embodiments, $R^{11}$ is alkoxy or substituted alkoxy. In certain embodiments, $R^{11}$ is amino or substituted amino. In certain embodiments, $R^{11}$ is carboxyl or carboxyl ester. In certain embodiments, $R^{11}$ is acyl or acyloxy. In certain embodiments, $R^{11}$ is acyl amino or amino acyl. In certain embodiments, $R^{11}$ is alkylamide or substituted alkylamide. In certain embodiments, $R^{11}$ is sulfonyl. In certain embodiments, $R^{11}$ is thioalkoxy or substituted thioalkoxy. In certain embodiments, $R^{11}$ is aryl or substituted aryl. In certain embodiments, $R^{11}$ is heteroaryl or substituted heteroaryl. In certain embodiments, $R^{11}$ is cycloalkyl or substituted cycloalkyl. In certain embodiments, $R^{11}$ is heterocyclyl or substituted heterocyclyl.

In certain embodiments, each $R^{12}$ (if present) is independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R^{12}$ is hydrogen. In certain embodiments, $R^{12}$ is halogen, such as F, Cl, Br or I. In certain embodiments, $R^{12}$ is F. In certain embodiments, $R^{12}$ is Cl. In certain embodiments, $R^{12}$ is Br. In certain embodiments, $R^{12}$ is I. In certain embodiments, $R^{12}$ is alkyl or substituted alkyl. In certain embodiments, $R^{12}$ is alkenyl or substituted alkenyl. In certain embodiments, $R^{12}$ is alkynyl or substituted alkynyl. In certain embodiments, $R^{12}$ is alkoxy or substituted alkoxy. In certain embodiments, $R^{12}$ is amino or substituted amino. In certain embodiments, $R^{12}$ is carboxyl or carboxyl ester. In certain embodiments, $R^{12}$ is acyl or acyloxy. In certain embodiments, $R^{12}$ is acyl amino or amino acyl. In certain embodiments, $R^{12}$ is alkylamide or substituted alkylamide. In certain embodiments, $R^{12}$ is sulfonyl. In certain embodiments, $R^{12}$ is thioalkoxy or substituted thioalkoxy. In certain embodiments, $R^{12}$ is aryl or substituted aryl. In certain embodiments, $R^{12}$ is heteroaryl or substituted heteroaryl. In certain embodiments, $R^{12}$ is cycloalkyl or substituted cycloalkyl. In certain embodiments, $R^{12}$ is heterocyclyl or substituted heterocyclyl.

In certain embodiments, $Y^5$ (if present) is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y^5$ is hydrogen. In certain embodiments, $Y^5$ is halogen, such as F, Cl, Br or I. In certain embodiments, $Y^5$ is F. In certain embodiments, $Y^5$ is Cl. In certain embodiments, $Y^5$ is Br. In certain embodiments, $Y^5$ is I. In certain embodiments, $Y^5$ is alkyl or substituted alkyl. In certain embodiments, $Y^5$ is alkenyl or substituted alkenyl. In certain embodiments, $Y^5$ is alkynyl or substituted alkynyl. In certain embodiments, $Y^5$ is alkoxy or substituted alkoxy. In certain embodiments, $Y^5$ is amino or substituted amino. In certain embodiments, $Y^5$ is carboxyl or carboxyl ester. In certain embodiments, $Y^5$ is acyl or acyloxy. In certain embodiments, $Y^5$ is acyl amino or amino acyl. In certain embodiments, $Y^5$ is alkylamide or substituted alkylamide. In certain embodiments, $Y^5$ is sulfonyl. In certain embodiments, $Y^5$ is thioalkoxy or substituted thioalkoxy. In certain embodiments, $Y^5$ is aryl or substituted aryl. In certain embodiments, $Y^5$ is heteroaryl or substituted heteroaryl. In certain embodiments, $Y^5$ is cycloalkyl or substituted cycloalkyl. In certain embodiments, $Y^5$ is heterocyclyl or substituted heterocyclyl.

In certain embodiments, $Q^1$ is a bond to either $Z^4$ or $X^5$. In certain embodiments, $Q^1$ is a bond to $Z^4$. In certain embodiments, if $Q^1$ is a bond to $Z^4$, then $Z^4$ is $CR^{11}$ and $R^{11}$ is absent. In certain embodiments, if $Q^1$ is a bond to $Z^4$, then $Z^4$ is $NR^{12}$ and $R^{12}$ is absent. In certain embodiments, $Q^1$ is a bond to $X^5$. In certain embodiments, if $Q^1$ is a bond to $X^5$, then $Y^5$ is absent.

In certain embodiments, $R^{15}$ is -L-$W^1$ or -L-$W^1$ is attached to one of $Z^1$, $Z^2$, $Z^3$ or $Z^4$. In certain embodiments, $R^{15}$ is -L-$W^1$. In certain embodiments, $R^{15}$ is not -L-$W^1$. In certain embodiments, -L-$W^1$ is attached to one of $Z^1$, $Z^2$, $Z^3$ or $Z^4$. In certain embodiments, -L-$W^1$ is attached to $Z^1$. In certain embodiments, -L-$W^1$ is attached to $Z^2$. In certain embodiments, -L-$W^1$ is attached to $Z^3$. In certain embodiments, -L-$W^1$ is attached to $Z^4$.

In certain embodiments, if -L-$W^1$ is attached to one of $Z^1$, $Z^2$, $Z^3$ or $Z^4$, then $R^{15}$ is is not -L-$W^1$. In these embodiments, $R^{15}$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl. In some instances, $R^{15}$ is hydrogen. In some instances, $R^{15}$ is alkyl or substituted alkyl. In some instances, $R^{15}$ is alkenyl or substituted alkenyl. In some instances, $R^{15}$ is alkynyl or substituted alkynyl. In some instances, $R^{15}$ is aryl or substituted aryl. In some instances, $R^{15}$ is heteroaryl or substituted heteroaryl. In some instances, $R^{15}$ is cycloalkyl or substituted cycloalkyl. In some instances, $R^{15}$ is heterocyclyl or substituted heterocyclyl.

In certain embodiments, L is an optional linker. In certain embodiments, L is not present, and thus the nitrogen of the indole ring is directly bonded to $W^1$. In certain embodiments, L is present, and thus the nitrogen of the indole ring is indirectly bonded to $W^1$ through the linker L. Further description of the linker, L, is found in the disclosure herein.

For instance, in certain embodiments, L includes a group selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl. In certain embodiments, L includes an alkyl or substituted alkyl group. In certain embodiments, L includes an alkenyl or substituted alkenyl group. In certain embodiments, L includes an alkynyl or substituted alkynyl group. In certain embodiments, L includes an alkoxy or substituted alkoxy group. In certain embodiments, L includes an amino or substituted amino group. In certain embodiments, L includes a carboxyl or carboxyl ester group. In certain embodiments, L includes an acyl amino group. In certain embodiments, L includes an alkylamide or substituted alkylamide group. In certain embodiments, L includes an aryl or substituted aryl group. In certain embodiments, L includes a heteroaryl or substituted heteroaryl group. In certain embodiments, L includes a cycloalkyl or substituted cycloalkyl group. In certain embodiments, L includes a heterocyclyl or substituted heterocyclyl group.

In certain embodiments, L includes a polymer. For example, the polymer may include a polyalkylene glycol and derivatives thereof, including polyethylene glycol, methoxypolyethylene glycol, polyethylene glycol homopolymers, polypropylene glycol homopolymers, copolymers of ethylene glycol with propylene glycol (e.g., where the homopolymers and copolymers are unsubstituted or substituted at one end with an alkyl group), polyvinyl alcohol, polyvinyl ethyl ethers, polyvinylpyrrolidone, combinations thereof, and the like. In certain embodiments, the polymer is a polyalkylene glycol. In certain embodiments, the polymer is a polyethylene glycol.

In some embodiments, L is a linker comprising -$(L^1)_a$-$(L^2)_b$-$(L^3)_c$-$(L^4)_d$-$(L^5)_e$-, wherein $L^1$, $L^2$, $L^3$, $L^4$ and $L^5$ are each a linker unit, and a, b, c, d and e are each independently 0 or 1, wherein the sum of a, b, c, d and e is 1 to 5. Other linkers are also possible, as shown in the conjugates and compounds described in more detail below.

In certain embodiments, $W^1$ is selected from a polypeptide and a chemical entity. In certain embodiments, $W^1$ is a chemical entity. In certain embodiments, the chemical entity is a drug. In certain embodiments, the chemical entity is a detectable label. In certain embodiments, $W^1$ is selected from a detectable label and a polypeptide. In certain embodiments, $W^1$ is selected from a drug, a detectable label and a polypeptide. In certain embodiments, $W^1$ is a polypeptide.

In certain embodiments, $W^2$ is selected from a drug and a chemical entity. In certain embodiments, $W^2$ is a chemical entity. In certain embodiments, the chemical entity is a drug. In certain embodiments, the chemical entity is a detectable label. In certain embodiments, $W^2$ is selected from a drug, a detectable label and a polypeptide. In certain embodiments, $W^2$ is a drug. In certain embodiments, $W^2$ is a detectable label. In certain embodiments, $W^2$ is a polypeptide.

In certain embodiments, one of $W^1$ and $W^2$ is a polypeptide and the other is a chemical entity. In certain embodiments, the chemical entity is a drug. In certain embodiments, the chemical entity is a detectable label. In certain embodiments, $W^1$ is the chemical entity, and $W^2$ is the polypeptide. In certain embodiments, $W^1$ is the polypeptide, and $W^2$ is the chemical entity.

In certain embodiments, the conjugate includes at least one modified amino acid residue of the formula (II):

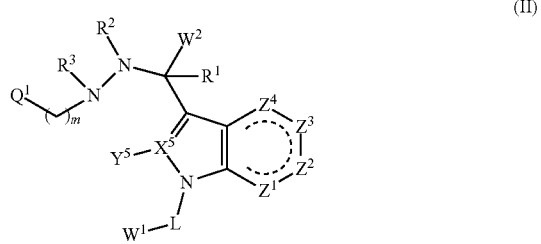

(II)

wherein m, $R^1$, $R^2$, $R^{3'}$ $X^5$, L, $Q^1$, $W^1$, $W^2$, $Y^5$, $Z^1$, $Z^2$, $Z^3$ and $Z^4$ are as defined in formula (I).

As described above, in formula (I), in some instances, $R^{15}$ is -L-$W^1$, which results in a modified amino acid residue of formula (II) as shown above.

In certain embodiments, the substituents for formula (II) are the same as for formula (I) described above. For example, in certain embodiments, m is 0 or 1. In certain embodiments, m is 0. In certain embodiments, m is 1. In certain embodiments, the substituents for formula (II), e.g., m, $R^1$, $R^2$, $R^{3'}$ $X^5$, L, $Q^1$, $W^1$, $W^2$, $Y^5$, $Z^1$, $Z^2$, $Z^3$ and $Z^4$ are as defined in formula (I).

In some embodiments, the conjugate includes at least one modified amino acid residue of formula (III):

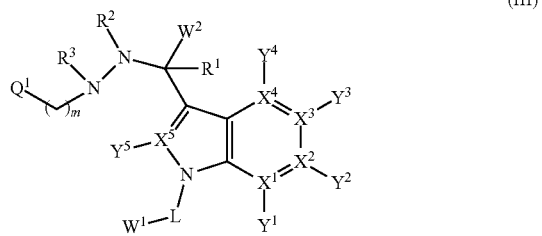

(III)

wherein m, $R^1$, $R^2$, $R^{3'}$ $X^5$, $Y^5$, L, $W^1$ and $W^2$ are as defined in formula (I);

$X^1$, $X^2$, $X^3$ and $X^4$ are each independently selected from C, N, O and S, wherein one of $X^1$, $X^2$, $X^3$ and $X^4$ is optional;

$Y^1$, $Y^2$, $Y^3$, $Y^4$ and $Y^5$, if present, are each independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, wherein $Y^1$ and $Y^2$, $Y^2$ and $Y^3$, or $Y^3$ and $Y^4$ are optionally cyclically linked; and $Q^1$ is a bond to either $X^4$ or $X^5$, wherein if $Q^1$ is a bond to $X^4$, then $Y^4$ is absent, or if $Q^1$ is a bond to $X^5$, then $Y^5$ is absent.

In certain embodiments, the substituents for formula (III) are the same as for formula (I) described above. For example, in certain embodiments, m is 0 or 1. In certain embodiments, m is 0. In certain embodiments, m is 1. In certain embodiments, the substituents for formula (III), e.g., m, $R^1$, $R^2$, $R^{3'}$ $X^5$, $Y^5$, L, $W^1$ and $W^2$, are as defined in formula (I).

In certain embodiments, $X^1$ is selected from C, N, O and S. In certain embodiments, $X^1$ is C. In certain embodiments, $X^1$ is N. In certain embodiments, $X^1$ is O. In certain embodiments, $X^1$ is S.

In certain embodiments, $X^2$ is selected from C, N, O and S. In certain embodiments, $X^2$ is C. In certain embodiments, $X^2$ is N. In certain embodiments, $X^2$ is O. In certain embodiments, $X^2$ is S.

In certain embodiments, $X^3$ is selected from C, N, O and S. In certain embodiments, $X^3$ is C. In certain embodiments, $X^3$ is N. In certain embodiments, $X^3$ is O. In certain embodiments, $X^3$ is S.

In certain embodiments, $X^4$ is selected from C, N, O and S. In certain embodiments, $X^4$ is C. In certain embodiments, $X^4$ is N. In certain embodiments, $X^4$ is O. In certain embodiments, $X^4$ is S.

In certain embodiments, one of $X^1$, $X^2$, $X^3$ and $X^4$ is optional. In certain embodiments, $X^1$ is absent. In certain embodiments, $X^2$ is absent. In certain embodiments, $X^3$ is absent. In certain embodiments, $X^4$ is absent.

Various combinations of $X^1$, $X^2$, $X^3$ and $X^4$ are possible. For example, in certain embodiments, each of $X^1$, $X^2$, $X^3$ and $X^4$ is C. In other instances, three of $X^1$, $X^2$, $X^3$ and $X^4$ are C and one of $X^1$, $X^2$, $X^3$ and $X^4$ is N. In other embodiments, two of $X^1$, $X^2$, $X^3$ and $X^4$ are C and two of $X^1$, $X^2$, $X^3$ and $X^4$ are N. In other embodiments, one of $X^1$, $X^2$, $X^3$ and $X^4$ is C and three of $X^1$, $X^2$, $X^3$ and $X^4$ is are N. Other combinations of C, N, O and S are possible for $X^1$, $X^2$, $X^3$ and $X^4$ as desired.

In certain embodiments, $Y^1$ (if present) is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y^1$ is hydrogen. In certain embodiments, $Y^1$ is halogen, such as F, Cl, Br or I. In certain embodiments, $Y^1$ is F. In certain embodiments, $Y^1$ is Cl. In certain embodiments, $Y^1$ is Br. In certain embodiments, $Y^1$ is I. In certain embodiments, $Y^1$ is alkyl or substituted alkyl. In certain embodiments, $Y^1$ is alkenyl or substituted alkenyl. In certain embodiments, $Y^1$ is alkynyl or substituted alkynyl. In certain embodiments, $Y^1$ is alkoxy or substituted alkoxy. In certain embodiments, $Y^1$ is amino or substituted amino. In certain embodiments, $Y^1$ is carboxyl or carboxyl ester. In certain embodiments, $Y^1$ is acyl or acyloxy. In certain embodiments, $Y^1$ is acyl amino or amino acyl. In certain embodiments, $Y^1$ is alkylamide or substituted alkylamide. In certain embodiments, $Y^1$ is sulfonyl. In certain embodiments, $Y^1$ is thioalkoxy or substituted thioalkoxy. In certain embodiments, $Y^1$ is aryl or substituted aryl. In certain embodiments, $Y^1$ is heteroaryl or substituted heteroaryl. In certain embodiments, $Y^1$ is cycloalkyl or substituted cycloalkyl. In certain embodiments, $Y^1$ is heterocyclyl or substituted heterocyclyl.

In certain embodiments, $Y^2$ (if present) is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y^2$ is hydrogen. In certain embodiments, $Y^2$ is halogen, such as F, Cl, Br or I. In certain embodiments, $Y^2$ is F. In certain embodiments, $Y^2$ is Cl. In certain embodiments, $Y^2$ is Br. In certain embodiments, $Y^2$ is I. In certain embodiments, $Y^2$ is alkyl or substituted alkyl. In certain embodiments, $Y^2$ is alkenyl or substituted alkenyl. In certain embodiments, $Y^2$ is alkynyl or substituted alkynyl. In certain embodiments, $Y^2$ is alkoxy or substituted alkoxy. In certain embodiments, $Y^2$ is amino or substituted amino. In certain embodiments, $Y^2$ is carboxyl or carboxyl ester. In certain embodiments, $Y^2$ is acyl or acyloxy. In certain embodiments, $Y^2$ is acyl amino or amino acyl. In certain embodiments, $Y^2$ is alkylamide or substituted alkylamide. In certain embodiments, $Y^2$ is sulfonyl. In certain embodiments, $Y^2$ is thioalkoxy or substituted thioalkoxy. In certain embodiments, $Y^2$ is aryl or substituted aryl. In certain embodiments, $Y^2$ is heteroaryl or substituted heteroaryl. In certain embodiments, $Y^2$ is cycloalkyl or substituted cycloalkyl. In certain embodiments, $Y^2$ is heterocyclyl or substituted heterocyclyl.

In certain embodiments, $Y^3$ (if present) is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y^3$ is hydrogen. In certain embodiments, $Y^3$ is halogen, such as F, Cl, Br or I. In certain embodiments, $Y^3$ is F. In certain embodiments, $Y^3$ is Cl. In certain embodiments, $Y^3$ is Br. In certain embodiments, $Y^3$ is I. In certain embodiments, $Y^3$ is alkyl or substituted alkyl. In certain embodiments, $Y^3$ is alkenyl or substituted alkenyl. In certain embodiments, $Y^3$ is alkynyl or substituted alkynyl. In certain embodiments, $Y^3$ is alkoxy or substituted alkoxy. In certain embodiments, $Y^3$ is amino or substituted amino. In certain embodiments, $Y^3$ is carboxyl or carboxyl ester. In certain embodiments, $Y^3$ is acyl or acyloxy. In certain embodiments, $Y^3$ is acyl amino or amino acyl. In certain embodiments, $Y^3$ is alkylamide or substituted alkylamide. In certain embodiments, $Y^3$ is sulfonyl. In certain embodiments, $Y^3$ is thioalkoxy or substituted thioalkoxy. In certain embodiments, $Y^3$ is aryl or substituted aryl. In certain embodiments, $Y^3$ is heteroaryl or substituted heteroaryl. In certain embodiments, $Y^3$ is cycloalkyl or substituted cycloalkyl. In certain embodiments, $Y^3$ is heterocyclyl or substituted heterocyclyl.

In certain embodiments, $Y^4$ (if present) is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y^4$ is hydrogen. In certain embodiments, $Y^4$ is halogen, such as F, Cl, Br or I. In certain embodiments, $Y^4$ is F. In certain embodiments, $Y^4$ is Cl. In certain embodiments, $Y^4$ is Br. In certain embodiments, $Y^4$ is I. In certain embodiments, $Y^4$ is alkyl or substituted alkyl. In certain embodiments, $Y^4$ is alkenyl or substituted alkenyl. In certain embodiments, $Y^4$ is alkynyl or substituted alkynyl. In certain embodiments, $Y^4$ is alkoxy or substituted alkoxy. In certain embodiments, $Y^4$ is amino or substituted amino. In certain embodiments, $Y^4$ is carboxyl or carboxyl ester. In certain embodiments, $Y^4$ is acyl or acyloxy. In certain embodiments, $Y^4$ is acyl amino or amino acyl. In certain embodiments, $Y^4$ is alkylamide or substituted alkylamide. In certain embodiments, $Y^4$ is sulfonyl. In certain embodiments, $Y^4$ is thioalkoxy or substituted thioalkoxy. In certain embodiments, $Y^4$ is aryl or substituted aryl. In certain embodiments, $Y^4$ is heteroaryl or substituted heteroaryl. In certain embodiments, $Y^4$ is cycloalkyl or substituted cycloalkyl. In certain embodiments, $Y^4$ is heterocyclyl or substituted heterocyclyl.

In certain embodiments, $Y^1$ and $Y^2$, $Y^2$ and $Y^3$, or $Y^3$ and $Y^4$ are cyclically linked to form a fused benzo ring. In certain embodiments, $Y^1$ and $Y^2$ are cyclically linked to form a fused benzo ring. In certain embodiments of formula, $Y^2$ and $Y^3$ are cyclically linked to form a fused benzo ring. In certain embodiments of formula, $Y^3$ and $Y^4$ are cyclically linked to form a fused benzo ring.

In certain embodiments, $Q^1$ is a bond to either $X^4$ or $X^5$, wherein if $Q^1$ is a bond to $X^4$, then $Y^4$ is absent, or if $Q^1$ is a bond to $X^5$, then $Y^5$ is absent. In certain embodiments, $Q^1$ is a bond to $X^4$, wherein if $Q^1$ is a bond to $X^4$, then $Y^4$ is absent. In certain embodiments, $Q^1$ is a bond to $X^5$, wherein if $Q^1$ is a bond to $X^5$, then $Y^5$ is absent.

In some embodiments, the conjugate includes at least one modified amino acid residue of formula (IVa) or (IVb):

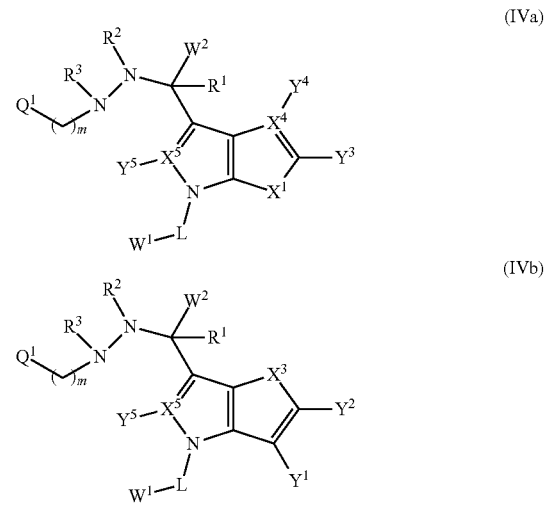

wherein m, $R^1$, $R^2$, $R^{3'}$ $R^{12'}$ $X^5$, $Y^{5'}$ L, $W^1$ and $W^2$ are as defined in formula (I);

$X^1$ and $X^3$ are each independently O, S or $NR^{12}$;

$Y^1$, $Y^2$, $Y^3$ and $Y^4$, if present, are each independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, wherein $Y^1$ and $Y^2$ or $Y^3$ and $Y^4$ are optionally cyclically linked;

$Q^1$ is a bond to either $X^4$ or $X^5$, wherein if $Q^1$ is a bond to $X^4$, then $X^4$ is C and $Y^4$ is absent, or if $Q^1$ is a bond to $X^5$, then $Y^5$ is absent; and $Q^2$ is a bond to either $X^3$ or $X^5$, wherein if $Q^2$ is a bond to $X^3$, then $X^3$ is $NR^{12}$ and $R^{12}$ is absent, or if $Q^2$ is a bond to $X^5$, then $Y^5$ is absent.

In certain embodiments, the substituents in formulae (IVa) and (IVb) are as described above for formula (I). In certain embodiments, the substituents m, $R^1$, $R^2$, $R^{3'}$ $R^{12'}$ $X^5$, $Y^{5'}$ L, $W^1$ and $W^2$ are as defined in formula (I).

In certain embodiments of formula (IVa), $X^1$ is O, S or $NR^{12}$. In certain embodiments of formula (IVa), $X^1$ is O. In certain embodiments of formula (IVa), $X^1$ is S. In certain embodiments of formula (IVa), $X^1$ is $NR^{12}$.

In certain embodiments of formula (IVb), $X^3$ is O, S or $NR^{12}$. In certain embodiments of formula (IVb), $X^3$ is O. In certain embodiments of formula (IVb), $X^3$ is S. In certain embodiments of formula (IVb), $X^3$ is $NR^{12}$.

In certain embodiments of formula (IVb), $Y^1$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y^1$ is hydrogen. In certain embodiments, $Y^1$ is halogen, such as F, Cl, Br or I. In certain embodiments, $Y^1$ is F. In certain embodiments, $Y^1$ is Cl. In certain embodiments, $Y^1$ is Br. In certain embodiments, $Y^1$ is I. In certain embodiments, $Y^1$ is alkyl or substituted alkyl. In certain embodiments, $Y^1$ is alkenyl or substituted alkenyl. In certain embodiments, $Y^1$ is alkynyl or substituted alkynyl. In certain embodiments, $Y^1$ is alkoxy or substituted alkoxy. In certain embodiments, $Y^1$ is amino or substituted amino. In certain embodiments, $Y^1$ is carboxyl or carboxyl ester. In certain embodiments, $Y^1$ is acyl or acyloxy. In certain embodiments, $Y^1$ is acyl amino or amino acyl. In certain embodiments, $Y^1$ is alkylamide or substituted alkylamide. In certain embodiments, $Y^1$ is sulfonyl. In certain embodiments, $Y^1$ is thioalkoxy or substituted thioalkoxy. In certain embodiments, $Y^1$ is aryl or substituted aryl. In certain embodiments, $Y^1$ is heteroaryl or substituted heteroaryl. In certain embodiments, $Y^1$ is cycloalkyl or substituted cycloalkyl. In certain embodiments, $Y^1$ is heterocyclyl or substituted heterocyclyl.

In certain embodiments of formula (IVb), $Y^2$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y^2$ is hydrogen. In certain embodiments, $Y^2$ is halogen, such as F, Cl, Br or I. In certain embodiments, $Y^2$ is F. In certain embodiments, $Y^2$ is Cl. In certain embodiments, $Y^2$ is Br. In certain embodiments, $Y^2$ is I. In certain embodiments, $Y^2$ is alkyl or substituted alkyl. In certain embodiments, $Y^2$ is alkenyl or substituted alkenyl. In certain embodiments, $Y^2$ is alkynyl or substituted alkynyl. In certain embodiments, $Y^2$ is alkoxy or substituted alkoxy. In certain embodiments, $Y^2$ is amino or substituted amino. In certain embodiments, $Y^2$ is carboxyl or carboxyl ester. In certain embodiments, $Y^2$ is acyl or acyloxy. In certain embodiments, $Y^2$ is acyl amino or amino acyl. In certain embodiments, $Y^2$ is alkylamide or substituted alkylamide. In certain embodiments, $Y^2$ is sulfonyl. In certain embodiments, $Y^2$ is thioalkoxy or substituted thioalkoxy. In certain embodiments, $Y^2$ is aryl or substituted aryl. In certain embodiments, $Y^2$ is heteroaryl or substituted heteroaryl. In certain embodiments, $Y^2$ is cycloalkyl or substituted cycloalkyl. In certain embodiments, $Y^2$ is heterocyclyl or substituted heterocyclyl.

In certain embodiments of formula (IVa), $Y^3$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y^3$ is hydrogen. In certain embodiments, $Y^3$ is halogen, such as F, Cl, Br or I. In certain embodiments, $Y^3$ is F. In certain embodiments, $Y^3$ is Cl. In certain embodiments, $Y^3$ is Br. In certain embodiments, $Y^3$ is I. In certain embodiments, $Y^3$ is alkyl or substituted alkyl. In certain embodiments, $Y^3$ is alkenyl or substituted alkenyl. In certain embodiments, $Y^3$ is alkynyl or substituted alkynyl. In certain embodiments, $Y^3$ is alkoxy or substituted alkoxy. In certain embodiments, $Y^3$ is amino or substituted amino. In certain embodiments, $Y^3$ is carboxyl or carboxyl ester. In certain embodiments, $Y^3$ is acyl or acyloxy. In certain embodiments, $Y^3$ is acyl amino or amino acyl. In certain embodiments, $Y^3$ is alkylamide or substituted alkylamide. In certain embodiments, $Y^3$ is sulfonyl. In certain embodiments, $Y^3$ is thioalkoxy or substituted thioalkoxy. In certain embodiments, $Y^3$ is aryl or substituted aryl. In certain embodiments, $Y^3$ is heteroaryl or substituted heteroaryl. In certain embodiments, $Y^3$ is cycloalkyl or substituted cycloalkyl. In certain embodiments, $Y^3$ is heterocyclyl or substituted heterocyclyl.

In certain embodiments of formula (IVa), $Y^4$ (if present) is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y^4$ is hydrogen. In certain embodiments, $Y^4$ is halogen, such as F, Cl, Br or I. In certain embodiments, $Y^4$ is F. In certain embodiments, $Y^4$ is Cl. In certain embodiments, $Y^4$ is Br. In certain embodiments, $Y^4$ is I. In certain embodiments, $Y^4$ is alkyl or substituted alkyl. In certain embodiments, $Y^4$ is alkenyl or substituted alkenyl. In certain embodiments, $Y^4$ is alkynyl or substituted alkynyl. In certain embodiments, $Y^4$ is alkoxy or substituted alkoxy. In certain embodiments, $Y^4$ is amino or substituted amino. In certain embodiments, $Y^4$ is carboxyl or carboxyl ester. In certain embodiments, $Y^4$ is acyl or acyloxy. In certain embodiments, $Y^4$ is acyl amino or amino acyl. In certain embodiments, $Y^4$ is alkylamide or substituted alkylamide. In certain embodiments, $Y^4$ is sulfonyl. In certain embodiments, $Y^4$ is thioalkoxy or substituted thioalkoxy. In certain embodiments, $Y^4$ is aryl or substituted aryl. In certain embodiments, $Y^4$ is heteroaryl or substituted heteroaryl. In certain embodiments, $Y^4$ is cycloalkyl or substituted cycloalkyl. In certain embodiments, $Y^4$ is heterocyclyl or substituted heterocyclyl.

In certain embodiments, $Y^1$ and $Y^2$ or $Y^3$ and $Y^4$ are cyclically linked to form a fused benzo ring. In certain embodiments of formula (IVa), $Y^3$ and $Y^4$ are cyclically linked to form a fused benzo ring. In certain embodiments of formula (IVb), $Y^1$ and $Y^2$ are cyclically linked to form a fused benzo ring.

In some embodiments of formula (IVa), $Q^1$ is a bond to $X^4$ and $Y^4$ is absent.

In some embodiments of formula (IVa), $Q^1$ is a bond to $X^5$, $X^5$ is C and $Y^5$ is absent.

In some embodiments of formula (IVb), $Q^2$ is a bond to $X^3$, $X^3$ is $NR^{12}$ and $R^{12}$ is absent.

In some embodiments of formula (IVb), $Q^2$ is a bond to $X^5$ and $Y^5$ is absent.

In some embodiments, $R^2$ and $R^3$ are each independently selected from alkyl and substituted alkyl.

In some embodiments of formulae (IVa) and (IVb), m is 1.

In some embodiments of formulae (IVa) and (IVb), $R^2$ and $R^3$ are each methyl.

In some embodiments of formulae (IVa) and (IVb), or $R^2$ and $R^3$ are optionally cyclically linked to form a 5 or 6-membered heterocyclyl as described above in formula (I).

In some embodiments of formulae (IVa) and (IVb), $X^1$, $X^3$, $X^4$ and $X^5$ are each C.

In some embodiments of formulae (IVa) and (IVb), $Y^1$, $Y^2$ and $Y^3$ are each H, and one of either $Y^4$ or $Y^5$ is H.

In some embodiments of formulae (IVa) and (IVb), the chemical entity is a drug or a detectable label.

In some embodiments of formulae (IVa) and (IVb), $W^1$ is the chemical entity, and $W^2$ is the polypeptide.

In some embodiments of formulae (IVa) and (IVb), $W^1$ is the polypeptide, and $W^2$ is the chemical entity.

In some embodiments, the conjugate comprises at least one modified amino acid residue of formula (IIIa):

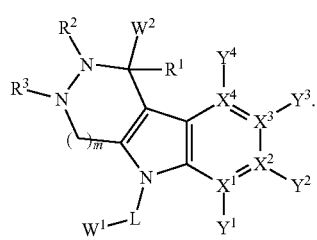

(IIIa)

In some embodiments, the conjugate comprises at least one modified amino acid residue of formula (IIIb):

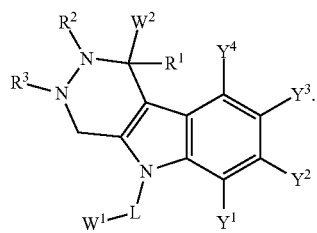

(IIIb)

In certain embodiments, the conjugate includes at least one modified amino acid residue of formula (IIIc):

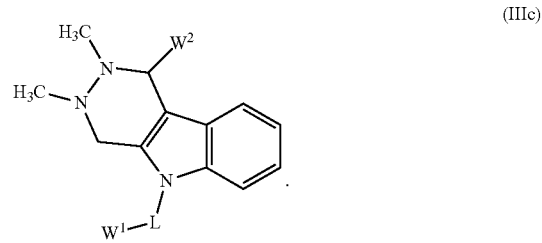

(IIIc)

In some embodiments, the conjugate comprises at least one modified amino acid residue of formula (IIId):

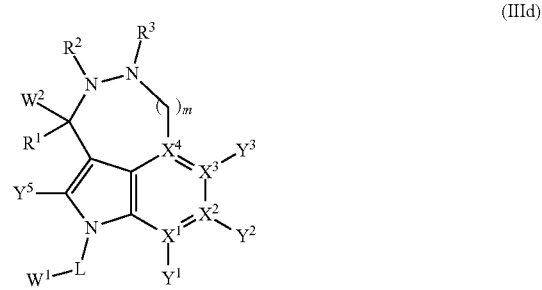

(IIId)

In some embodiments, the conjugate comprises at least one modified amino acid residue of formula (IIIe):

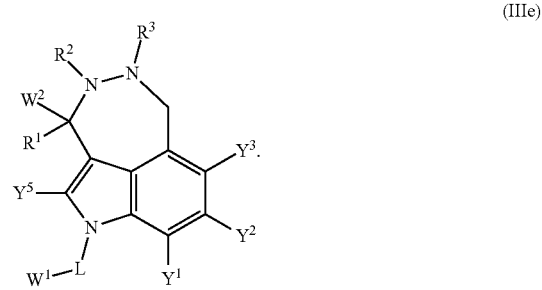

(IIIe)

In certain embodiments, the conjugate includes at least one modified amino acid residue of formula (IIIf):

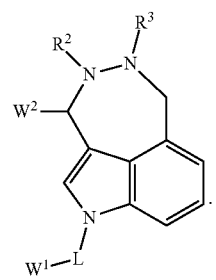

(IIIf)

In certain embodiments, the substituents in formulae (IIIa), (IIIb), (IIIc), (IIId), (IIIe) and (IIIf) are as described above for formula (III).

Linkers Useful for Conjugates and Compounds

The present disclosure provides linkers (L) useful for the conjugates and compounds described herein, such as conjugates and compounds of each of the formulae disclosed herein (e.g., formulae (I), (II), (III), (IIIa), (IIIb), (IIIc), (IIId), (IIIe), (IIIf), (IVa), (IVb), (V), (VI), (VIIa), (VIIb), (VIII), (VIIIa), (VIIIb), (IX), (IXa) and (IXb) as described herein). The linkers may be utilized to bind a coupling moiety to one or more moieties of interest and/or one or more polypeptides. In some embodiments, the linker binds a coupling moiety to either a polypeptide or a chemical entity. The linker may be bound (e.g., covalently bounded) to the coupling moiety (e.g., as described herein) at any convenient position.

In certain embodiments, the linker (L) is optional. In certain embodiments, L is not present, and thus the polypeptide or the chemical entity is directly bonded to the coupling moiety. In certain embodiments, L is present, and thus the coupling moiety is indirectly bonded to $W^1$ through the linker L.

Any convenient linkers may be utilized in the subject conjugates and compunds. In certain embodiments, L includes a group selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl. In certain embodiments, L includes an alkyl or substituted alkyl group. In certain embodiments, L includes an alkenyl or substituted alkenyl group. In certain embodiments, L includes an alkynyl or substituted alkynyl group. In certain embodiments, L includes an alkoxy or substituted alkoxy group. In certain embodiments, L includes an amino or substituted amino group. In certain embodiments, L includes a carboxyl or carboxyl ester group. In certain embodiments, L includes an acyl amino group. In certain embodiments, L includes an alkylamide or substituted alkylamide group. In certain embodiments, L includes an aryl or substituted aryl group. In certain embodiments, L includes a heteroaryl or substituted heteroaryl group. In certain embodiments, L includes a cycloalkyl or substituted cycloalkyl group. In certain embodiments, L includes a heterocyclyl or substituted heterocyclyl group.

In certain embodiments, L includes a polymer. For example, the polymer may include a polyalkylene glycol and derivatives thereof, including polyethylene glycol, methoxypolyethylene glycol, polyethylene glycol homopolymers, polypropylene glycol homopolymers, copolymers of ethylene glycol with propylene glycol (e.g., where the homopolymers and copolymers are unsubstituted or substituted at one end with an alkyl group), polyvinyl alcohol, polyvinyl ethyl ethers, polyvinylpyrrolidone, combinations thereof, and the like. In certain embodiments, the polymer is a polyalkylene glycol. In certain embodiments, the polymer is a polyethylene glycol. Other linkers are also possible, as shown in the conjugates and compounds described in more detail below.

In some embodiments, L is a linker described by the formula -$(L^1)_a$-$(L^2)_b$-$(L^3)_c$-$(L^4)_d$-$(L^5)_e$-, wherein $L^1$, $L^2$, $L^3$, $L^4$ and $L^5$ are each independently a linker unit, and a, b, c, d and e are each independently 0 or 1, wherein the sum of a, b, c, d and e is 1 to 5.

In certain embodiments, the sum of a, b, c, d and e is 1. In certain embodiments, the sum of a, b, c, d and e is 2. In certain embodiments, the sum of a, b, c, d and e is 3. In certain embodiments, the sum of a, b, c, d and e is 4. In certain embodiments, the sum of a, b, c, d and e is 5. In certain embodiments, a, b, c, d and e are each 1. In certain embodiments, a, b and c are each 1, and d and e are each 0. In certain embodiments, a and b are each 1, and c, d and e are each 0. In certain embodiments, a is 1 and b, c, d and e are each 0.

Any convenient linker units may be utilized in the subject linkers. Linker units of interest include, but are not limited to, units of polymers such as polyethylene glycols, polyethylenes and polyacrylates, amino acid residue(s), carbohydrate-based polymers or carbohydrate residues and derivatives thereof, polynucleotides, alkyl groups, aryl groups, heterocycle groups, cleavable linker groups, combinations thereof, and substituted versions thereof. In some embodiments, each of $L^1$, $L^2$, $L^3$, $L^4$ and $L^5$ (if present) include one or more groups independently selected from a polyethylene glycol, a modified polyethylene glycol, an amino acid residue, an alkyl group, a substituted alkyl, an aryl group, a substituted aryl group, a diamine (e.g., a linking group that includes an alkylene diamine), and a cleavable moiety (e.g., a chemically cleavable moiety, an enzymatically cleavable moiety (such as, but not limited to, a protease cleavable moiety, a glucuronidase cleavable moiety, a beta-lactamase cleavable moiety, etc.), a photocleavable moiety, and the like).

In some embodiments, $L^1$ (if present) comprises a polyethylene glycol, a modified polyethylene glycol, an amino acid residue, an alkyl group, a substituted alkyl, an aryl group, a substituted aryl group, a diamine or a cleavable moiety. In some embodiments, $L^1$ comprises a polyethylene glycol. In some embodiments, $L^1$ comprises a modified polyethylene glycol. In some embodiments, $L^1$ comprises an amino acid residue. In some embodiments, $L^1$ comprises an alkyl group or a substituted alkyl. In some embodiments, $L^1$ comprises an aryl group or a substituted aryl group. In some embodiments, $L^1$ comprises a diamine. In some embodiments, $L^1$ comprises a cleavable moiety.

In some embodiments, $L^2$ (if present) comprises a polyethylene glycol, a modified polyethylene glycol, an amino acid residue, an alkyl group, a substituted alkyl, an aryl group, a substituted aryl group, a diamine or a cleavable moiety. In some embodiments, $L^2$ comprises a polyethylene glycol. In some embodiments, $L^2$ comprises a modified polyethylene glycol. In some embodiments, $L^2$ comprises an amino acid residue. In some embodiments, $L^2$ comprises an alkyl group or a substituted alkyl. In some embodiments, $L^2$ comprises an aryl group or a substituted aryl group. In some embodiments, $L^2$ comprises a diamine. In some embodiments, $L^2$ comprises a cleavable moiety.

In some embodiments, $L^3$ (if present) comprises a polyethylene glycol, a modified polyethylene glycol, an amino acid residue, an alkyl group, a substituted alkyl, an aryl group, a substituted aryl group, a diamine or a cleavable moiety. In some embodiments, $L^3$ comprises a polyethylene glycol. In some embodiments, $L^3$ comprises a modified polyethylene glycol. In some embodiments, $L^3$ comprises an amino acid residue. In some embodiments, $L^3$ comprises an alkyl group or a substituted alkyl. In some embodiments, $L^3$ comprises an aryl group or a substituted aryl group. In some embodiments, $L^3$ comprises a diamine. In some embodiments, $L^3$ comprises a cleavable moiety.

In some embodiments, $L^4$ (if present) comprises a group independently selected from a polyethylene glycol, a modified polyethylene glycol, an amino acid residue, an alkyl group, a substituted alkyl, an aryl group, a substituted aryl group, a diamine (e.g., a linking group comprising an alkylene diamine), and a cleavable moiety. In some embodiments, $L^4$ comprises a polyethylene glycol. In some embodiments, $L^4$ comprises a modified polyethylene glycol. In some embodiments, $L^4$ comprises an amino acid residue. In some embodiments, $L^4$ comprises an alkyl group or a substituted alkyl. In some embodiments, $L^4$ comprises an aryl group or a substituted aryl group. In some embodiments, $L^4$ comprises a diamine. In some embodiments, $L^4$ comprises a cleavable moiety.

In some embodiments, $L^5$ (if present) comprises a group independently selected from a polyethylene glycol, a modified polyethylene glycol, an amino acid residue, an alkyl group, a substituted alkyl, an aryl group, a substituted aryl group, a diamine (e.g., a linking group comprising an alkylene diamine), and a cleavable moiety. In some embodiments, $L^5$ comprises a polyethylene glycol. In some embodiments, $L^5$ comprises a modified polyethylene glycol. In some embodiments, $L^5$ comprises an amino acid residue. In some embodiments, $L^5$ comprises an alkyl group or a substituted alkyl. In some embodiments, $L^5$ comprises an aryl group or a substituted aryl group. In some embodiments, $L^5$ comprises a diamine. In some embodiments, $L^5$ comprises a cleavable moiety.

Any convenient cleavable moieties may be utilized as a cleavable linker unit in the subject conjugates and compounds. In certain embodiments, the cleavable moiety is a para-amino-benzyloxycarbonyl group (PABC), a meta-amino-benzyloxycarbonyl group (MABC), a para-amino-benzyloxy group (PABO), a meta-amino-benzyloxy group (MABO), para-aminobenzyl, an acetal group, a disulfide, a hydrazine, a protease-cleavable moiety (e.g., a Cat B cleavable moiety), a glucuronidase cleavable moiety, a beta-lactamase cleavable moiety, or an ester.

In some embodiments, L is a linker comprising $-(L^1)_a$-$(L^2)_b$-$(L^3)_c$-$(L^4)_d$-$(L^5)_e$-, where:

$-(L^1)_a$- is $-(T^1$-$V^1)_a$—;

$-(L^2)_b$- is $-(T^2$-$V^2)_b$—;

$-(L^3)_c$- is $-(T^3$-$V^3)_c$—;

$-(L^4)_d$- is $-(T^4$-$V^4)_d$—; and $-(L^5)_e$- is $-(T^5$-$V^5)_e$—, wherein $T^1$, $T^2$, $T^3$, $T^4$ and $T^5$, if present, are tether groups; $V^1$, $V^2$, $V^3$, $Z^4$ and $V^5$, if present, are covalent bonds or linking functional groups; and a, b, c, d and e are each independently 0 or 1, wherein the sum of a, b, c, d and e is 1 to 5.

Regarding the tether groups, $T^1$, $T^2$, $T^3$, $T^4$ and $T^5$, any convenient tether groups may be utilized in the subject linkers. In some embodiments, $T^1$, $T^2$, $T^3$, $T^4$ and $T^5$ each comprise one or more groups independently selected from a $(C_1$-$C_{12})$alkyl, a substituted $(C_1$-$C_{12})$alkyl, an $(EDA)_w$, $(PEG)_n$, $(AA)_p$, —$(CR^{13}OH)_h$—, piperidin-4-amino (P4A), MABC, MABO, PABO, PABC, para-aminobenzyl, an acetal group, a disulfide, a hydrazine, a protease-cleavable moiety, a glucuronidase cleavable moiety, a beta-lactamase cleavable moiety, and an ester, where w is an integer from 1 to 20, n is an integer from 1 to 30, p is an integer from 1 to 20, and h is an integer from 1 to 12.

In certain embodiments, when the sum of a, b, c, d and e is 2 and one of $T^1$-$V^1$, $T^2$-$V^2$, $T^3$-$V^3$, $T^4$-$V^4$ or $T^5$-$V^5$ is $(PEG)_n$-CO, then n is not 6. For example, in some instances, the linker may have the following structure:

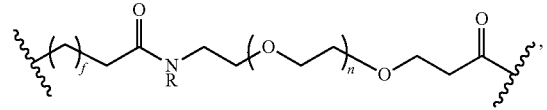

where n is not 6.

In certain embodiments, when the sum of a, b, c, d and e is 2 and one of $T^1$-$V^1$, $T^2$-$V^2$, $T^3$-$V^3$, $T^4$-$V^4$ or $T^5$-$V^5$ is $(C_1$-$C_{12})$alkyl-$NR^{11}$, then $(C_1$-$C_{12})$alkyl is not a $C_5$-alkyl. For example, in some instances, the linker may have the following structure:

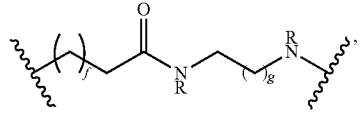

where g is not 4.

In certain embodiments, the tether group includes an ethylene diamine (EDA) moiety, e.g., an EDA containing tether. In certain embodiments, $(EDA)_w$ includes one or more EDA moieties, such as where w is an integer from 1 to 50, such as from 1 to 40, from 1 to 30, from 1 to 20, from 1 to 12 or from 1 to 6, such as 1, 2, 3, 4, 5 or 6). The linked ethylene diamine (EDA) moieties may optionally be substituted at one or more convenient positions with any convenient substituents, e.g., with an alkyl, a substituted alkyl, an acyl, a substituted acyl, an aryl or a substituted aryl. In certain embodiments, the EDA moiety is described by the structure:

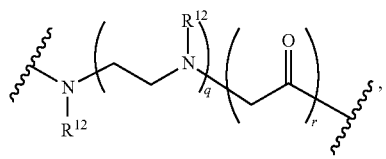

where q is an integer from 1 to 6 and r is 0 or 1 and each $R^{12}$ is independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, q is 1, 2, 3, 4, 5 or 6. In certain embodiments, q is 1 and r is 0. In certain embodiments, q is 1 and r is 1. In certain embodiments, q is 2 and r is 0. In certain embodiments, q is 2 and r is 1. In certain embodiments, each $R^{12}$ is independently selected from hydrogen, an alkyl, a substituted alkyl, an aryl and a substituted aryl. In certain embodiments, any two adjacent $R^{12}$ groups of the EDA may be cyclically linked, e.g., to form a piperazinyl ring. In certain embodiments, q is 1 and the two adjacent $R^{12}$ groups are an alkyl group, cyclically linked to form a piperazinyl ring. In certain embodiments, q is 1 and the adjacent $R^{12}$ groups are selected from hydrogen, an alkyl (e.g., methyl) and a substituted alkyl (e.g., lower alkyl-OH, such as ethyl-OH or propyl-OH).

In certain embodiments, the tether group includes a piperidin-4-amino (P4A) moiety. The P4A moiety may optionally be substituted at one or more convenient positions with any convenient substituents, e.g., with an alkyl, a substituted alkyl, a polyethylene glycol moiety, an acyl, a substituted acyl, an aryl or a substituted aryl. In certain embodiments, the P4A moiety is described by the structure:

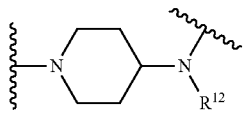

where $R^{12}$ is selected from hydrogen, alkyl, substituted alkyl, a polyethylene glycol moiety (e.g., a polyethylene glycol or a modified polyethylene glycol), alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R^{12}$ is a polyethylene glycol moiety. In certain embodiments, $R^{12}$ is a carboxy modified polyethylene glycol.

In certain embodiments, a tether is $(PEG)_n$ where $(PEG)_n$ is a polyethylene glycol or a modified polyethylene glycol linking unit. In certain embodiments, $(PEG)_n$ is described by the structure:

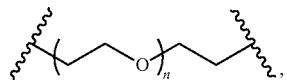

where n is an integer from 1 to 50, such as from 1 to 40, from 1 to 30, from 1 to 20, from 1 to 12 or from 1 to 6, such as 1, 2, 3, 4, 5, 6, 7, 8, 9, 10, 11, 12, 13, 14, 15, 16, 17, 18, 19 or 20. In some instances, n is 3. In some instances, n is 6. In some instances, n is 12.

In certain embodiments, a tether group includes $(AA)_p$, where AA is an amino acid residue. Any convenient amino acids may be utilized. Amino acids of interest include but are not limited to, L- and D-amino acids, naturally occurring amino acids such as any of the 20 primary alpha-amino acids and beta-alanine, non-naturally occurring amino acids (e.g., amino acid analogs), such as a non-naturally occurring alpha-amino acid or a non-naturally occurring beta-amino acid, etc. In certain embodiments, p is 1. In certain embodiments, p is an integer from 1 to 50, such as from 1 to 40, from 1 to 30, from 1 to 20, from 1 to 12 or from 1 to 6, such as 1, 2, 3, 4, 5, 6, 7, 8, 9, 10, 11, 12, 13, 14, 15, 16, 17, 18, 19 or 20.

In certain embodiments, a tether group includes a moiety described by the formula $-(CR^{13}OH)_h-$, where h is 0 or n is an integer from 1 to 50, such as from 1 to 40, from 1 to 30, from 1 to 20, from 1 to 12 or from 1 to 6, such as 1, 2, 3, 4, 5, 6, 7, 8, 9, 10, 11 or 12. In certain embodiments, $R^{13}$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R^{13}$ is hydrogen. In certain embodiments, $R^{13}$ is alkyl or substituted alkyl. In certain embodiments, $R^{13}$ is alkenyl or substituted alkenyl. In certain embodiments, $R^{13}$ is alkynyl or substituted alkynyl. In certain embodiments, $R^{13}$ is alkoxy or substituted alkoxy. In certain embodiments, $R^{13}$ is amino or substituted amino. In certain embodiments, $R^{13}$ is carboxyl or carboxyl ester. In certain embodiments, $R^{13}$ is acyl or acyloxy. In certain embodiments, $R^{13}$ is acyl amino or amino acyl. In certain embodiments, $R^{13}$ is alkylamide or substituted alkylamide. In certain embodiments, $R^{13}$ is sulfonyl. In certain embodiments, $R^{13}$ is thioalkoxy or substituted thioalkoxy. In certain embodiments, $R^{13}$ is aryl or substituted aryl. In certain embodiments, $R^{13}$ is heteroaryl or substituted heteroaryl. In certain embodiments, $R^{13}$ is cycloalkyl or substituted cycloalkyl. In certain embodiments, $R^{13}$ is heterocyclyl or substituted heterocyclyl. In certain embodiments, $R^{13}$ is selected from hydrogen, an alkyl, a substituted alkyl, an aryl, and a substituted aryl.

Regarding $V^1$, $V^2$, $V^3$, $V^4$ and $V^5$, any convenient linking functional groups may be utilized in the subject linkers. Linking functional groups of interest include, but are not limited to, amino, carbonyl, amido, oxycarbonyl, carboxy, sulfonyl, sulfoxide, sulfonylamino, aminosulfonyl, thio, oxy, phospho, phosphoramidate, thiophosphoraidate, and the like. In some embodiments, $V^1$, $V^2$, $V^3$, $V^4$ and $V^5$ are each independently selected from the group consisting of a covalent bond, $-CO-$, $-NR^{11}-$, $-CONR^{11}-$, $-NR^{11}CO-$, $-C(O)O-$, $-OC(O)-$, $-O-$, $-S-$, $-S(O)-$, $-SO_2-$, $-SO_2NR^{11}-$, $-NR^{11}SO_2-$ and $-P(O)OH-$. In some embodiment, $R^{11}$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R^{11}$ is hydrogen. In certain embodiments, $R^{11}$ is alkyl or substituted alkyl. In certain embodiments, $R^{11}$ is alkenyl or substituted alkenyl. In certain embodiments, $R^{11}$ is alkynyl or substituted alkynyl. In certain embodiments, $R^{11}$ is alkoxy or substituted alkoxy. In certain embodiments, $R^{11}$ is carboxyl or carboxyl ester. In certain embodiments, $R^{11}$ is acyl or acyloxy. In certain embodiments, $R^{11}$ is acyl amino or amino acyl. In certain embodiments, $R^{11}$ is alkylamide or substituted alkylamide. In certain embodiments, $R^{11}$ is sulfonyl. In certain embodiments, $R^{11}$ is thioalkoxy or substituted thioalkoxy. In certain embodiments, $R^{11}$ is aryl or substituted aryl. In certain embodiments, $R^{11}$ is heteroaryl or substituted heteroaryl. In certain embodiments, $R^{11}$ is cycloalkyl or substituted cycloalkyl. In certain embodiments, $R^{11}$ is heterocyclyl or substituted heterocyclyl.

In some embodiments, a tether includes a MABC group described by the following structure:

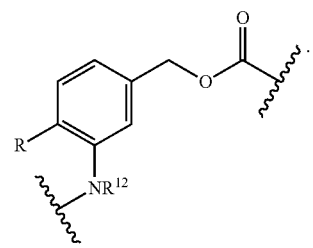

In some embodiments, a tether includes a MABO group described by the following structure:

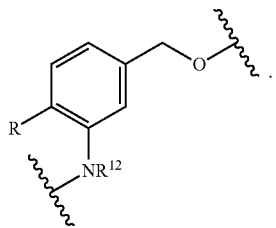

In some embodiments of the MABO and MABC tether structures shown above, R is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In some embodiments of the MABO and MABC tether structures shown above, R is a carbohydrate or carbohydrate derivative.

In some embodiments, a tether includes a PABC group described by the following structure:

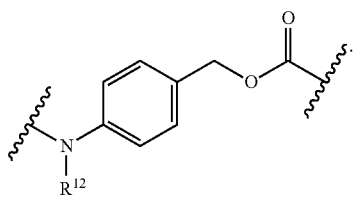

In some embodiments, a tether includes a PABO group described by the following structure:

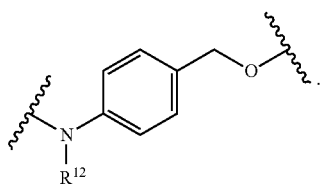

In some embodiments, a tether includes a para-aminobenzyl (PAB) group described by the following structure:

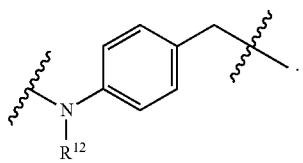

In some embodiments of the PABO, PABC, MABO, MABC and PAB tether structures shown above, $R^{12}$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments of PABO, PABC, MABO, MABC and PAB, $R^{12}$ is selected from hydrogen, an alkyl, a substituted alkyl, an aryl and a substituted aryl. In certain embodiments of PABO, PABC, MABO, MABC and PAB, $R^{12}$ is selected from hydrogen, an alkyl (e.g., methyl) and a substituted alkyl (e.g., lower alkyl-OH, such as ethyl-OH or propyl-OH). In some embodiments, any of the PABO, PABC, MABO, MABC and PAB tether structures shown above may be further substituted with one or more convenient aryl and/or alkyl substituents. In certain embodiments of PABO, PABC, MABO, MABC and PAB, $R^{12}$ is hydrogen. The divalent PABO, PABC, MABO, MABC and PAB tether groups may be covalently bound to adjacent moieties via any convenient chemistries.

In certain embodiments, the tether group includes an acetal group, a disulfide, a hydrazine, a glucuronidase cleavable moiety, a beta-lactamase cleavable moiety, or an ester. In some embodiments, the tether group is an acetal group. In some embodiments, the tether group is a disulfide. In some embodiments, the tether group is a hydrazine. In some embodiments, the tether group is a glucuronidase cleavable moiety. In some embodiments, the tether group is a beta-lactamase cleavable moiety. In some embodiments, the tether group is an ester.

In some embodiments, in the subject linker:
$T^1$ is selected from a $(C_1-C_{12})$alkyl and a substituted $(C_1-C_{12})$alkyl;
$T^2$, $T^3$, $T^4$ and $T^5$ are each independently selected from $(EDA)_w$, $(PEG)_n$, a $(C_1-C_{12})$alkyl, a substituted $(C_1-C_{12})$ alkyl, $(AA)_p$, —$(CR^{13}OH)_h$—, piperidin-4-amino (P4A), a MABC, a MABO, a PABO, a PABC, para-aminobenzyl, an acetal group, a disulfide, a hydrazine, a protease-cleavable moiety, a glucuronidase cleavable moiety, a beta-lactamase cleavable moiety, an ester, $(AA)_p$-MABC-$(AA)_p$, $(AA)_p$-MABO-$(AA)_p$, $(AA)_p$-PABO-$(AA)_p$ and $(AA)_p$-PABC-$(AA)_p$; and
$V^1$, $V^2$, $V^3$, $V^4$ and $V^5$ are each independently selected from the group consisting of: a covalent bond, —CO—, —$NR^{11}$—, —$CONR^{11}$—, —$NR^{11}CO$—, —C(O)O—, —OC(O)—, —O—, —S—, —S(O)—, —$SO_2$—, —$SO_2NR^{11}$—, —$NR^{11}SO_2$—, and —P(O)OH—;
wherein:
$(PEG)_n$ is

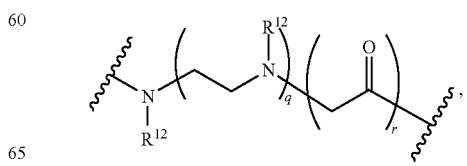

where n is an integer from 1 to 30;
EDA is an ethylene diamine moiety having the following structure:

where q is an integer from 1 to 6 and r is 0 or 1;
piperidin-4-amino (P4A) is

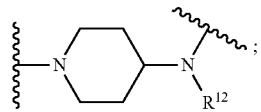

AA is an amino acid residue, where p is an integer from 1 to 20;

PABC is para-amino-benzyloxycarbonyl, MABC is meta-amino-benzyloxycarbonyl, PABO is para-amino-benzyloxy, and MABO is meta-amino-benzyloxy;

each $R^{11}$ and $R^{12}$ is independently selected from hydrogen, an alkyl, a substituted alkyl, a PEG, an aryl and a substituted aryl, wherein any two adjacent $R^{12}$ groups may be cyclically linked to form a piperazinyl ring; and $R^{13}$ is selected from hydrogen, an alkyl, a substituted alkyl, an aryl, and a substituted aryl.

In certain embodiments, $T^1$, $T^2$, $T^3$, $T^4$ and $T^5$ and $V^1$, $V^2$, $V^3$, $V^4$ and $V^5$ are selected from the following table, e.g., one row of the following table:

| $T^1$ | $V^1$ | $T^2$ | $V^2$ | $T^3$ | $V^3$ | $T^4$ | $V^4$ | $T^5$ | $V^5$ |
|---|---|---|---|---|---|---|---|---|---|
| $(C_1\text{-}C_{12})$alkyl | —$CONR^{11}$— | $(PEG)_n$ | —CO— | — | — | — | — | — | — |
| $(C_1\text{-}C_{12})$alkyl | —CO— | $(AA)_p$ | —$NR^{11}$— | $(PEG)_n$ | —CO— | — | — | — | — |
| $(C_1\text{-}C_{12})$alkyl | —CO— | $(AA)_p$ | — | — | — | — | — | — | — |
| $(C_1\text{-}C_{12})$alkyl | —$CONR^{11}$— | $(PEG)_n$ | —$NR^{11}$— | — | — | — | — | — | — |
| $(C_1\text{-}C_{12})$alkyl | —CO— | $(AA)_p$ | —$NR^{11}$— | $(PEG)_n$ | —$NR^{11}$— | — | — | — | — |
| $(C_1\text{-}C_{12})$alkyl | —CO— | $(EDA)_w$ | —CO— | — | — | — | — | — | — |
| $(C_1\text{-}C_{12})$alkyl | —$CONR^{11}$— | $(C_1\text{-}C_{12})$alkyl | —$NR^{11}$— | — | — | — | — | — | — |
| $(C_1\text{-}C_{12})$alkyl | —$CONR^{11}$— | $(PEG)_n$ | —CO— | $(EDA)_w$ | — | — | — | — | — |
| $(C_1\text{-}C_{12})$alkyl | —CO— | $(EDA)_w$ | — | — | — | — | — | — | — |
| $(C_1\text{-}C_{12})$alkyl | —CO— | $(EDA)_w$ | —CO— | $(CR^{13}OH)_h$ | —$CONR^{11}$— | $(C_1\text{-}C_{12})$alkyl | —CO— | — | — |
| $(C_1\text{-}C_{12})$alkyl | —CO— | $(AA)_p$ | —$NR^{11}$— | $(C_1\text{-}C_{12})$alkyl | —CO— | — | — | — | — |
| $(C_1\text{-}C_{12})$alkyl | —$CONR^{11}$— | $(PEG)_n$ | —CO— | $(AA)_p$ | — | — | — | — | — |
| $(C_1\text{-}C_{12})$alkyl | —$CONR^{11}$— | $(PEG)_n$ | —CO— | $(AA)_p$ | — | MABO | — | — | — |
| $(C_1\text{-}C_{12})$alkyl | —$CONR^{11}$— | $(PEG)_n$ | —CO— | $(AA)_p$ | — | PABO | — | — | — |
| $(C_1\text{-}C_{12})$alkyl | —$CONR^{11}$— | $(PEG)_n$ | —CO— | $(AA)_p$ | — | PABC | — | — | — |
| $(C_1\text{-}C_{12})$alkyl | —CO— | $(EDA)_w$ | —CO— | $(CR^{13}OH)_h$ | —CO— | $(AA)_p$ | — | — | — |
| $(C_1\text{-}C_{12})$alkyl | —CO— | $(AA)_p$ | —$NR^{11}$— | $(C_1\text{-}C_{12})$alkyl | —CO— | $(AA)_p$ | — | — | — |
| $(C_1\text{-}C_{12})$alkyl | —CO— | $(AA)_p$ | —$NR^{11}$— | $(PEG)_n$ | —CO— | $(AA)_p$ | — | — | — |
| $(C_1\text{-}C_{12})$alkyl | —CO— | $(AA)_p$ | —$NR^{11}$— | $(C_1\text{-}C_{12})$alkyl | —CO— | $(AA)_p$ | — | — | — |
| $(C_1\text{-}C_{12})$alkyl | —CO— | $(AA)_p$ | —$NR^{11}$— | $(PEG)_n$ | —CO— | $(AA)_p$-PABC-$(AA)_p$ | — | — | — |
| $(C_1\text{-}C_{12})$alkyl | —CO— | $(AA)_p$ | —$NR^{11}$— | $(PEG)_n$ | —CO— | $(AA)_p$- | — | PABC-$(AA)_p$ | — |
| $(C_1\text{-}C_{12})$alkyl | —CO— | $(AA)_p$ | —$NR^{11}$— | $(PEG)_n$ | —CO— | $(AA)_p$-PABO | — | — | — |
| $(C_1\text{-}C_{12})$alkyl | —CO— | $(AA)_p$ | —$NR^{11}$— | $(PEG)_n$ | —CO— | $(AA)_p$ | — | PABO | — |
| $(C_1\text{-}C_{12})$alkyl | —CO— | $(AA)_p$ | —$NR^{11}$— | $(PEG)_n$ | —$SO_2$— | $(AA)_p$ | — | — | — |
| $(C_1\text{-}C_{12})$alkyl | —$CONR^{11}$— | $(PEG)_n$ | —CO— | $(AA)_p$ | — | PABC-$(AA)_p$ | — | — | — |
| $(C_1\text{-}C_{12})$alkyl | —$CONR^{11}$— | $(PEG)_n$ | —CO— | $(AA)_p$ | — | PABC | — | $(AA)_p$ | — |
| $(C_1\text{-}C_{12})$alkyl | —CO— | $(EDA)_w$ | —CO— | $(CR^{13}OH)_h$ | —$CONR^{11}$— | $(PEG)_n$ | —CO— | — | — |
| $(C_1\text{-}C_{12})$alkyl | —CO— | $(AA)_p$ | —$NR^{11}$— | $(PEG)_n$ | —CO— | MABC-$(AA)_p$- | — | — | — |
| $(C_1\text{-}C_{12})$alkyl | —CO— | $(AA)_p$ | —$NR^{11}$— | $(PEG)_n$ | —CO— | MABC | — | $(AA)_p$ | — |
| $(C_1\text{-}C_{12})$alkyl | —$CONR^{11}$— | $(PEG)_n$ | —CO— | MABO | — | — | — | — | — |
| $(C_1\text{-}C_{12})$alkyl | —CO— | $(AA)_p$ | —$NR^{11}$— | $(PEG)_n$ | —CO— | MABO | — | — | — |
| $(C_1\text{-}C_{12})$alkyl | —CO— | $(AA)_p$ | —$NR^{11}$— | $(PEG)_n$ | —CO— | PABO | — | — | — |
| $(C_1\text{-}C_{12})$alkyl | —CO— | $(AA)_p$ | —$NR^{11}$— | $(PEG)_n$ | —CO— | PABC | — | — | — |
| $(C_1\text{-}C_{12})$alkyl | —$CONR^{11}$— | $(PEG)_n$ | —CO— | MABC | — | $(AA)_p$ | — | — | — |
| $(C_1\text{-}C_{12})$alkyl | —CO— | $(CR^{13}OH)_h$ | —CO— | — | — | — | — | — | — |
| $(C_1\text{-}C_{12})$alkyl | —$CONR^{11}$— | substituted $(C_1\text{-}C_{12})$alkyl | —$NR^{11}$— | $(PEG)_n$ | —CO— | — | — | — | — |
| $(C_1\text{-}C_{12})$alkyl | —$SO_2$— | $(C_1\text{-}C_{12})$alkyl | —CO— | — | — | — | — | — | — |
| $(C_1\text{-}C_{12})$alkyl | —$CONR^{11}$— | $(PEG)_n$ | —CO— | $(AA)_p$ | — | PABC | —$NR^{11}$— | — | — |
| $(C_1\text{-}C_{12})$alkyl | —$CONR^{11}$— | $(C_1\text{-}C_{12})$alkyl | — | $(CR^{13}OH)_h$ | —$CONR^{11}$— | — | — | — | — |
| $(C_1\text{-}C_{12})$alkyl | —CO— | P4A | —CO— | $(C_1\text{-}C_{12})$alkyl | —CO— | $(AA)_p$ | — | PABO | —CO— |
| $(C_1\text{-}C_{12})$alkyl | —CO— | P4A | —CO— | $(C_1\text{-}C_{12})$alkyl | —CO— | $(AA)_p$ | — | PABO | — |
| $(C_1\text{-}C_{12})$alkyl | —CO— | P4A | —CO— | $(C_1\text{-}C_{12})$alkyl | —CO— | $(AA)_p$ | — | PABC-$(AA)_p$ | — |
| $(C_1\text{-}C_{12})$alkyl | —CO— | P4A | —CO— | $(C_1\text{-}C_{12})$alkyl | —CO— | $(AA)_p$ | — | — | — |

In some embodiments, L is a linker comprising -(L$^1$)$_a$-(L$^2$)$_b$-(L$^3$)$_c$-(L$^4$)$_d$-(L$^5$)$_e$-, where -(L$^1$)$_a$ is -(T$^1$-V$^1$)$_a$—; -(L$^2$)$_b$ is -(T$^2$-V$^2$)$_b$—; -(L$^3$)$_c$ is -(T$^3$-V$^3$)$_c$—; -(L$^4$)$_d$ is -(T$^4$-V$^4$)$_d$—; and -(L$^5$)$_e$- is -(T$^5$-V$^5$)$_e$—. In certain embodiments, T$^1$ is (C$_1$-C$_{12}$)alkyl, V$^1$ is —CONR$^{11}$—, T$^2$ is (PEG)$_n$, V$^2$ is —CO—, T$^3$ is absent, V$^3$ is absent, T$^4$ is absent, V$^4$ is absent, T$^5$ is absent and V$^5$ is absent. In certain embodiments, T$^1$ is (C$_1$-C$_{12}$)alkyl, V$^1$ is —CO—, T$^2$ is (AA)$_p$, V$^2$ is —NR$^{11}$—, T$^3$ is (PEG)$_n$, V$^3$ is —CO—, T$^4$ is absent, V$^4$ is absent, T$^5$ is absent and V$^5$ is absent. In certain embodiments, T$^1$ is (C$_1$-C$_{12}$)alkyl, V$^1$ is —CO—, T$^2$ is (AA)$_p$, V$^2$ is absent, T$^3$ is absent, V$^3$ is absent, T$^4$ is absent, V$^4$ is absent, T$^5$ is absent and V$^5$ is absent. In certain embodiments, T$^1$ is (C$_1$-C$_{12}$)alkyl, V$^1$ is —CONR$^{11}$—, T$^2$ is (PEG)$_n$, V$^2$ is —NR$^{11}$—, T$^3$ is absent, V$^3$ is absent, T$^4$ is absent, V$^4$ is absent, T$^5$ is absent and V$^5$ is absent. In certain embodiments, T$^1$ is (C$_1$-C$_{12}$)alkyl, V$^1$ is —CO—, T$^2$ is (AA)$_p$, V$^2$ is NR$^{11}$—, T$^3$ is (PEG)$_n$, V$^3$ is, T$^4$ is absent, V$^4$ is absent, T$^5$ is absent and V$^5$ is absent. In certain embodiments, T$^1$ is (C$_1$-C$_{12}$)alkyl, V$^1$ is —CO—, T$^2$ is (EDA)$_w$, V$^2$ is —CO—, T$^3$ is absent, V$^3$ is absent, T$^4$ is absent, V$^4$ is absent, T$^5$ is absent and V$^5$ is absent. In certain embodiments, T$^1$ is (C$_1$-C$_{12}$)alkyl, V$^1$ is —CONR$^{11}$—, T$^2$ is (C$_1$-C$_{12}$)alkyl, V$^2$ is —NR$^{11}$—, T$^3$ is absent, V$^3$ is absent, T$^4$ is absent, V$^4$ is absent, T$^5$ is absent and V$^5$ is absent. In certain embodiments, T$^1$ is (C$_1$-C$_{12}$)alkyl, V$^1$ is —CONR$^{11}$—, T$^2$ is (PEG)$_n$, V$^2$ is —CO—, T$^3$ is (EDA)$_w$, V$^3$ is absent, T$^4$ is absent, V$^4$ is absent, T$^5$ is absent and V$^5$ is absent. In certain embodiments, T$^1$ is (C$_1$-C$_{12}$)alkyl, V$^1$ is —CO—, T$^2$ is (EDA)$_w$, V$^2$ is absent, T$^3$ is absent, V$^3$ is absent, T$^4$ is absent, V$^4$ is absent, T$^5$ is absent and V$^5$ is absent. In certain embodiments, T$^1$ is (C$_1$-C$_{12}$)alkyl, V$^1$ is —CO—, T$^2$ is (EDA)$_w$, V$^2$ is —CO—, T$^3$ is (CR$^{13}$OH)$_h$, V$^3$ is —CONR$^{11}$—, T$^4$ is (C$_1$-C$_{12}$)alkyl, V$^4$ is —CO—, T$^5$ is absent and V$^5$ is absent. In certain embodiments, T$^1$ is (C$_1$-C$_{12}$)alkyl, V$^1$ is —CO—, T$^2$ is (AA)$_p$, V$^2$ is —NR$^{11}$—, T$^3$ is (C$_1$-C$_{12}$)alkyl, V$^3$ is —CO—, T$^4$ is absent, V$^4$ is absent, T$^5$ is absent and V$^5$ is absent. In certain embodiments, T$^1$ is (C$_1$-C$_{12}$)alkyl, V$^1$ is —CONR$^{11}$—, T$^2$ is (PEG)$_n$, V$^2$ is —CO—, T$^3$ is (AA)$_p$, V$^3$ is absent, T$^4$ is absent, V$^4$ is absent, T$^5$ is absent and V$^5$ is absent. In certain embodiments, T$^1$ is (C$_1$-C$_{12}$)alkyl, V$^1$ is —CO—, T$^2$ is (EDA)$_w$, V$^2$ is —CO—, T$^3$ is (CR$^{13}$OH)$_h$, V$^3$ is —CO—, T$^4$ is (AA)$_p$, V$^4$ is absent, T$^5$ is absent and V$^5$ is absent. In certain embodiments, T$^1$ is (C$_1$-C$_{12}$)alkyl, V$^1$ is —CO—, T$^2$ is (AA)$_p$, V$^2$ is —NR$^{11}$—, T$^3$ is (C$_1$-C$_{12}$)alkyl, V$^3$ is —CO—, T$^4$ is (AA)$_p$, V$^4$ is absent, T$^5$ is absent and V$^5$ is absent. In certain embodiments, T$^1$ is (C$_1$-C$_{12}$)alkyl, V$^1$ is —CO—, T$^2$ is (AA)$_p$, V$^2$ is —NR$^{11}$—, T$^3$ is (PEG)$_n$, V$^3$ is —CO—, T$^4$ is (AA)$_p$, V$^4$ is absent, T$^5$ is absent and V$^5$ is absent. In certain embodiments, T$^1$ is (C$_1$-C$_{12}$)alkyl, V$^1$ is —CO—, T$^2$ is (AA)$_p$, V$^2$ is —NR$^{11}$—, T$^3$ is (C$_1$-C$_{12}$)alkyl, V$^3$ is —CO—, T$^4$ is (AA)$_p$, V$^4$ is absent, T$^5$ is absent and V$^5$ is absent. In certain embodiments, T$^1$ is (C$_1$-C$_{12}$)alkyl, V$^1$ is —CO—, T$^2$ is (AA)$_p$, V$^2$ is —NR$^{11}$—, T$^3$ is (PEG)$_n$, V$^3$ is —CO—, T$^4$ is (AA)$_p$-PABC-(AA)$_p$, where each p is independently 0, 1, 2, 3, 4, 5 or 6, V$^4$ is absent, T$^5$ is absent and V$^5$ is absent. In certain embodiments, T$^1$ is (C$_1$-C$_{12}$)alkyl, V$^1$ is —CO—, T$^2$ is (AA)$_p$, V$^2$ is —NR$^{11}$—, T$^3$ is (PEG)$_n$, V$^3$ is —CO—, T$^4$ is (AA)$_p$-PABO where p is 0, 1, 2, 3, 4, 5 or 6, V$^4$ is absent, T$^5$ is absent and V$^5$ is absent. In certain embodiments, T$^1$ is (C$_1$-C$_{12}$)alkyl, V$^1$ is —CO—, T$^2$ is (AA)$_p$, V$^2$ is —NR$^{11}$—, T$^3$ is (PEG)$_n$, V$^3$ is —SO$_2$—, T$^4$ is (AA)$_p$, V$^4$ is absent, T$^5$ is absent and V$^5$ is absent. In certain embodiments, T$^1$ is (C$_1$-C$_{12}$)alkyl, V$^1$ is —CONR$^{11}$—, T$^2$ is (PEG)$_n$, V$^2$ is —CO—, T$^3$ is (AA)$_p$, V$^3$ is absent, T$^4$ is PABC-(AA)$_p$ where p is 0, 1, 2, 3, 4, 5 or 6, V$^4$ is absent, T$^5$ is absent and V$^5$ is absent. In certain embodiments, T$^1$ is (C$_1$-C$_{12}$)alkyl, V$^1$ is —CO—, T$^2$ is (EDA)$_w$, V$^2$ is —CO—, T$^3$ is (CR$^{13}$OH)$_h$, V$^3$ is —CONR$^{11}$—, T$^4$ is (PEG)$_n$, V$^4$ is —CO—, T$^5$ is absent and V$^5$ is absent. In certain embodiments, T$^1$ is (C$_1$-C$_{12}$)alkyl, V$^1$ is —CO—, T$^2$ is (AA)$_p$, V$^2$ is —NR$^{11}$—, T$^3$ is (PEG)$_n$, V$^3$ is —CO—, T$^4$ is MABC-(AA)$_p$- where p is 0, 1, 2, 3, 4, 5 or 6, V$^4$ is absent, T$^5$ is absent and V$^5$ is absent. In certain embodiments, T$^1$ is (C$_1$-C$_{12}$)alkyl, V$^1$ is —CONR$^{11}$—, T$^2$ is (PEG)$_n$, V$^2$ is —CO—, T$^3$ is MABO, V$^3$ is absent, T$^4$ is absent, V$^4$ is absent, T$^5$ is absent and V$^5$ is absent. In certain embodiments, T$^1$ is (C$_1$-C$_{12}$)alkyl, V$^1$ is —CO—, T$^2$ is (AA)$_p$, V$^2$ is —NR$^{11}$—, T$^3$ is (PEG)$_n$, V$^3$ is —CO—, T$^4$ is MABO, V$^4$ is absent, T$^5$ is absent and V$^5$ is absent. In certain embodiments, T$^1$ is (C$_1$-C$_{12}$)alkyl, V$^1$ is —CONR$^{11}$—, T$^2$ is (PEG)$_n$, V$^2$ is —CO—, T$^3$ is MABC, V$^3$ is absent, T$^4$ is (AA)$_p$, V$^4$ is absent, T$^5$ is absent and V$^5$ is absent. In certain embodiments, T$^1$ is (C$_1$-C$_{12}$)alkyl, V$^1$ is —CO—, T$^2$ is (CR$^{13}$OH)$_h$, V$^2$ is —CO—, T$^3$ is absent, V$^3$ is absent, T$^4$ is absent, V$^4$ is absent, T$^5$ is absent and V$^5$ is absent. In certain embodiments, T$^1$ is (C$_1$-C$_{12}$)alkyl, V$^1$ is —CONR$^{11}$—, T$^2$ is substituted (C$_1$-C$_{12}$)alkyl, V$^2$ is —NR$^{11}$—, T$^3$ is (PEG)$_n$, V$^3$ is —CO—, T$^4$ is absent, V$^4$ is absent, T$^5$ is absent and V$^5$ is absent. In certain embodiments, T$^1$ is (C$_1$-C$_{12}$)alkyl, V$^1$ is —SO$_2$—, T$^2$ is (C$_1$-C$_{12}$)alkyl, V$^2$ is —CO—, T$^3$ is absent, V$^3$ is absent, T$^4$ is absent, V$^4$ is absent, T$^5$ is absent and V$^5$ is absent. In certain embodiments, T$^1$ is (C$_1$-C$_{12}$)alkyl, V$^1$ is —CONR$^{11}$—, T$^2$ is (PEG)$_n$, V$^2$ is —CO—, T$^3$ is (AA)$_p$, V$^3$ is absent, T$^4$ is PABC, V$^4$ is —NR$^{11}$—, T$^5$ is absent and V$^5$ is absent. In certain embodiments, T$^1$ is (C$_1$-C$_{12}$)alkyl, V$^1$ is —CONR$^{11}$—, T$^2$ is (C$_1$-C$_{12}$)alkyl, V$^2$ is absent, T$^3$ is (CR$^{13}$OH)$_h$, V$^3$ is —CONR$^{11}$—, T$^4$ is absent, V$^4$ is absent, T$^5$ is absent and V$^5$ is absent. In certain embodiments, T$^1$ is (C$_1$-C$_{12}$)alkyl, V$^1$ is —CO—, T$^2$ is P4A, V$^2$ is —CO—, T$^3$ is (C$_1$-C$_{12}$)alkyl, V$^3$ is —CO—, T$^4$ is (AA)$_p$, V$^4$ is absent, T$^5$ is absent and V$^5$ is absent. In certain embodiments, T$^1$ is (C$_1$-C$_{12}$)alkyl, V$^1$ is —CONR$^{11}$—, T$^2$ is (PEG)$_n$, V$^2$ is —CO—, T$^3$ is (AA)$_p$, V$^3$ is absent, T$^4$ is MABO, V$^4$ is absent, T$^5$ is absent and V$^5$ is absent. In certain embodiments, T$^1$ is (C$_1$-C$_{12}$)alkyl, V$^1$ is —CONR$^{11}$—, T$^2$ is (PEG)$_n$, V$^2$ is —CO—, T$^3$ is (AA)$_p$, V$^3$ is absent, T$^4$ is PABO, V$^4$ is absent, T$^5$ is absent and V$^5$ is absent. In certain embodiments, T$^1$ is (C$_1$-C$_{12}$)alkyl, V$^1$ is —CONR$^{11}$—, T$^2$ is (PEG)$_n$, V$^2$ is —CO—, T$^3$ is (AA)$_p$, V$^3$ is absent, T$^4$ is PABC, V$^4$ is absent, T$^5$ is absent and V$^5$ is absent. In certain embodiments, T$^1$ is (C$_1$-C$_{12}$)alkyl, V$^1$ is —CO—, T$^2$ is (AA)$_p$, V$^2$ is —NR$^{11}$—, T$^3$ is (PEG)$_n$, V$^3$ is —CO—, T$^4$ is PABO, V$^4$ is absent, T$^5$ is absent and V$^5$ is absent. In certain embodiments, T$^1$ is (C$_1$-C$_{12}$)alkyl, V$^1$ is —CO—, T$^2$ is (AA)$_p$, V$^2$ is —NR$^{11}$—, T$^3$ is (PEG)$_n$, V$^3$ is —CO—, T$^4$ is PABC, V$^4$ is absent, T$^5$ is absent and V$^5$ is absent.

In some embodiments, L is a linker comprising -(L$^1$)$_a$-(L$^2$)$_b$-(L$^3$)$_c$-(L$^4$)$_d$-(L$^5$)$_e$-, where -(L$^1$)$_a$- is -(T$^1$-V$^1$)$_a$—; -(L$^2$)$_b$- is -(T$^2$-V$^2$)$_b$—; -(L$^3$)$_c$- is -(T$^3$-V$^3$)$_c$—; -(L$^4$)$_d$- is -(T$^4$-V$^4$)$_d$—; and -(L$^5$)$_e$- is -(T$^5$-V$^5$)$_e$—. In certain embodiments, T$^1$ is (C$_1$-C$_{12}$)alkyl, V$^1$ is —CO—, T$^2$ is (AA)$_p$, V$^2$ is —NR$^{11}$—, T$^3$ is (PEG)$_n$, V$^3$ is —CO—, T$^4$ is (AA)p, V$^4$ is absent, T$^5$ is PABC-(AA)p, and V$^5$ is absent. In certain embodiments, T$^1$ is (C$_1$-C$_{12}$)alkyl, V$^1$ is —CO—, T$^2$ is (AA)$_p$, V$^2$ is —NR$^{11}$—, T$^3$ is (PEG)$_n$, V$^3$ is —CO—, T$^4$ is (AA)p, V$^4$ is absent, T$^5$ is PABO, and V$^5$ is absent. In certain embodiments, T$^1$ is (C$_1$-C$_{12}$)alkyl, V$^1$ is —CO—, T$^2$ is (PEG)$_n$, V$^2$ is —CO—, T$^3$ is (AA)p, V$^3$ is absent, T$^4$ is PABC, V$^4$ is absent, T$^5$ is (AA)p, and V$^5$ is absent. In certain embodiments, T$^1$ is (C$_1$-C$_{12}$)alkyl, V$^1$ is —CO—, T$^2$ is (AA)$_p$, V$^2$ is —NR$^{11}$—, T$^3$ is (PEG)$_n$, V$^3$ is —CO—, T$^4$ is MABC, V$^4$ is absent, T$^5$ is (AA)p, and V$^5$ is absent. In certain embodiments, T$^1$ is (C$_1$-C$_{12}$)alkyl, V$^1$ is —CO—, T$^2$ is P4A, V² is —CO—, T³ is (C₁-C₁₂)alkyl, V³ is —CO—, T⁴ is (AA)p, V⁴ is absent, T⁵ is PABO, and V⁵ is —CO—. In certain embodiments, T¹ is (C₁-C₁₂)alkyl, V¹ is —CO—, T² is P4A, V² is —CO—, T³ is (C₁-C₁₂)alkyl, V³ is —CO—, T⁴ is (AA)p, V⁴ is absent, T⁵ is PABO, and V⁵ is absent. In certain embodiments, T¹ is (C₁-C₁₂)alkyl, V¹ is —CO—, T² is P4A, V² is —CO—, T³ is (C₁-C₁₂)alkyl, V³ is —CO—, T⁴ is (AA)p, V⁴ is absent, T⁵ is PABC-(AA)p, and V⁵ is absent. In certain embodiments, T¹ is (C₁-C₁₂)alkyl, V¹ is —CO—, T² is P4A, V² is —CO—, T³ is (C₁-C₁₂)alkyl, V³ is —CO—, T⁴ is (AA)$_p$, V⁴ is absent, T⁵ is absent and V⁵ is absent.

In some embodiments, the linker is described by one of the following structures:

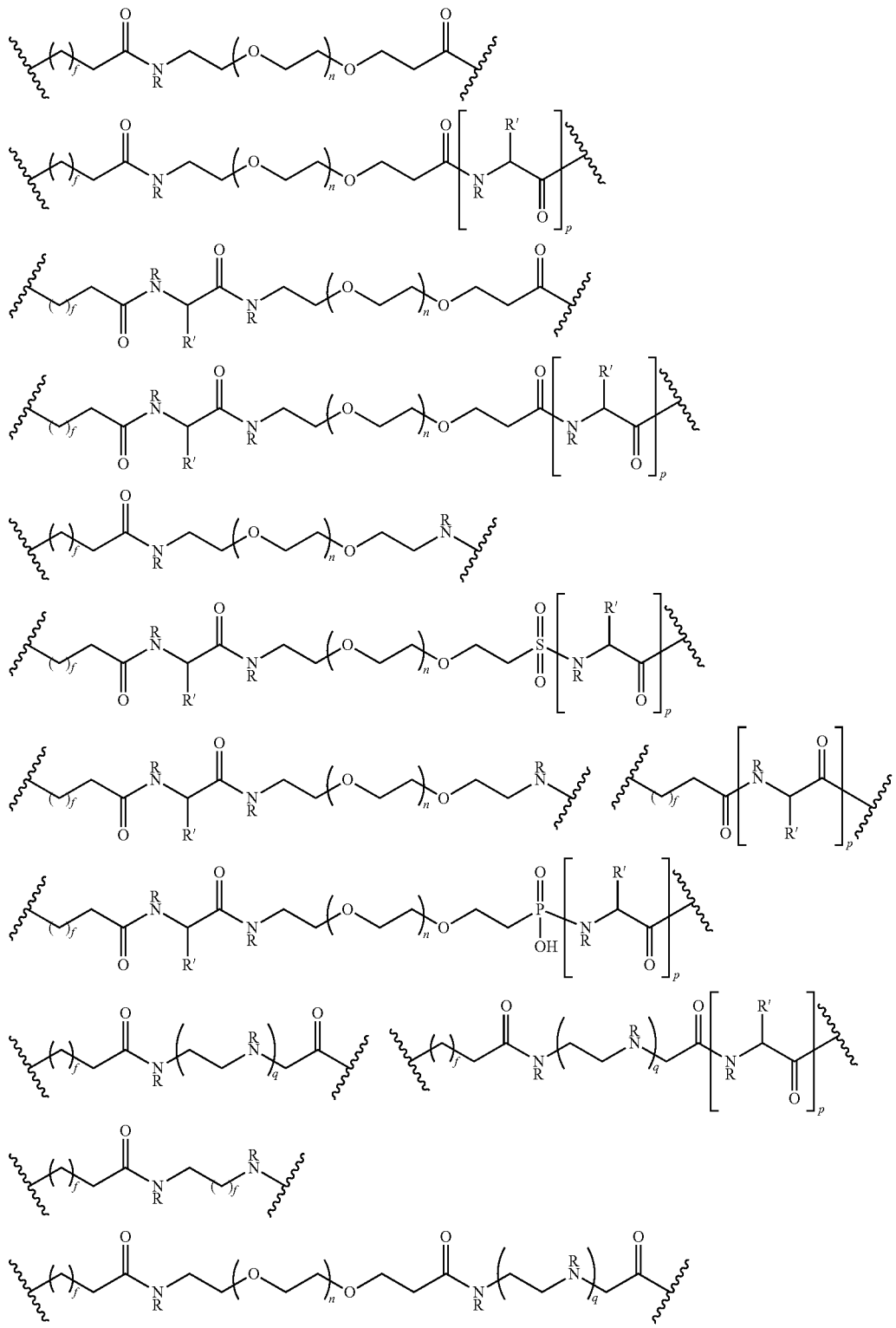

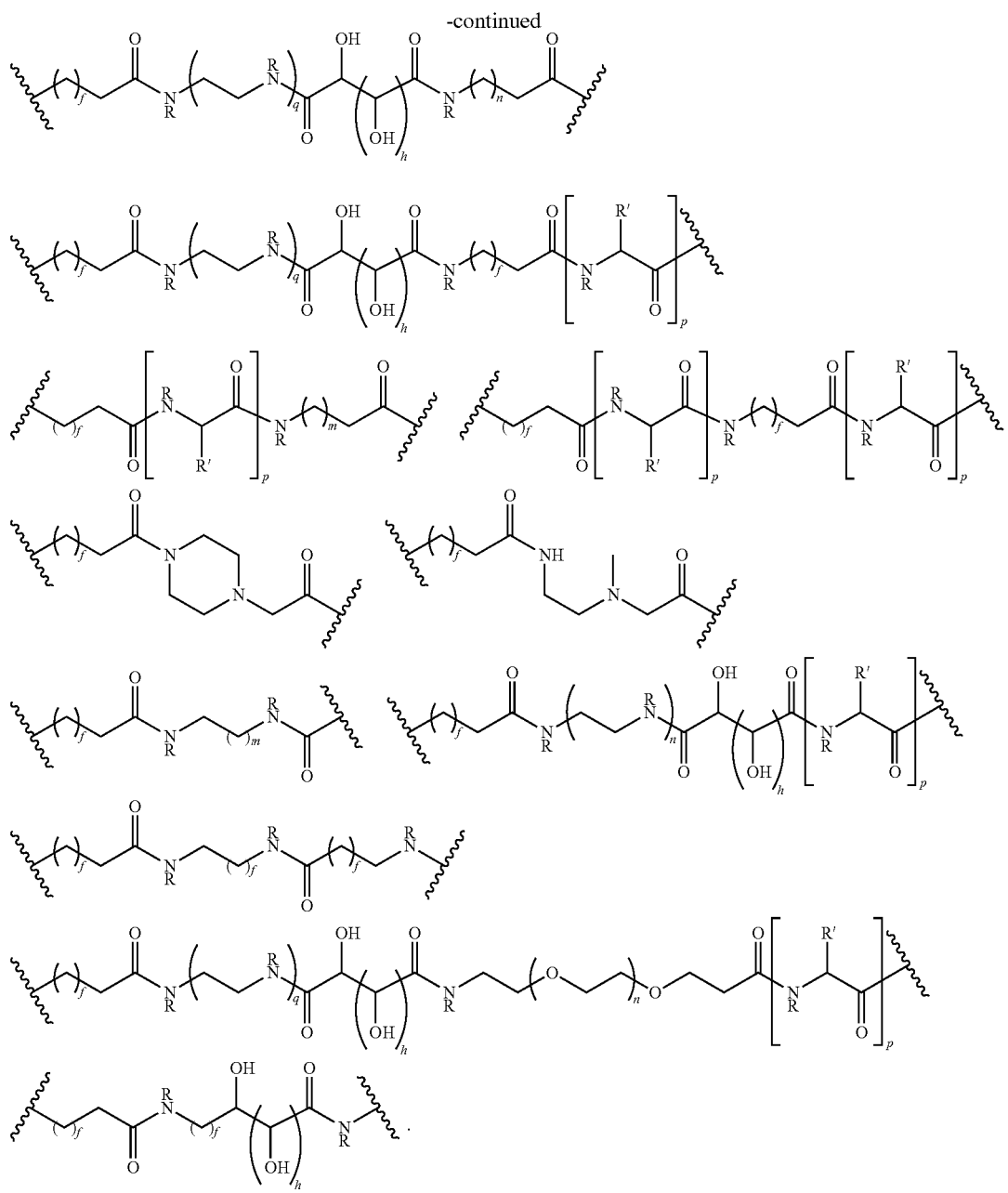

In certain embodiments of the linker structures depicted above, each f is independently 0 or an integer from 1 to 12; each w is independently 0 or an integer from 1 to 20; each n is independently 0 or an integer from 1 to 30; each p is independently 0 or an integer from 1 to 20; each h is independently 0 or an integer from 1 to 12; each R is independently hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl; and each R' is independently H, a sidechain of an amino acid, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments of the linker structures depicted above, each f is independently 0, 1, 2, 3, 4, 5 or 6; each w is independently 0, 1, 2, 3, 4, 5 or 6; each n is independently 0, 1, 2, 3, 4, 5 or 6; each p is independently 0, 1, 2, 3, 4, 5 or 6; and each h is independently 0, 1, 2, 3, 4, 5 or 6. In certain embodiments of the linker structures depicted above, each R is independently H, methyl or —(CH$_2$)$_m$—OH where m is 1, 2, 3 or 4 (e.g., 2).

In certain embodiments, the linker includes a cleavable group, e.g., as described in the following structures:

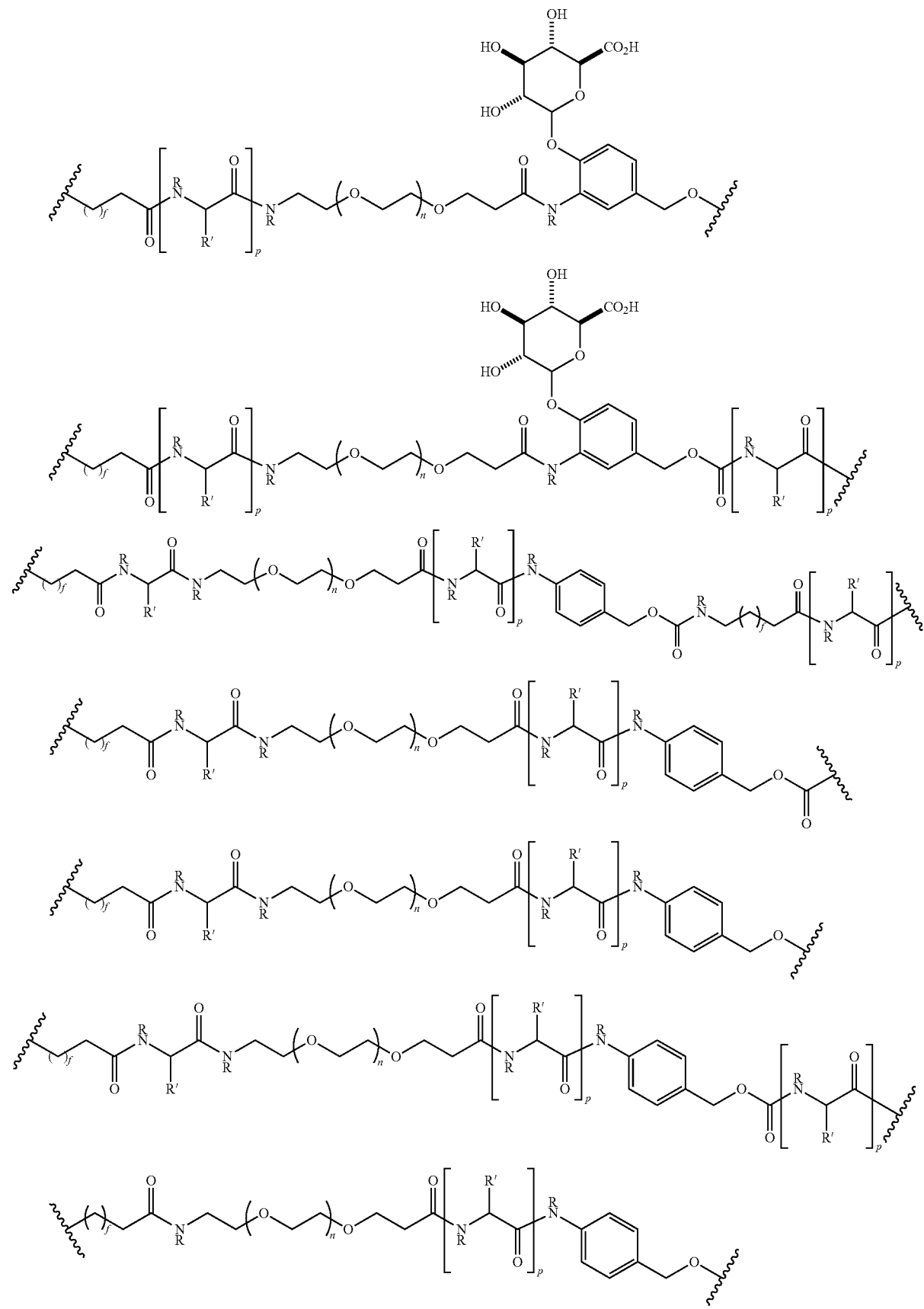

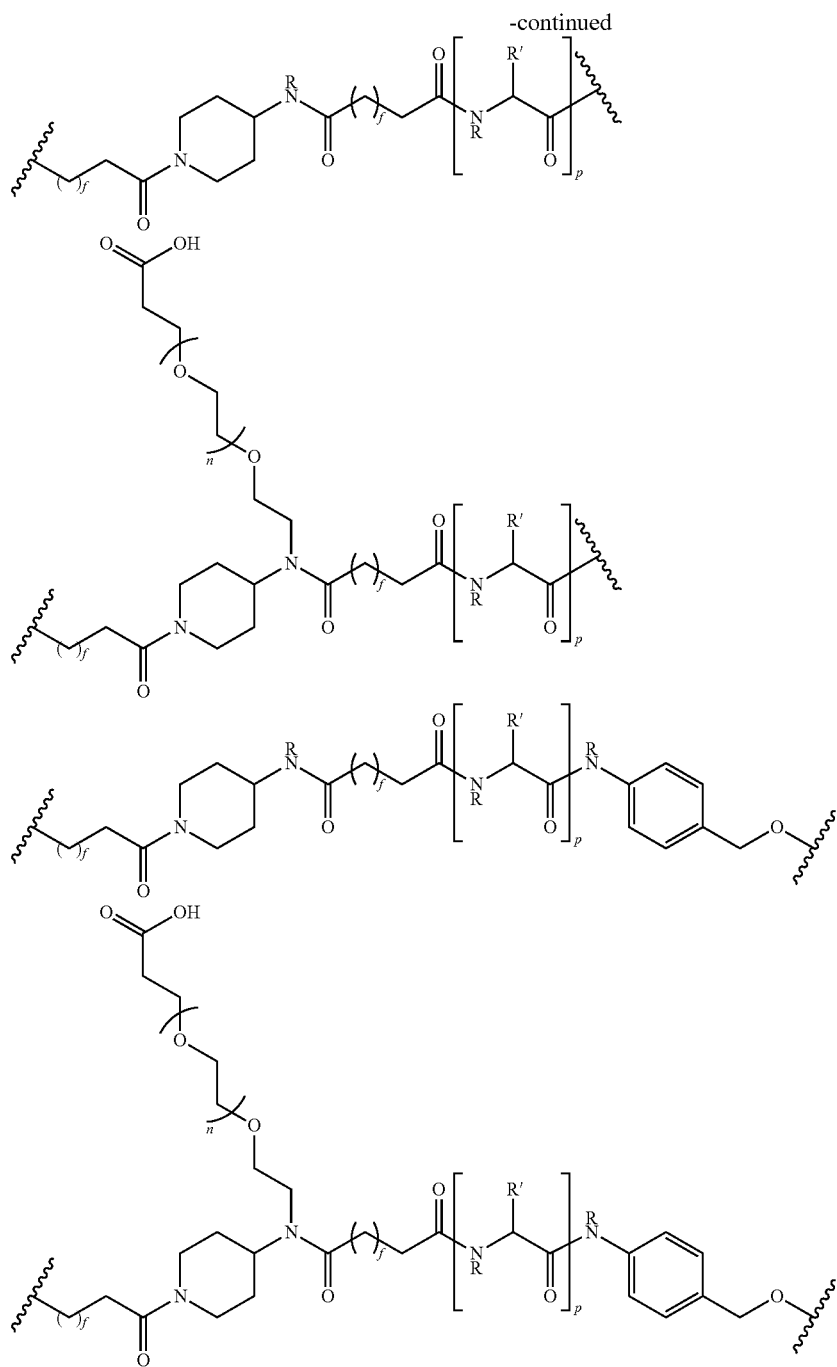

In certain embodiments of the linker structures depicted above, each f is independently 0 or an integer from 1 to 12; each w is independently 0 or an integer from 1 to 20; each n is independently 0 or an integer from 1 to 30; each p is independently 0 or an integer from 1 to 20; each h is independently 0 or an integer from 1 to 12; each R is independently hydrogen, alkyl, substituted alkyl, a polyethylene glycol moiety, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl; and each R' is independently H, a sidechain of an amino acid, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments of the linker structures depicted above, each f is independently 0, 1, 2, 3, 4, 5 or 6; each w is independently 0, 1, 2, 3, 4, 5 or 6; each n is independently 0, 1, 2, 3, 4, 5 or 6; each p is independently 0, 1, 2, 3, 4, 5 or 6; and each h is independently 0, 1, 2, 3, 4, 5 or 6. In certain embodiments of the linker structures depicted above, each R is independently H, methyl or —(CH$_2$)$_m$—OH where m is 1, 2, 3 or 4 (e.g., 2).

Compounds Useful for Producing Conjugates

The present disclosure provides hydrazinyl-pyrrolo compounds useful for producing the conjugates described herein. In certain embodiments, the hydrazinyl-pyrrolo compound may be a coupling moiety useful for conjugation of a polypeptide and a second moiety. For example, the hydrazinyl-pyrrolo compound may be bound to the polypeptide and also bound to the second moiety, thus indirectly binding the polypeptide and the second moiety together.

In certain instances, the hydrazinyl-pyrrolo compound may be a compound of formula (V):

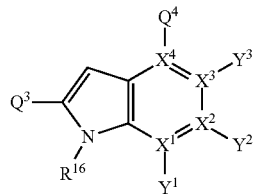

(V)

wherein
one of Q$^3$ and Q$^4$ is —(CH$_2$)$_m$NR$^3$NHR$^2$ and the other is Y$^4$;

m is 0 or 1;

R$^2$ and R$^3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, or R$^2$ and R$^3$ are optionally cyclically linked to form a 5 or 6-membered heterocyclyl;

X$^1$, X$^2$, X$^3$ and X$^4$ are each independently selected from C, N, O and S, wherein one of X$^1$, X$^2$, X$^3$ and X$^4$ is optional;

Y$^1$, Y$^2$, Y$^3$ and Y$^4$ are each independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, wherein Y$^1$ and Y$^2$ or Y$^2$ and Y$^3$ are optionally cyclically linked, and wherein when Q$^4$ is Y$^4$, then Y$^3$ and Y$^4$ are optionally cyclically linked;

one of R$^{16}$, Y$^1$, Y$^2$, Y$^3$ or Q$^4$ is -L-W$^1$, wherein if Q$^4$ is -L-W$^1$, then Q$^3$ is —(CH$_2$)$_m$NR$^3$NHR$^2$ and Y$^4$ is absent; and wherein if one of Y$^1$, Y$^2$, Y$^3$ or Q$^4$ is -L-W$^1$, then R$^{16}$ is selected from hydrogen, alkyl, substituted alkyl, alkenyl, substituted aryl, heteroaryl, substituted heteroaryl, cycloalkyl, substituted cycloalkyl, heterocyclyl, and substituted heterocyclyl;

L is an optional linker (e.g., a linker as described herein); and

W$^1$ is selected from a polypeptide and a chemical entity.

For example, L may be a linker such as where:
L is a linker comprising -(T$^1$-V$^1$)$_a$-(T$^2$-V$^2$)$_b$-(T$^3$-V$^3$)$_c$-(T$^4$-V$^4$)$_d$-(T$^5$-V$^5$)$_e$—, where a, b, c, d and e are each independently 0 or 1, where the sum of a, b, c, d and e is 1 to 5;

T$^1$, T$^2$, T$^3$, T$^4$ and T$^5$ are each independently selected from (C$_1$-C$_{12}$)alkyl, substituted (C$_1$-C$_{12}$)alkyl, (EDA)$_w$, (PEG)$_n$, (AA)$_p$, —(CR$^{13}$OH)$_h$—, piperidin-4-amino (P4A), para-amino-benzyloxycarbonyl (PABC), a meta-amino-benzyloxycarbonyl (MABC), a para-amino-benzyloxy (PABO), a meta-amino-benzyloxy (MABO), para-aminobenzyl, an acetal group, a disulfide, a hydrazine, a protease-cleavable moiety, a glucuronidase cleavable moiety, a beta-lactamase cleavable moiety, and an ester, where EDA is an ethylene diamine moiety, PEG is a polyethylene glycol or a modified polyethylene glycol, and AA is an amino acid residue;

w is an integer from 1 to 20;
n is an integer from 1 to 30;
p is an integer from 1 to 20;
h is an integer from 1 to 12; and
V$^1$, V$^2$, V$^3$, V$^4$ and V$^5$ are each independently selected from the group consisting of a covalent bond, —CO—, —NR$^{11}$—, —CONR$^{11}$—, —NR$^{11}$CO—, —C(O)O—, —OC(O)—, —O—, —S—, —S(O)—, —SO$_2$—, —SO$_2$NR$^{11}$—, —NR$^{11}$SO$_2$— and —P(O)OH—.

In certain embodiments, one of Q$^3$ and Q$^4$ is —(CH$_2$)$_m$NR$^3$NHR$^2$ and the other is Y$^4$. In certain embodiments, Q$^3$ is —(CH$_2$)$_m$NR$^3$NHR$^2$ and Q$^4$ is Y$^4$. In certain embodiments, Q$^4$ is —(CH$_2$)$_m$NR$^3$NHR$^2$ and Q$^3$ is Y$^4$. In certain embodiments, m is 0 or 1. In certain embodiments, m is 0. In certain embodiments, m is 1.

In certain embodiments, R$^2$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, R$^2$ is hydrogen. In certain embodiments, R$^2$ is alkyl or substituted alkyl. In certain embodiments, R$^2$ is alkenyl or substituted alkenyl. In certain embodiments, R$^2$ is alkynyl or substituted alkynyl. In certain embodiments, R$^2$ is alkoxy or substituted alkoxy. In certain embodiments, R$^2$ is amino or substituted amino. In certain embodiments, R$^2$ is carboxyl or carboxyl ester. In certain embodiments, R$^2$ is acyl or acyloxy. In certain embodiments, R$^2$ is acyl amino or amino acyl. In certain embodiments, R$^2$ is alkylamide or substituted alkylamide. In certain embodiments, R$^2$ is sulfonyl. In certain embodiments, R$^2$ is thioalkoxy or substituted thioalkoxy. In certain embodiments, R$^2$ is aryl or substituted aryl. In certain embodiments, R$^2$ is heteroaryl or substituted heteroaryl. In certain embodiments, R$^2$ is cycloalkyl or substituted cycloalkyl. In certain embodiments, R$^2$ is heterocyclyl or substituted heterocyclyl.

In certain embodiments, R$^2$ is alkyl or substituted alkyl. For example, R$^2$ may be alkyl or substituted alkyl, such as, C$_1$-C$_{10}$ alkyl or C$_1$-C$_{10}$ substituted alkyl (e.g., C$_1$-C$_6$ alkyl or C$_1$-C$_6$ substituted alkyl). In some cases, R$^2$ is methyl, ethyl, n-propyl, iso-propyl, n-butyl, sec-butyl, isobutyl, t-butyl, or the like. In certain cases, R$^2$ is methyl.

In certain embodiments, R$^3$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl.

In certain embodiments, $R^3$ is hydrogen. In certain embodiments, $R^3$ is alkyl or substituted alkyl. In certain embodiments, $R^3$ is alkenyl or substituted alkenyl. In certain embodiments, $R^3$ is alkynyl or substituted alkynyl. In certain embodiments, $R^3$ is alkoxy or substituted alkoxy. In certain embodiments, $R^3$ is amino or substituted amino. In certain embodiments, $R^3$ is carboxyl or carboxyl ester. In certain embodiments, $R^3$ is acyl or acyloxy. In certain embodiments, $R^3$ is acyl amino or amino acyl. In certain embodiments, $R^3$ is alkylamide or substituted alkylamide. In certain embodiments, $R^3$ is sulfonyl. In certain embodiments, $R^3$ is thioalkoxy or substituted thioalkoxy. In certain embodiments, $R^3$ is aryl or substituted aryl. In certain embodiments, $R^3$ is heteroaryl or substituted heteroaryl. In certain embodiments, $R^3$ is cycloalkyl or substituted cycloalkyl. In certain embodiments, $R^3$ is heterocyclyl or substituted heterocyclyl.

In certain embodiments, $R^3$ is alkyl or substituted alkyl. For example, $R^3$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R^3$ is methyl, ethyl, n-propyl, iso-propyl, n-butyl, sec-butyl, isobutyl, t-butyl, or the like. In certain cases, $R^3$ is methyl.

In certain embodiments, $R^2$ and $R^3$ are each independently selected from alkyl and substituted alkyl. For example, $R^2$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl), and $R^3$ may be alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl). In some cases, $R^2$ and $R^3$ are each independently selected from methyl, ethyl, n-propyl, iso-propyl, n-butyl, sec-butyl, isobutyl, t-butyl, or the like. In certain cases, $R^2$ and $R^3$ are each methyl.

In certain embodiments, $R^2$ and $R^3$ are optionally cyclically linked to form a 5 or 6-membered heterocyclyl. In some instances, $R^2$ and $R^3$ (together with the atoms to which they are attached) may be cyclically linked to form a 5-membered heterocyclyl. In some instances, $R^2$ and $R^3$ (together with the atoms to which they are attached) may be cyclically linked to form a 6-membered heterocyclyl. For example, $R^2$ and $R^3$ may each independently be an alkyl or substituted alkyl, such as, $C_1$-$C_{10}$ alkyl or $C_1$-$C_{10}$ substituted alkyl (e.g., $C_1$-$C_6$ alkyl or $C_1$-$C_6$ substituted alkyl), where $R^2$ and $R^3$ are optionally cyclically linked to form a 5 or 6-membered heterocyclyl, as described above. In some instances, one or more carbon atoms in $R^2$ and/or $R^3$ may be replaced with a heteroatom, such as N, O, or S.

In certain embodiments, $X^1$ is selected from C, N, O and S. In certain embodiments, $X^1$ is C. In certain embodiments, $X^1$ is N. In certain embodiments, $X^1$ is O. In certain embodiments, $X^1$ is S. In certain embodiments, $X^1$ is absent.

In certain embodiments, $X^2$ is selected from C, N, O and S. In certain embodiments, $X^2$ is C. In certain embodiments, $X^2$ is N. In certain embodiments, $X^2$ is O. In certain embodiments, $X^2$ is S. In certain embodiments, $X^2$ is absent.

In certain embodiments, $X^3$ is selected from C, N, O and S. In certain embodiments, $X^3$ is C. In certain embodiments, $X^3$ is N. In certain embodiments, $X^3$ is O. In certain embodiments, $X^3$ is S. In certain embodiments, $X^3$ is absent.

In certain embodiments, $X^4$ is selected from C, N, O and S. In certain embodiments, $X^4$ is C. In certain embodiments, $X^4$ is N. In certain embodiments, $X^4$ is O. In certain embodiments, $X^4$ is S. In certain embodiments, $X^4$ is absent.

Various combinations of $X^1$, $X^2$, $X^3$ and $X^4$ are possible. For example, in certain embodiments, each of $X^1$, $X^2$, $X^3$ and $X^4$ is C. In other instances, three of $X^1$, $X^2$, $X^3$ and $X^4$ are C and one of $X^1$, $X^2$, $X^3$ and $X^4$ is N. In other embodiments, two of $X^1$, $X^2$, $X^3$ and $X^4$ are C and two of $X^1$, $X^2$, $X^3$ and $X^4$ are N. In other embodiments, one of $X^1$, $X^2$, $X^3$ and $X^4$ is C and three of $X^1$, $X^2$, $X^3$ and $X^4$ is are N. In other embodiments, one of $X^1$, $X^2$, $X^3$ and $X^4$ is absent, two of $X^1$, $X^2$, $X^3$ and $X^4$ are C and one of $X^1$, $X^2$, $X^3$ and $X^4$ is N. In other embodiments, one of $X^1$, $X^2$, $X^3$ and $X^4$ is absent, two of $X^1$, $X^2$, $X^3$ and $X^4$ are C and one of $X^1$, $X^2$, $X^3$ and $X^4$ is S. In other embodiments, one of $X^1$, $X^2$, $X^3$ and $X^4$ is absent, two of $X^1$, $X^2$, $X^3$ and $X^4$ are C and one of $X^1$, $X^2$, $X^3$ and $X^4$ is O. Other combinations of C, N, O and S are possible for $X^1$, $X^2$, $X^3$ and $X^4$ as desired.

In certain embodiments, $Y^1$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y^1$ is hydrogen. In certain embodiments, $Y^1$ is halogen, such as F, Cl, Br or I. In certain embodiments, $Y^1$ is F. In certain embodiments, $Y^1$ is Cl. In certain embodiments, $Y^1$ is Br. In certain embodiments, $Y^1$ is I. In certain embodiments, $Y^1$ is alkyl or substituted alkyl. In certain embodiments, $Y^1$ is alkenyl or substituted alkenyl. In certain embodiments, $Y^1$ is alkynyl or substituted alkynyl. In certain embodiments, $Y^1$ is alkoxy or substituted alkoxy. In certain embodiments, $Y^1$ is amino or substituted amino. In certain embodiments, $Y^1$ is carboxyl or carboxyl ester. In certain embodiments, $Y^1$ is acyl or acyloxy. In certain embodiments, $Y^1$ is acyl amino or amino acyl. In certain embodiments, $Y^1$ is alkylamide or substituted alkylamide. In certain embodiments, $Y^1$ is sulfonyl. In certain embodiments, $Y^1$ is thioalkoxy or substituted thioalkoxy. In certain embodiments, $Y^1$ is aryl or substituted aryl. In certain embodiments, $Y^1$ is heteroaryl or substituted heteroaryl. In certain embodiments, $Y^1$ is cycloalkyl or substituted cycloalkyl. In certain embodiments, $Y^1$ is heterocyclyl or substituted heterocyclyl.

In certain embodiments, $Y^2$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y^2$ is hydrogen. In certain embodiments, $Y^2$ is halogen, such as F, Cl, Br or I. In certain embodiments, $Y^2$ is F. In certain embodiments, $Y^2$ is Cl. In certain embodiments, $Y^2$ is Br. In certain embodiments, $Y^2$ is I. In certain embodiments, $Y^2$ is alkyl or substituted alkyl. In certain embodiments, $Y^2$ is alkenyl or substituted alkenyl. In certain embodiments, $Y^2$ is alkynyl or substituted alkynyl. In certain embodiments, $Y^2$ is alkoxy or substituted alkoxy. In certain embodiments, $Y^2$ is amino or substituted amino. In certain embodiments, $Y^2$ is carboxyl or carboxyl ester. In certain embodiments, $Y^2$ is acyl or acyloxy. In certain embodiments, $Y^2$ is acyl amino or amino acyl. In certain embodiments, $Y^2$ is alkylamide or substituted alkylamide. In certain embodiments, $Y^2$ is sulfonyl. In certain embodiments, $Y^2$ is thioalkoxy or substituted thioalkoxy. In certain embodiments, $Y^2$ is aryl or substituted aryl. In certain embodiments, $Y^2$ is heteroaryl or substituted heteroaryl. In certain embodiments, $Y^2$ is cycloalkyl or substituted cycloalkyl. In certain embodiments, $Y^2$ is heterocyclyl or substituted heterocyclyl.

In certain embodiments, $Y^3$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y^3$ is hydrogen. In certain embodiments, $Y^3$ is halogen, such as F, Cl, Br or I. In certain embodiments, $Y^3$ is F. In certain embodiments, $Y^3$ is Cl. In certain embodiments, $Y^3$ is Br. In certain embodiments, $Y^3$ is I. In certain embodiments, $Y^3$ is alkyl or substituted alkyl. In certain embodiments, $Y^3$ is alkenyl or substituted alkenyl. In certain embodiments, $Y^3$ is alkynyl or substituted alkynyl. In certain embodiments, $Y^3$ is alkoxy or substituted alkoxy. In certain embodiments, $Y^3$ is amino or substituted amino. In certain embodiments, $Y^3$ is carboxyl or carboxyl ester. In certain embodiments, $Y^3$ is acyl or acyloxy. In certain embodiments, $Y^3$ is acyl amino or amino acyl. In certain embodiments, $Y^3$ is alkylamide or substituted alkylamide. In certain embodiments, $Y^3$ is sulfonyl. In certain embodiments, $Y^3$ is thioalkoxy or substituted thioalkoxy. In certain embodiments, $Y^3$ is aryl or substituted aryl. In certain embodiments, $Y^3$ is heteroaryl or substituted heteroaryl. In certain embodiments, $Y^3$ is cycloalkyl or substituted cycloalkyl. In certain embodiments, $Y^3$ is heterocyclyl or substituted heterocyclyl.

In certain embodiments, $Y^4$ is selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $Y^4$ is hydrogen. In certain embodiments, $Y^4$ is halogen, such as F, Cl, Br or I. In certain embodiments, $Y^4$ is F. In certain embodiments, $Y^4$ is Cl. In certain embodiments, $Y^4$ is Br. In certain embodiments, $Y^4$ is I. In certain embodiments, $Y^4$ is alkyl or substituted alkyl. In certain embodiments, $Y^4$ is alkenyl or substituted alkenyl. In certain embodiments, $Y^4$ is alkynyl or substituted alkynyl. In certain embodiments, $Y^4$ is alkoxy or substituted alkoxy. In certain embodiments, $Y^4$ is amino or substituted amino. In certain embodiments, $Y^4$ is carboxyl or carboxyl ester. In certain embodiments, $Y^4$ is acyl or acyloxy. In certain embodiments, $Y^4$ is acyl amino or amino acyl. In certain embodiments, $Y^4$ is alkylamide or substituted alkylamide. In certain embodiments, $Y^4$ is sulfonyl. In certain embodiments, $Y^4$ is thioalkoxy or substituted thioalkoxy. In certain embodiments, $Y^4$ is aryl or substituted aryl. In certain embodiments, $Y^4$ is heteroaryl or substituted heteroaryl. In certain embodiments, $Y^4$ is cycloalkyl or substituted cycloalkyl. In certain embodiments, $Y^4$ is heterocyclyl or substituted heterocyclyl.

In certain embodiments, $Y^1$ and $Y^2$ or $Y^2$ and $Y^3$ are cyclically linked to form a fused benzo ring. In certain embodiments, $Y^1$ and $Y^2$ are cyclically linked to form a fused benzo ring. In certain embodiments, $Y^2$ and $Y^3$ are cyclically linked to form a fused benzo ring. In certain embodiments, when $Q^4$ is $Y^4$, then $Y^3$ and $Y^4$ are optionally cyclically linked.

In certain embodiments, one of $R^{16}$, $Y^1$, $Y^2$, $Y^3$ or $Q^4$ is -L-$W^1$, wherein if $Q^4$ is -L-$W^1$, then $Q^3$ is —$(CH_2)_m NR^3 NHR^2$ and $Y^4$ is absent. In certain embodiments, $R^{16}$ is -L-$W^1$. In certain embodiments, $Y^1$ is -L-$W^1$. In certain embodiments, $Y^2$ is -L-$W^1$. In certain embodiments, $Y^3$ is -L-$W^1$. In certain embodiments, $Q^4$ is -L-$W^1$. In certain embodiments, if $Q^4$ is -L-$W^1$, then $Q^3$ is —$(CH_2)_m NR^3 NHR^2$ and $Y^4$ is absent.

In certain embodiments, if one of $Y^1$, $Y^2$, $Y^3$ or $Q^4$ is -L-$W^1$, then $R^{16}$ is is not -L-$W^1$. In these embodiments, $R^{16}$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl. In some instances, $R^{16}$ is hydrogen. In some instances, $R^{16}$ is alkyl or substituted alkyl. In some instances, $R^{16}$ is alkenyl or substituted alkenyl. In some instances, $R^{16}$ is alkynyl or substituted alkynyl. In some instances, $R^{16}$ is aryl or substituted aryl. In some instances, $R^{16}$ is heteroaryl or substituted heteroaryl. In some instances, $R^{16}$ is cycloalkyl or substituted cycloalkyl. In some instances, $R^{16}$ is heterocyclyl or substituted heterocyclyl.

In certain embodiments, L is an optional linker. In certain embodiments, L is not present, and thus the nitrogen of the indole ring is directly bonded to $W^1$. In certain embodiments, L is present, and thus the nitrogen of the indole ring is indirectly bonded to $W^1$ through the linker L. Further description of the linker, L, is found in the disclosure herein.

For instance, in certain embodiments, L includes a group selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl. In certain embodiments, L includes an alkyl or substituted alkyl group. In certain embodiments, L includes an alkenyl or substituted alkenyl group. In certain embodiments, L includes an alkynyl or substituted alkynyl group. In certain embodiments, L includes an alkoxy or substituted alkoxy group. In certain embodiments, L includes an amino or substituted amino group. In certain embodiments, L includes a carboxyl or carboxyl ester group. In certain embodiments, L includes an acyl amino group. In certain embodiments, L includes an alkylamide or substituted alkylamide group. In certain embodiments, L includes an aryl or substituted aryl group. In certain embodiments, L includes a heteroaryl or substituted heteroaryl group. In certain embodiments, L includes a cycloalkyl or substituted cycloalkyl group. In certain embodiments, L includes a heterocyclyl or substituted heterocyclyl group.

In certain embodiments, L includes a polymer. For example, the polymer may include a polyalkylene glycol and derivatives thereof, including polyethylene glycol, methoxypolyethylene glycol, polyethylene glycol homopolymers, polypropylene glycol homopolymers, copolymers of ethylene glycol with propylene glycol (e.g., where the homopolymers and copolymers are unsubstituted or substituted at one end with an alkyl group), polyvinyl alcohol, polyvinyl ethyl ethers, polyvinylpyrrolidone, combinations thereof, and the like. In certain embodiments, the polymer is a polyalkylene glycol. In certain embodiments, the polymer is a polyethylene glycol.

In some embodiments, L is a linker comprising -$(L^1)_a$-$(L^2)_b$-$(L^3)_c$-$(L^4)_d$-$(L^5)_e$-, wherein $L^1$, $L^2$, $L^3$, $L^4$ and $L^5$ are each a linker unit, and a, b, c, d and e are each independently 0 or 1, wherein the sum of a, b, c, d and e is 1 to 5. Other linkers are also possible, as shown in the conjugates and compounds described in more detail herein.

In certain embodiments, $W^1$ is selected from a chemical entity and a polypeptide. In certain embodiments, $W^1$ is a chemical entity (e.g., a drug or a detectable label). In certain embodiments, $W^1$ is a drug. In certain embodiments, $W^1$ is a detectable label. In certain embodiments, $W^1$ is a polypeptide.

In certain instances, the hydrazinyl-pyrrolo compound is a compound of formula (VI):

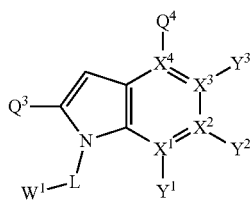

(VI)

wherein
$Q^3$, $Q^4$, $X^1$, $X^2$, $X^3$, $X^4$, L, $W^1$, $Y^1$, $Y^2$, and $Y^3$ are as defined in formula (V).

As described above, in formula (V), in some instances, $R^{16}$ is -L-$W^1$, which results in a compound of formula (VI) as shown above.

In certain embodiments, the substituents for formula (VI) are the same as for formula (V) described above. For example, in certain embodiments, the substituents for formula (VI), e.g., $Q^3$, $Q^4$, $X^1$, $X^2$, $X^3$, $X^4$, L, $W^1$, $Y^1$, $Y^2$, and $Y^3$ are as defined in formula (V).

In some embodiments, the compound is a compound of formula (VIIa) or (VIIb):

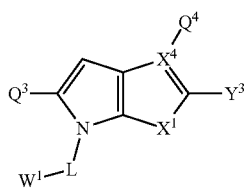

(VIIa)

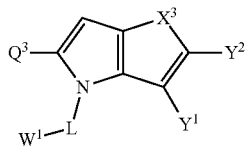

(VIIb)

wherein:
$X^1$ and $X^3$ are each independently O, S or $NR^{12}$;
$X^4$ is C;
in formula (VIIa), one of $Q^3$ and $Q^4$ is —$(CH_2)_m NR^3 NHR^2$ and the other is $Y^4$;
in formula (VIIb), one of $Q^3$ and $R^{12}$, if present, is —$(CH_2)_m NR^3 NHR^2$ and the other is $Y^3$;
$Y^1$, $Y^2$, $Y^3$ and $Y^4$, if present, are each independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, wherein $Y^1$ and $Y^2$ are optionally cyclically linked, and wherein when $Q^4$ is $Y^4$, then $Y^3$ and $Y^4$ are optionally cyclically linked; and n, $R^2$ and $R^3$ are as defined in formula (V).

In certain embodiments, the substituents for formulae (VIIa) and (VIIb) are the same as for formula (V) described above.

For example, in certain embodiments of formula (VIIa), $X^4$ is C, and one of $Q^3$ and $R^{12}$ is —$(CH_2)_m NR^3 NHR^2$ and the other is $Y^3$. In certain embodiments of formula (VIIa), $X^4$ is C, $Q^3$ is —$(CH_2)_m NR^3 NHR^2$ and $Q^4$ is $Y^3$. In certain embodiments of formula (VIIa), $X^4$ is C, $Q^4$ is —$(CH_2)_m NR^3 NHR^2$ and $Q^3$ is $Y^3$. In certain embodiments, m is 0 or 1. In certain $Q^4$ i embodiments, m is 0. In certain embodiments, m is 1.

In certain embodiments of formula (VIIb), $X^3$ is $NR^{12}$, and one of $Q^3$ and $R^{12}$ is —$(CH_2)_m NR^3 NHR^2$ and the other is $Y^3$. In certain embodiments of formula (VIIb), $X^3$ is $NR^{12}$, $Q^3$ is —$(CH_2)_m NR^3 NHR^2$ and $R^{12}$ is $Y^3$. In certain embodiments of formula (VIIb), $X^3$ is $NR^{12}$, $R^{12}$ is —$(CH_2)_m NR^3 NHR^2$ and $Q^3$ is $Y^3$. In certain embodiments, m is 0 or 1. In certain embodiments, m is 0. In certain embodiments, m is 1.

In certain embodiments, $Y^1$ and $Y^2$ are optionally cyclically linked, and wherein when $Q^4$ is $Y^4$, then $Y^3$ and $Y^4$ are optionally cyclically linked to form a fused benzo ring. In certain embodiments of formula (VIIb), $Y^1$ and $Y^2$ are cyclically linked to form a fused benzo ring. In certain embodiments of formula (VIIa), $Q^4$ is $Y^4$ and $Y^3$ and $Y^4$ are cyclically linked to form a fused benzo ring.

In some embodiments, in the compounds, $Q^2$ is —$(CH_2)_m NR^3 NHR^2$ and $Q^3$ is $Y^4$. In some embodiments, in the compounds, $Q^3$ is —$(CH_2)_m NR^3 NHR^2$ and $Q^2$ is $Y^4$. In certain embodiments, m is 1.

In some embodiments, $R^2$ and $R^3$ are each independently selected from alkyl and substituted alkyl. In certain embodiments, $R^2$ and $R^3$ are each methyl.

In some embodiments, $X^1$, $X^2$, $X^3$ and $X^4$ are each C.
In some embodiments, $Y^1$, $Y^2$, $Y^3$ and $Y^4$ are each H.
In some embodiments, $X^1$ and $X^3$ are each S and $X^4$ is C.
In some embodiments, $X^1$ and $X^3$ are each O and $X^4$ is C. In some embodiments of formula (VIIa), $X^1$ is S and $X^4$ is C. In some embodiments of formula (VIIa), $X^1$ is O and $X^4$ is C. In some embodiments of formula (VIIb), $X^3$ is S. In some embodiments of formula (VIIb), $X^3$ is O.

In some embodiments, $X^1$ and $X^3$ are each $NR^{12}$ and $X^4$ is C. In some embodiments of formula (VIIa), $X^1$ is $NR^{12}$ and $X^4$ is C. In some embodiments of formula (VIIa), $X^1$ is NH and $X^4$ is C. In some embodiments of formula (VIIb), $X^3$ is $NR^{12}$. In some embodiments of formula (VIIb), $X^3$ is NH.

In some embodiments, $W^1$ is a chemical entity. In some embodiments, $W^1$ is a drug or a detectable label. In certain embodiments, the detectable label comprises a fluorophore. In some embodiments, $W^2$ is the polypeptide.

In some embodiments, the compound is a compound of formula (VIII):

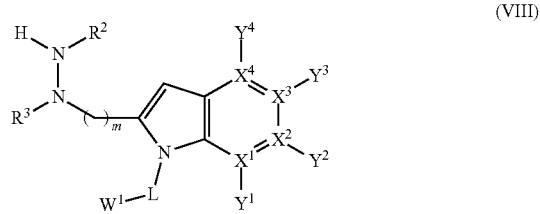

(VIII)

wherein m is 0 or 1;

$R^2$ and $R^3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, or $R^2$ and $R^3$ are optionally cyclically linked to form a 5 or 6-membered heterocyclyl;

$X^1$, $X^2$, $X^3$ and $X^4$ are each independently selected from C, N, O and S;

$Y^1$, $Y^2$, $Y^3$ and $Y^4$ are each independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, wherein $Y^1$ and $Y^2$, $Y^2$ and $Y^3$, or $Y^3$ and $Y^4$ are optionally cyclically linked;

L is an optional linker (e.g., a linker as described herein); and $W^1$ is selected from a chemical entity and a polypeptide.

In certain embodiments, the substituents for formula (VIII) are the same as for formula (V) described above.

In some embodiments, the compound is a compound of formula (VIIIa):

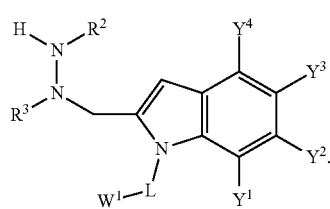

(VIIIa)

In certain embodiments, the substituents in formula (VIIIa) are as described above for formula (VIII).

Embodiments of the compound include a compound of formula (VIIIb):

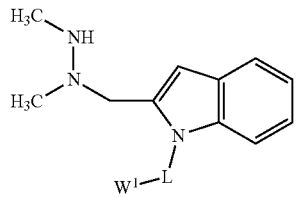

(VIIIb)

where $W^1$ and L are as as described above for formula (VIII).

In some embodiments, the compound is a compound of formula (IX):

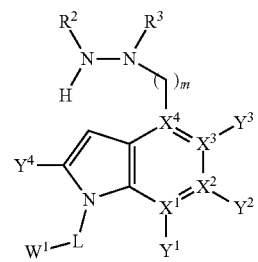

(IX)

wherein m is 0 or 1;

$R^2$ and $R^3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, or $R^2$ and $R^3$ are optionally cyclically linked to form a 5 or 6-membered heterocyclyl;

$X^1$, $X^2$, $X^3$ and $X^4$ are each independently selected from C, N, O and S;

$Y^1$, $Y^2$, $Y^3$ and $Y^4$ are each independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, wherein $Y^1$ and $Y^2$ or $Y^2$ and $Y^3$ are optionally cyclically linked;

L is an optional linker (e.g., a linker as described herein); and $W^1$ is selected from a chemical entity and a polypeptide.

In certain embodiments, the substituents in formula (IX) are as described above for formula (V). For example, in certain embodiments, m is 0 or 1. In certain embodiments, m is 0. In certain embodiments, m is 1.

In some embodiments, the compound is a compound of formula (IXa):

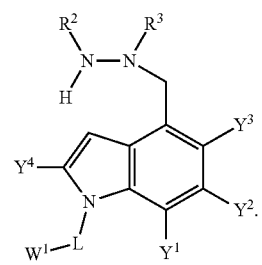

(IXa)

In certain embodiments, the substituents in formula (IXa) are as described above for formula (IX).

Embodiments of the compound include a compound of formula (IXb):

95

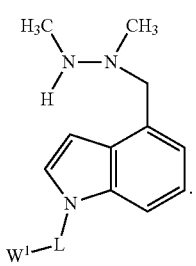

(IXb)

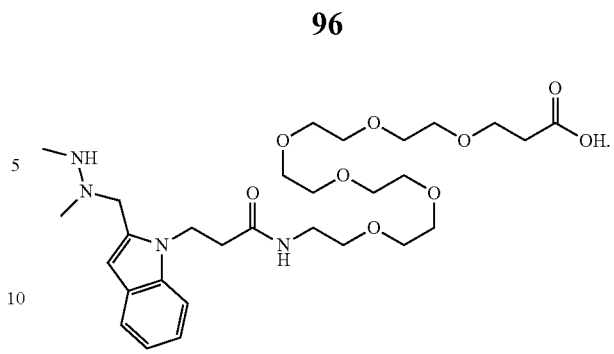

In certain embodiments, the substituents in formula (DO) are as described above for formula (IX).

In certain embodiments, the compound is of the following structure:

In certain embodiments, the compound is of the following structure:

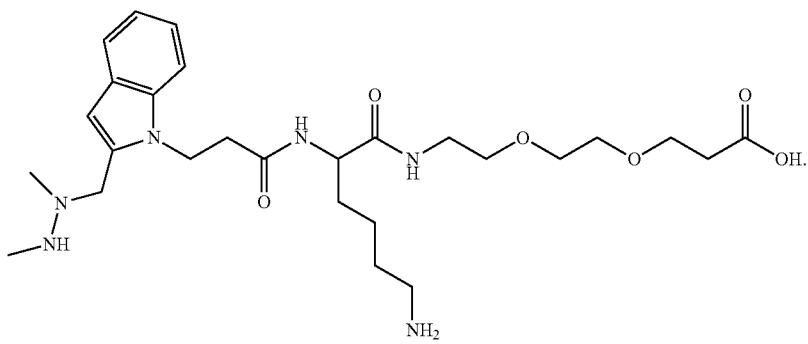 [SMILES: CNN(C)Cc1cc2ccccc2n1CCC(=O)NC(CCCCN)C(=O)NCCOCCOCCC(=O)O]

In certain embodiments, the compound is of the following structure:

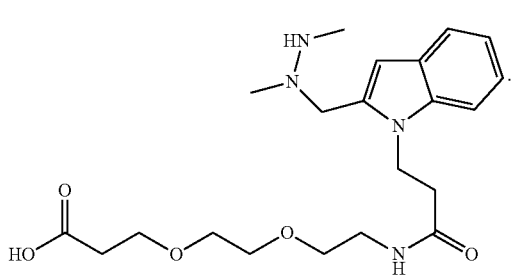 [SMILES: CNN(C)Cc1cc2ccccc2n1CCC(=O)NCCOCCOCCC(=O)O]

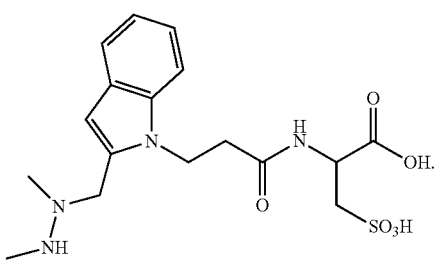 [SMILES: CNN(C)Cc1cc2ccccc2n1CCC(=O)NC(CS(=O)(=O)O)C(=O)O]

In certain embodiments, the compound is of the following structure:

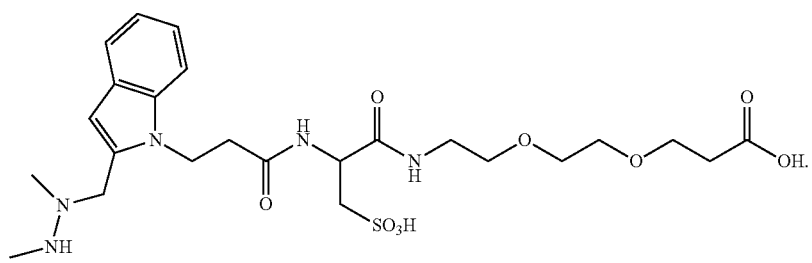 [SMILES: CNN(C)Cc1cc2ccccc2n1CCC(=O)NC(CS(=O)(=O)O)C(=O)NCCOCCOCCC(=O)O]

In certain embodiments, the compound is of the following structure:

In certain embodiments, the compound is of the following structure:

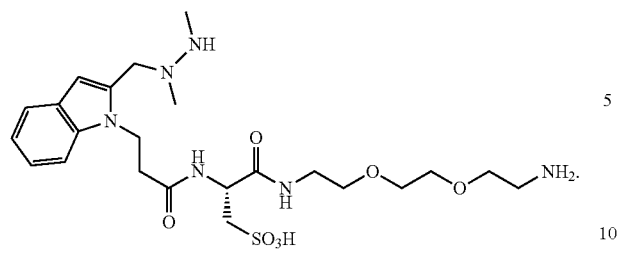
In certain embodiments, the compound is of the following structure:
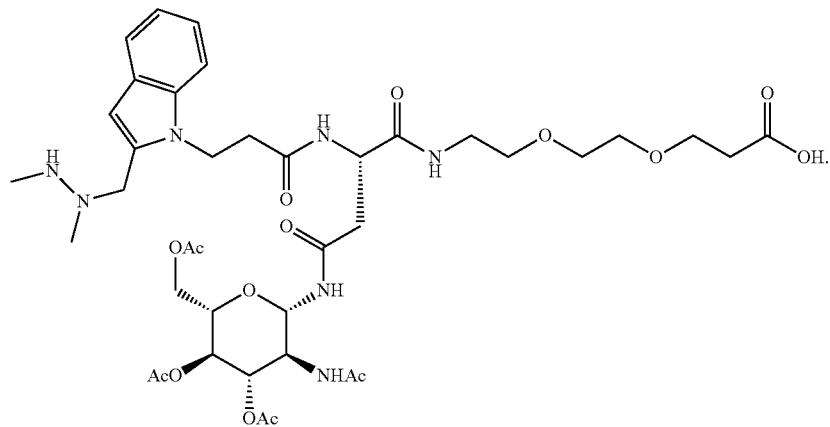 [SMILES: CNN(C)Cc1cc2ccccc2n1CCC(=O)N[C@@H](CC(=O)N[C@H]1O[C@@H](COC(C)=O)[C@H](OC(C)=O)[C@@H](OC(C)=O)[C@@H]1NC(C)=O)C(=O)NCCOCCOCCC(=O)O]
In certain embodiments, the compound is of the following structure:
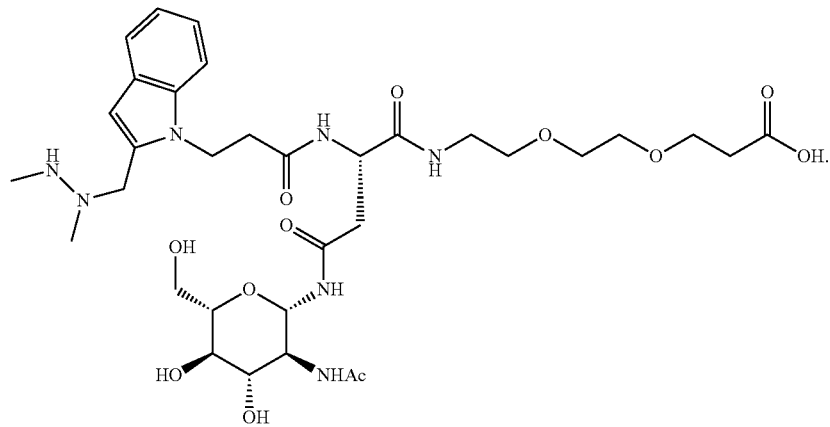 [SMILES: CNN(C)Cc1cc2ccccc2n1CCC(=O)N[C@@H](CC(=O)N[C@H]1O[C@@H](CO)[C@H](O)[C@@H](O)[C@@H]1NC(C)=O)C(=O)NCCOCCOCCC(=O)O]
In certain embodiments, the compound is of the following structure:
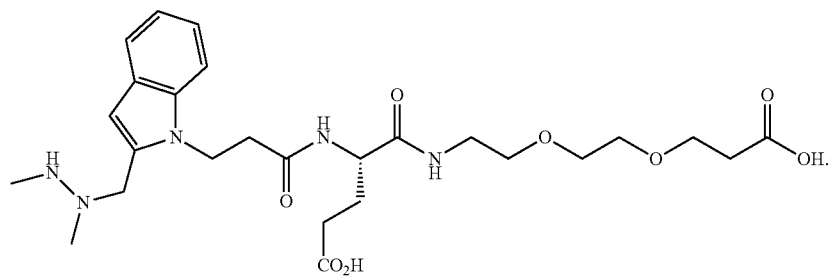 [SMILES: CNN(C)Cc1cc2ccccc2n1CCC(=O)N[C@@H](CCC(=O)O)C(=O)NCCOCCOCCC(=O)O]

In certain embodiments, the compound is of the following structure:
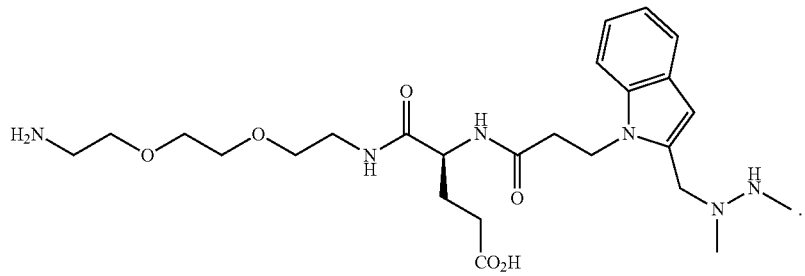 [SMILES: CNN(C)Cc1cc2ccccc2n1CCC(=O)N[C@@H](CCC(=O)O)C(=O)NCCOCCOCCN]
In certain embodiments, the compound is of the following structure:
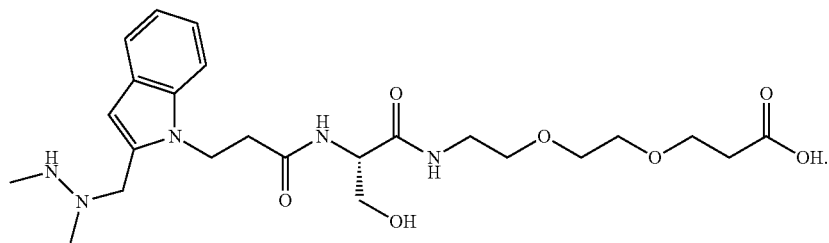 [SMILES: CNN(C)Cc1cc2ccccc2n1CCC(=O)N[C@@H](CO)C(=O)NCCOCCOCCC(=O)O]
In certain embodiments, the compound is of the following structure:
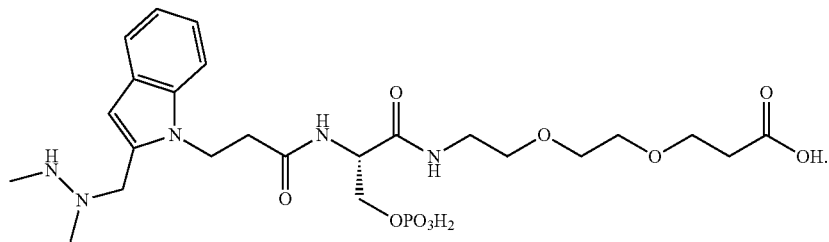
In certain embodiments, the compound is of the following structure:
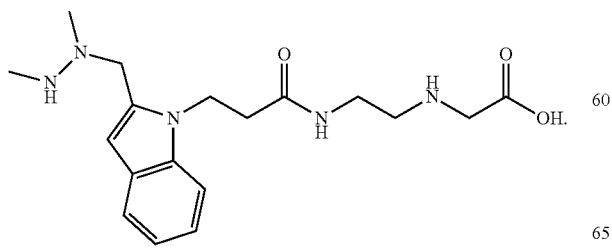

In certain embodiments, the compound is of the following structure:
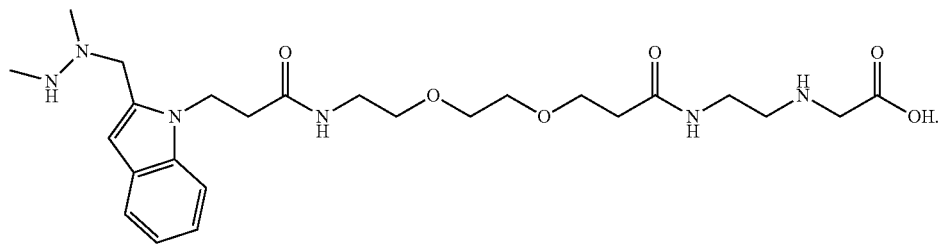 [SMILES: CNN(C)Cc1cc2ccccc2n1CCC(=O)NCCOCCOCCC(=O)NCCNCC(=O)O]
In certain embodiments, the compound is of the following structure:
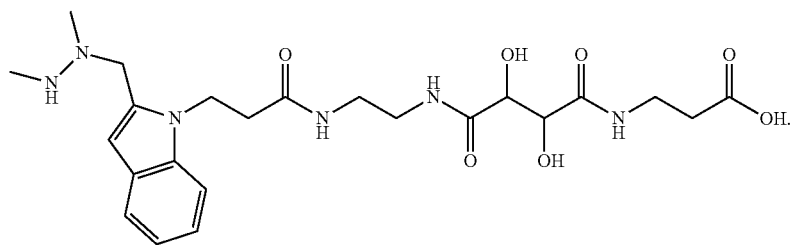 [SMILES: CNN(C)Cc1cc2ccccc2n1CCC(=O)NCCNC(=O)C(O)C(O)C(=O)NCCC(=O)O]
In certain embodiments, the compound is of the following structure:
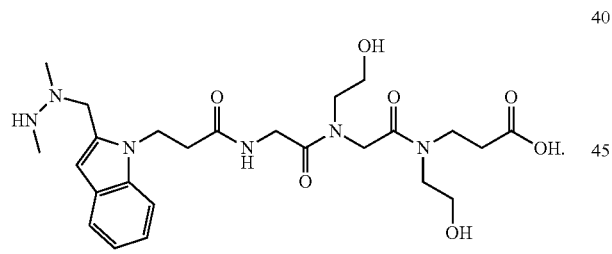
In certain embodiments, the compound is of the following structure:
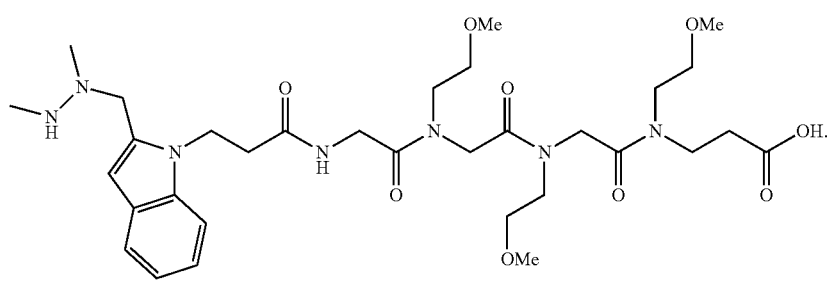 [SMILES: CNN(C)Cc1cc2ccccc2n1CCC(=O)NCC(=O)N(CCOC)CC(=O)N(CCOC)CC(=O)N(CCOC)CCC(=O)O]

In certain embodiments, the compound is of the following structure:

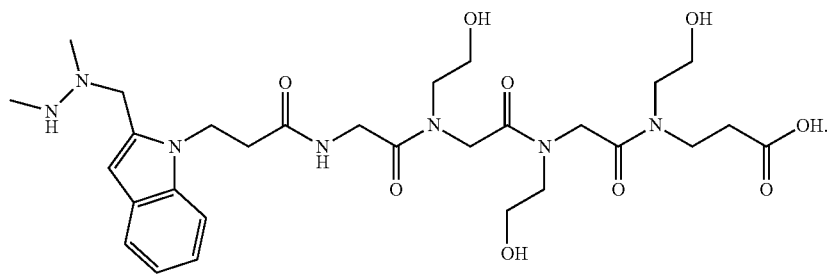 [SMILES: CNN(C)Cc1cc2ccccc2n1CCC(=O)NCC(=O)N(CCO)CC(=O)N(CCO)CC(=O)N(CCO)CCC(=O)O]

In certain embodiments, the compound is of the following structure:

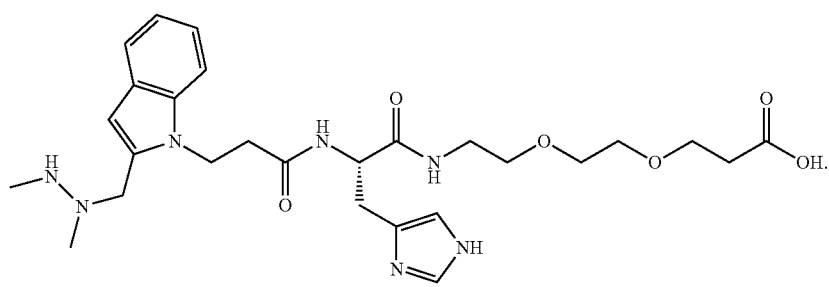 [SMILES: CNN(C)Cc1cc2ccccc2n1CCC(=O)N[C@@H](Cc1c[nH]cn1)C(=O)NCCOCCOCCC(=O)O]

In certain embodiments, the compound is of the following structure:

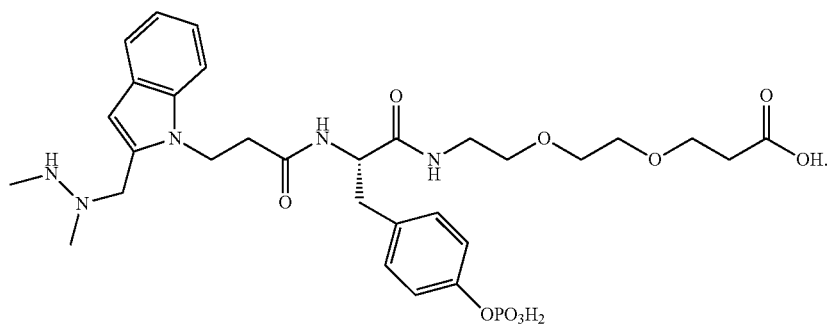

In certain embodiments, the compound is of the following structure:

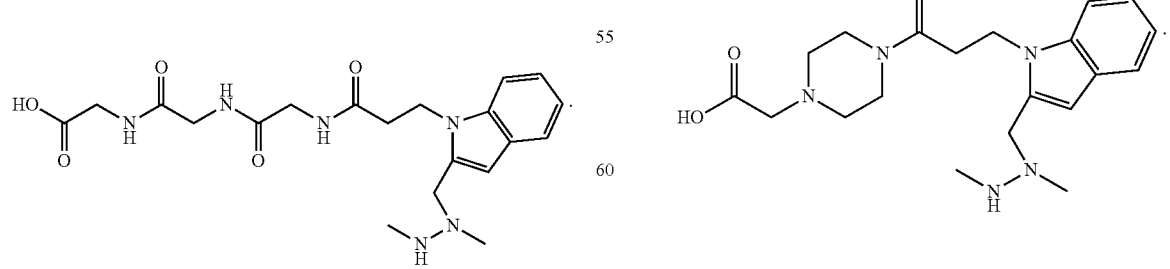

In certain embodiments, the compound is of the following structure:

In certain embodiments, the compound is of the following structure:

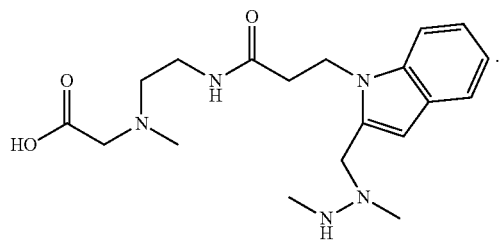 [SMILES: CNN(C)Cc1cc2ccccc2n1CCC(=O)NCCN(C)CC(=O)O]
In certain embodiments, the compound is of the following structure:
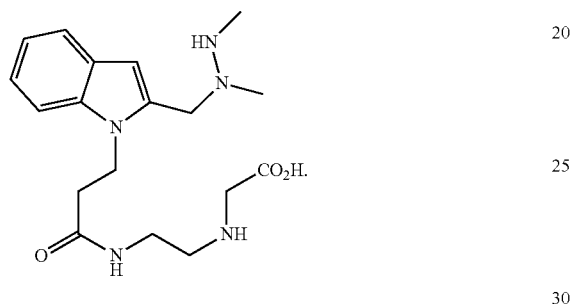
In certain embodiments, the compound is of the following structure:
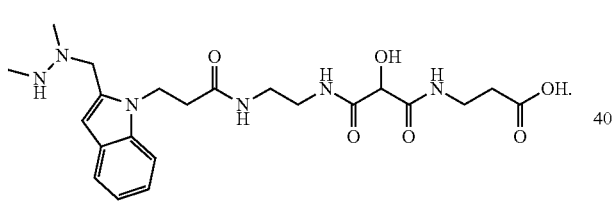
In certain embodiments, the compound is of the following structure:
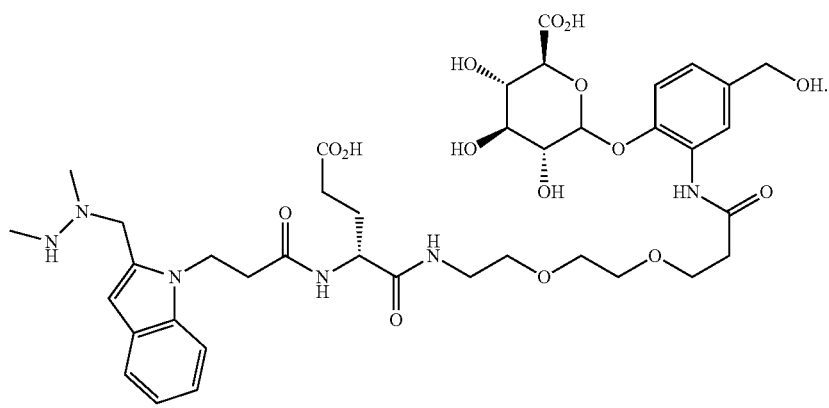

In certain embodiments, the compound is of the following structure:
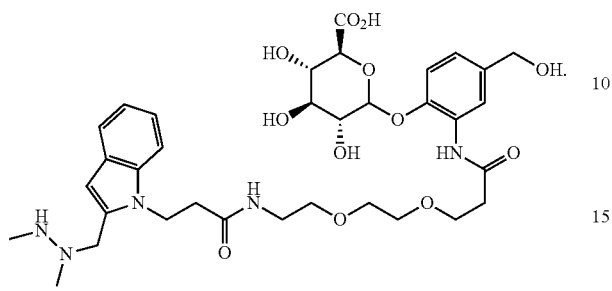
In certain embodiments, the compound is of the following structure:
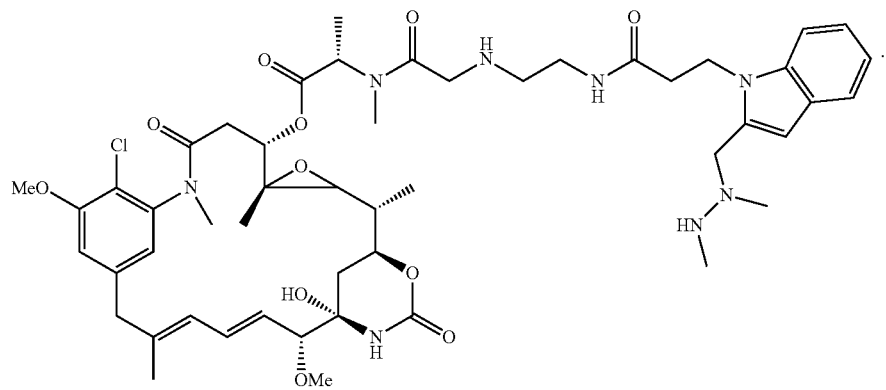
In certain embodiments, the compound is of the following structure:
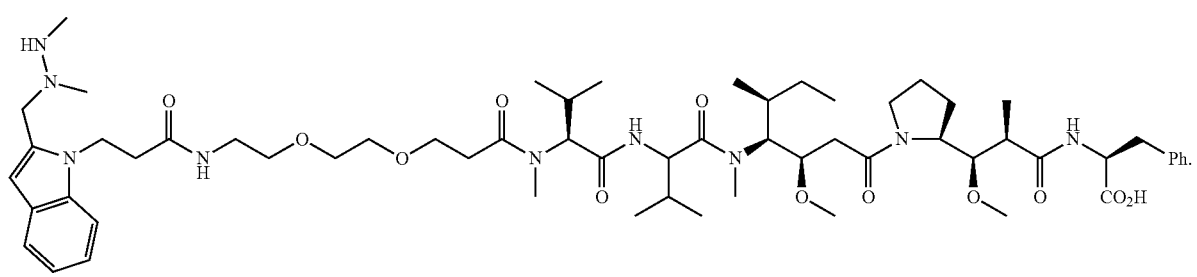 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)C(NC(=O)[C@H](C(C)C)N(C)C(=O)CCOCCOCCNC(=O)CCn1c(CN(C)NC)cc2ccccc21)C(C)C]

In certain embodiments, the compound is of the following structure:
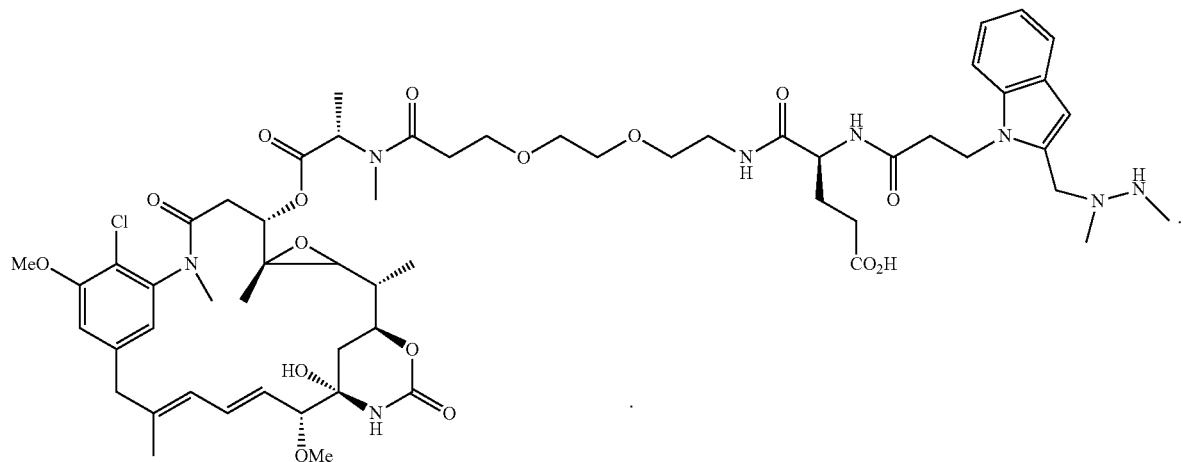
In certain embodiments, the compound is of the following structure:
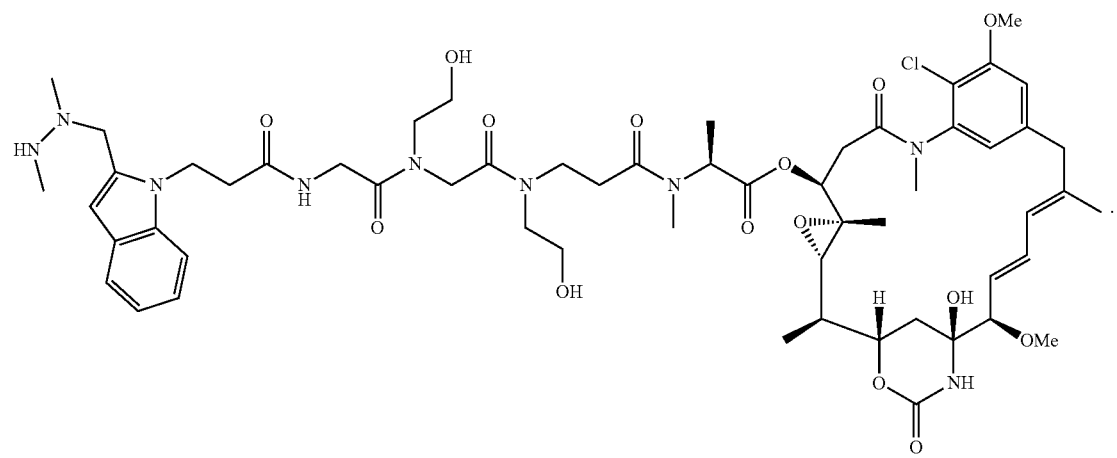
In certain embodiments, the compound is of the following structure:
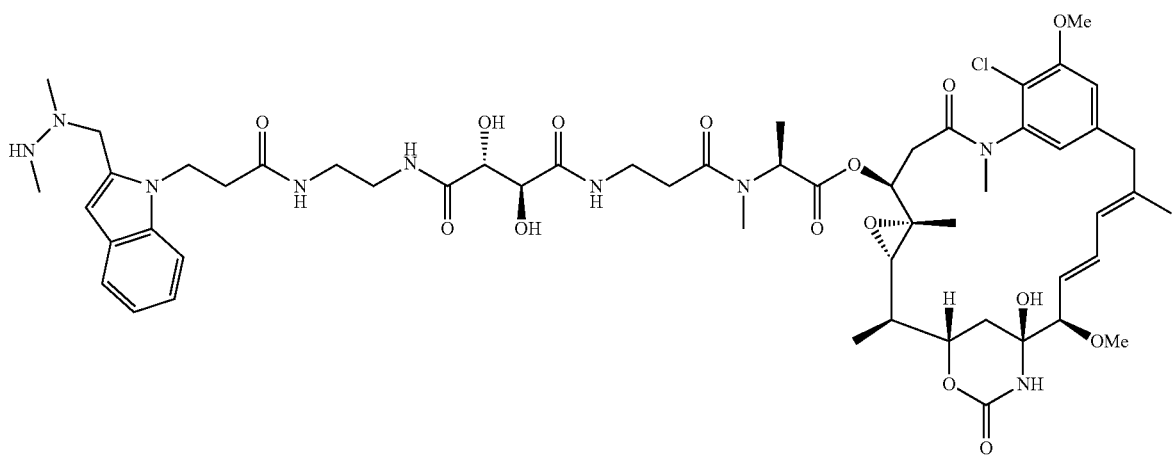

In certain embodiments, the compound is of the following structure:
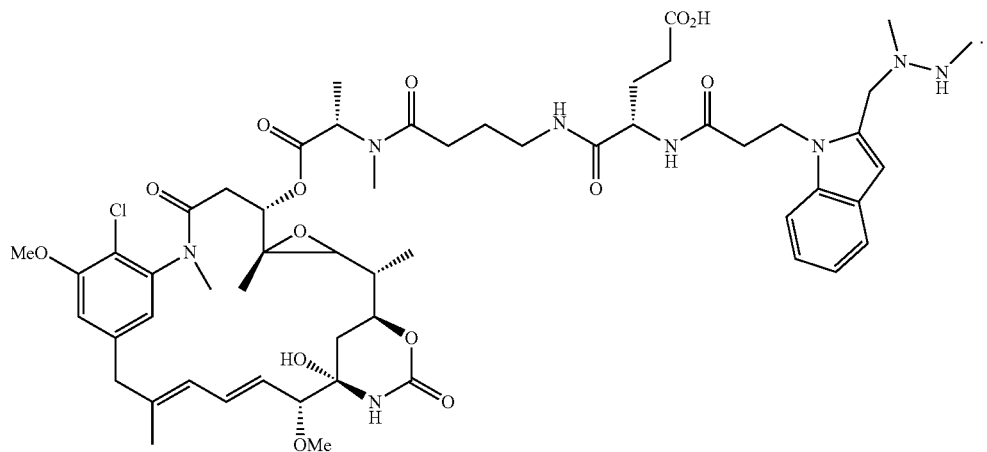
In certain embodiments, the compound is of the following structure:
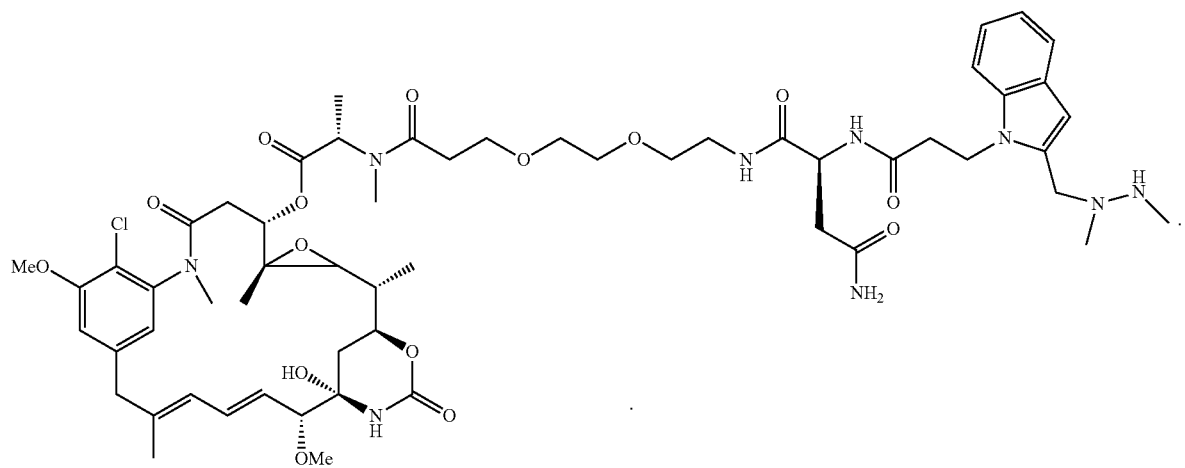
In certain embodiments, the compound is of the following structure:
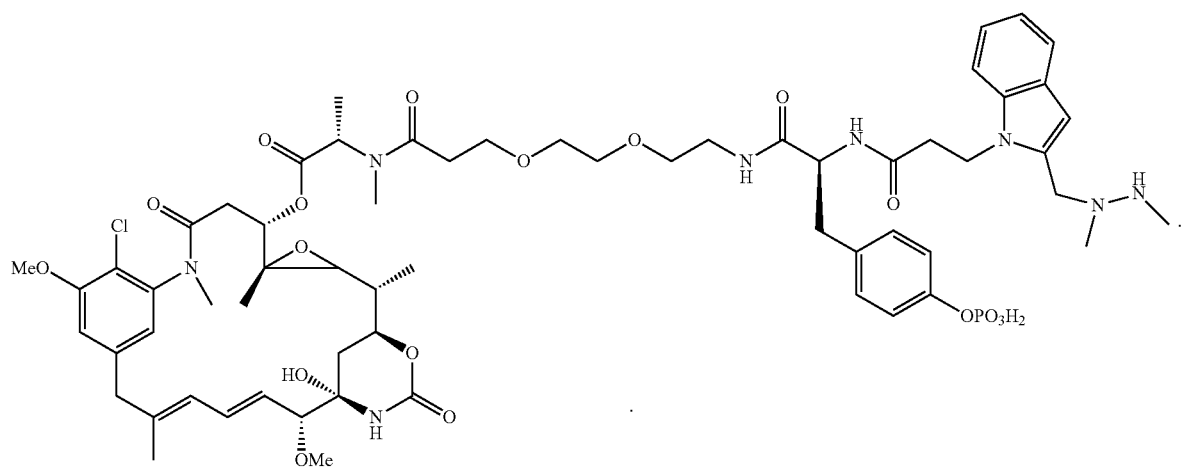

In certain embodiments, the compound is of the following structure:
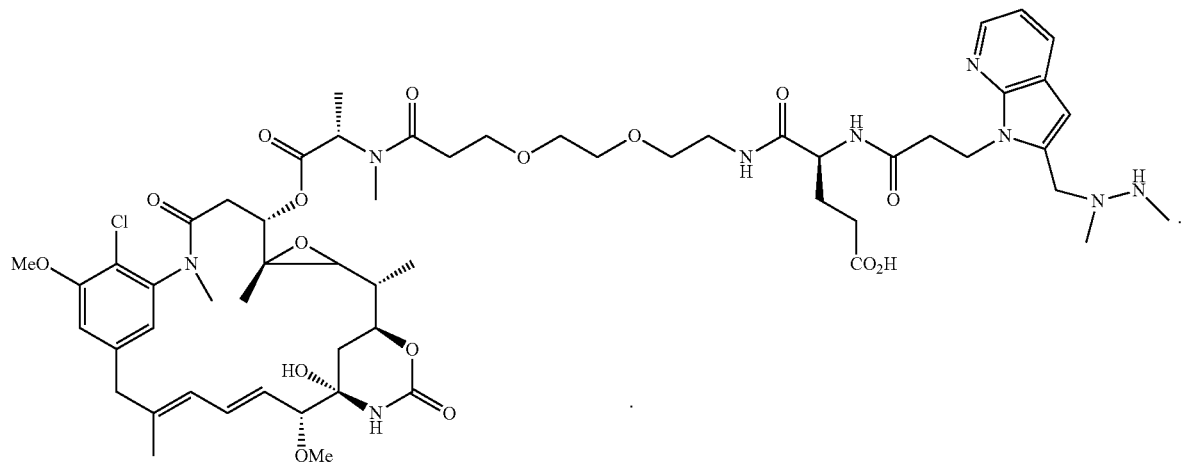
In certain embodiments, the compound is of the following structure:
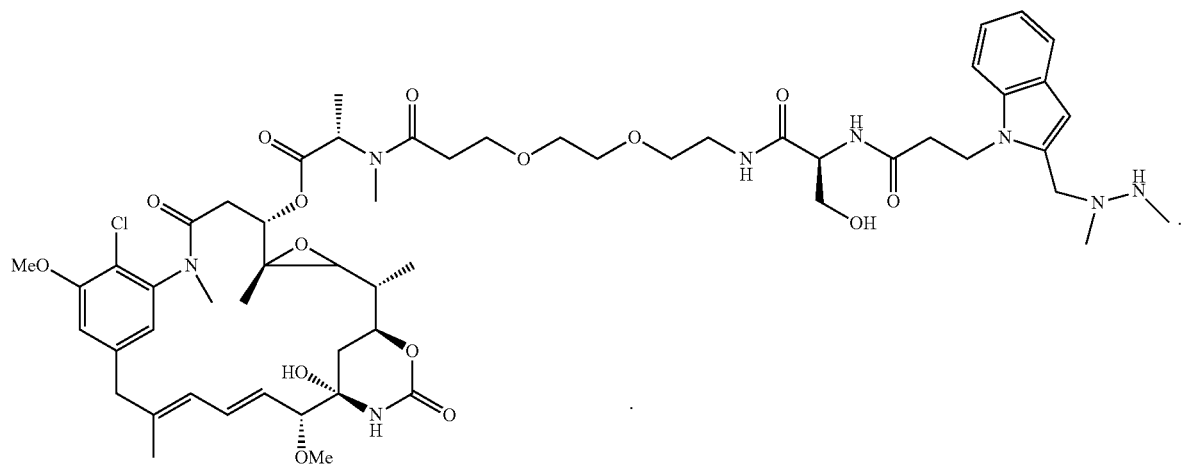
In certain embodiments, the compound is of the following structure:
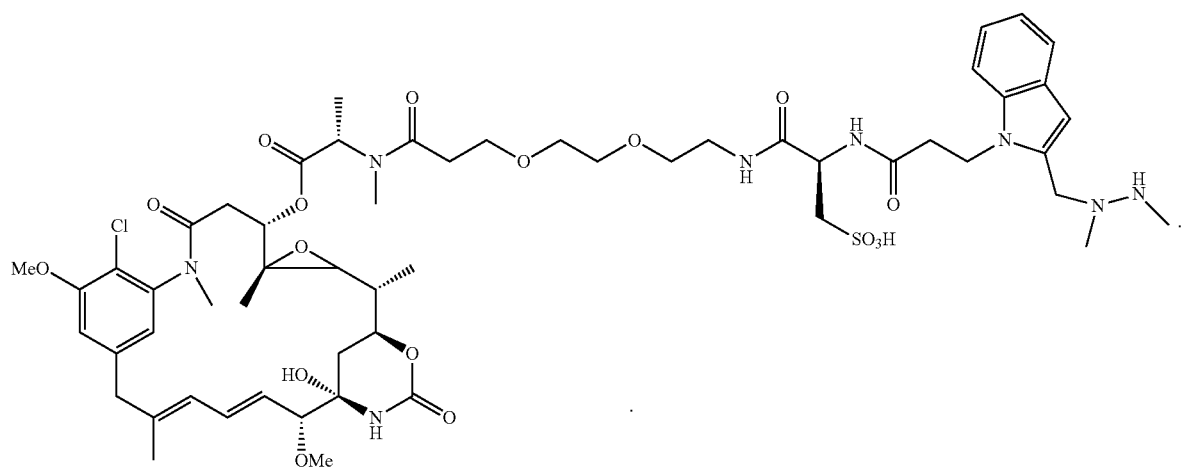

In certain embodiments, the compound is of the following structure:
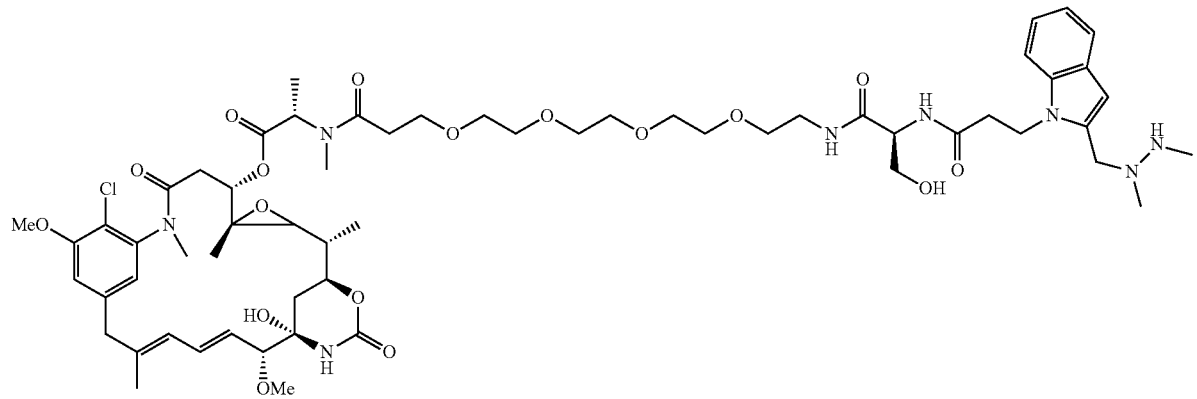
In certain embodiments, the compound is of the following structure:
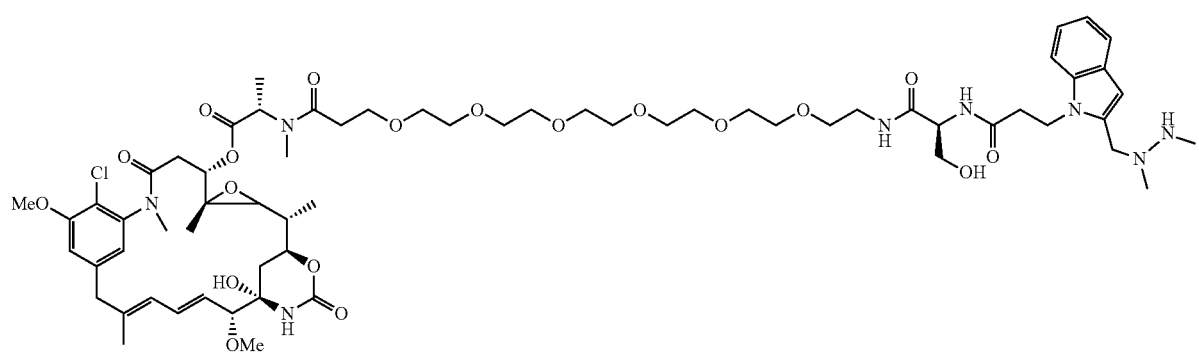
In certain embodiments, the compound is of the following structure:
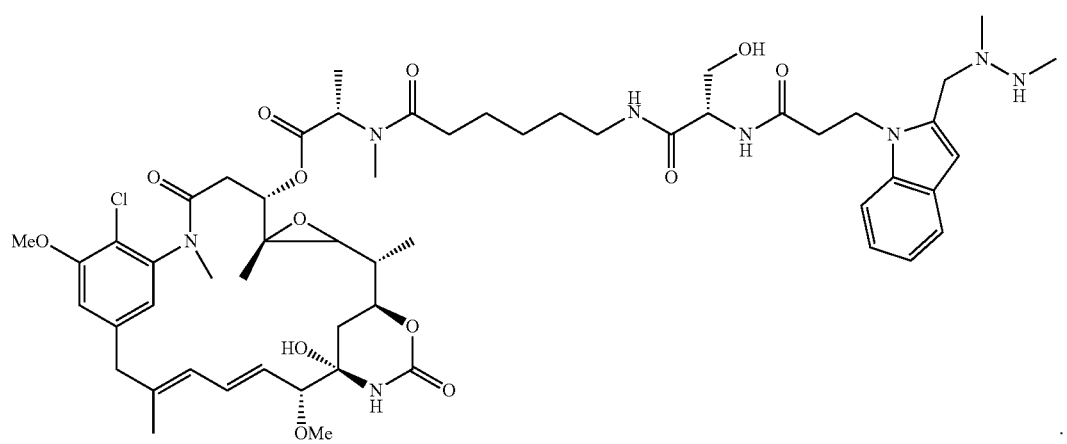

In certain embodiments, the compound is of the following structure:
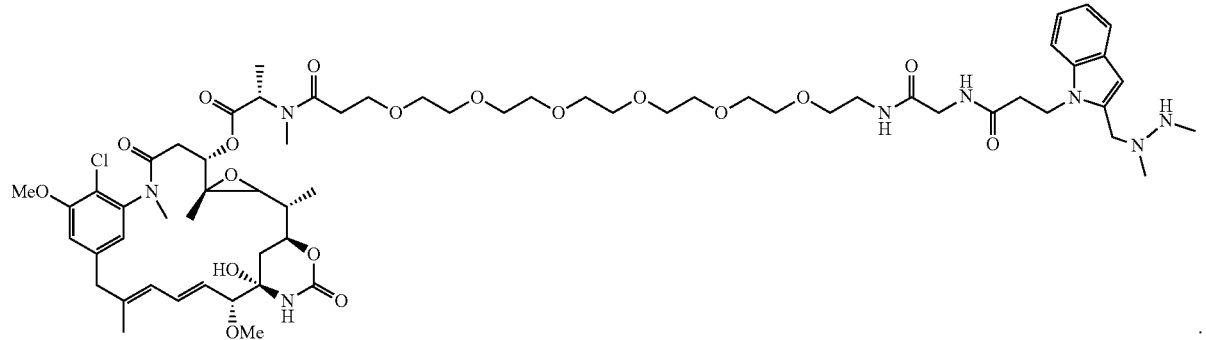
In certain embodiments, the compound is of the following structure:
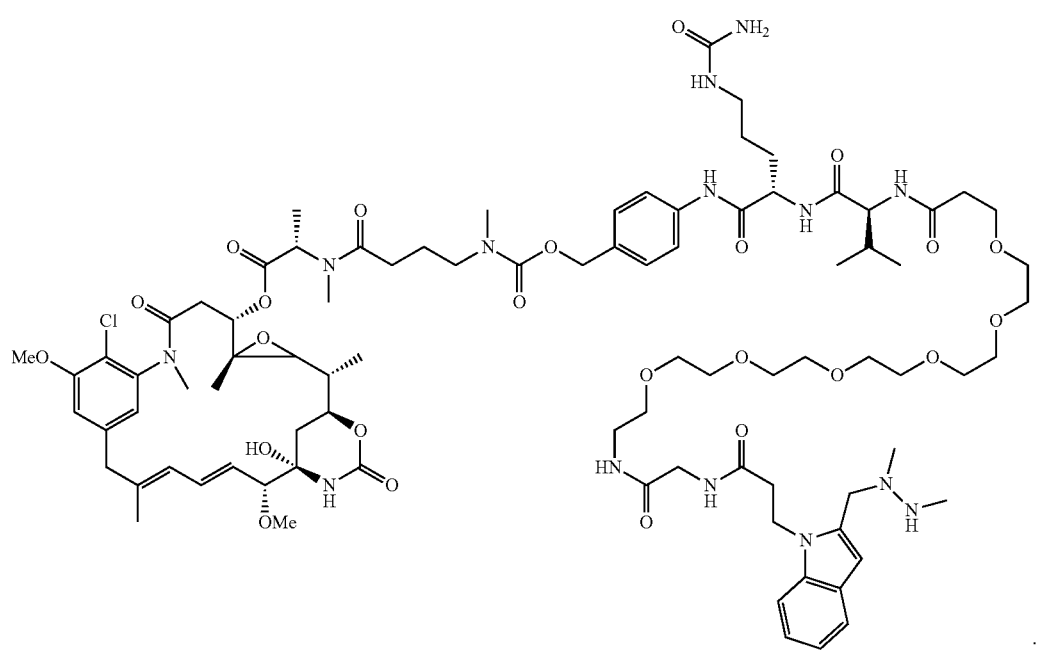

In certain embodiments, the compound is of the following structure:
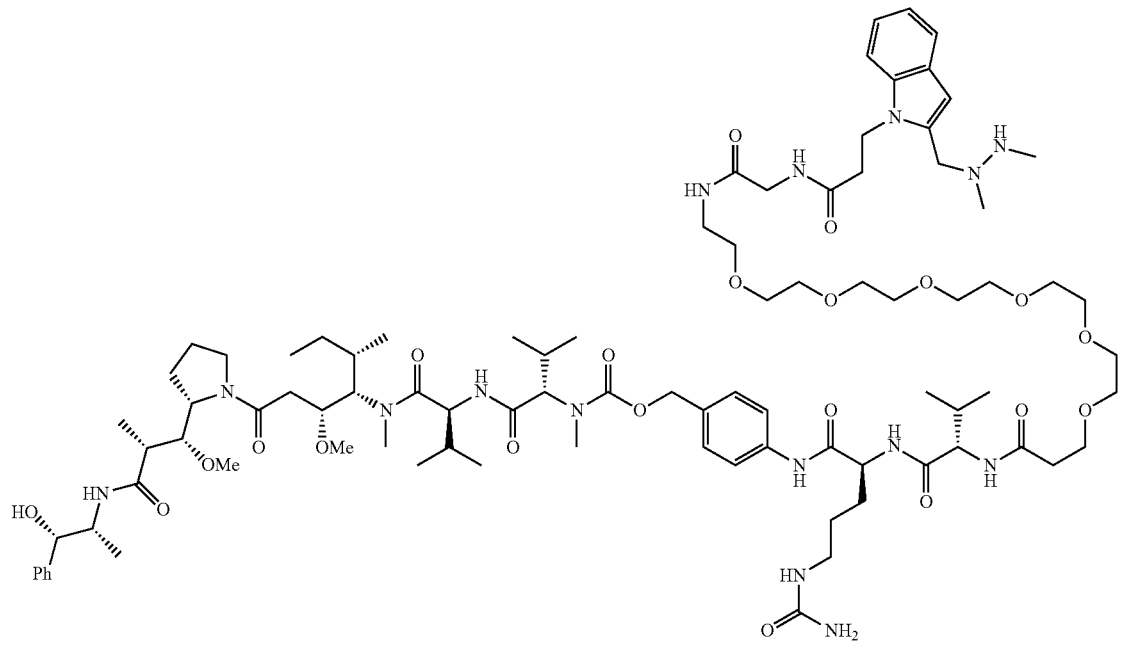 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCOCCOCCOCCOCCOCCOCCNC(=O)CNC(=O)CCn2c(CN(C)NC)cc3ccccc32)C(C)C)cc1)C(C)C]
In certain embodiments, the compound is of the following structure:
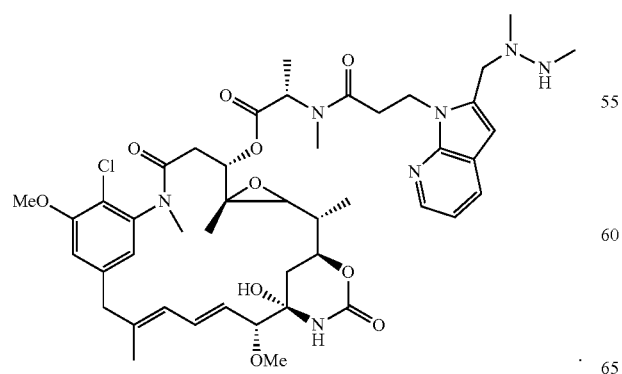

In certain embodiments, the compound is of the following structure:
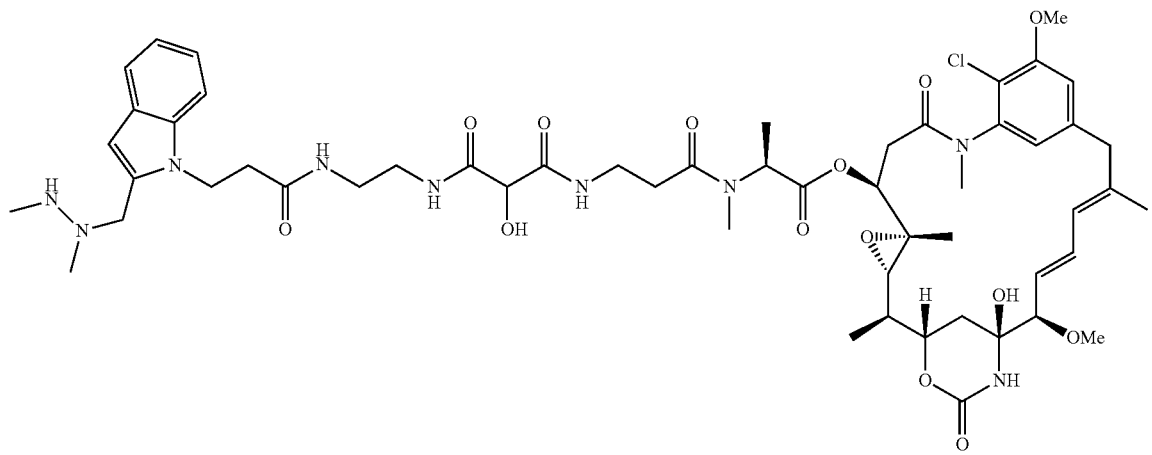
In certain embodiments, the compound is of the following structure:
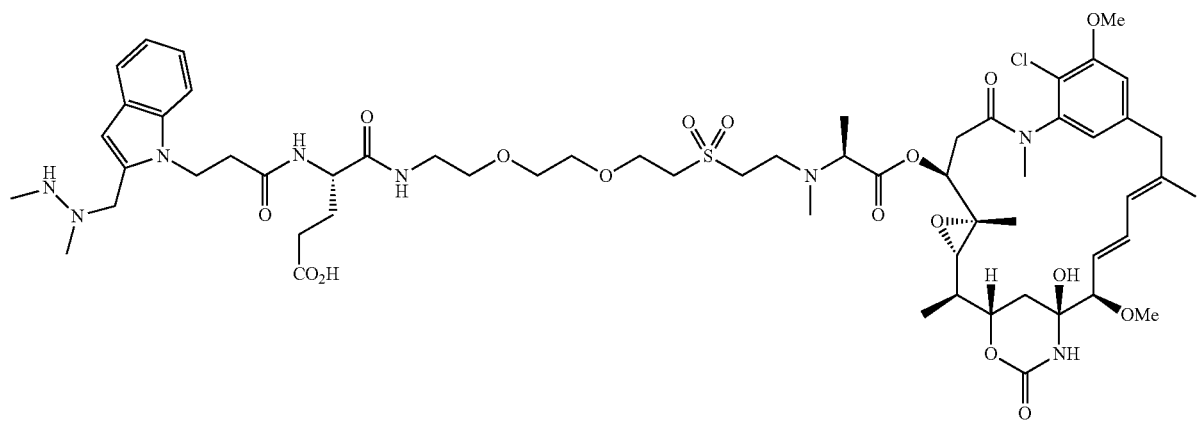
In certain embodiments, the compound is of the following structure:
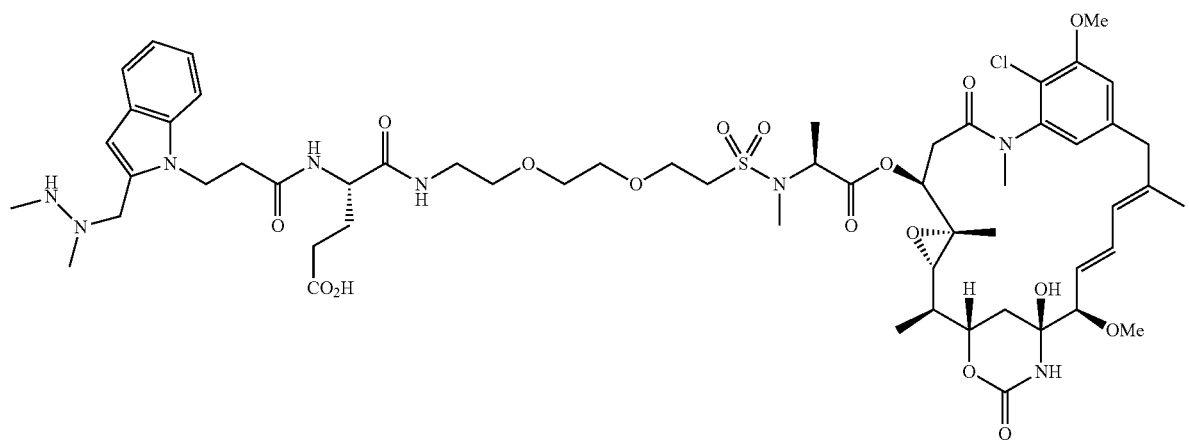

In certain embodiments, the compound is of the following structure:
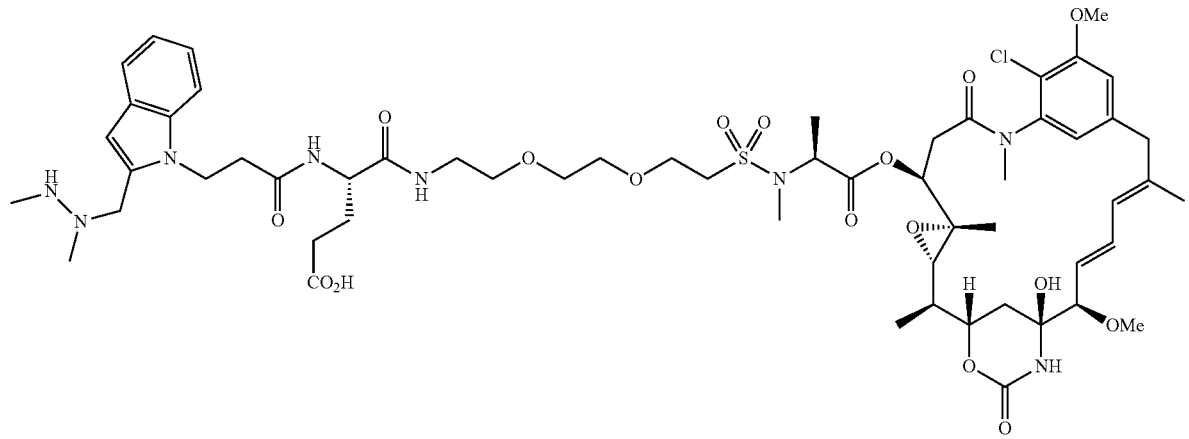
In certain embodiments, the compound is of the following structure:
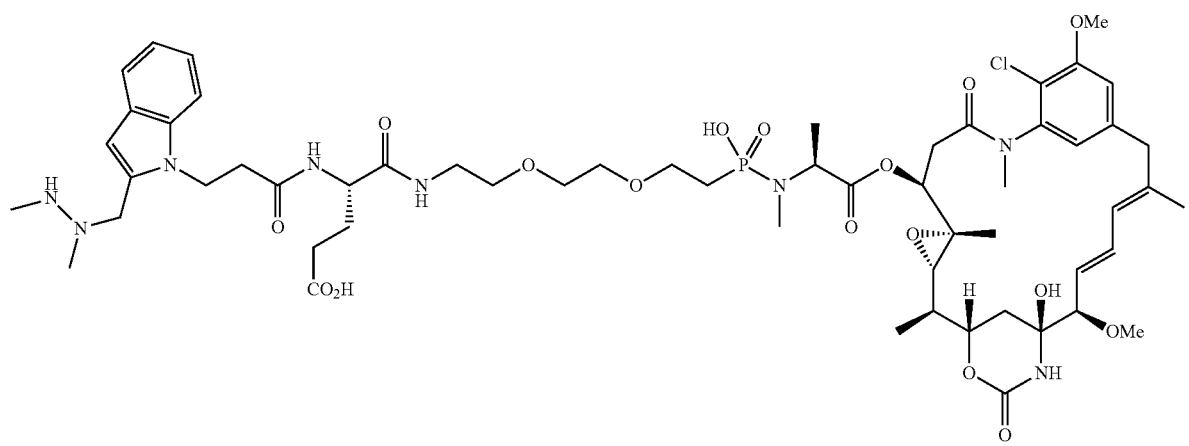
In certain embodiments, the compound is of the following structure:
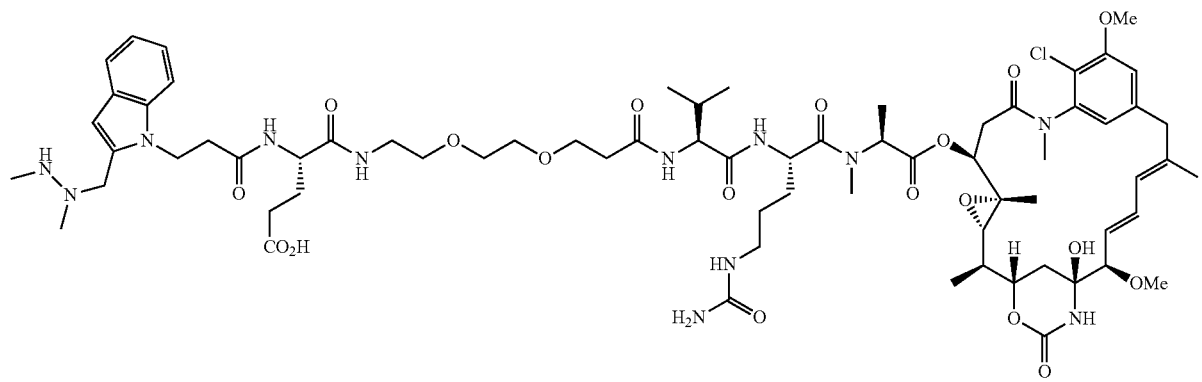

In certain embodiments, the compound is of the following structure:
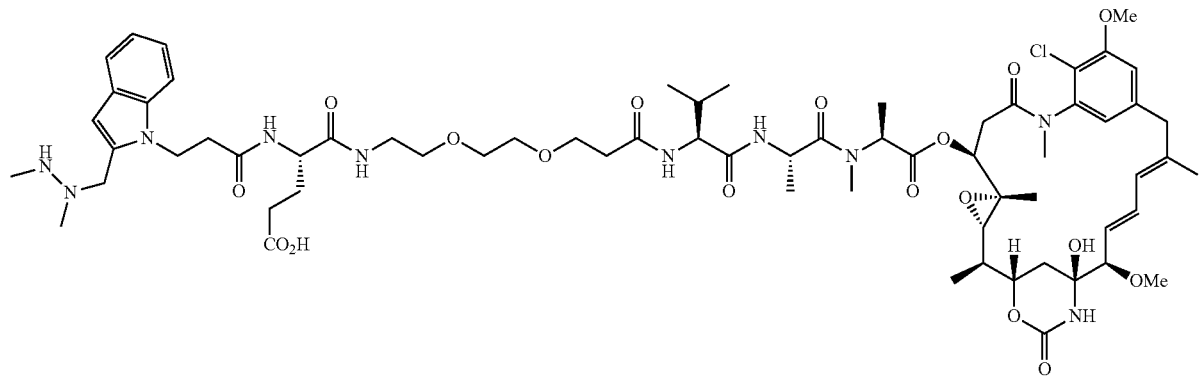
In certain embodiments, the compound is of the following structure:
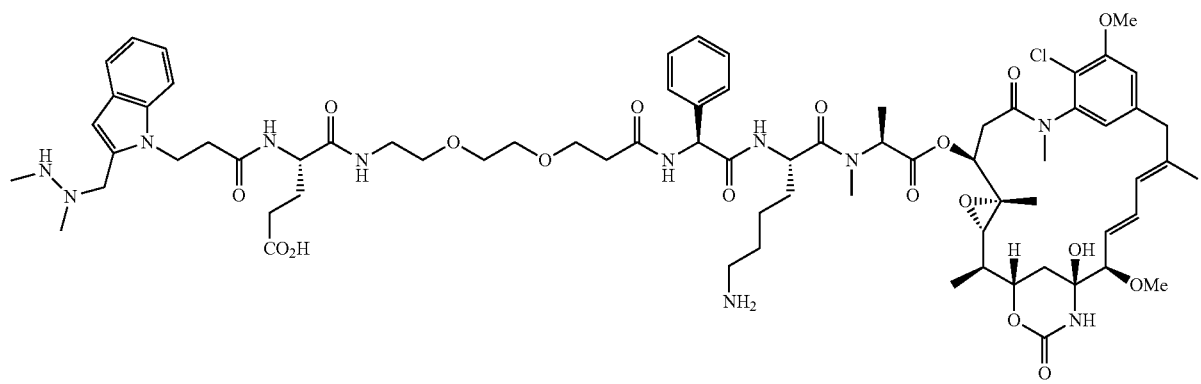
In certain embodiments, the compound is of the following structure:
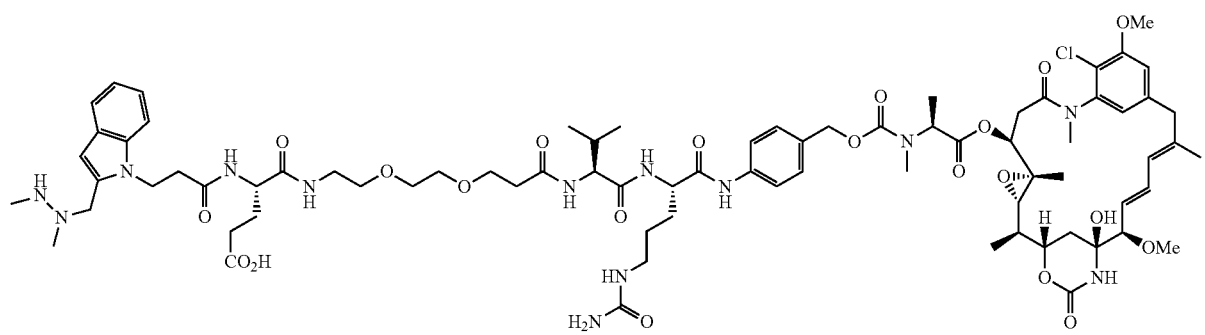

In certain embodiments, the compound is of the following structure:
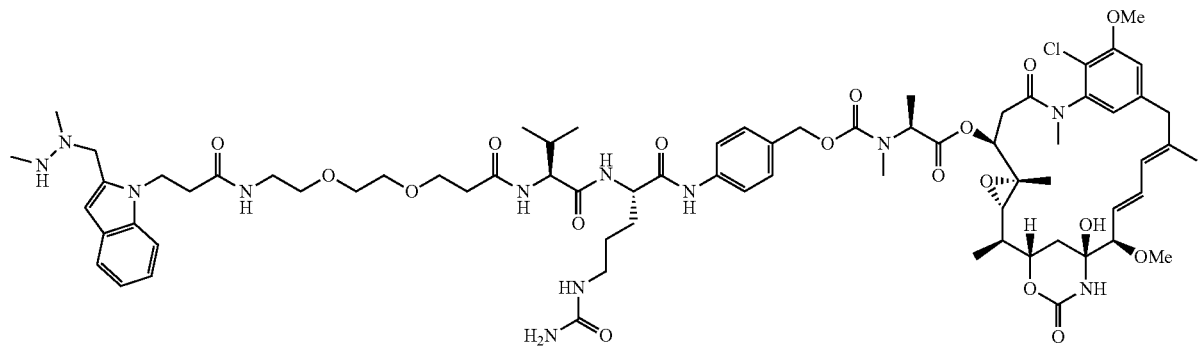
In certain embodiments, the compound is of the following structure:
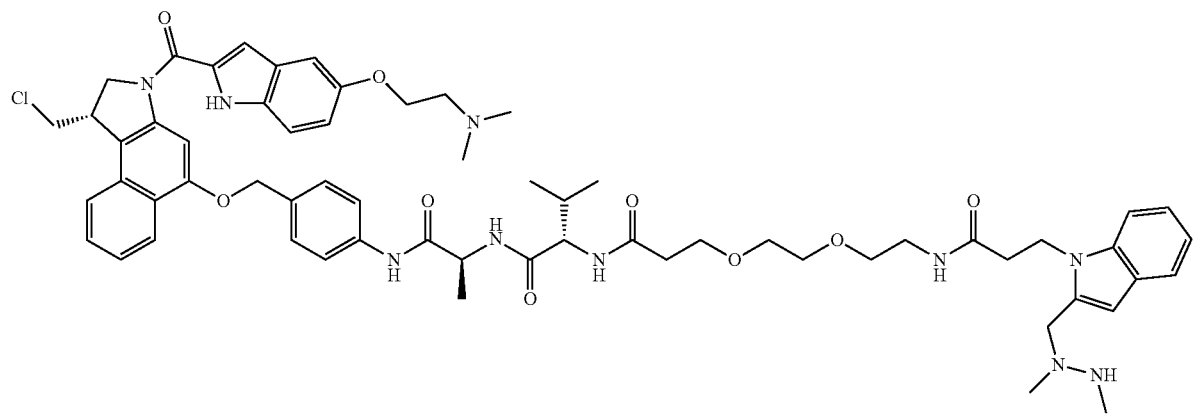 [SMILES: CNN(C)Cc1cc2ccccc2n1CCC(=O)NCCOCCOCCC(=O)N[C@H](C(=O)N[C@@H](C)C(=O)Nc1ccc(COc2cc3c(c4ccccc24)[C@H](CCl)CN3C(=O)c2cc3cc(OCCN(C)C)ccc3[nH]2)cc1)C(C)C]
In certain embodiments, the compound is of the following structure:
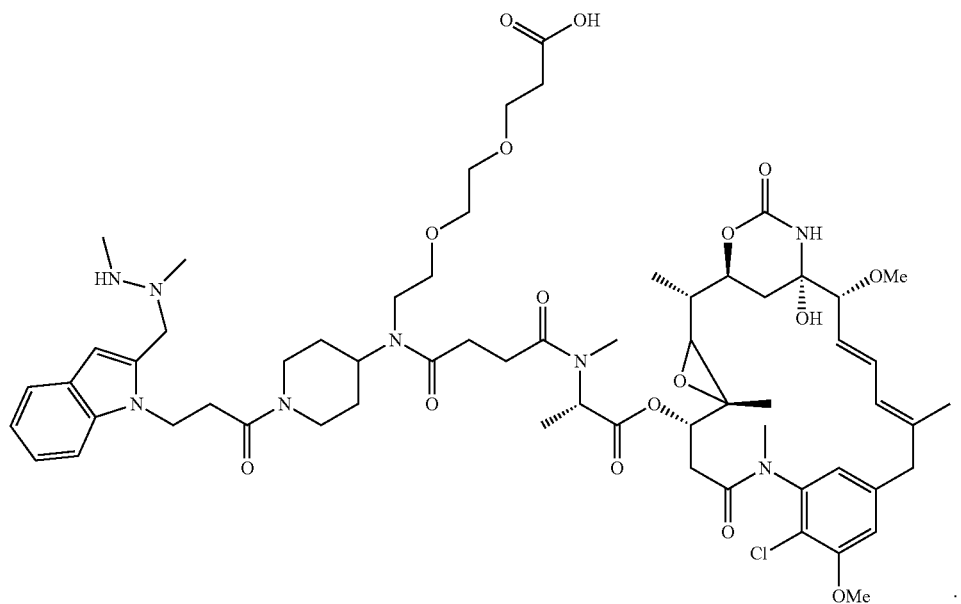 [SMILES: CNN(C)Cc1cc2ccccc2n1CCC(=O)N1CCC(N(CCOCCOCCC(=O)O)C(=O)CCC(=O)N(C)[C@@H](C)C(=O)O[C@H]2CC(=O)N(C)c3cc(cc(OC)c3Cl)C/C(C)=C/C=C/[C@@H](OC)[C@@]3(O)C[C@H](OC(=O)N3)[C@@H](C)C3O[C@]32C)CC1]

In certain embodiments, the compound is of the following structure:
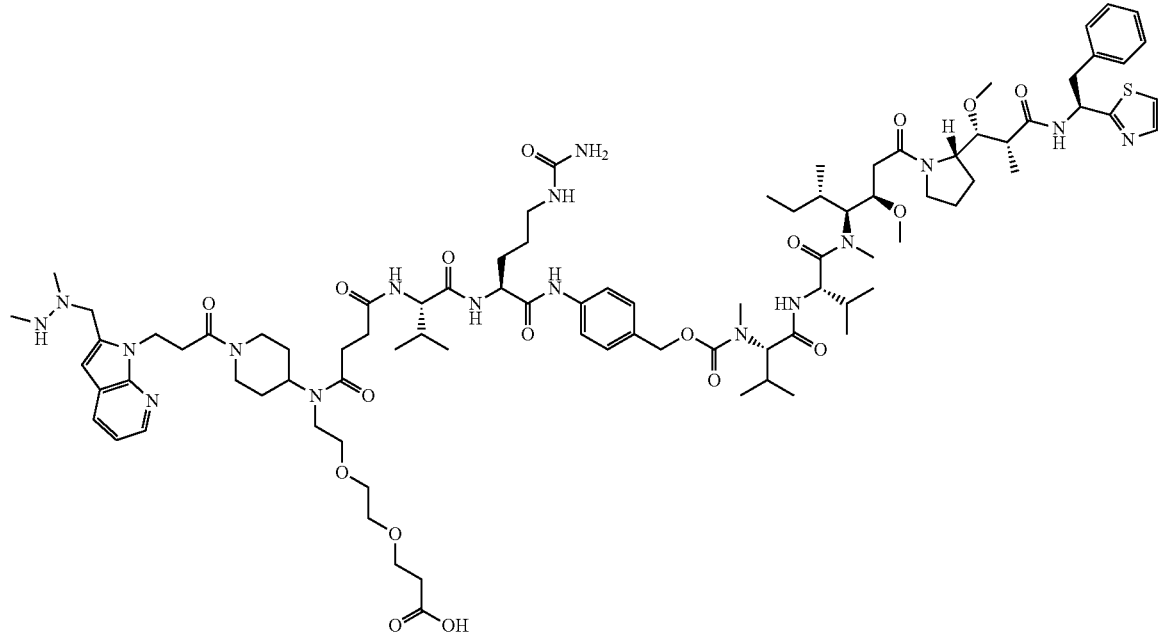 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCC(=O)N(CCOCCOCCC(=O)O)C2CCN(C(=O)CCn3c(CN(C)NC)cc4cccnc43)CC2)C(C)C)cc1)C(C)C]
In certain embodiments, the compound is of the following structure:
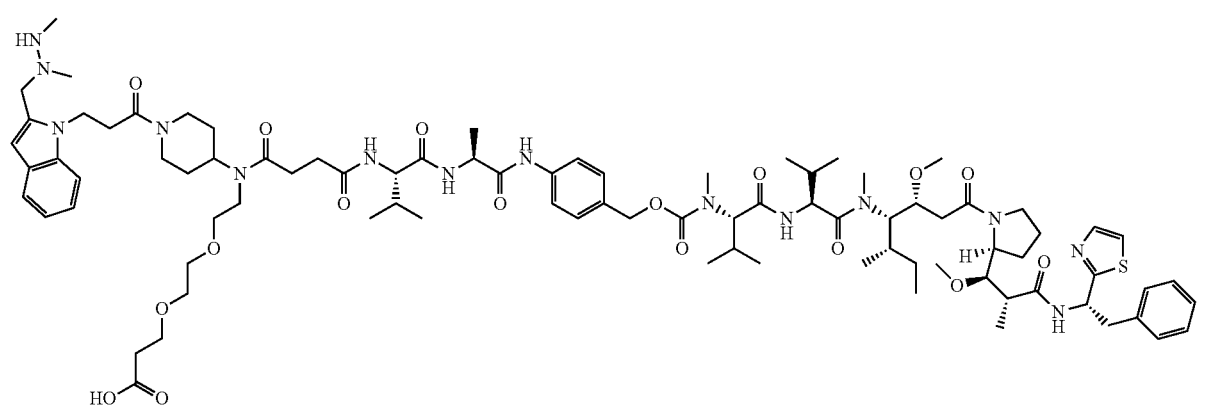 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)C(=O)OCc1ccc(NC(=O)[C@H](C)NC(=O)[C@@H](NC(=O)CCC(=O)N(CCOCCOCCC(=O)O)C2CCN(C(=O)CCn3c(CN(C)NC)cc4ccccc43)CC2)C(C)C)cc1)C(C)C]

In certain embodiments, the compound is of the following structure:
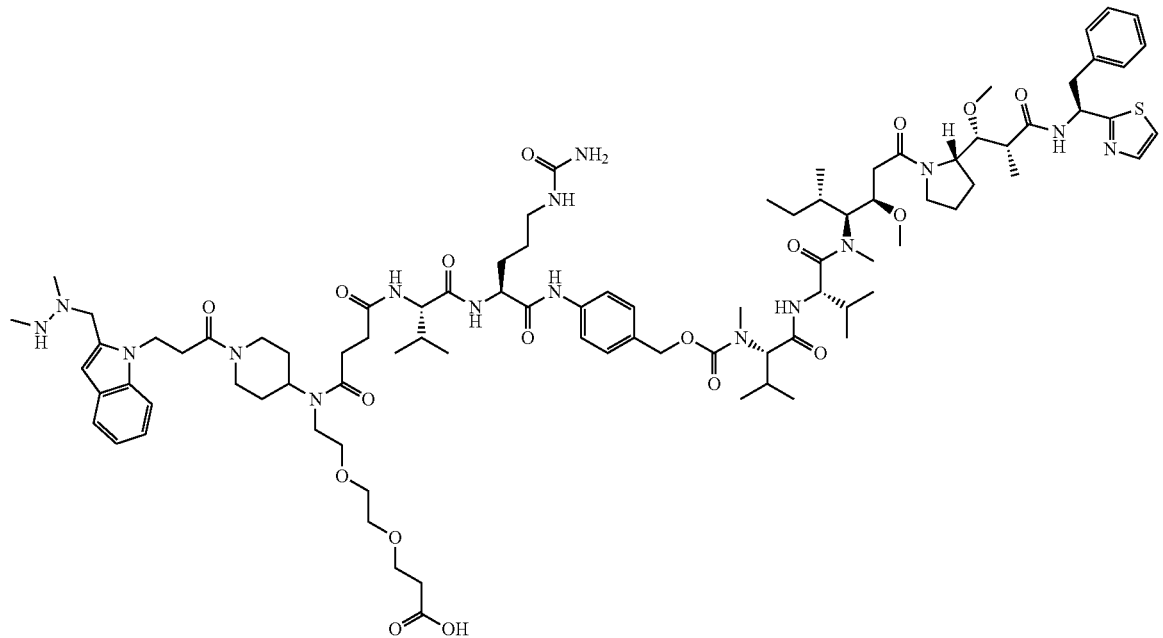 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCC(=O)N(CCOCCOCCC(=O)O)C2CCN(C(=O)CCn3c(CN(C)NC)cc4ccccc43)CC2)C(C)C)cc1)C(C)C]
In certain embodiments, the compound is of the following structure:
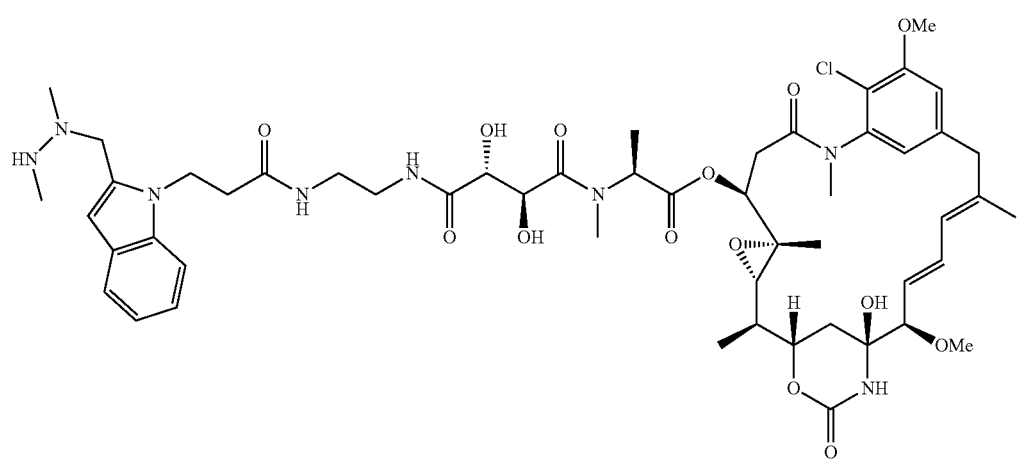

In certain embodiments, the compound is of the following structure:
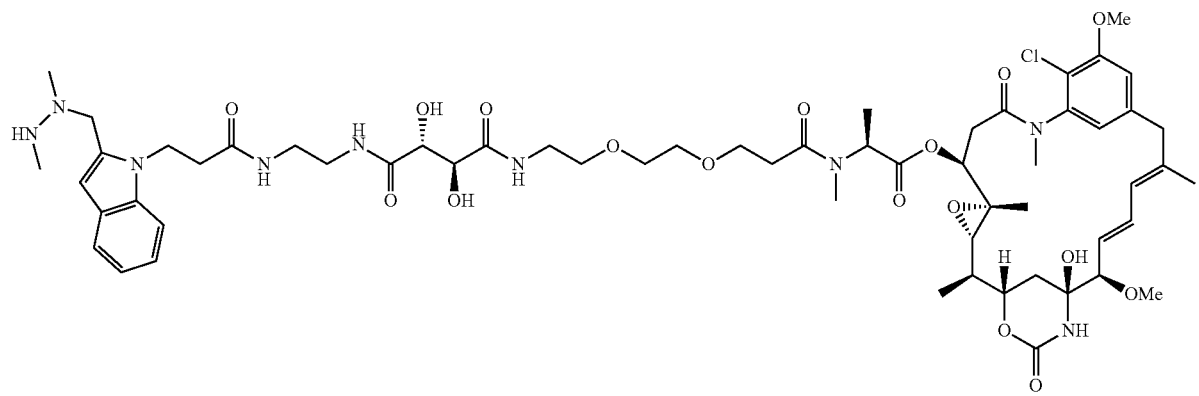
In certain embodiments, the compound is of the following structure:
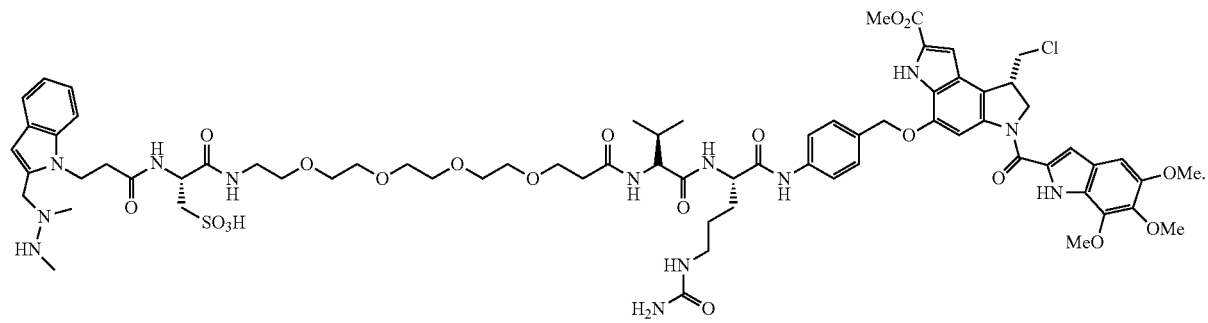
In certain embodiments, the compound is of the following structure:
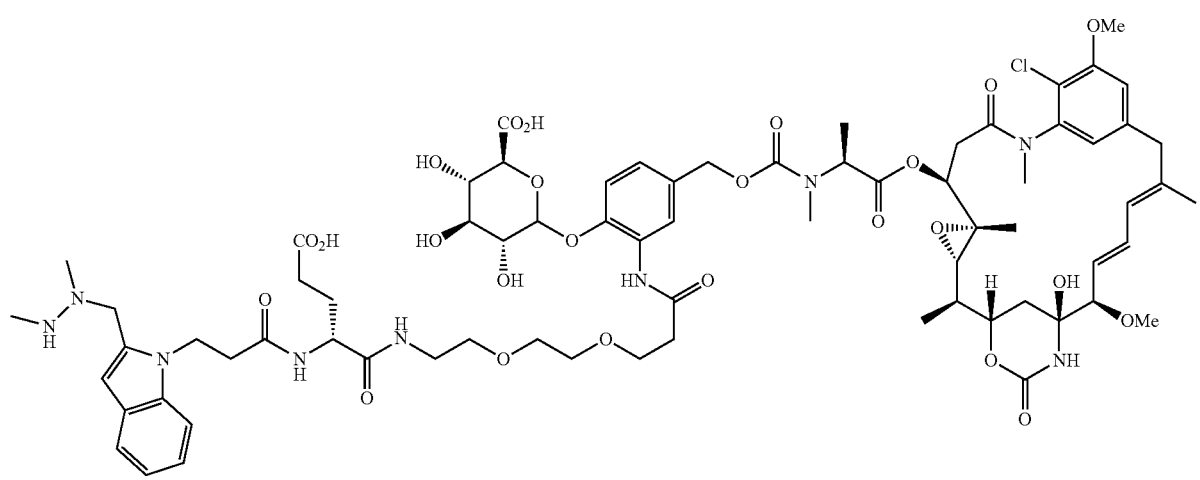

In certain embodiments, the compound is of the following structure:
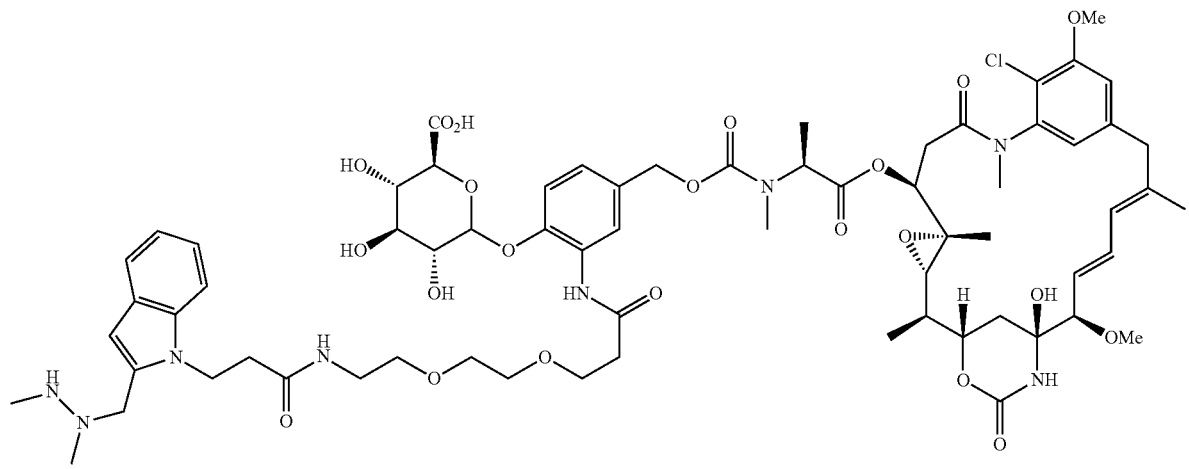
In certain embodiments, the compound is of the following structure:
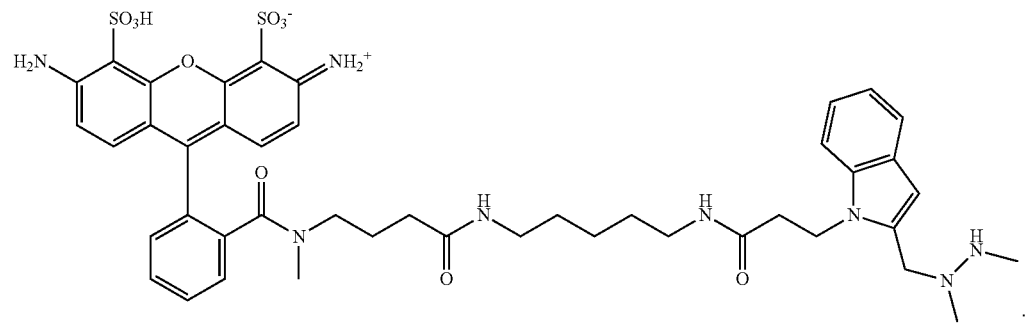
In certain embodiments, the compound is of the following structure:
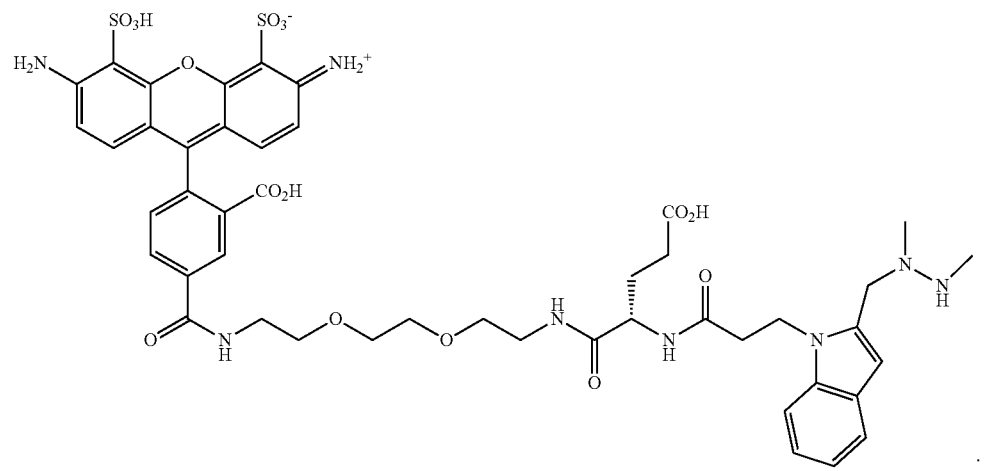

In certain embodiments, the compound is of the following structure:
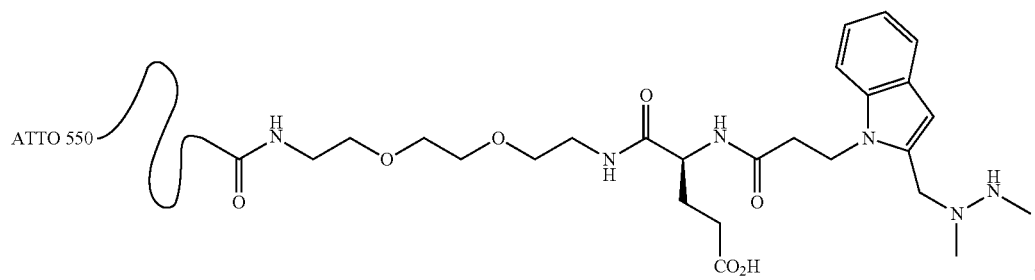 [SMILES: CNN(C)Cc1cc2ccccc2n1CCC(=O)N[C@@H](CCC(=O)O)C(=O)NCCOCCOCCNC(C)=O]
In certain embodiments, the compound is of the following structure:
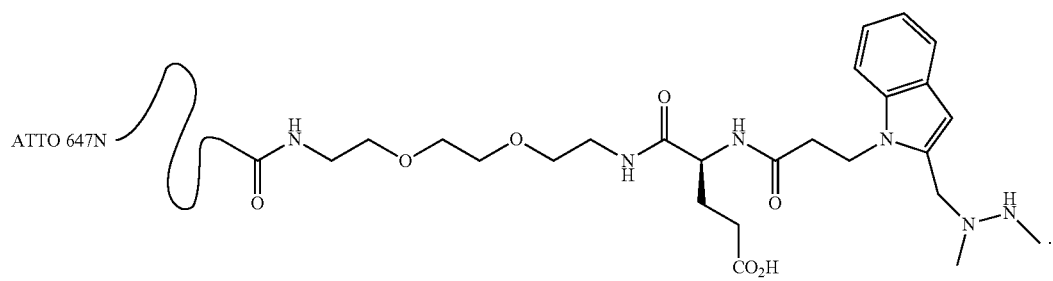 [SMILES: CNN(C)Cc1cc2ccccc2n1CCC(=O)N[C@@H](CCC(=O)O)C(=O)NCCOCCOCCNC(C)=O]
In certain embodiments, the compound is of the following structure:
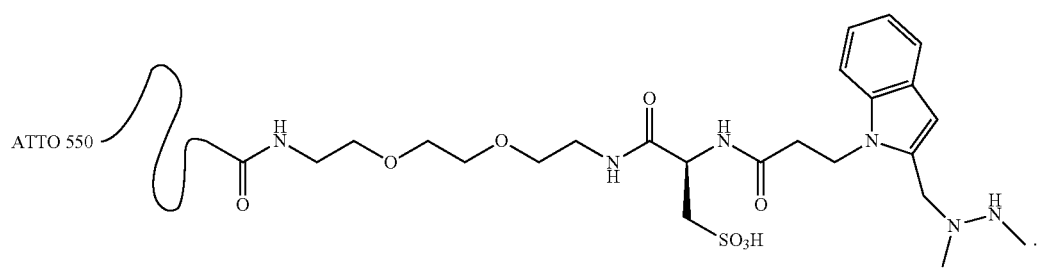 [SMILES: CNN(C)Cc1cc2ccccc2n1CCC(=O)N[C@@H](CS(=O)(=O)O)C(=O)NCCOCCOCCNC(C)=O]
In certain embodiments, the compound is of the following structure:
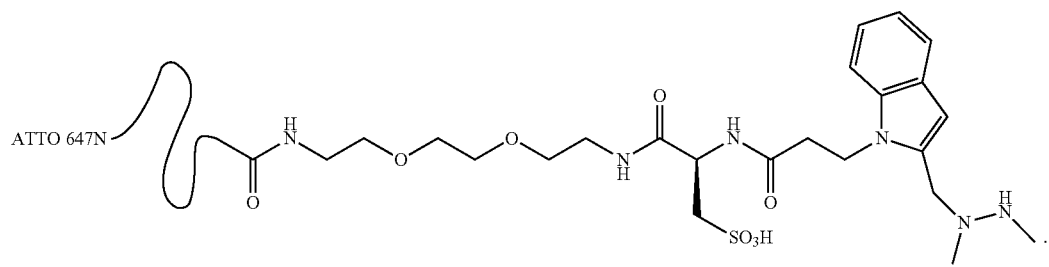 [SMILES: CNN(C)Cc1cc2ccccc2n1CCC(=O)N[C@@H](CS(=O)(=O)O)C(=O)NCCOCCOCCNC(C)=O]

In certain embodiments, the compound is of the following structure:

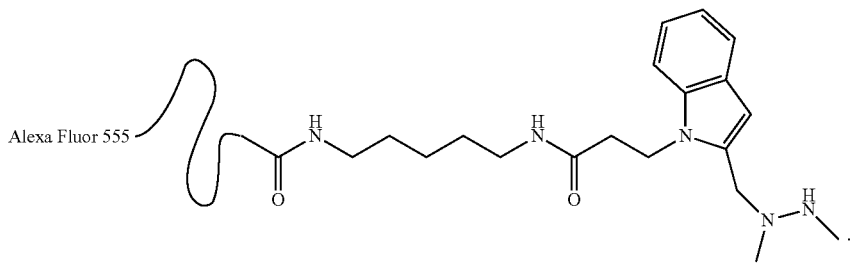

In certain embodiments, the compound is of the following structure:

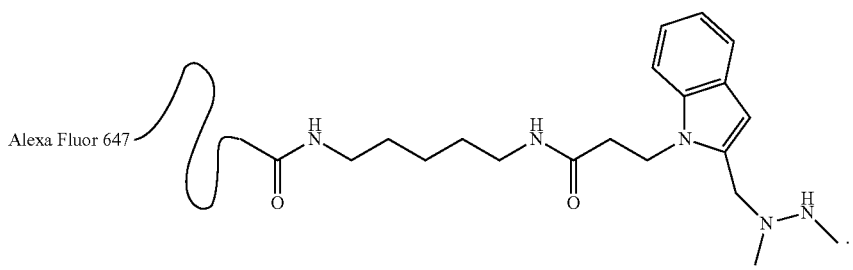 [SMILES: CNN(C)Cc1cc2ccccc2n1CCC(=O)NCCCCCNC(C)=O]

Any of the chemical entities, linkers and coupling moieties set forth in the structures above may be adapted for use in the subject compounds and conjugates.

Additional disclosure related to hydrazinyl-indole compounds and methods for producing a conjugate is found in U.S. application Ser. No. 13/794,159, filed Mar. 11, 2013, the disclosure of which is incorporated herein by reference.

Target Polypeptides

Any of a wide variety of polypeptides can be modified to be conjugated to a second moiety as described above. Polypeptides suitable for modification include both proteins having a naturally-occurring amino acid sequence, fragments of naturally-occurring polypeptides, and non-naturally occurring polypeptides and fragments thereof.

The following are examples of classes and types of polypeptides which are of interest for modification using the compounds and methods described herein to produce the polypeptide conjugates described herein.

Therapeutic Polypeptides

In certain embodiments, the methods of producing a conjugate are applied to modification of polypeptides that may provide for a therapeutic benefit, such as those polypeptides for which attachment to a moiety can provide for one or more of, for example, an increase in serum half-life, a decrease in an adverse immune response, additional or alternate biological activity or functionality, and the like, or other benefit or reduction of an adverse side effect. Where the therapeutic polypeptide is an antigen for a vaccine, modification can provide for an enhanced immunogenicity of the polypeptide.

Examples of classes of therapeutic proteins include those that are cytokines, chemokines, growth factors, hormones, antibodies, and antigens. Further examples include, but are not limited to, the following: erythropoietin (EPO, e.g., native EPO or synthetic EPO (see, e.g., US 2003/0191291), such as, but not limited to, e.g., PROCRIT®, EPREX®, or EPOGEN® (epoetin-α), ARANESP® (darbepoietin-α), NEORECORMON®, EPOGIN® (epoetin-β), and the like); a growth hormone (e.g., a somatotropin, e.g., GENOTROPIN®, NUTROPIN®, NORDITROPIN®, SAIZEN®, SEROSTIM®, HUMATROPE®, etc.); human growth hormone (hGH); bovine growth hormone (bGH); follicle stimulating hormone (FSH); interferon (e.g., IFN-γ, IFN-α, IFN-β, IFN-ω; IFN-τ, consensus interferon, and the like); insulin (e.g., Novolin, Humulin, Humalog, Lantus, Ultralente, etc.), insulin-like growth factor (e.g., IGF-I, IGF-II); blood factors (e.g., Factor X, tissue plasminogen activator (TPA), and the like, such as, but not limited to, e.g., ACTIVASE® (alteplase) tissue plasminogen activator, NOVOSEVEN® (recombinant human factor VIIa), Factor VIIa, Factor VIII (e.g., KOGENATE®), Factor IX, β-globin, hemoglobin, and the like); colony stimulating factors (e.g., granulocyte-CSF (G-CSF, e.g., NEUPOGEN® (filgrastim)), macrophage-CSF (M-CSF), granulocyte-macrophage-CSF (GM-CSF), Neulasta (pegfilgrastim), granulocyte-monocyte colony stimulating factor, megakaryocyte colony stimulating factor, and the like), transforming growth factors (e.g., TGF-beta, TGF-alpha); interleukins (e.g., IL-1, IL-2 (e.g., Proleukin®), IL-3, IL-4, IL-5, IL-6, IL-7, IL-8, IL-9, IL-12, and the like); a growth factor (e.g., epidermal growth factor (EGF), platelet-derived growth factor (PDGF, e.g., REGRANEX® (beclapermin)), fibroblast growth factors (FGFs, e.g., aFGF, bFGF, such as FIBLAST® (trafermin)), glial cell line-derived growth factor (GDNF), nerve growth factor (NGF), stem cell factor (e.g., STEMGEN® (ancestim)), keratinocyte growth factor, a hepatocyte growth factor, and the like); a soluble receptor (e.g., a TNF-α-binding soluble receptor such as ENBREL® (etanercept), a soluble VEGF receptor, a soluble interleukin receptor, a soluble γ/δ T cell receptor, and the like); an enzyme (e.g., α-glucosidase, CERAZYME® (imiglucarase, β-glucocerebrosidase, CEREDASE® (alglucerase); an enzyme activator (e.g., tissue plasminogen activator); a chemokine (e.g., IP-10, Mig, Groα/IL-8, regulated and normal T cell expressed and secreted (RANTES), MIP-1α, MIP-1β, MCP-1, PF-4, and the like); an angiogenic agent (e.g., vascular endothelial growth factor (VEGF); an anti-angiogenic agent (e.g., a soluble VEGF receptor); a protein vaccine; a neuroactive peptide such as bradykinin, cholecystokinin, gastin, secretin, oxytocin, gonadotropin-releasing hormone, beta-endorphin, enkephalin, substance P, somatostatin, galanin, growth hormone-releasing hormone, bombesin, warfarin, dynorphin, neurotensin, motilin, thyrotropin, neuropeptide Y, luteinizing hormone, calcitonin, insulin, glucagon, vasopressin, angiotensin II, thyrotropin-releasing hormone, vasoactive intestinal peptide, a sleep peptide, etc.; other proteins such as a thrombolytic agent, an atrial natriuretic peptide, bone morphogenic protein, thrombopoietin, relaxin, glial fibrillary acidic protein, follicle stimulating hormone, a human alpha-1 antitrypsin, a leukemia inhibitory factor, a transforming growth factor, a tissue factor, an insulin-like growth factor, a luteinizing hormone, a follicle stimulating hormone, a macrophage activating factor, tumor necrosis factor, a neutrophil chemotactic factor, a nerve growth factor, a tissue inhibitor of metalloproteinases; a vasoactive intestinal peptide, angiogenin, angiotropin, fibrin; hirudin; a leukemia inhibitory factor; an IL-1 receptor antagonist (e.g., Kineret® (anakinra)); and the like. It will be readily appreciated that native forms of the above therapeutic proteins are also of interest as target polypeptides in the present disclosure.

Further examples include antibodies, e.g., polyclonal antibodies, monoclonal antibodies, humanized antibodies, antigen-binding fragments (e.g., F(ab)', Fab, Fv), single chain antibodies, and the like (e.g., RITUXAN® (rituximab); REMICADE® (infliximab); HERCEPTIN® (trastuzumab); HUMIRA™ (adalimumab); XOLAIR® (omalizumab); BEXXAR® (tositumomab); RAPTIVA™ (efalizumab); ERBITUX™ (cetuximab); and the like). In some instances, antibodies include antibodies that specifically bind to a tumor antigen, an immune cell antigen (e.g., CD4, CD8, and the like), an antigen of a microorganism, particularly a pathogenic microorganism (e.g., a bacterial, viral, fungal, or parasitic antigen), and the like.

In some instances, the methods, conjugates and compounds described herein can be applied to provide for a moiety (e.g., a water-soluble polymer) at a native or engineered site of glycosylation, such as found in hyperglycosylated forms of a therapeutic protein.

The biological activity of a modified target polypeptide can be assayed according to methods known in the art. Modified polypeptides that retain at least one desired pharmacologic activity of the corresponding parent protein are of interest.

Immunogenic Compositions

The methods, conjugates and compounds disclosed herein also find application in production of components of immunogenic compositions (e.g., therapeutic vaccines). For example, the compounds can be used to facilitate attachment of moieties that increase serum half-life of a polypeptide antigen, that increase immunogenicity of the polypeptide, or that link a non-amino acid antigen to a polypeptide carrier. In this regard, the compounds can be used to facilitate modification of microbial antigens (e.g., a bacterial, viral, fungal, or parasitic antigen), tumor antigens, and other antigens which are of interest for administration to a subject to elicit an immune response in the subject. Also of interest is modification of antigens that are useful in eliciting antibodies which can be useful as research tools.

Further examples of polypeptides of interest for modification using the compounds disclosed herein include those that are of interest for detection or functional monitoring in an assay (e.g., as a research tool, in a drug screening assay, and the like). Examples of polypeptides of this type include receptors (e.g., G-protein coupled receptors (GPCRs, including orphan GPCRs)), receptor ligands (including naturally-occurring and synthetic), protein channels (e.g., ion channels (e.g., potassium channels, calcium channels, sodium channels, and the like), and other polypeptides. In some embodiments, modification of cell surface-associated polypeptides, such as transmembrane polypeptides) is of interest, for example where such modification is accomplished while the polypeptide is present in a membrane. Methods for modification of a polypeptide under physiological conditions are described further below.

Methods of Polypeptide Production

In general, the polypeptides described herein may be expressed in prokaryotes or eukaryotes in accordance with conventional ways, depending upon the purpose for expression. Thus, the present invention further provides a host cell, e.g., a genetically modified host cell that comprises a nucleic acid encoding a polypeptide.

Host cells for production (including large scale production) of an unconjugated or modified polypeptide suitable to form a conjugate as described herein can be selected from any of a variety of available host cells. Examples of host cells include those of a prokaryotic or eukaryotic unicellular organism, such as bacteria (e.g., *Escherichia coli* strains, *Bacillus* spp. (e.g., *B. subtilis*), and the like) yeast or fungi (e.g., *S. cerevisiae, Pichia* spp., and the like), and other such host cells can be used. Examples of host cells originally derived from a higher organism such as insects, vertebrates, including mammals, (e.g., CHO, HEK, and the like), may be used as the expression host cells.

Suitable mammalian cell lines include, but are not limited to, HeLa cells (e.g., American Type Culture Collection (ATCC) No. CCL-2), CHO cells (e.g., ATCC Nos. CRL9618 and CRL9096), CHO DG44 cells (Urlaub (1983) *Cell* 33:405), CHO-K1 cells (ATCC CCL-61), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

Specific expression systems of interest include bacterial, yeast, insect cell and mammalian cell derived expression systems.

The expressed polypeptide can be recovered by any appropriate means known in the art. Further, any convenient protein purification procedures may be employed, where suitable protein purification methodologies are described in Guide to Protein Purification, (Deuthser ed.) (Academic Press, 1990). For example, a lysate may prepared from a cell comprising the expression vector expressing the desired polypeptide, and purified using high performance liquid chromatography (HPLC), exclusion chromatography, gel electrophoresis, affinity chromatography, and the like.

Methods for Modification of a Polypeptide

In certain embodiments, the polypeptide may be conjugated to a moiety of interest without first modifying the polypeptide. For instance, the polypeptide may include one or more reactive groups suitable for conjugation to the moiety of interest (e.g., a moiety comprising a coupling moiety, such as a pyrazolinone or pyrazolinone derivative as described herein). In other embodiments, the polypeptide may be modified before conjugation to the moiety of interest. Modification of the polypeptide may produce a modified polypeptide that contains one or more reactive groups suitable for conjugation to the moiety of interest.

In some cases, the polypeptide may be modified at one or more amino acid residues to provide one or more reactive groups suitable for conjugation to the moiety of interest (e.g., a moiety comprising a coupling moiety, such as a pyrazalinone or pyrazalinone derivative as described herein). For example, carbonyls introduced into a polypeptide can be selectively reacted with α-nucleophiles, such as aminooxy- and hydrazide-bearing compounds. Chemistries selective for carbonyl functional groups on a protein with enhanced kinetics, site selectivity and conjugate stability may result in improved bioconjugates and provide access to new products and therapeutic targets as disclosed herein.

In certain embodiments, the polypeptide may be modified to include a reactive aldehyde group (e.g., a reactive aldehyde). A reactive aldehyde may be included in an "aldehyde tag" or "ald-tag", which is meant to refer to an amino acid sequence derived from a sulfatase motif that has been converted by action of a formylglycine generating enzyme (FGE) to contain a 2-formylglycine residue (referred to herein as "fGly"). The fGly residue generated by an FGE is also referred to in the literature as a "formylglycine". Stated differently, the term "aldehyde tag" is used herein to refer to an amino acid sequence comprising a "converted" sulfatase motif (i.e., a sulfatase motif in which the cysteine or the serine residue has been converted to fGly by action of an FGE, e.g., L(fGly)TPSR). A converted sulfatase motif may be derived from an amino acid sequence comprising an "unconverted" sulfatase motif (i.e., a sulfatase motif in which the cysteine or serine residues has not been converted to fGly by an FGE, but is capable of being converted, e.g., an unconverted sulfatase motif with the sequence: L(C/S)TPSR). By "conversion" as used in the context of action of a formylglycine generating enzyme (FGE) on a sulfatase motif refers to biochemical modification of a cysteine or serine residue in a sulfatase motif to a formylglycine (fGly) residue (e.g., Cys to fGly, or Ser to fGly). Additional aspects of aldehyde tags and uses thereof in site-specific protein modification are described in U.S. Pat. No. 7,985,783 and U.S. Application Publication No. 2011/0117621, filed Mar. 20, 2009, the disclosures of each of which are incorporated herein by reference.

Conversion of a polypeptide to include fGly can be accomplished by cell-based (in vivo) or cell-free methods (in vitro). Similarly, modification of a polypeptide to produce a polypeptide suitable for conjugation (e.g., modification to produce a polypeptide containing a reactive group suitable for conjugation) can be accomplished by cell-based (in vivo) or cell-free methods (in vitro).

Alternatively, isolated, unmodified polypeptides can be isolated following recombinant production in a host cell lacking a suitable enzyme or by synthetic production. The isolated polypeptide may then be contacted with a suitable enzyme under conditions to provide for the desired modification of the polypeptide to include fGly. The polypeptide can be unfolded by methods known in the art (e.g., using heat, adjustment of pH, chaotropic agents, (e.g., urea, and the like), organic solvents (e.g., hydrocarbons: octane, benzene, chloroform), etc.) and the denatured protein contacted with a suitable enzyme. The modified polypeptide can then be refolded under suitable conditions.

In some cases, the modified polypeptide containing the fGly residue may be conjugated to the moiety of interest by reaction of the fGly with a compound as described herein (e.g., a compound containing a coupling moiety, such as a pyrazalinone or pyrazalinone derivative as described herein). For example, an fGly-containing polypeptide may be isolated from a production source (e.g., recombinant host cell production, synthetic production), and contacted with a reactive partner-containing drug or other moiety (e.g., detectable label) under conditions suitable to provide for conjugation of the drug or other moiety to the polypeptide. For example, the reactive partner-containing drug or other moiety may include a reactive moiety (e.g., a pyrazalinone or pyrazalinone derivative as described herein). The pyrazalinone-containing drug or other moiety may be reacted with the polypeptide to produce a polypeptide conjugate as described herein. For example, FIG. 1 shows schematic drawings of polypeptide conjugates according to embodiments of the present disclosure. FIG. 1A shows a reaction scheme for the production of a polypeptide conjugate that includes a cyclic coupling moiety. In FIG. 1A, a polypeptide that includes an fGly is reacted with a cyclic coupling moiety (e.g., a pyrazalinone or pyrazalinone derivative) to produce a polypeptide conjugate that includes the cyclic coupling moiety. FIG. 1B shows a reaction scheme for the production of a polypeptide conjugate that includes an acyclic coupling moiety. In FIG. 1B, a polypeptide that includes an fGly is reacted with an acyclic coupling moiety to produce a polypeptide conjugate that includes the acyclic coupling moiety.

In some cases, the modified polypeptide containing the fGly residue may be conjugated to the moiety of interest by reaction of the fGly with a compound such as, but not limited to, one of the following compounds:

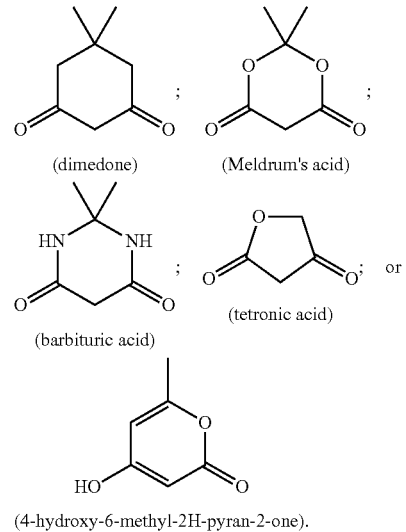

Polypeptide Conjugates

The polypeptides can be subjected to conjugation to provide for attachment of a wide variety of moieties. Examples of moieties of interest include, but are not limited to, a drug, a detectable label, a small molecule, a water-soluble polymer, a peptide, and the like (also referred to a "payload" or "cargo" herein). Thus, the present disclosure provides a polypeptide conjugate as described above.

The moiety of interest is provided as a component of a reactive partner for reaction with a residue of a polypeptide. In certain embodiments, the methods of polypeptide conjugation are compatible with reaction conditions suitable for the polypeptide. For example, the reaction conditions may include a reaction mixture that includes water. In some cases, the reaction mixture may have a pH compatible with the polypeptide, such as, but not limited to, a pH of 4 to 11, or a pH of 5 to 10, or a pH of 6 to 9, or a pH of 6 to 8. In certain instances, the reaction mixture has a pH of 7. In some embodiments, the reaction conditions are performed at a temperature compatible with the polypeptide. For example, the reaction conditions may be at a temperature of 20° C. to 45° C., such as 25° C. to 40° C., or 30° C. to 40° C., or 35° C. to 40° C. In some cases, the reaction conditions are at room temperature (e.g., 25° C.). In some instances, the reaction conditions are at a temperature of 37° C.

Provided the present disclosure, the ordinarily skilled artisan can readily adapt any of a variety of moieties to provide a reactive partner for conjugation to a polypeptide as contemplated herein. The ordinarily skilled artisan will appreciate that factors such as pH and steric hindrance (i.e., the accessibility of the modified amino acid residue to reaction with a reactive partner of interest) are of importance. Modifying reaction conditions to provide for optimal conjugation conditions is well within the skill of the ordinary artisan, and is routine in the art. Where conjugation is conducted with a polypeptide present in or on a living cell, the conditions are selected so as to be physiologically compatible. For example, the pH can be dropped temporarily for a time sufficient to allow for the reaction to occur but within a period tolerated by the cell (e.g., from about 30 min to 1 hour). Physiological conditions for conducting modification of polypeptides on a cell surface can be similar to those used in a ketone-azide reaction in modification of cells bearing cell-surface azides (see, e.g., U.S. Pat. No. 6,570, 040).

In certain embodiments, the present disclosure provides a polypeptide conjugate, where the polypeptide is an antibody. As such, embodiments include an antibody conjugated to a moiety of interest, where an antibody conjugated to a moiety of interest is referred to as an "antibody conjugate." An Ig polypeptide generally includes at least an Ig heavy chain constant region or an Ig light chain constant region, and can further include an Ig variable region (e.g., a $V_L$ region and/or a $V_H$ region). Ig heavy chain constant regions include Ig constant regions of any heavy chain isotype, non-naturally occurring Ig heavy chain constant regions (including consensus Ig heavy chain constant regions). An Ig constant region can be modified to be conjugated to a moiety of interest, where the moiety of interest is present in or adjacent a solvent-accessible loop region of the Ig constant region.

In some cases, an antibody conjugate of the present disclosure can include: 1) Ig heavy chain constant region conjugated to one or more moieties of interest, and an Ig light chain constant region conjugated to one or more moieties of interest; 2) an Ig heavy chain constant region conjugated to one or more moieties of interest, and an Ig light chain constant region that is not conjugated to a moiety of interest; or 3) an Ig heavy chain constant region that is not conjugated to a moiety of interest, and an Ig light chain constant region conjugated to one or more moieties of interest. A subject antibody conjugate can also include variable VH and/or VL domains. As described above, the one or more moieties of interest may be conjugated to the Ig heavy chain constant region or the Ig light chain constant region at a single amino acid residue (e.g., one or two moieties of interest conjugated to a single amino acid residue), or conjugated to the Ig heavy chain constant region and/or the Ig light chain constant region at two or more different amino acid residues.

An antibody conjugate of the present disclosure can include, as the conjugated moiety, any of a variety of compounds, as described herein, e.g., a drug (e.g., a peptide drug, a small molecule drug, and the like), a water-soluble polymer, a detectable label, a synthetic peptide, etc.

An antibody conjugate can have any of a variety of antigen-binding specificities, as described above, including, e.g., an antigen present on a cancer cell; an antigen present on an autoimmune cell; an antigen present on a pathogenic microorganism; an antigen present on a virus-infected cell (e.g., a human immunodeficiency virus-infected cell), e.g., CD4 or gp120; an antigen present on a diseased cell; and the like. For example, an antibody conjugate can bind an antigen, as noted above, where the antigen is present on the surface of the cell. An antibody conjugate of the present disclosure can bind antigen with a suitable binding affinity, e.g., from $5 \times 10^{-6}$ M to $10^{-7}$ M, from $10^{-7}$ M to $5 \times 10^{-7}$ M, from $5 \times 10^{-7}$ M to $10^{-8}$ M, from $10^{-8}$ M to $5 \times 10^{-8}$ M, from $5 \times 10^{-8}$ M to $10^{-9}$ M, or a binding affinity greater than $10^{-9}$ M.

As non-limiting examples, a subject antibody conjugate can bind an antigen present on a cancer cell (e.g., a tumor-specific antigen; an antigen that is over-expressed on a cancer cell; etc.), and the conjugated moiety can be a cytotoxic compound (e.g., a cytotoxic small molecule, a cytotoxic synthetic peptide, etc.). For example, a subject antibody conjugate can be specific for an antigen on a cancer cell, where the conjugated moiety is a cytotoxic compound (e.g., a cytotoxic small molecule, a cytotoxic synthetic peptide, etc.).

As further non-limiting examples, a subject antibody conjugate can bind an antigen present on a cell infected with a virus (e.g., where the antigen is encoded by the virus; where the antigen is expressed on a cell type that is infected by a virus; etc.), and the conjugated moiety can be a viral fusion inhibitor. For example, a subject antibody conjugate can bind an antigen present on a cell infected with a virus, and the conjugated moiety can be a viral fusion inhibitor.

Embodiments of the present disclosure also include polypeptide conjugates where the polypeptide is a carrier protein. For example, carrier proteins can be covalently and site-specifically bound to drug to provide a drug-containing scaffold. A carrier protein can be site-specifically conjugated to a covalently bound molecule of interest, such as a drug (e.g., a peptide, a small molecule drug, and the like), detectable label, etc. In certain embodiments, drug-scaffold conjugates can provide for enhanced serum half-life of the drug.

In general a "carrier protein" is a protein that is biologically inert, is susceptible to modification as disclosed herein, and which can provide for solvent-accessible presentation of the moiety of interest conjugated to the carrier protein through a modified amino acid residue in the carrier protein (e.g., through an oxime or hydrazone bond within the converted sulfatase motif of an aldehyde tagged carrier protein) in a physiological environment. "Biologically inert" is meant to indicate the carrier protein exhibits clinically insignificant or no detectable biological activity when administered to the appropriate subject, such as when administered to a human subject. Thus, carrier proteins are biologically inert in that they, for example, are of low immunogenicity, do not exhibit significant or detectable targeting properties (e.g., do not exhibit significant or detectable activity in binding to a specific receptor), and exhibit little or no detectable biological activity that may interfere with activity of the moiety (e.g., drug or detectable label) conjugated to the aldehyde-tagged carrier protein. By "low immunogenicity" is meant that the carrier protein elicits little or no detectable immune response upon administration to a subject, such as a mammalian subject, e.g., a human subject. Carrier proteins can be provided in monomeric or multimeric (e.g., dimeric) forms.

Carrier proteins having a three-dimensional structure when folded that provides for multiple different solvent-accessible sites that are amenable to modification (and thus conjugation to a moiety of interest) are of interest. In general, carrier proteins of interest are those that are of a size and three-dimensional folded structure so as to provide for presentation of the conjugated moiety of interest on solvent accessible surfaces in a manner that is sufficiently spatially separated so as to provide for activity and bioavailability of the conjugated moiety or moieties of interest. The carrier protein may be selected according to a variety of factors including, but not limited to, the moiety (e.g., drug or detectable label) to be conjugated to the carrier protein.

Accordingly, any of a wide variety of polypeptides can be suitable for use as carrier proteins for use in the carrier protein conjugates of the present disclosure. Such carrier proteins can include those having a naturally-occurring amino acid sequence, fragments of naturally-occurring polypeptides, and non-naturally occurring polypeptides and fragments thereof.

Examples of carrier proteins include, but are not limited to, albumin and fragments thereof (e.g., human serum albumin, bovine serum albumin, and the like), transferrin and fragments thereof (e.g. human transferrin), and Fc fragments having reduced binding to a mammalian Fc receptor, particularly a human Fc receptor (e.g., a modified Fc fragment of an antibody (e.g., IgG), such as a mammalian antibody, e.g., a human antibody). Examples of modified Fc fragments having reduced Fc receptor binding are exemplified by the Fc fragments of Herceptin (trastuzumab) and Rituxan (Rituximab), which contain point mutations that provide for reduced Fc receptor binding (see, e.g., Clynes et al., Nature Medicine (2000), 6, 443-446). Alternatively or in addition, the isotype of the Fc fragment can be selected according to a desired level of Fc receptor binding (e.g., use of an Fc fragment of an IgG4 isotype human heavy chain constant region rather than from IgG1 or IgG3. (see, e.g., Fridman FASEB J 1991 September; 5 (12): 2684-90). In general, carrier proteins can be at least about 4 kDa (e.g., about 50 amino acid residues in length), usually at least about 25 kDa, and can be larger in size (e.g., transferrin has a molecular weight of 90 kDa while Fc fragments can have molecular weights of 30 kDa to 50 kDa).

The conjugates described herein can be used for a variety of applications including, but not limited to, visualization using fluorescence or epitope labeling (e.g., electron microscopy using gold particles equipped with reactive groups for conjugation to the compounds and conjugates described herein); protein immobilization (e.g., protein microarray production); protein dynamics and localization studies and applications; and conjugation of proteins with a moiety of interest (e.g., moieties that improve a parent protein's half-life (e.g., poly(ethylene glycol)), targeting moieties (e.g., to enhance delivery to a site of action), and biologically active moieties (e.g., a therapeutic moiety).

The polypeptide conjugate may include a polypeptide conjugated to a moiety or moieties that provide for one or more of a wide variety of functions or features. In general, examples of moieties include, but are not limited to, the following: detectable labels (e.g., fluorescent labels); light-activated dynamic moieties (e.g., azobenzene mediated pore closing, azobenzene mediated structural changes, photo-decaging recognition motifs); water soluble polymers (e.g., PEGylation); purification tags (e.g., to facilitate isolation by affinity chromatography (e.g., attachment of a FLAG epitope); membrane localization domains (e.g., lipids or glycophosphatidylinositol (GPI)-type anchors); immobilization tags (e.g., to facilitate attachment of the polypeptide to a surface, including selective attachment); drugs (e.g., to facilitate drug targeting, e.g., through attachment of the drug to an antibody); targeted delivery moieties, (e.g., ligands for binding to a target receptor (e.g., to facilitate viral attachment, attachment of a targeting protein present on a liposome, etc.)), and the like.

Specific, non-limiting examples are provided below.

Drugs for Conjugation to a Polypeptide

Any of a number of drugs are suitable for use, or can be modified to be rendered suitable for use, as a reactive partner to conjugate to a polypeptide. Examples of drugs include small molecule drugs and peptide drugs. Thus, the present disclosure provides drug-polypeptide conjugates.

"Small molecule drug" as used herein refers to a compound, e.g., an organic compound, which exhibits a pharmaceutical activity of interest and which is generally of a molecular weight of 800 Da or less, or 2000 Da or less, but can encompass molecules of up to 5 kDa and can be as large as 10 kDa. A small inorganic molecule refers to a molecule containing no carbon atoms, while a small organic molecule refers to a compound containing at least one carbon atom.

"Peptide drug" as used herein refers to amino-acid containing polymeric compounds, and is meant to encompass naturally-occurring and non-naturally-occurring peptides, oligopeptides, cyclic peptides, polypeptides, and proteins, as well as peptide mimetics. The peptide drugs may be obtained by chemical synthesis or be produced from a genetically encoded source (e.g., recombinant source). Peptide drugs can range in molecular weight, and can be from 200 Da to 10 kDa or greater in molecular weight.

In some cases, the drug is a cancer chemotherapeutic agent. For example, where the polypeptide is an antibody (or fragment thereof) that has specificity for a tumor cell, the antibody can be modified as described herein to include a modified amino acid, which can be subsequently conjugated to a cancer chemotherapeutic agent. Cancer chemotherapeutic agents include non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones. Peptidic compounds can also be used.

Suitable cancer chemotherapeutic agents include dolastatin and active analogs and derivatives thereof; and auristatin and active analogs and derivatives thereof (e.g., Monomethyl auristatin D (MMAD), monomethyl auristatin E (MMAE), monomethyl auristatin F (MMAF), and the like). See, e.g., WO 96/33212, WO 96/14856, and U.S. Pat. No. 6,323,315. For example, dolastatin 10 or auristatin PE can be included in an antibody-drug conjugate of the present disclosure. Suitable cancer chemotherapeutic agents also include maytansinoids and active analogs and derivatives thereof (see, e.g., EP 1391213; and Liu et al (1996) *Proc. Natl. Acad. Sci. USA* 93:8618-8623); duocarmycins and active analogs and derivatives thereof (e.g., including the synthetic analogues, KW-2189 and CB 1-TM1); and benzodiazepines and active analogs and derivatives thereof (e.g., pyrrolobenzodiazepine (PBD)).

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation; therefore compounds that bind to the estrogen receptor are used to block this activity. Corticosteroids may inhibit T cell proliferation.

Other suitable chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

Taxanes are suitable for use. "Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from Taxus brevifolia; or T-1912 from Taxus yannanensis).

Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Biological response modifiers suitable for use include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) IFN-α; (7) IFN-γ; (8) colony-stimulating factors; and (9) inhibitors of angiogenesis.

Methods for Modification of Drugs to Contain a Reactive Partner

Drugs to be conjugated to a polypeptide may be modified to incorporate a reactive partner for reaction with the polypeptide. Where the drug is a peptide drug, the reactive moiety (e.g., aminooxy or hydrazide can be positioned at an N-terminal region, the N-terminus, a C-terminal region, the C-terminus, or at a position internal to the peptide. For example, an example of a method involves synthesizing a peptide drug having an aminooxy group. In this example, the peptide is synthesized from a Boc-protected precursor. An amino group of a peptide can react with a compound comprising a carboxylic acid group and oxy-N-Boc group. As an example, the amino group of the peptide reacts with 3-(2,5-dioxopyrrolidin-1-yloxy)propanoic acid. Other variations on the compound comprising a carboxylic acid group and oxy-N-protecting group can include different number of carbons in the alkylene linker and substituents on the alkylene linker. The reaction between the amino group of the peptide and the compound comprising a carboxylic acid group and oxy-N-protecting group occurs through standard peptide coupling chemistry. Examples of peptide coupling reagents that can be used include, but not limited to, DCC (dicyclohexylcarbodiimide), DIC (diisopropylcarbodiimide), di-p-toluoylcarbodiimide, BDP (1-benzotriazole diethylphosphate-1-cyclohexyl-3-(2-morpholinylethyl)carbodiimide), EDC (1-(3-dimethylaminopropyl-3-ethylcarbodiimide hydrochloride), cyanuric fluoride, cyanuric chloride, TFFH (tetramethyl fluoroformamidinium hexafluorophosphate), DPPA (diphenylphosphorazidate), BOP (benzotriazol-1-yloxytris(dimethylamino)phosphonium hexafluorophosphate), HBTU (O-benzotriazol-1-yl-N,N,N',N'-tetramethyluronium hexafluorophosphate), TBTU (O-benzotriazol-1-yl-N,N,N',N'-tetramethyluronium tetrafluoroborate), TSTU (O—(N-succinimidyl)-N,N,N',N'-tetramethyluronium tetrafluoroborate), HATU (N-[(dimethylamino)-1-H-1,2,3-triazolo[4,5,6]-pyridin-1-ylmethylene]--N-methylmethanaminium hexafluorophosphate N-oxide), BOP-Cl (bis(2-oxo-3-oxazolidinyl)phosphinic chloride), PyBOP ((1-H-1,2,3-benzotriazol-1-yloxy)-tris(pyrrolidino) phosphonium tetrafluorophopsphate), BrOP (bromotris(dimethylamino)phosphonium hexafluorophosphate), DEPBT (3-(diethoxyphosphoryloxy)-1,2,3-benzotriazin-4(3H)-one) PyBrOP (bromotris(pyrrolidino)phosphonium hexafluorophosphate). As a non-limiting example, HOBt and DIC can be used as peptide coupling reagents.

Deprotection to expose the amino-oxy functionality is performed on the peptide comprising an N-protecting group. Deprotection of the N-oxysuccinimide group, for example, occurs according to standard deprotection conditions for a cyclic amide group. Deprotecting conditions can be found in Greene and Wuts, Protective Groups in Organic Chemistry, 3rd Ed., 1999, John Wiley & Sons, NY and Harrison et al. Certain deprotection conditions include a hydrazine reagent, amino reagent, or sodium borohydride. Deprotection of a Boc protecting group can occur with TFA. Other reagents for deprotection include, but are not limited to, hydrazine, methylhydrazine, phenylhydrazine, sodium borohydride, and methylamine. The product and intermediates can be purified by conventional means, such as HPLC purification.

The ordinarily skilled artisan will appreciate that factors such as pH and steric hindrance (i.e., the accessibility of the amino acid residue to reaction with a reactive partner of interest) are of importance, Modifying reaction conditions to provide for optimal conjugation conditions is well within the skill of the ordinary artisan, and is routine in the art. Where conjugation is conducted with a polypeptide present in or on a living cell, the conditions are selected so as to be physiologically compatible. For example, the pH can be dropped temporarily for a time sufficient to allow for the reaction to occur but within a period tolerated by the cell (e.g., from about 30 min to 1 hour). Physiological conditions for conducting modification of polypeptides on a cell surface can be similar to those used in a ketone-azide reaction in modification of cells bearing cell-surface azides (see, e.g., U.S. Pat. No. 6,570,040).

Small molecule compounds containing, or modified to contain, an α-nucleophilic group that serves as a reactive partner with a compound or conjugate disclosed herein are also contemplated for use as drugs in the polypeptide-drug conjugates of the present disclosure. General methods are known in the art for chemical synthetic schemes and conditions useful for synthesizing a compound of interest (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Peptide Drugs

In some cases, a conjugate comprises a covalently linked peptide. Suitable peptides include, but are not limited to, cytotoxic peptides; angiogenic peptides; anti-angiogenic peptides; peptides that activate B cells; peptides that activate T cells; anti-viral peptides; peptides that inhibit viral fusion; peptides that increase production of one or more lymphocyte populations; anti-microbial peptides; growth factors; growth hormone-releasing factors; vasoactive peptides; anti-inflammatory peptides; peptides that regulate glucose metabolism; an anti-thrombotic peptide; an anti-nociceptive peptide; a vasodilator peptide; a platelet aggregation inhibitor; an analgesic; and the like.

In some embodiments, the peptide can be chemically synthesized to include a group reactive with an amino acid residue or a modified amino acid residue of the polypeptide. A suitable synthetic peptide has a length of from 5 amino acids to 100 amino acids, or longer than 100 amino acids; e.g., a suitable peptide has a length of from 5 amino acids (aa) to 10 aa, from 10 aa to 15 aa, from 15 aa to 20 aa, from 20 aa to 25 aa, from 25 aa to 30 aa, from 30 aa to 40 aa, from 40 aa to 50 aa, from 50 aa to 60 aa, from 60 aa to 70 aa, from 70 aa to 80 aa, from 80 aa to 90 aa, or from 90 aa to 100 aa.

In certain embodiments, a peptide can be modified to contain an α-nucleophile-containing moiety (e.g., an aminooxy or hydrazide moiety), e.g., can be reacted with an fGly-containing polypeptide to yield a conjugate in which the polypeptide and peptide are linked by a hydrazone or oxime bond, respectively. Examples of methods of synthesizing a peptide, such that the synthetic peptide comprising a reactive group reactive with an amino acid residue or a modified amino acid residue of the polypeptide, are described above.

Suitable peptides include, but are not limited to, hLF-11 (an 11-amino acid N-terminal fragment of lactoferrin), an anti-microbial peptide; granulysin, an anti-microbial peptide; Plectasin (NZ2114; SAR 215500), an anti-microbial peptide; viral fusion inhibitors such as Fuzeon (enfuvirtide), TRI-1249 (T-1249; see, e.g., Matos et al. (2010) PLoS One 5:e9830), TRI-2635 (T-2635; see, e.g., Eggink et al. (2009) J. Biol. Chem. 284:26941), T651, and TRI-1144; C5a receptor inhibitors such as PMX-53, JPE-1375, and JSM-7717; POT-4, a human complement factor C3 inhibitor; Pancreate (an INGAP derivative sequence, a HIP-human proislet protein); somatostatin; a somatostatin analog such as DEBIO 8609 (Sanvar), octreotide, octreotide (C2L), octreotide QLT, octreotide LAR, Sandostatin LAR, SomaLAR, Somatuline (lanreotide), see, e.g., Deghenghi et al. (2001) Endocrine 14:29; TH9507 (Tesamorelin, a growth hormone-releasing factor); POL7080 (a protegrin analog, an anti-microbial peptide); relaxin; a corticotropin releasing factor agonist such as urotensin, sauvagine, and the like; a heat shock protein derivative such as DiaPep277; a human immunodeficiency virus entry inhibitor; a heat shock protein-20 mimic such as AZX100; a thrombin receptor activating peptide such as TP508 (Chrysalin); a urocortin 2 mimic (e.g., a CRF2 agonist) such as urocortin-2; an immune activator such as Zadaxin (thymalfasin; thymosin-α1), see, e.g., Sjogren (2004) J. Gastroenterol. Hepatol. 19:S69; a hepatitis C virus (HCV) entry inhibitorE2 peptide such as HCV3; an atrial natriuretic peptide such as HANP (Sun 4936; carperitide); an annexin peptide; a defensin (anti-microbial peptide) such as hBD2-4; a defensin (anti-microbial peptide) such as hBD-3; a defensin (anti-microbial peptide) such as PMX-30063; a histatin (anti-microbial peptide) such as histatin-3, histatin-5, histatin-6, and histatin-9; a histatin (anti-microbial peptide) such as PAC-113; an indolicidin (anti-microbial peptide) such as MX-594AN (Omniganin; CLS001); an indolicidin (anti-microbial peptide) such as Omnigard (MBI-226; CPI-226); an anti-microbial peptide such as an insect cecropin; an anti-microbial peptide such as a lactoferrin (talactoferrin); an LL-37/cathelicidin derivative (an anti-microbial peptide) such as P60.4 (OP-145); a magainin (an anti-microbial peptide) such as Pexiganan (MSI-78; Suponex); a protegrin (an anti-microbial peptide) such as IB-367 (Iseganan); an agan peptide; a beta-natriuretic peptide such as Natrecor, or Noratak (Nesiritide), or ularitide; bivalarudin (Angiomax), a thrombin inhibitor; a C peptide derivative; a calcitonin such as Miacalcin (Fortical); an enkephalin derivative; an erythropoiesis-stimulating peptide such as Hematide; a gap junction modulator such as Danegaptide (ZP1609); a gastrin-releasing peptide; a ghrelin; a glucagon-like peptide; a glucagon-like peptide-2 analog such as ZP1846 or ZP1848; a glucosaminyl muramyl dipeptide such as GMDP; a glycopeptide antibiotic such as Oritavancin; a teicoplanin derivative such as Dalbavancin; a gonadotropin releasing hormone (GnRH) such as Zoladex (Lupon) or Triptorelin; a histone deacetylase (HDAC) inhibitor depsipeptide such as PMO2734 (Irvalec); an integrin such as eptifibatide; an insulin analog such as Humulog; a kahalalide depsipeptide such as PMO2734; a kallikrein inhibitor such as Kalbitor (ecallantide); an antibiotic such as Telavancin; a lipopeptide such as Cubicin or MX-2401; a lutenizing hormone releasing hormone (LHRH) such as goserelin; an LHRH synthetic decapeptide agonist analog such as Treistar (triptorelin pamoate); an LHRH such as Eligard; an M2 protein channel peptide inhibitor; metreleptin; a melanocortin receptor agonist peptide such as bremalanotide/PT-141; a melanocortin; a muramyl tripeptide such as Mepact (mifamurtide); a myelin basic protein peptide such as MBP 8298 (dirucotide); an N-type voltage-gated calcium channel blocker such as Ziconotide (Prialt); a parathyroid hormone peptide; a parathyroid analog such as 768974; a peptide hormone analog such as UGP281; a prostaglandin F2-a receptor inhibitor such as PDC31; a protease inhibitor such as PPL-100; surfaxin; a thrombospondin-1 (TSP-1) mimetic such as CVX-045 or ABT 510; a vasoactive intestinal peptide; vasopressin; a Y2R agonist peptide such as RG7089; obinepeptide; and TM30339.

Detectable Labels

The conjugates, compounds and methods of the present disclosure can be used to conjugate a detectable label to polypeptide. Examples of detectable labels include, but are not limited to, fluorescent molecules (e.g., autofluorescent molecules, molecules that fluoresce upon contact with a reagent, etc.), radioactive labels (e.g., $^{111}$In, $^{125}$I $^{131}$I, $^{212}$B, $^{90}$Y, $^{186}$Rh, and the like), biotin (e.g., to be detected through reaction of biotin and avidin), fluorescent tags, imaging reagents, and the like. Detectable labels also include peptides or polypeptides that can be detected by antibody binding, e.g., by binding of a detectably labeled antibody or by detection of bound antibody through a sandwich-type assay. Further examples of detectable labels include, but are not limited to, dye labels (e.g., chromophores, fluorophores, such as, but not limited to, Alexa Fluor® fluorescent dyes (e.g., Alexa Fluor® 350, 405, 430, 488, 532, 546, 555, 568, 594, 595, 610, 633, 635, 647, 660, 680, 700, 750, 790, and the like), coumarins, rhodamines (5-carboxyrhodamine and sulfo derivates thereof, e.g., 5-carboxy-disulfo-rhodamine, carbopyranins and oxazines, such as ATTO dyes (e.g., ATTO 390, 425, 465, 488, 495, 520, 532, 550, 565, 590, 594, 610, 611X, 620, 633, 635, 637, 647, 647N, 655, 665, 680, 700, 725 or 740), biophysical probes (spin labels, nuclear magnetic resonance (NMR) probes), Förster Resonance Energy Transfer (FRET)-type labels (e.g., at least one member of a FRET pair, including at least one member of a fluorophore/quencher pair), Bioluminescence Resonance Energy Transfer (BRET)-type labels (e.g., at least one member of a BRET pair), immunodetectable tags (e.g., FLAG, His(6), and the like), localization tags (e.g., to identify association of a tagged polypeptide at the tissue or molecular cell level (e.g., association with a tissue type, or particular cell membrane), and the like.

Attachment of Moieties for Delivery to a Target Site

Embodiments of the present disclosure also include a polypeptide conjugated to one or more moieties, such as, but not limited to, a drug (e.g., a small molecule drug), toxin, or other molecule for delivery to a target site (e.g., a cell) and which can provide for a pharmacological activity or can serve as a target for delivery of other molecules.

Also contemplated are conjugates that include one of a pair of binding partners (e.g., a ligand, a ligand-binding portion of a receptor, a receptor-binding portion of a ligand, etc.). For example, the conjugate can include a polypeptide that serves as a viral receptor and, upon binding with a viral envelope protein or viral capsid protein, facilitates attachment of virus to the cell surface on which the modified polypeptide is expressed. Alternatively, the conjugate may include an antigen that is specifically bound by an antibody (e.g., monoclonal antibody), to facilitate detection and/or separation of host cells expressing the modified polypeptide.

Attachment of Target Molecules to a Support

The methods can provide for conjugation of a polypeptide to a moiety to facilitate attachment of the polypeptide to a solid substrate (e.g., to facilitate assays), or to a moiety to facilitate easy separation (e.g., a hapten recognized by an antibody bound to a magnetic bead). In some embodiments, the methods are used to provide for attachment of a protein to an array (e.g., chip) in a defined orientation. For example, a polypeptide modified at a selected site (e.g., at or near the N-terminus) can be generated, and the methods, conjugates and compounds used to deliver a moiety to the modified polypeptide. The moiety can then be used as the attachment site for affixing the polypeptide to a support (e.g., solid or semi-solid support, such as a support suitable for use as a microchip in high-throughput assays).

Water-Soluble Polymers

In some cases, a conjugate includes a covalently linked water-soluble polymer. A moiety of particular interest is a water-soluble polymer. A "water-soluble polymer" refers to a polymer that is soluble in water and is usually substantially non-immunogenic, and usually has an atomic molecular weight greater than 1,000 Daltons. The methods, conjugates and compounds described herein can be used to attach one or more water-soluble polymers to a polypeptide. Attachment of a water-soluble polymer (e.g., PEG) to a polypeptide, such as a pharmaceutically active (e.g., therapeutic) polypeptide can be desirable as such modification can increase the therapeutic index by increasing serum half-life as a result of increased proteolytic stability and/or decreased renal clearance. Additionally, attachment of one or more polymers (e.g., PEGylation) can reduce immunogenicity of protein pharmaceuticals.

In some embodiments, the water-soluble polymer has an effective hydrodynamic molecular weight of greater than 5,000 Da, greater than 10,000 Da, greater than 20,000 to 500,000 Da, greater than 40,000 Da to 300,000 Da, greater than 50,000 Da to 70,000 Da, such as greater than 60,000 Da. In some embodiments, the water-soluble polymer has an effective hydrodynamic molecular weight of from 10 kDa to 20 kDa, from 20 kDa to 25 kDa, from 25 kDa to 30 kDa, from 30 kDa to 50 kDa, or from 50 kDa to 100 kDa. By "effective hydrodynamic molecular weight" is intended the effective water-solvated size of a polymer chain as determined by aqueous-based size exclusion chromatography (SEC). When the water-soluble polymer contains polymer chains having polyalkylene oxide repeat units, such as ethylene oxide repeat units, each chain can have an atomic molecular weight of 200 Da to 80,000 Da, or 1,500 Da to 42,000 Da, including 2,000 to 20,000 Da. Unless referred to specifically, molecular weight is intended to refer to atomic molecular weight. Linear, branched, and terminally charged water soluble polymers (e.g., PEG) may be used.

Polymers useful as moieties to be attached to a polypeptide can have a wide range of molecular weights, and polymer subunits. These subunits may include a biological polymer, a synthetic polymer, or a combination thereof. Examples of such water-soluble polymers include: dextran and dextran derivatives, including dextran sulfate, P-amino cross linked dextrin, and carboxymethyl dextrin, cellulose and cellulose derivatives, including methylcellulose and carboxymethyl cellulose, starch and dextrines, and derivatives and hydroylactes of starch, polyalkylene glycol and derivatives thereof, including polyethylene glycol, methoxy-polyethylene glycol, polyethylene glycol homopolymers, polypropylene glycol homopolymers, copolymers of ethylene glycol with propylene glycol, wherein said homopolymers and copolymers are unsubstituted or substituted at one end with an alkyl group, heparin and fragments of heparin, polyvinyl alcohol and polyvinyl ethyl ethers, polyvinylpyrrolidone, aspartamide, and polyoxyethylated polyols, with the dextran and dextran derivatives, dextrine and dextrine derivatives. It will be appreciated that various derivatives of the specifically recited water-soluble polymers are also contemplated.

Water-soluble polymers such as those described above include polyalkylene oxide based polymers, such as polyethylene glycol "PEG" (See. e.g., "Poly(ethylene glycol) Chemistry: Biotechnical and Biomedical Applications", J. M. Harris, Ed., Plenum Press, New York, N.Y. (1992); and "Poly(ethylene glycol) Chemistry and Biological Applications", J. M. Harris and S. Zalipsky, Eds., ACS (1997); and International Patent Applications: WO 90/13540, WO 92/00748, WO 92/16555, WO 94/04193, WO 94/14758, WO 94/17039, WO 94/18247, WO 94/28937, WO 95/11924, WO 96/00080, WO 96/23794, WO 98/07713, WO 98/41562, WO 98/48837, WO 99/30727, WO 99/32134, WO 99/33483, WO 99/53951, WO 01/26692, WO 95/13312, WO 96/21469, WO 97/03106, WO 99/45964, and U.S. Pat. Nos. 4,179,337; 5,075,046; 5,089, 261; 5,100,992; 5,134,192; 5,166,309; 5,171,264; 5,213, 891; 5,219,564; 5,275,838; 5,281,698; 5,298,643; 5,312, 808; 5,321,095; 5,324,844; 5,349,001; 5,352,756; 5,405, 877; 5,455,027; 5,446,090; 5,470,829; 5,478,805; 5,567, 422; 5,605,976; 5,612,460; 5,614,549; 5,618,528; 5,672, 662; 5,637,749; 5,643,575; 5,650,388; 5,681,567; 5,686, 110; 5,730,990; 5,739,208; 5,756,593; 5,808,096; 5,824, 778; 5,824,784; 5,840,900; 5,874,500; 5,880,131; 5,900, 461; 5,902,588; 5,919,442; 5,919,455; 5,932,462; 5,965, 119; 5,965,566; 5,985,263; 5,990,237; 6,011,042; 6,013, 283; 6,077,939; 6,113,906; 6,127,355; 6,177,087; 6,180, 095; 6,194,580; 6,214,966).

Examples of polymers of interest include those containing a polyalkylene oxide, polyamide alkylene oxide, or derivatives thereof, including polyalkylene oxide and polyamide alkylene oxide comprising an ethylene oxide repeat unit of the formula $—(CH_2—CH_2—O)—$. Further examples of polymers of interest include a polyamide having a molecular weight greater than 1,000 Daltons of the formula $—[C(O)—X—C(O)—NH—Y—NH]n-$ or $—[NH—Y—NH—C(O)—X—C(O)]_n—$, where X and Y are divalent radicals that may be the same or different and may be branched or linear, and n is a discrete integer from 2-100, such as from 2 to 50, and where either or both of X and Y comprises a biocompatible, substantially non-antigenic water-soluble repeat unit that may be linear or branched. Further examples of water-soluble repeat units comprise an ethylene oxide of the formula $—(CH_2—CH_2—O)—$ or $—(O—CH_2—CH_2)—$. The number of such water-soluble repeat units can vary significantly, with the number of such units being from 2 to 500, 2 to 400, 2 to 300, 2 to 200, 2 to 100, for example from 2 to 50. An example of an embodiment is one in which one or both of X and Y is selected from: $—((CH_2)_{n1}—(CH_2—CH_2—O)_{n2}—(CH_2)—$ or $—((CH_2)_{n1}—(O—CH_2—CH_2)_{n2}—(CH_2)_{n-1}—)$, where n1 is 1 to 6, 1 to 5, 1 to 4, or 1 to 3, and where n2 is 2 to 50, 2 to 25, 2 to 15, 2 to 10, 2 to 8, or 2 to 5. A further example of an embodiment is one in which X is $—(CH_2—CH_2)—$, and where Y is $—(CH_2—(CH_2—CH_2—O)_3—CH_2—CH_2—CH_2)—$ or $—(CH_2—CH_2—CH_2—(O—CH_2—CH_2)_3—CH_2)—$.

The polymer can include one or more spacers or linkers. Examples of spacers or linkers include linear or branched moieties comprising one or more repeat units employed in a water-soluble polymer, diamino and or diacid units, natural or unnatural amino acids or derivatives thereof, as well as aliphatic moieties, including alkyl, aryl, heteroalkyl, heteroaryl, alkoxy, and the like, which can contain, for example, up to 18 carbon atoms or even an additional polymer chain.

The polymer moiety, or one or more of the spacers or linkers of the polymer moiety when present, may include polymer chains or units that are biostable or biodegradable. For example, polymers with repeat linkages have varying degrees of stability under physiological conditions depending on bond lability. Polymers with such bonds can be categorized by their relative rates of hydrolysis under physiological conditions based on known hydrolysis rates of low molecular weight analogs, e.g., from less stable to more stable, e.g., polyurethanes $(—NH—C(O)—O—)$>polyorthoesters $(—O—C((OR)(R'))—O—)$>polyamides $(—C(O)—NH—)$. Similarly, the linkage systems attaching a water-soluble polymer to a target molecule may be biostable or biodegradable, e.g., from less stable to more stable: carbonate $(—O—C(O)—O—)$>ester $(—C(O)—O—)$>urethane $(—NH—C(O)—O—)$>orthoester $(—O—C((OR)(R'))—O—)$>amide $(—C(O)—NH—)$. In general, it may be desirable to avoid use of a sulfated polysaccharide, depending on the lability of the sulfate group. In addition, it may be less desirable to use polycarbonates and polyesters. These bonds are provided by way of example, and are not intended to limit the types of bonds employable in the polymer chains or linkage systems of the water-soluble polymers useful in the modified aldehyde tagged polypeptides disclosed herein.

Formulations

The conjugates (including antibody conjugates) of the present disclosure can be formulated in a variety of different ways. In general, where the conjugate is a polypeptide-drug conjugate, the conjugate is formulated in a manner compatible with the drug conjugated to the polypeptide, the condition to be treated, and the route of administration to be used.

The conjugate (e.g., polypeptide-drug conjugate) can be provided in any suitable form, e.g., in the form of a pharmaceutically acceptable salt, and can be formulated for any suitable route of administration, e.g., oral, topical or parenteral administration. Where the conjugate is provided as a liquid injectable (such as in those embodiments where they are administered intravenously or directly into a tissue), the conjugate can be provided as a ready-to-use dosage form, or as a reconstitutable storage-stable powder or liquid composed of pharmaceutically acceptable carriers and excipients.

Methods for formulating conjugates can be adapted from those available in the art. For example, conjugates can be provided in a pharmaceutical composition comprising a therapeutically effective amount of a conjugate and a pharmaceutically acceptable carrier (e.g., saline). The pharmaceutical composition may optionally include other additives (e.g., buffers, stabilizers, preservatives, and the like). In some embodiments, the formulations are suitable for administration to a mammal, such as those that are suitable for administration to a human.

Methods of Treatment

The polypeptide-drug conjugates of the present disclosure find use in treatment of a condition or disease in a subject that is amenable to treatment by administration of the parent drug (i.e., the drug prior to conjugation to the polypeptide). By "treatment" is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition. Thus treatment includes: (i) prevention, that is, reducing the risk of development of clinical symptoms, including causing the clinical symptoms not to develop, e.g., preventing disease progression to a harmful state; (ii) inhibition, that is, arresting the development or further development of clinical symptoms, e.g., mitigating or completely inhibiting an active disease; and/or (iii) relief, that is, causing the regression of clinical symptoms.

In the context of cancer, the term "treating" includes any or all of: reducing growth of a solid tumor, inhibiting replication of cancer cells, reducing overall tumor burden, and ameliorating one or more symptoms associated with a cancer.

The subject to be treated can be one that is in need of therapy, where the host to be treated is one amenable to treatment using the parent drug. Accordingly, a variety of subjects may be amenable to treatment using the polypeptide-drug conjugates disclosed herein. Generally, such subjects are "mammals", with humans being of interest. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys).

The amount of polypeptide-drug conjugate administered can be initially determined based on guidance of a dose and/or dosage regimen of the parent drug. In general, the polypeptide-drug conjugates can provide for targeted delivery and/or enhanced serum half-life of the bound drug, thus providing for at least one of reduced dose or reduced administrations in a dosage regimen. Thus, the polypeptide-drug conjugates can provide for reduced dose and/or reduced administration in a dosage regimen relative to the parent drug prior to being conjugated in an polypeptide-drug conjugate of the present disclosure.

Furthermore, as noted above, because the polypeptide-drug conjugates can provide for controlled stoichiometry of drug delivery, dosages of polypeptide-drug conjugates can be calculated based on the number of drug molecules provided on a per polypeptide-drug conjugate basis.

In some embodiments, multiple doses of a polypeptide-drug conjugate are administered. The frequency of administration of a polypeptide-drug conjugate can vary depending on any of a variety of factors, e.g., severity of the symptoms, condition of the subject, etc. For example, in some embodiments, a polypeptide-drug conjugate is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

Methods of Treating Cancer

The present disclosure provides methods for delivering a cancer chemotherapeutic agent to an individual having a cancer. The methods are useful for treating a wide variety of cancers, including carcinomas, sarcomas, leukemias, and lymphomas.

Carcinomas that can be treated using a subject method include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma, etc.

Sarcomas that can be treated using a subject method include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Other solid tumors that can be treated using a subject method include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Leukemias that can be treated using a subject method include, but are not limited to, a) chronic myeloproliferative syndromes (neoplastic disorders of multipotential hematopoietic stem cells); b) acute myelogenous leukemias (neoplastic transformation of a multipotential hematopoietic stem cell or a hematopoietic cell of restricted lineage potential; c) chronic lymphocytic leukemias (CLL; clonal proliferation of immunologically immature and functionally incompetent small lymphocytes), including B-cell CLL, T-cell CLL prolymphocytic leukemia, and hairy cell leukemia; and d) acute lymphoblastic leukemias (characterized by accumulation of lymphoblasts). Lymphomas that can be treated using a subject method include, but are not limited to, B-cell lymphomas (e.g., Burkitt's lymphoma); Hodgkin's lymphoma; non-Hodgkin's B cell lymphoma; and the like.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. By "average" is meant the arithmetic mean. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

General Synthetic Procedures

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any purification protocol known in the art, including chromatography, such as HPLC, preparative thin layer chromatography, flash column chromatography and ion exchange chromatography. Any suitable stationary phase can be used, including normal and reversed phases as well as ionic resins. In certain embodiments, the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, $4^{th}$ edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

The subject compounds can be synthesized via a variety of different synthetic routes using commercially available starting materials and/or starting materials prepared by conventional synthetic methods. A variety of examples of synthetic routes that can be used to synthesize the compounds disclosed herein are described in the schemes below.

HPLC Analyses

HPLC analyses were conducted on an Agilent 1100 Series Analytical HPLC equipped with a Model G1322A Degasser, Model G1311A Quarternary Pump, Model G1329A Autosampler, Model G1314 Variable Wavelength Detector, and Model G1364C Fraction Collector at room temperature according to the methods described below.

Method A: Agilent Poroshell 120 SB C18, 4.6 mm×150 mm (2.7 um) (1.0 mL min$^{-1}$). Solvent A: H$_2$O (0.1% HCO$_2$H), Solvent B: CH$_3$CN (0.1% HCO$_2$H).

| Time (min) | Solvent B (%) |
|---|---|
| 0.0 | 10 |
| 15.0 | 100 |
| 17.5 | 100 |
| 18.0 | 10 |
| 20.5 | 10 |

Method B: Agilent Poroshell 120 SB C18, 4.6 mm×50 mm (2.7 um) (2.5 mL min$^{-1}$). Solvent A: H$_2$O (0.1% HCO$_2$H), Solvent B: CH$_3$CN (0.1% HCO$_2$H)

| Time (min) | Solvent B (%) |
|---|---|
| 0.0 | 10 |
| 5.0 | 100 |
| 6.0 | 100 |
| 6.1 | 10 |
| 7.1 | 10 |

Method C: Agilent Poroshell 120 SB C18, 4.6 mm×150 mm (2.7 um) (1.0 mL min$^{-1}$). Solvent A: H$_2$O (0.1% HCO$_2$H), Solvent B: CH$_3$CN (0.1% HCO$_2$H)

| Time (min) | Solvent B (%) |
|---|---|
| 0.0 | 5 |
| 15.0 | 95 |
| 17.5 | 95 |
| 18.0 | 5 |
| 20.5 | 5 |

Method D: Agilent Zorbax 300 SB CN, 4.6 mm×250 mm (5.0 um) (1.0 mL min$^{-1}$). Solvent A: NH$_4$OAc (10 mM), Solvent B: H$_2$O, CH$_3$CN (0.05, 0.95)

| Time (min) | Solvent B (%) |
|---|---|
| 0.0 | 10 |
| 30.0 | 100 |
| 33.0 | 100 |
| 36.0 | 10 |
| 45.0 | 10 |

Example 1

Method 1—Preparation of (2S,15S)-1-((S)-3-maytansinyl)-15-(3-(2-((1,2-dimethylhydrazinyl)methyl)-1H-indol-1-yl)propanamido)-2,3-dimethyl-1,4,14-trioxo-7,10-dioxa-3,13-diazaoctadecan-18-oic acid (HIPS Indole E (CO$_2$H) PEG$_2$ Maytansine)

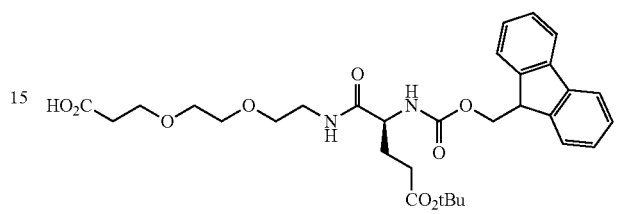
(Compound 1)

Figure 3:
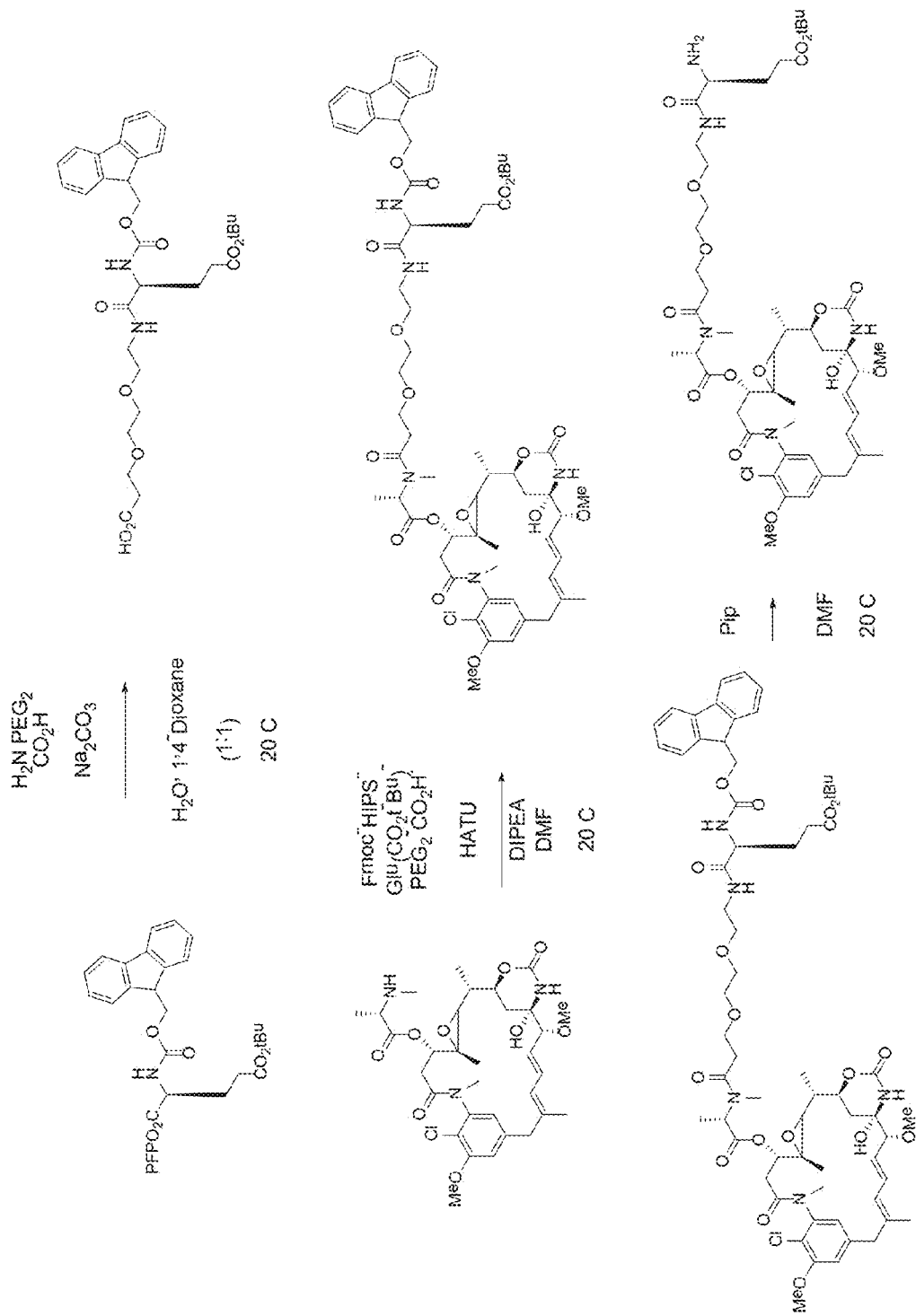
FIG. 3 and FIG. 4 show reaction schemes for the synthesis of compound HIPS Indole E ($CO_2H$) $PEG_2$ Maytansine, according to embodiments of the present disclosure, see e.g., Example 1.
Figure 4:
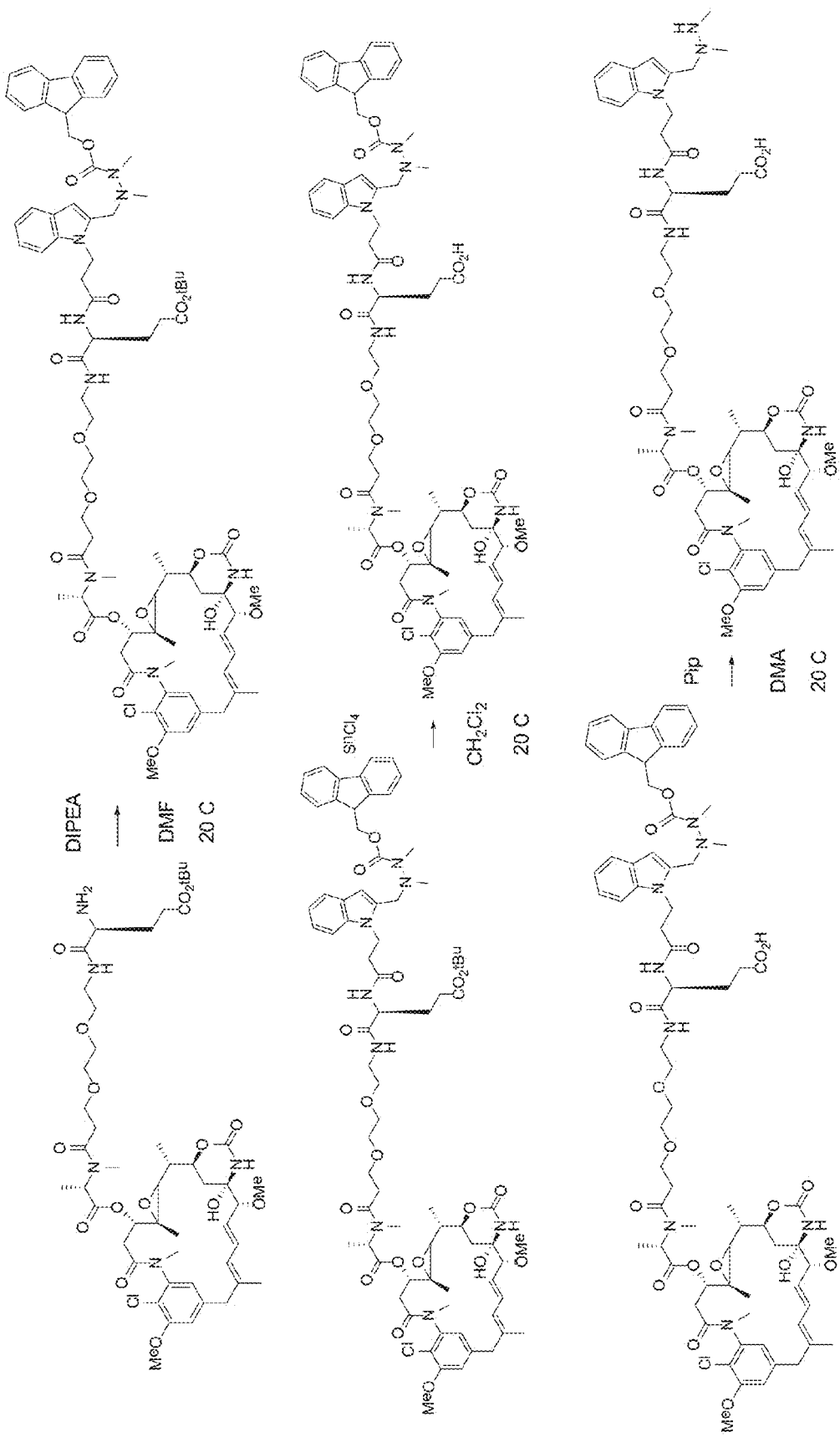

Reaction schemes for the synthesis of compound HIPS Indole E (CO$_2$H) PEG$_2$ Maytansine are shown in FIG. 3 and FIG. 4.

Preparation of (S)-5-(3-(tert-butoxy)-3-oxopropyl)-1-(9H-fluoren-9-yl)-3,6-dioxo-2,10,13-trioxa-4,7-diazahexadecan-16-oic acid (FMOC E (CO$_2$tBu) PEG$_2$ CO$_2$H) (Compound 2) (FIG. 3)

To a 20 mL glass scintillation vial containing a pea stir bar was added H$_2$N PEG$_2$ CO$_2$H (710.3 mg, 4.0 mmol), Na$_2$CO$_3$ (637.9 mg, 6.0 mmol), and H$_2$O (10 mL). The clear, colorless solution was stirred at room temperature. N-α-Fmoc-L-glutamic acid γ-t.-butyl ester pentafluorophenyl ester (1185.7 mg, 2.0 mmol) was added to a separate 20 mL glass scintillation vial, dissolved in anhydrous 1,4-dioxane (10 mL), and added dropwise, slowly, to the aqueous solution. A white precipitate evolved with continued stirring. The reaction was stirred at room temperature for 4 h, diluted with H$_2$O (70 mL), acidified to pH 3 with dropwise addition of 1 M HCl, and extracted with 2×50 mL EtOAc. The organic fractions were combined, dried over Na$_2$SO$_4$, concentrated, adsorbed onto a Biotage KP C18 HS 12 g samplet, and purified on a Biotage KP C18 HS 60 g cartridge using a gradient of 0-100% CH$_3$CN in H$_2$O, giving the desired product as a clear, viscous oil (1137.3 mg, 97% yield). HPLC retention time 12.260 min. Method A.

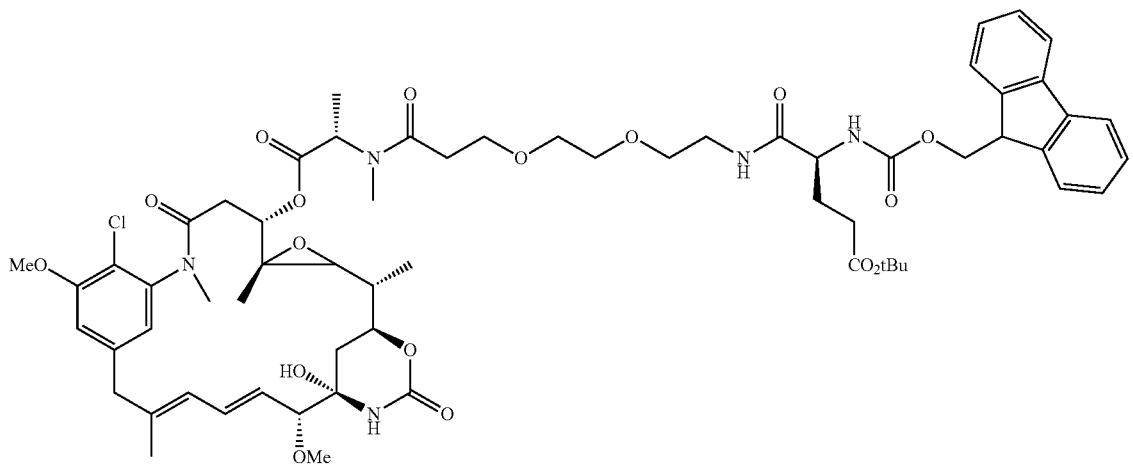

Preparation of (2S,15S)-18-tert-butyl 1-((S)-3-maytansinyl) 15-((((9H-fluoren-9-yl)methoxy)carbonyl)amino)-2,3-dimethyl-4,14-dioxo-7,10-dioxa-3,13-diazaoctadecane-1,18-dioate (FMOC E (CO$_2$tBu) PEG$_2$ Maytansine) (Compound 3) (FIG. 3)

To a dried 20 mL glass scintillation vial containing a dried flea stir bar was added FMOC E (CO$_2$tBu) PEG$_2$ CO$_2$H (311.3 mg, 0.5 mmol), HATU (201.0 mg, 0.5 mmol), and anhydrous DMF (2 mL). The clear, colorless solution was stirred at room temperature for 15 min. Deacyl maytansine (343.4 mg, 0.5 mmol), DIPEA (204.8 mg, 276.0 uL, 1.6 mmol), and anhydrous DMF (1 mL) were combined in a separate, dried 4 mL glass scintillation vial and added dropwise, slowly, to the stirring solution. The reaction was allowed to stir at room temperature for 2 h, adsorbed directly onto a Biotage KP C18 HS 12 g samplet, and purified on a Biotage KP C18 HS 60 g cartridge using a gradient of 0-100% CH$_3$CN in H$_2$O, giving the title compound as a white solid (377.8 mg, 59% yield). HPLC retention time 14.385 min. Method A.

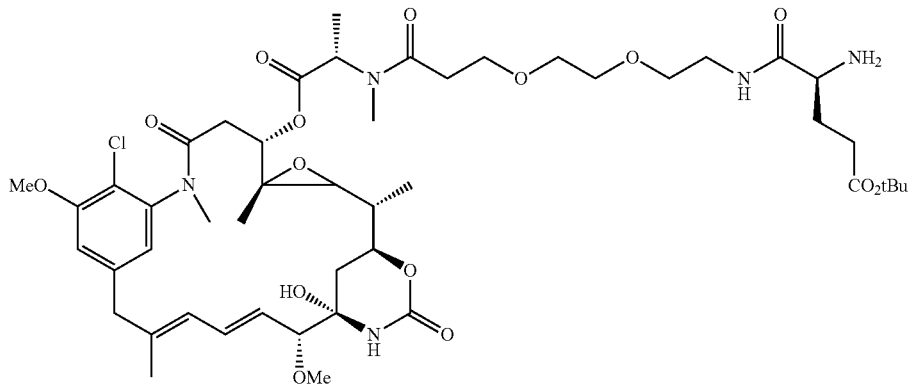

Preparation of (2S,15S)-18-tert-butyl 1-((S)-3-maytansinyl) 15-amino-2,3-dimethyl-4,14-dioxo-7,10-dioxa-3,13-diazaoctadecane-1,18-dioate (E (CO$_2$tBu) PEG$_2$ Maytansine) (Compound 4) (FIG. 3)

To a dried 20 mL glass scintillation vial containing a dried flea stir bar was added FMOC E (CO$_2$tBu) PEG$_2$ Maytansine (377.8 mg, 0.3 mmol). Piperidine (528.8 mg, 0.613 mL, 6.2 mmol) in DMF (2.452 mL) was added by syringe. The solution was stirred at room temperature for 20 min, adsorbed directly onto a Biotage KP C18 HS 12 g samplet, and purified on a Biotage KP C18 HS 60 g cartridge using a gradient of 0-100% CH$_3$CN in H$_2$O, giving the desired product as a pale yellow solid (269.2 mg, 87% yield). HPLC retention time 9.683 min. Method A.

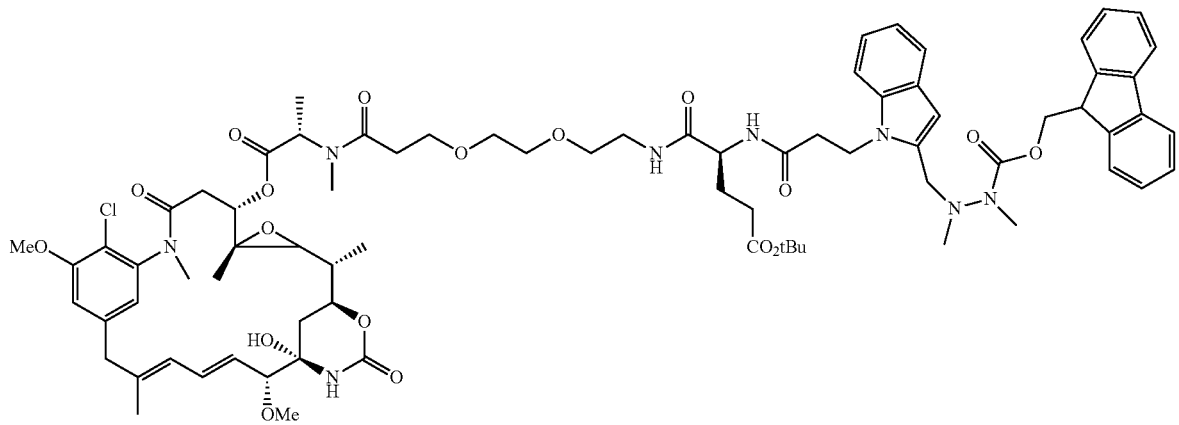

Preparation of (2S,15S)-18-tert-butyl 1-((S)-3-maytansinyl) 15-(3-(2-((2-(((9H-fluoren-9-yl)methoxy)carbonyl)-1,2-dimethylhydrazinyl)methyl)-1H-indol-1-yl)propanamido)-2,3-dimethyl-4,14-dioxo-7,10-dioxa-3,13-diazaoctadecane-1,18-dioate (FMOC HIPS Indole E (CO₂tBu) PEG₂ Maytansine) (Compound 5) (FIG. 4)

To a dried 4 mL glass scintillation vial containing a dried flea stir bar was added E (CO₂tBu) PEG₂ Maytansine (269.2 mg, 0.3 mmol), FMOC HIPS Indole CO₂PFP (211.5 mg, 0.3 mmol), DIPEA (105.1 mg, 141.6 uL, 0.8 mmol), and anhydrous DMF (1 mL). The solution was stirred at room temperature for 2 h, adsorbed directly onto a Biotage KP C18 HS 3 g samplet, and purified on a Biotage KP C18 HS 30 g cartridge using a gradient of 0-100% CH₃CN in H₂O, giving the title compound as a pale yellow solid (361.6 mg, 92% yield). HPLC retention time 15.989 min. Method A.

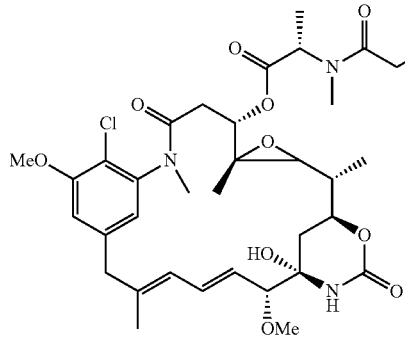
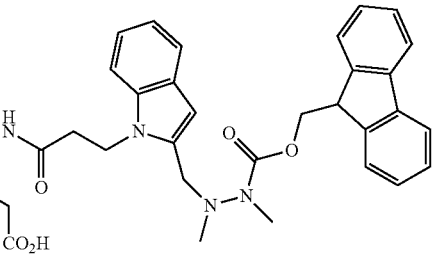

Preparation of (2S,15S)-15-(3-(2-((2-(((9H-fluoren-9-yl)methoxy)carbonyl)-1,2-dimethylhydrazinyl)methyl)-1H-indol-1-yl)propanamido)-1-((S)-3-maytansinyl)-2,3-dimethyl-1,4,14-trioxo-7,10-dioxa-3,13-diazaoctadecan-18-oic acid (FMOC HIPS Indole E (CO₂H) PEG₂ Maytansine) (Compound 6) (FIG. 4)

To a dried 20 mL glass scintillation vial containing a dried flea stir bar was added FMOC HIPS Indole E (CO₂tBu) PEG₂ Maytansine (361.6 mg, 0.2 mmol) and anhydrous CH₂Cl₂ (3 mL). The solution was cooled to 0° C. in an ice, H₂O bath and SnCl₄ (1.2 mL, 1.2 mmol, 1.0 M solution in anhydrous CH₂Cl₂) was added dropwise by syringe, giving a pale yellow precipitate. The solution was stirred at 0° C. for 5 min, whereupon the ice, H₂O bath was removed and the solution warmed to room temperature. The reaction was stirred for 1 h, adsorbed directly onto a Biotage KP C18 HS 3 g samplet, and purified on a Biotage KP C18 HS 30 g cartridge using a gradient of 0-100% CH₃CN in H₂O, giving the desired product as a pale yellow solid (260.9 mg, 75% yield). HPLC retention time 13.833 min. Method A.

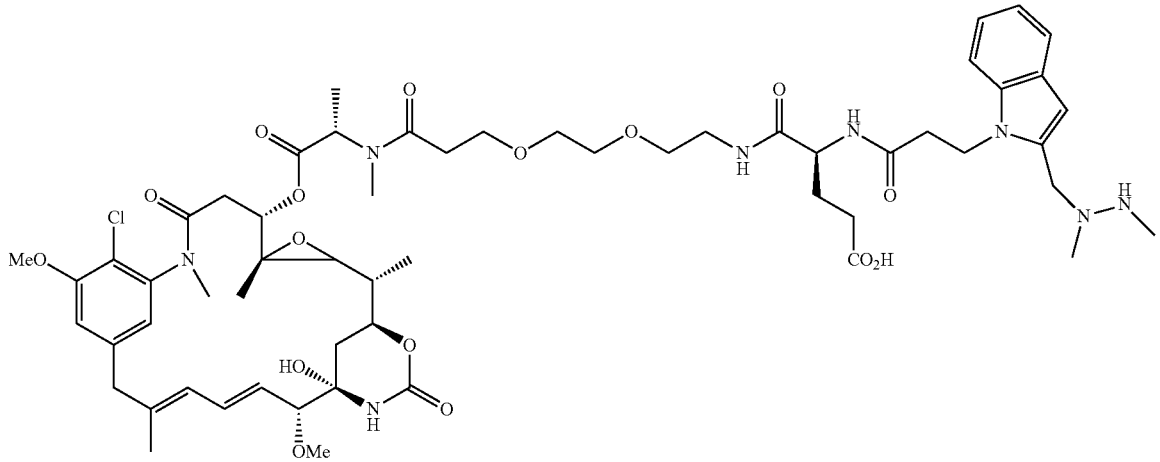

Preparation of (2S,15S)-1-((S)-3-maytansinyl)-15-(3-(2-((1,2-dimethylhydrazinyl)methyl)-1H-indol-1-yl)propanamido)-2,3-dimethyl-1,4,14-trioxo-7,10-dioxa-3,13-diazaoctadecan-18-oic acid (HIPS Indole E (CO₂H) PEG₂ Maytansine) (Compound 7) (FIG. 4)

To a dried 20 mL glass scintillation vial containing a dried flea stir bar was added FMOC HIPS Indole E (CO₂H) PEG₂ Maytansine (260.9 mg, 0.2 mmol). Piperidine (344.8 mg, 0.4 mL, 4.0 mmol) in DMA (1.6 mL) was added by syringe. The solution was stirred at room temperature for 20 min, adsorbed directly onto a Biotage KP C18 HS 3 g samplet, and purified on a Biotage KP C18 HS 30 g cartridge using a gradient of 0-100% CH₃CN in H₂O, giving the title compound as a white solid (218.1 mg, 99% yield).

HPLC retention time 9.372 min. Method A. LRMS (ESI) calcd for $C_{58}H_{82}ClN_8O_{16}$ [M+H]⁺: 1181.6 found 1181.3.

Example 2

Method 2—Preparation of (2S,15S)-1-((S)-3-maytansinyl)-15-(3-(2-((1,2-dimethylhydrazinyl)methyl)-1H-indol-1-yl)propanamido)-2,3-dimethyl-1,4,14-trioxo-7,10-dioxa-3,13-diazaoctadecan-18-oic acid (HIPS Indole E (CO₂H) PEG₂ Maytansine)

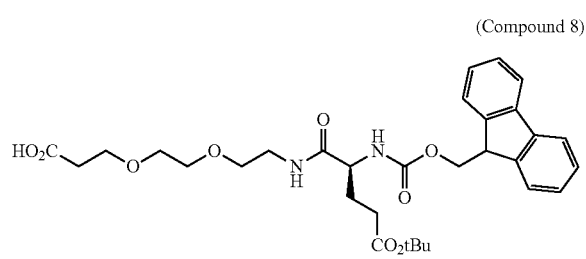 [SMILES: CC(C)(C)OC(=O)CC[C@H](NC(=O)OCC1c2ccccc2-c2ccccc21)C(=O)NCCOCCOCCC(=O)O]

(Compound 8)

Figure 5:
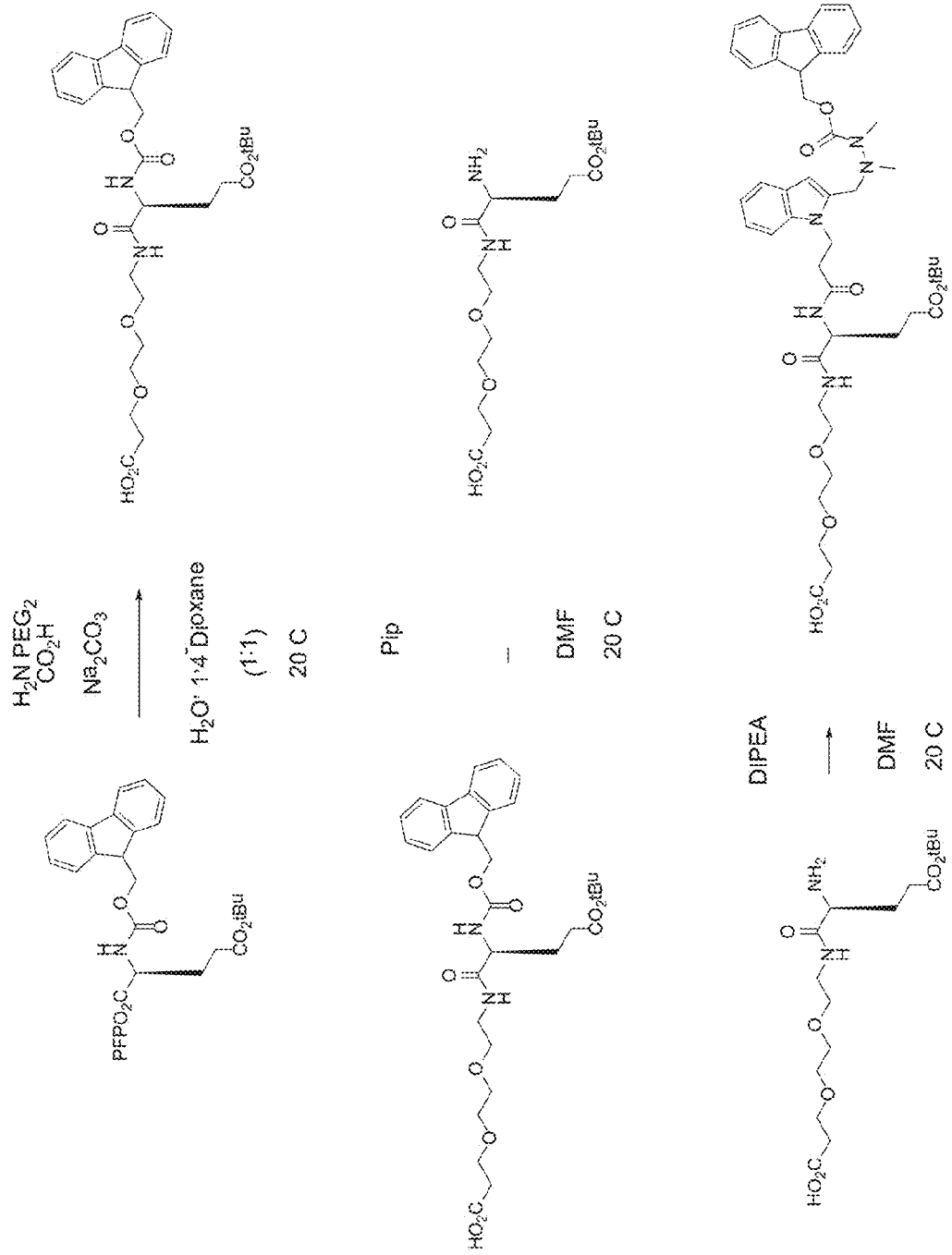
FIG. 5 and FIG. 6 show reaction schemes for the synthesis of compound HIPS Indole E ($CO_2H$) $PEG_2$ Maytansine according to embodiments of the present disclosure, see e.g., Example 2.
Figure 6:
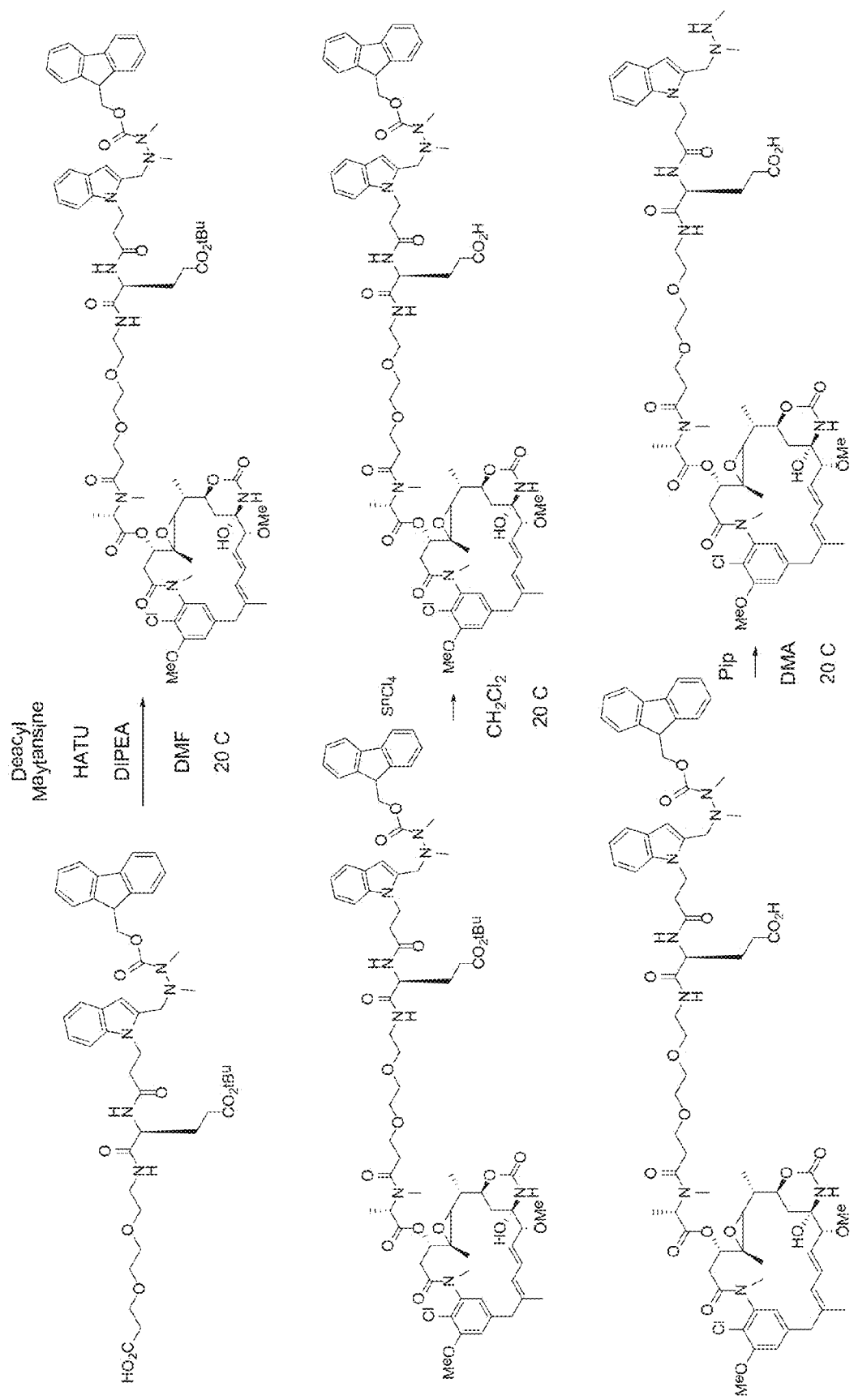

Reaction schemes for the synthesis of compound HIPS Indole E (CO₂H) PEG₂ Maytansine are shown in FIG. 5 and FIG. 6.

Preparation of (S)-5-(3-(tert-butoxy)-3-oxopropyl)-1-(9H-fluoren-9-yl)-3,6-dioxo-2,10,13-trioxa-4,7-diazahexadecan-16-oic acid (FMOC E (CO₂tBu) PEG₂CO₂H) (FIG. 5)

Prepared as in Method 1. HPLC retention time 12.260 min. Method A.

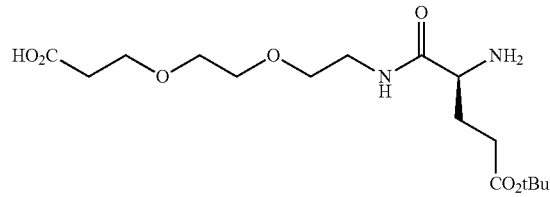 [SMILES: CC(C)(C)OC(=O)CC[C@H](N)C(=O)NCCOCCOCCC(=O)O]

Preparation of (S)-7-amino-2,2-dimethyl-4,8-dioxo-3,12,15-trioxa-9-azaoctadecan-18-oic acid (E (CO₂tBu) PEG₂ CO₂H) (Compound 8) (FIG. 5)

To a dried 20 mL glass scintillation vial containing a dried flea stir bar was added FMOC E (CO₂tBu) PEG₂ CO₂H (2638.7 mg, 4.5 mmol). Piperidine (1921.4 mg, 2.229 mL, 22.6 mmol) in DMF (8.871 mL) was added by syringe. The solution was stirred at room temperature for 20 min, giving a large amount of white precipitate. The reaction was filtered, adsorbed directly onto a Biotage KP C18 HS 12 g samplet (×2), and purified on a Biotage KP C18 HS 60 g cartridge (×2) using a gradient of 0-100% CH₃CN in H₂O, giving the desired product as a colorless, viscous oil (813.1 mg, 50% yield). HPLC retention time 5.480 min. Method A.

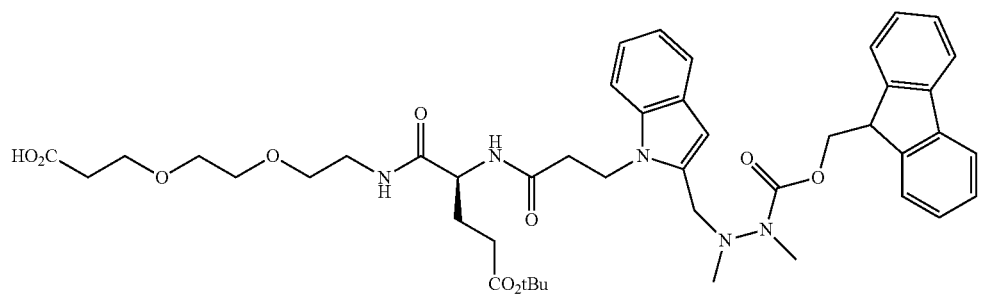 [SMILES: CN(Cc1cc2ccccc2n1CCC(=O)N[C@@H](CCC(=O)OC(C)(C)C)C(=O)NCCOCCOCCC(=O)O)N(C)C(=O)OCC1c2ccccc2-c2ccccc21]

Preparation of (S)-7-(3-(2-((2-(((9H-fluoren-9-yl)methoxy)carbonyl)-1,2-dimethylhydrazinyl)methyl)-1H-indol-1-yl)propanamido)-2,2-dimethyl-4,8-dioxo-3,12,15-trioxa-9-azaoctadecan-18-oic acid (FMOC HIPS Indole E (CO$_2$tBu) PEG$_2$ CO$_2$H) (Compound 9) (FIG. 5)

To a 20 mL glass scintillation vial containing a pea stir bar was added E (CO$_2$tBu) PEG$_2$ CO$_2$H (582.4 mg, 1.6 mmol), FMOC HIPS Indole CO$_2$PFP (1253.7 mg, 1.9 mmol), DIPEA (623.1 mg, 839.8 uL, 4.8 mmol), and anhydrous DMF (5 mL). The solution was stirred at room temperature for 2 h, adsorbed directly onto a Biotage KP C18 HS 12 g samplet, and purified on a Biotage KP C18 HS 60 g cartridge using a gradient of 0-100% CH$_3$CN in H$_2$O, giving the title compound as a waxy solid (406.3 mg, 31% yield). HPLC retention time 4.037 min. Method B.

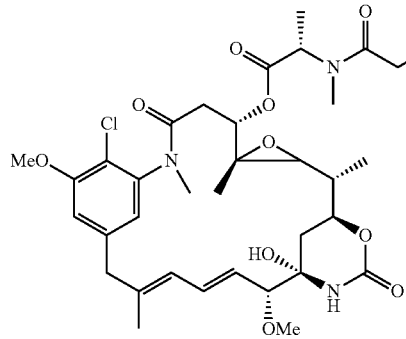
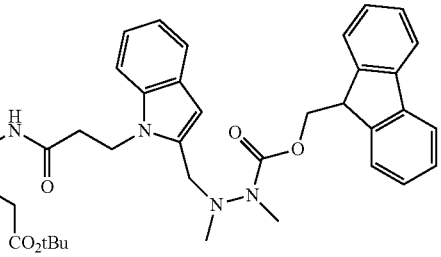

Preparation of (2S,15S)-18-tert-butyl 1-((S)-3-maytansinyl) 15-(3-(2-((2-(((9H-fluoren-9-yl)methoxy)carbonyl)-1,2-dimethylhydrazinyl)methyl)-1H-indol-1-yl)propanamido)-2,3-dimethyl-4,14-dioxo-7,10-dioxa-3,13-diazaoctadecane-1,18-dioate (FMOC HIPS Indole E (CO$_2$tBu) PEG$_2$ Maytansine) (Compound 10) (FIG. 6)

To a dried 4 mL glass scintillation vial containing a dried flea stir bar was added FMOC HIPS Indole E (CO$_2$tBu) PEG$_2$ CO$_2$H (289.8 mg, 0.4 mmol), HATU (133.7 mg, 0.4 mmol), and anhydrous DMF (1 mL). The clear, colorless solution was stirred at room temperature for 15 min. Deacyl maytansine (227.5 mg, 0.4 mmol), DIPEA (135.7 mg, 182.9 uL, 1.1 mmol), and anhydrous DMF (1 mL) were combined in a separate, dried 4 mL glass scintillation vial and added dropwise, slowly, to the stirring solution. The reaction was allowed to stir at room temperature for 2 h, adsorbed directly onto a Biotage KP C18 HS 3 g samplet, and purified on a Biotage KP C18 HS 30 g cartridge using a gradient of 0-100% CH$_3$CN in H$_2$O, giving the desired product as a white solid (268.4 mg, 53% yield). HPLC retention time 13.833 min. Method A.

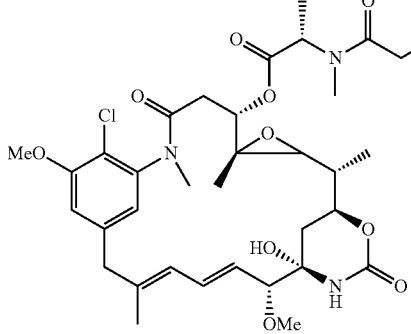
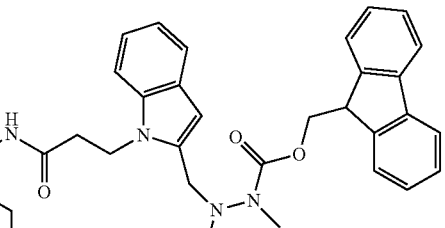

Preparation of (2S,15S)-15-(3-(2-((2-(((9H-fluoren-9-yl)methoxy)carbonyl)-1,2-dimethylhydrazinyl)methyl)-1H-indol-1-yl)propanamido)-1-((S)-3-maytansinyl)-2,3-dimethyl-1,4,14-trioxo-7,10-dioxa-3,13-diazaoctadecan-18-oic acid (FMOC HIPS Indole E (CO$_2$H) PEG$_2$ Maytansine) (FIG. 6)

Prepared as in Method 1. HPLC retention time 13.833 min. Method A.

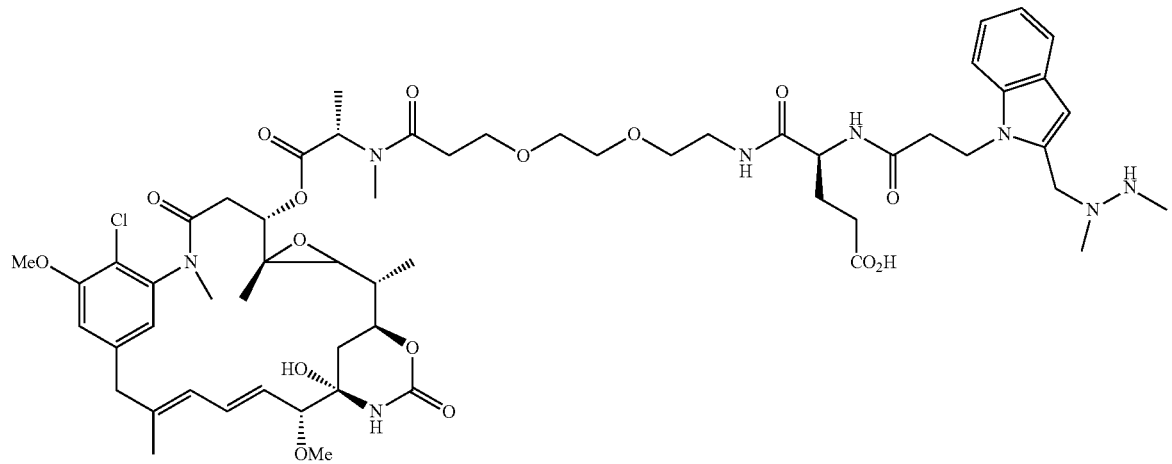

Preparation of (2S,15S)-1-((S)-3-maytansinyl)-15-(3-(2-((1,2-dimethylhydrazinyl)methyl)-1H-indol-1-yl)propanamido)-2,3-dimethyl-1,4,14-trioxo-7,10-dioxa-3,13-diazaoctadecan-18-oic acid (HIPS Indole E (CO$_2$H) PEG$_2$ Maytansine) (FIG. 6)

Prepared as in Method 1. HPLC retention time 9.372 min. Method A. LRMS (ESI) calcd for $C_{58}H_{82}ClN_8O_{16}$ [M+H]$^+$: 1181.6 found 1181.3.

Example 3

Method 3—Preparation of (2S,15S)-1-((S)-3-maytansinyl) 15-(2-amino-2-oxoethyl)-19-(2-((1,2-dimethylhydrazinyl)methyl)-1H-indol-1-yl)-2,3-dimethyl-4,14,17-trioxo-7,10-dioxa-3,13,16-triazanonadecan-1-oate (HIPS Indole N (CONH$_2$) PEG$_2$ Maytansine) (Acidic Deprotection)

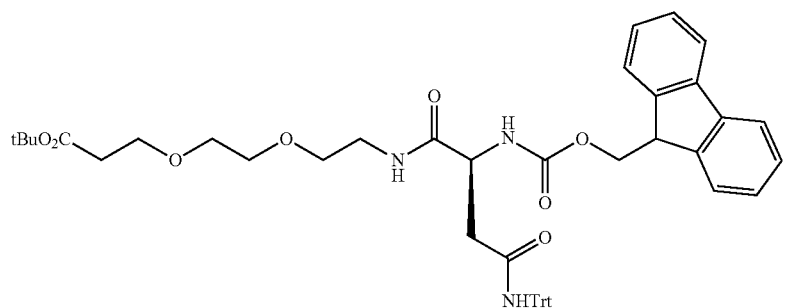

Figure 7:
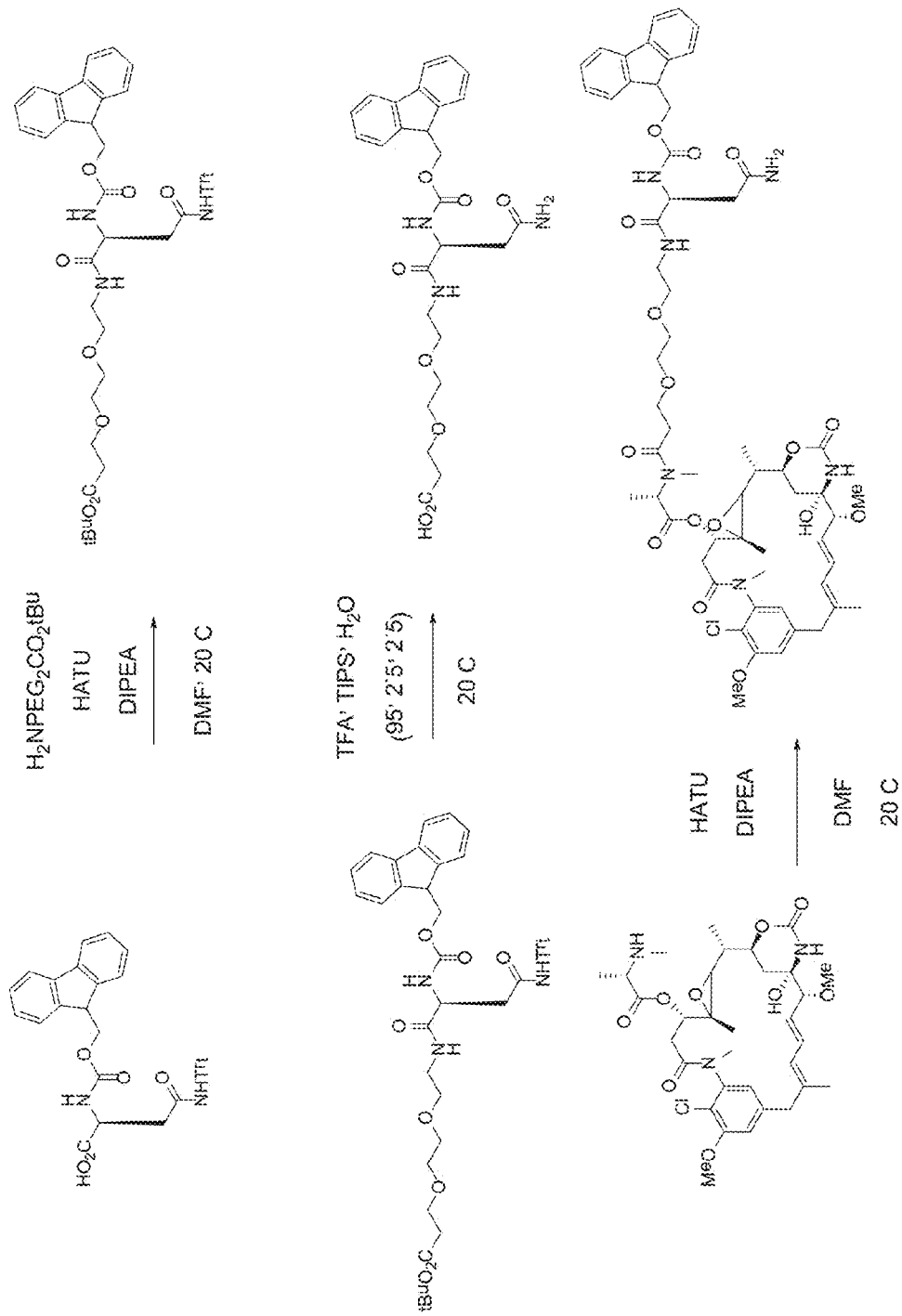
FIG. 7 and FIG. 8 show reaction schemes for the synthesis of compound HIPS Indole N ($CONH_2$) $PEG_2$ Maytansine according to embodiments of the present disclosure, see e.g., Example 3.
Figure 8:
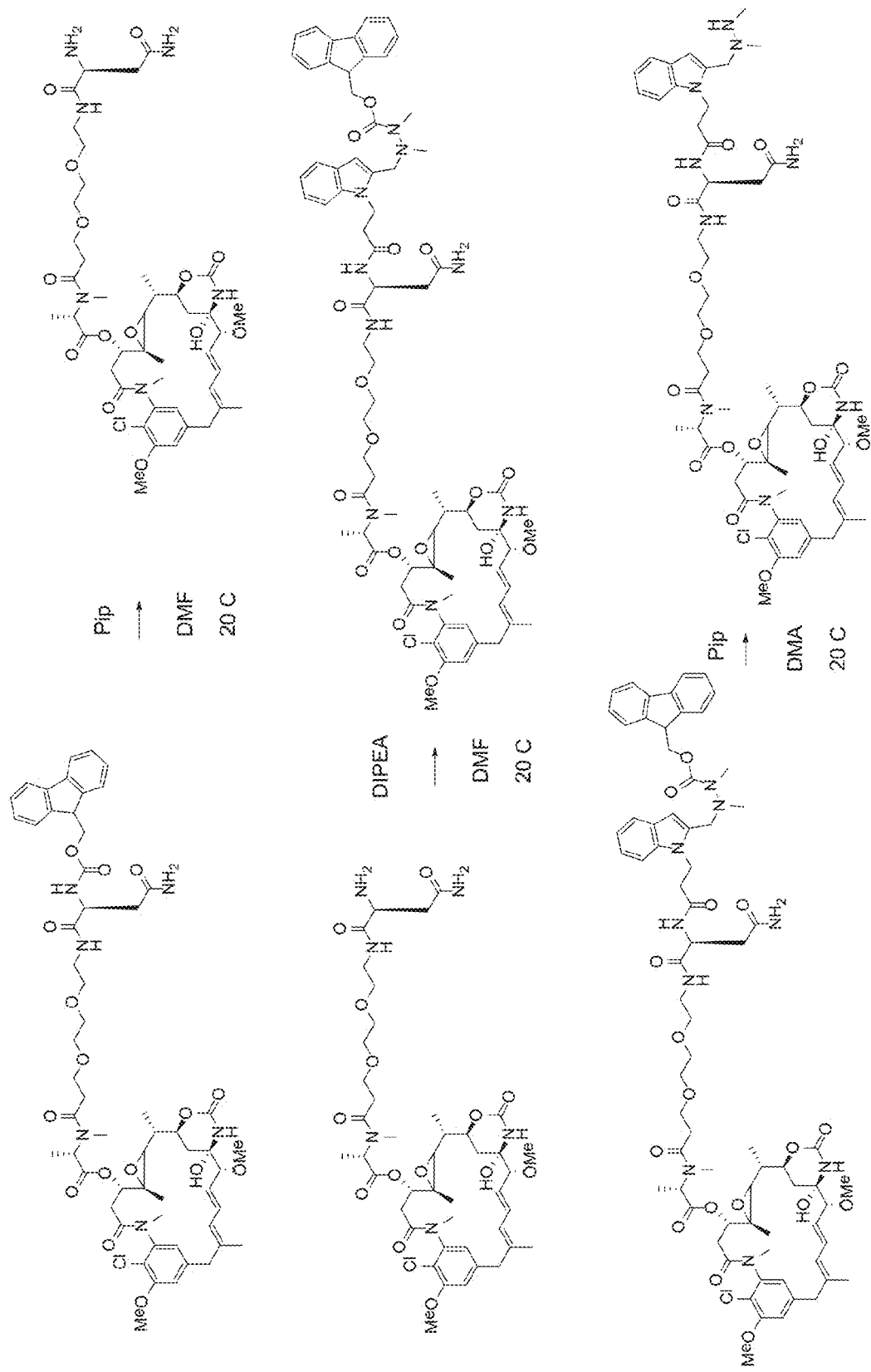

Reaction schemes for the synthesis of compound HIPS Indole N (CONH$_2$) PEG$_2$ Maytansine are shown in FIG. 7 and FIG. 8.

Preparation of (S)-tert-butyl 1-(9H-fluoren-9-yl)-3,6-dioxo-5-(2-oxo-2-(tritylamino)ethyl)-2,10,13-trioxa-4,7-diazahexadecan-16-oate (FMOC N (Trt) PEG$_2$ CO$_2$tBu) (Compound 11) (FIG. 7)

To a dried 20 mL glass scintillation vial containing a dried pea stir bar was added FMOC N (Trt) CO$_2$H (597.0 mg, 1.0 mmol), HATU (380.9 mg, 1.0 mmol), and anhydrous DMF (3 mL). The clear, colorless solution was stirred at room temperature for 15 min. H$_2$N PEG$_2$ CO$_2$tBu (238.2 mg, 1.0 mmol), DIPEA (258.5 mg, 348.4 uL, 2.0 mmol), and anhydrous DMF (3 mL) were combined in a separate, dried 4 mL glass scintillation vial and added dropwise, slowly, to the stirring solution. The reaction was stirred at room temperature for 2 h, added to H$_2$O (100 mL) and 5 M NaCl (25 mL) in a separatory funnel, and extracted with 5×25 mL EtOAc. The organic fractions were combined, washed with 1×25 mL H$_2$O, 1×25 mL 1.2 M NaHCO$_3$, and 1×25 mL 5 M NaCl, dried over Na$_2$SO$_4$, concentrated, adsorbed onto a Biotage KP C18 HS 12 g samplet, and purified on a Biotage KP C18 HS 60 g cartridge using a gradient of 0-100% CH$_3$CN in H$_2$O, giving the title compound as a white, crystalline solid (708.4 mg, 87% yield). HPLC retention time 15.971 min. Method A.

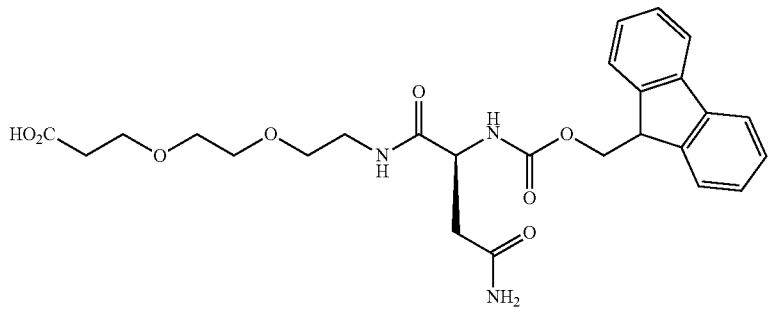 [SMILES: NC(=O)C[C@H](NC(=O)OCC1c2ccccc2-c2ccccc21)C(=O)NCCOCCOCCC(=O)O]

Preparation of (S)-5-(2-amino-2-oxoethyl)-1-(9H-fluoren-9-yl)-3,6-dioxo-2,10,13-trioxa-4,7-diazahexadecan-16-oic acid (FMOC N (CONH$_2$) PEG$_2$ CO$_2$H) (Compound 12) (FIG. 7)

To a 20 mL glass scintillation vial containing a pea stir bar was added a solution of TFA, TIPS, H$_2$O (6.8 ml, 0.2 mL, 0.2 mL). FMOC N (Trt) PEG$_2$ CO$_2$tBu (708.4 mg, 0.9 mmol) was added in small portions and the reaction was stirred at room temperature for 4 h. The solution was evaporated, adsorbed onto a Biotage KP C18 HS 12 g samplet, and purified on a Biotage KP C18 HS 60 g cartridge using a gradient of 0-100% CH$_3$CN in H$_2$O, giving the desired product as a white solid (385.3 mg, 86% yield). HPLC retention time 8.084 min. Method A.

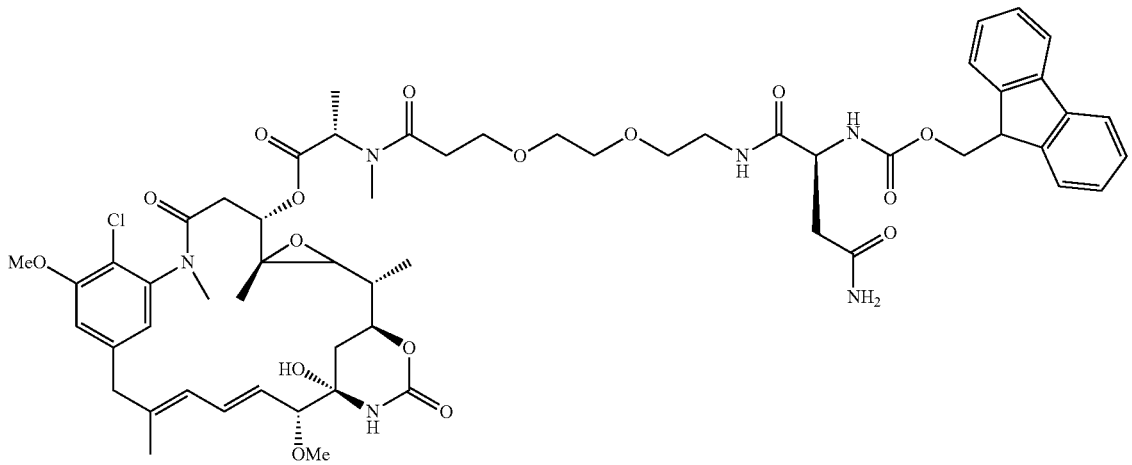

Preparation of (5S,18S)-1-((S)-3-maytansinyl) 5-(2-amino-2-oxoethyl)-1-(9H-fluoren-9-yl)-17,18-dimethyl-3,6,16-trioxo-2,10,13-trioxa-4,7,17-triazanonadecan-19-oate (FMOC N (CONH$_2$) PEG$_2$ Maytansine) (Compound 13) (FIG. 7)

To a dried 4 mL glass scintillation vial containing a dried flea stir bar was added FMOC N (CONH$_2$) PEG$_2$ CO$_2$H (98.6 mg, 0.2 mmol), HATU (72.9 mg, 0.2 mmol), and anhydrous DMF (1 mL). The clear, colorless solution was stirred at room temperature for 15 min. Deacyl maytansine (122.1 mg, 0.2 mmol), DIPEA (72.8 mg, 98.1 uL, 0.6 mmol), and anhydrous DMF (1 mL) were combined in a separate, dried 4 mL glass scintillation vial and added dropwise, slowly, to the stirring solution. The reaction was allowed to stir at room temperature for 2 h, adsorbed directly onto a Biotage KP C18 HS 3 g samplet, and purified on a Biotage KP C18 HS 30 g cartridge using a gradient of 0-100% CH$_3$CN in H$_2$O, giving the title compound as a white solid (149.1 mg, 69% yield). HPLC retention time 11.569 min. Method A.

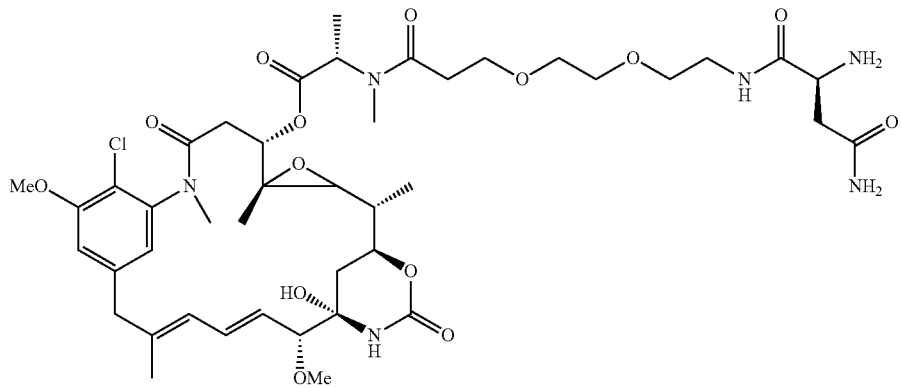

Preparation of (2S,15S)-1-((S)-3-maytansinyl) 15,17-diamino-2,3-dimethyl-4,14,17-trioxo-7,10-dioxa-3,13-diazaheptadecan-1-oate (N (CONH$_2$) PEG$_2$ Maytansine) (Compound 14) (FIG. 8)

To a dried 20 mL glass scintillation vial containing a dried flea stir bar was added FMOC N (CONH$_2$) PEG$_2$ Maytansine (149.1 mg, 0.1 mmol). Piperidine (221.6 mg, 0.26 mL) in DMF (1.03 mL) was added by syringe. The solution was stirred at room temperature for 20 min, adsorbed directly onto a Biotage KP C18 HS 3 g samplet, and purified on a Biotage KP C18 HS 30 g cartridge using a gradient of 0-100% CH$_3$CN in H$_2$O, giving the desired product as a white solid (115.0 mg, 96% yield). HPLC retention time 8.154 min. Method A.

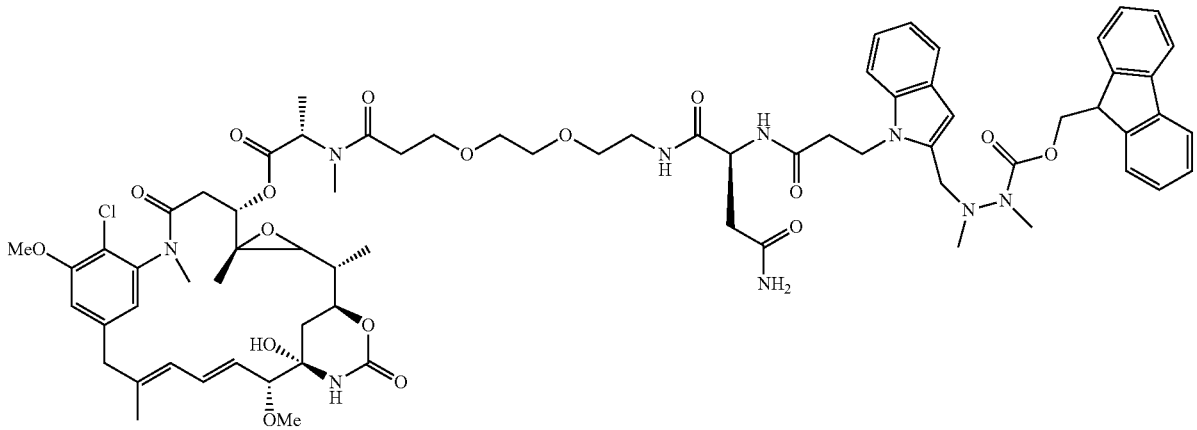

Preparation of (2S,15S)-1-((S)-3-maytansinyl) 19-(2-((2-(((9H-fluoren-9-yl)methoxy)carbonyl)-1,2-dimethylhydrazinyl)methyl)-1H-indol-1-yl)-15-(2-amino-2-oxoethyl)-2,3-dimethyl-4,14,17-trioxo-7,10-dioxa-3,13,16-triazanonadecan-1-oate (FMOC HIPS Indole N (CONH$_2$) PEG$_2$ Maytansine) (Compound 15) (FIG. 8)

To a dried 4 mL glass scintillation vial containing a dried flea stir bar was added N (CONH$_2$) PEG$_2$ Maytansine (115.0 mg, 0.1 mmol), FMOC HIPS Indole CO$_2$PFP (86.1 mg, 0.1 mmol), DIPEA (32.3 mg, 43.5 uL, 0.3 mmol), and anhydrous DMF (1 mL). The solution was stirred at room temperature for 2 h, adsorbed directly onto a Biotage KP C18 HS 3 g samplet, and purified on a Biotage KP C18 HS 30 g cartridge using a gradient of 0-100% CH$_3$CN in H$_2$O, giving the title compound as a very pale yellow solid (143.3 mg, 83% yield). HPLC retention time 13.557 min. Method A.

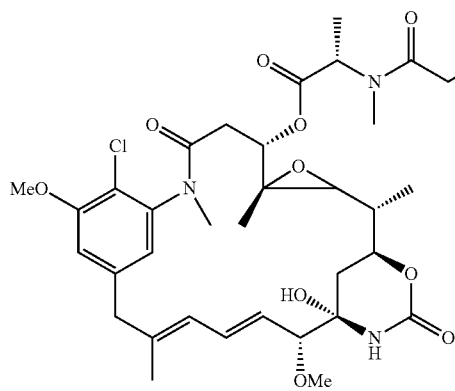
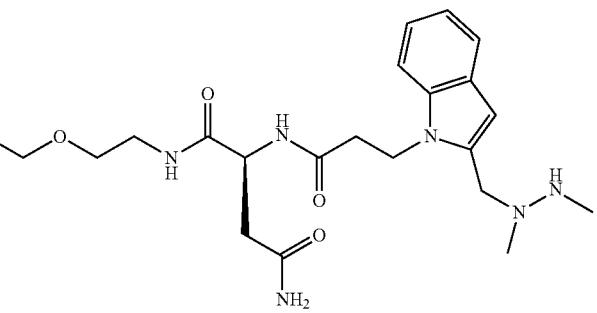

Preparation of (2S,15S)-1-((S)-3-maytansinyl) 15-(2-amino-2-oxoethyl)-19-(2-((1,2-dimethylhydrazinyl)methyl)-1H-indol-1-yl)-2,3-dimethyl-4,14,17-trioxo-7,10-dioxa-3,13,16-triazanonadecan-1-oate (HIPS Indole N (CONH$_2$) PEG$_2$ Maytansine) (Compound 16) (FIG. 8)

To a dried 4 mL glass scintillation vial containing a dried flea stir bar was added FMOC HIPS Indole N (CONH$_2$) PEG$_2$ Maytansine (83.3 mg, 0.1 mmol). Piperidine (102.1 mg, 0.118 mL, 1.2 mmol) in DMA (0.474 mL) was added by syringe. The solution was stirred at room temperature for 20 min, adsorbed directly onto a Biotage KP C18 HS 1.2 g samplet, and purified on a Biotage KP C18 HS 12 g cartridge using a gradient of 0-100% CH$_3$CN in H$_2$O, giving the desired product as a white solid (38.8 mg, 55% yield). HPLC retention time 9.084 min. Method A. LRMS (ESI) calcd for C$_{57}$H$_{80}$ClN$_9$NaO$_{15}$ [M+Na]$^+$: 1188.5 found 1188.5.

Example 4

Method 4—Preparation of HIPS Indole Cadaverine Alexa Fluor 555

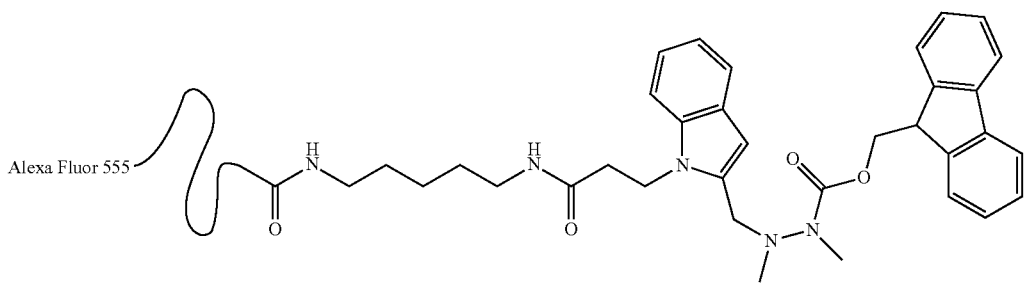 [SMILES: CC(=O)NCCCCCNC(=O)CCn1c(CN(C)N(C)C(=O)OCC2c3ccccc3-c3ccccc32)cc2ccccc21]

Figure 9:
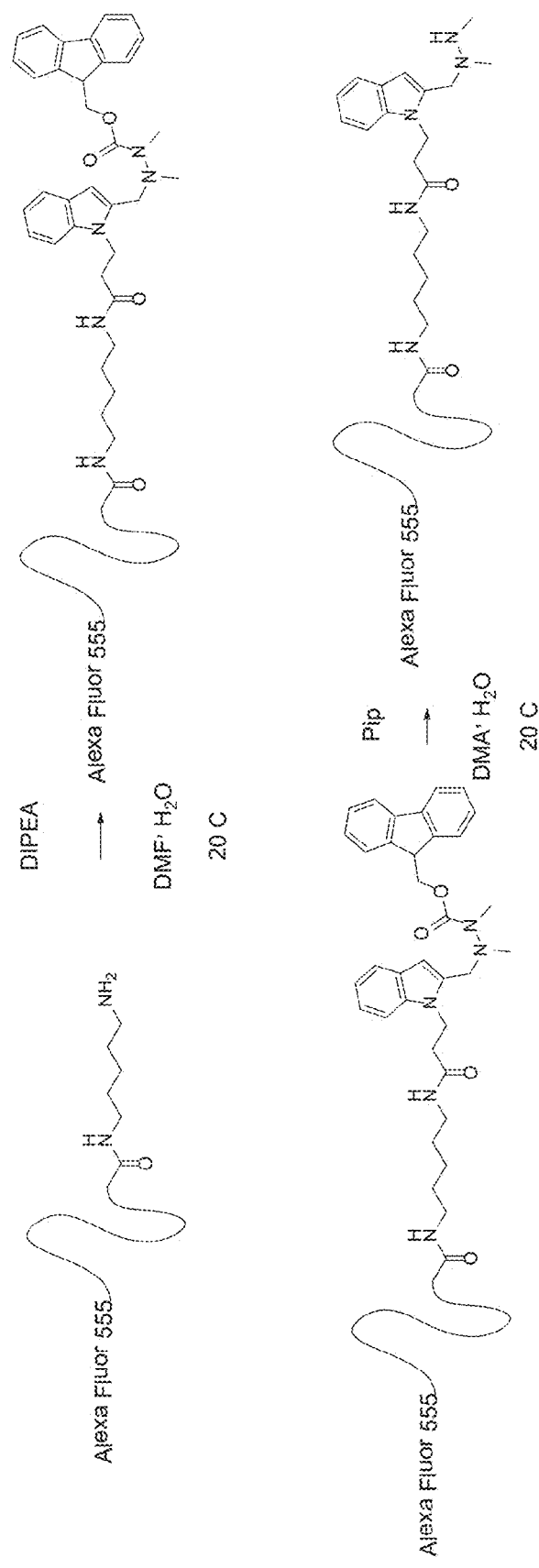
FIG. 9 shows a reaction scheme for the synthesis of compound HIPS Indole Cadaverine Alexa Fluor 555 according to embodiments of the present disclosure, see e.g., Example 4.

A reaction scheme for the synthesis of compound HIPS Indole Cadaverine Alexa Fluor 555 is shown in FIG. 9.

Preparation of (9H-fluoren-9-yl)methyl 2-((1-(3-((5-(carboxamido)pentyl)amino)-3-oxopropyl)-1H-indol-2-yl)methyl)-1,2-dimethylhydrazinecarboxylate Alexa Fluor 555 (FMOC HIPS Indole Cadaverine Alexa Fluor 555) (Compound 17) (FIG. 9)

To a 4 mL glass scintillation vial containing a flea stir bar was added Alexa Fluor 555 Cadaverine (8 mg, 0.01 mmol) in DMF, $H_2O$ (285 uL, 15 uL), FMOC HIPS Indole $CO_2$PFP (36.1 mg, 0.06 mmol), and DIPEA (5.4 mg, 7.3 uL, 0.04 mmol). The reaction was stirred at room temperature for 2 h, adsorbed directly onto a Biotage KP C18 HS 1.2 g samplet, and purified on a Biotage KP C18 HS 12 g cartridge using a gradient of 0-100% $CH_3CN$ in $H_2O$, giving the title compound as a purplish red film (11.8 mg, 99% yield). HPLC retention time 6.092 min. Method A.

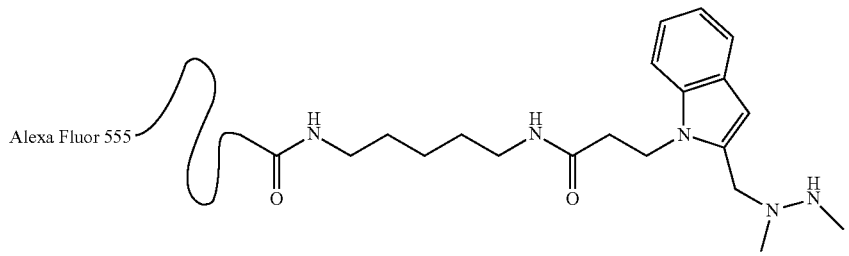 [SMILES: CNN(C)Cc1cc2ccccc2n1CCC(=O)NCCCCCNC(C)=O]

Preparation of N-(5-carboxamidopentyl)-3-(2-((1,2-dimethylhydrazinyl)methyl)-1H-indol-1-yl)propanamide Alexa Fluor 555 (HIPS Indole Cadaverine Alexa Fluor 555) (Compound 18) (FIG. 9)

To a 4 mL glass scintillation vial containing a flea stir bar was added FMOC HIPS Indole Cadaverine Alexa Fluor 555 (22.1 mg, 0.02 mmol). Piperidine (51.7 mg, 0.06 mL, 0.6 mmol) in DMA, $H_2O$ (228 uL, 12 uL) was added by syringe. The solution was stirred at room temperature for 20 min, adsorbed directly onto a Biotage KP C18 HS 1.2 g samplet, and purified on a Biotage KP C18 HS 12 g cartridge using a gradient of 0-100% $CH_3CN$ in $H_2O$, giving the desired product as a purplish red film (18.4 mg, 99% yield). HPLC retention time 5.085 min. Method A.

Example 5

Method 5—Preparation of (S)-1-carboxamido-13-(3-(2-((1,2-dimethylhydrazinyl)methyl)-1H-indol-1-yl)propanamido)-1,12-dioxo-5,8-dioxa-2,11-diazahexadecan-16-oic acid ATTO 550 (HIPS Indole E ($CO_2H$) $PEG_2$ NH ATTO 550)

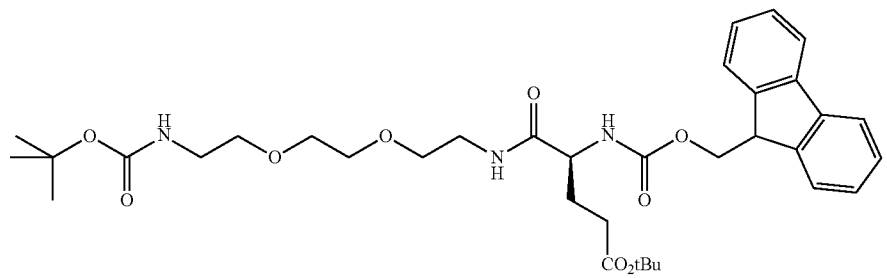 [SMILES: CC(C)(C)OC(=O)CC[C@H](NC(=O)OCC1c2ccccc2-c2ccccc21)C(=O)NCCOCCOCCNC(=O)OC(C)(C)C]

Figure 10:
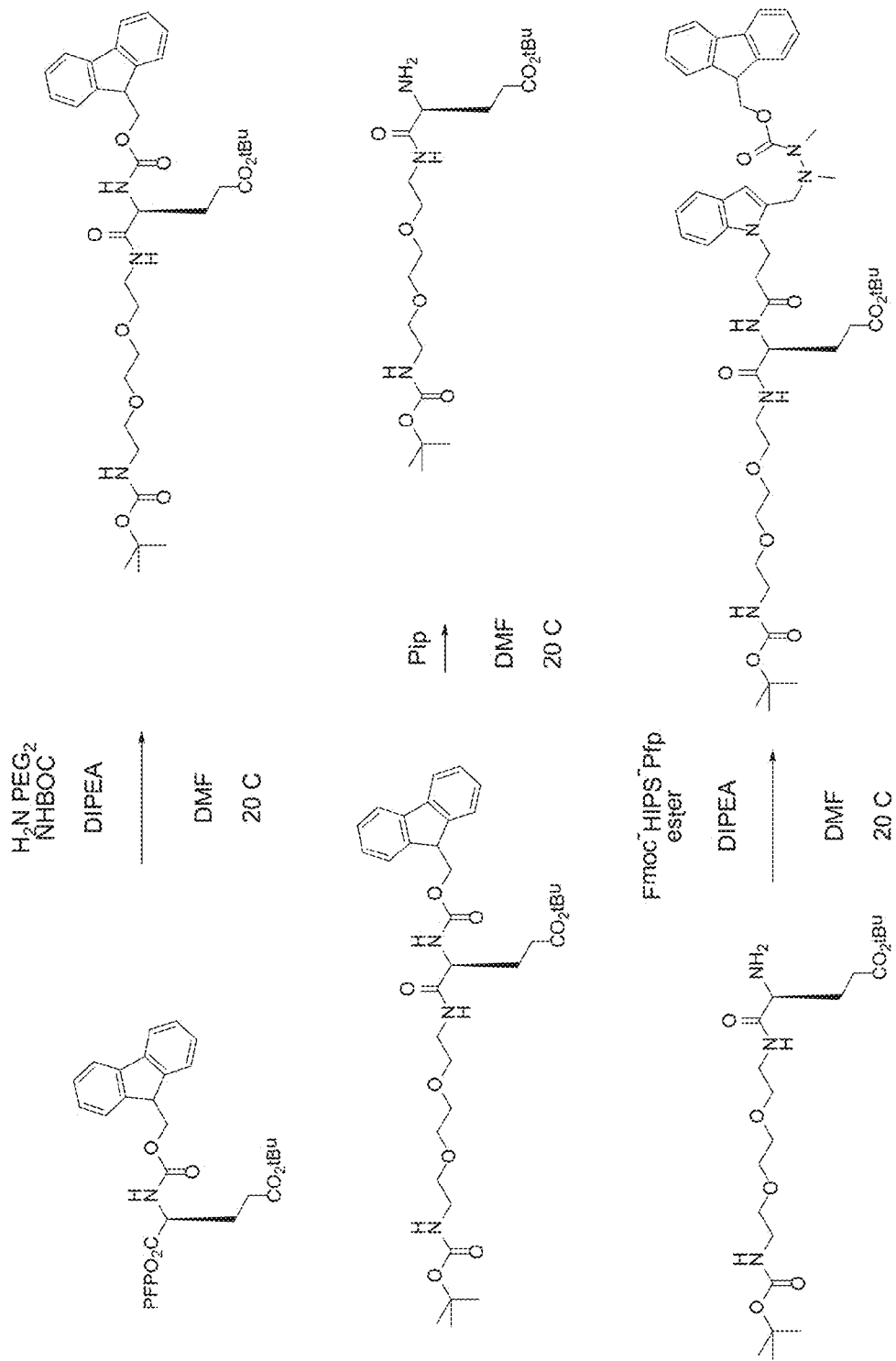
FIG. 10 and FIG. 11 show reaction schemes for the synthesis of compound HIPS Indole E ($CO_2H$) $PEG_2$ NH ATTO 550 according to embodiments of the present disclosure, see e.g., Example 5.
Figure 11:
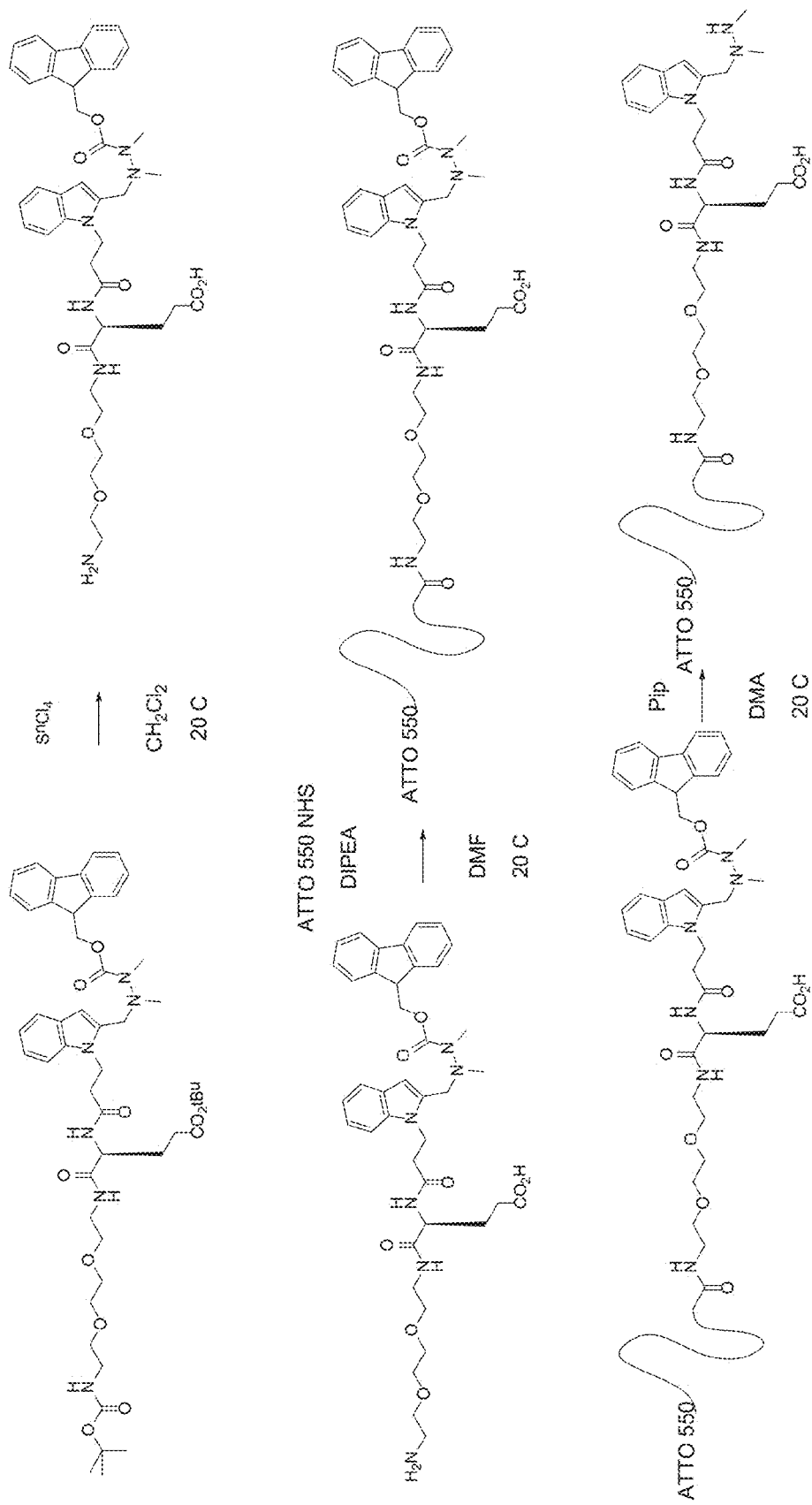

Reaction schemes for the synthesis of compound HIPS Indole E (CO₂H) PEG₂ NH ATTO 550 are shown in FIG. 10 and FIG. 11.

Preparation of (S)-tert-butyl 16-((((9H-fluoren-9-yl)methoxy)carbonyl)amino)-2,2-dimethyl-4,15-dioxo-3,8,11-trioxa-5,14-diazanonadecan-19-oate (FMOC E (CO₂tBu) PEG₂ NHBOC) (Compound 19) (FIG. 10)

To a dried 4 mL glass scintillation vial containing a dried flea stir bar was added N-α-Fmoc-L-glutamic acid γ-tert-butyl ester pentafluorophenyl ester (296.2 mg, 0.5 mmol), H₂N PEG₂ NHBOC (124.5 mg, 0.5 mmol), DIPEA (129.2 mg, 174.2 uL, 1.0 mmol), and anhydrous DMF (0.5 mL). The clear, colorless solution was stirred at room temperature for 2 h, diluted with H₂O (8 mL) and 5 M NaCl (2 mL), and extracted with 3×5 mL EtOAc. The organic fractions were washed with 1×5 mL H₂O, 1×5 mL 1.2 M NaHCO₃, and 1×5 mL 5 M NaCl, dried over Na₂SO₄, concentrated, adsorbed onto a Biotage KP C18 HS 3 g samplet, and purified on a Biotage KP C18 HS 30 g cartridge using a gradient of 0-100% CH₃CN in H₂O, giving the title compound as a white, crystalline solid (253.9 mg, 77% yield). HPLC retention time 14.333 min. Method A.

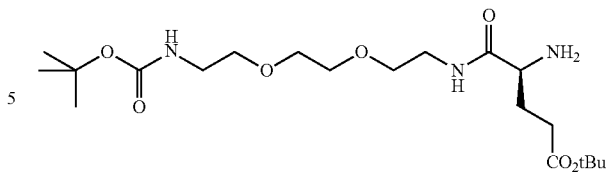

Preparation of (S)-tert-butyl 16-amino-2,2-dimethyl-4,15-dioxo-3,8,11-trioxa-5,14-diazanonadecan-19-oate (E (CO₂tBu) PEG₂ NHBOC) (Compound 20) (FIG. 10)

To a dried 20 mL glass scintillation vial containing a dried flea stir bar was added FMOC E (CO₂tBu) PEG₂ NHBOC (253.9 mg, 0.4 mmol). Piperidine (659.4 mg, 0.765 mL 7.7 mmol) in DMF (3.1 mL) was added by syringe. The solution was stirred at room temperature for 20 min, adsorbed directly onto a Biotage KP C18 HS 12 g samplet, and purified on a Biotage KP C18 HS 60 g cartridge using a gradient of 0-100% CH₃CN in H₂O, giving the desired product as a colorless solid (165.7 mg, 99% yield). HPLC retention time 7.599 min. Method A.

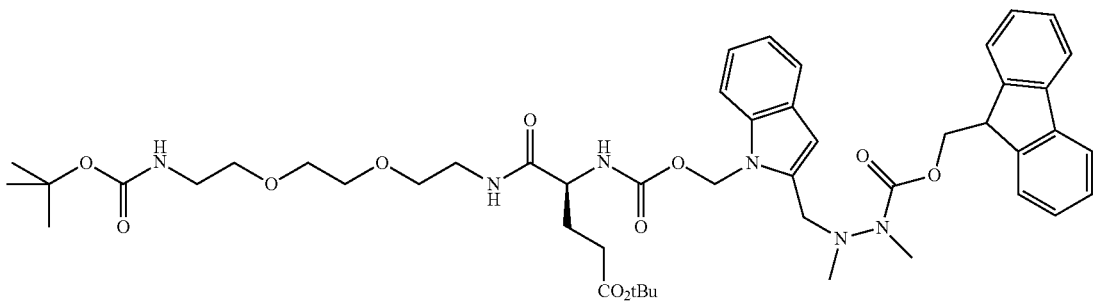 [SMILES: CN(Cc1cc2ccccc2n1COC(=O)N[C@@H](CCC(=O)OC(C)(C)C)C(=O)NCCOCCOCCNC(=O)OC(C)(C)C)N(C)C(=O)OCC1c2ccccc2-c2ccccc21]

Preparation of (S)-tert-butyl 16-(3-(2-((2-(((9H-fluoren-9-yl)methoxy)carbonyl)-1,2-dimethylhydrazinyl)methyl)-1H-indol-1-yl)propanamido)-2,2-dimethyl-4,15-dioxo-3,8,11-trioxa-5,14-diazanonadecan-19-oate (FMOC HIPS Indole E (CO₂tBu) PEG₂ NHBOC) (Compound 21) (FIG. 10)

To a dried 4 mL glass scintillation vial containing a dried flea stir bar was added E (CO₂tBu) PEG₂ NHBOC (64.8 mg, 0.15 mmol), FMOC HIPS Indole CO₂PFP (98.4 mg, 0.15 mmol), DIPEA (58.0 mg, 78.2 uL, 0.45 mmol), and anhydrous DMF (0.3 mL). The solution was stirred at room temperature for 2 h, adsorbed directly onto a Biotage KP C18 HS 1.2 g samplet, and purified on a Biotage KP C18 HS 12 g cartridge using a gradient of 0-100% CH₃CN in H₂O, giving the title compound as a colorless solid (83.4 mg, 62% yield). HPLC retention time 16.054 min. Method A.

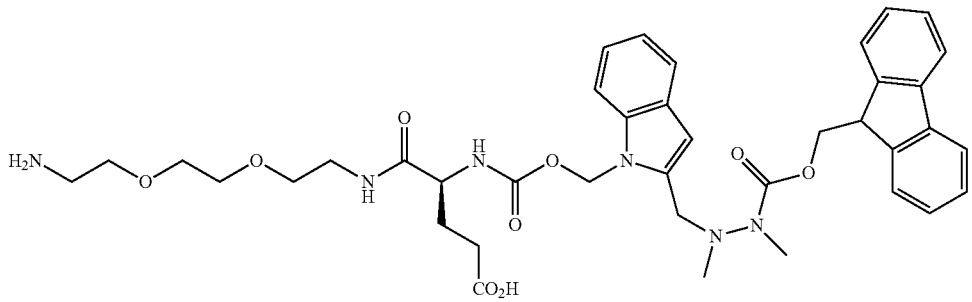 [SMILES: CN(Cc1cc2ccccc2n1COC(=O)N[C@@H](CCC(=O)O)C(=O)NCCOCCOCCN)N(C)C(=O)OCC1c2ccccc2-c2ccccc21]

Preparation of (S)-4-(3-(2-((2-(((9H-fluoren-9-yl)methoxy)carbonyl)-1,2-dimethylhydrazinyl)methyl)-1H-indol-1-yl)propanamido)-5-((2-(2-(2-aminoethoxy)ethoxy)ethyl)amino)-5-oxopentanoic acid (FMOC HIPS Indole E (CO₂H) PEG₂ NH₂) (Compound 22) (FIG. 11)

To a dried 4 mL glass scintillation vial containing a dried flea stir bar was added FMOC HIPS Indole E (CO₂tBu) PEG₂ NHBOC (83.4 mg, 0.1 mmol) and anhydrous CH₂Cl₂ (1 mL). The solution was cooled to 0° C. in an ice, H₂O bath and SnCl₄ (0.928 mL, 0.928 mmol, 1.0 M solution in anhydrous CH₂Cl₂) was added dropwise by syringe, giving a pale yellow precipitate. The solution was stirred at 0° C. for 5 min, whereupon the ice, H₂O bath was removed and the solution warmed to room temperature. The reaction was stirred for 1 h, adsorbed directly onto a Biotage KP C18 HS 3 g samplet, and purified on a Biotage KP C18 HS 30 g cartridge using a gradient of 0-100% CH₃CN in H₂O, giving the desired product as a white film (36.2 mg, 52% yield). HPLC retention time 10.380 min. Method A.

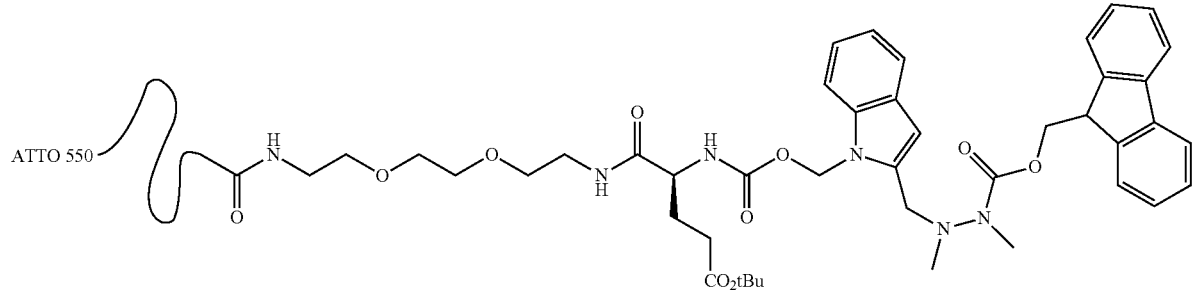 [SMILES: CC(=O)NCCOCCOCCNC(=O)[C@H](CCC(=O)OC(C)(C)C)NC(=O)OCn1c(CN(C)N(C)C(=O)OCC2c3ccccc3-c3ccccc32)cc2ccccc21]

Preparation of (S)-13-(3-(2-((2-(((9H-fluoren-9-yl)methoxy)carbonyl)-1,2-dimethylhydrazinyl)methyl)-1H-indol-1-yl)propanamido)-1-carboxamido-1,12-dioxo-5,8-dioxa-2,11-diazahexadecan-16-oic acid ATTO 550 (FMOC HIPS Indole E (CO₂H) PEG₂ NH ATTO 550) (Compound 23) (FIG. 11)

To a dried 4 mL glass scintillation vial containing a dried flea stir bar was added FMOC HIPS Indole E (CO₂H) PEG₂ NH₂ (5.3 mg, 7.1 umol), ATTO 550 NHS (5.0 mg, 6.3 umol), DIPEA (2.5 mg, 3.4 uL, 19.3 umol), and anhydrous DMF (0.3 mL). The solution was stirred at room temperature for 2 h, adsorbed directly onto a Biotage SNAP Ultra 1 g samplet, and purified on a Biotage SNAP Ultra 10 g cartridge using a step gradient of 0% MeOH (0.1% AcOH) in CH₂Cl₂ (0.1% AcOH) to 10% MeOH (0.1% AcOH) in CH₂Cl₂ (0.1% AcOH), giving the title compound as a purplish red film (4.9 mg, 54% yield). TLC $R_f$ (SiO₂) 0.308 (10% MeOH, 0.1% AcOH, 89.9% CH₂Cl₂).

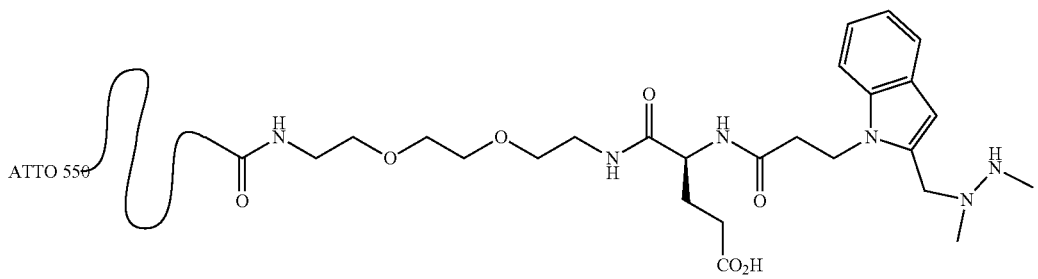 [SMILES: CNN(C)Cc1cc2ccccc2n1CCC(=O)N[C@@H](CCC(=O)O)C(=O)NCCOCCOCCNC(C)=O]

Preparation of (S)-1-carboxamido-13-(3-(2-((1,2-dimethylhydrazinyl)methyl)-1H-indol-1-yl)propanamido)-1,12-dioxo-5,8-dioxa-2,11-diazahexadecan-16-oic acid ATTO 550 (HIPS Indole E ($CO_2H$) $PEG_2$ NH ATTO 550) (Compound 24) (FIG. 11)

To a dried 4 mL glass scintillation vial containing a dried flea stir bar was added FMOC HIPS Indole E ($CO_2H$) $PEG_2$ NH ATTO 550 (4.9 mg, 3.4 umol). Piperidine (51.7 mg, 60.0 uL, 0.6 mmol) in DMA (240 uL) was added by syringe. The solution was stirred at room temperature for 20 min, adsorbed directly onto a Biotage KP C18 HS 1.2 g samplet, and purified on a Biotage KP C18 HS 12 g cartridge using a gradient of 0-100% $CH_3CN$ in $H_2O$, giving the desired product as a dark red film (3.2 mg, 78% yield). HPLC retention time 10.568 min, 10.689 min, 10.947 min (mixture of cadaverine isomers).

Example 6

Method 6—Preparation of (R)-1-carboxamido-13-(3-(2-((1,2-dimethylhydrazinyl)methyl)-1H-indol-1-yl)propanamido)-1,12-dioxo-5,8-dioxa-2,11-diazatetradecane-14-sulfonic acid ATTO 550 (HIPS Indole C ($SO_3H$) $PEG_2$ NH ATTO 550)

0.9 mmol), HATU (403.0 mg, 1.1 mmol), DIPEA (252.0 mg, 339.6 uL, 2.0 mmol), and anhydrous DMF (10 mL). The clear, colorless solution was stirred at room temperature for 15 min. $H_2N$ $PEG_2$ NHBOC (258.0 mg, 1.0 mmol) and anhydrous DMF (1 mL) were combined in a separate, dried 4 mL glass scintillation vial and added dropwise, slowly, to the stirring solution. The reaction was stirred at room temperature for 16 h, concentrated, adsorbed onto a Biotage KP C18 HS 12 g samplet, and purified on a Biotage KP C18 HS 100 g cartridge using a gradient of 0-100% $CH_3CN$ in $H_2O$, giving the title compound as a colorless, glassy solid (262.0 mg, 46% yield). HPLC retention time 8.961 min. Method A.

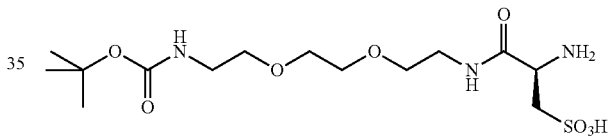

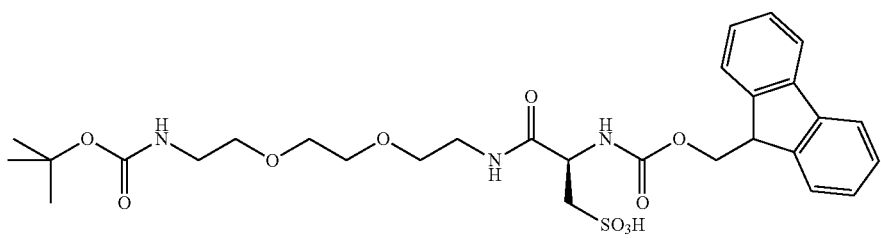 [SMILES: CC(C)(C)OC(=O)NCCOCCOCCNC(=O)[C@H](CS(=O)(=O)O)NC(=O)OCC1c2ccccc2-c2ccccc21]

Figure 12:
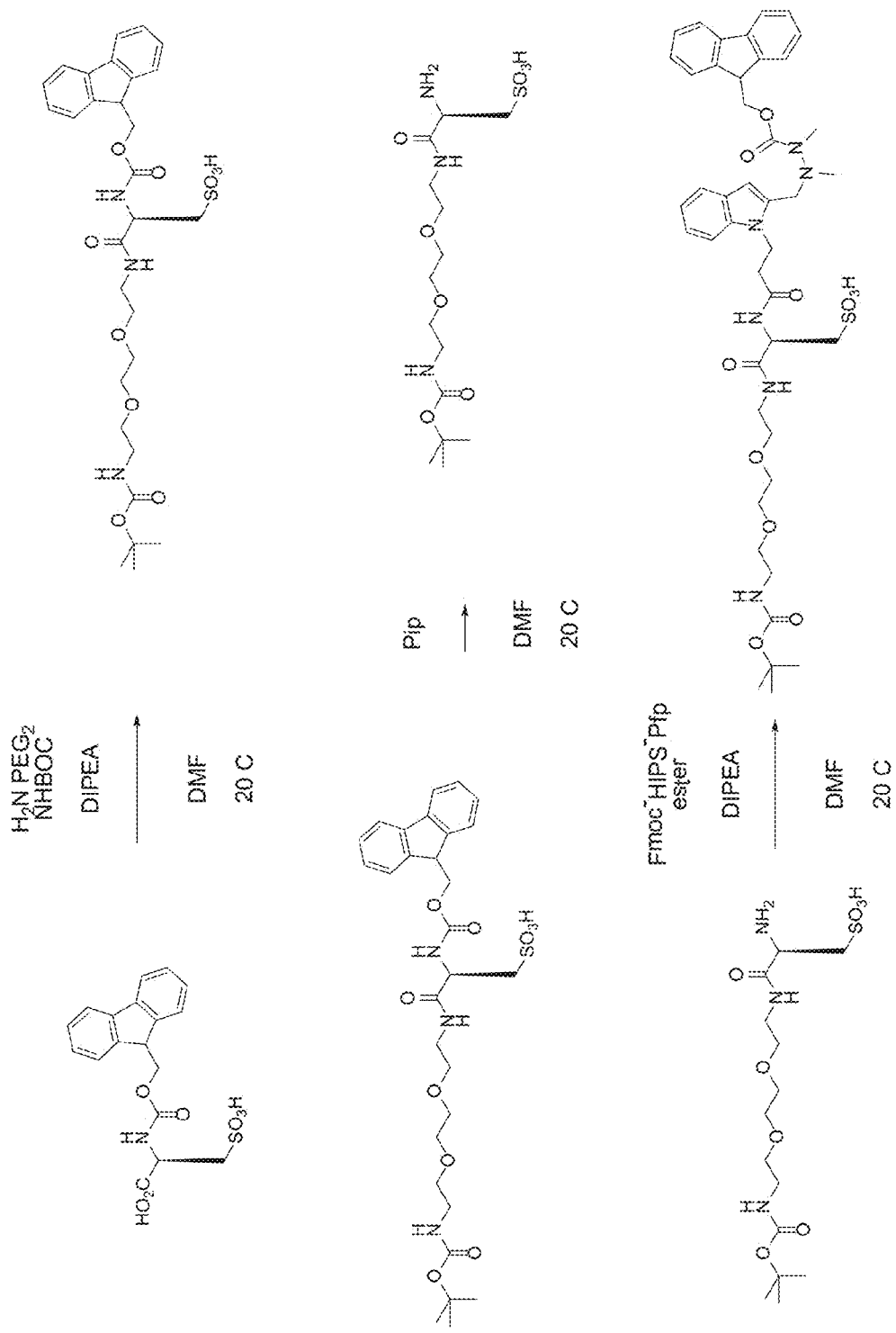
FIG. 12 and FIG. 13 show reaction schemes for the synthesis of compound HIPS Indole C ($SO_3H$) $PEG_2$ NH ATTO 550 according to embodiments of the present disclosure, see e.g., Example 6.
Figure 13:
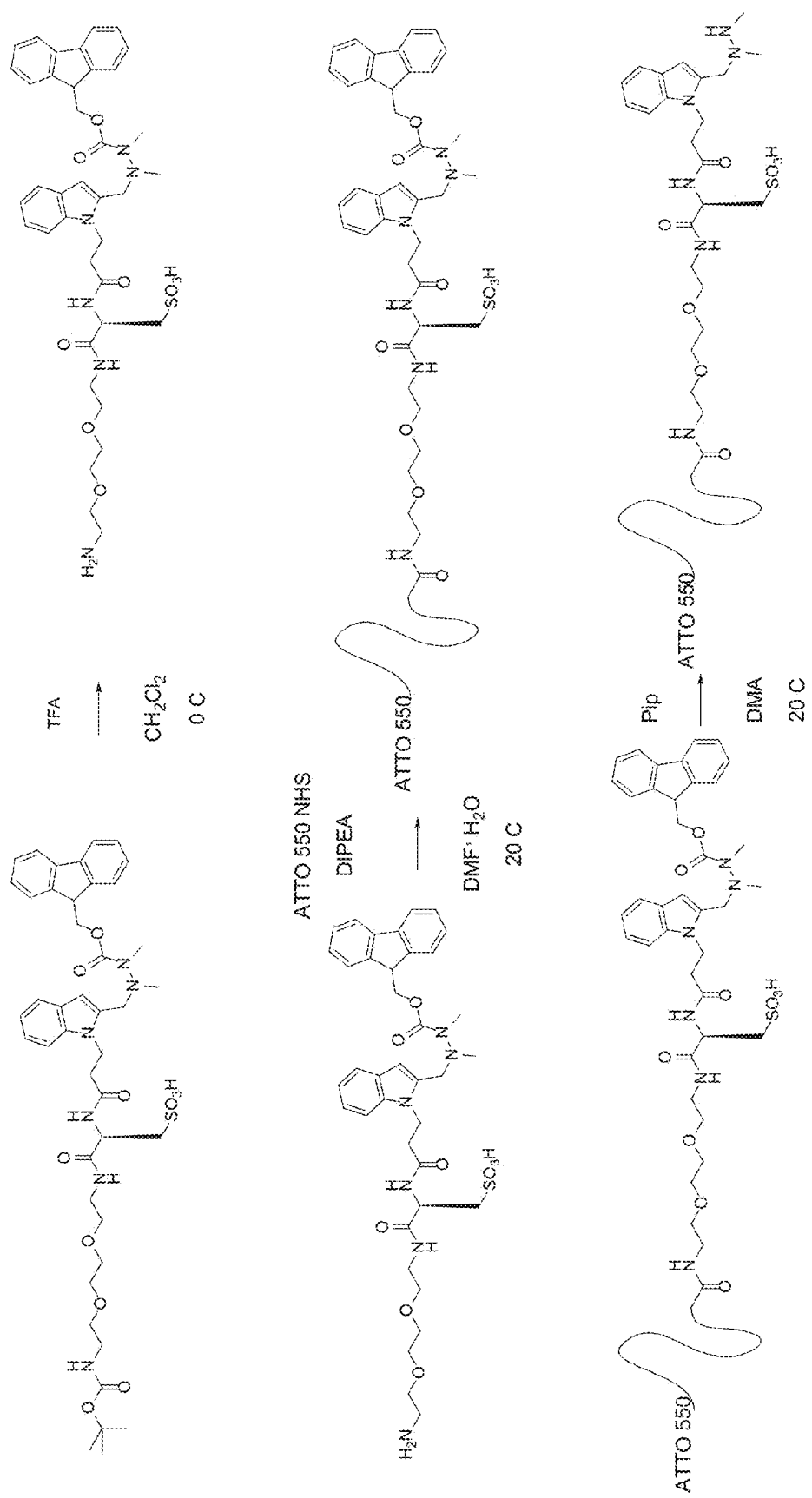

Reaction schemes for the synthesis of compound HIPS Indole C ($SO_3H$) $PEG_2$ NH ATTO 550 are shown in FIG. 12 and FIG. 13.

Preparation of (R)-16-((((9H-fluoren-9-yl)methoxy)carbonyl)amino)-2,2-dimethyl-4,15-dioxo-3,8,11-trioxa-5,14-diazaheptadecane-17-sulfonic acid (FMOC C ($SO_3H$) $PEG_2$ NHBOC) (FIG. 12)

To a dried 20 mL glass scintillation vial containing a dried pea stir bar was added FMOC C ($SO_3H$) $CO_2H$ (361.0 mg, Preparation of (R)-16-amino-2,2-dimethyl-4,15-dioxo-3,8,11-trioxa-5,14-diazaheptadecane-17-sulfonic acid (C ($SO_3H$) $PEG_2$ NHBOC) (FIG. 12)

To a dried 4 mL glass scintillation vial containing a dried flea stir bar was added FMOC C ($SO_3H$) $PEG_2$ NHBOC (248.0 mg, 0.4 mmol). Piperidine (681.2 mg, 0.790 mL 8.0 mmol) in DMF (2.0 mL) was added by syringe. The solution was stirred at room temperature for 1.5 h, concentrated, adsorbed directly onto a Biotage KP C18 HS 3 g samplet, and purified on a Biotage KP C18 HS 30 g cartridge using a gradient of 0-100% $CH_3CN$ in $H_2O$, giving the desired product as a white solid (250.0 mg, 31% yield). HPLC retention time 2.311 min. Method A.

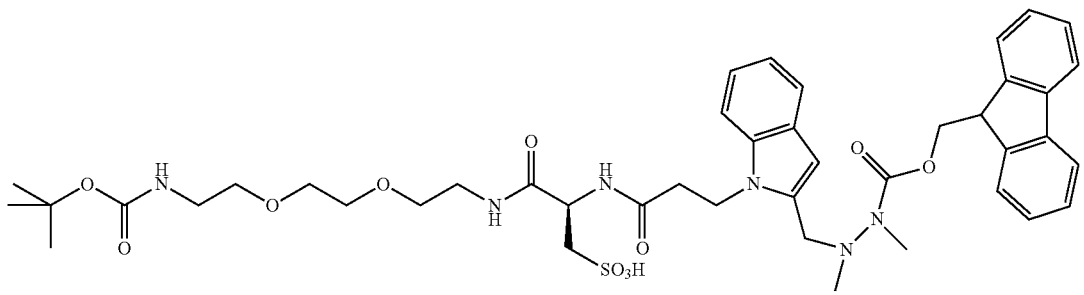 [SMILES: CN(Cc1cc2ccccc2n1CCC(=O)N[C@@H](CS(=O)(=O)O)C(=O)NCCOCCOCCNC(=O)OC(C)(C)C)N(C)C(=O)OCC1c2ccccc2-c2ccccc21]

Preparation of (R)-16-(3-(2-((2-(((9H-fluoren-9-yl)methoxy)carbonyl)-1,2-dimethylhydrazinyl)methyl)-1H-indol-1-yl)propanamido)-2,2-dimethyl-4,15-dioxo-3,8,11-trioxa-5,14-diazaheptadecane-17-sulfonic acid (FMOC HIPS Indole C (SO$_3$H) PEG$_2$ NHBOC) (FIG. 12)

To a dried 4 mL glass scintillation vial containing a dried flea stir bar was added C (SO$_3$H) PEG$_2$ NHBOC (50.0 mg, 0.13 mmol), FMOC HIPS Indole CO$_2$PFP (85.0 mg, 0.13 mmol), NaHCO$_3$ (51.0 mg, 0.61 mmol), and DMA (2.0 mL). The solution was stirred at room temperature for 1.5 h, adsorbed directly onto a Biotage KP C18 HS 3 g samplet, and purified on a Biotage KP C18 HS 30 g cartridge using a gradient of 0-100% CH$_3$CN in H$_2$O, giving the title compound as a white, foamy solid (41.0 mg, 36% yield). HPLC retention time 11.024 min. Method A.

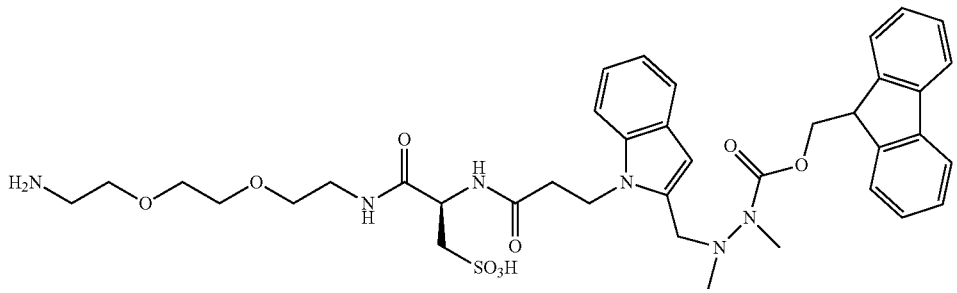 [SMILES: CN(Cc1cc2ccccc2n1CCC(=O)N[C@@H](CS(=O)(=O)O)C(=O)NCCOCCOCCN)N(C)C(=O)OCC1c2ccccc2-c2ccccc21]

Preparation of (R)-2-(3-(2-((2-(((9H-fluoren-9-yl)methoxy)carbonyl)-1,2-dimethylhydrazinyl)methyl)-1H-indol-1-yl)propanamido)-3-((2-(2-(2-aminoethoxy)ethoxy)ethyl)amino)-3-oxopropane-1-sulfonic acid (FMOC HIPS Indole C (SO$_3$H) PEG$_2$ NH$_2$) (FIG. 13)

To a dried 20 mL glass scintillation vial containing a dried flea stir bar was added FMOC HIPS Indole C (SO$_3$H) PEG$_2$ NHBOC (41.0 mg, 0.05 mmol) and anhydrous CH$_2$Cl$_2$ (5 mL). The solution was cooled to 0° C. in an ice, H$_2$O bath and TFA (273.6 mg, 0.184 mL, 2.4 mmol) was added dropwise by syringe. The solution was stirred at 0° C. for 2 h, adsorbed directly onto a Biotage SNAP Ultra 3 g samplet, and purified on a Biotage SNAP Ultra 25 g cartridge using 10% MeOH in CH$_2$Cl$_2$, giving the desired product as a white solid (31.0 mg, 86% yield). HPLC retention time 10.284 min. Method A.

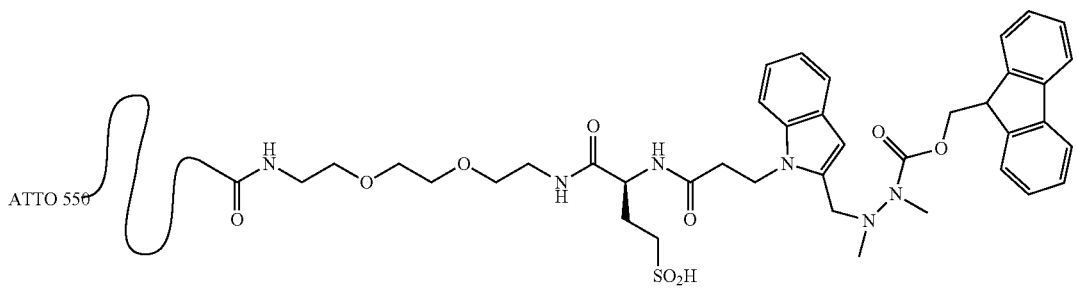

Preparation of (R)-13-(3-(2-((2-(((9H-fluoren-9-yl)methoxy)carbonyl)-1,2-dimethylhydrazinyl)methyl)-1H-indol-1-yl)propanamido)-1-carboxamido-1,12-dioxo-5,8-dioxa-2,11-diazatetradecane-14-sulfonic acid ATTO 550 (FMOC HIPS Indole C (SO$_3$H) PEG$_2$ NH ATTO 550) (Compound 25) (FIG. 13)

To a 4 mL glass scintillation vial containing a flea stir bar was added FMOC HIPS Indole C (SO$_3$H) PEG$_2$ NH$_2$ (5.3 mg, 7.0 umol), ATTO 550 NHS (5.0 mg, 6.3 umol), DIPEA (4.0 mg, 5.5 uL, 31.6 umol), DMF (270.0 uL), and H$_2$O (30.0 uL). The solution was stirred at room temperature for 2 h, adsorbed directly onto a Biotage SNAP Ultra 1 g samplet, and purified on a Biotage SNAP Ultra 10 g cartridge using a step gradient of 0% MeOH (0.1% AcOH) in CH$_2$Cl$_2$ (0.1% AcOH) to 10% MeOH (0.1% AcOH) in CH$_2$Cl$_2$ (0.1% AcOH), giving the title compound as a purplish red film (10.0 mg, 99% yield). HPLC retention time 15.220 min, 15.366 min, 15.573 min (mixture of isomers). Method A.

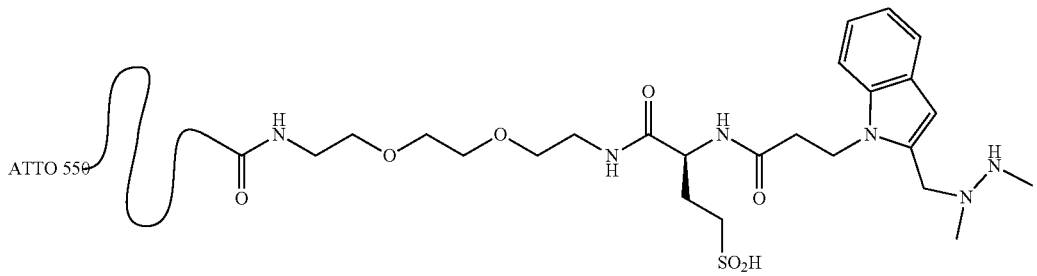

Preparation of (R)-1-carboxamido-13-(3-(2-((1,2-dimethylhydrazinyl)methyl)-1H-indol-1-yl)propanamido)-1,12-dioxo-5,8-dioxa-2,11-diazatetradecane-14-sulfonic acid ATTO 550 (HIPS Indole C (SO$_3$H) PEG$_2$ NH ATTO 550) (Compound 26) (FIG. 13)

To a dried 4 mL glass scintillation vial containing a dried flea stir bar was added FMOC HIPS Indole C (SO$_3$H) PEG$_2$ NH ATTO 550 (10.0 mg, 6.3 umol). Piperidine (51.7 mg, 60.0 uL, 0.6 mmol) in DMA (240 uL) was added by syringe. The solution was stirred at room temperature for 20 min, adsorbed directly onto a Biotage KP C18 HS 1.2 g samplet, and purified on a Biotage KP C18 HS 12 g cartridge using a gradient of 0-100% CH$_3$CN in H$_2$O, giving the desired product as a dark red film (3.3 mg, 38% yield). HPLC retention time 11.343 min, 11.499 min, 11.771 min. Method A.

Example 7

Method 7—Preparation of (S)-1-((S)-3-maytansinyl) 2-(4-((((4-(2S,5S)-34-(2-((1,2-dimethylhydrazinyl)methyl)-1H-indol-1-yl)-5-isopropyl-4,7,29,32-tetraoxo-2-(3-ureidopropyl)-10,13,16,19,22,25-hexaoxa-3,6,28,31-tetraazatetratriacontanamido)benzyl)oxy)carbonyl)(methyl)amino)-N-methylbutanamido)propanoate (HIPS Indole G PEG$_6$ Val Cit PABC NMC$_3$ Maytansine)

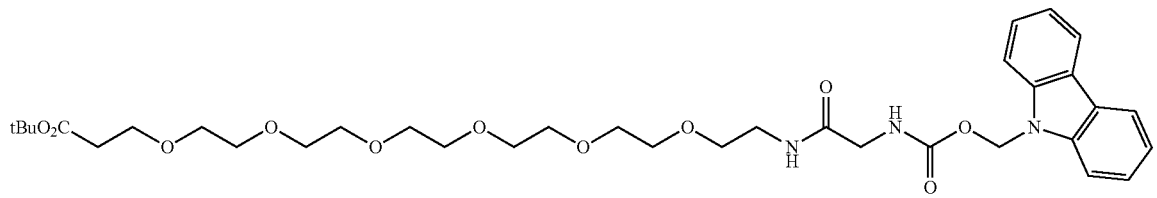 [SMILES: CC(C)(C)OC(=O)CCOCCOCCOCCOCCOCCOCCNC(=O)CNC(=O)OCn1c2ccccc2c2ccccc21]

Reaction schemes for the synthesis of compound HIPS Indole G PEG$_6$ Val Cit PABC NMC$_3$ Maytansine are shown in FIGS. 14 to 19; where NMC$_3$ represents the group —N(CH$_3$)—(CH$_2$)$_3$—.

Preparation of tert-butyl 1-(9H-fluoren-9-yl)-3,6-dioxo-2,10,13,16,19,22,25-heptaoxa-4,7-diazaoctacosan-28-oate (FMOC G PEG$_6$ CO$_2$tBu) (Compound 27)

To a dried 20 mL glass scintillation vial containing a dried pea stir bar was added FMOC G CO$_2$H (297.6 mg, 1.0 mmol), HATU (381.0 mg, 1.0 mmol), and anhydrous DMF (3 mL). The clear, colorless solution was stirred at room temperature for 15 min. H$_2$N PEG$_6$ CO$_2$tBu (415.7 mg, 1.0 mmol), DIPEA (387.7 mg, 522.5 uL, 3.0 mmol), and anhydrous DMF (1 mL) were combined in a separate, dried 4 mL glass scintillation vial and added dropwise, slowly, to the stirring solution. The reaction was stirred at room temperature for 2 h, adsorbed directly onto a Biotage KP C18 HS 12 g samplet, and purified on a Biotage KP C18 HS 60 g cartridge using a gradient of 0-100% CH$_3$CN in H$_2$O, giving the title compound as a pale yellow, viscous oil (669.0 mg, 97% yield). HPLC retention time 12.481 min. Method A.

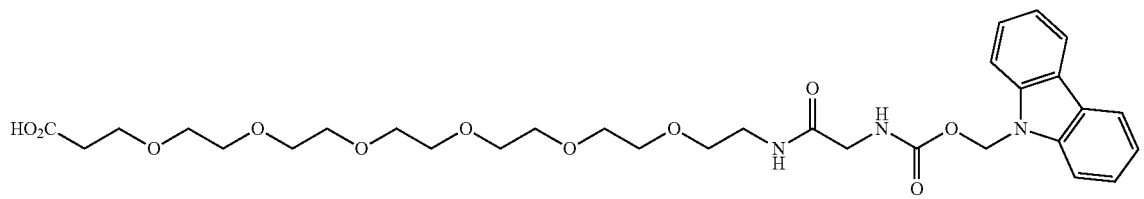 [SMILES: O=C(O)CCOCCOCCOCCOCCOCCOCCNC(=O)CNC(=O)OCn1c2ccccc2c2ccccc21]

Figure 14:
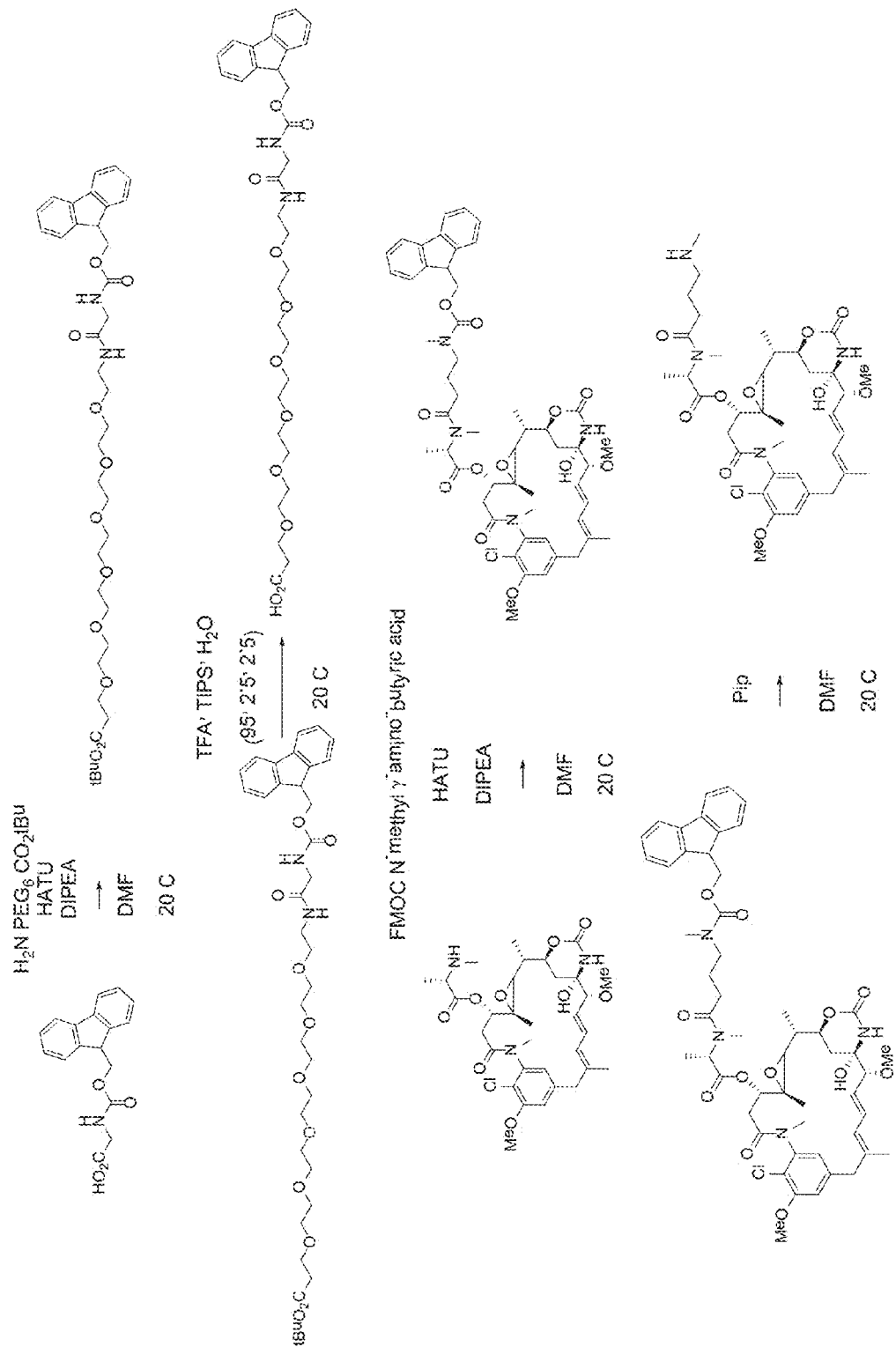
FIGS. 14 to 19 show reaction schemes for the synthesis of compound HIPS Indole G $PEG_6$ Val Cit PABC $NMC_3$ Maytansine according to embodiments of the present disclosure, see e.g., Example 7 (where, as used herein, $NMC_3$ represents the group —$N(CH_3)$—$(CH_2)_3$—).

Preparation of 1-(9H-fluoren-9-yl)-3,6-dioxo-2,10,13,16,19,22,25-heptaoxa-4,7-diazaoctacosan-28-oic acid (FMOC G $PEG_6$ $CO_2H$) (Compound 28) (FIG. 14)

To a 20 mL glass scintillation vial containing a pea stir bar was added a solution of TFA, TIPS, $H_2O$ (7.6 ml, 0.2 mL, 0.2 mL). FMOC G $PEG_6$ $CO_2tBu$ (669.0 mg, 1.0 mmol) was added in small portions and the reaction was stirred at room temperature for 1 h. The solution was evaporated, adsorbed onto a Biotage KP C18 HS 12 g samplet, and purified on a Biotage KP C18 HS 60 g cartridge using a gradient of 0-100% $CH_3CN$ in $H_2O$, giving the desired product as a white solid (500.2 mg, 79% yield). HPLC retention time 9.686 min. Method A.

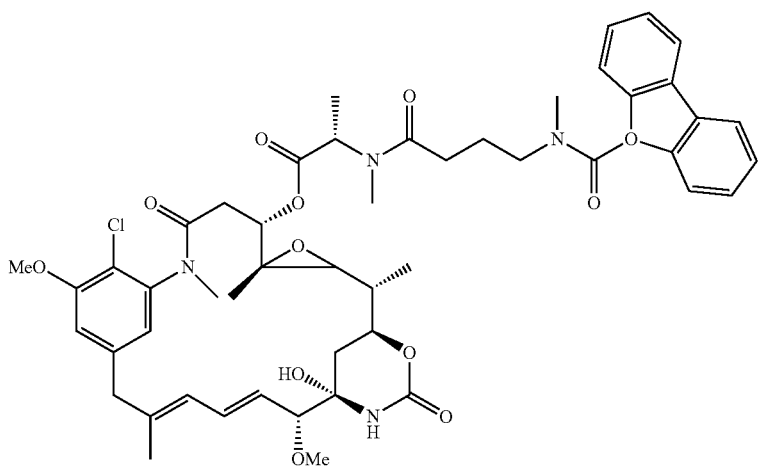

Preparation of (S)-1-((S)-3-maytansinyl)2-(4-((((9H-fluoren-9-yl)methoxy)carbonyl)(methyl)amino)-N-methylbutanamido)propanoate (FMOC $NMC_3$ Maytansine) (Compound 29) (FIG. 14)

To a dried 4 mL glass scintillation vial containing a dried flea stir bar was added FMOC N methyl γ-amino butyric acid (76.3 mg, 0.2 mmol), HATU (85.4 mg, 0.2 mmol), and anhydrous DMF (0.6 mL). The clear, colorless solution was stirred at room temperature for 15 min. Deacyl maytansine (145.4 mg, 0.2 mmol), DIPEA (86.7 mg, 116.9 uL, 0.7 mmol), and anhydrous DMF (0.3 mL) were combined in a separate, dried 4 mL glass scintillation vial and added dropwise, slowly, to the stirring solution. The reaction was allowed to stir at room temperature for 2 h, adsorbed directly onto a Biotage KP C18 HS 3 g samplet, and purified on a Biotage KP C18 HS 30 g cartridge using a gradient of 0-100% $CH_3CN$ in $H_2O$, giving the title compound as a white solid (182.7 mg, 84% yield). HPLC retention time 14.220 min. Method A.

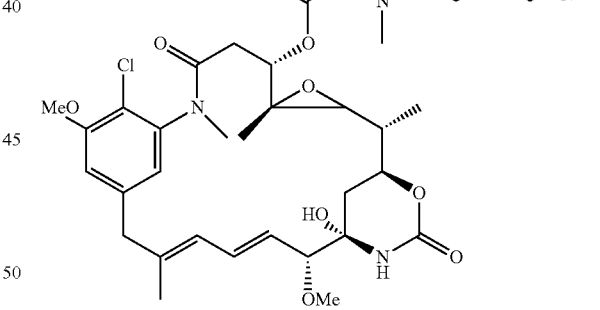

Preparation of (S)-1-((S)-3-maytansinyl)2-(N-methyl-4-(methylamino)butanamido)propanoate ($NMC_3$ Maytansine) (Compound 30) (FIG. 14)

To a dried 4 mL glass scintillation vial containing a dried flea stir bar was added FMOC $NMC_3$ Maytansine (182.7 mg, 0.2 mmol). Piperidine (344.8 mg, 0.4 mL, 4.0 mmol) in DMF (1.6 mL) was added by syringe. The solution was stirred at room temperature for 20 min, adsorbed directly onto a Biotage KP C18 HS 3 g samplet, and purified on a Biotage KP C18 HS 30 g cartridge using a gradient of 0-100% $CH_3CN$ in $H_2O$, giving the desired product as a white solid (110.6 mg, 79% yield). HPLC retention time 13.510 min. Method A.

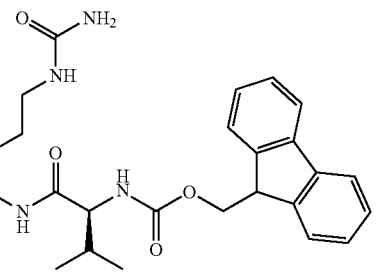
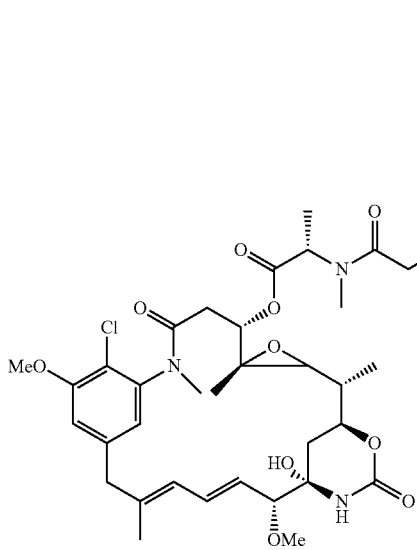

Figure 15:
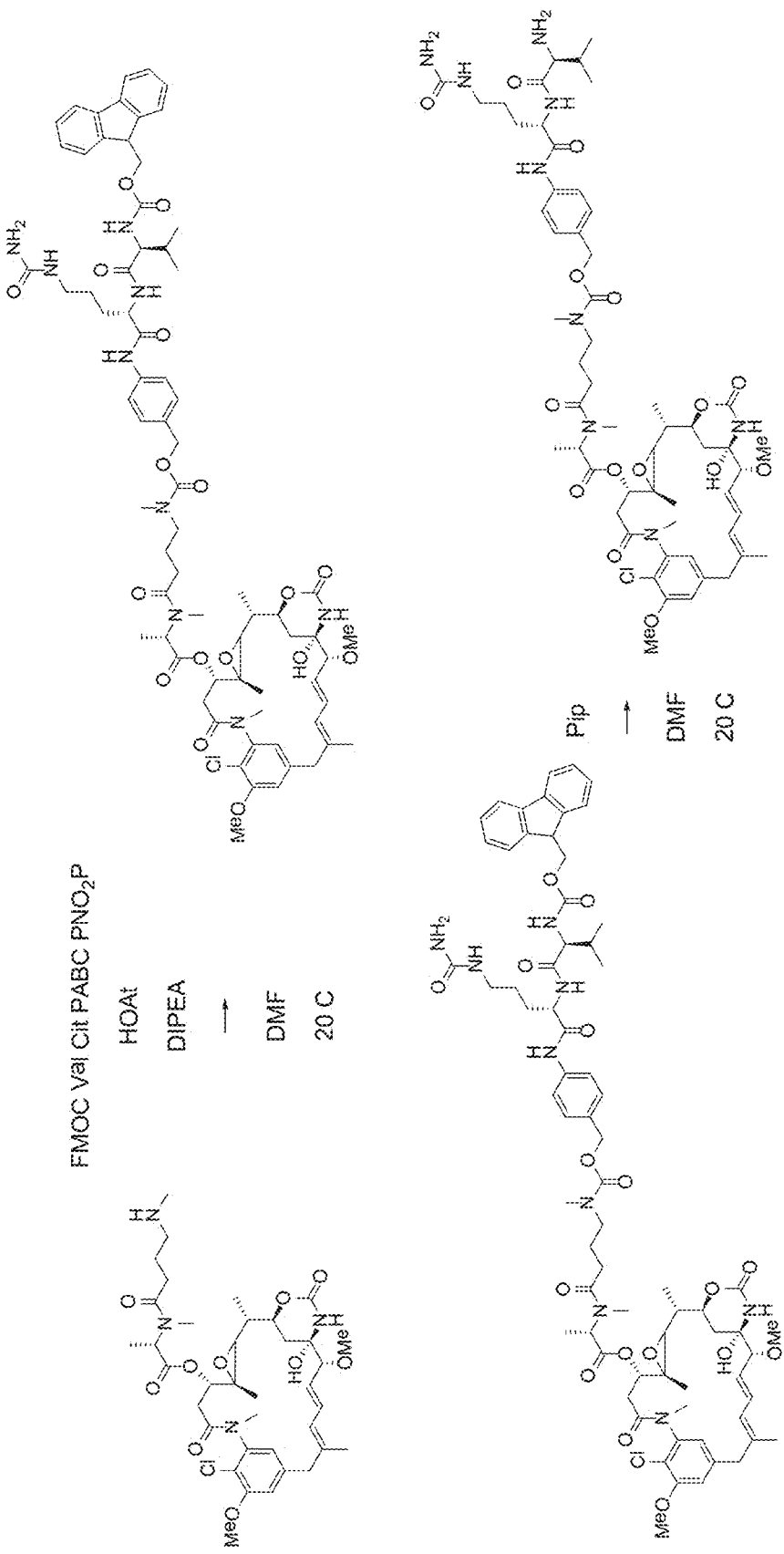

Preparation of (S)-1-((S)-3-maytansinyl) 2-(4-(((((4-((S)-2-((S)-2-((((9H-fluoren-9-yl)methoxy)carbonyl)amino)-3-methylbutanamido)-5-ureidopentanamido)benzyl)oxy)carbonyl)(methyl)amino)-N-methylbutanamido)propanoate (FMOC Val Cit PABC NMC$_3$ Maytansine) (Compound 31) (FIG. 15)

To a dried 4 mL glass scintillation vial containing a dried flea stir bar was added NMC$_3$ Maytansine (39.8 mg, 0.05 mmol), FMOC Val Cit PABC PNO$_2$P (42.0 mg, 0.06 mmol), HOAt (12.8 mg, 0.09 mmol), DIPEA (20.6 mg, 27.8 uL, 0.16 mmol), and anhydrous DMF (0.7 mL). The solution was stirred at room temperature for 24 h, adsorbed directly onto a Biotage KP C18 HS 1.2 g samplet, and purified on a Biotage KP C18 HS 12 g cartridge using a gradient of 0-100% CH$_3$CN in H$_2$O, giving the title compound as a pale yellow solid (46.9 mg, 64% yield). HPLC retention time 12.702 min. Method A.

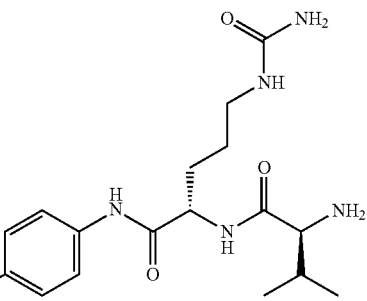
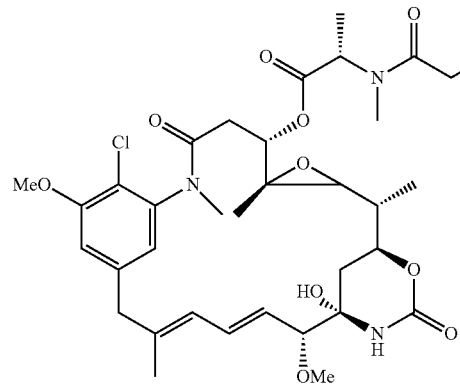

Preparation of (S)-1-((S)-3-maytansinyl) 2-(4-((((4-((S)-2-((S)-2-amino-3-methylbutanamido)-5-ureidopentanamido)benzyl)oxy)carbonyl)(methyl)amino)-N-methylbutanamido)propanoate (Val Cit PABC NMC₃ Maytansine) (Compound 32) (FIG. 15)

To a dried 4 mL glass scintillation vial containing a dried flea stir bar was added FMOC Val Cit PABC NMC₃ Maytansine (46.9 mg, 0.03 mmol). Piperidine (86.2 mg, 0.1 mL, 1.0 mmol) in DMF (0.4 mL) was added by syringe. The solution was stirred at room temperature for 20 min, adsorbed directly onto a Biotage KP C18 HS 1.2 g samplet, and purified on a Biotage KP C18 HS 12 g cartridge using a gradient of 0-100% CH₃CN in H₂O, giving the desired product as a white solid (31.1 mg, 79% yield). HPLC retention time 8.774 min. Method A.

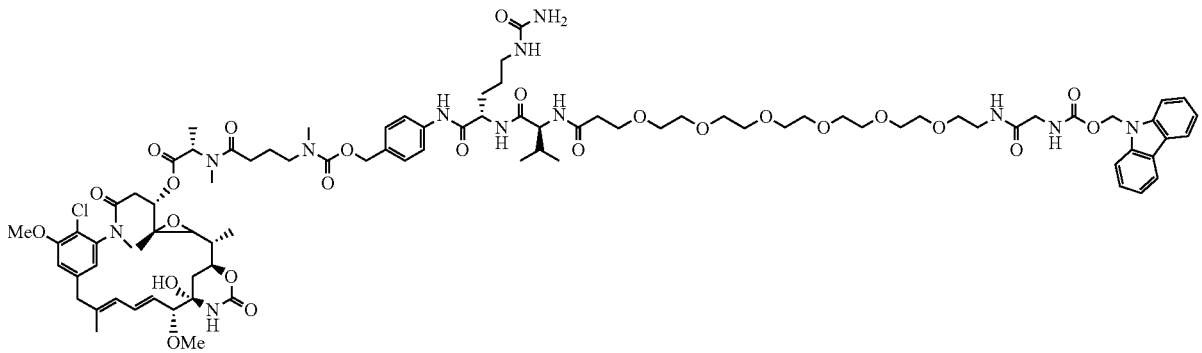 [SMILES: COc1cc2cc(c1Cl)N(C)C(=O)C[C@H](OC(=O)[C@H](C)N(C)C(=O)CCCN(C)C(=O)OCc1ccc(NC(=O)[C@H](CCCNC(N)=O)NC(=O)[C@@H](NC(=O)CCOCCOCCOCCOCCOCCOCCNC(=O)CNC(=O)OCn3c4ccccc4c4ccccc43)C(C)C)cc1)[C@]1(C)OC1[C@H](C)[C@@H]1C[C@@](O)(NC(=O)O1)[C@H](OC)/C=C/C=C(\C)C2]

Figure 16:
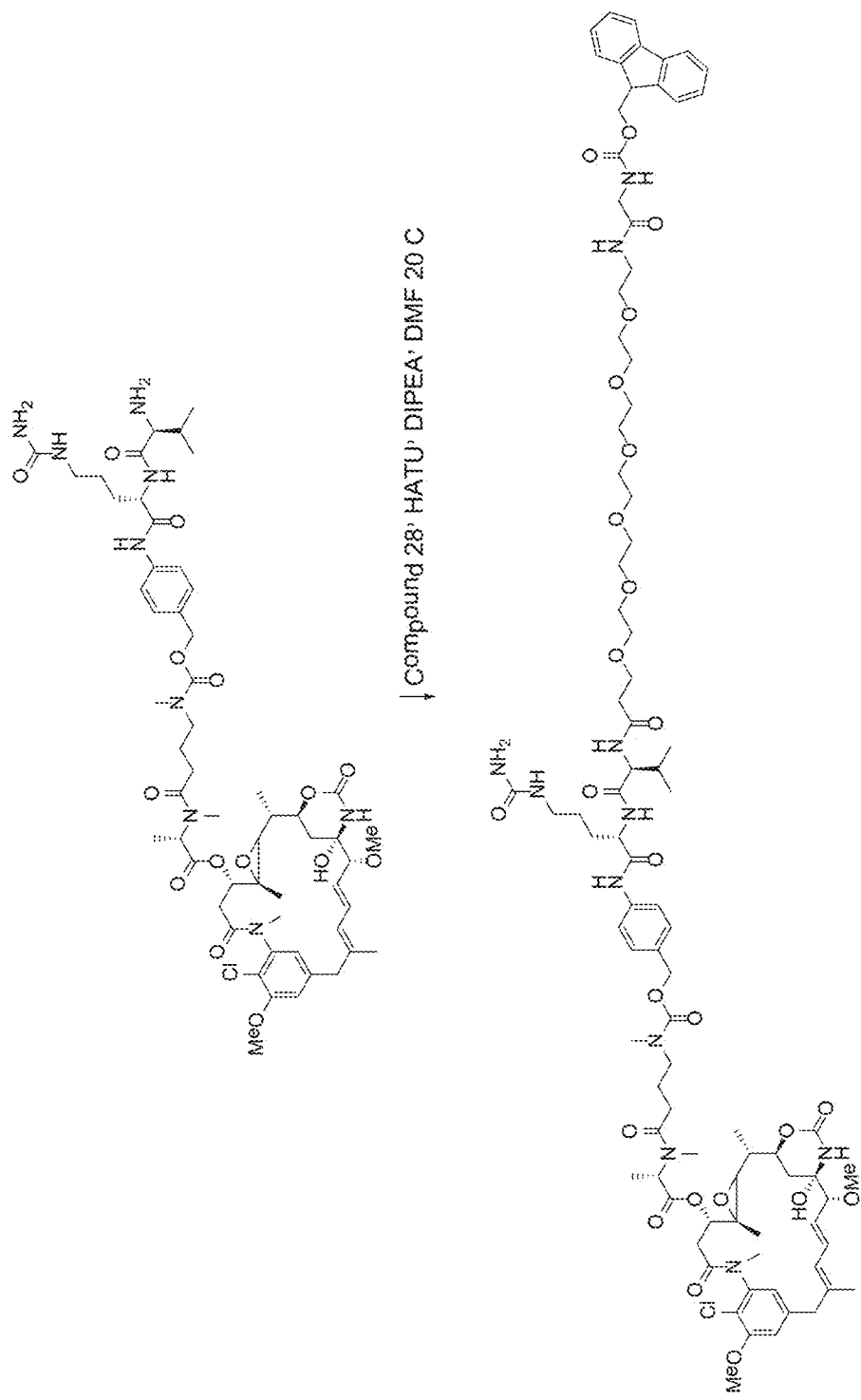

Preparation of (S)-1-((S)-3-maytansinyl)2-(4-((((4-((30S,33S)-1-(9H-fluoren-9-yl)-30-isopropyl-3,6,28,31-tetraoxo-33-(3-ureidopropyl)-2,10,13,16,19,22,25-heptaoxa-4,7,29,32-tetraazatetratriacontanamido)benzyl)oxy)carbonyl)(methyl)amino)-N-methylbutanamido)propanoate (FMOC G PEG₆ Val Cit PABC NMC₃ Maytansine) (Compound 33) (FIG. 16)

To a dried 4 mL glass scintillation vial containing a dried flea stir bar was added FMOC G PEG₆ CO₂H (21.5 mg, 0.03 mmol), HATU (12.7 mg, 0.03 mmol), and anhydrous DMF (0.2 mL). The clear, colorless solution was stirred at room temperature for 15 min. Val Cit PABC NMC₃ Maytansine (31.1 mg, 0.03 mmol), DIPEA (10.5 mg, 14.2 uL, 0.08 mmol), and anhydrous DMF (0.2 mL) were combined in a separate, dried 4 mL glass scintillation vial and added dropwise, slowly, to the stirring solution. The reaction was stirred at room temperature for 2 h, adsorbed directly onto a Biotage KP C18 HS 1.2 g samplet, and purified on a Biotage KP C18 HS 12 g cartridge using a gradient of 0-100% CH₃CN in H₂O, giving the title compound as a white solid (43.6 mg, 91% yield). HPLC retention time 11.305 min. Method A.

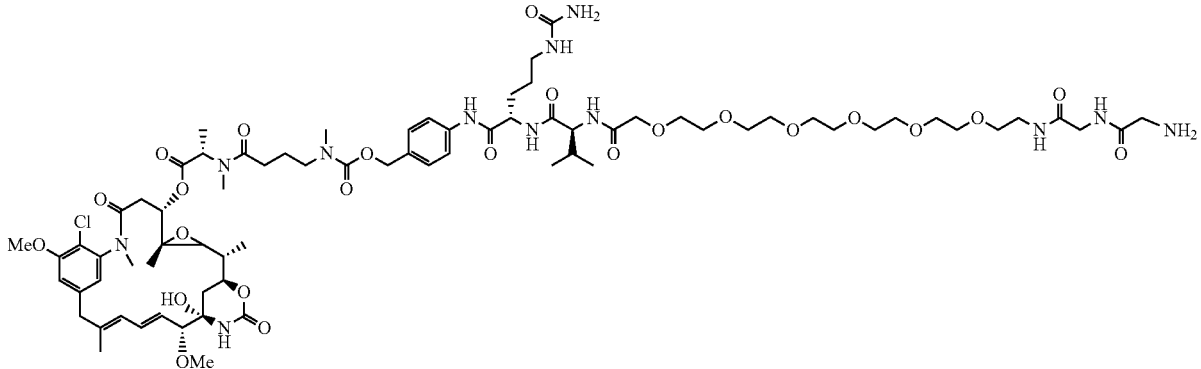 [SMILES: COc1cc2cc(c1Cl)N(C)C(=O)C[C@H](OC(=O)[C@H](C)N(C)C(=O)CCCN(C)C(=O)OCc1ccc(NC(=O)[C@H](CCCNC(N)=O)NC(=O)[C@@H](NC(=O)COCCOCCOCCOCCOCCOCCNC(=O)CNC(=O)CN)C(C)C)cc1)[C@]1(C)OC1[C@H](C)[C@@H]1C[C@@](O)(NC(=O)O1)[C@H](OC)/C=C/C=C(\C)C2]

Figure 17:
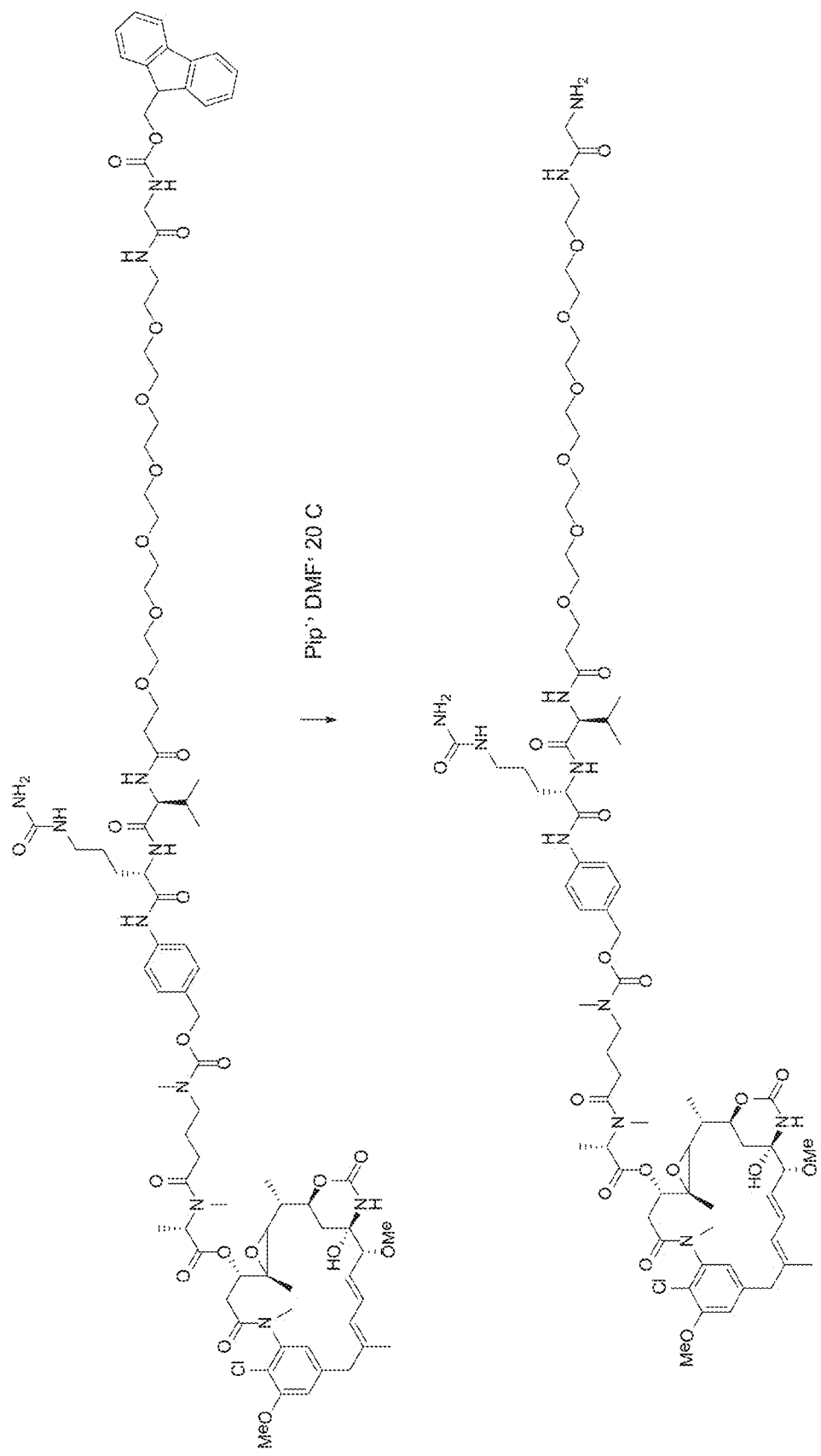

Preparation of (S)-1-((S)-3-maytansinyl) 2-(4-((((4-((26S,29S)-1-amino-26-isopropyl-2,24,27-trioxo-29-(3-ureidopropyl)-6,9,12,15,18,21-hexaoxa-3,25,28-triazatriacontanamido)benzyl)oxy)carbonyl)(methyl)amino)-N-methylbutanamido)propanoate (G PEG$_6$ Val Cit PABC NMC$_3$ Maytansine) (Compound 34) (FIG. 17)

To a dried 4 mL glass scintillation vial containing a dried flea stir bar was added FMOC Val Cit PABC NMC$_3$ Maytansine (43.6 mg, 0.03 mmol). Piperidine (86.2 mg, 0.1 mL, 1.0 mmol) in DMF (0.4 mL) was added by syringe. The solution was stirred at room temperature for 20 min, adsorbed directly onto a Biotage KP C18 HS 1.2 g samplet, and purified on a Biotage KP C18 HS 12 g cartridge using a gradient of 0-100% CH$_3$CN in H$_2$O, giving the desired product as a white solid (33.7 mg, 89% yield). HPLC retention time 8.817 min. Method A.

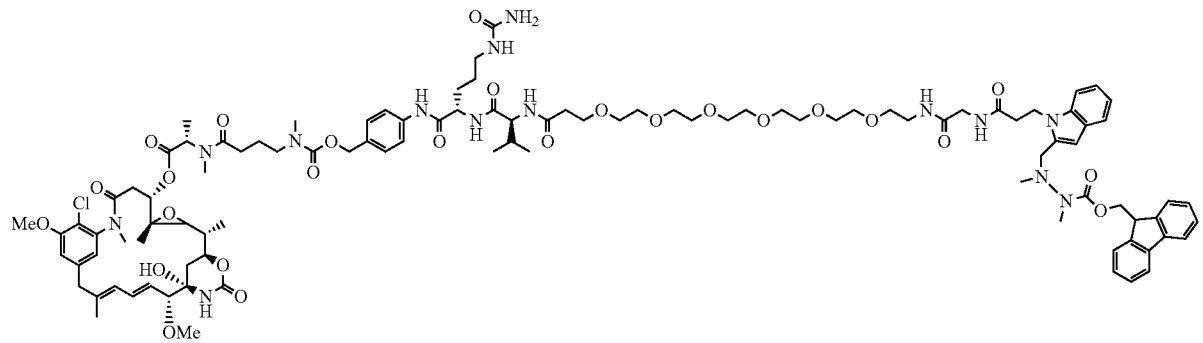

Figure 18:
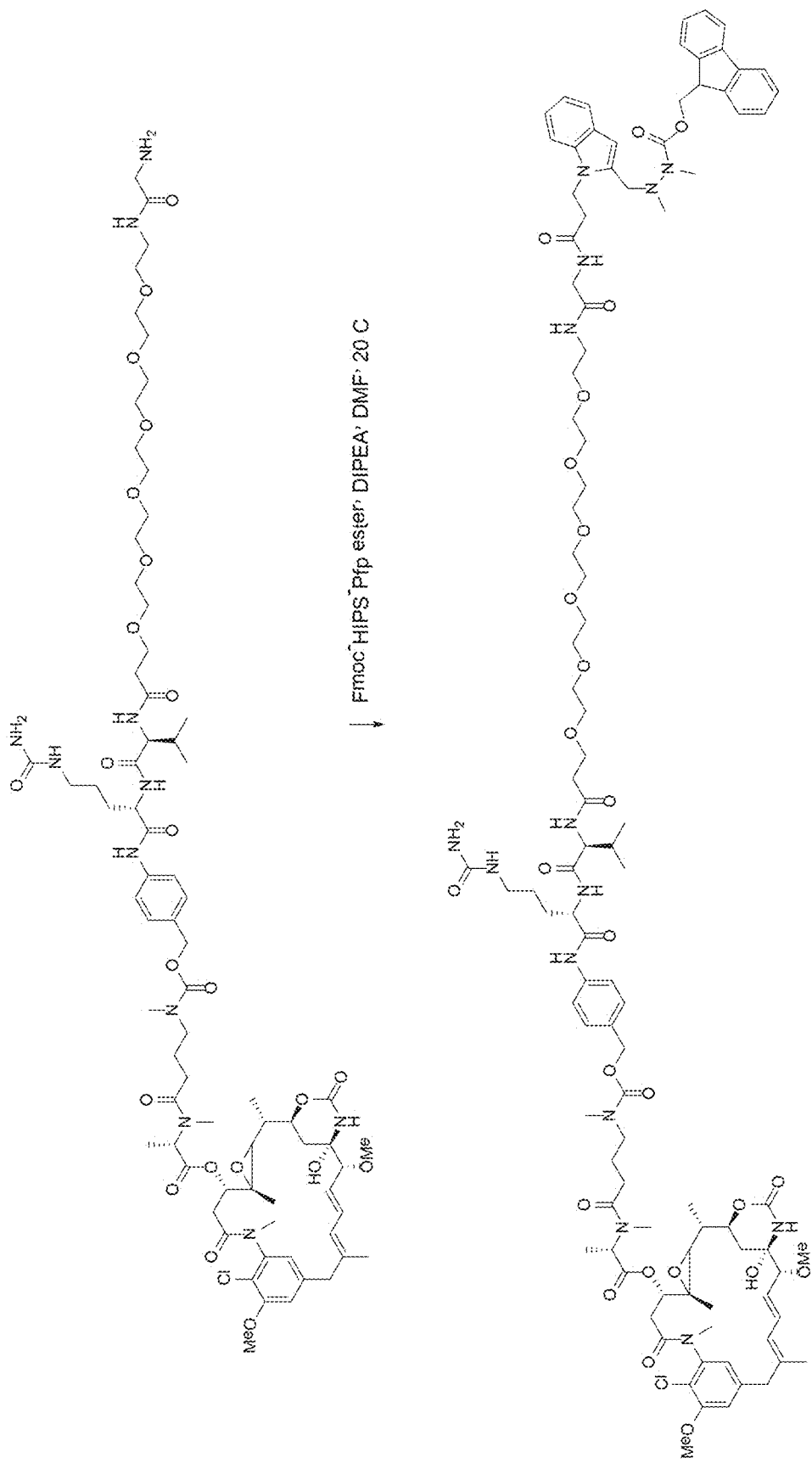

Preparation of (9H-fluoren-9-yl)methyl 2-((1-((6S,9S)-1-amino-6-((4-((10S,13S)-13-((S)-3-maytansinyl)-4,9,10-trimethyl-3,8,11-trioxo-2,12-dioxa-4,9-diazatetradecyl)phenyl)carbamoyl)-9-isopropyl-1,8,11,33,36-pentaoxo-14,17,20,23,26,29-hexaoxa-2,7,10,32,35-pentaazaoctatriacontan-38-yl)-1H-indol-2-yl)methyl)-1,2-dimethylhydrazinecarboxylate (FMOC HIPS Indole G PEG$_6$ Val Cit PABC NMC$_3$ Maytansine) (Compound 35) (FIG. 18)

To a dried 4 mL glass scintillation vial containing a dried flea stir bar was added G PEG$_6$ Val Cit PABC NMC$_3$ Maytansine (33.7 mg, 0.02 mmol), FMOC HIPS Indole CO$_2$PFP (17.4 mg, 0.03 mmol), DIPEA (8.5 mg, 11.5 uL, 0.07 mmol), and anhydrous DMF (0.3 mL). The solution was stirred at room temperature for 2 h, adsorbed directly onto a Biotage KP C18 HS 1.2 g samplet, and purified on a Biotage KP C18 HS 12 g cartridge using a gradient of 0-100% CH$_3$CN in H$_2$O, giving the title compound as a pale yellow solid (39.3 mg, 90% yield). HPLC retention time 12.900 min. Method A.

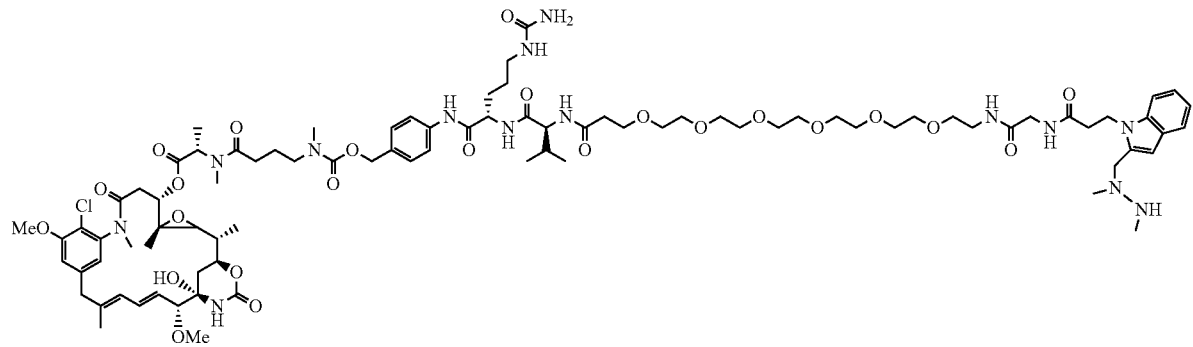

Figure 19:
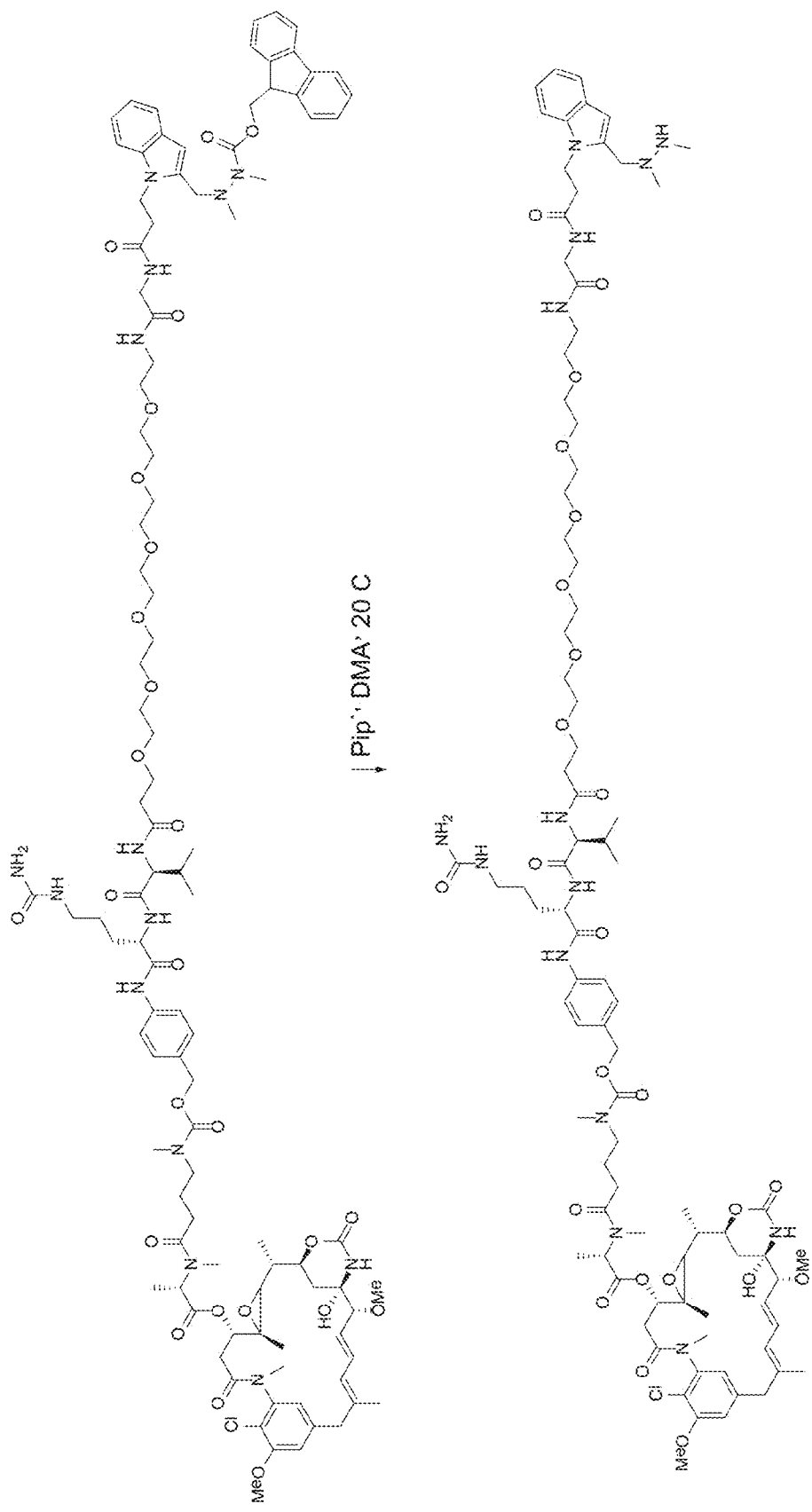

Preparation of (S)-1-((S)-3-maytansinyl) 2-(4-((((4-((2S,5S)-34-(2-((1,2-dimethylhydrazinyl)methyl)-1H-indol-1-yl)-5-isopropyl-4,7,29,32-tetraoxo-2-(3-ureidopropyl)-10,13,16,19,22,25-hexaoxa-3,6,28,31-tetraazatetratriacontanamido)benzyl)oxy)carbonyl)(methyl)amino)-N-methylbutanamido)propanoate (HIPS Indole G PEG6 Val Cit PABC NMC₃ Maytansine) (Compound 36) (FIG. 19)

Figure 20:
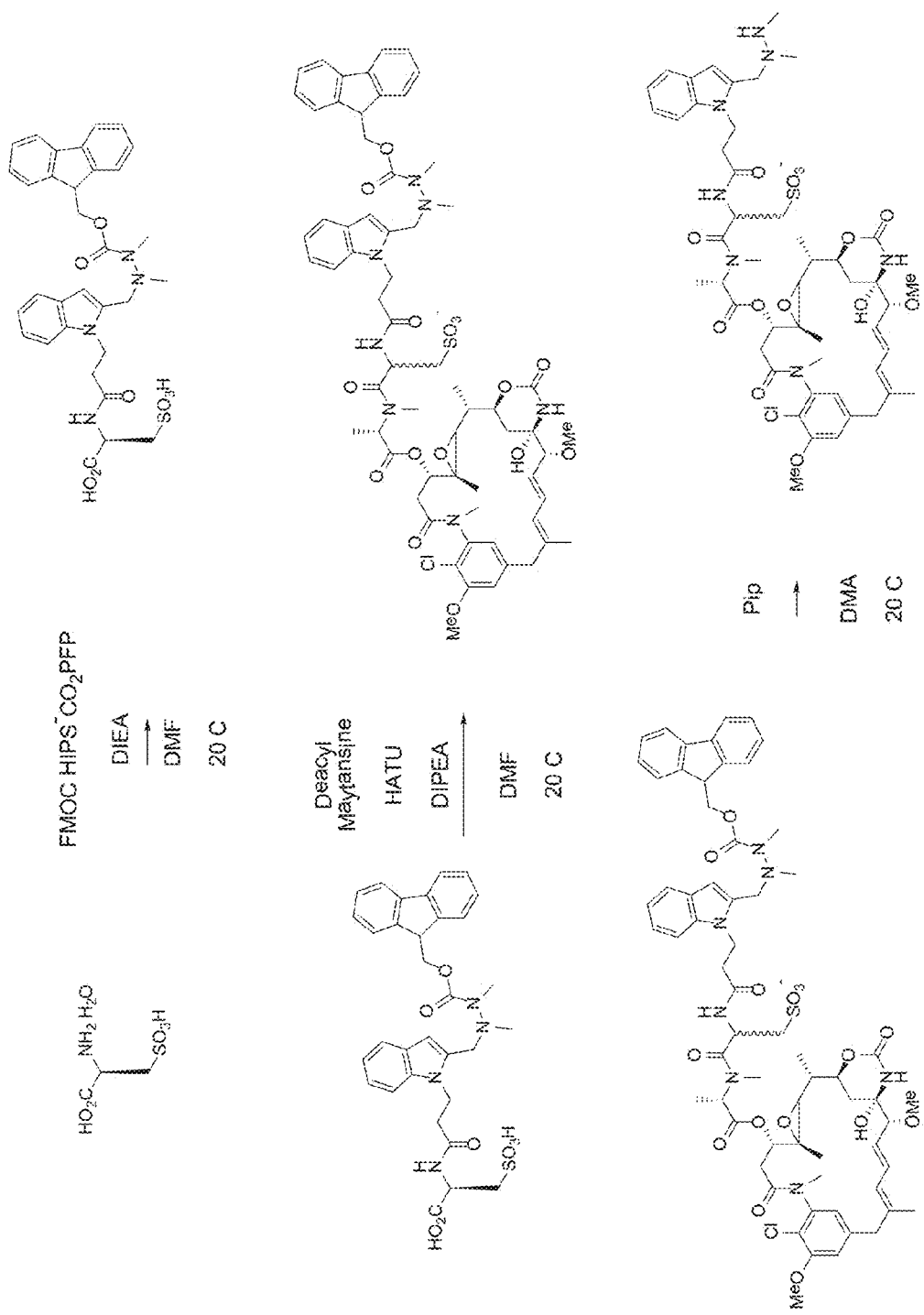
FIG. 20 shows a reaction scheme for the synthesis of compound HIPS Indole C ($SO_3H$) Maytansine according to embodiments of the present disclosure, see e.g., Example 8.

To a dried 4 mL glass scintillation vial containing a dried flea stir bar was added FMOC HIPS Indole G PEG₆ Val Cit PABC NMC₃ Maytansine (39.3 mg, 0.02 mmol). Piperidine (86.2 mg, 0.1 mL, 1.0 mmol) in DMA (0.4 mL) was added by syringe. The solution was stirred at room temperature for 20 min, adsorbed directly onto a Biotage KP C18 HS 1.2 g samplet, and purified on a Biotage KP C18 HS 12 g cartridge using a gradient of 0-100% CH₃CN in H₂O, giving the Preparation of (R)-2-(3-(2-((2-(((9H-fluoren-9-yl)methoxy)carbonyl)-1,2-dimethylhydrazinyl)methyl)-1H-indol-1-yl)propanamido)-3-sulfopropanoic acid (FMOC HIPS Indole C (SO₃H) CO₂H) (Compound 36) (FIG. 20)

To a dried 20 mL glass scintillation vial containing a dried pea stir bar was added L-cysteic acid monohydrate (411.1 mg, 2.2 mmol), FMOC HIPS Indole CO₂PFP (704.6 mg, 1.1 mmol), DIPEA (851.8 mg, 1.148 mL, 6.6 mmol), and anhydrous DMF (5 mL). The solution was stirred at room temperature for 4 h, adsorbed directly onto a Biotage KP C18 HS 12 g samplet, and purified on a Biotage KP C18 HS 60 g cartridge using a gradient of 0-100% CH₃CN in H₂O, giving the title compound as a white solid (654.2 mg, 95% yield). HPLC retention time 10.725 min. Method C.

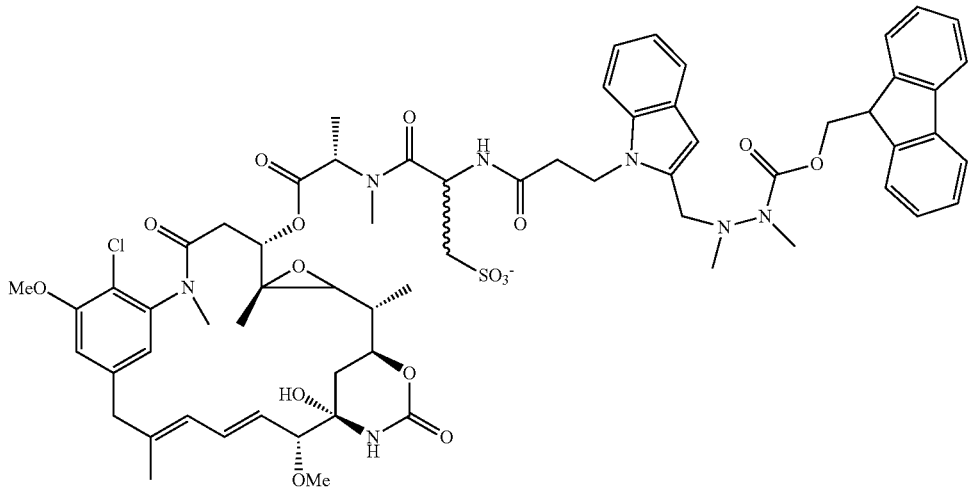

desired product as a white solid (31.3 mg, 90% yield). HPLC retention time 9.425 min. Method A. LRMS (ESI) calcd for $C_{87}H_{129}ClN_{14}NaO_{24}^+$ [M+Na]⁺: 1811.9 found 1811.7.

Example 8

Method 8—Preparation of 3-(((S)-1-((S)-1-cyclopropylethoxy)-1-oxopropan-2-yl)(methyl)amino)-2-(3-(2-((1,2-dimethylhydrazinyl)methyl)-1H-indol-1-yl)propanamido)-3-oxopropane-1-sulfonate (HIPS Indole C (SO₃H) Maytansine)

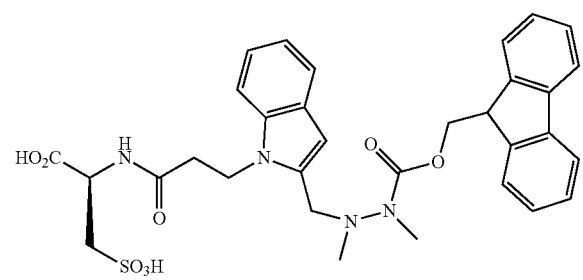 [SMILES: CN(Cc1cc2ccccc2n1CCC(=O)N[C@@H](CS(=O)(=O)O)C(=O)O)N(C)C(=O)OCC1c2ccccc2-c2ccccc21]

A reaction scheme for the synthesis of compound HIPS Indole C (SO₃H) Maytansine is shown in FIG. 20.

Preparation of 2-(3-(2-((2-(((9H-fluoren-9-yl)methoxy)carbonyl)-1,2-dimethylhydrazinyl)methyl)-1H-indol-1-yl)propanamido)-3-(((S)-1-((S)-3-maytansinyl)-1-oxopropan-2-yl)(methyl)amino)-3-oxopropane-1-sulfonate (FMOC HIPS Indole C (SO₃H) Maytansine) (Compound 37) (FIG. 20)

To a dried 20 mL glass scintillation vial containing a dried pea stir bar was added FMOC HIPS Indole C (SO₃H) CO₂H (586.2 mg, 0.9 mmol), HATU (351.3 mg, 0.9 mmol), and anhydrous DMF (3 mL). The clear, colorless solution was stirred at room temperature for 15 min. Deacyl maytansine (316.9 mg, 0.5 mmol), DIPEA (388.3 mg, 523.3 uL, 3.0 mmol), and anhydrous DMF (3 mL) were combined in a separate, dried 4 mL glass scintillation vial and added dropwise, slowly, to the stirring solution. The reaction was allowed to stir at room temperature for 2 h, adsorbed directly onto a Biotage KP C18 HS 12 g samplet, and purified on a Biotage KP C18 HS 60 g cartridge using a gradient of 0-100% CH₃CN in H₂O, giving the desired product as a white solid (505.9 mg, 82% yield). HPLC retention time 16.493 min, 16.899 min (mixture of diastereomers). Method C.

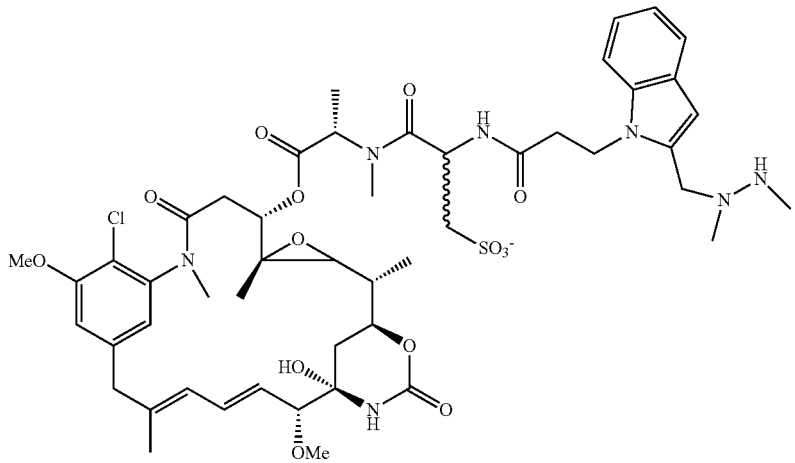

Preparation of 3-(((S)-1-((S)-3-maytansinyl)-1-oxo-propan-2-yl)(methyl)amino)-2-(3-(2-((1,2-dimethylhydrazinyl)methyl)-1H-indol-1-yl)propanamido)-3-oxopropane-1-sulfonate (HIPS Indole C (SO₃H) Maytansine) (Compound 38) (FIG. 20)

To a dried 4 mL glass scintillation vial containing a dried flea stir bar was added FMOC HIPS Indole C (SO₃H) Maytansine (253.0 mg, 0.2 mmol). Piperidine (172.4 mg, 0.2 mL, 2.0 mmol) in DMA (0.8 mL) was added by syringe. The solution was stirred at room temperature for 20 min, adsorbed directly onto a Biotage KP C18 HS 1.2 g samplet, and purified on a Biotage KP C18 HS 12 g cartridge using a gradient of 0-100% CH₃CN in H₂O, giving the title compound as a white solid (83.2 mg, 40% yield). HPLC retention time 13.643 min, 13.968 min (mixture of diastereomers). Method C. LRMS (ESI) calcd for $C_{49}H_{65}ClN_7O_{14}S$— [M–H]⁻: 1042.4 found 1042.1.

Example 9

Method 9—Preparation of (S)-1-((S)-3-maytansinyl) 31-(2-((1,2-dimethylhydrazinyl)methyl)-1H-indol-1-yl)-2,3-dimethyl-4,26,29-trioxo-7,10,13,16,19,22-hexaoxa-3,25,28-triazahentriacontan-1-oate (HIPS Indole G PEG₆ Maytansine)

Figure 21:
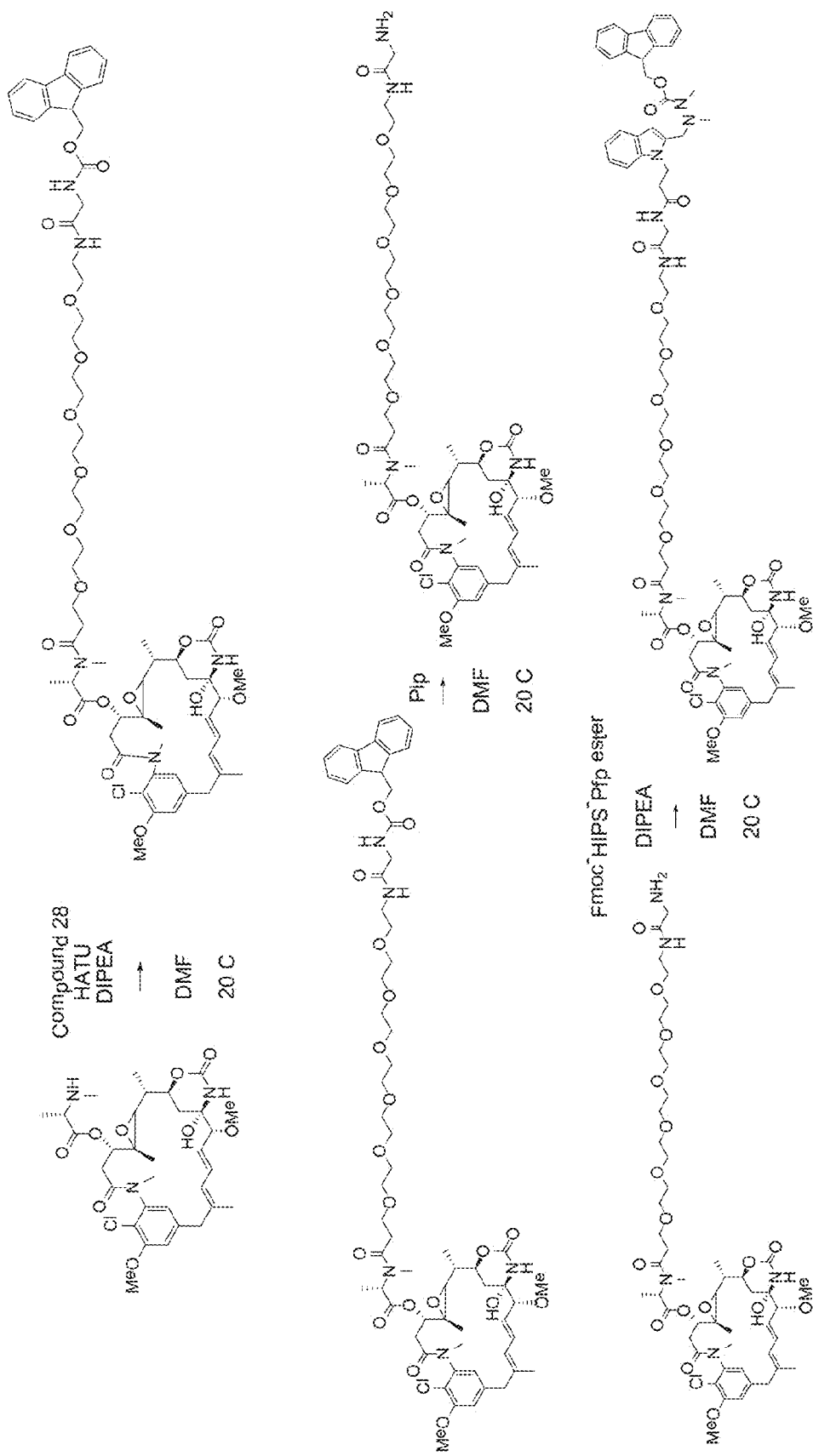
FIG. 21 and FIG. 22 show reaction schemes for the synthesis of compound HIPS Indole G $PEG_6$ Maytansine according to embodiments of the present disclosure, see e.g., Example 9.
Figure 22:
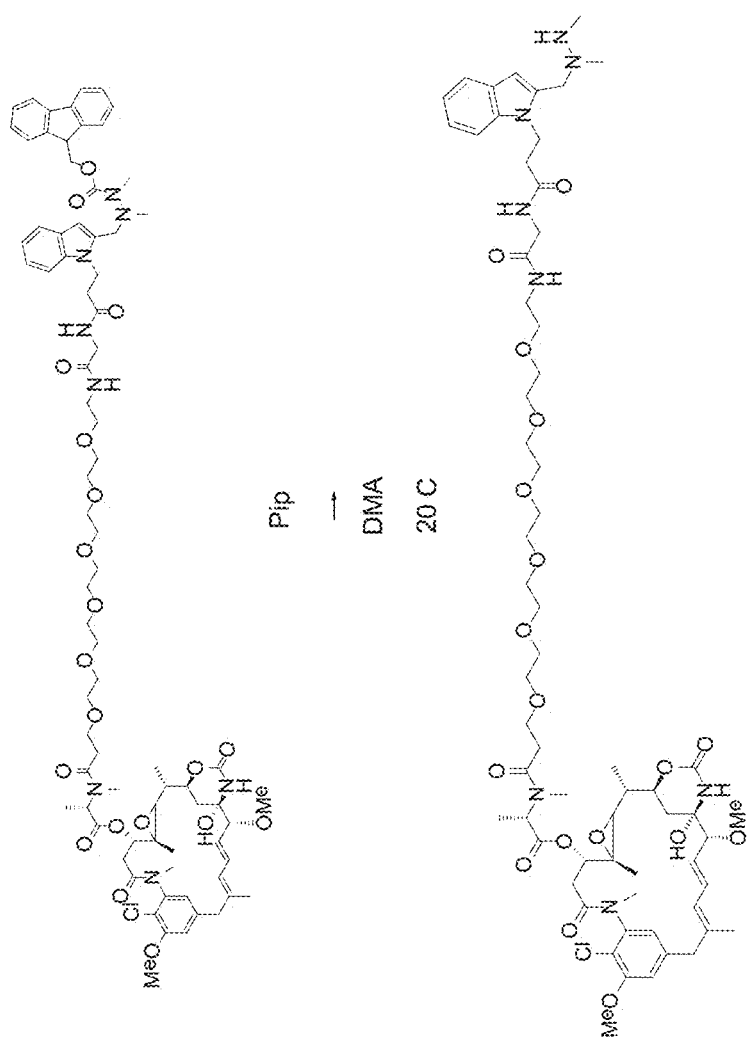

Reaction schemes for the synthesis of compound HIPS Indole G PEG₆ Maytansine are shown in FIG. 21 and FIG. 22.

Preparation of (S)-1-((S)-3-maytansinyl) 1-(9H-fluoren-9-yl)-29,30-dimethyl-3,6,28-trioxo-2,10,13,16,19,22,25-heptaoxa-4,7,29-triazahentriacontan-31-oate (FMOC G PEG₆ Maytansine) (Compound 39) (FIG. 21)

To a dried 4 mL glass scintillation vial containing a dried flea stir bar was added FMOC G PEG₆ CO₂H (62.3 mg, 0.1 mmol), HATU (37.8 mg, 0.1 mmol), and anhydrous DMF (0.2 mL). The clear, colorless solution was stirred at room temperature for 15 min. Deacyl maytansine (63.8 mg, 0.1 mmol), DIPEA (38.2 mg, 51.4 uL, 0.3 mmol), and anhydrous DMF (0.2 mL) were combined in a separate, dried 4 mL glass scintillation vial and added dropwise, slowly, to the stirring solution. The reaction was allowed to stir at room temperature for 2 h, adsorbed directly onto a Biotage KP C18 HS 1.2 g samplet, and purified on a Biotage KP C18 HS 12 g cartridge using a gradient of 0-100% CH₃CN in H₂O, giving the desired product as a white solid (87.3 mg, 70% yield). HPLC retention time 12.122 min. Method A.

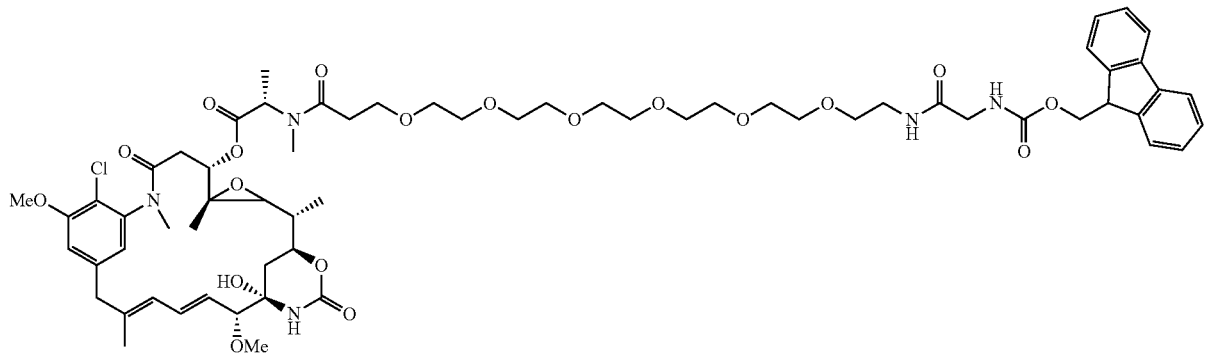

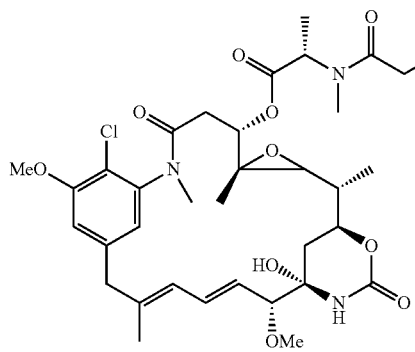
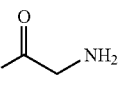

Preparation of (S)-1-((S)-3-maytansinyl) 1-amino-25,26-dimethyl-2,24-dioxo-6,9,12,15,18,21-hexaoxa-3,25-diazaheptacosan-27-oate (G PEG$_6$ Maytansine) (Compound 40) (FIG. 21)

To a dried 4 mL glass scintillation vial containing a dried flea stir bar was added FMOC G PEG$_6$ Maytansine (87.3 mg, 0.07 mmol). Piperidine (172.4 mg, 0.2 mL, 2.0 mmol) in DMF (0.8 mL) was added by syringe. The solution was stirred at room temperature for 20 min, adsorbed directly onto a Biotage KP C18 HS 1.2 g samplet, and purified on a Biotage KP C18 HS 12 g cartridge using a gradient of 0-100% CH$_3$CN in H$_2$O, giving the title compound as a white solid (59.1 mg, 82% yield). HPLC retention time 14.090 min. Method A.

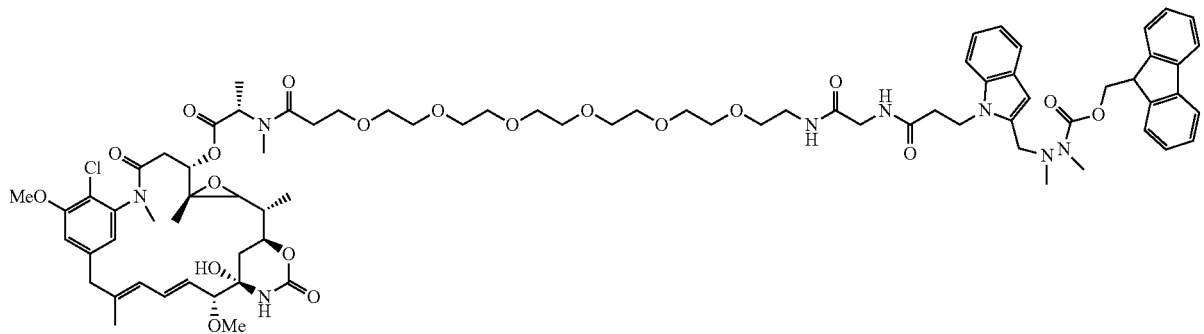

Preparation of (S)-1-((S)-3-maytansinyl) 31-(2-((2-(((9H-fluoren-9-yl)methoxy)carbonyl)-1,2-dimethyl-hydrazinyl)methyl)-1H-indol-1-yl)-2,3-dimethyl-4,26,29-trioxo-7,10,13,16,19,22-hexaoxa-3,25,28-triazahentriacontan-1-oate (FMOC HIPS Indole G PEG$_6$ Maytansine) (Compound 41) (FIG. 21)

To a dried 4 mL glass scintillation vial containing a dried flea stir bar was added G PEG$_6$ Maytansine (59.1 mg, 0.06 mmol), FMOC HIPS Indole CO$_2$PFP (44.0 mg, 0.07 mmol), DIPEA (36.6 mg, 49.4 uL, 0.3 mmol), and anhydrous DMF (0.3 mL). The solution was stirred at room temperature for 2 h, adsorbed directly onto a Biotage KP C18 HS 1.2 g samplet, and purified on a Biotage KP C18 HS 12 g cartridge using a gradient of 0-100% CH$_3$CN in H$_2$O, giving the desired product as a white solid (67.2 mg, 79% yield). HPLC retention time 13.963 min. Method A.

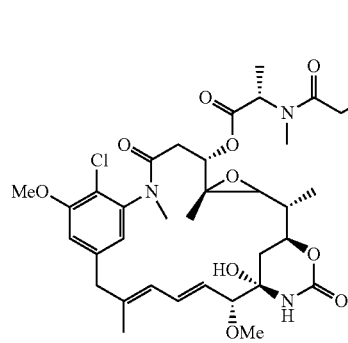
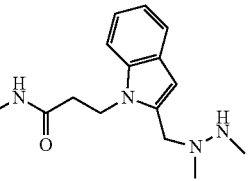

Preparation of (S)-1-((S)-3-maytansinyl) 31-(2-((1,2-dimethylhydrazinyl)methyl)-1H-indol-1-yl)-2,3-dimethyl-4,26,29-trioxo-7,10,13,16,19,22-hexaoxa-3,25,28-triazahentriacontan-1-oate (HIPS Indole G PEG$_6$ Maytansine) (Compound 42) (FIG. 22)

To a dried 4 mL glass scintillation vial containing a dried flea stir bar was added FMOC HIPS Indole G PEG$_6$ Maytansine (67.2 mg, 0.05 mmol). Piperidine (86.2 mg, 0.1 mL, 1.0 mmol) in DMA (0.4 mL) was added by syringe. The solution was stirred at room temperature for 20 min, adsorbed directly onto a Biotage KP C18 HS 1.2 g samplet, and purified on a Biotage KP C18 HS 12 g cartridge using a gradient of 0-100% CH$_3$CN in H$_2$O, giving the title compound as a white solid (48.0 mg, 84% yield). HPLC retention time 9.416 min. Method A. LRMS (ESI) calcd for C$_{63}$H$_{94}$ClN$_8$O$_{18}$$^+$ [M+H]$^+$: 1285.6 found 1285.5.

Example 10

Method 10—Preparation of (2S,15S)-1-((S)-3-maytansinyl) 15-(2-(((2R,3R,4R,5S,6R)-3-acetamido-4,5-dihydroxy-6-(hydroxymethyl)tetrahydro-2H-pyran-2-yl)amino)-2-oxoethyl)-19-(2-((1,2-dimethylhydrazinyl)methyl)-1H-indol-1-yl)-2,3-dimethyl-4,14,17-trioxo-7,10-dioxa-3,13,16-triazanonadecan-1-oate (HIPS Indole N ((OH)$_3$AcNH-β-Glc) PEG$_2$ Maytansine)

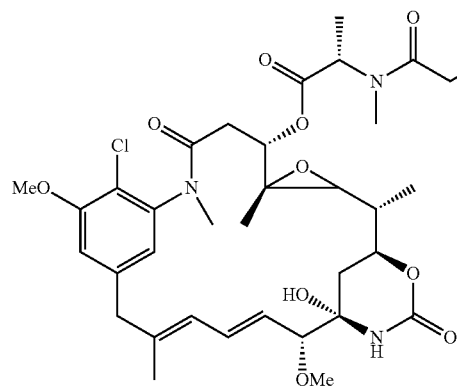
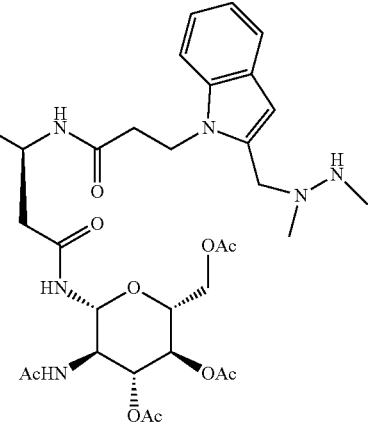

A reaction scheme for the synthesis of compound HIPS Indole N ((OH)$_3$AcNH-β-Glc) PEG$_2$ Maytansine is shown in FIG. 23.

Preparation of (2R,3S,4R,5R,6R)-5-acetamido-2-(acetoxymethyl)-6-((2S,15S)-1-((S)-3-maytansinyl)-15-(3-(2-((1,2-dimethylhydrazinyl)methyl)-1H-indol-1-yl)propanamido)-2,3-dimethyl-1,4,14-trioxo-7,10-dioxa-3,13-diazaheptadecanamido)tetrahydro-2H-pyran-3,4-diyl diacetate (HIPS Indole N ((Ac)$_3$AcNH-β-Glc) PEG$_2$ Maytansine) (Compound 43) (FIG. 23)

Prepared as in Method 3. HPLC retention time 9.451 min. Method A. LRMS (ESI) calcd for C$_{71}$H$_{100}$ClN$_{10}$O$_{23}$$^+$ [M+H]$^+$: 1495.7 found 1495.4.

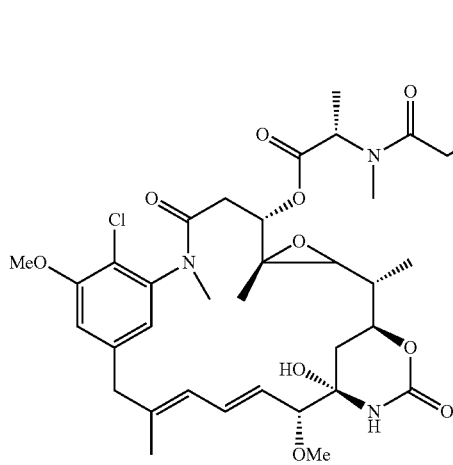
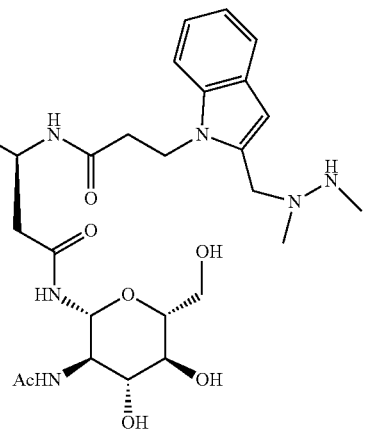

Preparation of (2S,15S)-1-((S)-3-maytansinyl) 15-(2-(((2R,3R,4R,5S,6R)-3-acetamido-4,5-dihydroxy-6-(hydroxymethyl)tetrahydro-2H-pyran-2-yl)amino)-2-oxoethyl)-19-(2-((1,2-dimethylhydrazinyl)methyl)-1H-indol-1-yl)-2,3-dimethyl-4,14,17-trioxo-7,10-dioxa-3,13,16-triazanonadecan-1-oate (HIPS Indole N ((OH)$_3$AcNH-β-Glc) PEG$_2$ Maytansine) (Compound 44) (FIG. 23)

To a dried 4 mL glass scintillation vial containing a dried flea stir bar was added HIPS Indole N ((Ac)$_3$AcNH-β-Glc) PEG$_2$ Maytansine (7.2 mg, 4.8 umol) and anhydrous MeOH (1.0 mL). NH$_3$ (1.0 mL, 2.0 mmol, 2.0 M solution in anhydrous MeOH) was added by syringe. The solution was stirred at room temperature for 4 h, evaporated, adsorbed directly onto a Biotage KP C18 HS 1.2 g samplet, and purified on a Biotage KP C18 HS 12 g cartridge using a gradient of 0-100% CH$_3$CN in H$_2$O, giving the desired product as a white film (6.5 mg, 99% yield). HPLC retention time 8.520 min. Method A. LRMS (ESI) calcd for C$_{65}$H$_{94}$ClN$_{10}$O$_{20}$$^+$ [M+H]$^+$: 1369.6 found 1369.5.

Example 11

Method 11—Preparation of (2S,9S,10R)-1-((S)-3-maytansinyl) 18-(2-((1,2-dimethylhydrazinyl)methyl)-1H-indol-1-yl)-9,10-dihydroxy-2,3-dimethyl-4,8,11,16-tetraoxo-3,7,12,15-tetraazaoctadecan-1-oate (HIPS Indole Ethylenediamine Tartaric Acid (OH)$_2$ Beta Alanine Maytansine) (from intermediate Compound 45)

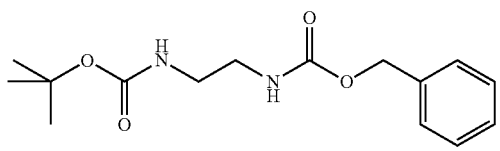 [SMILES: CC(C)(C)OC(=O)NCCNC(=O)OCc1ccccc1]

Figure 24:
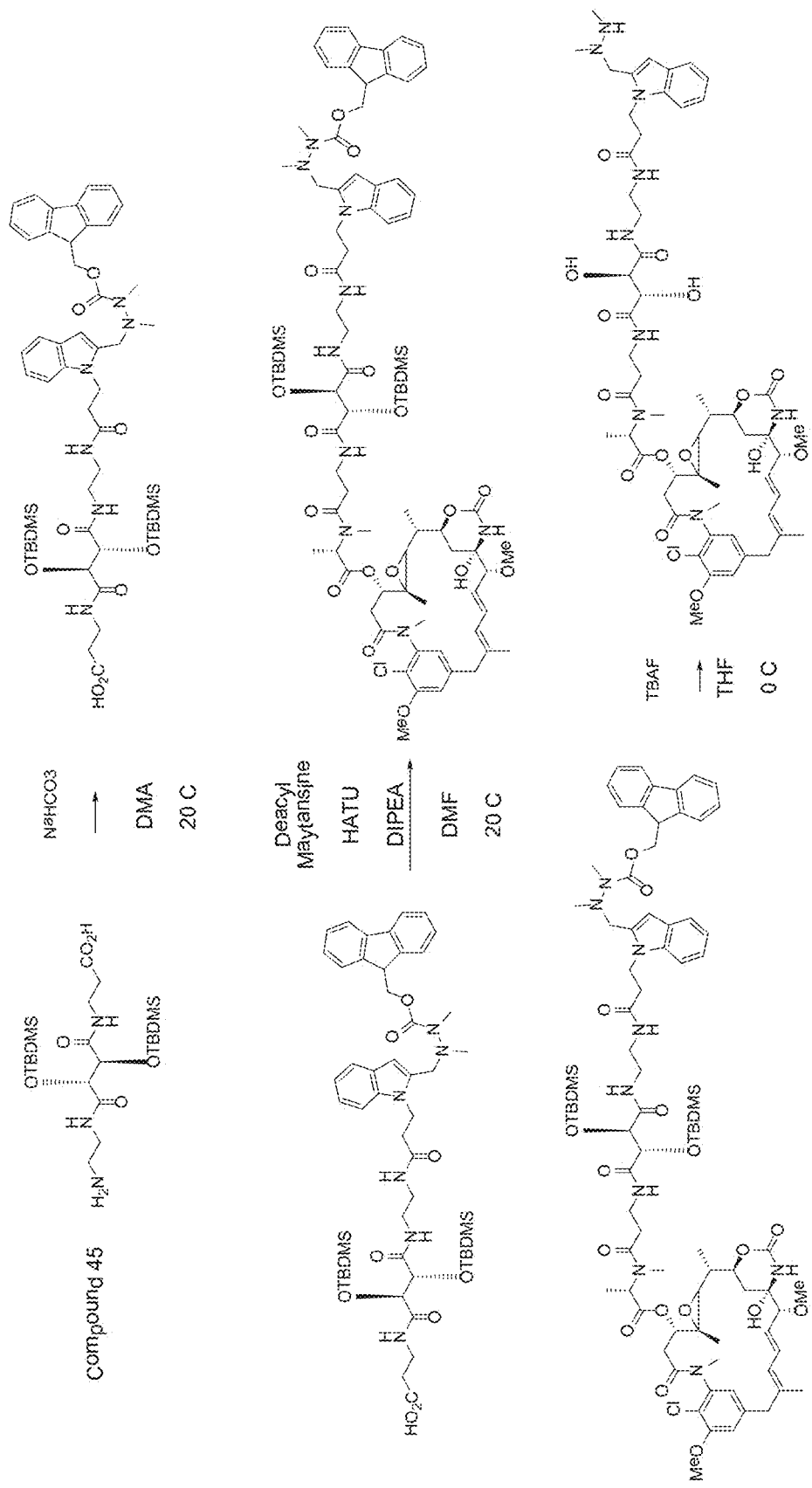
FIG. 24 shows a reaction scheme for the synthesis of compound HIPS Indole Ethylenediamine Tartaric Acid $(OH)_2$ Beta Alanine Maytansine according to embodiments of the present disclosure, see e.g., Example 11.

A reaction scheme for the synthesis of compound HIPS Indole Ethylenediamine Tartaric Acid (OH)$_2$ Beta Alanine Maytansine is shown in FIG. 24.

Preparation of benzyl tert-butyl ethane-1,2-diyldicarbamate

To a solution of tert-butyl (2-aminoethyl)carbamate (1.0 g, 6.3 mmol), Et$_3$N (0.94 g, 9.4 mmol), and THF (20 mL) was added CbzCl (1.2 g, 7.5 mmol) over 10 min. The reaction was stirred at room temperature for 10 h and concentrated to afford a white solid, which was purified by column chromatography on silica gel (PE: EtOAc=10:1~3:1) to give the desired compound (1.5 g, 83% yield).

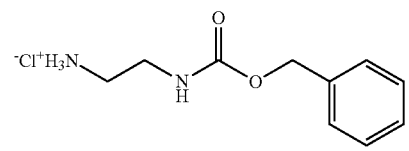

Preparation of 2-(((benzyloxy)carbonyl)amino)ethanaminium chloride

Benzyl tert-butyl ethane-1,2-diyldicarbamate (1.5 g, 6.3 mmol) in MeOH (10 mL) was treated with HCl/EtOAc (2 mL). The reaction was stirred at room temperature for 10 h and concentrated to give the title compound (1.0 g, 85% yield).

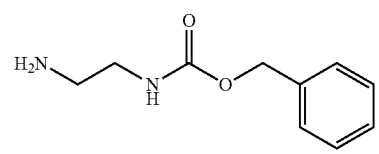 [SMILES: NCCNC(=O)OCc1ccccc1]

Preparation of benzyl (2-aminoethyl)carbamate

To a solution of 2-(((benzyloxy)carbonyl)amino)ethan-aminium chloride (1.0 g, 4.3 mmol) in water (5 mL) was added anhydrous Na₂CO₃ until litmus testing indicated pH 9. Solvent removal afforded a residue that was triturated with CH₂Cl₂ and filtered. The filtrate was concentrated to afford the desired free amine (0.93 g, 99% yield).

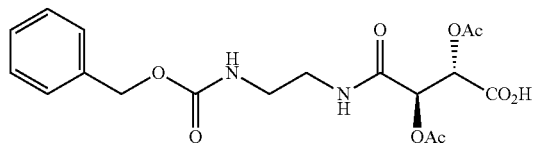 [SMILES: CC(=O)O[C@H](C(=O)O)[C@@H](OC(C)=O)C(=O)NCCNC(=O)OCc1ccccc1]

Preparation of (2S,3R)-2,3-diacetoxy-4-((2-(((benzyloxy)carbonyl)amino)ethyl)amino)-4-oxobutanoic acid To benzyl (2-aminoethyl)carbamate (100 mg, 0.52 mmol) in THF (2 mL) at 0° C. was added (+)-diacetyl-L-tartaric anhydride (37 mg, 0.17 mmol). The mixture was warmed to room temperature and stirred overnight. The solvent was removed to afford the title compound as a pale yellow solid (212 mg, 83% yield). The compound was used in subsequent steps without additional purification.

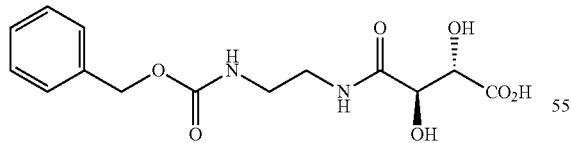

Preparation of (2S,3R)-4-((2-(((benzyloxy)carbonyl)amino)ethyl)amino)-2,3-dihydroxy-4-oxobutanoic acid To a suspension of (2S,3R)-2,3-diacetoxy-4-((2-(((benzyloxy)carbonyl)amino)ethyl)amino)-4-oxobutanoic acid (3.3 g, 8 mmol) in H₂O (40 mL) was added potassium hydroxide (0.9 g, 16 mmol). The solution was stirred at room temperature for 1.5 h and acidified to pH 5 with HCl (1 M), giving a white precipitate. The solid was filtered, washed with water, and dried to give the title compound (1.2 g, 45% yield). The compound was used in subsequent steps without additional purification.

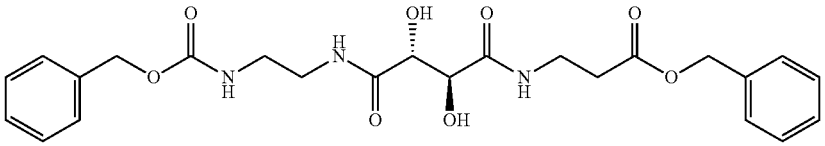 [SMILES: O=C(CCNC(=O)[C@@H](O)[C@@H](O)C(=O)NCCNC(=O)OCc1ccccc1)OCc1ccccc1]

Preparation of (9R,10S)-benzyl 9,10-dihydroxy-3,8,11-trioxo-1-phenyl-2-oxa-4,7,12-triazapentadecan-15-oate To a solution of (2S,3R)-4-((2-(((benzyloxy)carbonyl)amino)ethyl)amino)-2,3-dihydroxy-4-oxobutanoic acid (4 g, 12 mmol) in DMF (100 mL) was added HOBT (1.66 g, 12 mmol) and EDCI (2.3 g, 12 mmol). The reaction was stirred at room temperature for 30 min, whereupon benzyl 3-aminopropanoate (2.1 g, 12 mmol) was added. The reaction was allowed to stir at room temperature overnight and added dropwise to a 10% Na₂CO₃ solution, giving a white precipitate. The solid was filtered, washed with water and dried under vacuum to afford the title compound (5.2 g, 78% yield).

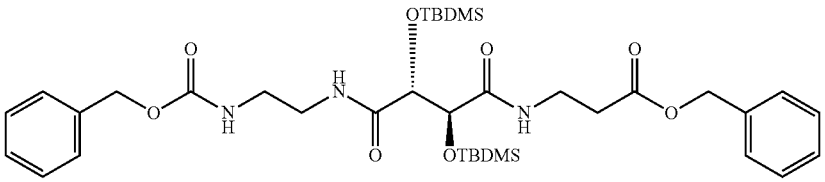 [SMILES: CC(C)(C)[Si](C)(C)O[C@H](C(=O)NCCC(=O)OCc1ccccc1)[C@@H](O[Si](C)(C)C(C)(C)C)C(=O)NCCNC(=O)OCc1ccccc1]

Preparation of (9R,10S)-benzyl 9,10-bis((tert-butyldimethylsilyl)oxy)-3,8,11-trioxo-1-phenyl-2-oxa-4,7,12-triazapentadecan-15-oate To a solution of (9R,10S)-benzyl 9,10-dihydroxy-3,8,11-trioxo-1-phenyl-2-oxa-4,7,12-triazapentadecan-15-oate (5.8 g, 12 mmol) in DMF (20 mL) was added TBSCl (18 g, 0.72 mol) and imidazole (8.1 g, 0.72 mol). The reaction was stirred at room temperature overnight, diluted with EtOAc (200 mL), washed with 1×5 M NaCl and 2×H₂O, dried over Na₂SO₄, and concentrated to give a pale yellow viscous oil. The oil was purified by flash column chromatography on silica gel (PE:EA=6:1~2:1) to afford the title compound as pale pink solid (4.9 g, 87% yield).

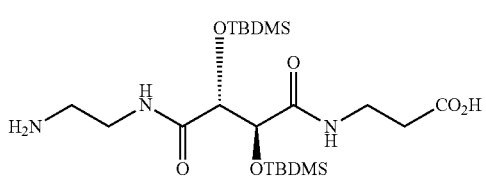 [SMILES: CC(C)(C)[Si](C)(C)O[C@H](C(=O)NCCC(=O)O)[C@@H](O[Si](C)(C)C(C)(C)C)C(=O)NCCN]

Preparation of 3-((2S,3R)-4-((2-aminoethyl)amino)-2,3-bis((tert-butyldimethylsilyl)oxy)-4-oxobutanamido)propanoic acid (Compound 45) (FIG. 24)

To a solution of (9R,10S)-benzyl 9,10-bis((tert-butyldimethylsilyl)oxy)-3,8,11-trioxo-1-phenyl-2-oxa-4,7,12-triazapentadecan-15-oate (4.0 g, 2.46 mmol) in THF (400 mL) was added 10% Pd/C (3.7 g, 50% wt). The mixture was stirred at room temperature under a double-layer $H_2$ balloon overnight. The reaction mixture was filtered and washed with THF. The filtrate was concentrated to afford the title compound (3.7 g, 91% yield). MS: m/z (ESI+): $(M+H)^+$=492.55. 1H NMR (400 MHz, CDCl3) δ 4.18 (d, J=2.0 Hz, 1H), 4.15 (d, J=2.0 Hz, 1H), 3.37-3.40 (m, 2H), 3.34-3.36 (m, 1H), 3.30-3.32 (m, 1H), 2.74 (s, 2H), 2.17-2.24 (m, 2H), 0.88 (s, 18H), 0.02 (s, 6H), −0.04 (s, 6H).

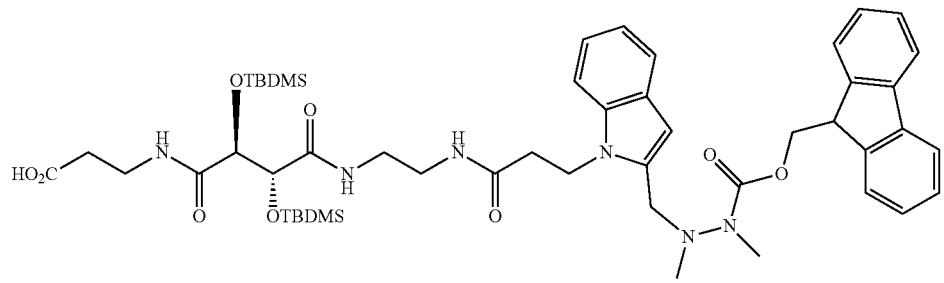 [SMILES: CN(Cc1cc2ccccc2n1CCC(=O)NCCNC(=O)[C@H](O[Si](C)(C)C(C)(C)C)[C@H](O[Si](C)(C)C(C)(C)C)C(=O)NCCC(=O)O)N(C)C(=O)OCC1c2ccccc2-c2ccccc21]

Preparation of 3-((2S,3R)-4-((2-(3-(2-((2-(((9H-fluoren-9-yl)methoxy)carbonyl)-1,2-dimethylhydrazinyl)methyl)-1H-indol-1-yl)propanamido)ethyl)amino)-2,3-bis((tert-butyldimethylsilyl)oxy)-4-oxobutanamido)propanoic acid (FIG. 24)

To a dried 20 mL glass scintillation vial containing a dried pea stir bar was added 3-((2S,3R)-4-((2-aminoethyl)amino)-2,3-bis((tert-butyldimethylsilyl)oxy)-4-oxobutanamido)propanoic acid (236.0 mg, 0.5 mmol), FMOC HIPS Indole $CO_2$PFP (206.0 mg, 0.3 mmol), NaHCO$_3$ (134.0 mg, 1.6 mmol), and DMA (5 mL). The solution was stirred at room temperature for 1 h, poured into $H_2O$ (25 mL), and extracted with 3×10 mL EtOAc. The organic fractions were combined, washed with 1×10 mL 5 M NaCl, dried over Na$_2$SO$_4$, concentrated, adsorbed onto a Biotage KP C18 HS 3 g samplet, and purified on a Biotage KP C18 HS 30 g cartridge using a gradient of 0-100% CH$_3$CN in H$_2$O, giving the desired product as a white solid (230.0 mg, 76% yield). HPLC retention time 16.21 min. Method A.

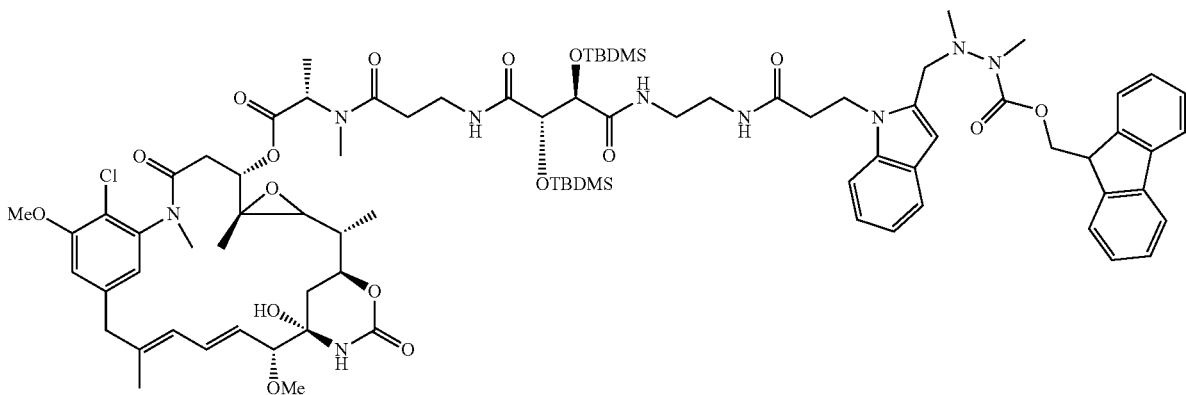

215

Preparation of (2S,9S,10R)-1-((S)-3-maytansinyl) 18-(2-((2-(((9H-fluoren-9-yl)methoxy)carbonyl)-1,2-dimethylhydrazinyl)methyl)-1H-indol-1-yl)-9,10-bis((tert-butyldimethylsilyl)oxy)-2,3-dimethyl-4,8,11,16-tetraoxo-3,7,12,15-tetraazaoctadecan-1-oate (FMOC HIPS Indole Ethylenediamine Tartaric Acid (OTBDMS)₂ Beta Alanine Maytansine) (FIG. 24)

To a dried 4 mL glass scintillation vial containing a dried flea stir bar was added 3-((2S,3R)-4-((2-(3-(2-((2-(((9H-fluoren-9-yl)methoxy)carbonyl)-1,2-dimethylhydrazinyl)methyl)-1H-indol-1-yl)propanamido)ethyl)amino)-2,3-bis((tert-butyldimethylsilyl)oxy)-4-oxobutanamido)propanoic acid (129.0 mg, 0.1 mmol), HATU (52.0 mg, 0.1 mmol), and anhydrous DMF (0.5 mL). The clear, colorless solution was stirred at room temperature for 15 min. Deacyl maytansine (96.0 mg, 0.1 mmol), DIPEA (36.0 mg, 48.5 uL, 0.3 mmol), and anhydrous DMF (0.5 mL) were combined in a separate, dried 4 mL glass scintillation vial and added dropwise, slowly, to the stirring solution. The reaction was allowed to stir at room temperature for 2 h, adsorbed directly onto a Biotage KP C18 HS 3 g samplet, and purified on a Biotage KP C18 HS 30 g cartridge using a gradient of 0-100% CH₃CN in H₂O, giving the title compound as a white solid (103.0 mg, 48% yield). HPLC retention time 17.23 min. Method A.

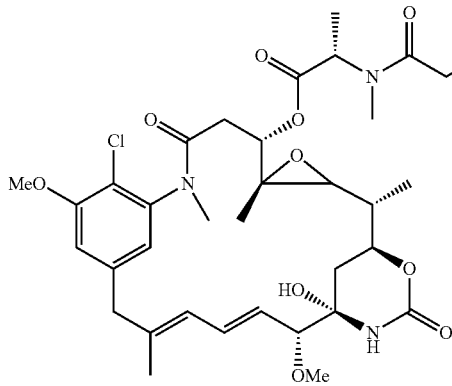

Preparation of (2S,9S,10R)-1-((S)-3-maytansinyl) 18-(2-((1,2-dimethylhydrazinyl)methyl)-1H-indol-1-yl)-9,10-dihydroxy-2, 3-dimethyl-4,8,11,16-tetraoxo-3,7,12,15-tetraazaoctadecan-1-oate (HIPS Indole Ethylenediamine Tartaric Acid (OH)₂ Beta Alanine Maytansine) (FIG. 24)

To a dried 4 mL glass scintillation vial containing a dried flea stir bar was added FMOC HIPS Indole Ethylenediamine Tartaric Acid (OTBDMS)₂ Beta Alanine Maytansine (102.0 mg, 0.06 mmol) and anhydrous THF (0.6 mL). The solution was cooled to 0° C. in an ice, H₂O bath and TBAF (0.225 mL, 0.225 mmol, 1.0 M solution in anhydrous THF) was added dropwise by syringe. The solution was stirred at 0° C. for 35 min, adsorbed directly onto a Biotage KP C18 HS 1.2 g samplet, and purified on a Biotage KP C18 HS 12 g cartridge using a gradient of 0-100% CH₃CN in H₂O, giving the desired product as a white solid (45.0 mg, 60% yield). HPLC retention time 8.72 min. Method A. LRMS (ESI) calcd for $C_{55}H_{76}ClN_9NaO_{15}^+$ [M+Na]⁺: 1160.5 found 1160.5.

216

Example 12

Method 12—Preparation of (S)-(S)-1-cyclopropylethyl 16-(2-((1,2-dimethylhydrazinyl)methyl)-1H-indol-1-yl)-7,10-bis(2-hydroxyethyl)-2,3-dimethyl-4,8,11,14-tetraoxo-3,7,10,13-tetraazahexadecan-1-oate (HIPS Indole Glycine Dihydroxypeptoid (OH)₂ Beta Alanine Maytansine) (from intermediate Compound 46)

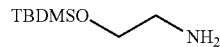

Figure 25:
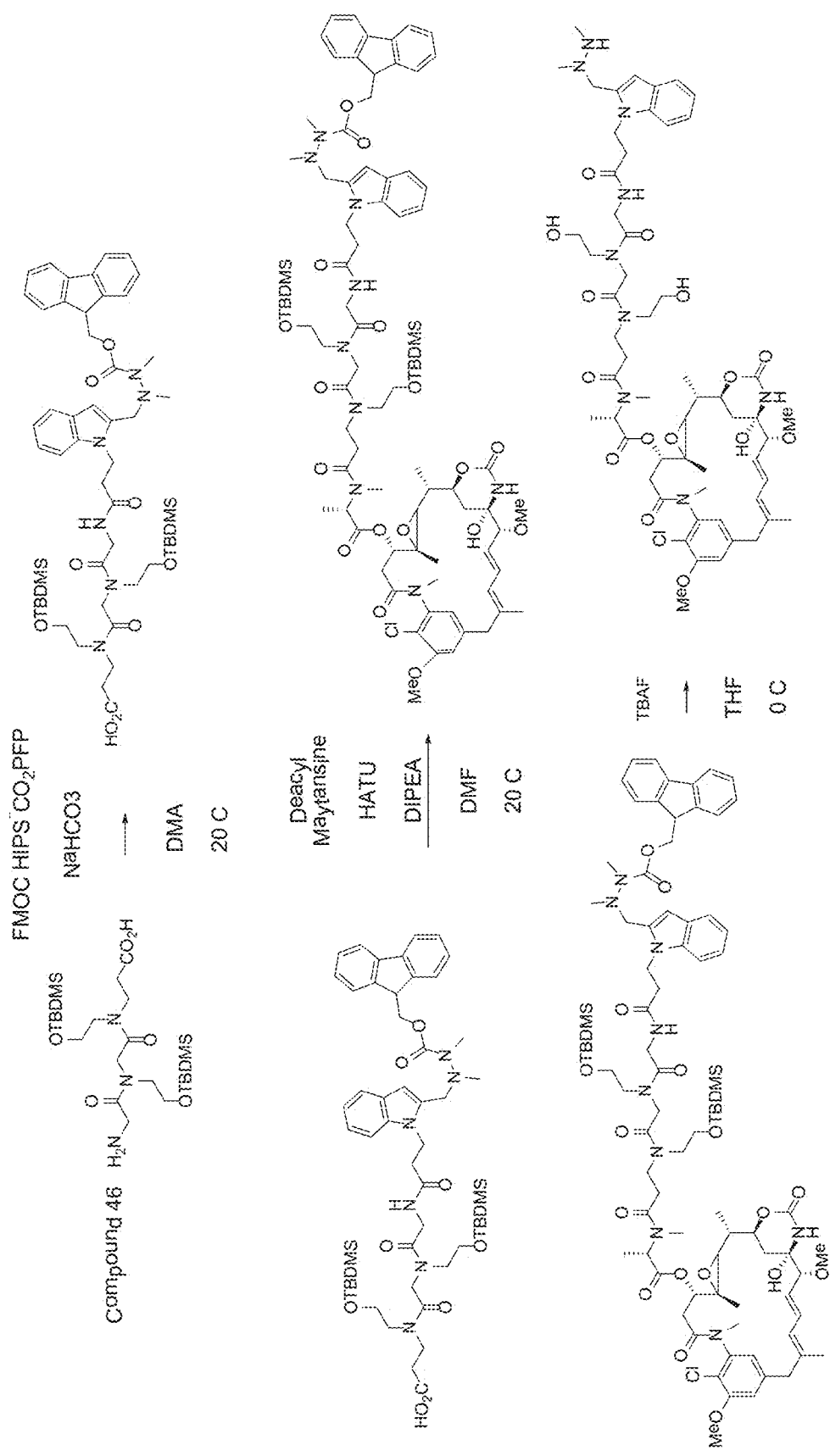
FIG. 25 shows a reaction scheme for the synthesis of compound HIPS Indole Glycine Dihydroxypeptoid $(OH)_2$ Beta Alanine Maytansine according to embodiments of the present disclosure, see e.g., Example 12.

A reaction scheme for the synthesis of compound HIPS Indole Glycine Dihydroxypeptoid (OH)₂ Beta Alanine Maytansine is shown in FIG. 25.

Preparation of 2-((tert-butyldimethylsilyl)oxy)ethanamine (Compound 1)

To a stirred solution of 2-aminoethanol (50 g, 0.82 mol), Et₃N (124 g, 1.23 mol), and DMAP (2 g) in anhydrous DCM (1 L) was added TBSCl (135 g, 0.9016 mol). The reaction was stirred at room temperature overnight, quenched with aqueous NH₄Cl, and extracted with DCM (×3). The combined organic layers were washed with H₂O, dried over MgSO₄, filtered, concentrated, and purified by flash column chromatography to give the title compound (30.5 g, 22% yield). 1H NMR (400 MHz, CDCl3) δ 3.6 (t, J=5.5 Hz, 2H), 2.74 (t, J=5.5 Hz, 2H), 1.36 (brs, 1H), 0.87 (s, 9H), 0.04 (s, 6H).

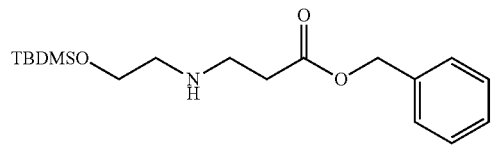 [SMILES: CC(C)(C)[Si](C)(C)OCCNCCC(=O)OCc1ccccc1]

Preparation of benzyl 3-((2-((tert-butyldimethylsilyl)oxy)ethyl)amino)propanoate (Compound 2)

To a stirred solution of lithium chloride (20 mg) and Compound 1 (1.0 g, 5.71 mmol) in MeOH (25 mL) and THF (25 mL) at 0° C. was added benzyl acrylate (1.0 g, 6.28 mmol) dropwise over 10 min. The reaction mixture was allowed to warm to room temperature gradually and stirred at room temperature overnight. The reaction mixture was concentrated under reduced pressure, extracted with EtOAc (250 mL), washed with 5 M NaCl (200 mL), dried over Na$_2$SO$_4$, and evaporated. The residue was purified by flash column chromatography (PE:EA=5:1 to 0:1) to afford compound the desired compound (0.7 g, 37% yield).

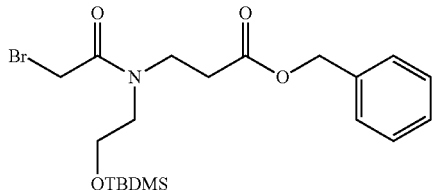 [SMILES: CC(C)(C)[Si](C)(C)OCCN(CCC(=O)OCc1ccccc1)C(=O)CBr]

Preparation of benzyl 3-(2-bromo-N-(2-((tert-butyldimethylsilyl)oxy)ethyl)acetamido)propanoate (Compound 3)

To a solution of Compound 2 (0.7 g, 2.07 mmol) in THF (20 mL) at 0° C. under nitrogen were added Et$_3$N (1.2 equiv, 0.25 g, 2.49 mmol) and bromoacetyl bromide (1.2 equiv, 0.5 g, 2.49 mmol). The reaction was stirred at 0° C. for 1 h, diluted with EtOAc (10 mL), and filtered. The solid was rinsed with EtOAc and the filtrate dried in vacuo to yield the crude bromoacetyl amide. The product was purified by flash column chromatography (PE:EA=10:1 to 5:1) to afford pure Compound 3 (0.3 g, 31% yield). MS+: 459[M+H]$^+$.

Preparation of benzyl 10-(2-((tert-butyldimethylsilyl)oxy)ethyl)-2,2,3,3-tetramethyl-9-oxo-4-oxa-7,10-diaza-3-silatridecan-13-oate (Compound 4)

To a solution of Compound 3 (36.8 g, 80.3 mmol, 1.0 eq) in THF (350 mL) at 0° C. under nitrogen were added Et$_3$N (16.3 g, 160.7 mmol, 2 eq) and 2-((tert-butyldimethylsilyl)oxy)ethanamine (28.1 g, 160.7 mmol, 2 eq). The reaction was stirred at room temperature overnight, diluted with EtOAc (100 mL), and filtered. The solid was rinsed with EtOAc and the filtrate concentrated to give the crude amine. The product was purified by flash column chromatography (PE:EA=3:1) to afford Compound 4 (27 g, 60% yield).

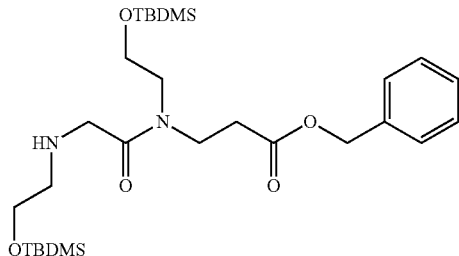 [SMILES: CC(C)(C)[Si](C)(C)OCCNCC(=O)N(CCO[Si](C)(C)C(C)(C)C)CCC(=O)OCc1ccccc1]

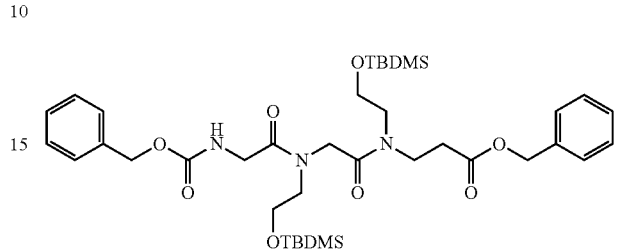

Preparation of benzyl 7,10-bis(2-((tert-butyldimethylsilyl)oxy)ethyl)-3,6,9-trioxo-1-phenyl-2-oxa-4,7,10-triazatridecan-13-oate (Compound 5)

To a solution of Cbz-glycine (2.5 g, 12 mmol), EDCI (2.5 g, 13 mmol), and HOBT (1.75 g, 13 mmol) in DCM (20 mL) at 0° C. was added DIPEA (4.2 g, 32.5 mmol). The mixture was stirred at 0° C. for 30 min. To the solution was added Compound 4 (6 g, 11 mmol) dropwise. The reaction was stirred at room temperature overnight, evaporated to dryness, suspended in DCM, and filtered. The filtrate was washed with H$_2$O and 5 M NaCl, dried over Na$_2$SO$_4$, and concentrated. The residue was purified by flash column chromatography to afford Compound 5 (3.01 g, 38% yield).

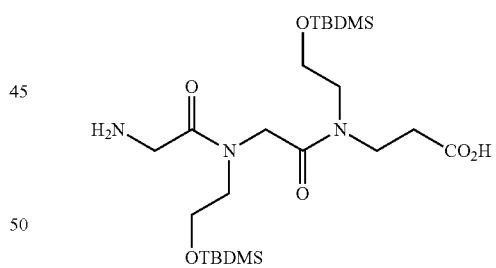

Preparation of 7-(2-aminoacetyl)-10-(2-((tert-butyldimethylsilyl)oxy)ethyl)-2,2,3,3-tetramethyl-9-oxo-4-oxa-7,10-diaza-3-silatridecan-13-oic acid (Compound 46) (FIG. 25)

A mixture of Compound 5 (1.9 g, 2.55 mmol) and Pd/C (500 mg) in EtOAc (50 mL) in a Parr shaker was stirred under H$_2$ (50 psi) at room temperature overnight. The mixture was filtered though a pad of Celite, and concentrated to give the title compound (AB4296) (730 mg, 55% yield). LC-MS: 520 (M+1).

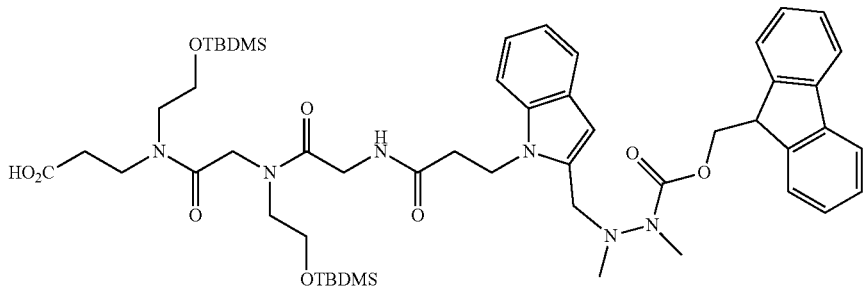 [SMILES: CN(Cc1cc2ccccc2n1CCC(=O)NCC(=O)N(CCO[Si](C)(C)C(C)(C)C)CC(=O)N(CCO[Si](C)(C)C(C)(C)C)CCC(=O)O)N(C)C(=O)OCC1c2ccccc2-c2ccccc21]

Preparation of 7-(2-(3-(2-((2-(((9H-fluoren-9-yl) methoxy)carbonyl)-1,2-dimethylhydrazinyl)methyl)-1H-indol-1-yl)propanamido)acetyl)-10-(2-((tert-butyldimethylsilyl)oxy)ethyl)-2,2,3,3-tetramethyl-9-oxo-4-oxa-7,10-diaza-3-silatridecan-13-oic acid (FIG. 25)

To a dried 20 mL glass scintillation vial containing a dried pea stir bar was added peptoid AB4296 (264.0 mg, 0.5 mmol), FMOC HIPS Indole CO$_2$PFP (220.0 mg, 0.3 mmol), NaHCO$_3$ (120.0 mg, 1.4 mmol), and DMA (5 mL). The solution was stirred at room temperature for 6 h, poured into H$_2$O (25 mL), and extracted with 3×10 mL EtOAc. The organic fractions were combined, washed with 1×10 mL 5 M NaCl, dried over Na$_2$SO$_4$, concentrated, adsorbed onto a Biotage KP C18 HS 3 g samplet, and purified on a Biotage KP C18 HS 30 g cartridge using a gradient of 0-100% CH$_3$CN in H$_2$O, giving the title compound as a white solid (184.0 mg, 55% yield). HPLC retention time 18.88 min. Method A.

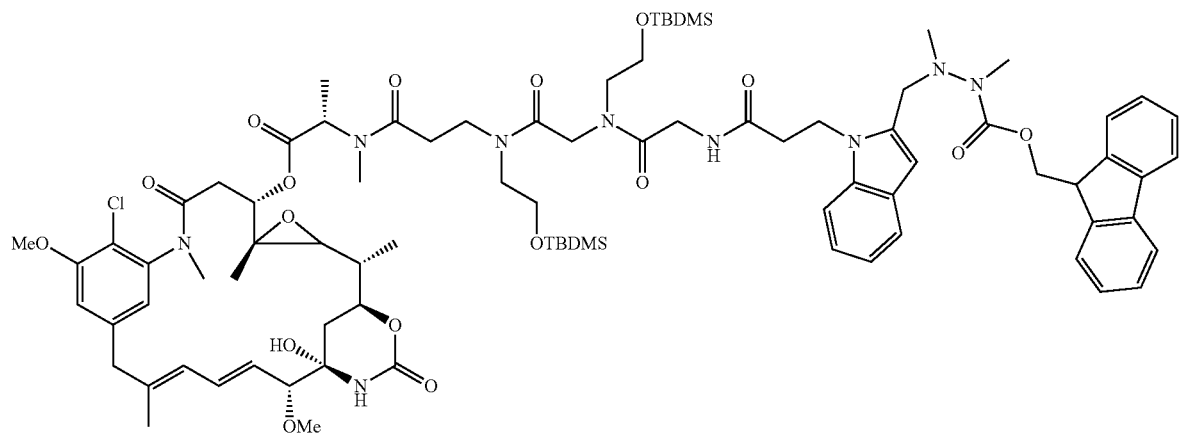

Preparation of (S)-1-((S)-3-maytansinyl) 7-(2-(3-(2-((2-(((9H-fluoren-9-yl)methoxy)carbonyl)-1,2-dimethylhydrazinyl)methyl)-1H-indol-1-yl)propanamido)acetyl)-10-(2-((tert-butyldimethylsilyl)oxy) ethyl)-2,2,3,3,14,15-hexamethyl-9,13-dioxo-4-oxa-7,10,14-triaza-3-silahexadecan-16-oate (FMOC HIPS Indole Glycine Dihydroxypeptoid (OTBDMS)$_2$ Beta Alanine Maytansine) (FIG. 25)

To a dried 4 mL glass scintillation vial containing a dried flea stir bar was added 7-(2-(3-(2-((2-(((9H-fluoren-9-yl) methoxy)carbonyl)-1,2-dimethylhydrazinyl)methyl)-1H-indol-1-yl)propanamido)acetyl)-10-(2-((tert-butyldimethylsilyl)oxy)ethyl)-2,2,3,3-tetramethyl-9-oxo-4-oxa-7,10-diaza-3-silatridecan-13-oic acid (180.0 mg, 0.2 mmol), HATU (72.0 mg, 0.2 mmol), and anhydrous DMF (0.5 mL). The clear, colorless solution was stirred at room temperature for 15 min. Deacyl maytansine (123.0 mg, 0.2 mmol), DIPEA (51.0 mg, 68.7 uL, 0.4 mmol), and anhydrous DMF (0.5 mL) were combined in a separate, dried 4 mL glass scintillation vial and added dropwise, slowly, to the stirring solution. The reaction was allowed to stir at room temperature for 2 h, adsorbed directly onto a Biotage KP C18 HS 3 g samplet, and purified on a Biotage KP C18 HS 30 g cartridge using a gradient of 0-100% CH$_3$CN in H$_2$O, giving the desired product as a white solid (235.0 mg, 80% yield). HPLC retention time 20.21 min. Method A.

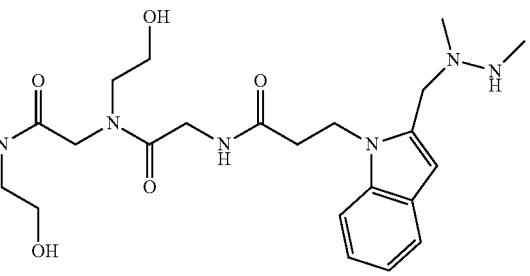
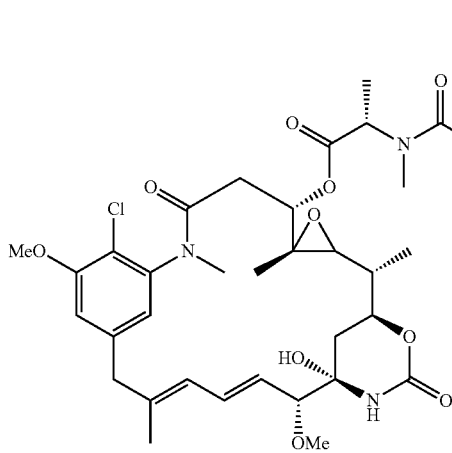

Preparation of (S)-1-((S)-3-maytansinyl) 16-(2-((1,2-dimethylhydrazinyl)methyl)-1H-indol-1-yl)-7,10-bis(2-hydroxyethyl)-2,3-dimethyl-4,8,11,14-tetraoxo-3,7,10,13-tetraazahexadecan-1-oate (HIPS Indole Glycine Dihydroxypeptoid (OH)$_2$ Beta Alanine Maytansine) (FIG. 25)

To a dried 4 mL glass scintillation vial containing a dried flea stir bar was added FMOC HIPS Indole Glycine Dihydroxypeptoid (OTBDMS)$_2$ Beta Alanine Maytansine (114.0 mg, 0.07 mmol) and anhydrous THF (0.5 mL). The solution was cooled to 0° C. in an ice, H$_2$O bath and TBAF (0.3 mL, 0.3 mmol, 1.0 M solution in anhydrous THF) was added dropwise by syringe. The solution was stirred at 0° C. for 1 h, adsorbed directly onto a Biotage KP C18 HS 1.2 g samplet, and purified on a Biotage KP C18 HS 12 g cartridge using a gradient of 0-100% CH$_3$CN in H$_2$O, giving the title compound as an off-white solid (41.7 mg, 51% yield). HPLC retention time 8.03 min. Method A. LRMS (ESI) calcd for C$_{57}$H$_{80}$ClN$_9$NaO$_{15}{}^+$ [M+Na]$^+$: 1188.5 found 1188.4.

Example 13

Method 13—Preparation of (S)-1-((S)-3-maytansinyl) 19-(2-((1,2-dimethylhydrazinyl)methyl)-1H-indol-1-yl)-7,10,13-tris(2-hydroxyethyl)-2,3-dimethyl-4,8,11,14,17-pentaoxo-3,7,10,13,16-pentaazanonadecan-1-oate (HIPS Indole Glycine Trihydroxypeptoid (OH)$_3$ Beta Alanine Maytansine) (from intermediate Compound 47)

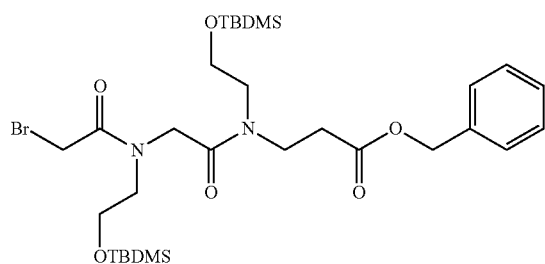 [SMILES: CC(C)(C)[Si](C)(C)OCCN(CCC(=O)OCc1ccccc1)C(=O)CN(CCO[Si](C)(C)C(C)(C)C)C(=O)CBr]

Figure 26:
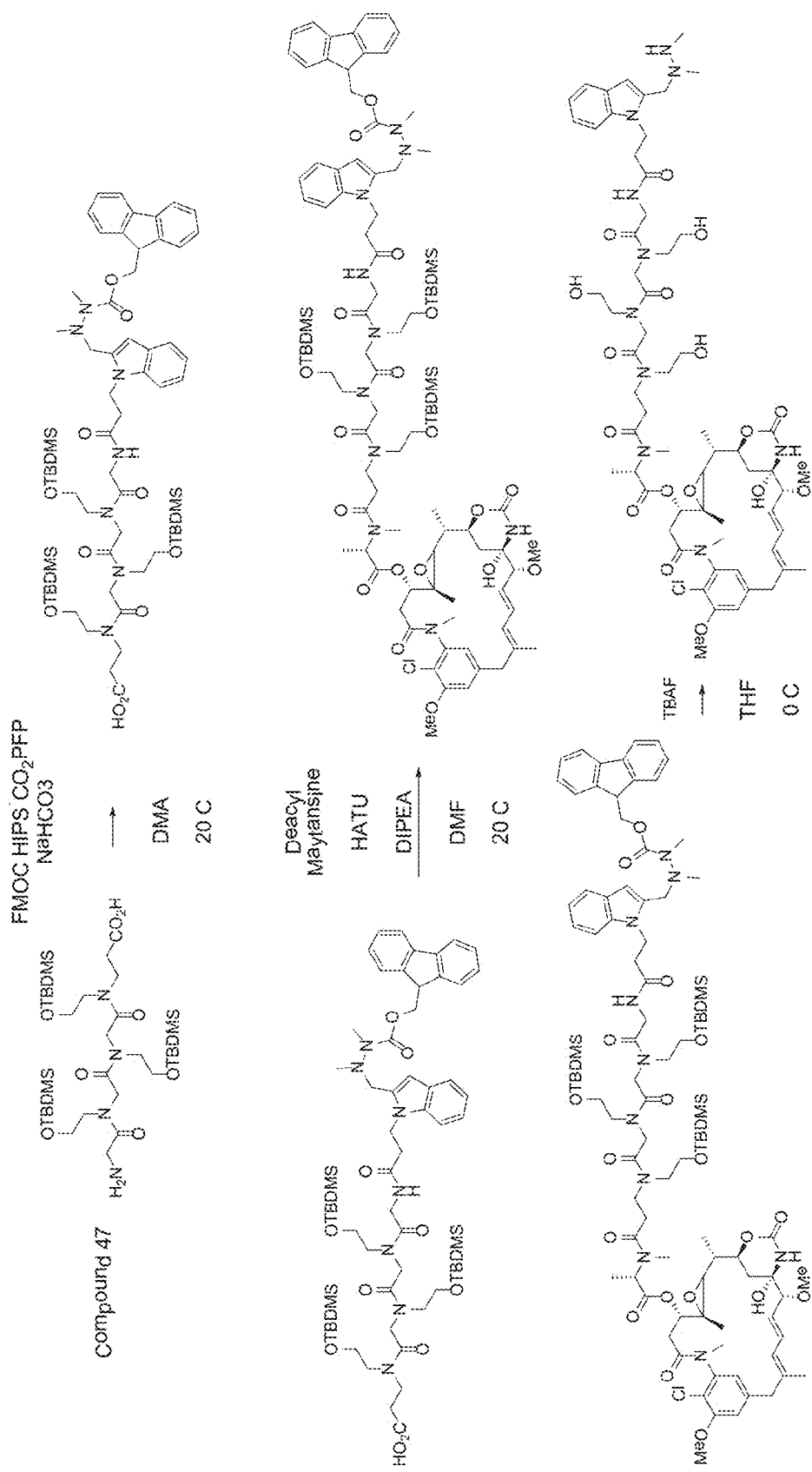
FIG. 26 shows a reaction scheme for the synthesis of compound HIPS Indole Glycine Trihydroxypeptoid $(OH)_3$ Beta Alanine Maytansine according to embodiments of the present disclosure, see e.g., Example 13.

A reaction scheme for the synthesis of compound HIPS Indole Glycine Trihydroxypeptoid (OH)$_3$ Beta Alanine Maytansine is shown in FIG. 26.

Preparation of benzyl 7-(2-bromoacetyl)-10-(2-((tert-butyldimethylsilyl)oxy)ethyl)-2,2,3,3-tetramethyl-9-oxo-4-oxa-7,10-diaza-3-silatridecan-13-oate (Compound 6)

To a solution of Compound 4 (16 g, 29 mmol) in THF (150 mL) at 0° C. under nitrogen were added Et$_3$N (3.5 g, 34.7 mmol) and bromoacetyl bromide (7 g, 34.7 mmol), dropwise. The reaction was stirred at 0° C. for 1 h, diluted with EtOAc (100 mL) and filtered. The solid was rinsed with EtOAc and the filtrate was concentrated to give the crude bromoacetyl amide. The product was purified by flash column chromatography (PE:EA=10:1) to afford Compound 6 (12.6 g, 64% yield).

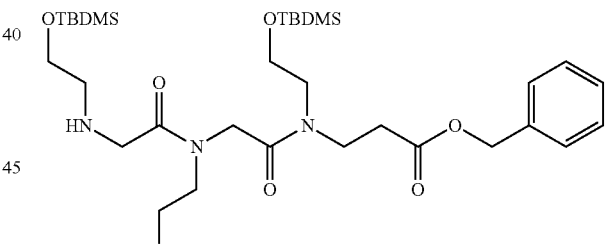

Preparation of benzyl 10,13-bis(2-((tert-butyldimethylsilyl)oxy)ethyl)-2,2,3,3-tetramethyl-9,12-dioxo-4-oxa-7,10,13-triaza-3-silahexadecan-16-oate (Compound 7)

To a solution of Compound 6 (12.6 g, 18.5 mmol) in THF (150 mL) at 0° C. under nitrogen, were added Et$_3$N (3.75 g, 37 mmol) and 2-((tert-butyldimethylsilyl)oxy)ethanamine (6.5 g, 37 mmol). The reaction was stirred at room temperature overnight, diluted with EtOAc (100 mL), filtered, and the solid washed with EtOAc. The filtrate was concentrated in vacuo to yield the crude amine. The product was purified by flash column chromatography (PE:EA=3:1) to afford pure Compound 7 (5.8 g, 41% yield).

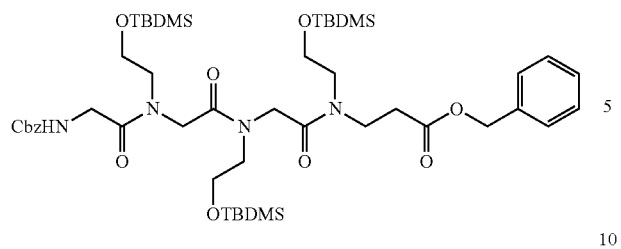

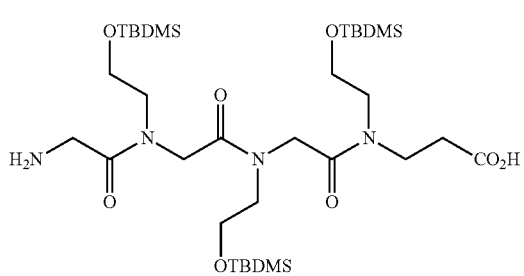 [SMILES: CC(C)(C)[Si](C)(C)OCCN(CCC(=O)O)C(=O)CN(CCO[Si](C)(C)C(C)(C)C)C(=O)CN(CCO[Si](C)(C)C(C)(C)C)C(=O)CN]

Preparation of benzyl 7,10,13-tris(2-((tert-butyldimethylsilyl)oxy)ethyl)-3,6,9,12-tetraoxo-1-phenyl-2-oxa-4,7,10,13-tetraazahexadecan-16-oate (Compound 8)

To a solution of Cbz-glycine (1.74 g, 8.3 mmol), EDCI (1.73 g, 9.06 mmol), and HOBT (1.22 g, 9.06 mmol) in DCM (50 mL) at 0° C. was added DIPEA (2.91 g, 22.6 mmol). The solution was stirred for 30 min. To the solution was added Compound 7 (5.8 g, 7.54 mmol), dropwise, in DCM (5 mL). The mixture was stirred at room temperature overnight, concentrated, suspended in DCM, and filtered. The filtrate was washed with H₂O and 5 M NaCl, and the product purified by flash column chromatography to afford pure Compound 8 (2.72 g, 38% yield). LC-MS: 960 (M+1).

Preparation of 7-(2-aminoacetyl)-10,13-bis(2-((tert-butyldimethylsilyl)oxy)ethyl)-2,2,3,3-tetramethyl-9,12-dioxo-4-oxa-7,10,13-triaza-3-silahexadecan-16-oic acid (Compound 47) (FIG. 26)

A mixture of Compound 8 (2.7 g, 2.81 mmol) and Pd/C (1 g) in EtOAc (60 mL) in a Parr shaker was stirred under H₂ (60 psi) at room temperature overnight. The mixture was filtered though a pad of Celite, washed with MeOH, and concentrated to give a residue that was lyophilized to afford AB4297 (1.7 g, 55% yield). LC-MS: 735.6 (M+1).

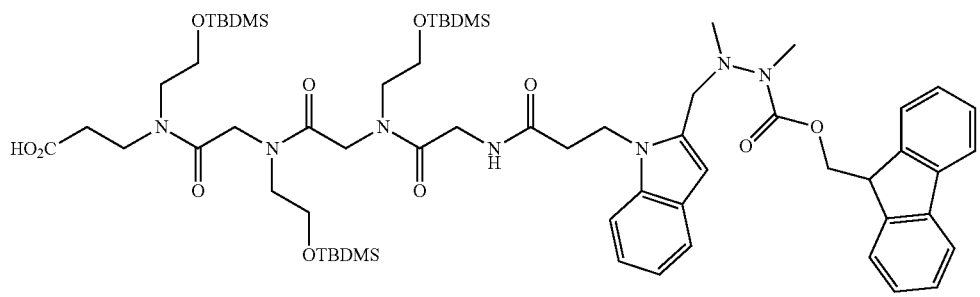 [SMILES: CN(Cc1cc2ccccc2n1CCC(=O)NCC(=O)N(CCO[Si](C)(C)C(C)(C)C)CC(=O)N(CCO[Si](C)(C)C(C)(C)C)CC(=O)N(CCO[Si](C)(C)C(C)(C)C)CCC(=O)O)N(C)C(=O)OCC1c2ccccc2-c2ccccc21]

Preparation of 7-(2-(3-(2-((2-(((9H-fluoren-9-yl)methoxy)carbonyl)-1,2-dimethylhydrazinyl)methyl)-1H-indol-1-yl)propanamido)acetyl)-10,13-bis(2-((tert-butyldimethylsilyl)oxy)ethyl)-2,2,3,3-tetramethyl-9,12-dioxo-4-oxa-7,10,13-triaza-3-silahexadecan-16-oic acid (FIG. 26)

To a dried 4 mL glass scintillation vial containing a dried flea stir bar was added peptoid AB4297 (50.0 mg, 0.07 mmol), FMOC HIPS Indole CO₂PFP (38.6 mg, 0.06 mmol), NaHCO₃ (14.2 mg, 0.2 mmol), and DMA (0.4 mL). The solution was stirred at room temperature for 16 h, acidified to pH 2 with 1 M HCl, and extracted with 1×10 mL EtOAc. The organic fraction was washed with a mixture of 1×10 mL 1 M HCl/5 M NaCl (1/1), dried over MgSO₄, filtered, concentrated, adsorbed onto a Biotage SNAP Ultra 1 g samplet, and purified on a Biotage SNAP Ultra 10 g cartridge using a gradient of 0-10% MeOH in CH₂Cl₂, giving the title compound as a white solid (40.0 mg, 49% yield). HPLC retention time 7.12 min. Method A. LRMS (ESI) calcd for $C_{47}H_{87}N_7O_9Si_3$ [M−H]⁻: 1198.6; found 1198.0.

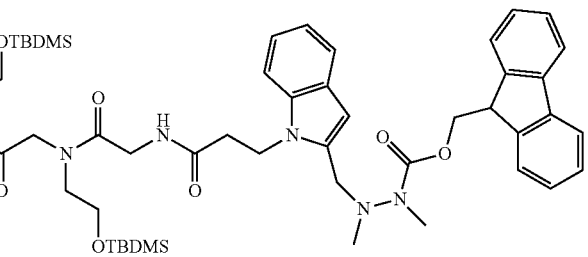
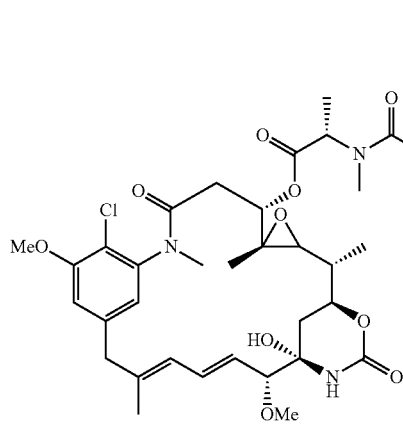

Preparation of (S)-1-((S)-3-maytansinyl) 7-(2-(3-(2-((2-(((9H-fluoren-9-yl)methoxy)carbonyl)-1,2-dimethylhydrazinyl)methyl)-1H-indol-1-yl)propanamido)acetyl)-10,13-bis(2-((tert-butyldimethylsilyl)oxy)ethyl)-2,2,3,3,17,18-hexamethyl-9,12,16-trioxo-4-oxa-7,10,13,17-tetraaza-3-silanonadecan-19-oate (FMOC HIPS Indole Glycine Trihydroxypeptoid (OTBDMS)₃ Beta Alanine Maytansine) (FIG. 26)

To a dried 4 mL glass scintillation vial containing a dried flea stir bar was added 7-(2-(3-(2-((2-(((9H-fluoren-9-yl)methoxy)carbonyl)-1,2-dimethylhydrazinyl)methyl)-1H-indol-1-yl)propanamido)acetyl)-10,13-bis(2-((tert-butyldimethylsilyl)oxy)ethyl)-2,2,3,3-tetramethyl-9,12-dioxo-4-oxa-7,10,13-triaza-3-silahexadecan-16-oic acid (28.1 mg, 0.03 mmol), deacyl maytansine (15.2 mg, 0.02 mmol), and DMA (0.13 mL). The solution was cooled to 0° C. in an ice, H₂O bath whereupon 2,4,6-trimethylpyridine (5.7 mg, 6.2 uL, 0.05 mmol) and COMU (10.0 mg, 0.02 mmol) were added. The reaction was allowed to stir at 0° C. for 15 min, then warmed to room temperature and stirred for 3 h. The reaction mixture was diluted with EtOAc (7 mL), washed with 3×2 mL 0.5 M HCl, 3×2 mL 1.2 M NaHCO₃, and 3×2 mL 5 M NaCl, dried over MgSO₄, filtered, and concentrated to a viscous oil. The product was adsorbed onto a Biotage KP C18 HS 1.2 g samplet and purified on a Biotage KP C18 HS 12 g cartridge using a gradient of 0-100% CH₃CN in H₂O, giving the desired product as a white solid (11.7 mg, 32% yield). HPLC retention time 18.72 min. Method A. LRMS (ESI) calcd for $C_{94}H_{139}ClN_{10}O_{19}Si_3$ [M+Na]⁺: 1853.9 found 1854.7.

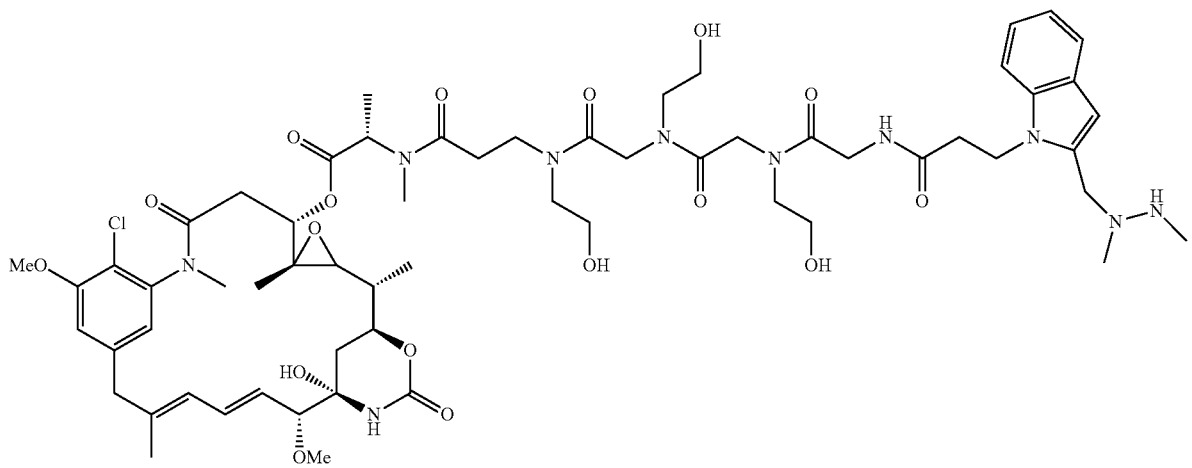

Preparation of (S)-1-((S)-3-maytansinyl) 19-(2-((1,2-dimethylhydrazinyl)methyl)-1H-indol-1-yl)-7,10,13-tris(2-hydroxyethyl)-2,3-dimethyl-4,8,11,14,17-pentaoxo-3,7,10,13,16-pentaazanonadecan-1-oate (HIPS Indole Glycine Trihydroxypeptoid (OH)₃ Beta Alanine Maytansine) (FIG. 26)

To a dried 4 mL glass scintillation vial containing a dried flea stir bar was added FMOC HIPS Indole Glycine Trihydroxypeptoid (OTBDMS)₃ Beta Alanine Maytansine (11.7 mg, 6.4 umol) and anhydrous THF (63.4 uL). The solution was cooled to 0° C. in an ice, H₂O bath and TBAF (25.0 uL, 0.25 mmol, 1.0 M solution in anhydrous THF) was added dropwise by micropipettor. The solution was stirred at 0° C. for 1 h, adsorbed directly onto a Biotage KP C18 HS 1.2 g samplet, and purified on a Biotage KP C18 HS 12 g cartridge using a gradient of 0-100% CH₃CN in H₂O, giving the title compound as an off-white solid (4.9 mg, 61% yield). HPLC retention time 8.50 min. Method A. LRMS (ESI) calcd for $C_{61}H_{87}ClN_{10}O_{17}$ [M+H]⁺: 1267.6 found 1267.3.

Example 14

Method 14—Preparation of (S)-1-((S)-3-maytansinyl) 19-(2-((1,2-dimethylhydrazinyl)methyl)-1H-indol-1-yl)-7,10,13-tris(2-methoxyethyl)-2,3-dimethyl-4,8,11,14,17-pentaoxo-3,7,10,13,16-pentaazanonadecan-1-oate (HIPS Indole Glycine Trimethoxypeptoid Beta Alanine Maytansine) (from intermediate Compound 48)

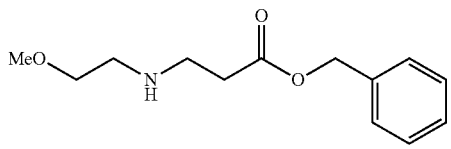 [SMILES: COCCNCCC(=O)OCc1ccccc1]

Figure 27:
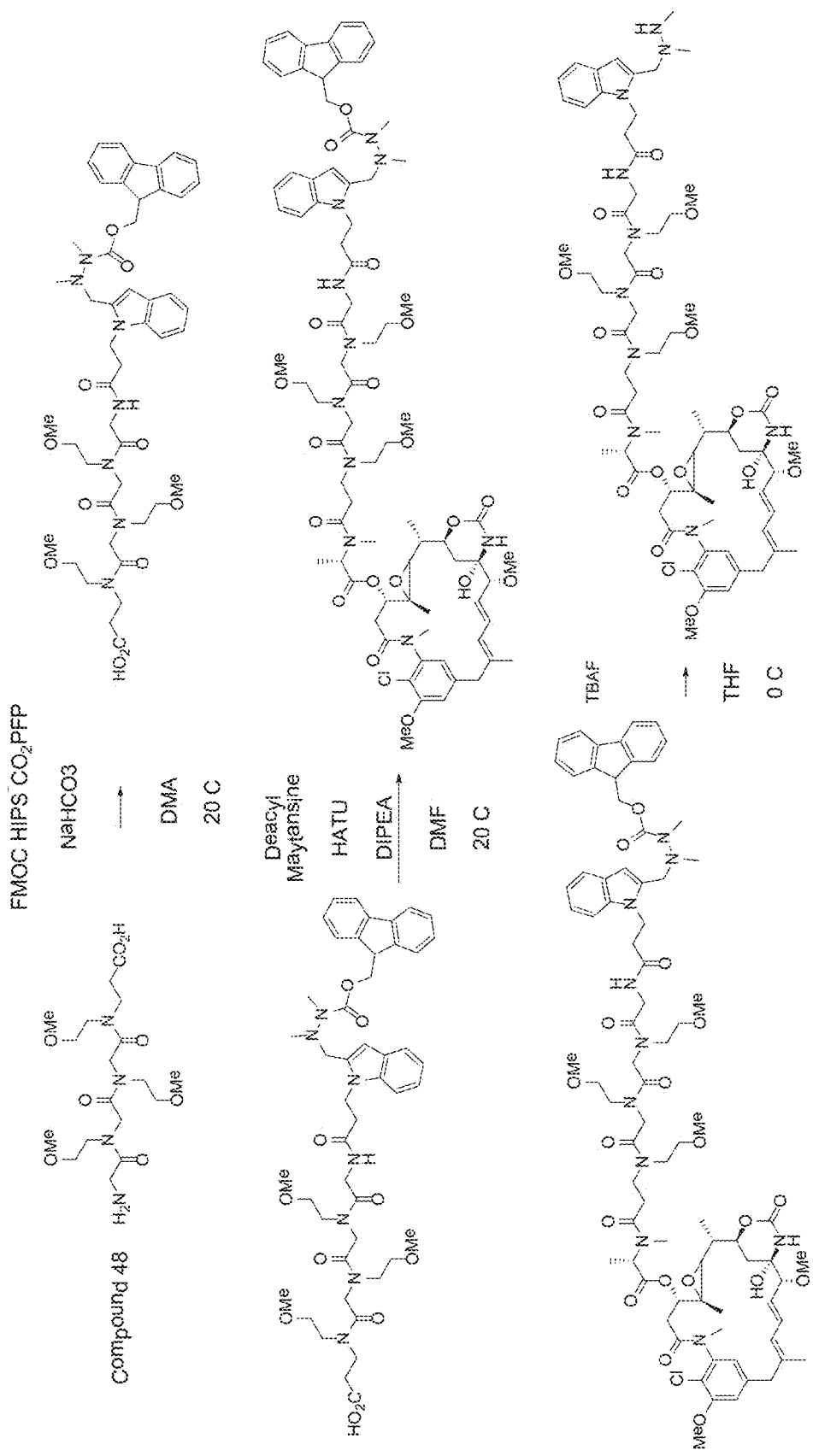
FIG. 27 shows a reaction scheme for the synthesis of compound HIPS Indole Glycine Trimethoxypeptoid Beta Alanine Maytansine according to embodiments of the present disclosure, see e.g., Example 14.

A reaction scheme for the synthesis of compound HIPS Indole Glycine Trimethoxypeptoid Beta Alanine Maytansine is shown in FIG. 27.

Preparation of benzyl 3-((2-methoxyethyl)amino)propanoate (Compound 1)

To a solution of 2-methoxyethanamine (0.42 g, 5.6 mmol) and lithium chloride (20 mg) in MeOH (25 mL) and THF (25 mL) at 0° C. was added benzyl acrylate (1.0 g, 6.16 mmol) dropwise over 10 min. The reaction was allowed to warm to room temperature gradually and stirred at room temperature overnight. The solvent was removed under reduced pressure and the resulting residue dissolved in EtOAc (250 mL). The organic fraction was washed with 5 M NaCl (200 mL), dried over Na₂SO₄, and concentrated to give a residue. The product was purified by flash column chromatography (PE:EA=5:1 to 0:1) to afford Compound 1 (0.95 g, 71% yield).

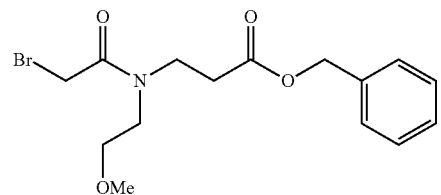 [SMILES: COCCN(CCC(=O)OCc1ccccc1)C(=O)CBr]

Preparation of benzyl 3-(2-bromo-N-(2-methoxyethyl)acetamido)propanoate (Compound 2)

To a solution of Compound 1 (0.95 g, 4 mmol) in THF (20 mL) at 0° C. were added Et₃N (0.49 g, 4.8 mmol) and bromoacetyl bromide (0.97 g, 4.8 mmol). The reaction was stirred at 0° C. for 1 h, diluted with EtOAc (20 mL), filtered, and washed with EtOAc. The filtrate was concentrated and dried in vacuo to yield the crude bromoacetyl amide which was purified by flash column chromatography (PE:EA=5:1) to afford pure Compound 2 (1.15 g, 80% yield). (MS+: 358, 360).

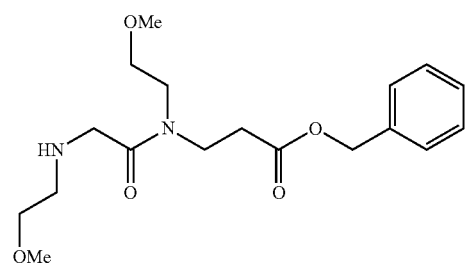 [SMILES: COCCNCC(=O)N(CCOC)CCC(=O)OCc1ccccc1]

Preparation of benzyl 3-(N-(2-methoxyethyl)-2-((2-methoxyethyl)amino)acetamido)propanoate (Compound 3)

To a solution of Compound 2 (1.15 g, 3.2 mmol) in THF (20 mL) at 0° C. were added Et₃N (0.647 g, 6.4 mmol) and 2-methoxyethanamine (0.48 g, 6.4 mmol). The reaction was stirred overnight, diluted with EtOAc (10 mL), filtered, and washed with EtOAc. The filtrate was concentrated and dried in vacuo to yield the crude amine which was purified by flash column chromatography (PE:EA=5:1 to 0:1) to afford pure Compound 3 (0.35 g, 31% yield). LC-MS: 353 [M+H]⁺.

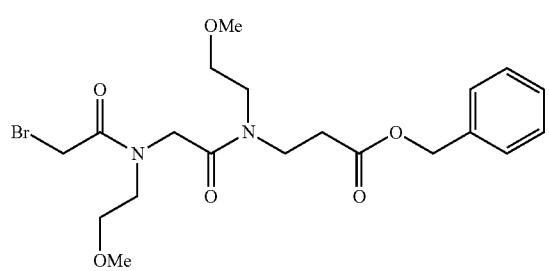 [SMILES: COCCN(CCC(=O)OCc1ccccc1)C(=O)CN(CCOC)C(=O)CBr]

Preparation of benzyl 3-(2-(2-bromo-N-(2-methoxyethyl)acetamido)-N-(2-methoxyethyl)acetamido)propanoate (Compound 4)

To a solution of Compound 3 (0.35 g, 1 mmol) in THF (15 mL) at 0° C. were added Et₃N (0.121 g, 1.2 mmol) and bromoacetyl bromide (0.242 g, 1.2 mmol). The reaction was at 0° C. for 1 h, diluted with EtOAc (10 mL), and filtered. The solid was washed with EtOAc and the filtrate concentrated in vacuo to give the crude bromoacetyl amide. Purification by flash column chromatography (EA) afforded Compound 4 (0.29 g, 61% yield). LC-MS: 473, 475.

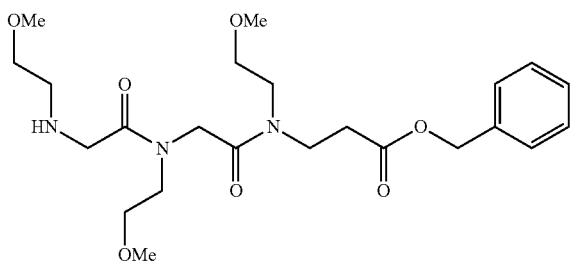 [SMILES: COCCNCC(=O)N(CCOC)CC(=O)N(CCOC)CCC(=O)OCc1ccccc1]

Preparation of benzyl 8,11-bis(2-methoxyethyl)-7,10-dioxo-2-oxa-5,8,11-triazatetradecan-14-oate (Compound 5)

To a solution of Compound 4 (0.29 g, 0.61 mmol) in THF (10 mL) at 0° C. were added Et$_3$N (0.124 g, 1.23 mmol) and 2-methoxyethanamine (91 mg, 1.23 mmol). The reaction was stirred at room temperature overnight, diluted with EtOAc (10 mL), and filtered. The solid was washed with EtOAc and the filtrate concentrated to give the crude amine which was purified by flash column chromatography (MeOH:EA=1:5) to afford pure Compound 5 (0.15 g, 52% yield). LC-MS: 468 (M+1).

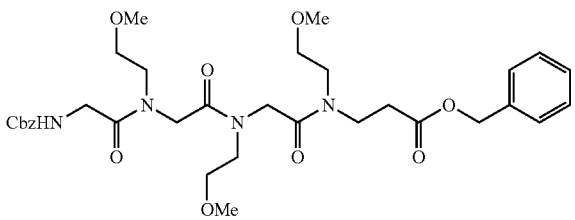 [SMILES: COCCN(CCC(=O)OCc1ccccc1)C(=O)CN(CCOC)C(=O)CN(CCOC)C(=O)CNC(=O)OCc1ccccc1]

Preparation of benzyl 7,10,13-tris(2-methoxyethyl)-3,6,9,12-tetraoxo-1-phenyl-2-oxa-4,7,10,13-tetraazahexadecan-16-oate (Compound 6)

To a mixture of Cbz-glycine (181 mg, 0.87 mmol), DCM (10 mL), EDCI (200 mg, 1.04 mmol) and HOBt (140 mg, 1.04 mmol) at 0° C. was added DIPEA (400 mg, 3.13 mmol). The mixture was stirred at 0° C. for 15 min whereupon Compound 5 (400 mg, 0.87 mmol) was added. The reaction was stirred at room temperature overnight, washed with H$_2$O and 5 M NaCl, and dried over Na$_2$SO$_4$. The crude product was concentrated and purified by flash column chromatography (PE:EA=1:3) to afford Compound 6 (300 mg, 62% yield). LC-MS: 660 (M+1).

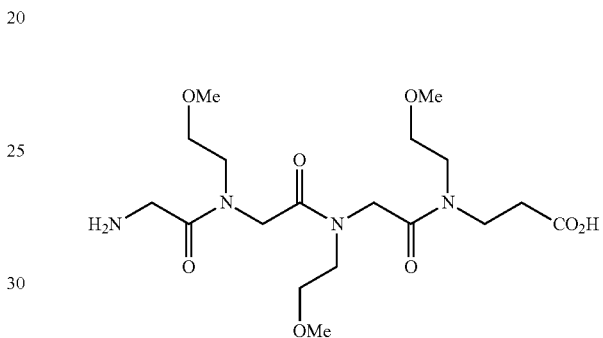

Preparation of 5-(2-aminoacetyl)-8,11-bis(2-methoxyethyl)-7,10-dioxo-2-oxa-5,8,11-triazatetradecan-14-oic acid (Compound 48) (FIG. 27)

A mixture of Compound 6 (2.63 g, 4.0 mmol) and Pd/C (500 mg) in EtOAc (60 mL) in a Parr shaker was stirred under H$_2$ (65 psi) at room temperature overnight. The mixture was filtered though a pad of Celite, washed with MeOH, and concentrated to give a residue which was lyophilized to afford AB4298 (1.2 g, 69% yield). LC-MS: 435 (M+1).

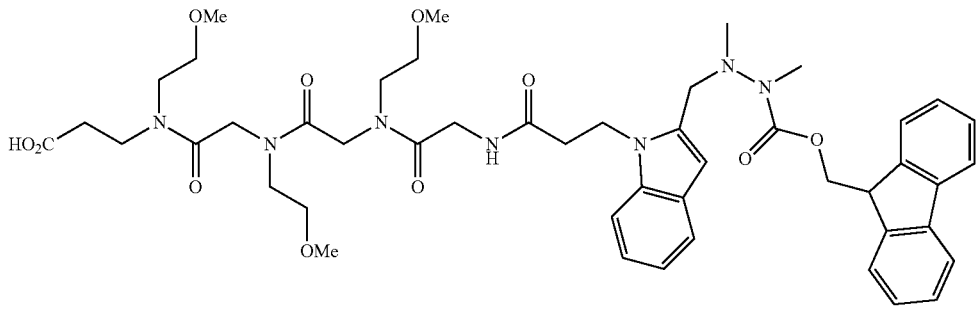 [SMILES: COCCN(CCC(=O)O)C(=O)CN(CCOC)C(=O)CN(CCOC)C(=O)CNC(=O)CCn1c(CN(C)N(C)C(=O)OCC2c3ccccc3-c3ccccc32)cc2ccccc21]

Preparation of 16-(2-((2-(((9H-fluoren-9-yl)methoxy)carbonyl)-1,2-dimethylhydrazinyl)methyl)-1H-indol-1-yl)-4,7,10-tris(2-methoxyethyl)-5,8,11,14-tetraoxo-4,7,10,13-tetraazahexadecan-1-oic acid (FIG. 27)

To a dried 4 mL glass scintillation vial containing a dried flea stir bar was added peptoid AB4298 (22.0 mg, 0.05 mmol), FMOC HIPS Indole CO$_2$PFP (33.1 mg, 0.05 mmol), NaHCO$_3$ (4.3 mg, 0.05 mmol), and DMA (0.4 mL). The solution was stirred at room temperature for 16 h, acidified to pH 2 with 1 M HCl, and extracted with 1×10 mL EtOAc. The organic fraction was washed with a mixture of 1×10 mL 1 M HCl/5 M NaCl (1/1), dried over MgSO$_4$, filtered, concentrated, adsorbed onto a Biotage SNAP Ultra 1 g samplet, and purified on a Biotage SNAP Ultra 10 g cartridge using a gradient of 0-10% MeOH in CH$_2$Cl$_2$, giving the title compound as a white solid (28.4 mg, 63% yield). HPLC retention time 12.68 min. Method A. LRMS (ESI) calcd for C$_{47}$H$_{61}$N$_7$O$_{11}$ [M−H]$^-$: 898.4; found 897.7.

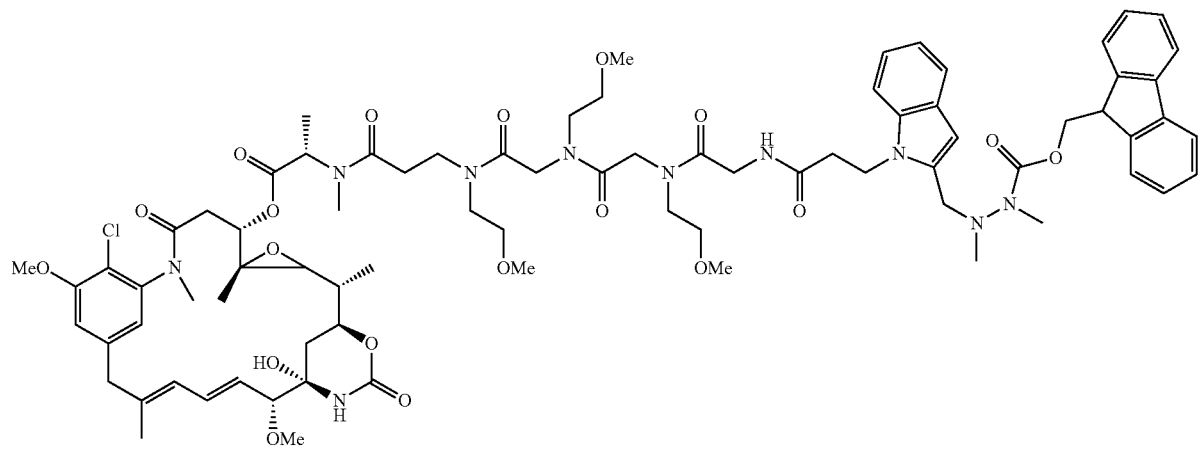

Preparation of (S)-1-((S)-3-maytansinyl) 19-(2-((2-(((9H-fluoren-9-yl)methoxy)carbonyl)-1,2-dimethylhydrazinyl)methyl)-1H-indol-1-yl)-7,10,13-tris(2-methoxyethyl)-2,3-dimethyl-4,8,11,14,17-pentaoxo-3,7,10,13,16-pentaazanonadecan-1-oate (FMOC HIPS Indole Glycine Trimethoxypeptoid Beta Alanine Maytansine) (FIG. 27)

To a dried 4 mL glass scintillation vial containing a dried flea stir bar was added 16-(2-((2-(((9H-fluoren-9-yl)methoxy)carbonyl)-1,2-dimethylhydrazinyl)methyl)-1H-indol-1-yl)-4,7,10-tris(2-methoxyethyl)-5,8,11,14-tetraoxo-4,7,10,13-tetraazahexadecan-1-oic acid (21.3 mg, 0.02 mmol), deacyl maytansine (15.4 mg, 0.02 mmol), and DMA (0.13 mL). The solution was cooled to 0° C. in an ice, H$_2$O bath whereupon 2,4,6-trimethylpyridine (5.7 mg, 6.2 uL, 0.05 mmol) and COMU (13.2 mg, 0.03 mmol) were added. The reaction was allowed to stir at 0° C. for 15 min, then warmed to room temperature and stirred for 3 h. The reaction mixture was diluted with EtOAc (7 mL), washed with 3×2 mL 0.5 M HCl, 3×2 mL 1.2 M NaHCO$_3$, and 3×2 mL 5 M NaCl, dried over MgSO$_4$, filtered, and concentrated to a viscous oil. The product was adsorbed onto a Biotage SNAP Ultra 1 g samplet and purified on a Biotage SNAP Ultra 10 g cartridge using a gradient of 2-15% MeOH in CH$_2$Cl$_2$, giving the desired product as a white solid (13.2 mg, 36% yield). HPLC retention time 14.40 min. Method A. LRMS (ESI) calcd for C$_{79}$H$_{103}$ClN$_{10}$O$_{19}$ [M+Na]$^+$: 1553.7 found 1553.6.

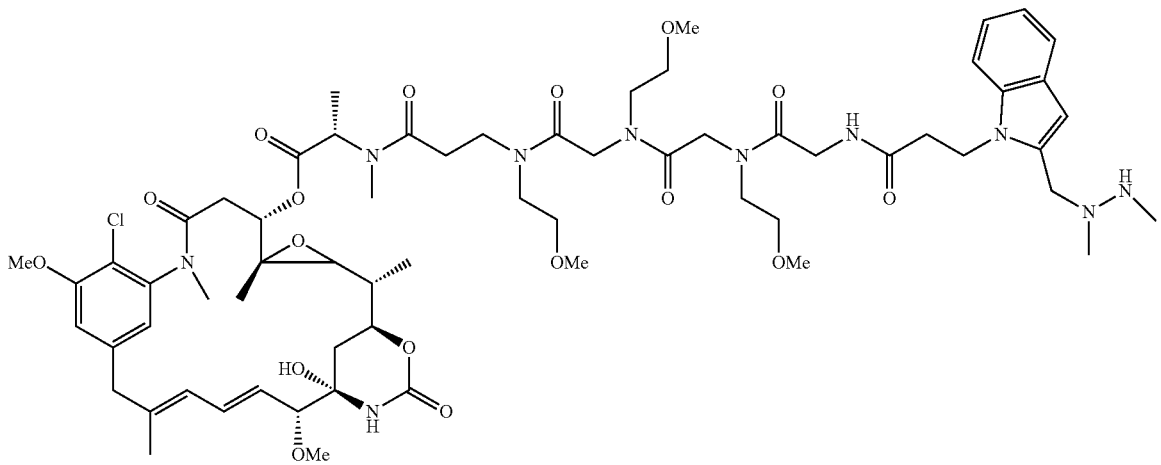

Preparation of (S)-1-((S)-3-maytansinyl) 19-(2-((1,2-dimethylhydrazinyl)methyl)-1H-indol-1-yl)-7,10,13-tris(2-methoxyethyl)-2,3-dimethyl-4,8,11,14,17-pentaoxo-3,7,10,13,16-pentaazanonadecan-1-oate (HIPS Indole Glycine Trimethoxypeptoid Beta Alanine Maytansine) (FIG. 27)

To a dried 4 mL glass scintillation vial containing a dried flea stir bar was added FMOC HIPS Indole Glycine Trimethoxypeptoid Beta Alanine Maytansine (13.2 mg, 8.6 umol). Piperidine (14.7 mg, 17.0 uL, 0.17 mmol) in DMA (0.3 mL) was added by syringe. The solution was stirred at room temperature for 1 h, adsorbed directly onto a Biotage KP C18 HS 1.2 g samplet, and purified on a Biotage KP C18 HS 12 g cartridge using a gradient of 0-100% $CH_3CN$ in $H_2O$, giving the title compound as a white solid (9.3 mg, 82% yield). HPLC retention time 9.71 min. Method A.

Example 15

Method 15—Preparation of (S)-1-((S)-3-maytansinyl) 15-(2-((1,2-dimethylhydrazinyl)methyl)-1H-indol-1-yl)-2,3-dimethyl-4,7,10,13-tetraoxo-3,6,9,12-tetraazapentadecan-1-oate (HIPS Indole Glycine₃ Maytansine)

Figure 28:
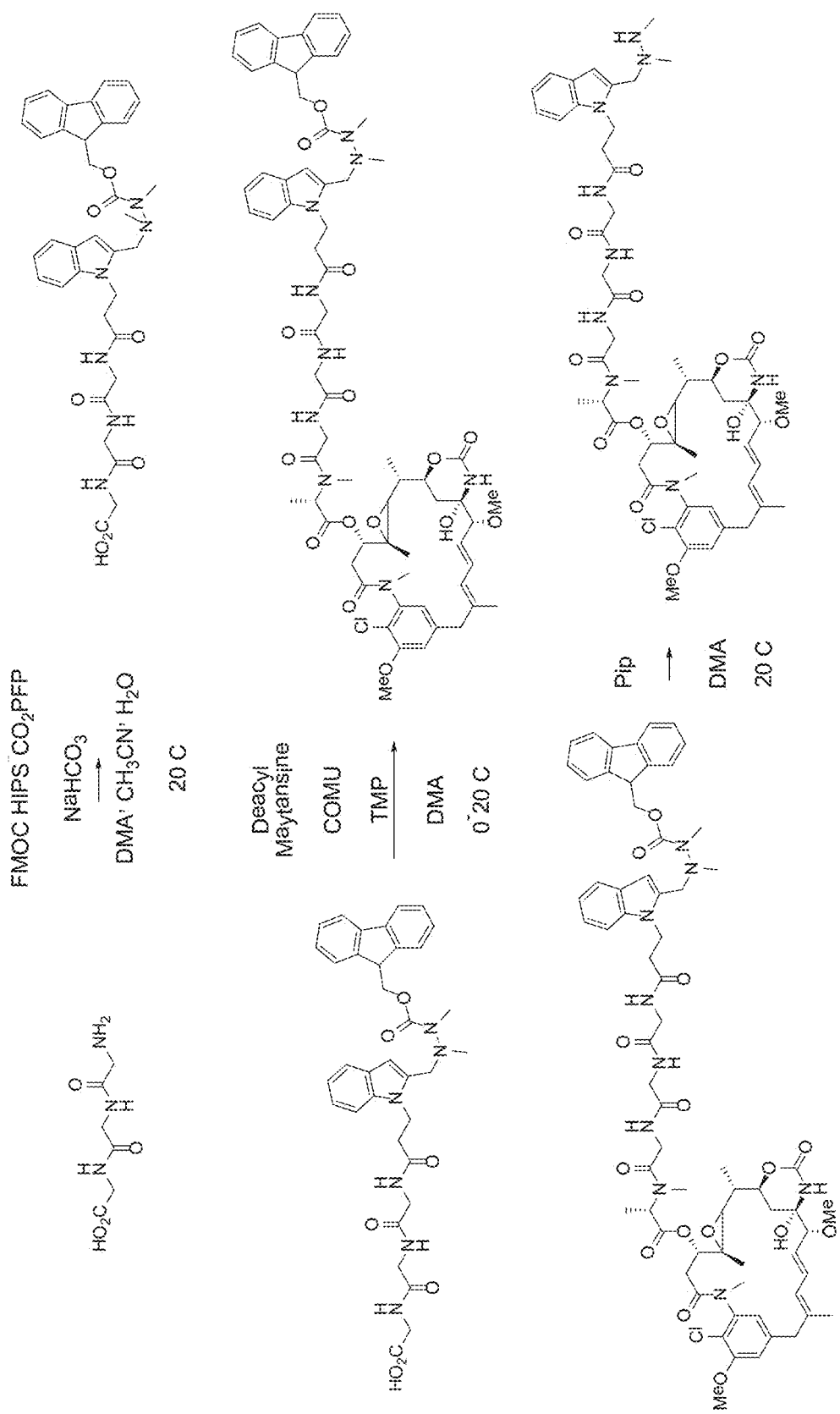
FIG. 28 shows a reaction scheme for the synthesis of compound HIPS Indole Glycine$_3$ Maytansine according to embodiments of the present disclosure, see e.g., Example 15.

A reaction scheme for the synthesis of compound HIPS Indole Glycine₃ Maytansine is shown in FIG. 28.

Preparation of 2-(2-(2-(3-(2-(((9H-fluoren-9-yl)methoxy)carbonyl)-1,2-dimethylhydrazinyl)methyl)-1H-indol-1-yl)propanamido)acetamido)acetamido) acetic acid (FIG. 28)

To a dried 4 mL glass scintillation vial containing a dried flea stir bar was added Triglycine (27.4 mg, 0.15 mmol), FMOC HIPS Indole $CO_2PFP$ (46.4 mg, 0.07 mmol), $NaHCO_3$ (25.9 mg, 0.3 mmol), DMA (0.6 mL), $H_2O$ (0.3 mL), and $CH_3CN$ (0.3 mL). The solution was stirred at room temperature for 22 h, acidified to pH 2 with 1 M HCl, and extracted with 1×10 mL EtOAc. The organic fraction was washed with a mixture of 1×10 mL 1 M HCl/5 M NaCl (1/1), dried over $MgSO_4$, filtered, concentrated, adsorbed onto a Biotage SNAP Ultra 1 g samplet, and purified on a Biotage SNAP Ultra 10 g cartridge using a gradient of 0-10% MeOH in $CH_2Cl_2$, giving the desired product as a white solid (53.4 mg, 82% yield). HPLC retention time 11.41 min. Method A. LRMS (ESI) calcd for $C_{35}H_{37}N_6O_7$ [M–H]⁻: 653.3; found 652.9.

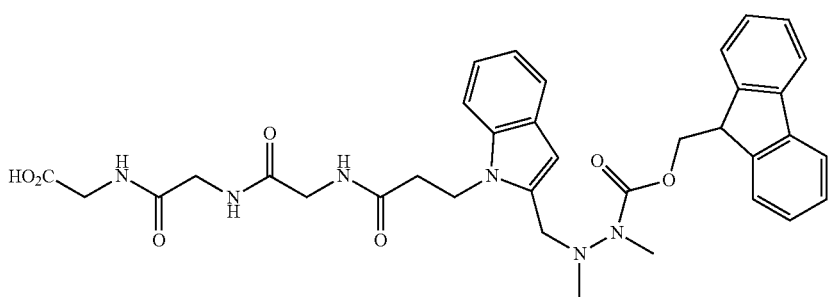 [SMILES: CN(Cc1cc2ccccc2n1CCC(=O)NCC(=O)NCC(=O)NCC(=O)O)N(C)C(=O)OCC1c2ccccc2-c2ccccc21]

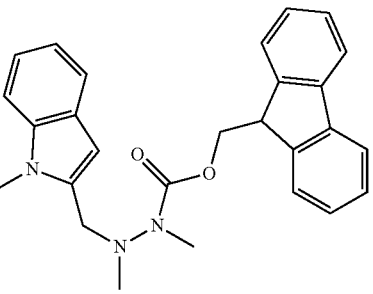
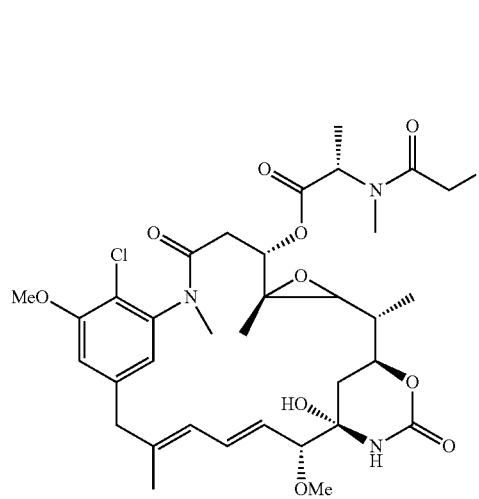

Preparation of (S)-1-((S)-3-maytansinyl) 15-(2-((2-(((9H-fluoren-9-yl)methoxy)carbonyl)-1,2-dimethylhydrazinyl)methyl)-1H-indol-1-yl)-2, 3-dimethyl-4,7,10,13-tetraoxo-3,6,9,12-tetraazapentadecan-1-oate (FMOC HIPS Indole Glycine$_3$ Maytansine) (FIG. 28)

To a dried 4 mL glass scintillation vial containing a dried flea stir bar was added 2-(2-(2-(3-(2-((2-(((9H-fluoren-9-yl)methoxy)carbonyl)-1,2-dimethylhydrazinyl)methyl)-1H-indol-1-yl)propanamido)acetamido)acetamido)acetic acid (28.5 mg, 0.03 mmol), deacyl maytansine (28.3 mg, 0.04 mmol), and DMA (0.2 mL). The solution was cooled to 0° C. in an ice, H$_2$O bath whereupon 2,4,6-trimethylpyridine (10.5 mg, 11.5 uL, 0.09 mmol) and COMU (20.5 mg, 0.05 mmol) were added. The reaction was allowed to stir at 0° C. for 15 min, then warmed to room temperature and stirred for 16 h. The reaction mixture was diluted with EtOAc (7 mL), washed with 3×2 mL 0.5 M HCl, 3×2 mL 1.2 M NaHCO$_3$, and 3×2 mL 5 M NaCl, dried over MgSO$_4$, filtered, and concentrated to a viscous oil. The product was adsorbed onto a Biotage SNAP Ultra 1 g samplet and purified on a Biotage SNAP Ultra 10 g cartridge using a gradient of 2-15% MeOH in CH$_2$Cl$_2$, giving the title compound as a white solid (3.2 mg, 6% yield). HPLC retention time 13.63 min. Method A. LRMS (ESI) calcd for C$_{67}$H$_{80}$ClN$_9$O$_{15}$ [M+Na]$^+$: 1308.5 found 1308.7.

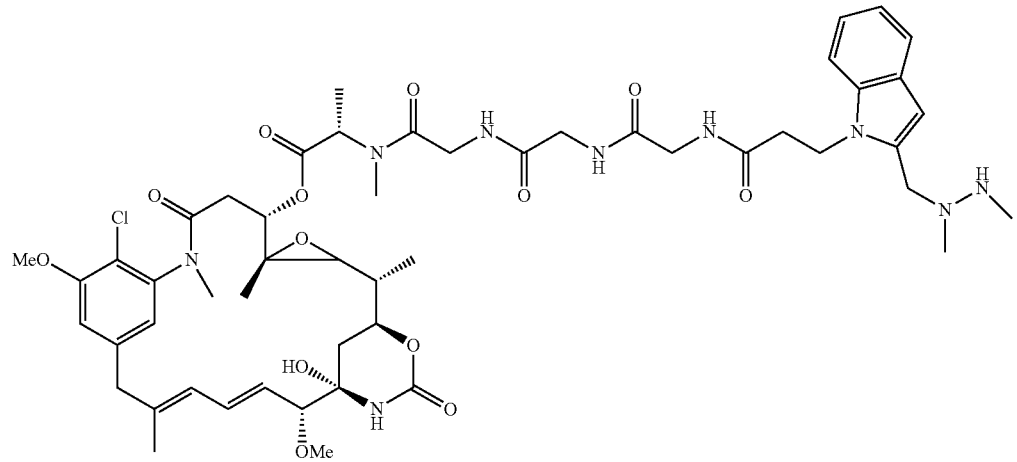

Preparation of (S)-1-((S)-3-maytansinyl) 15-(2-((1,2-dimethylhydrazinyl)methyl)-1H-indol-1-yl)-2,3-dimethyl-4,7,10,13-tetraoxo-3,6,9,12-tetraazapentadecan-1-oate (HIPS Indole Glycine$_3$ Maytansine) (FIG. 28)

To a dried 4 mL glass scintillation vial containing a dried flea stir bar was added FMOC HIPS Indole Glycine$_3$ Maytansine (3.2 mg, 2.5 umol). Piperidine (30.2 mg, 35.0 uL, 0.35 mmol) in DMA (0.2 mL) was added by syringe. The solution was stirred at room temperature for 1 h and purified by preparative thin layer chromatography on a Whatman 1000 um preparative thin layer chromatography plate (SiO$_2$) using 14% MeOH in CH$_2$Cl$_2$, giving the desired product as a white solid (1.8 mg, 68% yield). HPLC retention time 8.81 min. Method A. LRMS (ESI) calcd for $C_{52}H_{70}ClN_9O_{13}$ [M+H]$^+$: 1063.5 found 1064.2.

Example 16

Method 16—Preparation of (S)-1-((S)-3-maytansinyl) 22-(2-(((1,2-dimethylhydrazinyl)methyl)-1H-indol-1-yl)-2,3-dimethyl-4,14,20-trioxo-7,10-dioxa-3,13,16,19-tetraazadocosan-1-oate (HIPS Indole Aminoethylglycine PEG$_2$ Maytansine)

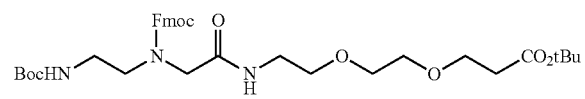

Figure 29:
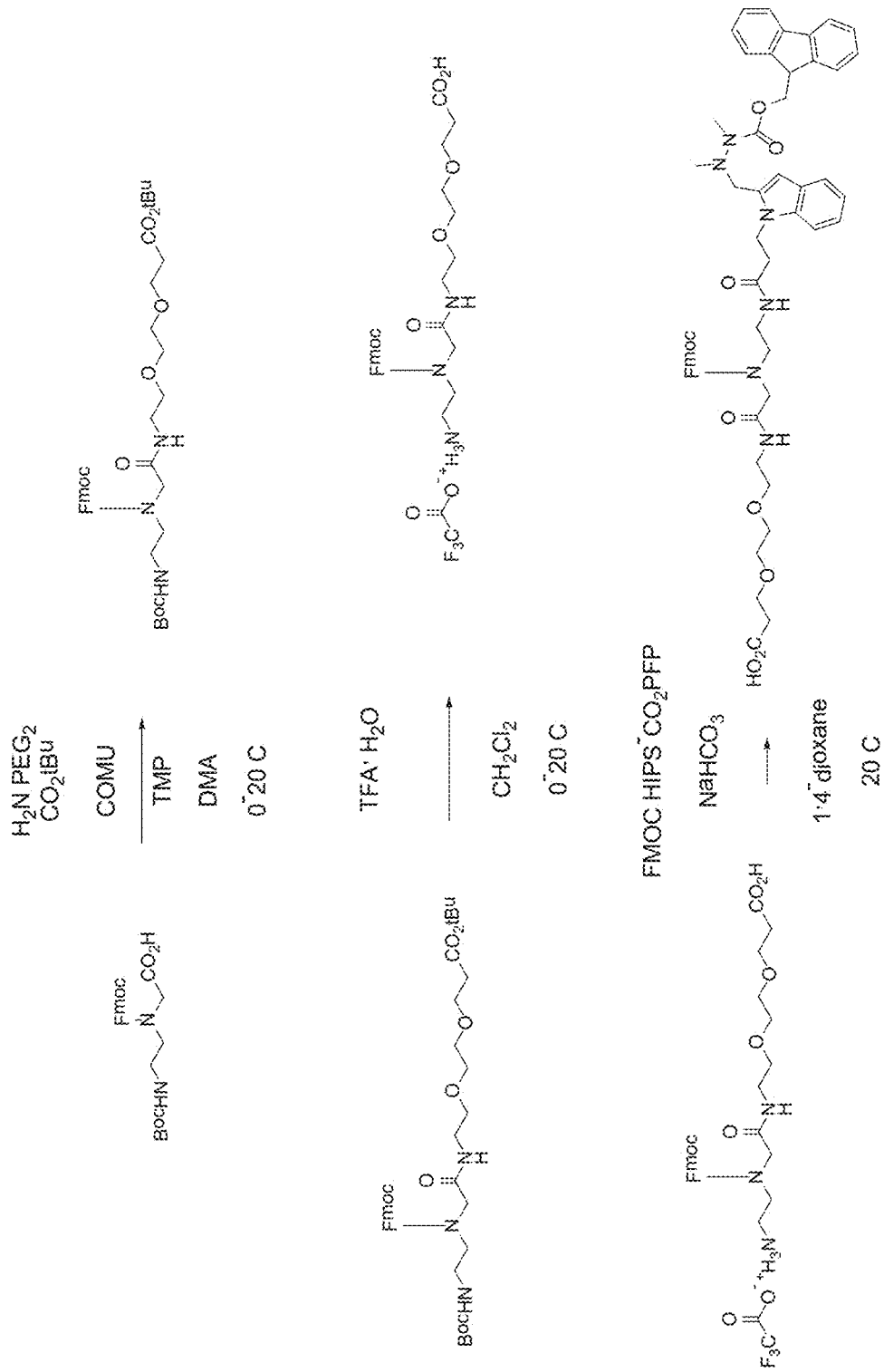
FIG. 29 and FIG. 30 show reaction schemes for the synthesis of compound HIPS Indole Aminoethylglycine $PEG_2$ Maytansine according to embodiments of the present disclosure, see e.g., Example 16.
Figure 30:
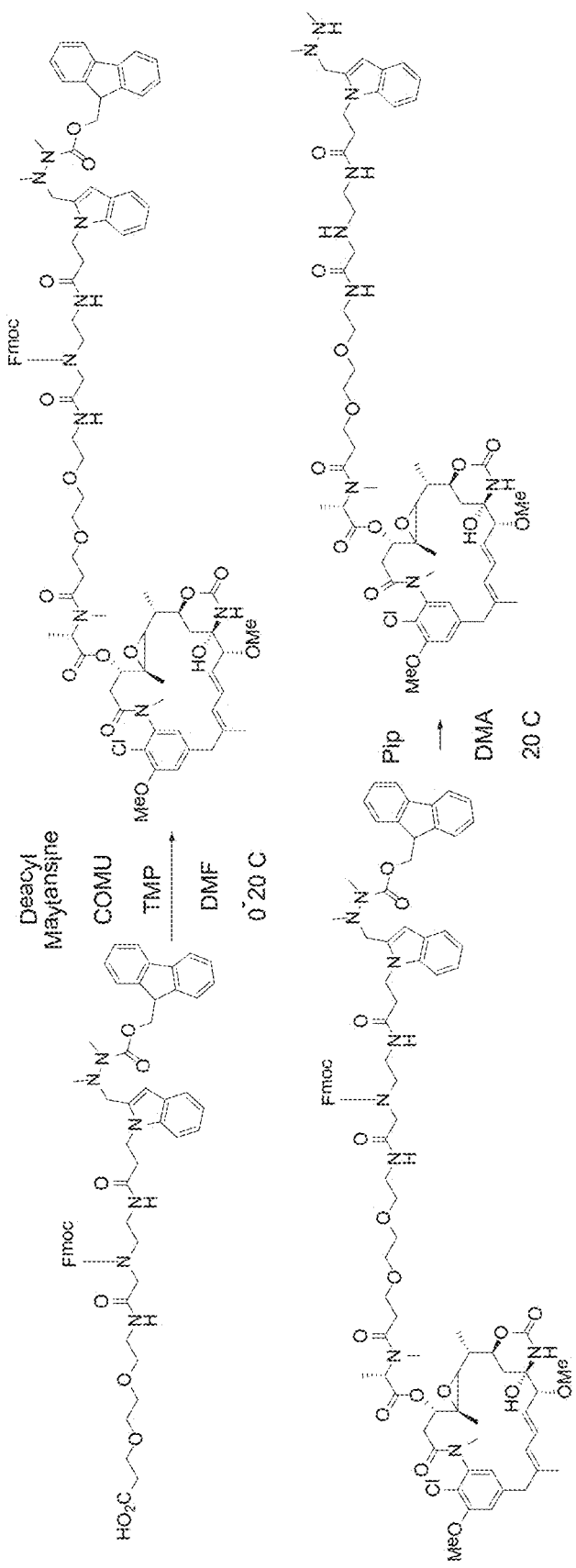

Reaction schemes for the synthesis of compound HIPS Indole Aminoethylglycine PEG$_2$ Maytansine are shown in FIG. 29 and FIG. 30.

Preparation of tert-butyl 8-(((9H-fluoren-9-yl) methoxy)carbonyl)-2,2-dimethyl-4,10-dioxo-3,14, 17-trioxa-5,8,11-triazaicosan-20-oate (FIG. 29)

To a dried 4 mL glass scintillation vial containing a dried flea stir bar was added 2-((((9H-fluoren-9-yl)methoxy)carbonyl)(2-((tert-butoxycarbonyl)amino)ethyl)amino)acetic acid (90.7 mg, 0.2 mmol), H$_2$N PEG$_2$ CO$_2$tBu (62.0 mg, 0.3 mmol), and DMA (0.8 mL). The solution was cooled to 0° C. in an ice, H$_2$O bath whereupon 2,4,6-trimethylpyridine (49.5 mg, 54.0 uL, 0.4 mmol) and COMU (97.0 mg, 0.2 mmol) were added. The reaction was allowed to stir at 0° C. for 15 min, then warmed to room temperature and stirred for 1 h. The reaction mixture was diluted with EtOAc (20 mL), washed with 3×7 mL 0.5 M HCl, 3×7 mL 1.2 M NaHCO$_3$, and 3×7 mL 5 M NaCl, dried over MgSO$_4$, filtered, and concentrated to a viscous oil. The product was adsorbed onto a Biotage SNAP Ultra 3 g samplet and purified on a Biotage SNAP Ultra 25 g cartridge using a gradient of 2-15% MeOH in CH$_2$Cl$_2$, giving the title compound as a white solid (132.0 mg, 98% yield).

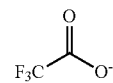
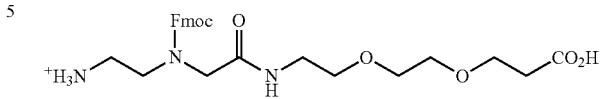

Preparation of 3-(((9H-fluoren-9-yl)methoxy)carbonyl)-14-carboxy-5-oxo-9,12-dioxa-3,6-diazatetradecan-1-aminium 2,2,2-trifluoroacetate (FIG. 29)

To a dried 4 mL glass scintillation vial containing a dried flea stir bar was added tert-butyl 8-(((9H-fluoren-9-yl) methoxy)carbonyl)-2,2-dimethyl-4,10-dioxo-3,14,17-trioxa-5,8,11-triazaicosan-20-oate (65.5 mg, 0.1 mmol), CH$_2$Cl$_2$ (0.5 mL), TFA (0.18 mL), and H$_2$O (0.02 mL). The reaction was stirred for 2.5 h, dried in vacuo, and azeotroped with 3×2 mL Tol, giving the desired product as a waxy residue (55.0 mg, 90% yield). The compound was used in subsequent steps without additional purification.

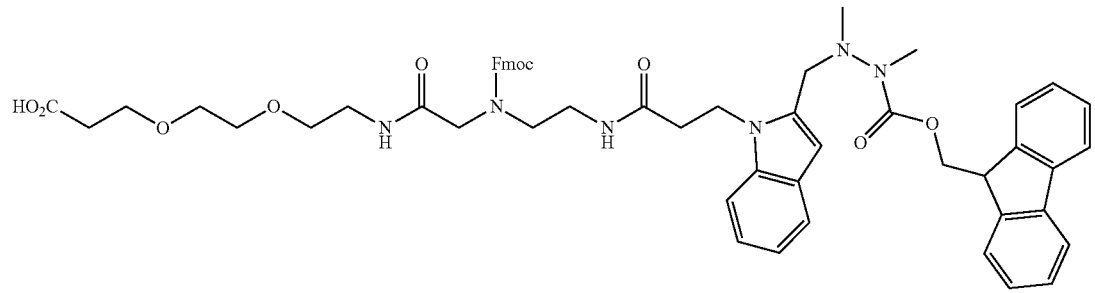

Preparation of 7-(((9H-fluoren-9-yl)methoxy)carbonyl)-1-(2-((2-(((9H-fluoren-9-yl)methoxy)carbonyl)-1,2-dimethylhydrazinyl)methyl)-1H-indol-1-yl)-3,9-dioxo-13,16-dioxa-4,7,10-triazanonadecan-19-oic acid (FIG. 29)

To a dried 4 mL glass scintillation vial containing a dried flea stir bar was added 3-(((9H-fluoren-9-yl)methoxy)carbonyl)-14-carboxy-5-oxo-9,12-dioxa-3,6-diazatetradecan-1-aminium 2,2,2-trifluoroacetate (55.0 mg, 0.09 mmol), FMOC HIPS Indole CO$_2$PFP (38.8 mg, 0.06 mmol), NaHCO$_3$ (30.0 mg, 0.4 mmol), and 1,4 dioxane (0.5 mL). The solution was stirred at room temperature for 16 h, acidified to pH 2 with 1 M HCl, and extracted with 1×10 mL EtOAc. The organic fraction was washed with a mixture of 1×10 mL 1 M HCl/5 M NaCl (1/1), dried over MgSO$_4$, filtered, concentrated, adsorbed onto a Biotage SNAP Ultra 1 g samplet, and purified on a Biotage SNAP Ultra 10 g cartridge using a gradient of 2-8% MeOH in CH$_2$Cl$_2$, giving the title compound as a white solid (28.4 mg, 49% yield). HPLC retention time 15.04 min. Method A. LRMS (ESI) calcd for $C_{55}H_{60}N_6O_{10}$ [M+H]$^+$: 965; found 965.

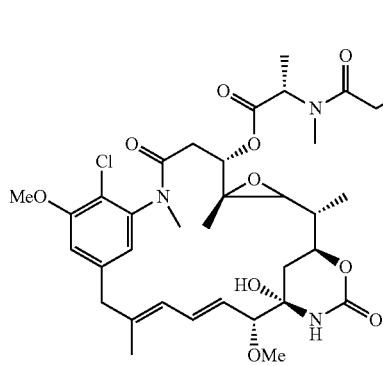 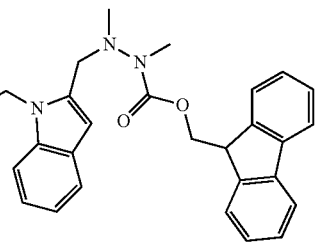

Preparation of (S)-1-((S)-3-maytansinyl) 16-(((9H-fluoren-9-yl)methoxy)carbonyl)-22-(2-((2-(((9H-fluoren-9-yl)methoxy)carbonyl)-1,2-dimethylhydrazinyl)methyl)-1H-indol-1-yl)-2,3-dimethyl-4,14,20-trioxo-7,10-dioxa-3,13,16,19-tetraazadocosan-1-oate (FMOC HIPS Indole Aminoethylglycine (FMOC) $PEG_2$ Maytansine) (FIG. 30)

To a dried 4 mL glass scintillation vial containing a dried flea stir bar was added 7-(((9H-fluoren-9-yl)methoxy)carbonyl)-1-(2-((2-(((9H-fluoren-9-yl)methoxy)carbonyl)-1,2-dimethylhydrazinyl)methyl)-1H-indol-1-yl)-3,9-dioxo-13,16-dioxa-4,7,10-triazanonadecan-19-oic acid (30.0 mg, 0.03 mmol), deacyl maytansine (23.7 mg, 0.04 mmol), and anhydrous DMF (0.3 mL). The solution was cooled to 0° C. in an ice, $H_2O$ bath whereupon 2,4,6-trimethylpyridine (7.4 mg, 8.1 uL, 0.06 mmol) and COMU (15.6 mg, 0.04 mmol) were added. The reaction was allowed to stir at 0° C. for 30 min, then warmed to room temperature and stirred for 2 h. The reaction mixture was diluted with EtOAc (7 mL), washed with 3×2 mL 0.5 M HCl, 3×2 mL 1.2 M $NaHCO_3$, and 3×2 mL 5 M NaCl, dried over $MgSO_4$, filtered, and concentrated to a viscous oil. The product was adsorbed onto a Biotage SNAP Ultra 1 g samplet and purified on a Biotage SNAP Ultra 10 g cartridge using a gradient of 2-7% MeOH in $CH_2Cl_2$, giving the desired product as a white solid (26.7 mg, 56% yield). HPLC retention time 16.28 min. Method A. LRMS (ESI) calcd for $C_{87}H_{102}ClN_9O_{18}$ $[M+Na]^+$: 1618.7; found 1619.7.

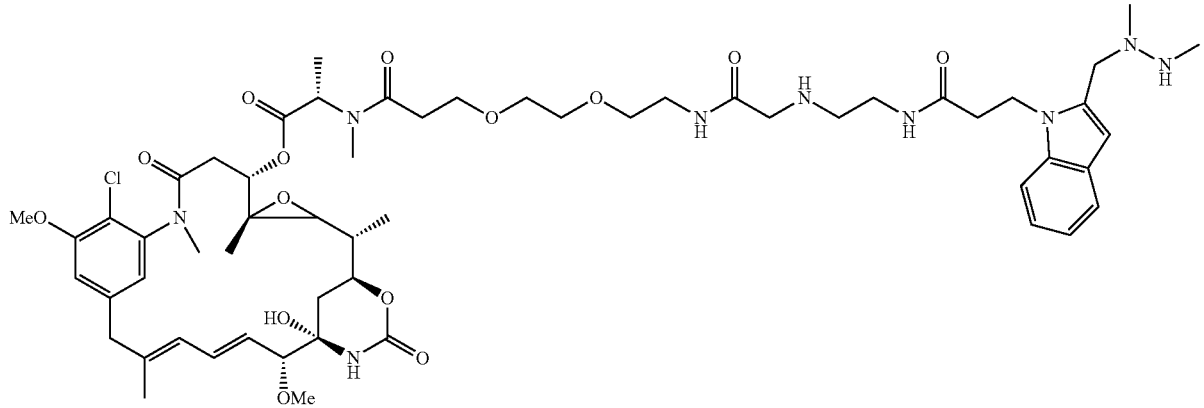

Preparation of (S)-1-((S)-3-maytansinyl)22-(2-((1,2-dimethylhydrazinyl)methyl)-1H-indol-1-yl)-2,3-dimethyl-4,14,20-trioxo-7,10-dioxa-3,13,16,19-tetraazadocosan-1-oate (HIPS Indole Aminoethylglycine PEG$_2$ Maytansine) (FIG. 30)

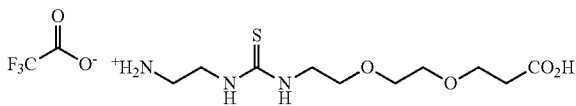 [SMILES: O=C([O-])C(F)(F)F ; [NH3+]CCNC(=S)NCCOCCOCCC(=O)O]

To a dried 4 mL glass scintillation vial containing a dried flea stir bar was added FMOC HIPS Indole Aminoethylglycine (FMOC) PEG$_2$ Maytansine (26.6 mg, 17 umol). Piperidine (28.4 mg, 33.0 uL, 0.3 mmol) in DMA (0.16 mL) was added by syringe. The solution was stirred at room temperature for 1 h, adsorbed onto a Biotage SNAP Ultra 1 g samplet and purified on a Biotage SNAP Ultra 10 g cartridge using 5% MeOH in CH$_2$Cl$_2$, giving the title compound as a white solid (5.6 mg, 29% yield). HPLC retention time 8.10 min. Method A. LRMS (ESI) calcd for C$_{72}$H$_{92}$ClN$_9$O$_{16}$ [M+H]$^+$: 1152.5 found 1152.4.

Figure 31:
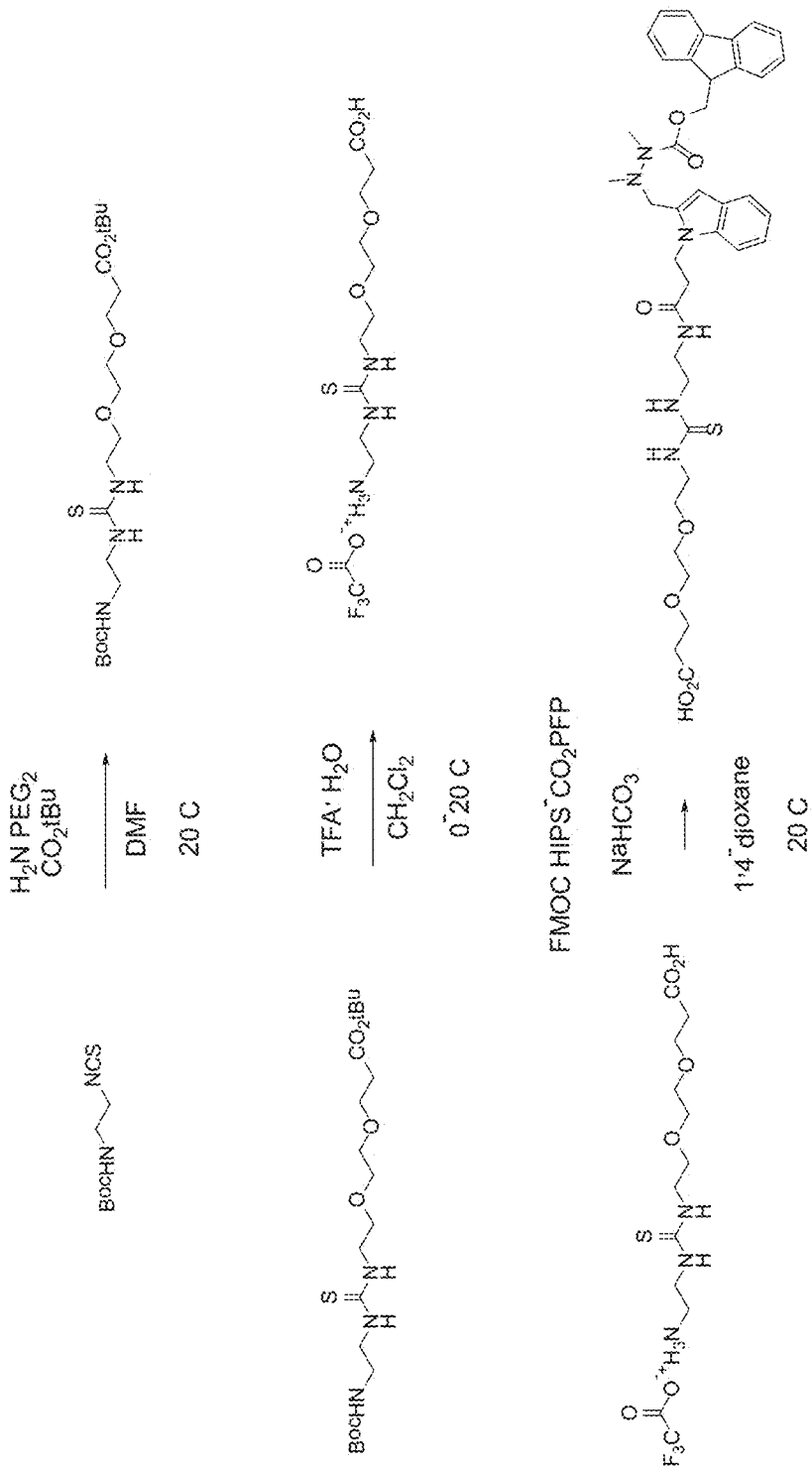
FIG. 31 and FIG. 32 show reaction schemes for the synthesis of compound HIPS Indole Ethylenediamine Thiourea $PEG_2$ Maytansine according to embodiments of the present disclosure, see e.g., Example 17.

Preparation of 13-carboxy-4-thioxo-8,11-dioxa-3,5-diazatridecan-1-aminium 2,2,2-trifluoroacetate (FIG. 31)

To a dried 4 mL glass scintillation vial containing a dried flea stir bar was added tert-butyl 2,2-dimethyl-4-oxo-9-thioxo-3,13,16-trioxa-5,8,10-triazanonadecan-19-oate (130.0 mg, 0.3 mmol), CH$_2$Cl$_2$ (0.5 mL), TFA (0.18 mL), and H$_2$O (0.02 mL). The reaction was stirred for 2.5 h, dried in vacuo, and azeotroped with 3×2 mL Tol, giving the title compound as a waxy residue (116.0 mg, 99% yield). The compound was used in subsequent steps without additional purification.

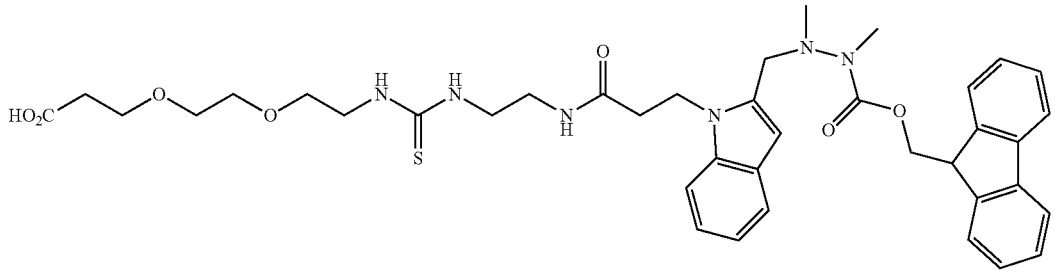 [SMILES: CN(Cc1cc2ccccc2n1CCC(=O)NCCNC(=S)NCCOCCOCCC(=O)O)N(C)C(=O)OCC1c2ccccc2-c2ccccc21]

Example 17

Method 17—Preparation of (S)-1-((S)-3-maytansinyl) 21-(2-((1,2-dimethylhydrazinyl)methyl)-1H-indol-1-yl)-2,3-dimethyl-4,19-dioxo-14-thioxo-7,10-dioxa-3,13,15,18-tetraazahenicosan-1-oate (HIPS Indole Ethylenediamine Thiourea PEG$_2$ Maytansine)

Preparation of 1-(2-((2-(((9H-fluoren-9-yl)methoxy)carbonyl)-1,2-dimethylhydrazinyl)methyl)-1H-indol-1-yl)-3-oxo-8-thioxo-12,15-dioxa-4,7,9-triazaoctadecan-18-oic acid (FIG. 31)

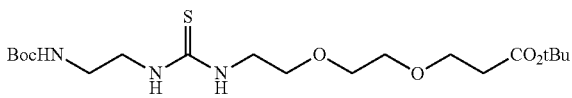

Figure 32:
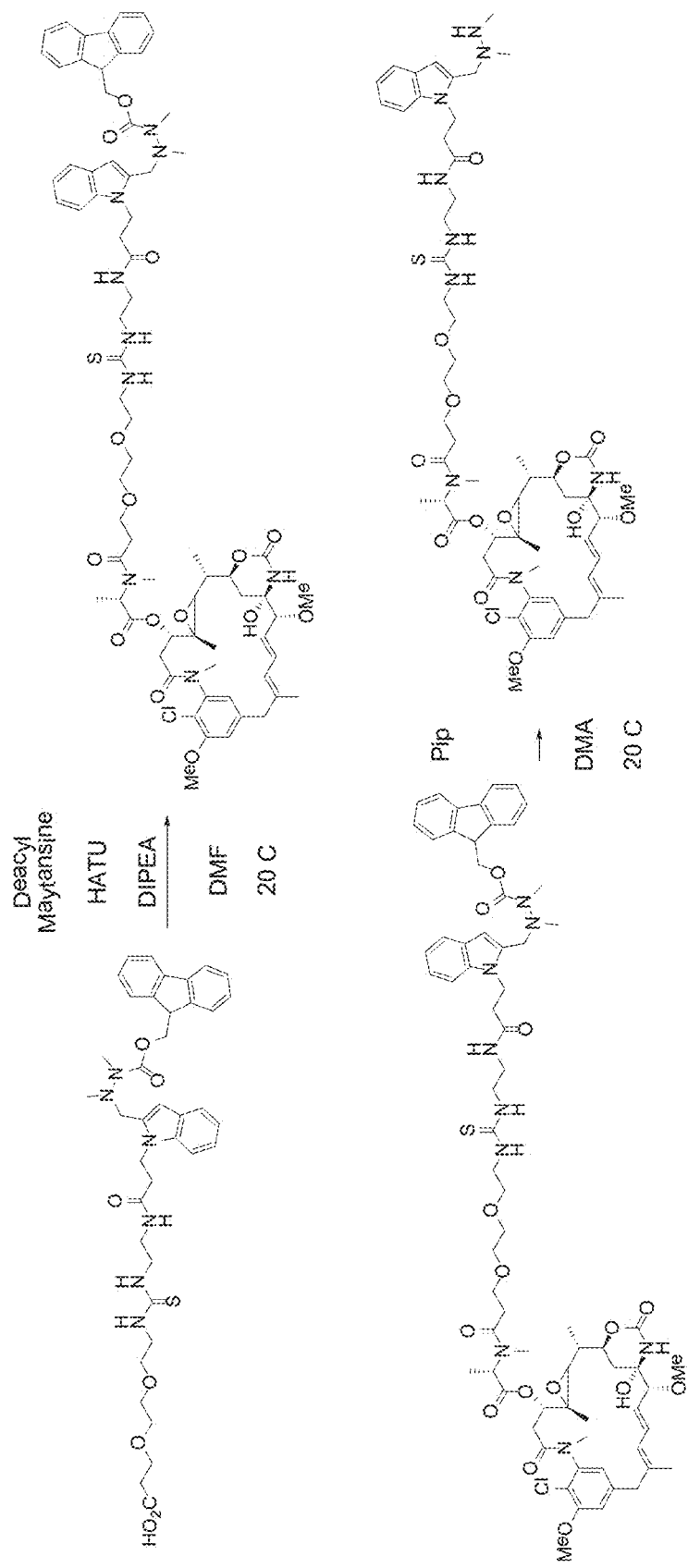

Reaction schemes for the synthesis of compound HIPS Indole Ethylenediamine Thiourea PEG$_2$ Maytansine are shown in FIG. 31 and FIG. 32.

Preparation of tert-butyl 2,2-dimethyl-4-oxo-9-thioxo-3,13,16-trioxa-5,8,10-triazanonadecan-19-oate (FIG. 31)

To a dried 4 mL glass scintillation vial containing a dried flea stir bar was added tert-butyl (2-isothiocyanatoethyl) carbamate (129.0 mg, 0.6 mmol), H$_2$N PEG$_2$ CO$_2$tBu (166.0 mg, 0.7 mmol), and anhydrous DMF (2.0 mL). The reaction was stirred for 16 h, concentrated in vacuo, adsorbed onto a Biotage SNAP Ultra 3 g samplet and purified on a Biotage SNAP Ultra 25 g cartridge using 30% EtOAc in Hex, giving the desired product as a white residue (268.0 mg, 96% yield).

To a dried 4 mL glass scintillation vial containing a dried flea stir bar was added 13-carboxy-4-thioxo-8,11-dioxa-3,5-diazatridecan-1-aminium 2,2,2-trifluoroacetate (38.4 mg, 0.1 mmol), FMOC HIPS Indole CO$_2$PFP (38.2 mg, 0.06 mmol), NaHCO$_3$ (30.0 mg, 0.4 mmol), and 1,4 dioxane (0.5 mL). The solution was stirred at room temperature for 16 h, acidified to pH 2 with 1 M HCl, and extracted with 1×10 mL EtOAc. The organic fraction was washed with a mixture of 1×10 mL 1 M HCl/5 M NaCl (1/1), dried over MgSO$_4$, filtered, concentrated, adsorbed onto a Biotage SNAP Ultra 1 g samplet, and purified on a Biotage SNAP Ultra 10 g cartridge using a gradient of 3-8% MeOH in CH$_2$Cl$_2$, giving the desired product as a white solid (17.6 mg, 40% yield). HPLC retention time 13.02 min. Method A. LRMS (ESI) calcd for C$_{39}$H$_{48}$N$_6$O$_7$S [M+H]$^+$: 743.3; found 743.1.

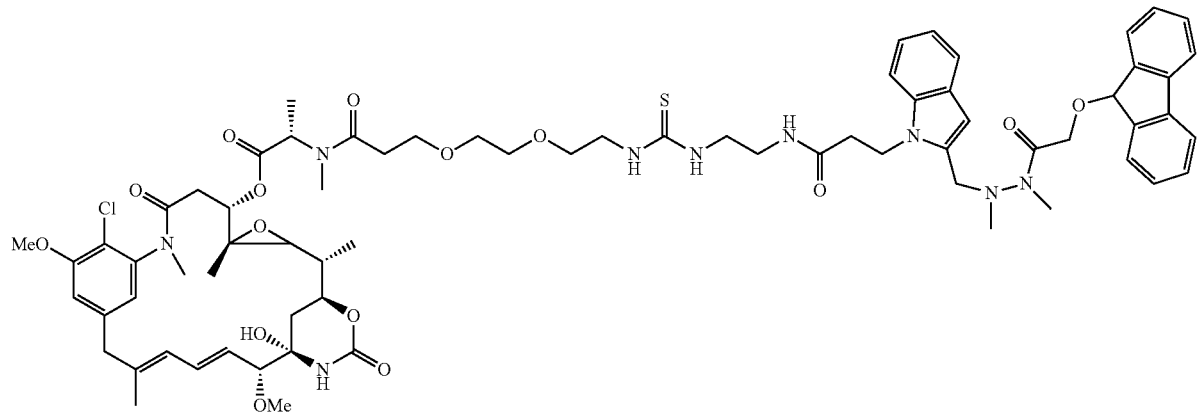

Preparation of (S)-1-((S)-3-maytansinyl) 21-(2-((2-(((9H-fluoren-9-yl)methoxy)carbonyl)-1,2-dimethyl-hydrazinyl)methyl)-1H-indol-1-yl)-2,3-dimethyl-4,19-dioxo-14-thioxo-7,10-dioxa-3,13,15,18-tetraazahenicosan-1-oate (FMOC HIPS Indole Ethylenediamine Thiourea PEG$_2$ Maytansine) (FIG. 32)

To a dried 4 mL glass scintillation vial containing a dried flea stir bar was added 1-(2-((2-(((9H-fluoren-9-yl)methoxy)carbonyl)-1,2-dimethylhydrazinyl)methyl)-1H-indol-1-yl)-3-oxo-8-thioxo-12,15-dioxa-4,7,9-triazaoctadecan-18-oic acid (17.4 mg, 0.02 mmol), HATU (8.9 mg, 0.02 mmol), and DMA (0.1 mL). The clear, colorless solution was stirred at room temperature for 15 min. Deacyl maytansine (15.2 mg, 0.02 mmol), DIPEA (6.1 mg, 8.2 uL, 0.05 mmol), and anhydrous DMF (0.06 mL) were combined in a separate 1.5 mL microcentrifuge tube and added dropwise, slowly, to the stirring solution. The reaction was allowed to stir at room temperature for 2 h, adsorbed directly onto a Biotage KP C18 HS 1.2 g samplet, and purified on a Biotage KP C18 HS 12 g cartridge using a gradient of 0-100% CH$_3$CN in H$_2$O, giving the title compound as a white solid (12.7 mg, 39% yield). HPLC retention time 14.71 min. Method A. LRMS (ESI) calcd for C$_{87}$H$_{102}$ClN$_9$O$_{18}$ [M+Na]$^+$: 1398.6; found 1398.5.

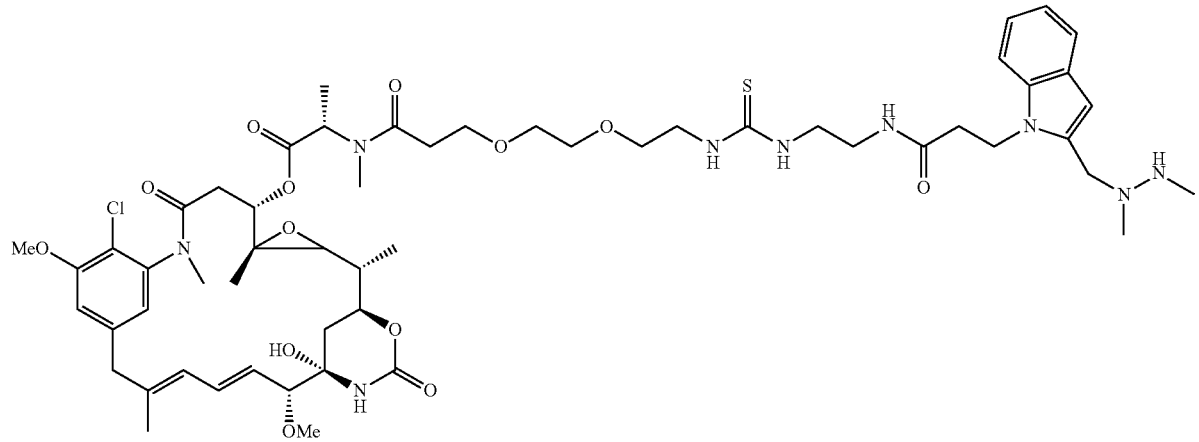

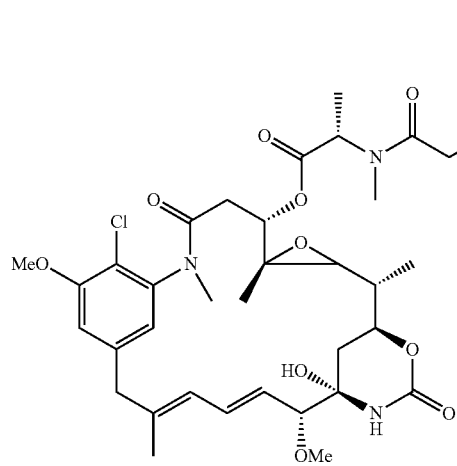
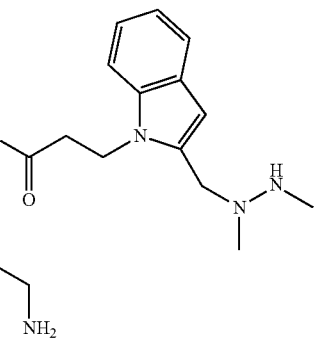
Preparation of (2S,15S)-1-((S)-3-maytansinyl) 15-(4-aminobutyl)-19-(2-((1,2-dimethylhydrazinyl)methyl)-1H-indol-1-yl)-2,3-dimethyl-4,14,17-trioxo-7,10-dioxa-3,13,16-triazanonadecan-1-oate (HIPS Indole K (NH$_2$) PEG$_2$ Maytansine) (Compound 49)
Prepared as in Method 1. HPLC retention time 8.921 min. Method D. LRMS (ESI) calcd for C$_{59}$H$_{86}$ClN$_9$NaO$_{14}$$^+$ [M+Na]$^+$: 1202.6 found 1202.7.
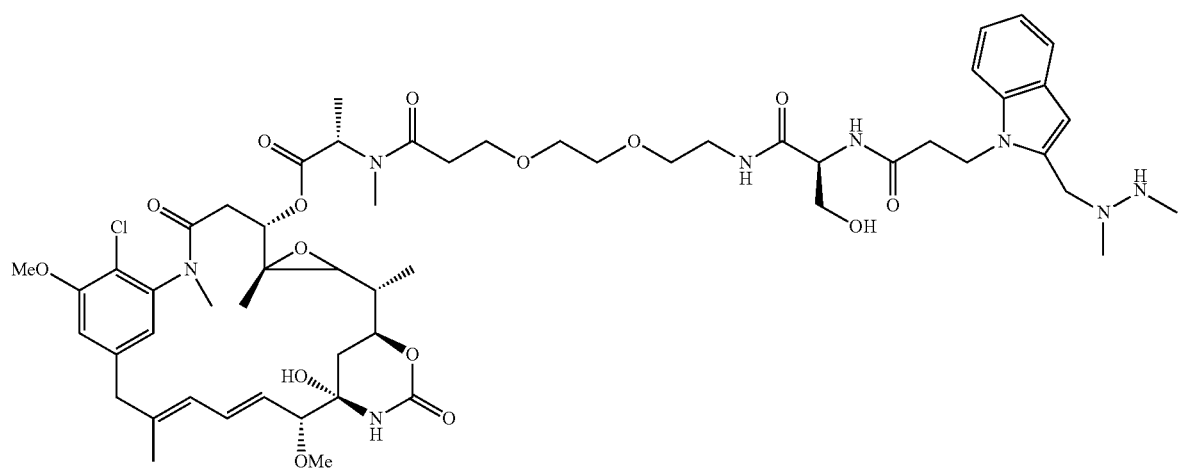

Preparation of (2S,15S)-1-((S)-3-maytansinyl) 19-(2-((1,2-dimethylhydrazinyl)methyl)-1H-indol-1-yl)-15-(hydroxymethyl)-2,3-dimethyl-4,14,17-trioxo-7,10-dioxa-3,13,16-triazanonadecan-1-oate (HIPS Indole S (OH) PEG$_2$ Maytansine)

Prepared as in Method 3. HPLC retention time 9.147 min. Method A. LRMS (ESI) calcd for $C_{56}H_{79}ClN_8NaO_{15}^+$ [M+Na]$^+$: 1161.5 found 1161.5.

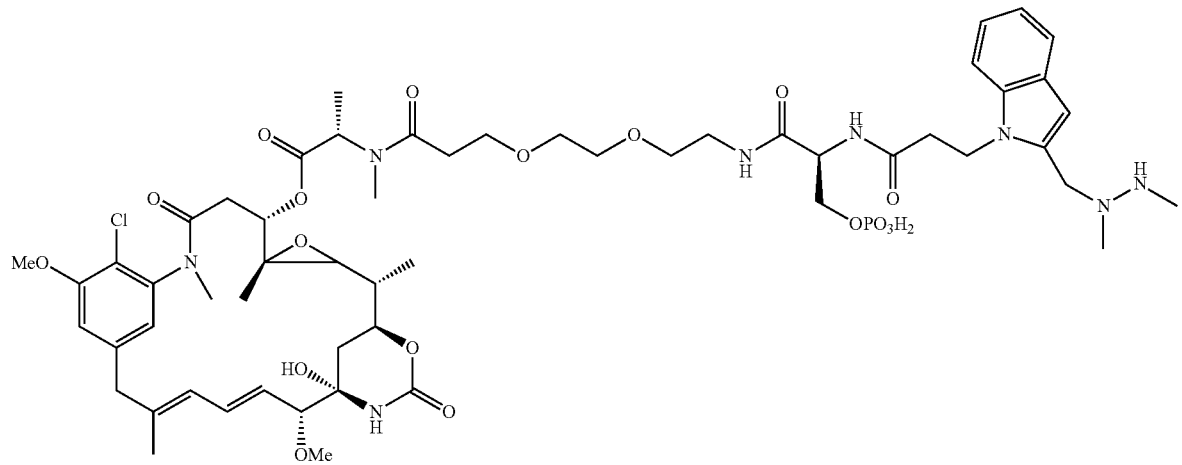

Preparation of (2S,15S)-1-((S)-3-maytansinyl) 19-(2-((1,2-dimethylhydrazinyl)methyl)-1H-indol-1-yl)-2,3-dimethyl-4,14,17-trioxo-15-((phosphonooxy)methyl)-7,10-dioxa-3,13,16-triazanonadecan-1-oate (HIPS Indole S (OPO$_3$H$_2$) PEG$_2$ Maytansine)

Prepared as in Method 3. HPLC retention time 8.916 min. Method A. LRMS (ESI) calcd for $C_{56}H_{79}ClN_8O_{18}P^-$ [M−H]$^-$: 1217.5 found 1217.2.

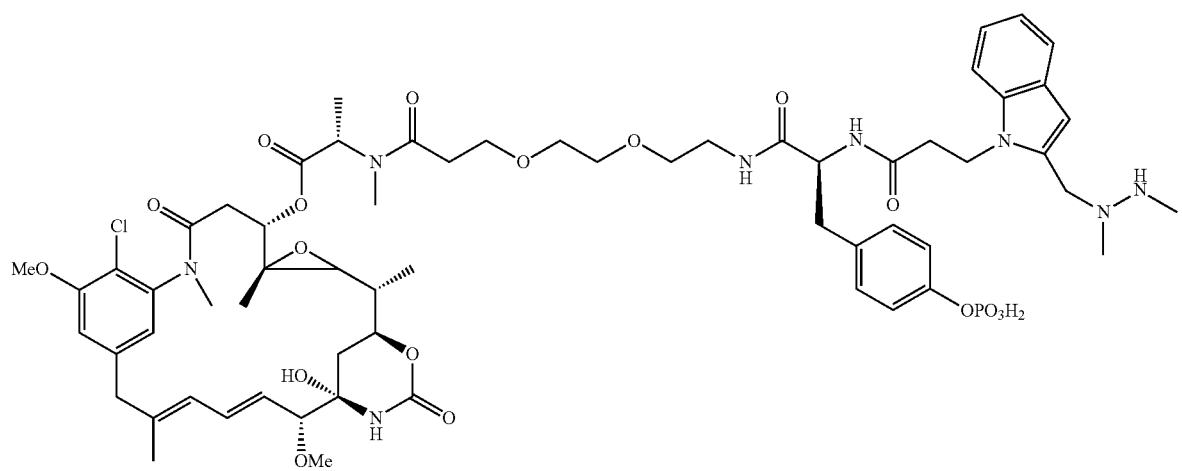

Preparation of (2S,15S)-1-((S)-3-maytansinyl) 19-(2-((1,2-dimethylhydrazinyl)methyl)-1H-indol-1-yl)-2,3-dimethyl-4,14,17-trioxo-15-(4-(Phosphonooxy)benzyl)-7,10-dioxa-3,13,16-triazanonadecan-1-oate (HIPS Indole Y (OPO$_3$H$_2$) PEG$_2$ Maytansine)

Prepared as in Method 3. HPLC retention time 9.070 min. Method A. LRMS (ESI) calcd for $C_{62}H_{83}ClN_8O_{18}P^-$ [M−H]$^-$: 1293.5 found 1293.3.

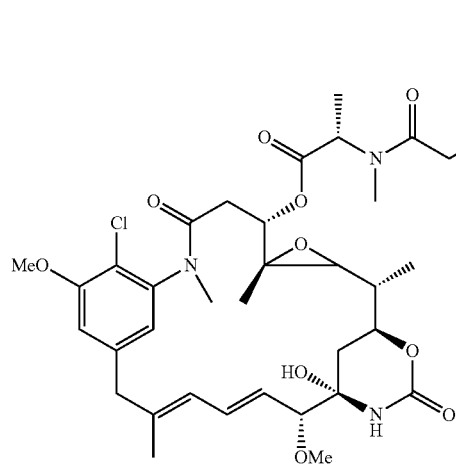
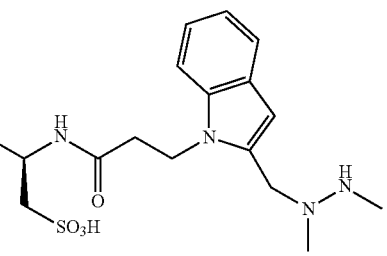

Preparation of (2S,5S,18R)-2-((S)-3-maytansinyl)-18-(3-(2-((1,2-dimethylhydrazinyl)methyl)-1H-indol-1-yl)propanamido)-5,6-dimethyl-4,7,17-trioxo-3,10,13-trioxa-6,16-diazanonadecane-19-sulfonic acid (HIPS Indole C (SO₃H) PEG₂ Maytansine)

Prepared as in Method 3. HPLC retention time 9.128 min. Method A. LRMS (ESI) calcd for $C_{56}H_{78}ClN_8O_{17}S^-$ [M−H]⁻: 1201.5 found 1201.4.

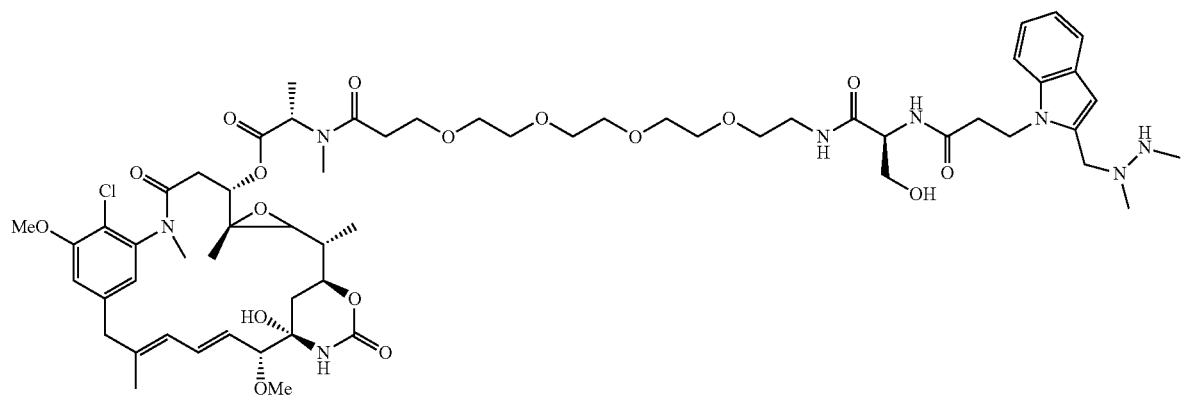

Preparation of (2S,21S)-1-((S)-3-maytansinyl) 25-(2-((1,2-dimethylhydrazinyl)methyl)-1H-indol-1-yl)-21-(hydroxymethyl)-2,3-dimethyl-4,20,23-trioxo-7,10,13,16-tetraoxa-3,19,22-triazapentacosan-1-oate (HIPS Indole S (OH) PEG₄ Maytansine)

Prepared as in Method 3. HPLC retention time 9.228 min. Method A. LRMS (ESI) calcd for $C_{60}H_{87}ClN_8NaO_{17}^+$ [M+Na]⁺: 1249.6 found 1249.6.

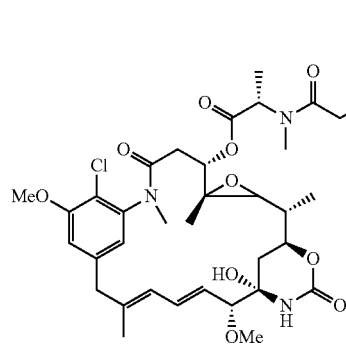
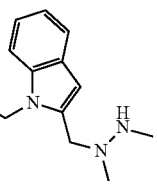

Preparation of (2S,27S)-1-((S)-3-maytansinyl) 31-(2-((1,2-dimethylhydrazinyl)methyl)-1H-indol-1-yl)-27-(hydroxymethyl)-2,3-dimethyl-4,26,29-trioxo-7,10,13,16,19,22-hexaoxa-3,25,28-triazahentriacontan-1-oate (HIPS Indole S (OH) PEG$_6$ Maytansine)

Prepared as in Method 3. HPLC retention time 9.305 min. Method A. LRMS (ESI) calcd for $C_{64}H_{95}ClN_8NaO_{19}^+$ [M+Na]$^+$: 1337.6 found 1337.6.

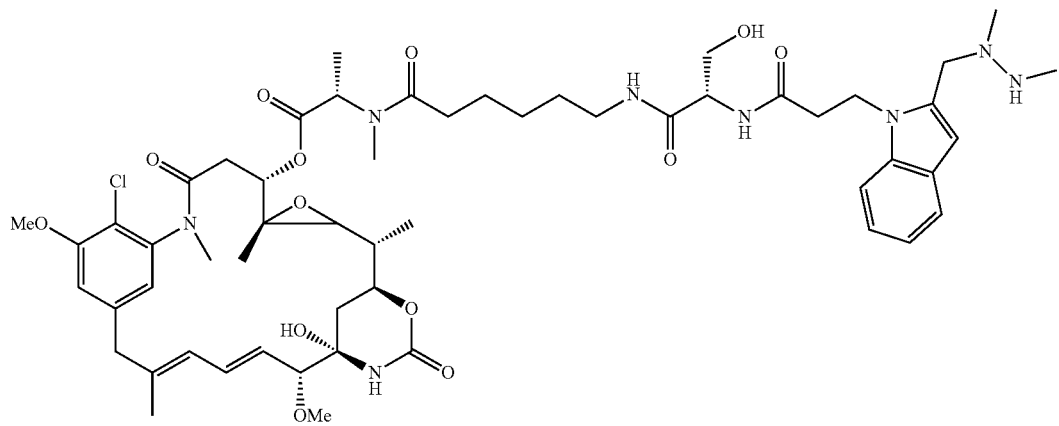

Preparation of (S)-1-((S)-3-maytansinyl) 2-(6-((S)-2-(3-(2-((1,2-dimethylhydrazinyl)methyl)-1H-indol-1-yl)propanamido)-3-hydroxypropanamido)-N-methylhexanamido)propanoate (HIPS Indole S (OH) C$_5$ Maytansine)

Prepared as in Method 3. HPLC retention time 9.307 min. Method A. LRMS (ESI) calcd for $C_{55}H_{78}ClN_8O_{13}^+$ [M+H]$^+$: 1093.5 found 1093.4.

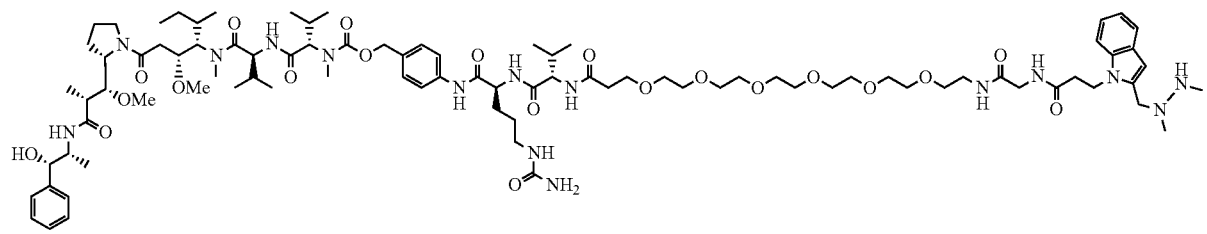 [SMILES: CCC(C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCOCCOCCOCCOCCOCCOCCNC(=O)CNC(=O)CCn2c(CN(C)NC)cc3ccccc32)C(C)C)cc1)C(C)C]

Preparation of 4-((2S,5S)-34-(2-((1,2-dimethylhydrazinyl)methyl)-1H-indol-1-yl)-5-isopropyl-4,7,29,32-tetraoxo-2-(3-ureidopropyl)-10,13,16,19,22,25-hexaoxa-3,6,28,31-tetraazatetratriacontanamido)benzyl ((S)-1-(((S)-1-(((3R,4S,5R)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)amino)-3-methyl-1-oxobutan-2-yl)(methyl)carbamate (HIPS Indole G PEG$_6$ Val Cit PABC Monomethyl Auristatin E)

Prepared as in Method 7. HPLC retention time 9.832 min. Method A. LRMS (ESI) calcd for $C_{89}H_{143}N_{15}NaO_{21}^{+}$ [M+Na]$^{+}$: 1781.1 found 1780.9.

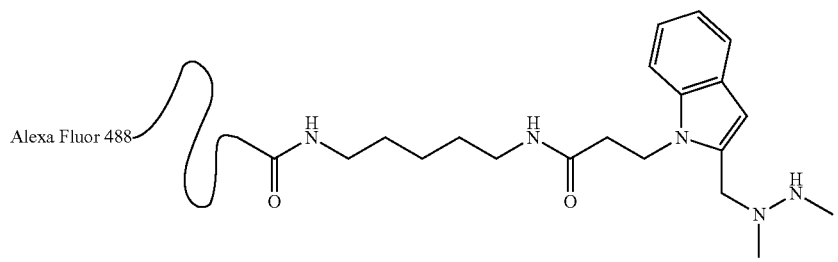 [SMILES: CNN(C)Cc1cc2ccccc2n1CCC(=O)NCCCCCNC(C)=O]

Preparation of N-(5-carboxamidopentyl)-3-(2-((1,2-dimethylhydrazinyl)methyl)-1H-indol-1-yl)propanamide Alexa Fluor 488 (HIPS Indole Cadaverine Alexa Fluor 488)

Prepared as in Method 4. HPLC retention time 6.448 min. Method A.

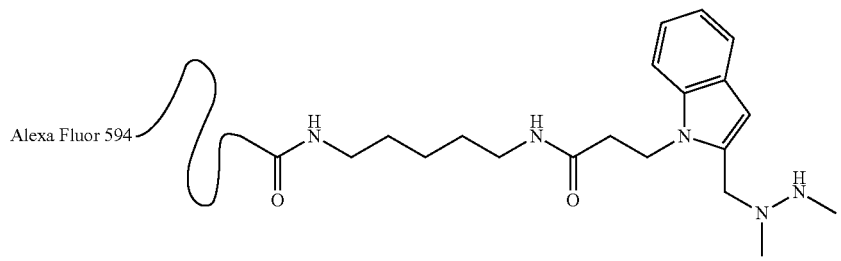 [SMILES: CNN(C)Cc1cc2ccccc2n1CCC(=O)NCCCCCNC(C)=O]

Preparation of N-(5-carboxamidopentyl)-3-(2-((1,2-dimethylhydrazinyl)methyl)-1H-indol-1-yl)propanamide Alexa Fluor 594 (HIPS Indole Cadaverine Alexa Fluor 594)

Prepared as in Method 4. HPLC retention time 7.666 min. Method A. LRMS (ESI) calcd for $C_{54}H_{62}N_7O_{11}S_2^{-}$ [M−H]$^{-}$: 1048.4 found 1048.2.

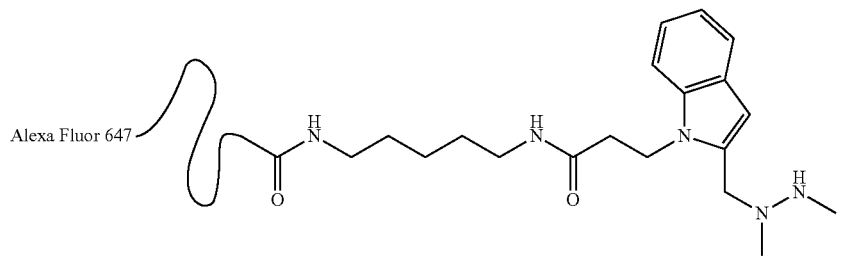 [SMILES: CNN(C)Cc1cc2ccccc2n1CCC(=O)NCCCCCNC(C)=O]

Preparation of N-(5-carboxamidopentyl)-3-(2-((1,2-dimethylhydrazinyl)methyl)-1H-indol-1-yl)propanamide Alexa Fluor 647 (HIPS Indole Cadaverine Alexa Fluor 647)

Prepared as in Method 4. HPLC retention time 5.415 min. Method A.

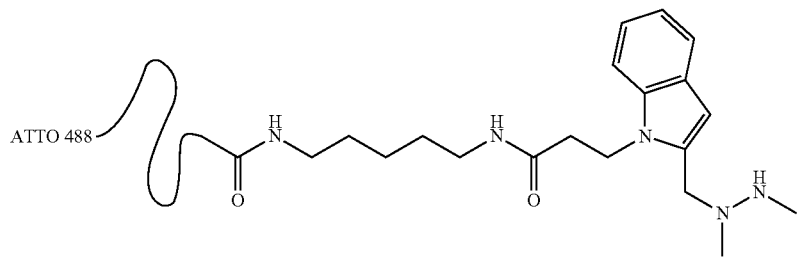 [SMILES: CNN(C)Cc1cc2ccccc2n1CCC(=O)NCCCCCNC(C)=O]

Preparation of N-(5-carboxamidopentyl)-3-(2-((1,2-dimethylhydrazinyl)methyl)-1H-indol-1-yl)propanamide ATTO 488 (HIPS Indole Cadaverine ATTO 488)

Prepared as in Method 4. HPLC retention time 6.699 min. Method A.

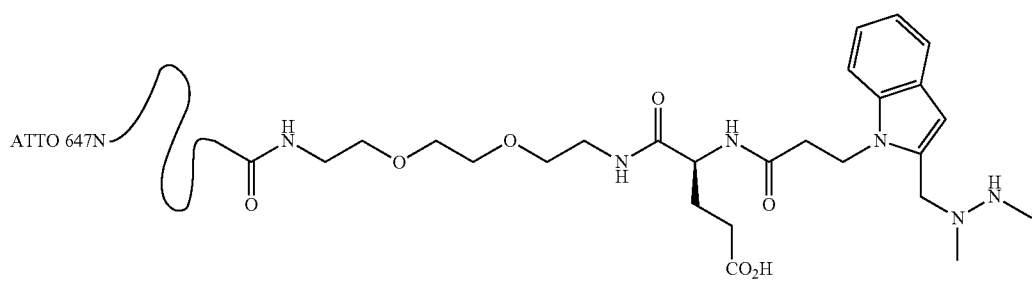 [SMILES: CNN(C)Cc1cc2ccccc2n1CCC(=O)N[C@@H](CCC(=O)O)C(=O)NCCOCCOCCNC(C)=O]

Preparation of (S)-1-carboxamido-13-(3-(2-((1,2-dimethylhydrazinyl)methyl)-1H-indol-1-yl)propanamido)-1,12-dioxo-5,8-dioxa-2,11-diazahexadecan-16-oic acid ATTO 647N (HIPS Indole E ($CO_2H$) $PEG_2$ NH ATTO 647N)

Prepared as in Method 5. HPLC retention time 11.595 min, 11.896 min (mixture of isomers). Method A.

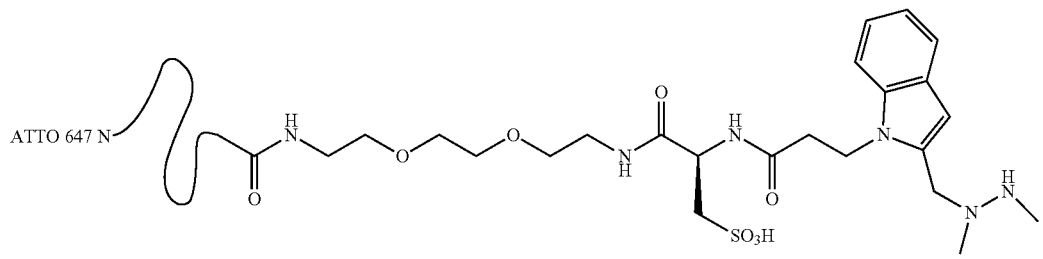 [SMILES: CNN(C)Cc1cc2ccccc2n1CCC(=O)N[C@@H](CS(=O)(=O)O)C(=O)NCCOCCOCCNC(C)=O]

Preparation of (R)-1-carboxamido-13-(3-(2-((1,2-dimethylhydrazinyl)methyl)-1H-indol-1-yl)propanamido)-1,12-dioxo-5,8-dioxa-2,11-diazatetradecane-14-sulfonic acid ATTO 647N (HIPS Indole C (SO$_3$H) PEG$_2$ NH ATTO 647N)

Prepared as in Method 6. HPLC retention time 12.519 min, 12.884 min (mixture of isomers). Method A.

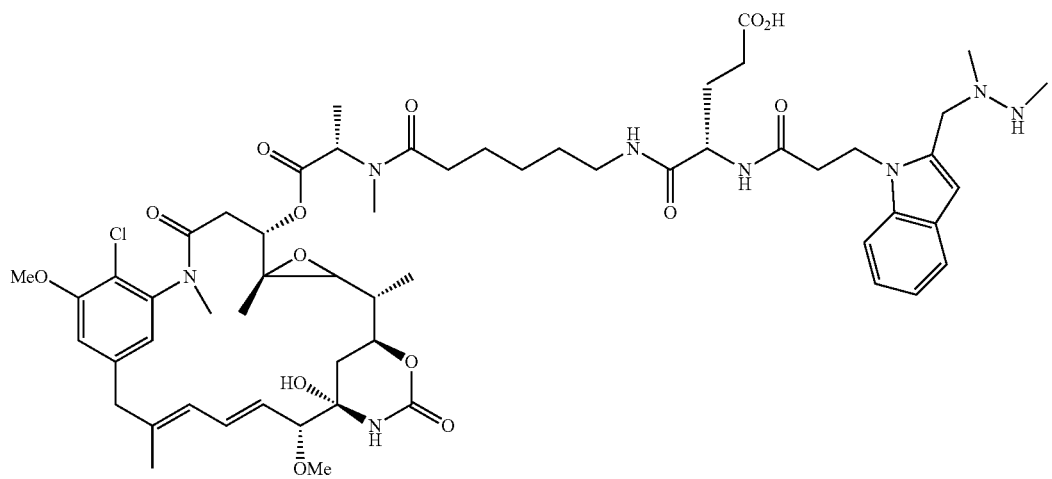

Preparation of (S)-5-((6-(((S)-1-((S)-3-maytansinyl)-1-oxopropan-2-yl)(methyl)amino)-6-oxohexyl)amino)-4-(3-(2-((1,2-dimethylhydrazinyl)methyl)-1H-indol-1-yl)propanamido)-5-oxopentanoic acid (HIPS Indole E (CO$_2$H) C$_5$ Maytansine)

Prepared as in Method 1. HPLC retention time 9.361 min. Method A. LRMS (ESI) calcd for $C_{57}H_{80}ClN_8O_{14}^+$ [M+H]$^+$: 1135.6 found 1135.4.

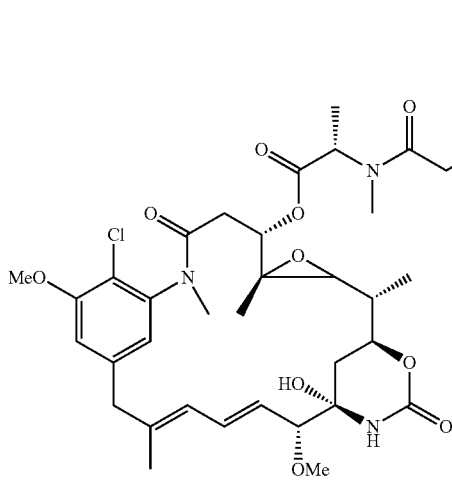
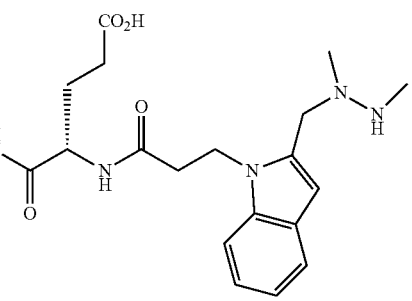

Preparation of (S)-5-((4-(((S)-1-((S)-3-maytansinyl)-1-oxopropan-2-yl)(methyl)amino)-4-oxobutyl)amino)-4-(3-(2-((1,2-dimethylhydrazinyl)methyl)-1H-indol-1-yl)propanamido)-5-oxopentanoic acid (HIPS Indole E (CO$_2$H) C$_3$ Maytansine)

Prepared as in Method 1. HPLC retention time 9.067 min. Method A. LRMS (ESI) calcd for $C_{55}H_{76}ClN_8O_{14}^+$ [M+H]$^+$: 1107.5 found 1107.3.

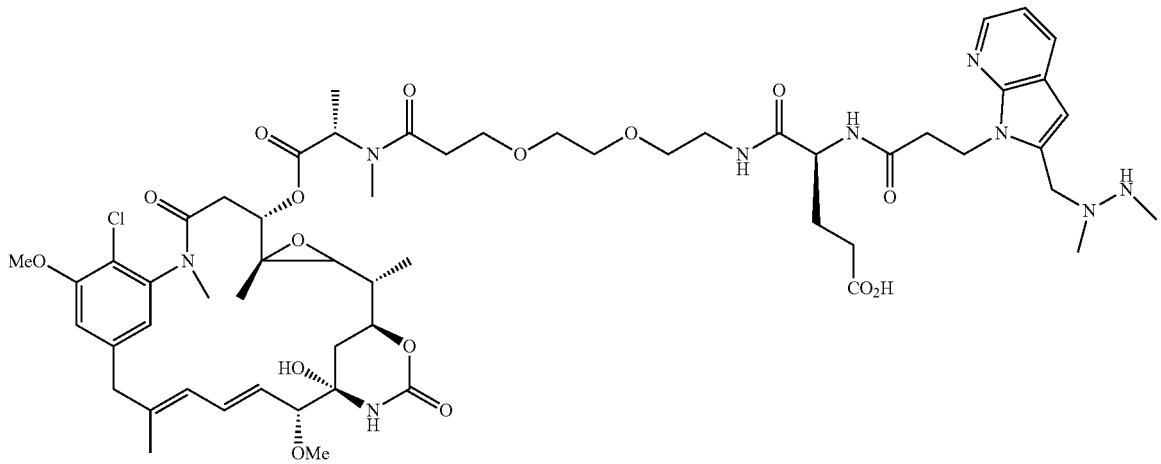

Preparation of (2S,5S,18S)-2-((S)-3-maytansinyl)-18-(3-(2-((1,2-dimethylhydrazinyl)methyl)-1H-pyrrolo[2,3-b]pyridin-1-yl)propanamido)-5,6-dimethyl-4,7,17-trioxo-3,10,13-trioxa-6,16-diazahenicosan-21-oic acid (HIPS Azaindole E (CO$_2$H) PEG$_2$ Maytansine)

Prepared as in Method 1. HPLC retention time 8.534 min. Method A. LRMS (ESI) calcd for $C_{57}H_{80}ClN_9NaO_{16}^+$ [M+H]$^+$: 1204.5 found 1204.5.

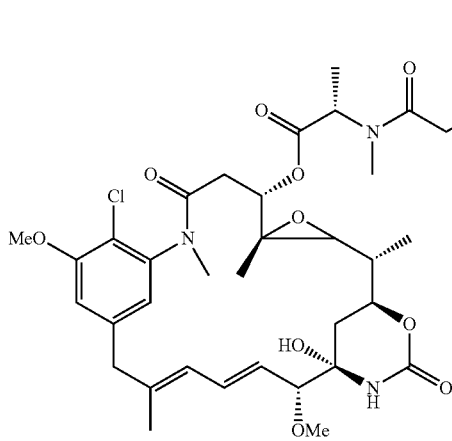

Preparation of (S)-1-((S)-3-maytansinyl) 16-(2-((1,2-dimethylhydrazinyl)methyl)-1H-pyrrolo[2,3-b]pyridin-1-yl)-2,3-dimethyl-4,14-dioxo-7,10-dioxa-3,13-diazahexadecan-1-oate (HIPS Azaindole PEG$_2$ Maytansine)

Prepared as in Method 1. HPLC retention time 8.867 min. Method A. LRMS (ESI) calcd for $C_{52}H_{74}ClN_8O_{13}^+$ [M+H]$^+$: 1053.5 found 1053.3.

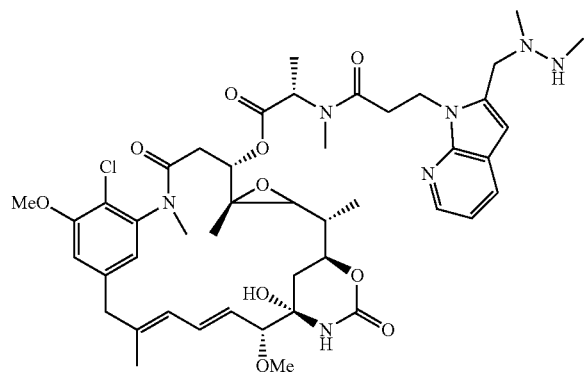

Preparation of (S)-1-((S)-3-maytansinyl)2-(3-(2-((1,2-dimethylhydrazinyl)methyl)-1H-pyrrolo[2,3-b]pyridin-1-yl)-N-methylpropanamido)propanoate (HIPS Azaindole Maytansine)

Prepared as in Method 1. HPLC retention time 9.198 min. Method A. LRMS (ESI) calcd for $C_{45}H_{61}ClN_7O_{10}^+$ [M+H]$^+$: 894.4 found 894.3.

Example 19

General Procedure for Conjugation of HIPS-Linker-Drug to an Aldehyde-Tagged Antibody To conjugate a HIPS-linker-drug to an aldehyde-tagged antibody as described herein, the following general protocol was used. 1.85 mM HIPS-linker-drug (e.g., HIPS-linker-Maytansine) was reacted with 102 μM aldehyde-tagged antibody (e.g., an aldehyde-tagged antibody (dimer) with one aldehyde tag per chain) in PBS with 50 mM sodium citrate pH 5.5, 2.5% DMA, and 0.25% Triton X-100 at 37° C. for 16-24 h. After the reaction was complete, unreacted drug was removed using diafiltration. Mono- and di-conjugated species were then purified away from unconjugated material using a hydrophobic interaction column (GE Healthcare Life Sciences #17-5195-01; Mobile Phase A: 25 mM NaPO$_4$, 1.0M NH$_4$SO$_4$, pH 7.0; Mobile Phase B: 18.75 mM NaPO$_4$, 25% IPA, pH 7.0). The enriched sample was put into a final formulation buffer of PBS using diafiltration. The final sample was analyzed using hydrophobic interaction chromatography to determine DAR (Tosoh #14947; Mobile Phase A: 25 mM NaPO$_4$, 1.5 M NH$_4$SO$_4$, pH 7.0; Mobile Phase B: 18.75 mM NaPO$_4$, 25% IPA, pH 7.0) and size exclusion chromatography determine the level of aggregation (Tosoh #08541; Mobile Phase A: 25 mM NaPO$_4$ buffer, 300 mM NaCl, pH 6.8).

Conjugation of HIPS Serine PEG$_2$ Maytansine to an Aldehyde-Tagged Antibody

HIPS Serine PEG$_2$ Maytansine was reacted with an aldehyde-tagged antibody according to the conjugation method described above.

Figure 33A:
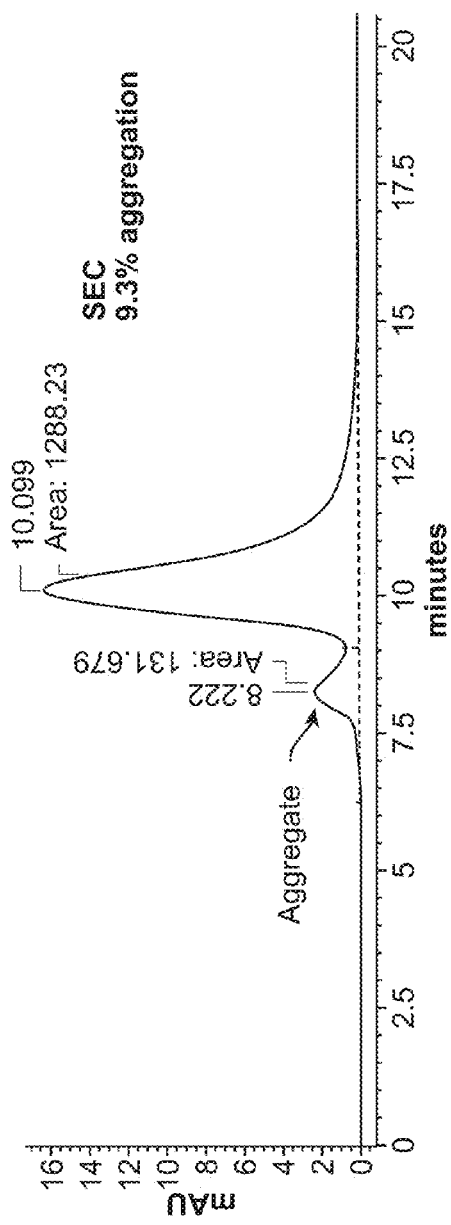
FIGS. 33A-33C show a size exclusion chromatography (SEC) trace (FIG. 33A), a hydrophobic interaction column (HIC) trace (FIG. 33B), and a mass spectrometer (MS) trace (FIG. 33C) of an aldehyde-tagged antibody conjugated to HIPS Serine $PEG_2$ Maytansine, according to embodiments of the present disclosure.
Figure 33B:
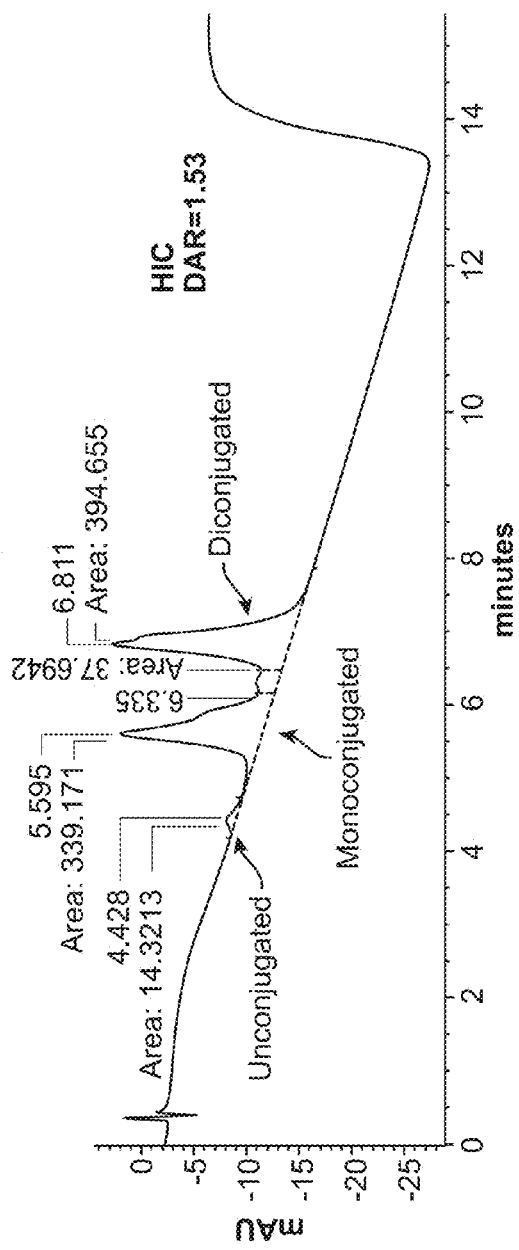
Figure 33C:
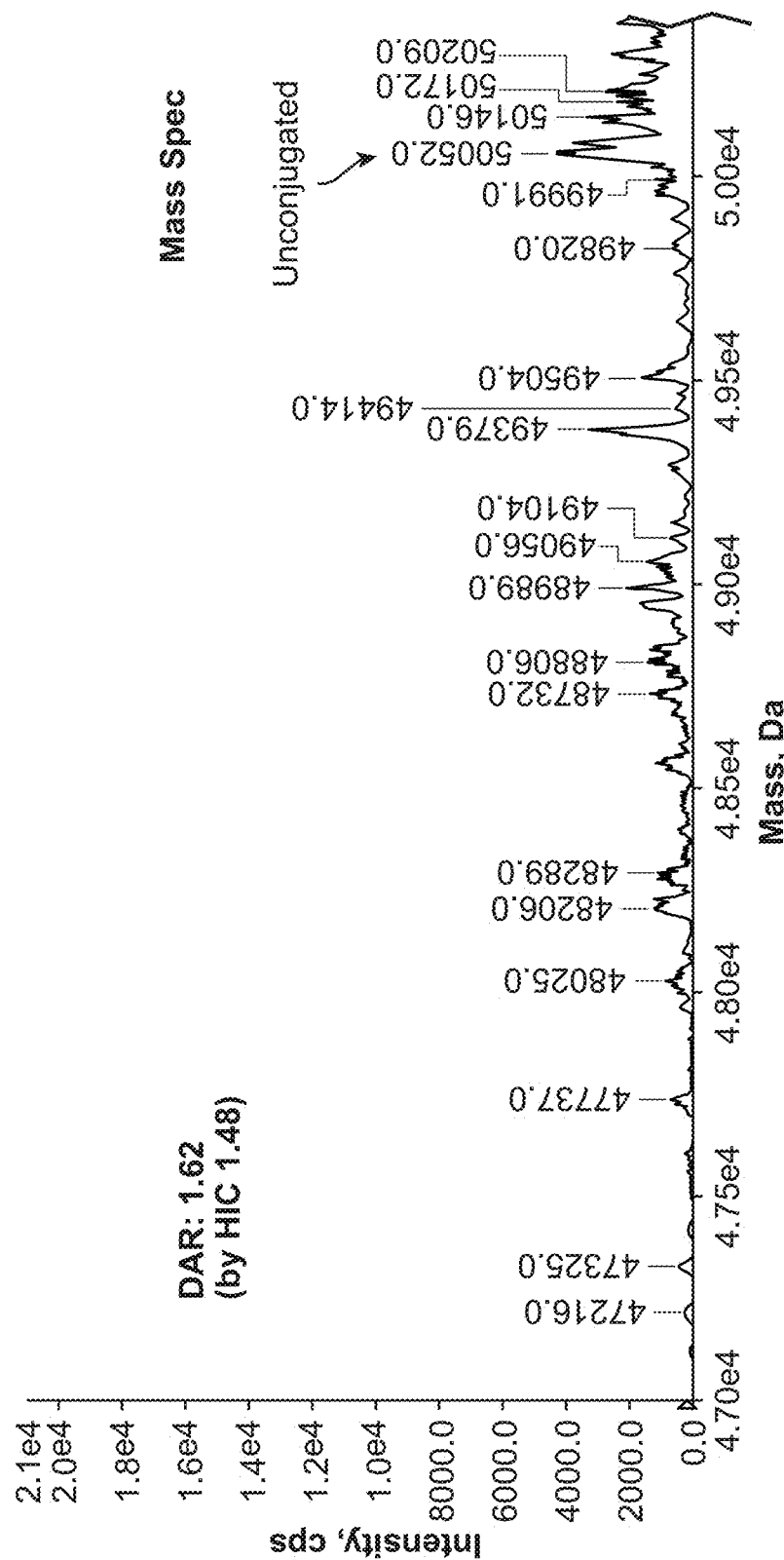
Figure 33C:
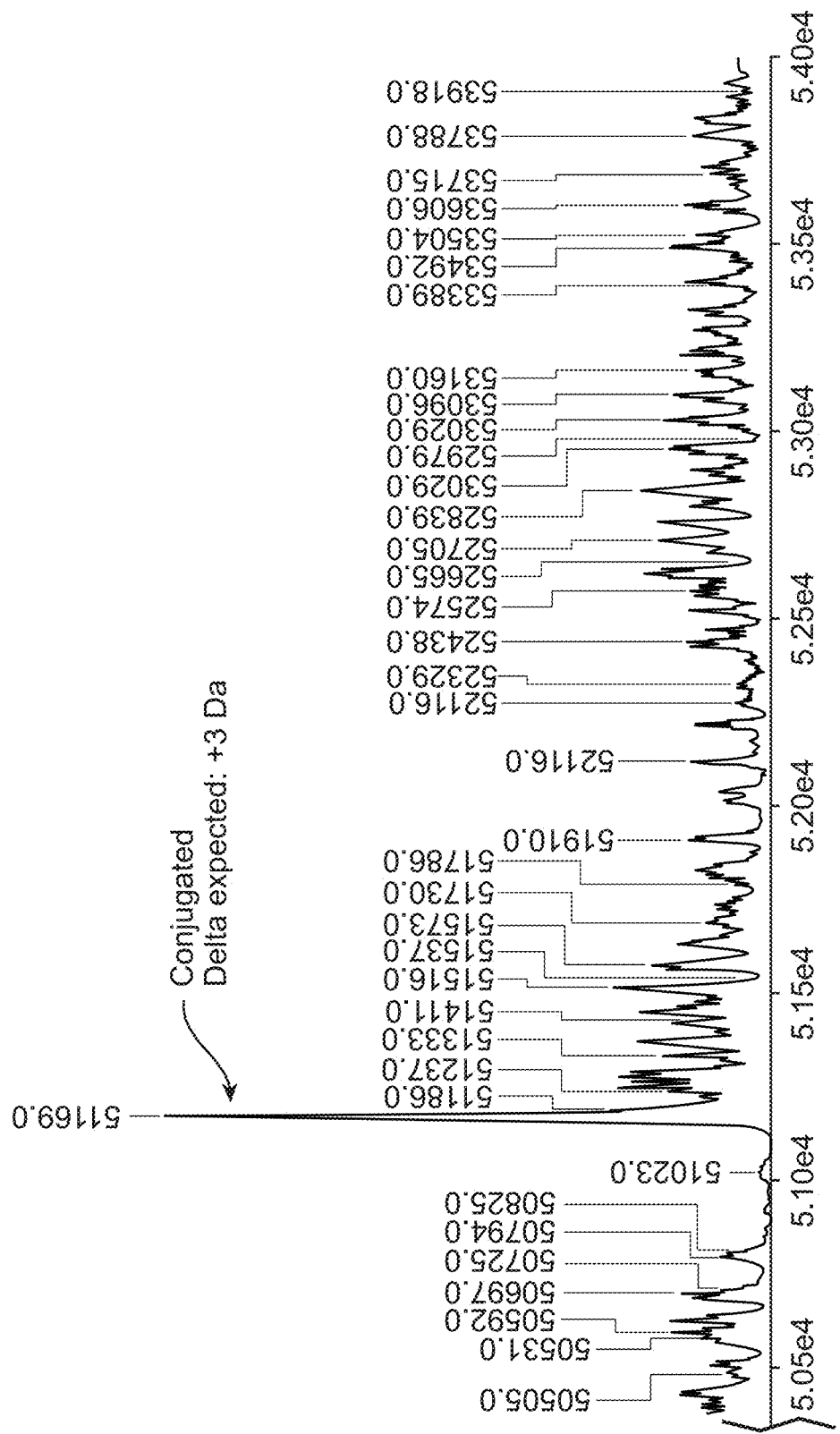

Results are shown in FIGS. 33A-33C, which shows a size exclusion chromatography (SEC) trace (FIG. 33A), a hydrophobic interaction column (HIC) trace (FIG. 33B), and a mass spectrometer (MS) trace (FIG. 33C) of the aldehyde-tagged antibody conjugated to HIPS Serine PEG$_2$ Maytansine. The unconjugated, mono-conjugated, and di-conjugated protein conjugates were observed.

Conjugation of HIPS Phosphoserine PEG$_2$ Maytansine to an Aldehyde-Tagged Antibody HIPS Phosphoserine PEG$_2$ Maytansine was reacted with an aldehyde-tagged antibody according to the conjugation method described above.

Figure 34A:
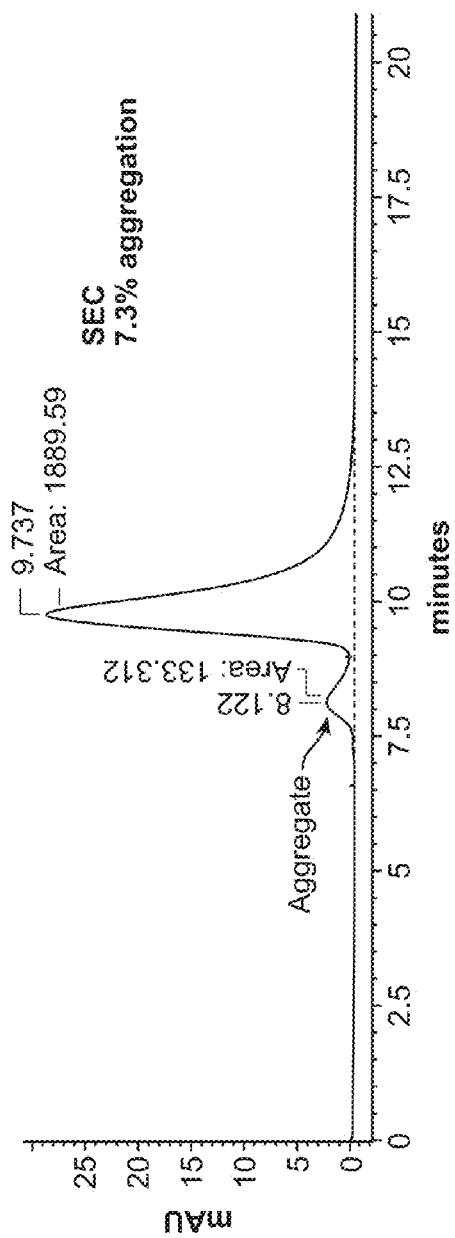
FIGS. 34A-34C show a size exclusion chromatography (SEC) trace (FIG. 34A), a hydrophobic interaction column (HIC) trace (FIG. 34B), and a mass spectrometer (MS) trace (FIG. 34C) of an aldehyde-tagged antibody conjugated to HIPS Phosphoserine $PEG_2$ Maytansine, according to embodiments of the present disclosure.
Figure 34B:
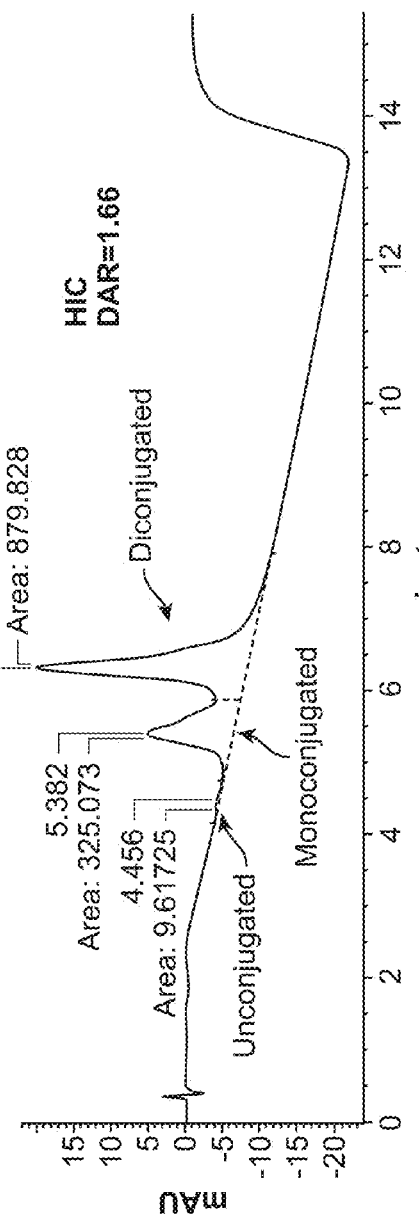
Figure 34C:
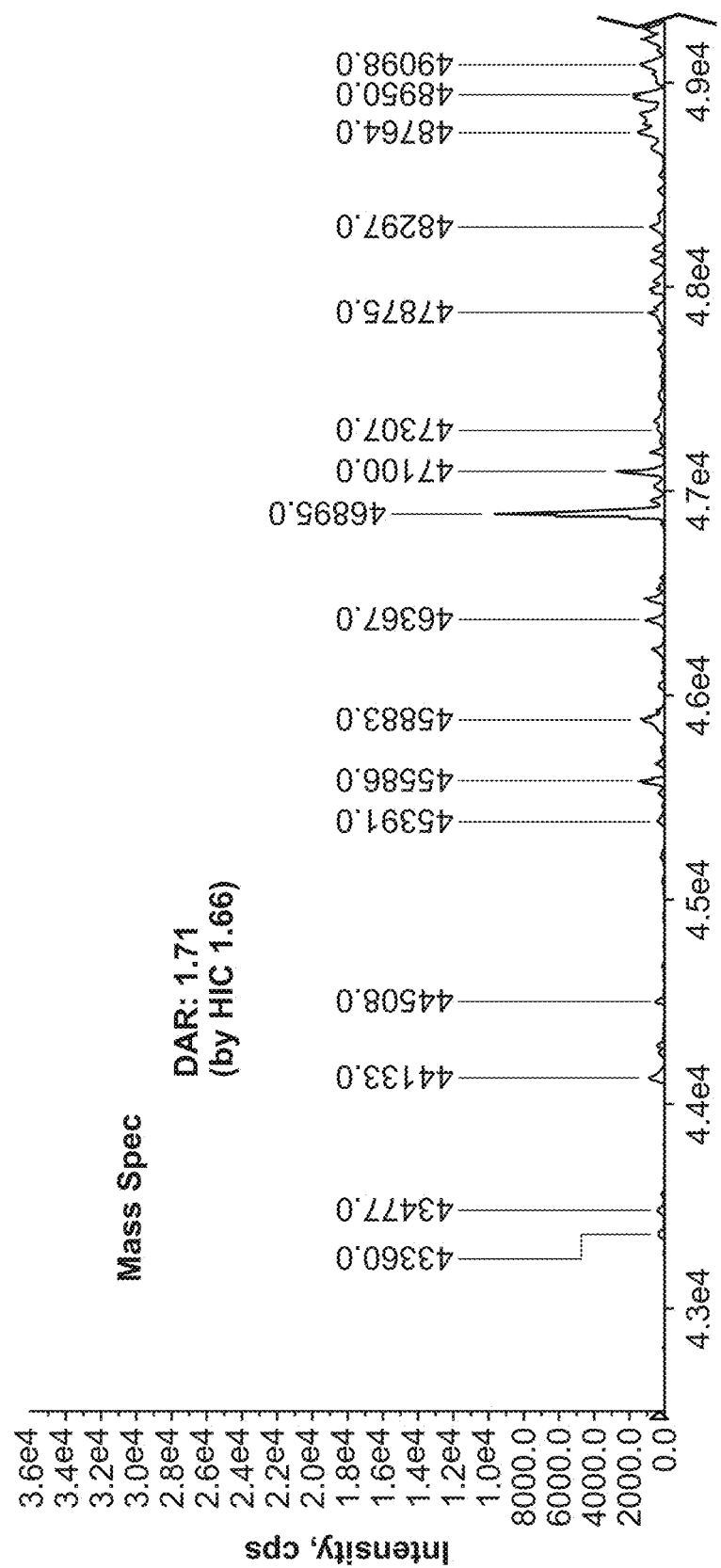
Figure 34C:
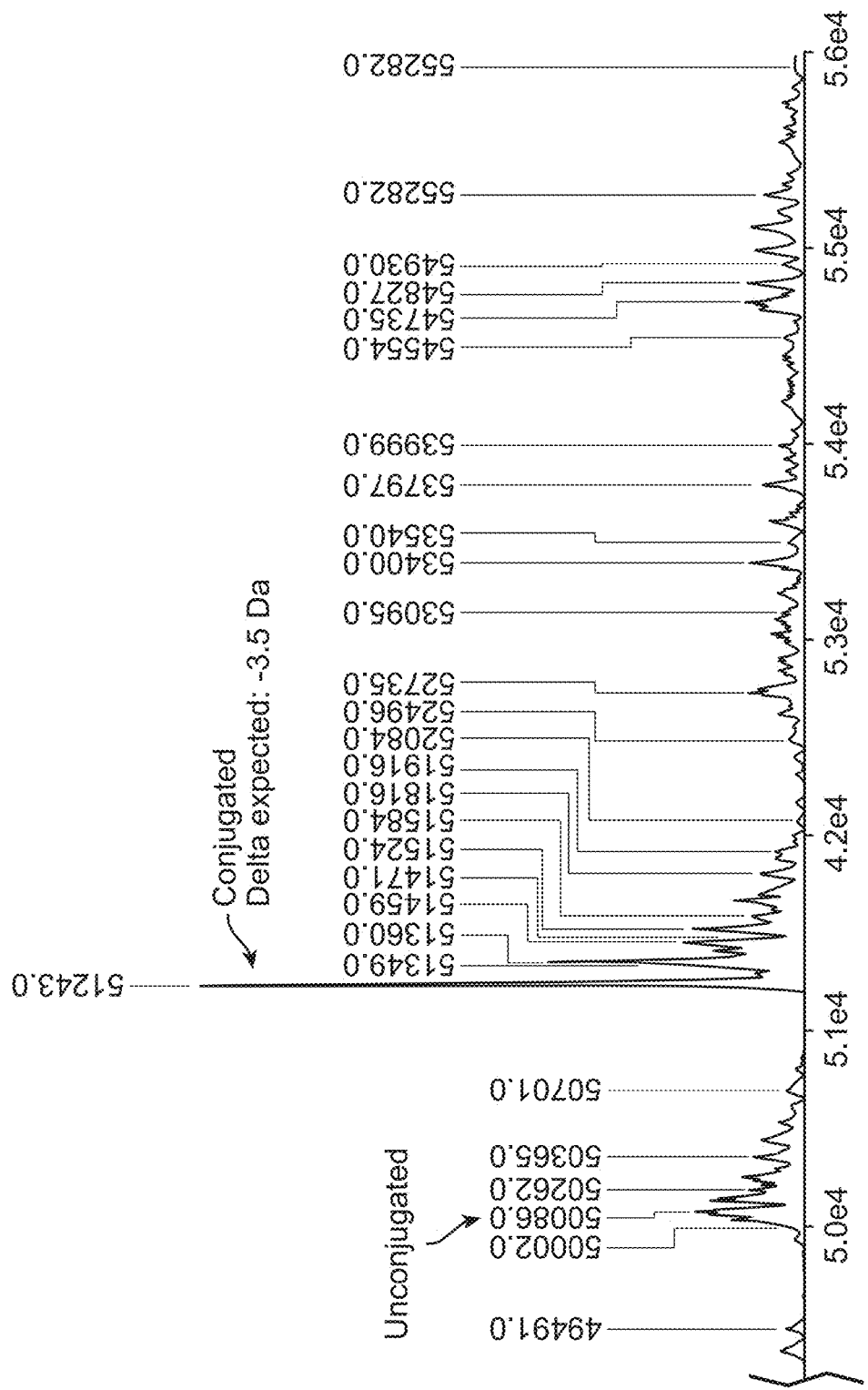

Results are shown in FIGS. 34A-34C, which shows a size exclusion chromatography (SEC) trace (FIG. 34A) and a hydrophobic interaction column (HIC) trace (FIG. 34B), and a mass spectrometer (MS) trace (FIG. 34C) of the aldehyde-tagged antibody conjugated to HIPS Phosphoserine PEG$_2$ Maytansine. The unconjugated, mono-conjugated, and di-conjugated protein conjugates were observed.

Conjugation of HIPS Cysteic Acid PEG$_2$ Maytansine to an Aldehyde-Tagged Antibody HIPS Cysteic Acid PEG$_2$ Maytansine was reacted with an aldehyde-tagged antibody according to the conjugation method described above.

Figure 35C:
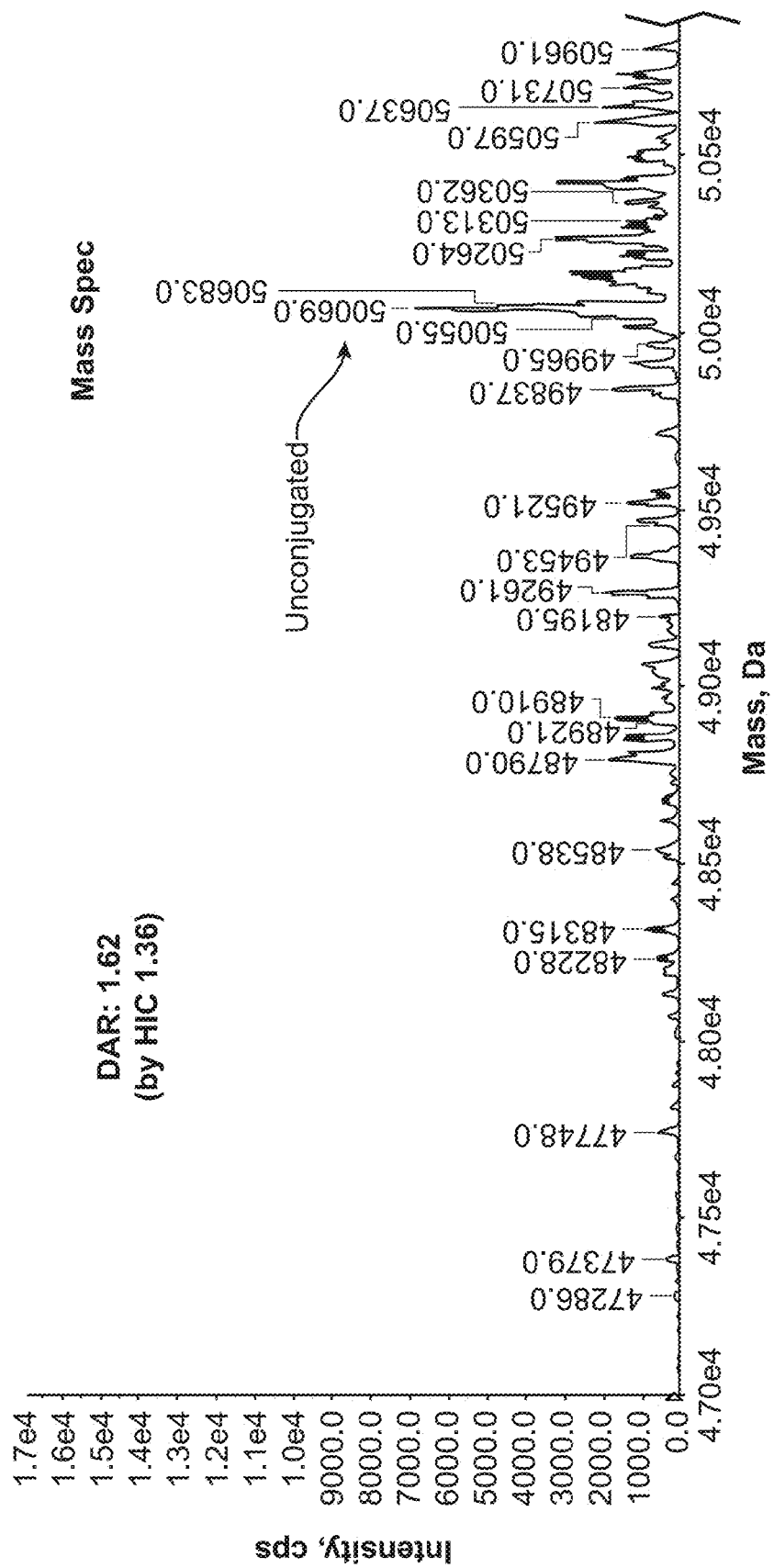
Figure 35C:
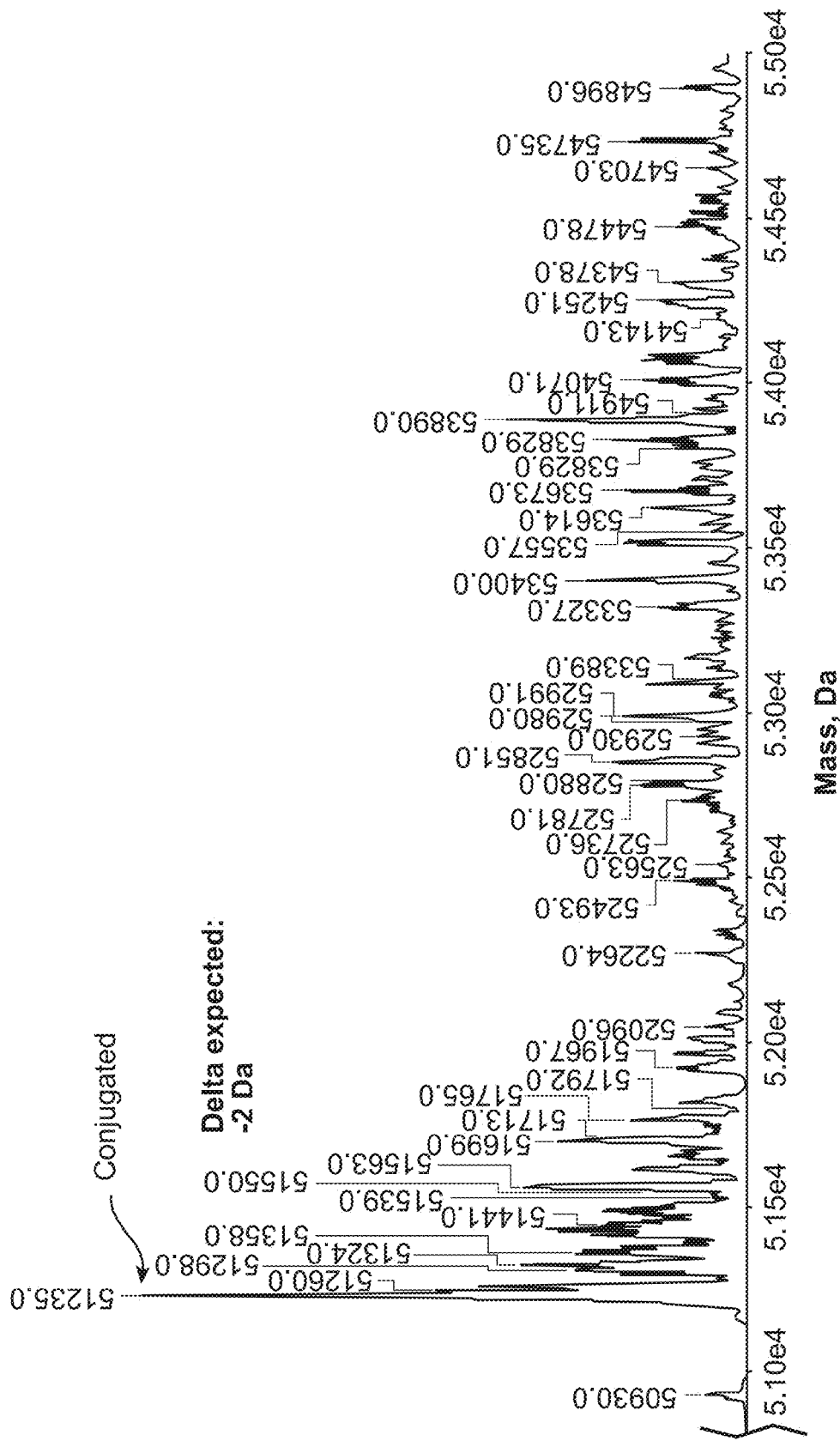

Results are shown in FIGS. 35A-35C, which shows a size exclusion chromatography (SEC) trace (FIG. 35A), a hydrophobic interaction column (HIC) trace (FIG. 35B), and a mass spectrometer (MS) trace (FIG. 35C) of the aldehyde-tagged antibody conjugated to HIPS HIPS Cysteic Acid $PEG_2$ Maytansine. The unconjugated, mono-conjugated, and di-conjugated protein conjugates were observed.

Conjugation of HIPS Glutamic Acid $PEG_2$ Maytansine to an Aldehyde-Tagged Antibody HIPS Glutamic Acid $PEG_2$ Maytansine was reacted with an aldehyde-tagged antibody according to the conjugation method described above.

Figure 36A:
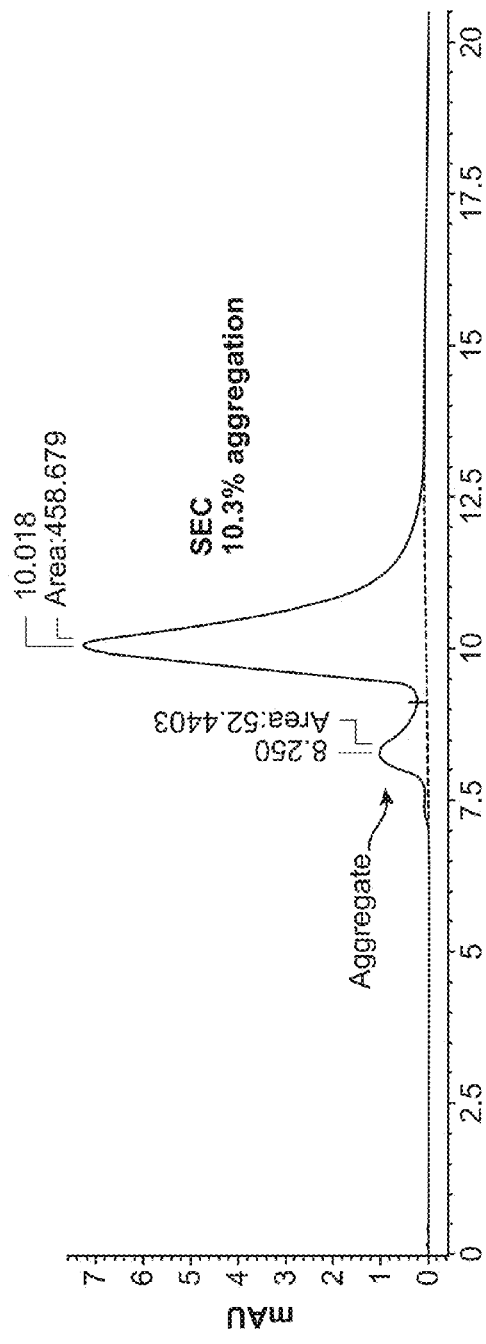
FIGS. 36A-36C show a size exclusion chromatography (SEC) trace (FIG. 36A), a hydrophobic interaction column (HIC) trace (FIG. 36B), and a mass spectrometer (MS) trace (FIG. 36C) of an aldehyde-tagged antibody conjugated to HIPS Glutamic Acid $PEG_2$ Maytansine, according to embodiments of the present disclosure.
Figure 36B:
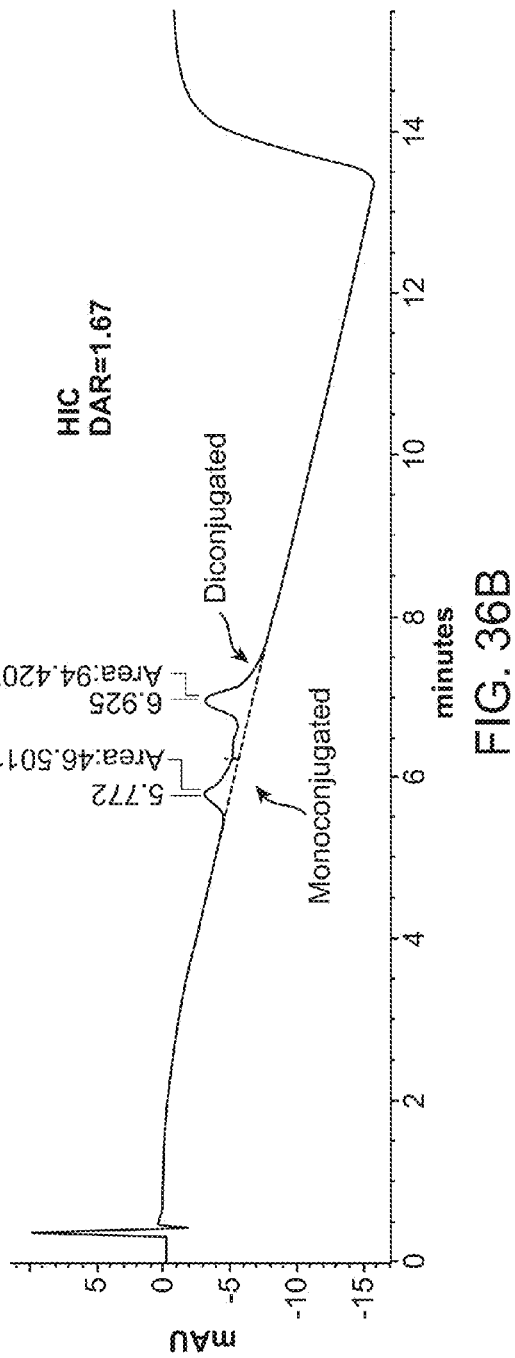
Figure 36C:
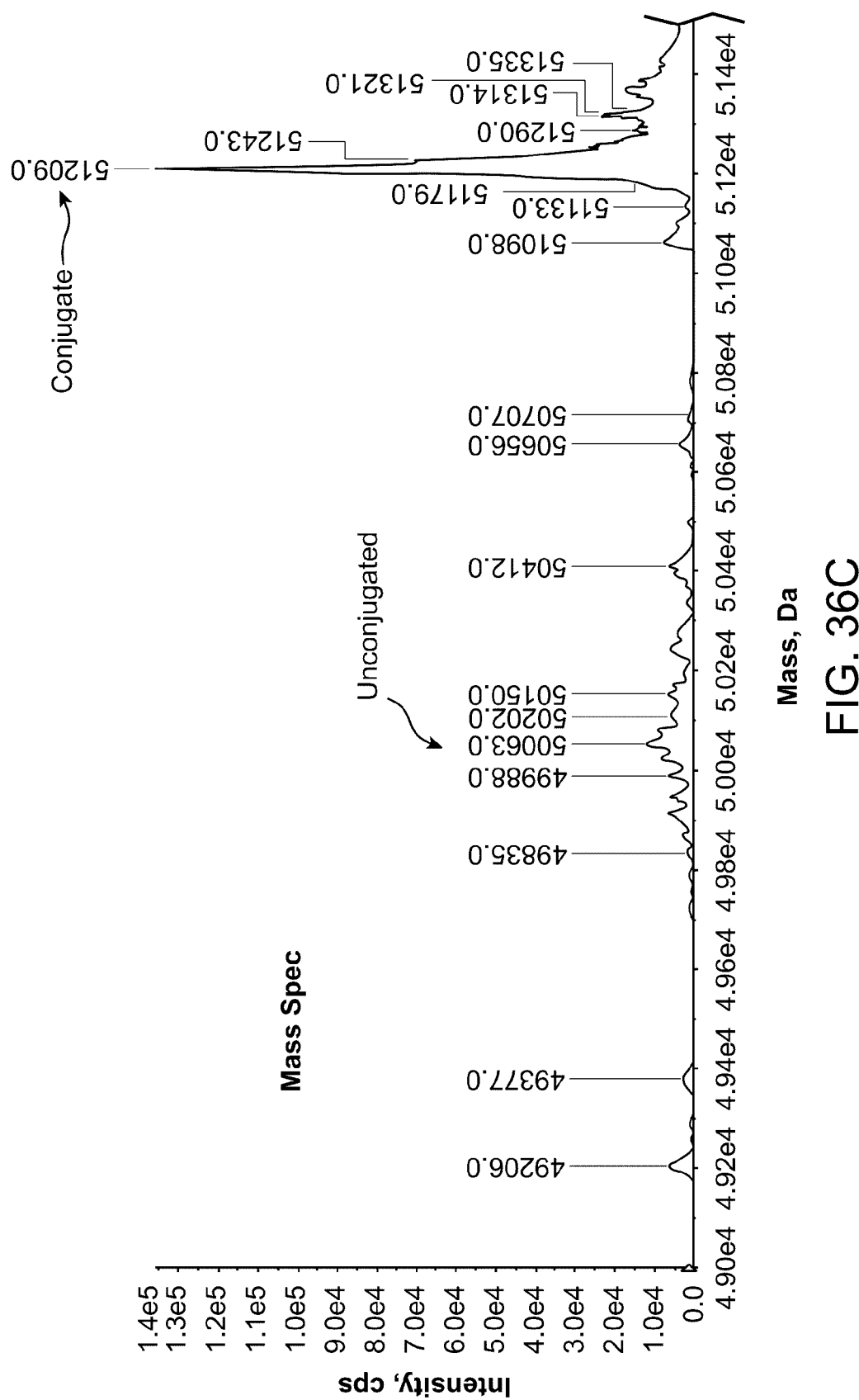
Figure 36C:
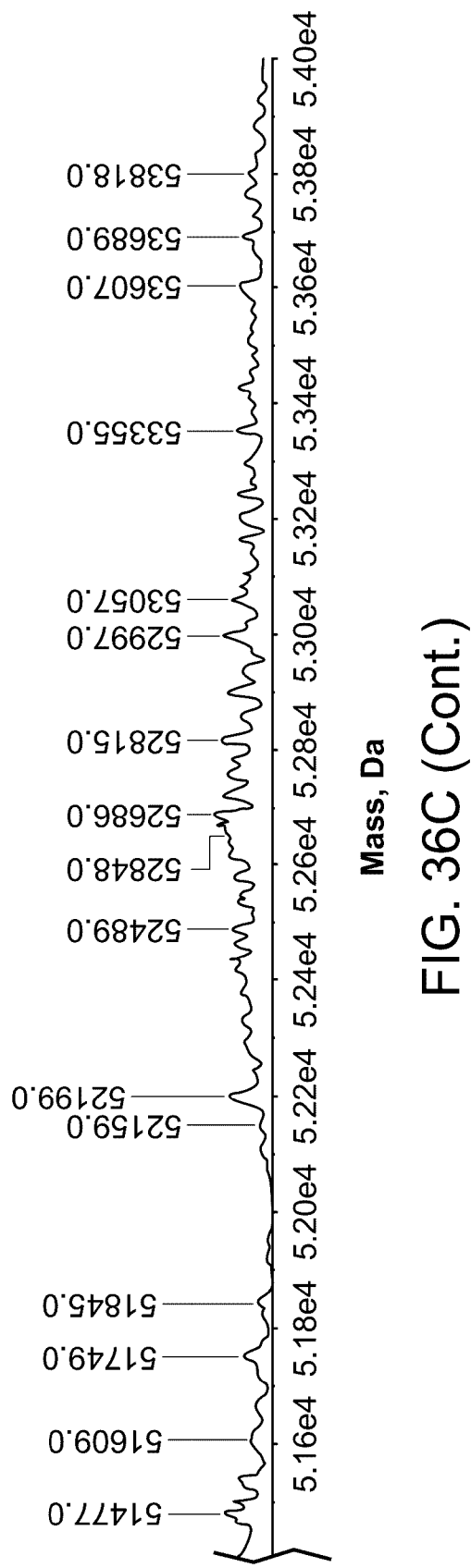

Results are shown in FIGS. 36A-36C, which shows a size exclusion chromatography (SEC) trace (FIG. 36A), a hydrophobic interaction column (HIC) trace (FIG. 36B), and a mass spectrometer (MS) trace (FIG. 36C) of the aldehyde-tagged antibody conjugated to HIPS Glutamic Acid $PEG_2$ Maytansine. The mono-conjugated and di-conjugated protein conjugates were observed.

Conjugation of HIPS Asparagine $PEG_2$ Maytansine to an Aldehyde-Tagged Antibody HIPS Asparagine $PEG_2$ Maytansine was reacted with an aldehyde-tagged antibody according to the conjugation method described above.

Results are shown in FIGS. 37A-37B, which shows a size exclusion chromatography (SEC) trace (FIG. 37A) and a hydrophobic interaction column (HIC) trace (FIG. 37B) of the aldehyde-tagged antibody conjugated to HIPS Asparagine $PEG_2$ Maytansine. The unconjugated, mono-conjugated and di-conjugated protein conjugates were observed.

Conjugation of HIPS Phosphotyrosine $PEG_2$ Maytansine to an Aldehyde-Tagged Antibody HIPS Phosphotyrosine $PEG_2$ Maytansine was reacted with an aldehyde-tagged antibody according to the conjugation method described above.

Figure 38A:
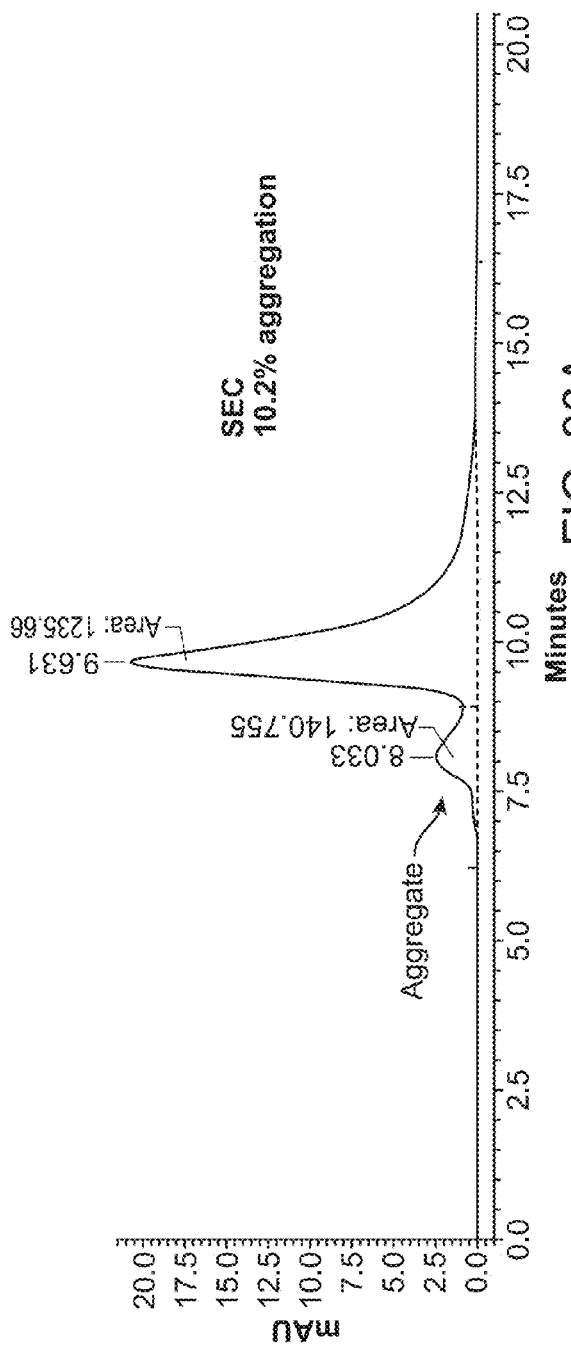
FIGS. 38A-38B show a size exclusion chromatography (SEC) trace (FIG. 38A) and a hydrophobic interaction column (HIC) trace (FIG. 38B) of an aldehyde-tagged antibody conjugated to HIPS Phosphotyrosine $PEG_2$ Maytansine, according to embodiments of the present disclosure.
Figure 38B:
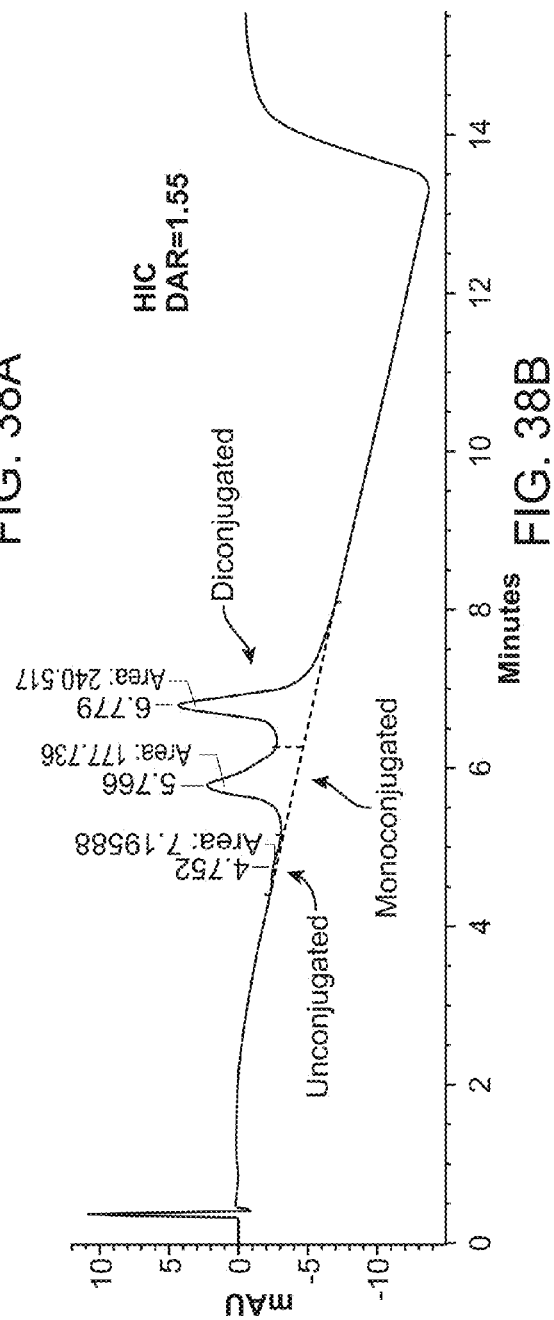

Results are shown in FIGS. 38A-38B, which shows a size exclusion chromatography (SEC) trace (FIG. 38A) and a hydrophobic interaction column (HIC) trace (FIG. 38B) of the aldehyde-tagged antibody conjugated to HIPS Phosphotyrosine $PEG_2$ Maytansine. The unconjugated, mono-conjugated and di-conjugated protein conjugates were observed.

Conjugation of AzaHIPS Glutamic Acid $PEG_2$ Maytansine to an Aldehyde-Tagged Antibody AzaHIPS Glutamic Acid $PEG_2$ Maytansine was reacted with an aldehyde-tagged antibody according to the conjugation method described above.

Figure 39C:
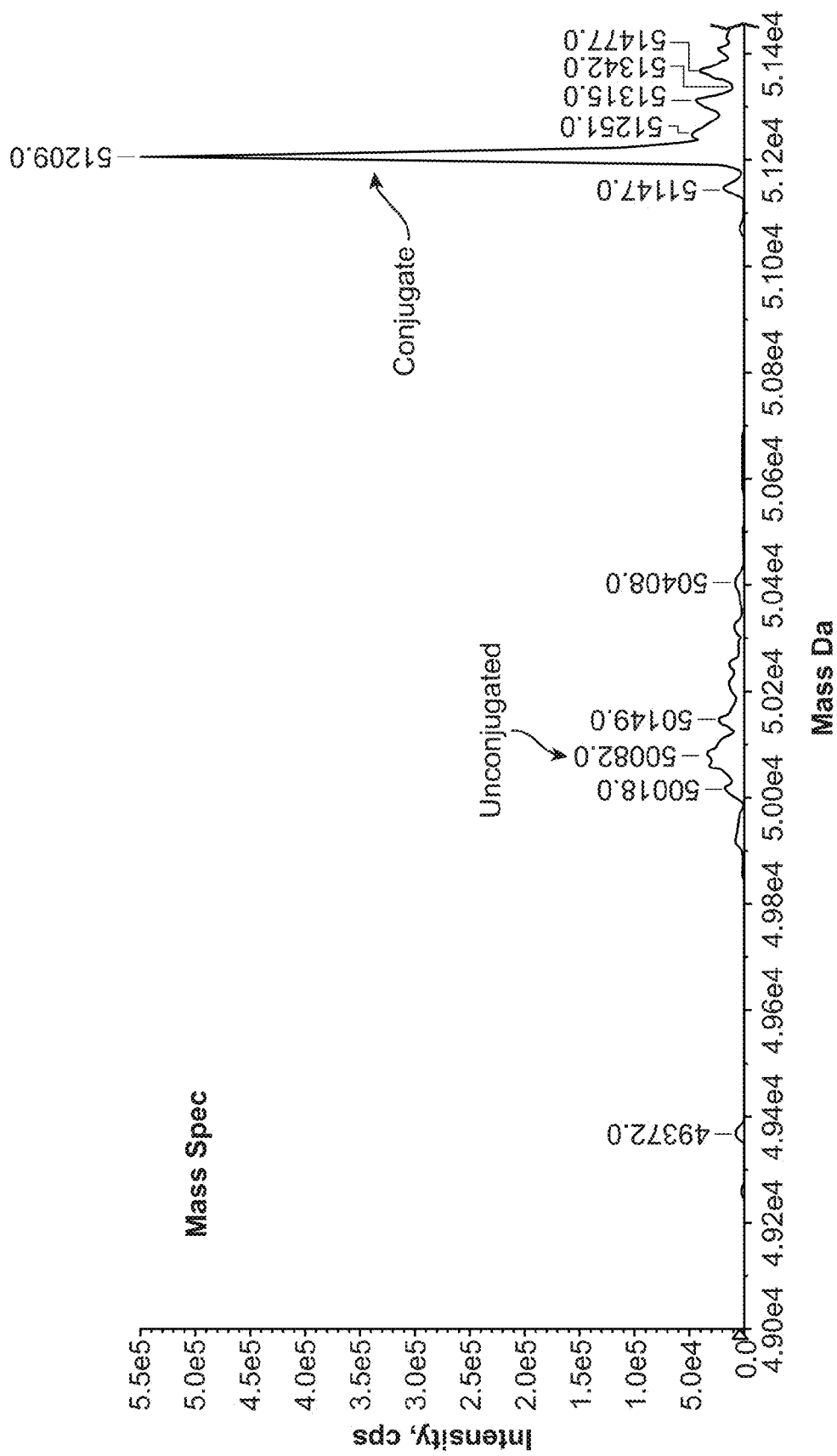
Figure 39C:
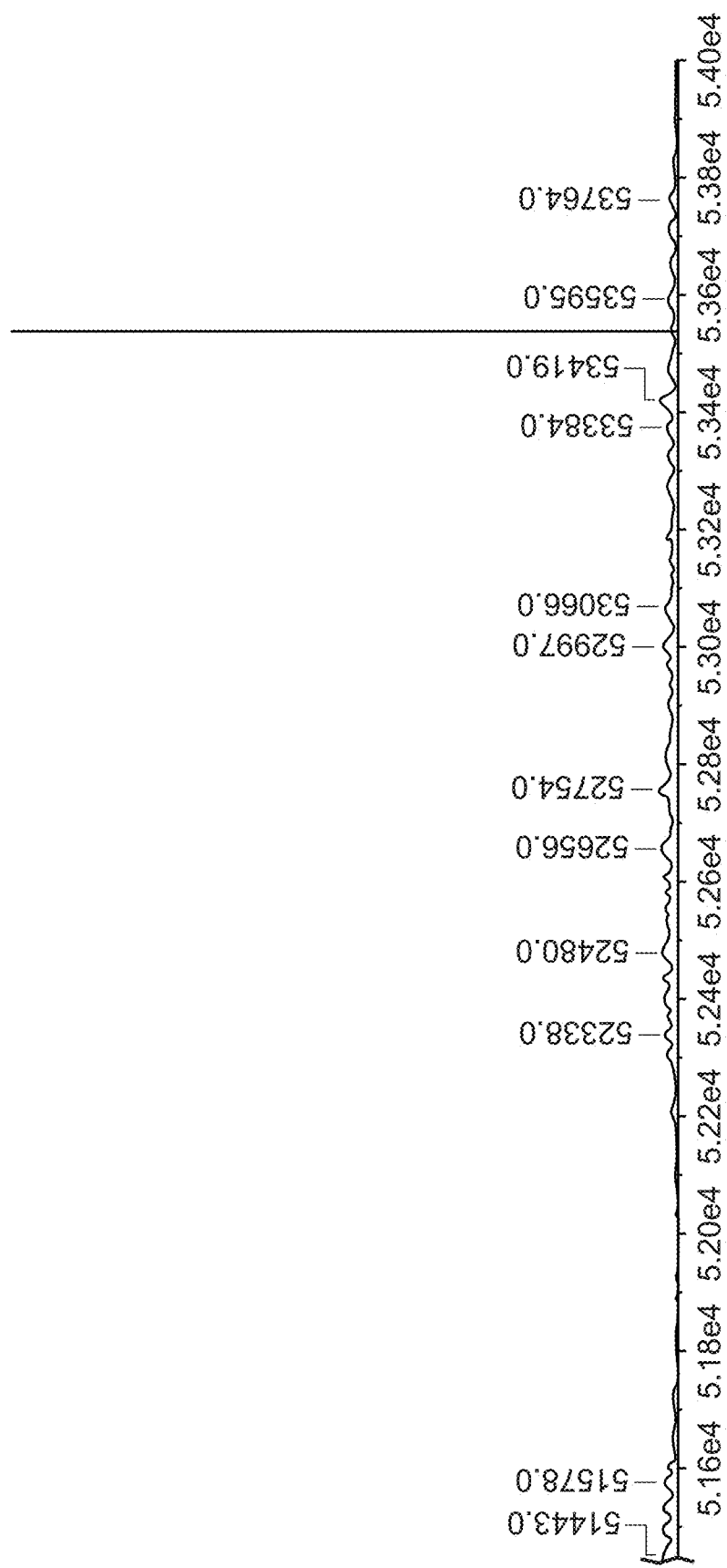

Results are shown in FIGS. 39A-39C, which shows a size exclusion chromatography (SEC) trace (FIG. 39A), a hydrophobic interaction column (HIC) trace (FIG. 39B), and a mass spectrometer (MS) trace (FIG. 39C) of the aldehyde-tagged antibody conjugated to AzaHIPS Glutamic Acid $PEG_2$ Maytansine. The unconjugated, mono-conjugated and di-conjugated protein conjugates were observed.

Conjugation of HIPS Tartaric Acid Maytansine to an Aldehyde-Tagged Antibody

HIPS Tartaric Acid Maytansine was reacted with an aldehyde-tagged antibody according to the conjugation method described above.

Figure 40C:
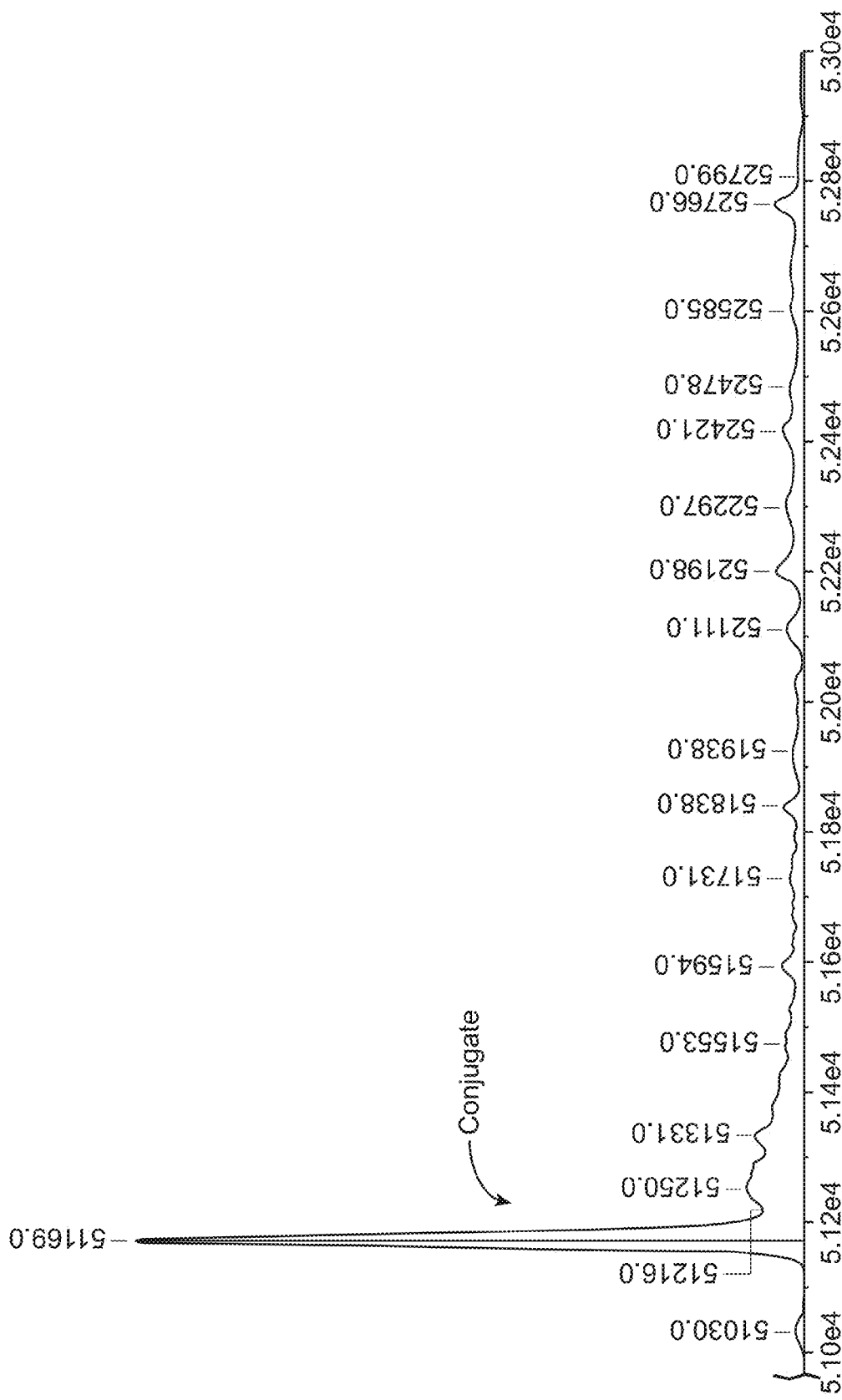

Results are shown in FIGS. 40A-40C, which shows a size exclusion chromatography (SEC) trace (FIG. 40A), a hydrophobic interaction column (HIC) trace (FIG. 40B), and a mass spectrometer (MS) trace (FIG. 40C) of the aldehyde-tagged antibody conjugated to HIPS Tartaric Acid Maytansine. The unconjugated, mono-conjugated and di-conjugated protein conjugates were observed.

Conjugation of HIPS Dihydroxy Maytansine to an Aldehyde-Tagged Antibody

HIPS Dihydroxy Maytansine was reacted with an aldehyde-tagged antibody according to the conjugation method described above.

Figure 41C:
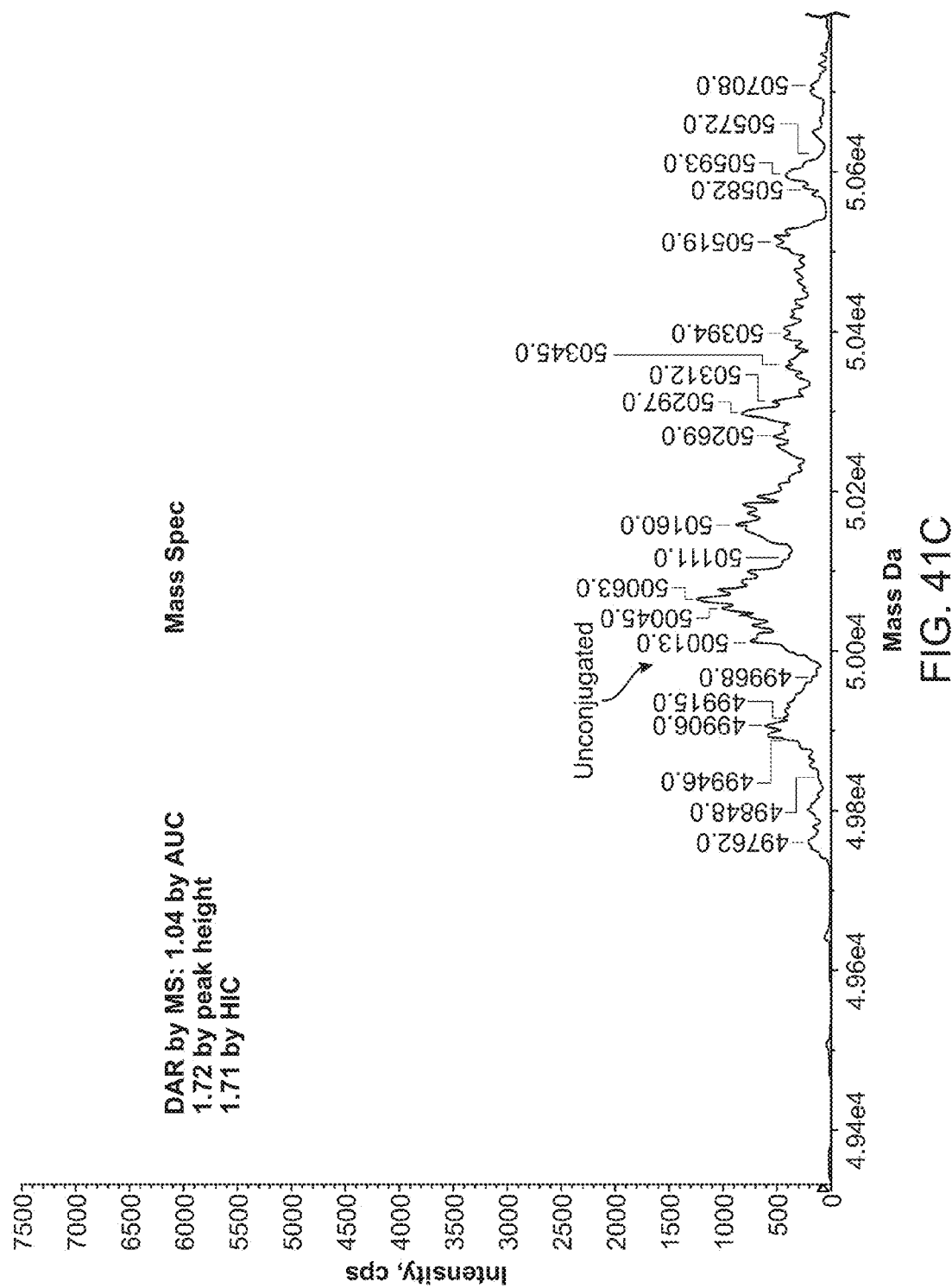

Results are shown in FIGS. 41A-41C, which shows a size exclusion chromatography (SEC) trace (FIG. 41A), a hydrophobic interaction column (HIC) trace (FIG. 41B), and a mass spectrometer (MS) trace (FIG. 41C) of the aldehyde-tagged antibody conjugated to HIPS Dihydroxy Maytansine. The mono-conjugated and di-conjugated protein conjugates were observed.

Conjugation of HIPS Glutamic Acid $C_3$ Maytansine to an Aldehyde-Tagged Antibody HIPS Glutamic Acid $C_3$ Maytansine was reacted with an aldehyde-tagged antibody according to the conjugation method described above.

Figure 42C:
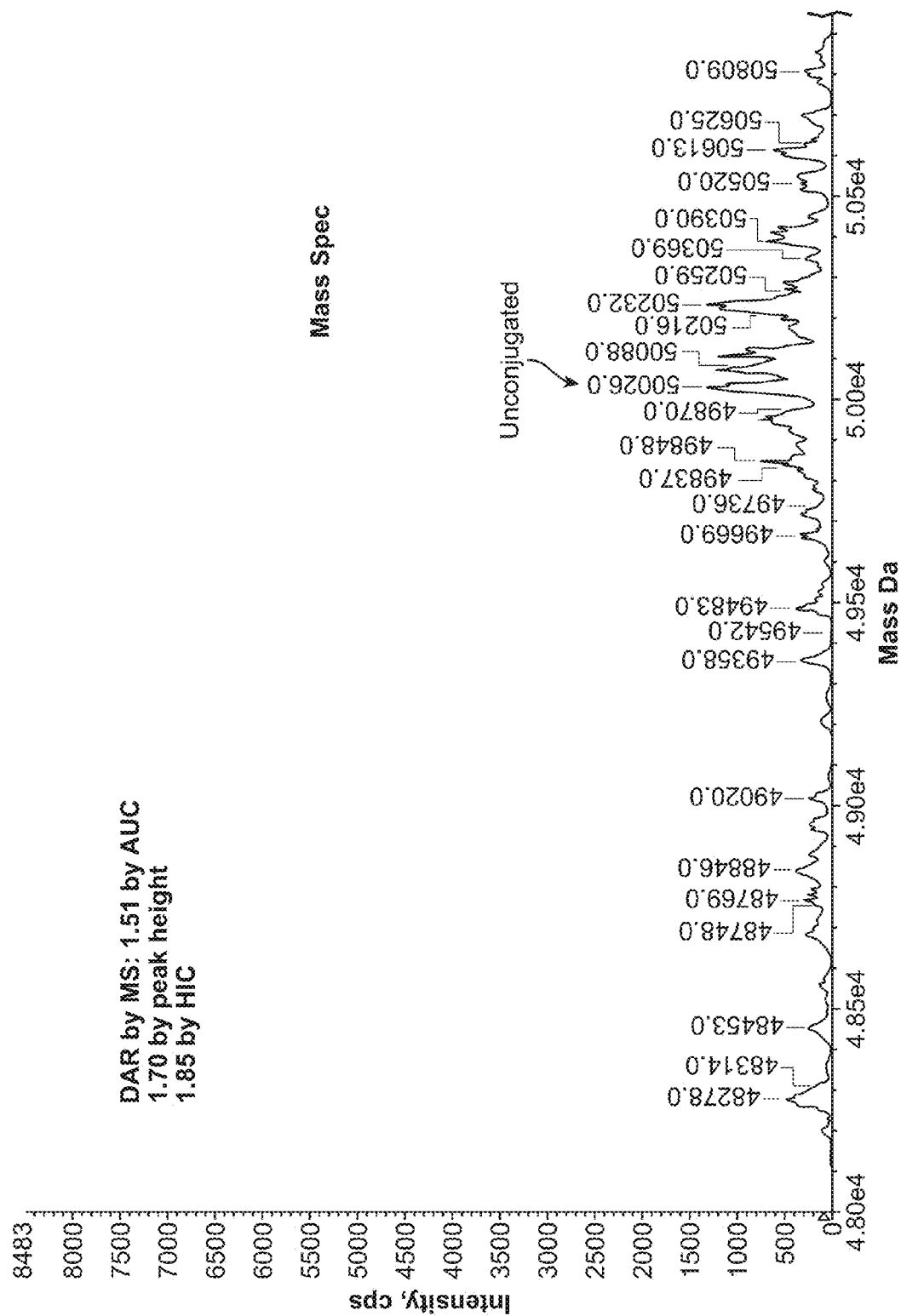
Figure 42C:
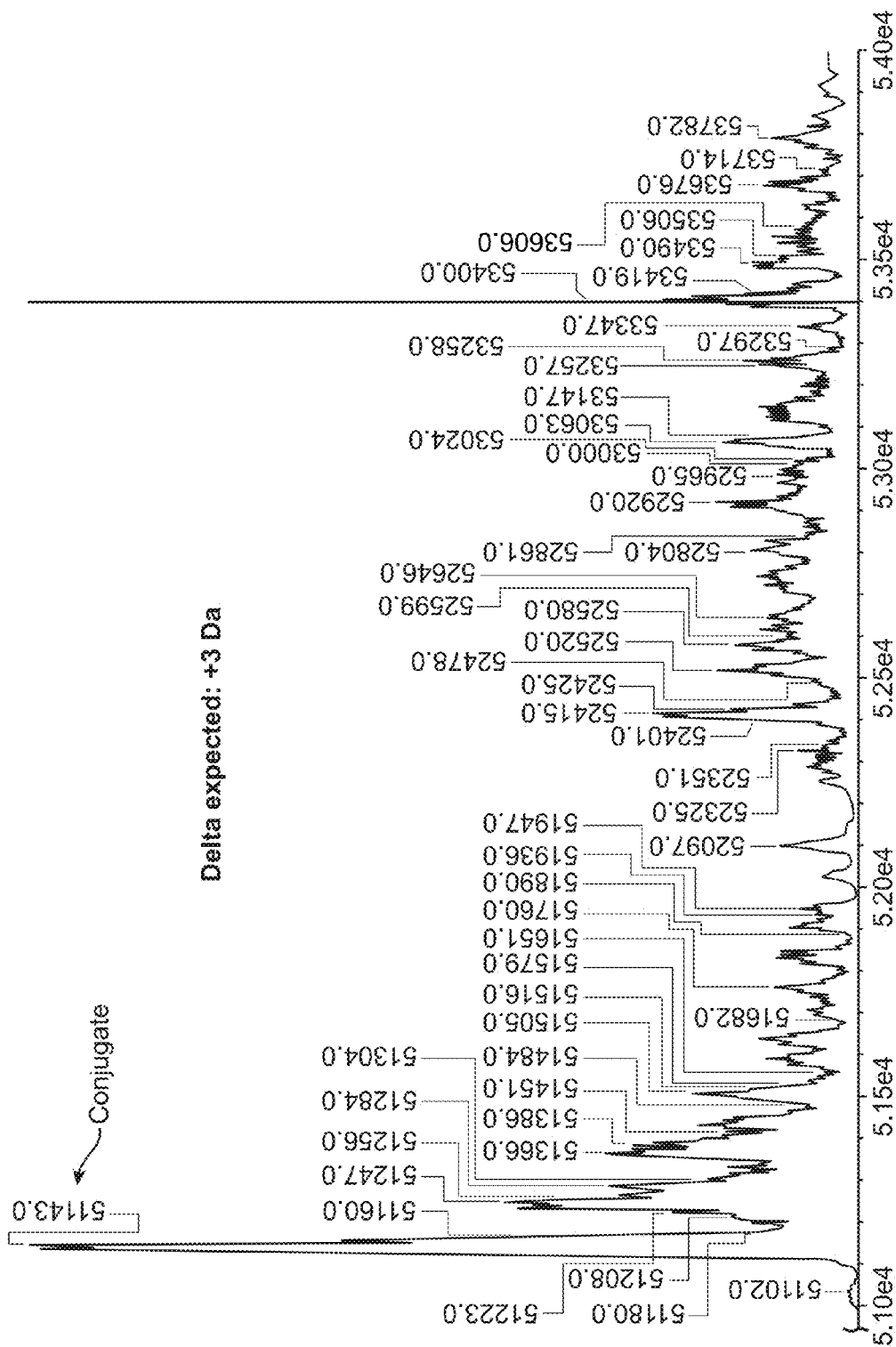

Results are shown in FIGS. 42A-42C, which shows a size exclusion chromatography (SEC) trace (FIG. 42A), a hydrophobic interaction column (HIC) trace (FIG. 42B), and a mass spectrometer (MS) trace (FIG. 42C) of the aldehyde-tagged antibody conjugated to HIPS Glutamic Acid $C_3$ Maytansine. The unconjugated, mono-conjugated and di-conjugated protein conjugates were observed.

Conjugation of HIPS Trimethoxy Maytansine to an Aldehyde-Tagged Antibody

HIPS Trimethoxy Maytansine was reacted with an aldehyde-tagged antibody according to the conjugation method described above.

Figure 43A:
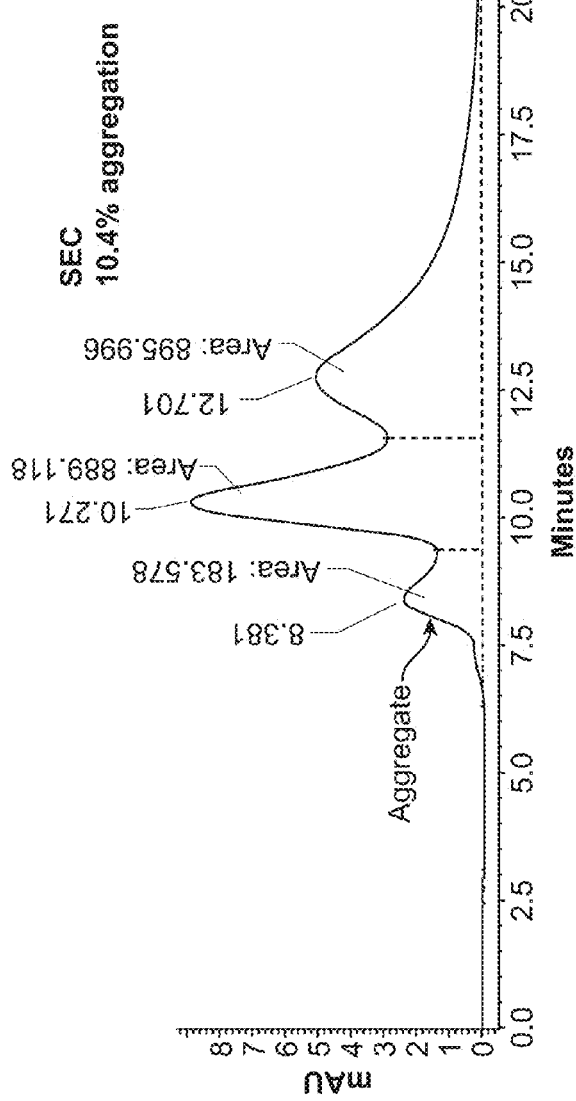
FIGS. 43A-43C show a size exclusion chromatography (SEC) trace (FIG. 43A), a hydrophobic interaction column (HIC) trace (FIG. 43B), and a mass spectrometer (MS) trace (FIG. 43C) of an aldehyde-tagged antibody conjugated to HIPS Trimethoxy Maytansine, according to embodiments of the present disclosure.
Figure 43B:
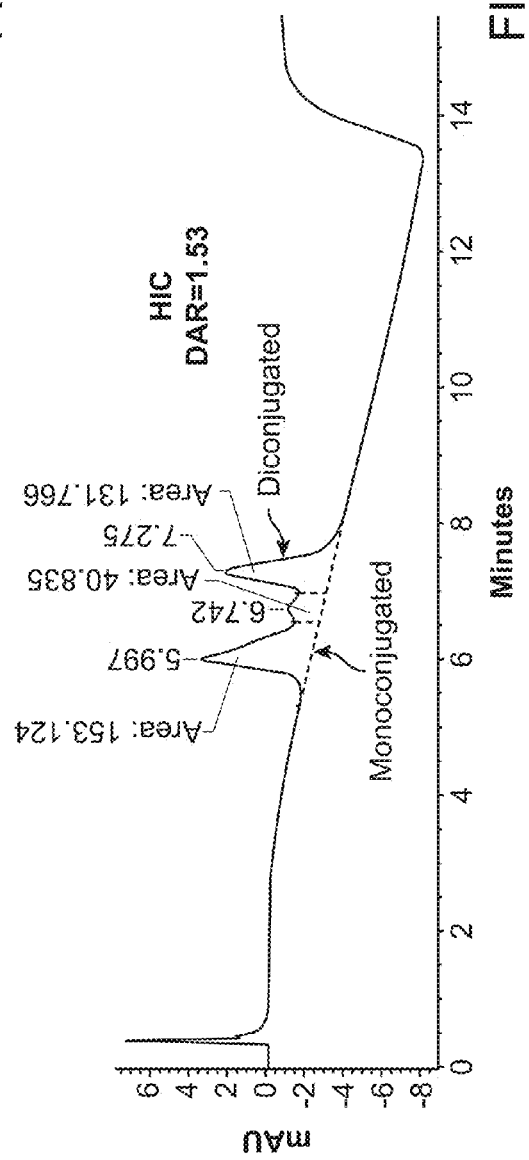
Figure 43C:
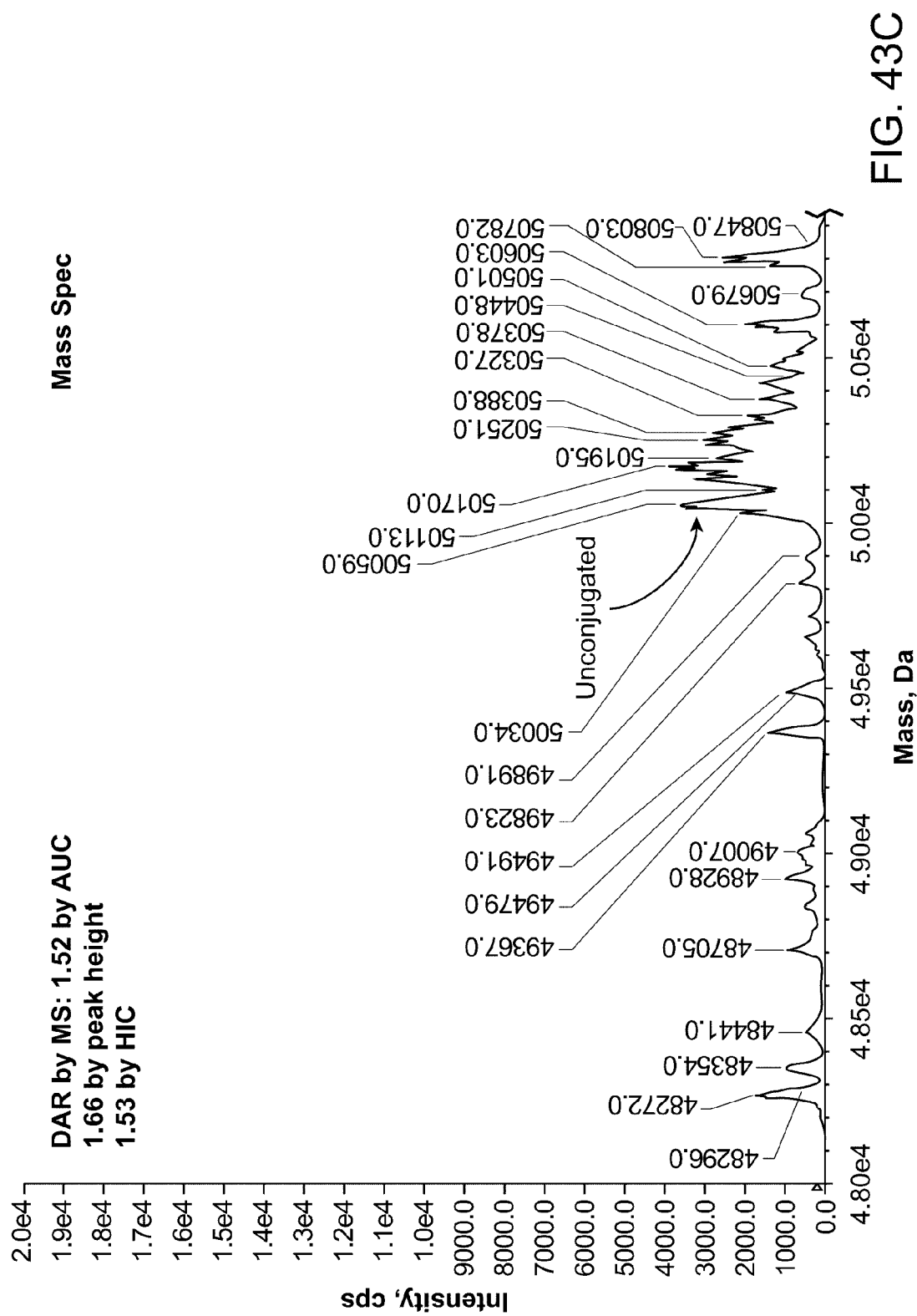

Results are shown in FIGS. 43A-43C, which shows a size exclusion chromatography (SEC) trace (FIG. 43A), a hydrophobic interaction column (HIC) trace (FIG. 43B), and a mass spectrometer (MS) trace (FIG. 43C) of the aldehyde-tagged antibody conjugated to HIPS Trimethoxy Maytansine. The mono-conjugated and di-conjugated protein conjugates were observed.

Conjugation of HIPS Glc NAc $PEG_2$ $Ac_3$ Maytansine to an Aldehyde-Tagged Antibody HIPS Glc NAc $PEG_2$ $Ac_3$ Maytansine was reacted with an aldehyde-tagged antibody according to the conjugation method described above.

Results are shown in FIG. 44, which shows a hydrophobic interaction column (HIC) trace of the aldehyde-tagged antibody conjugated to HIPS Glc NAc $PEG_2$ $Ac_3$ Maytansine. The unconjugated, mono-conjugated and di-conjugated protein conjugates were observed.

Conjugation of HIPS Glc NAc $PEG_2$ Maytansine to an Aldehyde-Tagged Antibody

HIPS Glc NAc $PEG_2$ Maytansine was reacted with an aldehyde-tagged antibody according to the conjugation method described above.

Results are shown in FIG. 45, which shows a hydrophobic interaction column (HIC) trace of the aldehyde-tagged antibody conjugated to HIPS Glc NAc $PEG_2$ Maytansine. The unconjugated, mono-conjugated and di-conjugated protein conjugates were observed.

Conjugation of HIPS Nit $PEG_2$ Maytansine to an Aldehyde-Tagged Antibody

HIPS Nit $PEG_2$ Maytansine was reacted with an aldehyde-tagged antibody according to the conjugation method described above.

Figure 46A:
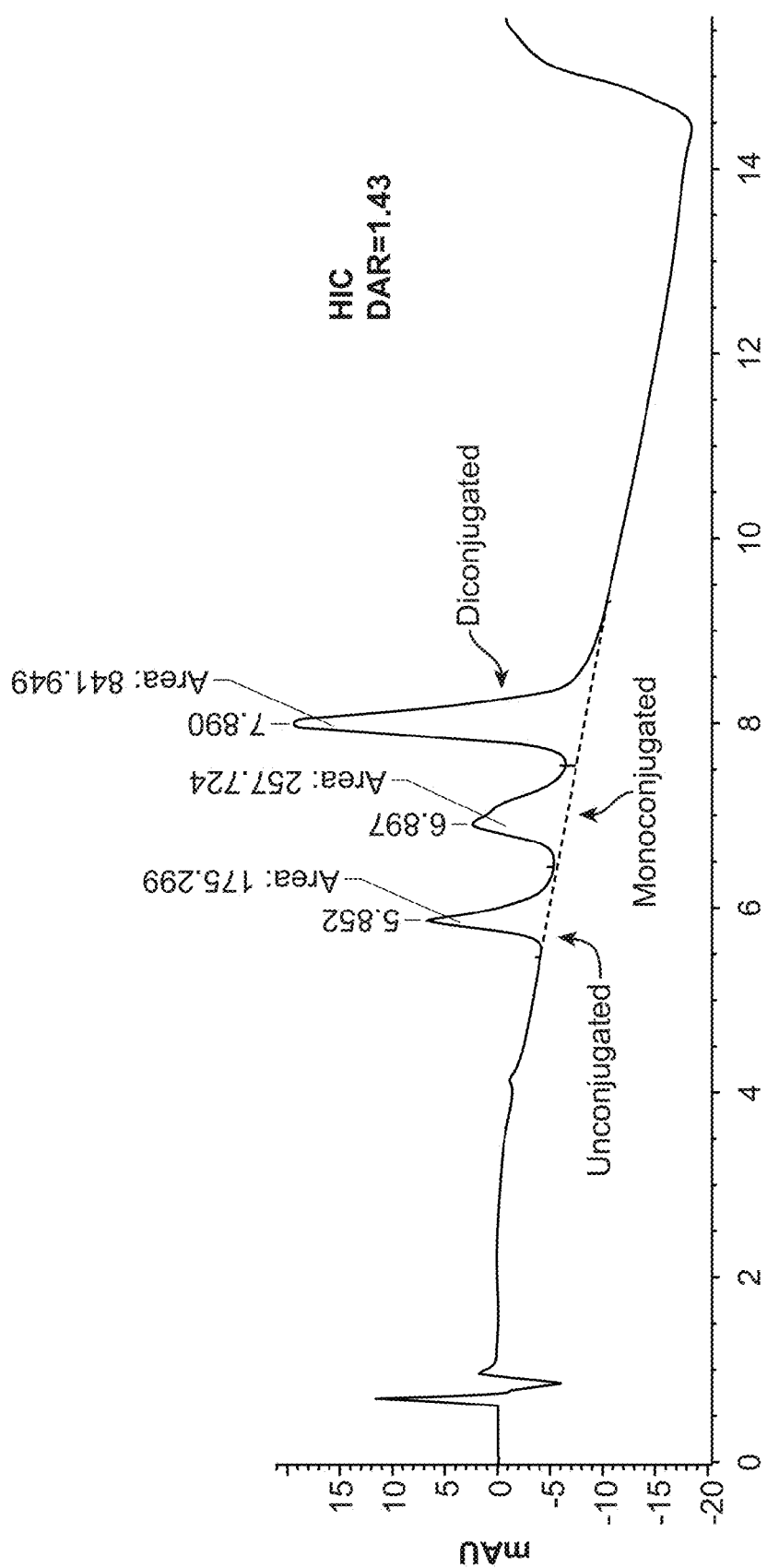
FIGS. 46A-46B show a hydrophobic interaction column (HIC) trace (FIG. 46A) and a mass spectrometer (MS) trace (FIG. 46B) of an aldehyde-tagged antibody conjugated to HIPS Nit $PEG_2$ Maytansine, according to embodiments of the present disclosure.
Figure 46B:
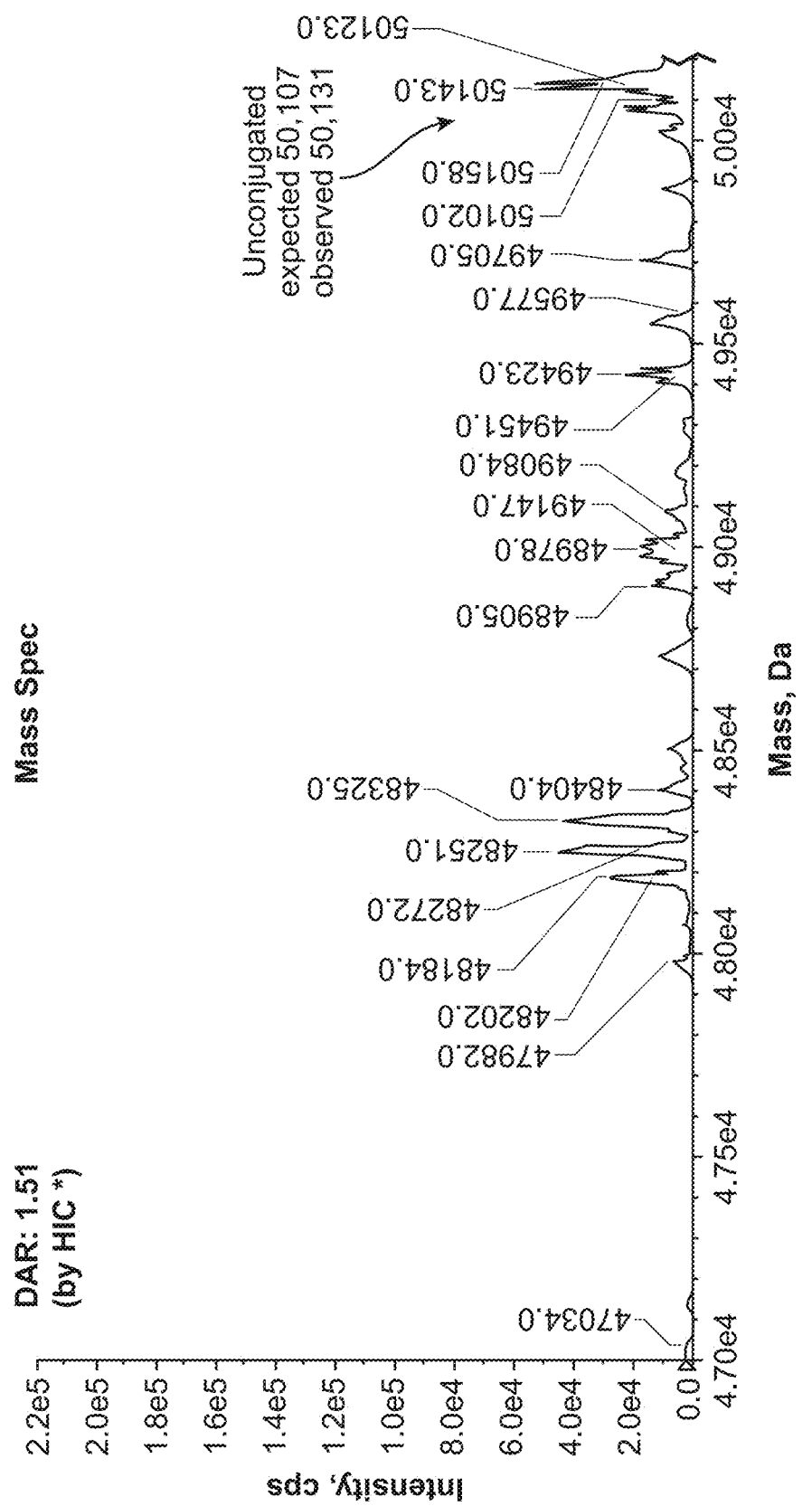
Figure 46B:
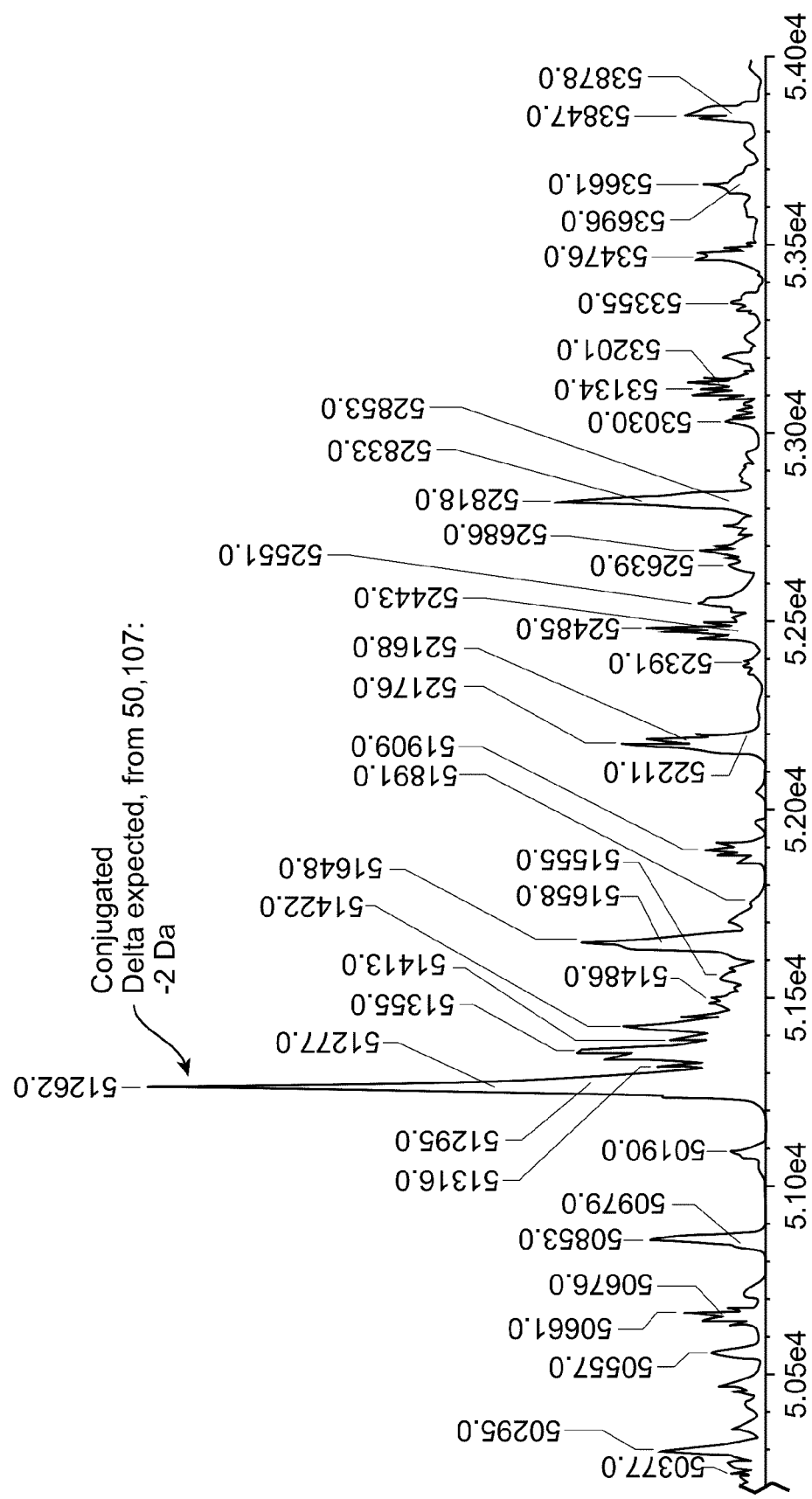

Results are shown in FIGS. 46A-46B, which shows a hydrophobic interaction column (HIC) trace (FIG. 46A) and a mass spectrometer (MS) trace (FIG. 46B) of the aldehyde-tagged antibody conjugated to HIPS Nit $PEG_2$ Maytansine. The unconjugated, mono-conjugated and di-conjugated protein conjugates were observed.

Conjugation of HIPS $PEG_2$ MMAF to an Aldehyde-Tagged Antibody

HIPS $PEG_2$ MMAF was reacted with an aldehyde-tagged antibody according to the conjugation method described above.

Figure 47A:
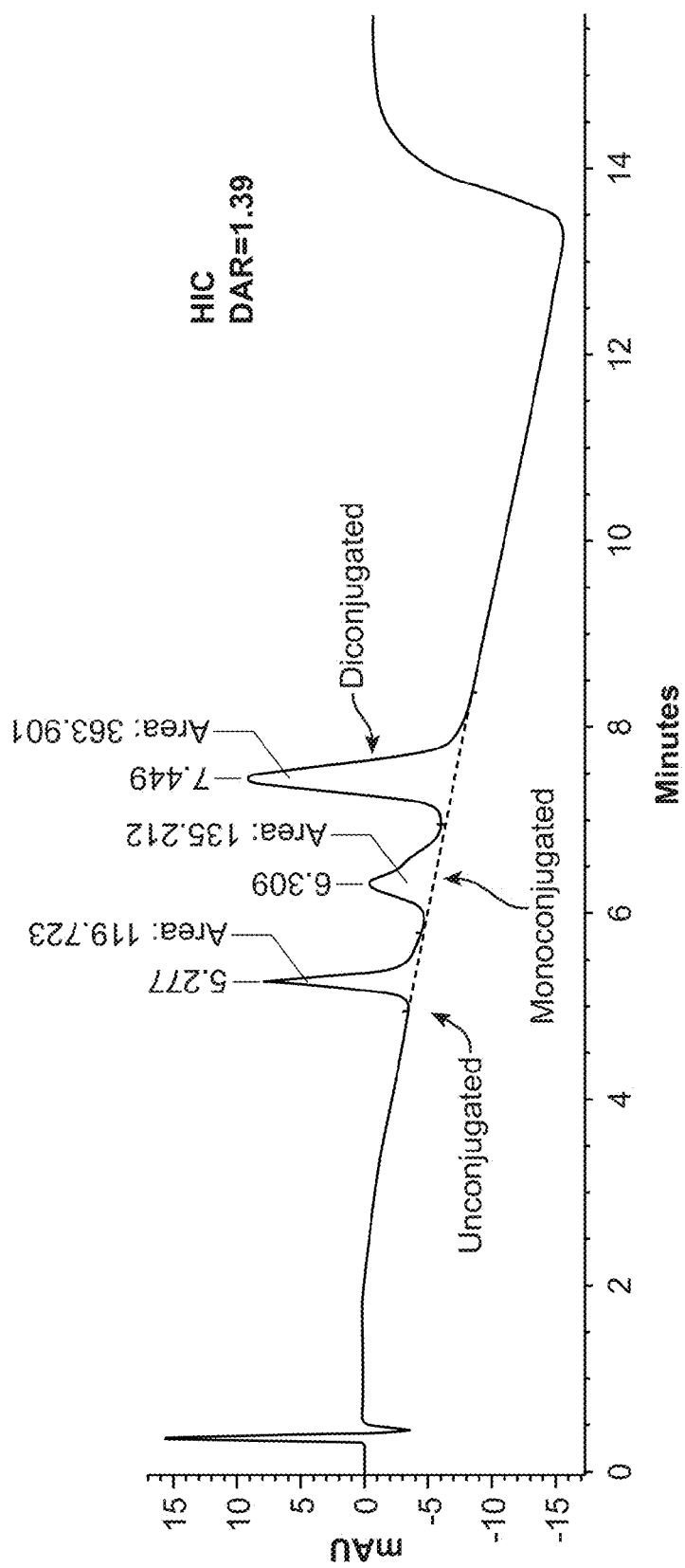
FIGS. 47A-47B show a hydrophobic interaction column (HIC) trace (FIG. 47A) and a mass spectrometer (MS) trace (FIG. 47B) of an aldehyde-tagged antibody conjugated to HIPS $PEG_2$ MMAF, according to embodiments of the present disclosure.
Figure 47B:
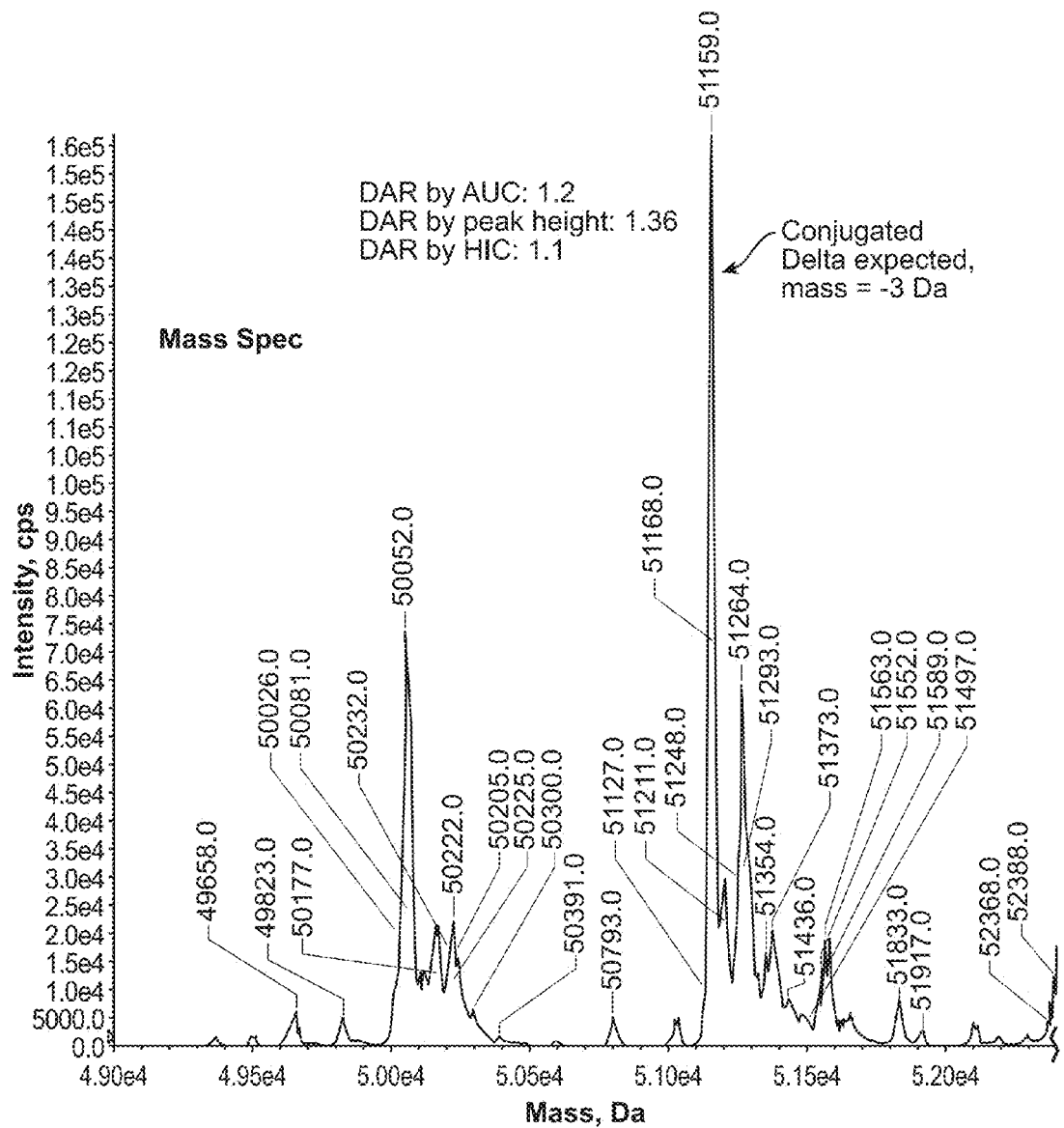
Figure 47B:
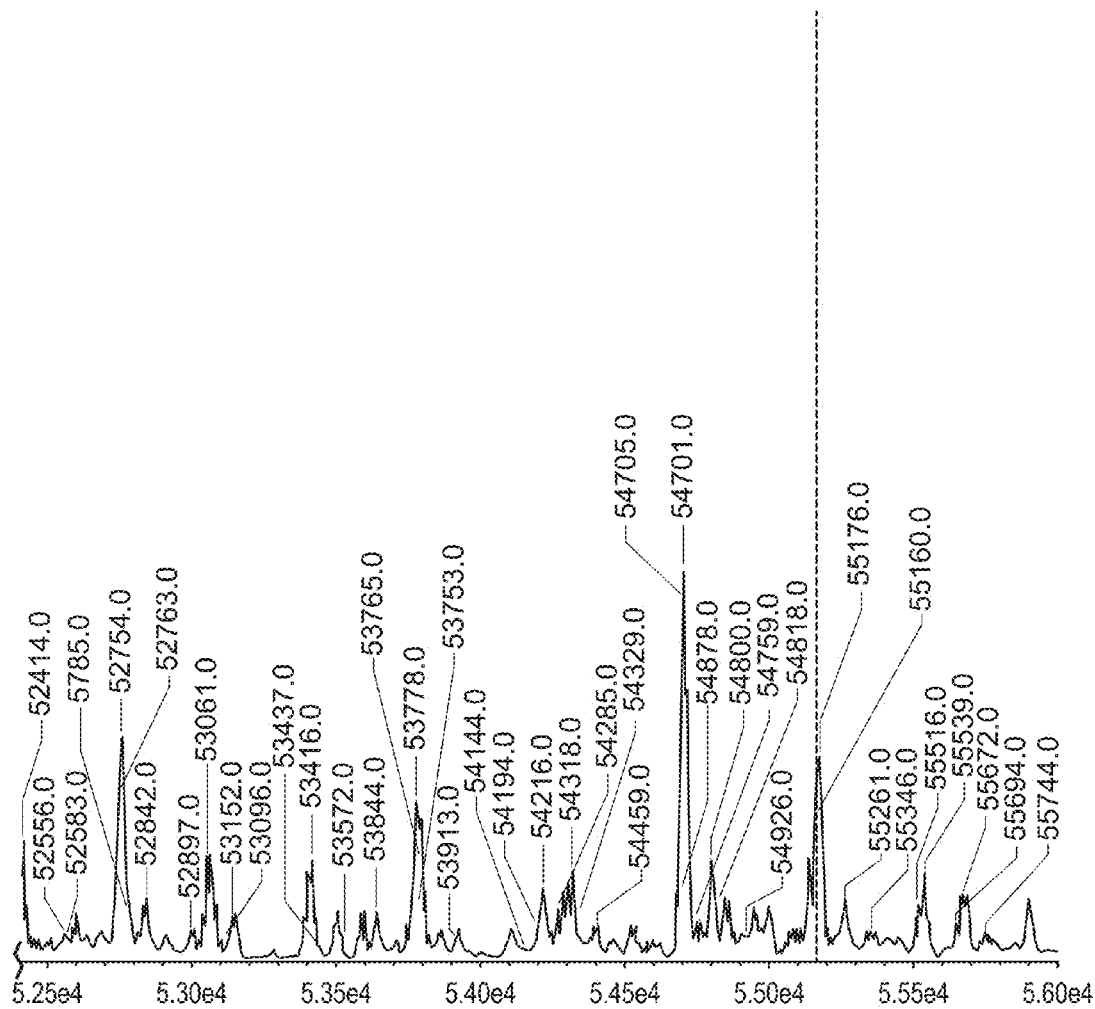

Results are shown in FIGS. 47A-47B, which shows a hydrophobic interaction column (HIC) trace (FIG. 47A) and a mass spectrometer (MS) trace (FIG. 47B) of the aldehyde-tagged antibody conjugated to HIPS $PEG_2$ MMAF. The unconjugated, mono-conjugated and di-conjugated protein conjugates were observed.

Conjugation of HIPS S $PEG_4$ Maytansine to an Aldehyde-Tagged Antibody

HIPS S $PEG_4$ Maytansine was reacted with an aldehyde-tagged antibody according to the conjugation method described above.

Figure 48:
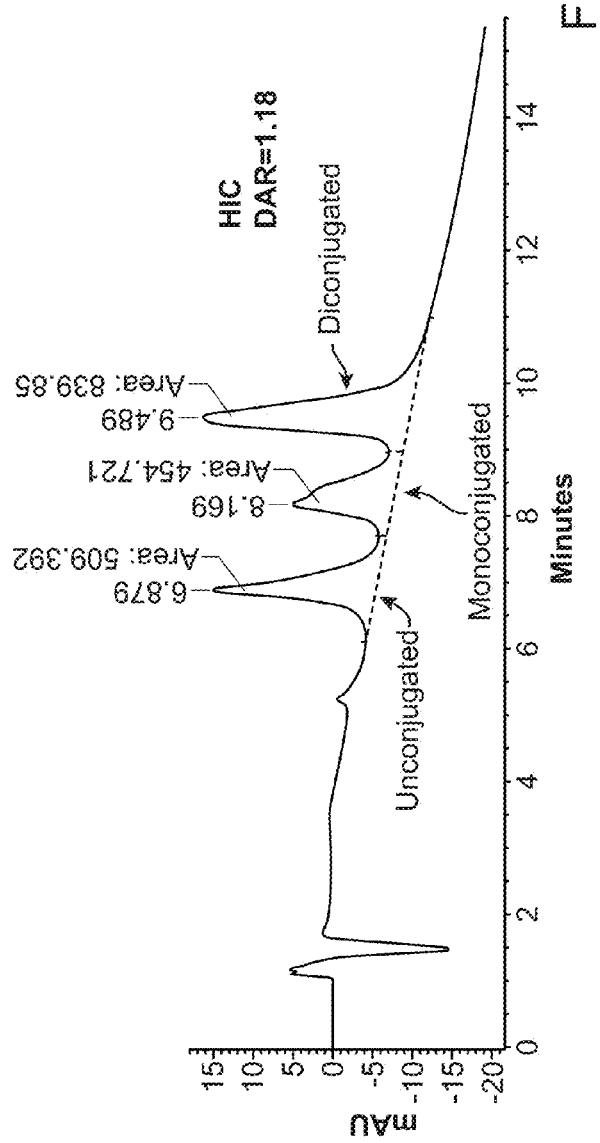
FIG. 48 shows a hydrophobic interaction column (HIC) trace of an aldehyde-tagged antibody conjugated to HIPS S $PEG_4$ Maytansine, according to embodiments of the present disclosure.

Results are shown in FIG. 48, which shows a hydrophobic interaction column (HIC) trace of the aldehyde-tagged antibody conjugated to HIPS S $PEG_4$ Maytansine. The unconjugated, mono-conjugated and di-conjugated protein conjugates were observed.

Conjugation of HIPS S $PEG_6$ Maytansine to an Aldehyde-Tagged Antibody

HIPS S $PEG_6$ Maytansine was reacted with an aldehyde-tagged antibody according to the conjugation method described above.

Figure 49:
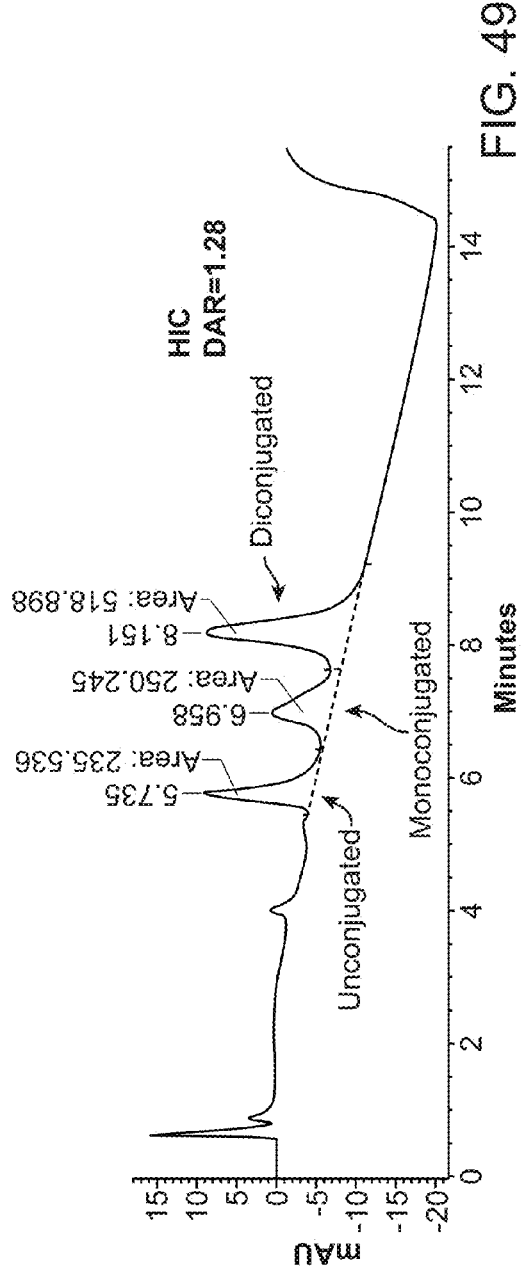
FIG. 49 shows a hydrophobic interaction column (HIC) trace of an aldehyde-tagged antibody conjugated to HIPS S $PEG_6$ Maytansine, according to embodiments of the present disclosure.

Results are shown in FIG. 49, which shows a hydrophobic interaction column (HIC) trace of the aldehyde-tagged antibody conjugated to HIPS S $PEG_6$ Maytansine. The unconjugated, mono-conjugated and di-conjugated protein conjugates were observed.

Conjugation of HIPS S $C_5$ Maytansine to an Aldehyde-Tagged Antibody

HIPS S $C_5$ Maytansine was reacted with an aldehyde-tagged antibody according to the conjugation method described above.

Figure 50:
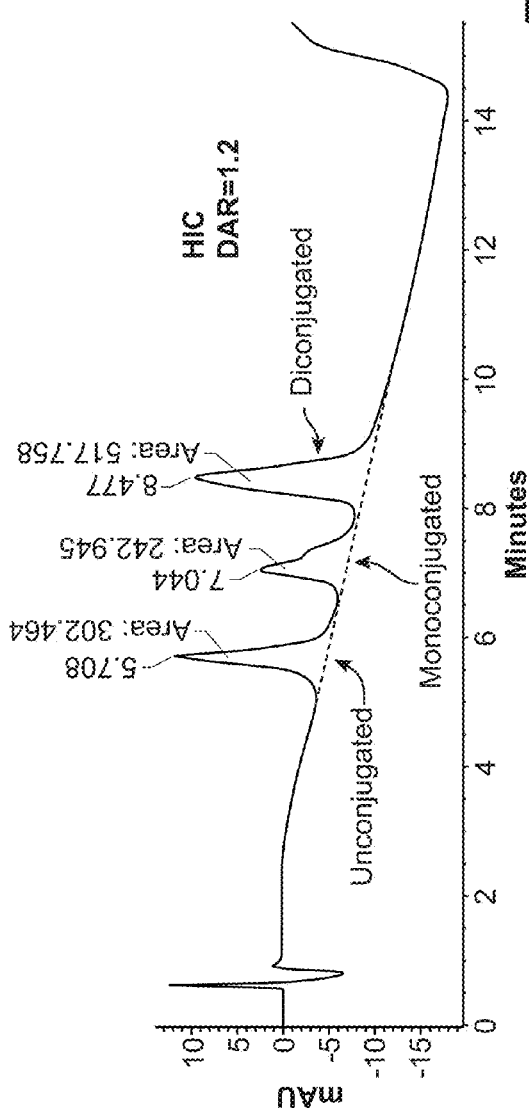
FIG. 50 shows a hydrophobic interaction column (HIC) trace of an aldehyde-tagged antibody conjugated to HIPS-S—$C_5$-Maytansine, according to embodiments of the present disclosure.

Results are shown in FIG. 50, which shows a hydrophobic interaction column (HIC) trace of the aldehyde-tagged antibody conjugated to HIPS S $C_5$ Maytansine. The unconjugated, mono-conjugated and di-conjugated protein conjugates were observed.

Conjugation of HIPS G $PEG_6$ Maytansine to an Aldehyde-Tagged Antibody

HIPS G $PEG_6$ Maytansine was reacted with an aldehyde-tagged antibody according to the conjugation method described above.

Figure 51:
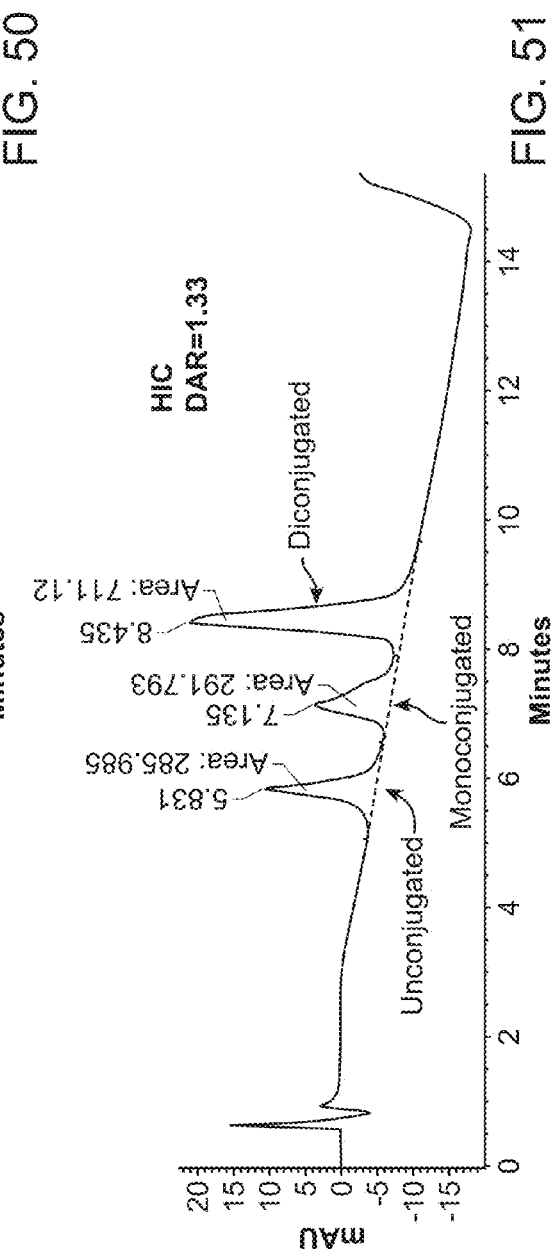
FIG. 51 shows a hydrophobic interaction column (HIC) trace of an aldehyde-tagged antibody conjugated to HIPS G $PEG_6$ Maytansine, according to embodiments of the present disclosure.

Results are shown in FIG. 51, which shows a hydrophobic interaction column (HIC) trace of the aldehyde-tagged antibody conjugated to HIPS G $PEG_6$ Maytansine. The unconjugated, mono-conjugated and di-conjugated protein conjugates were observed.

Conjugation of HIPS $PEG_6$ Val Cit PABC $NMC_3$ Maytansine to an Aldehyde-Tagged Antibody HIPS $PEG_6$ Val Cit PABC $NMC_3$ Maytansine was reacted with an aldehyde-tagged antibody according to the conjugation method described above.

Figure 52:
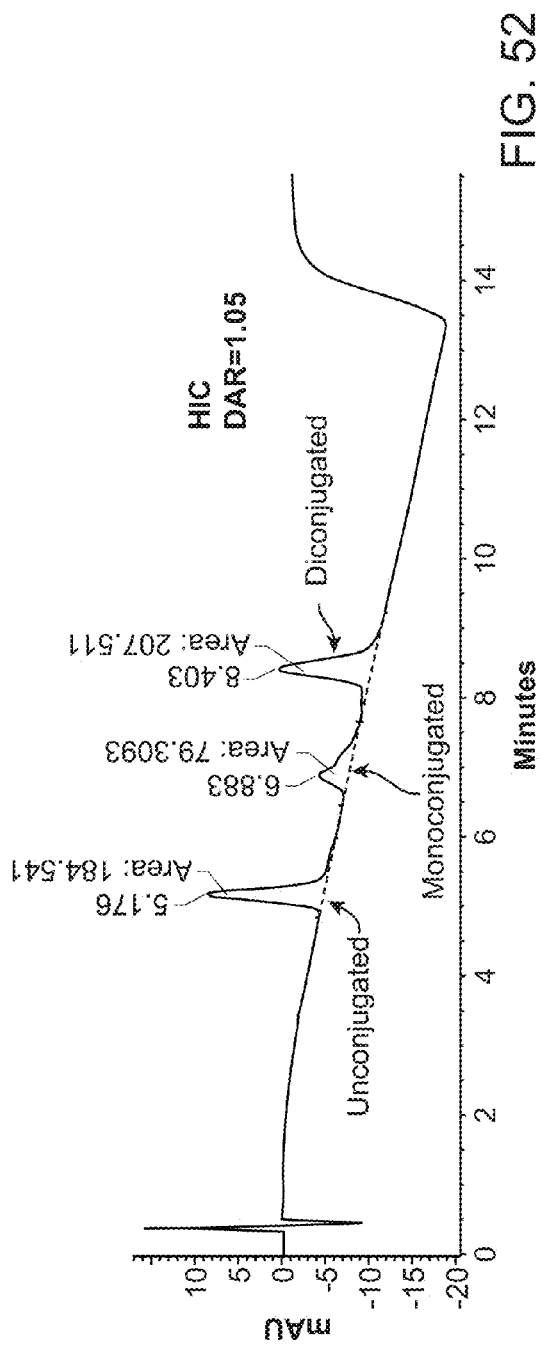
FIG. 52 shows a hydrophobic interaction column (HIC) trace of an aldehyde-tagged antibody conjugated to HIPS $PEG_6$ Val Cit PABC $NMC_3$ Maytansine, according to embodiments of the present disclosure.

Results are shown in FIG. 52, which shows a hydrophobic interaction column (HIC) trace of the aldehyde-tagged antibody conjugated to HIPS $PEG_6$ Val Cit PABC $NMC_3$ Maytansine. The unconjugated, mono-conjugated and di-conjugated protein conjugates were observed.

Conjugation of HIPS Gly $PEG_6$ Val Cit PABC MMAE to an Aldehyde-Tagged Antibody HIPS Gly $PEG_6$ Val Cit PABC MMAE was reacted with an aldehyde-tagged antibody according to the conjugation method described above.

Figure 53:
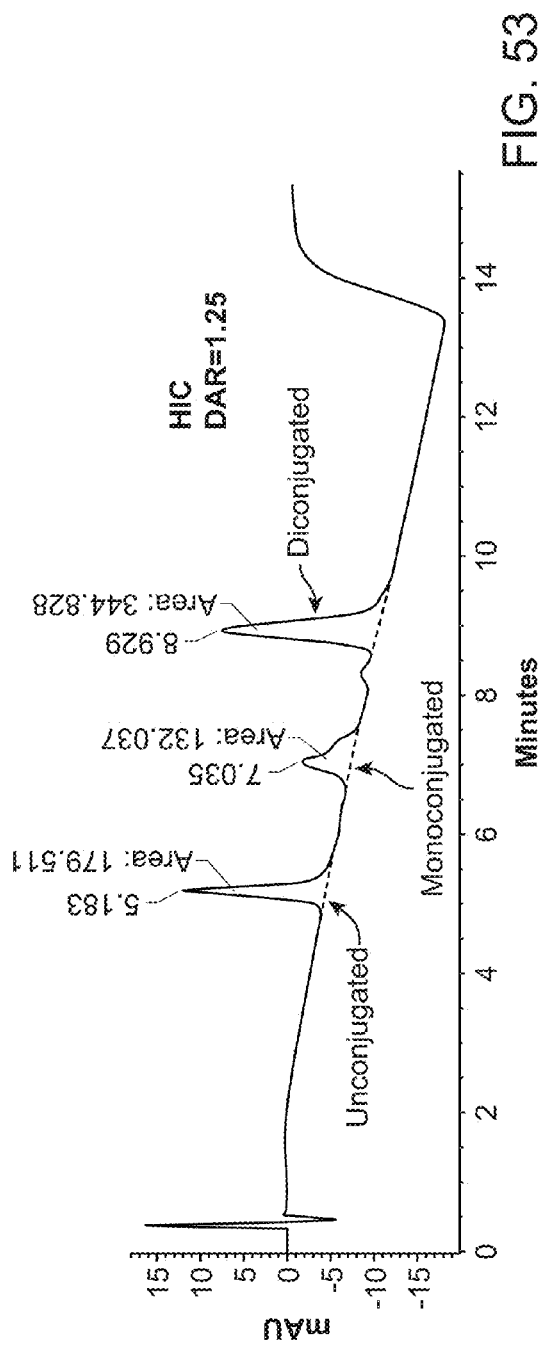
FIG. 53 shows a hydrophobic interaction column (HIC) trace of an aldehyde-tagged antibody conjugated to HIPS Gly $PEG_6$ Val Cit PABC MMAE, according to embodiments of the present disclosure.

Results are shown in FIG. 53, which shows a hydrophobic interaction column (HIC) trace of the aldehyde-tagged antibody conjugated to HIPS Gly $PEG_6$ Val Cit PABC MMAE. The unconjugated, mono-conjugated and di-conjugated protein conjugates were observed.

Conjugation of HIPS Cysteic Acid Maytansine to an Aldehyde-Tagged Antibody

HIPS Cysteic Acid Maytansine was reacted with an aldehyde-tagged antibody according to the conjugation method described above.

Figure 54:
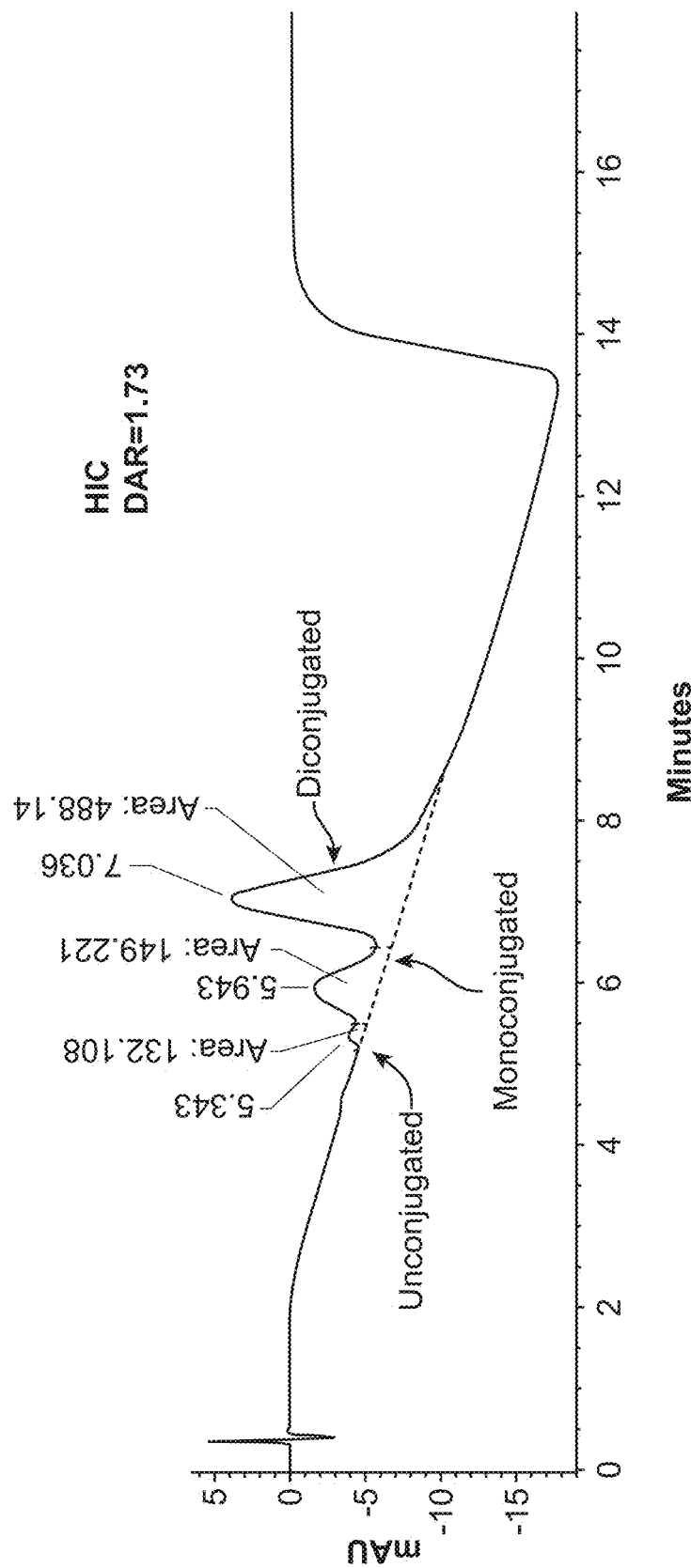
FIG. 54 shows a hydrophobic interaction column (HIC) trace of an aldehyde-tagged antibody conjugated to HIPS Cysteic Acid Maytansine, according to embodiments of the present disclosure.

Results are shown in FIG. 54, which shows a hydrophobic interaction column (HIC) trace of the aldehyde-tagged antibody conjugated to HIPS Cysteic Acid Maytansine. The unconjugated, mono-conjugated and di-conjugated protein conjugates were observed.

Conjugation of HIPS Indole E ($CO_2H$) $PEG_2$ NH Alexa Fluor 488 to an Aldehyde-Tagged Antibody HIPS Indole E ($CO_2H$) $PEG_2$ NH Alexa Fluor 488 was reacted with an aldehyde-tagged antibody according to the conjugation method described above.

Figure 55:
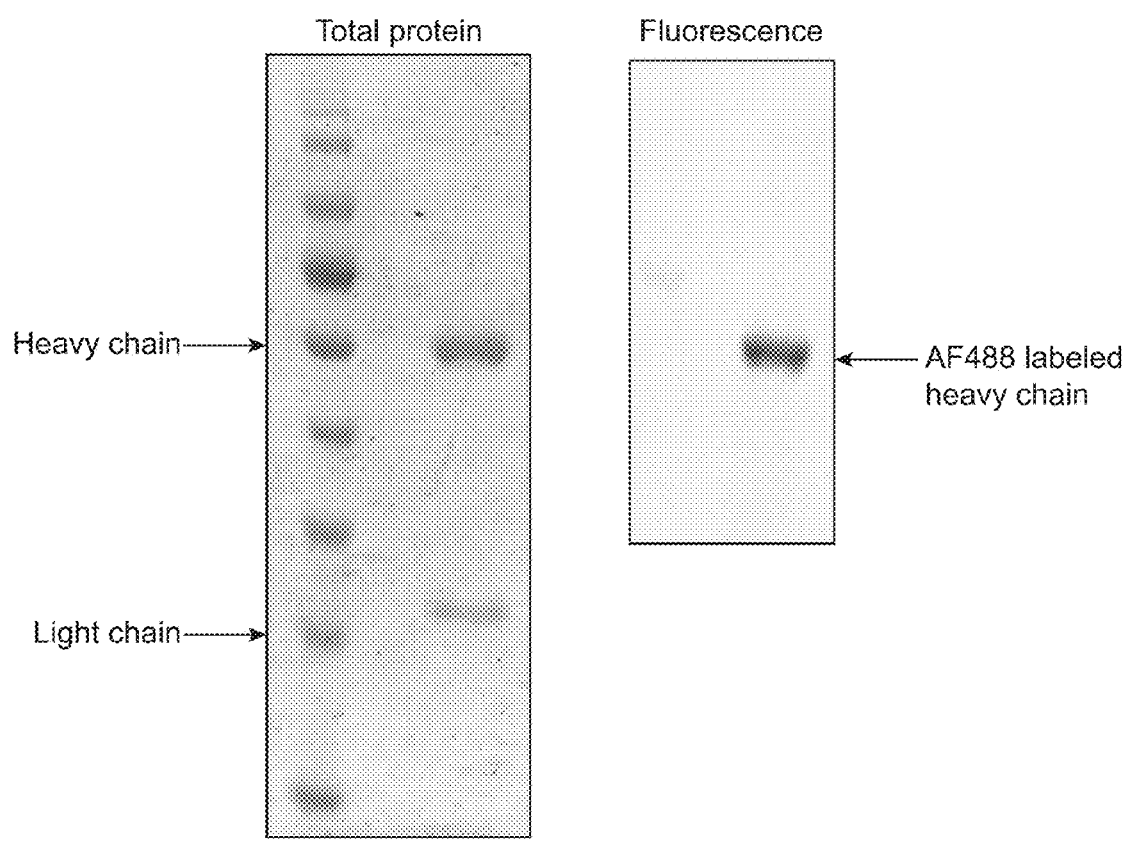
FIG. 55 shows images of SDS-PAGE gels showing an aldehyde-tagged antibody conjugated to HIPS Indole E ($CO_2H$) $PEG_2$ NH Alexa Fluor 488, according to embodiments of the present disclosure.

Results are shown in FIG. 55, which shows images of SDS-PAGE gels of the aldehyde-tagged antibody conjugated to HIPS Indole E ($CO_2H$) $PEG_2$ NH Alexa Fluor 488. Conjugates to the heavy chain and the light chain of the aldehyde-tagged antibody were observed.

Conjugation of HIPS $PEG_6$ Maytansine to an Aldehyde-Tagged Antibody

HIPS $PEG_6$ Maytansine was reacted with an aldehyde-tagged antibody according to the conjugation method described above.

Figure 56:
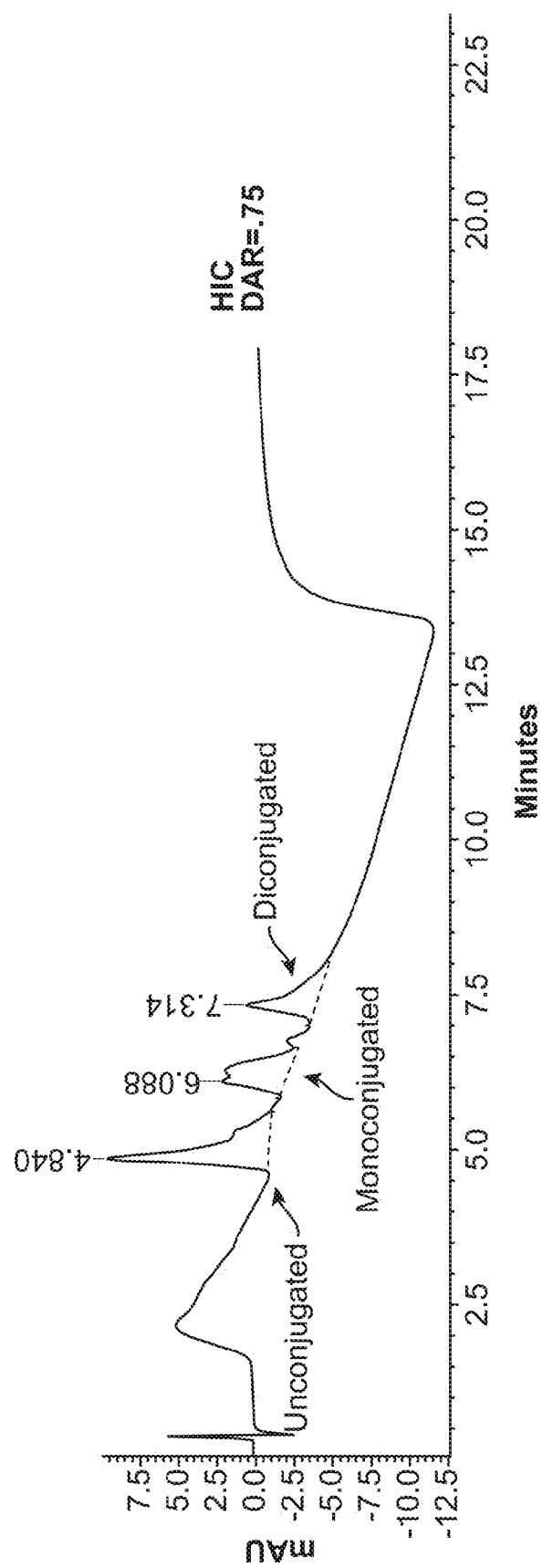
FIG. 56 shows a hydrophobic interaction column (HIC) trace of an aldehyde-tagged antibody conjugated to HIPS $PEG_6$ Maytansine, according to embodiments of the present disclosure.

Results are shown in FIG. 56, which shows a hydrophobic interaction column (HIC) trace of the aldehyde-tagged antibody conjugated to HIPS $PEG_6$ Maytansine. The unconjugated, mono-conjugated and di-conjugated protein conjugates were observed.

Conjugation of PIPS $PEG_2$ Maytansine to an Aldehyde-Tagged Antibody

PIPS $PEG_2$ Maytansine was reacted with an aldehyde-tagged antibody according to the conjugation method described above.

Figure 57:
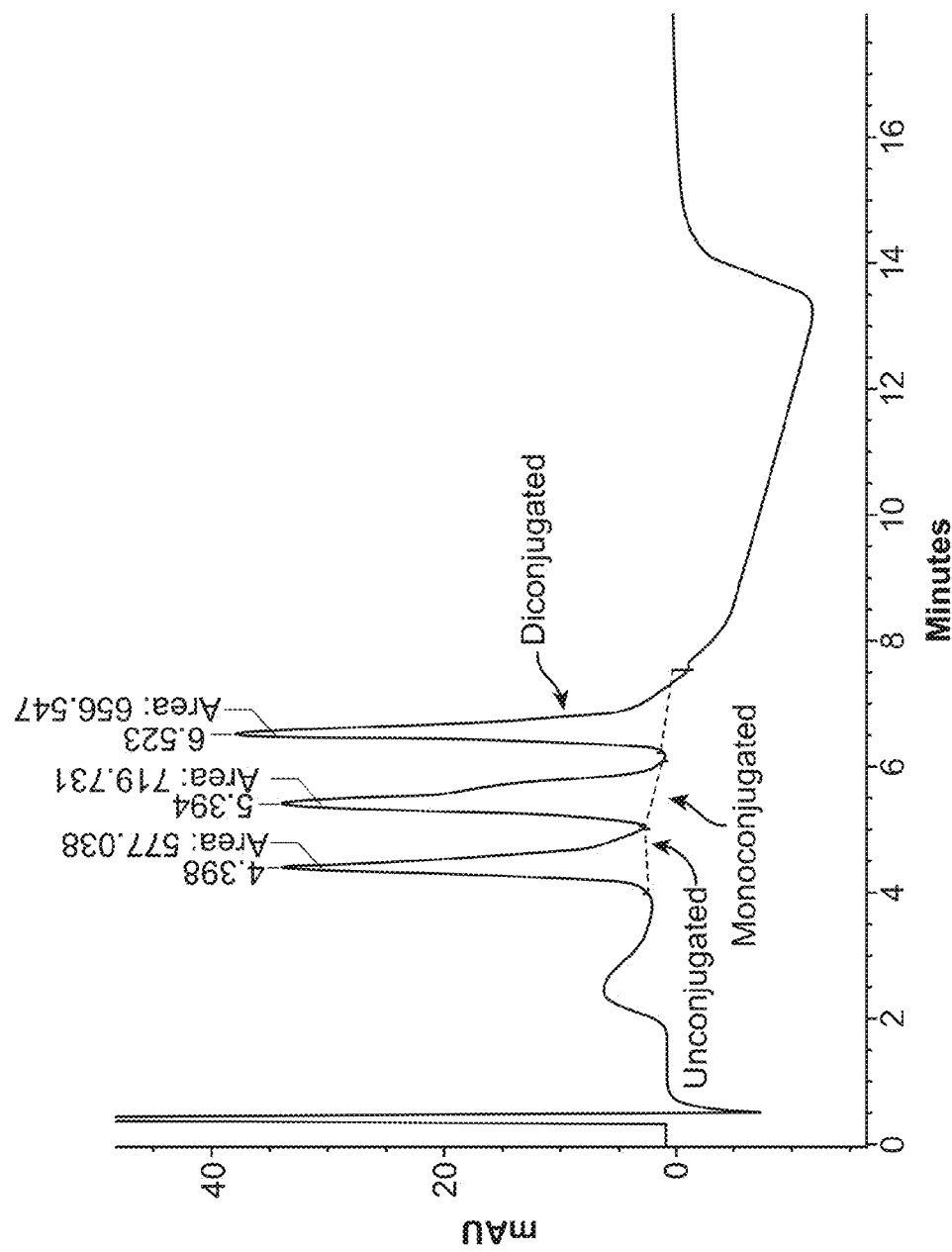
FIG. 57 shows a hydrophobic interaction column (HIC) trace of an aldehyde-tagged antibody conjugated to PIPS $PEG_2$ Maytansine, according to embodiments of the present disclosure.

Results are shown in FIG. 57, which shows a hydrophobic interaction column (HIC) trace of the aldehyde-tagged antibody conjugated to PIPS $PEG_2$ Maytansine. The unconjugated, mono-conjugated and di-conjugated protein conjugates were observed.

Conjugation of HIPS Trihydroxy Maytansine to an Aldehyde-Tagged Antibody

HIPS Trihydroxy Maytansine was reacted with an aldehyde-tagged antibody according to the conjugation method described above.

Results are shown in FIG. 58, which shows a hydrophobic interaction column (HIC) trace of the aldehyde-tagged antibody conjugated to HIPS Trihydroxy Maytansine. The unconjugated and conjugated protein conjugates were observed.

Conjugation of HIPS Lysine $PEG_2$ Maytansine to an Aldehyde-Tagged Antibody

HIPS Lysine $PEG_2$ Maytansine was reacted with an aldehyde-tagged antibody according to the conjugation method described above.

Results are shown in FIG. 59, which shows a hydrophobic interaction column (HIC) trace of the aldehyde-tagged antibody conjugated to HIPS Lysine $PEG_2$ Maytansine. The unconjugated and conjugated protein conjugate was observed.

Conjugation of HIPS-PAPip(PEG2(CO2H)-Maytansine to an Aldehyde-Tagged Antibody

HIPS-PAPip(PEG2(CO2H))-Maytansine was reacted with an aldehyde-tagged antibody according to the conjugation method described above.

Figure 66A:
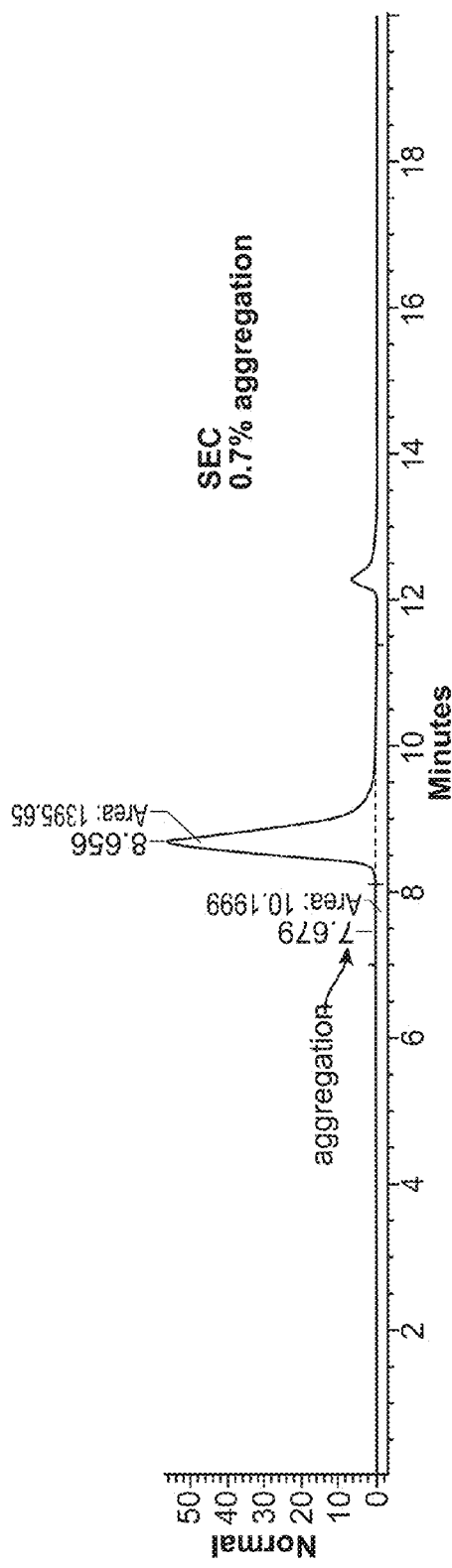
FIGS. 66A-66C show a size exclusion chromatography (SEC) trace (FIG. 66A), a hydrophobic interaction column (HIC) trace (FIG. 66B), and a mass spectrometer (MS) trace (FIG. 66C) of an aldehyde-tagged antibody conjugated to HIPS-PAPip(PEG2(CO2H))-Maytansine, according to embodiments of the present disclosure.
Figure 66B:
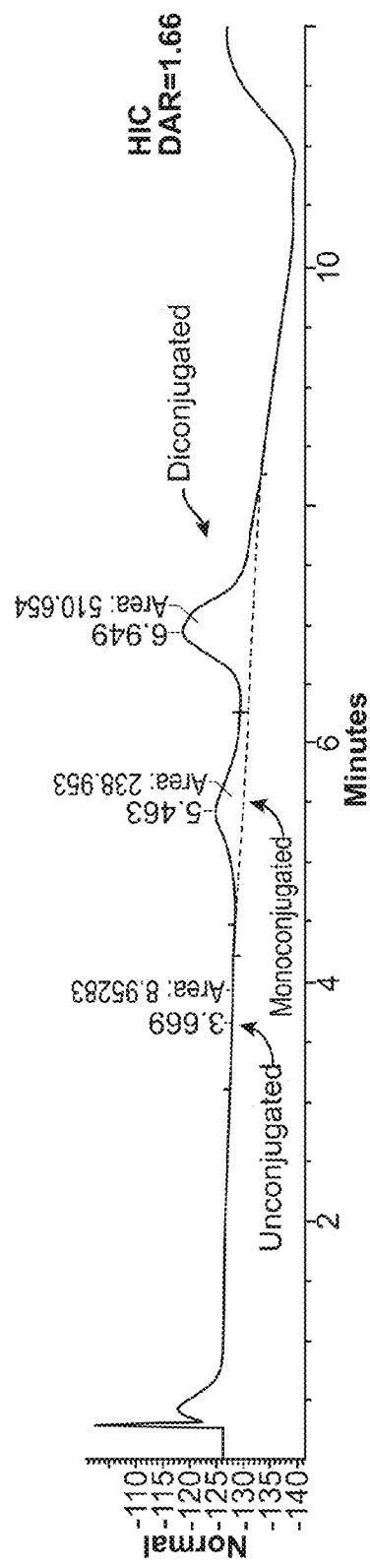
Figure 66C:
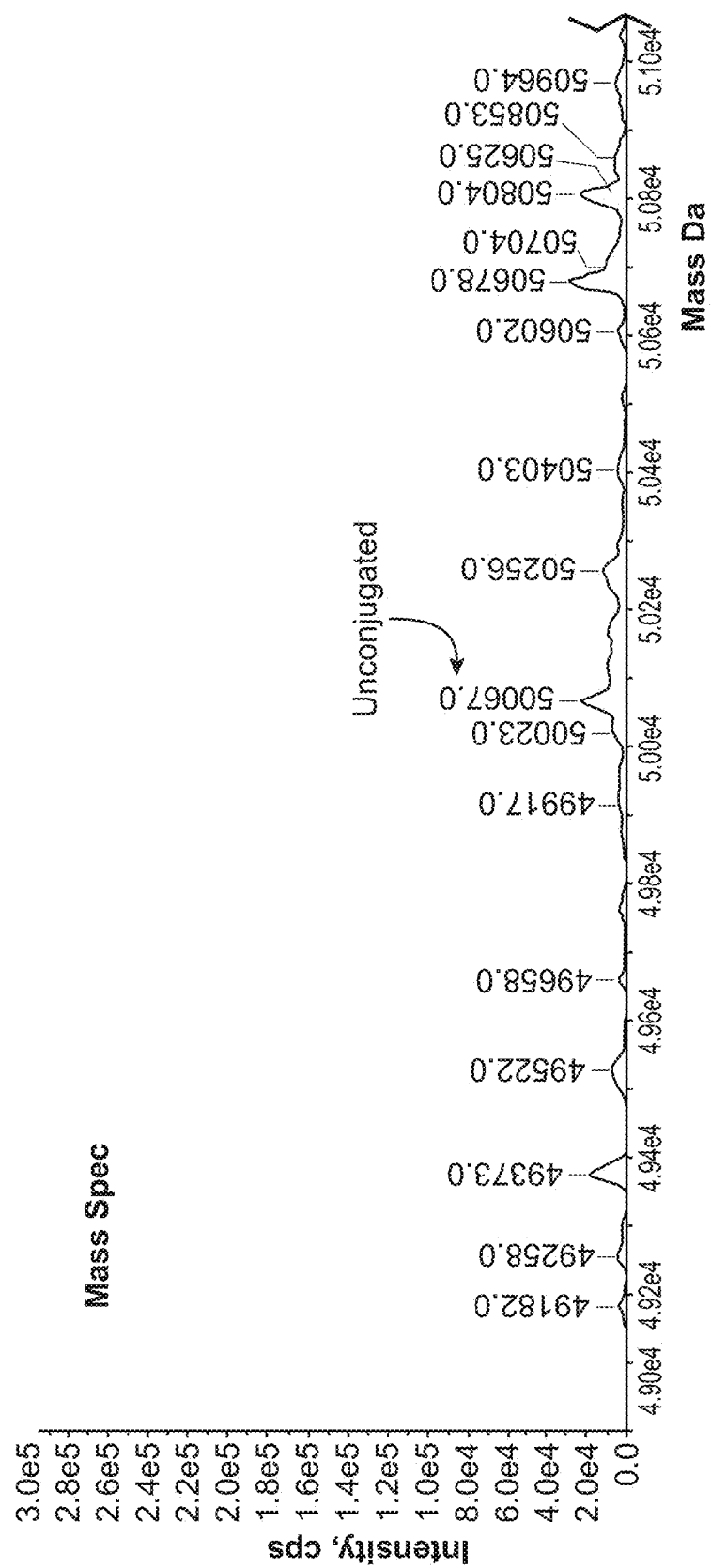
Figure 66C:
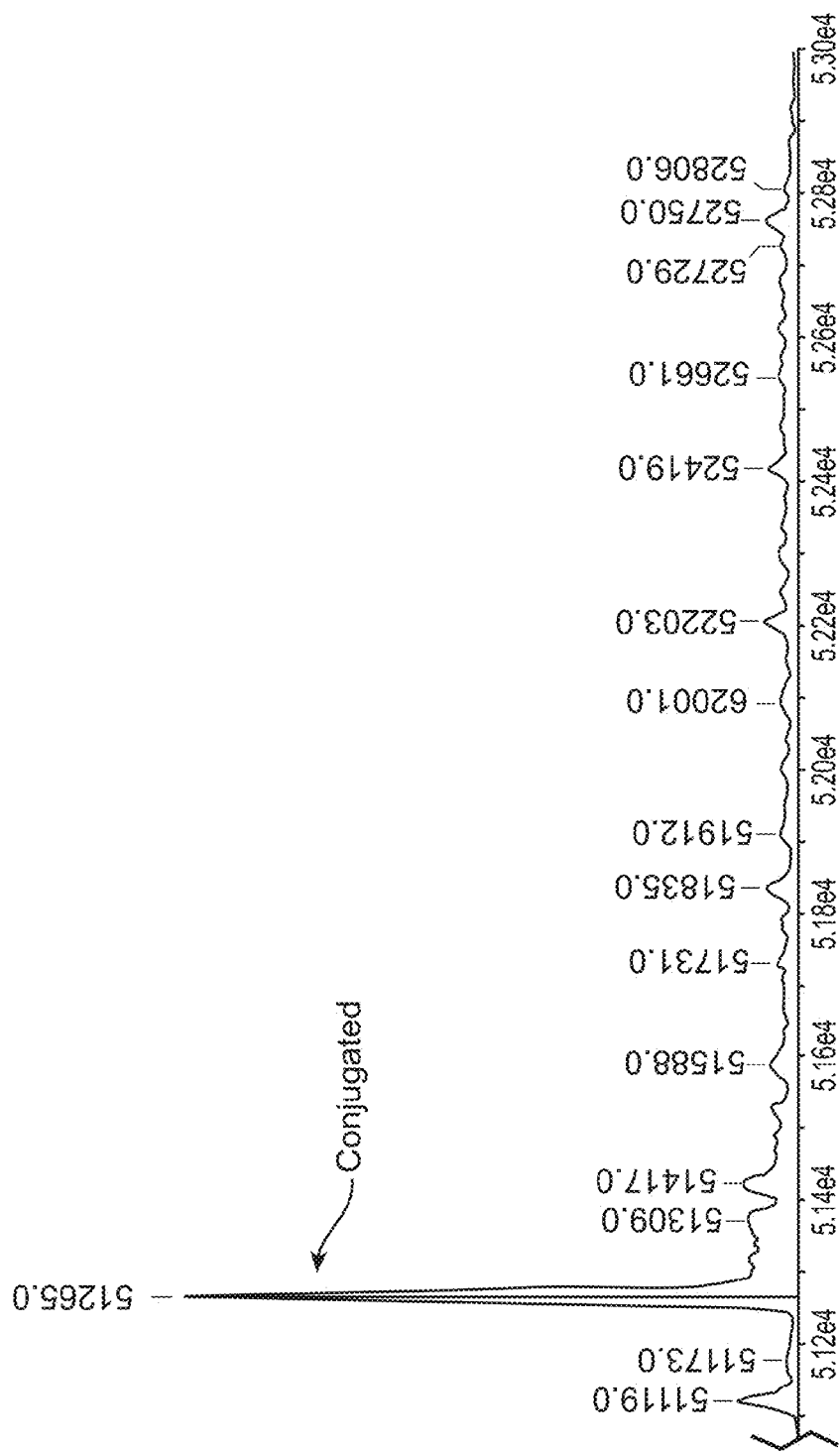

Results are shown in FIGS. 66A-66C, which shows a size exclusion chromatography (SEC) trace (FIG. 66A), a hydrophobic interaction column (HIC) trace (FIG. 66B), and a mass spectrometer (MS) trace (FIG. 66C) of the aldehyde-tagged antibody conjugated to HIPS-PAPip(PEG2(CO2H))-Maytansine. The unconjugated, mono-conjugated and di-conjugated protein conjugates were observed.

Conjugation of HIPS-Glutamic Acid-PEG2-Valine-Alanine-PABC-Maytansine to an Aldehyde-Tagged Antibody HIPS-Glutamic Acid-PEG2-Valine-Alanine-PABC-Maytansine was reacted with an aldehyde-tagged antibody according to the conjugation method described above.

Figure 67:
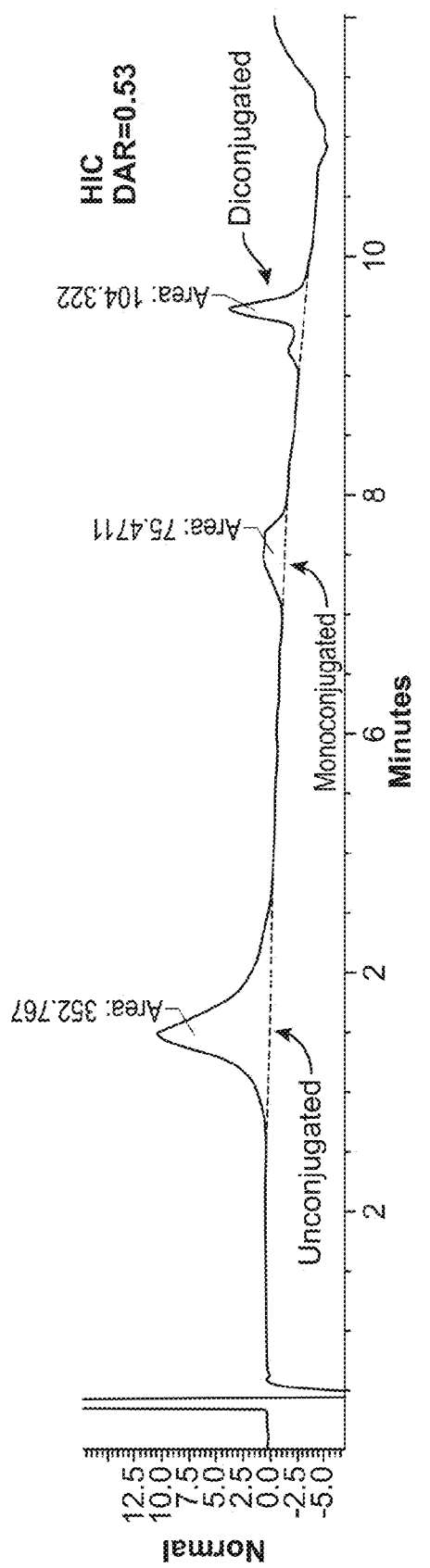
FIG. 67 shows a hydrophobic interaction column (HIC) trace of an aldehyde-tagged antibody conjugated to HIPS-Glutamic Acid-PEG2-Valine-Alanine-PABC-Maytansine, according to embodiments of the present disclosure.

Results are shown in FIG. 67, which shows a hydrophobic interaction column (HIC) trace of the aldehyde-tagged antibody conjugated to HIPS-Glutamic Acid-PEG2-Valine-Alanine-PABC-Maytansine. The unconjugated, mono-conjugated and di-conjugated protein conjugates were observed.

Conjugation of HIPS-PAPip(PEG2(CO2H))-Valine-Alanine-PABC-MMAD to an Aldehyde-Tagged Antibody HIPS-PAPip(PEG2(CO2H))-Valine-Alanine-PABC-MMAD was reacted with an aldehyde-tagged antibody according to the conjugation method described above.

Figure 68:
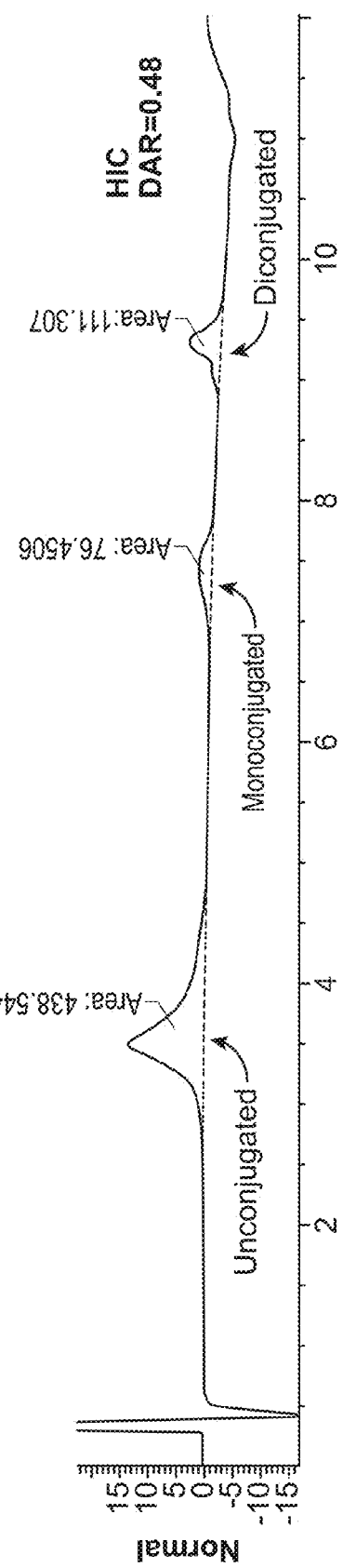
FIG. 68 shows a hydrophobic interaction column (HIC) trace of an aldehyde-tagged antibody conjugated to HIPS-PAPip(PEG2(CO2H))-Valine-Alanine-PABC-MMAD, according to embodiments of the present disclosure.

Results are shown in FIG. 68, which shows a hydrophobic interaction column (HIC) trace of the aldehyde-tagged antibody conjugated to HIPS-PAPip(PEG2(CO2H))-Valine-Alanine-PABC-MMAD. The unconjugated, mono-conjugated and di-conjugated protein conjugates were observed.

Conjugation of HIPS-PAPip(PEG2(CO2H))-Valine-Citrulline-PABC-MMAD to an Aldehyde-Tagged Antibody HIPS-PAPip(PEG2(CO2H))-Valine-Citrulline-PABC-MMAD was reacted with an aldehyde-tagged antibody according to the conjugation method described above.

Figure 69A:
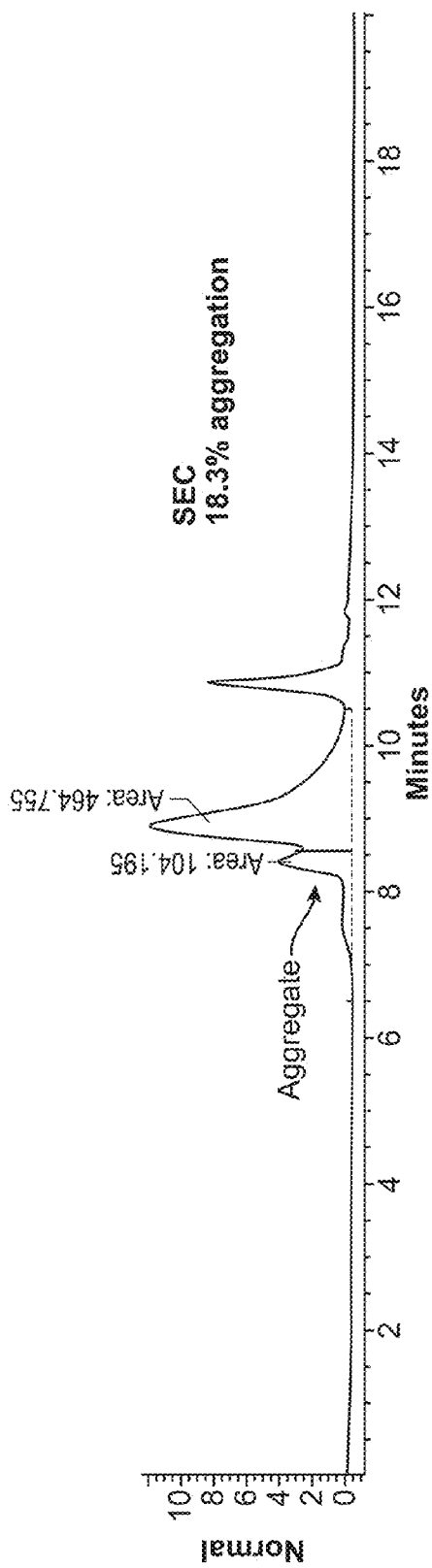
FIGS. 69A-69B show a size exclusion chromatography (SEC) trace (FIG. 69A) and a hydrophobic interaction column (HIC) trace (FIG. 69B) of an aldehyde-tagged antibody conjugated to HIPS-PAPip(PEG2(CO2H))-Valine-Citrulline-PABC-MMAD, according to embodiments of the present disclosure.
Figure 69B:
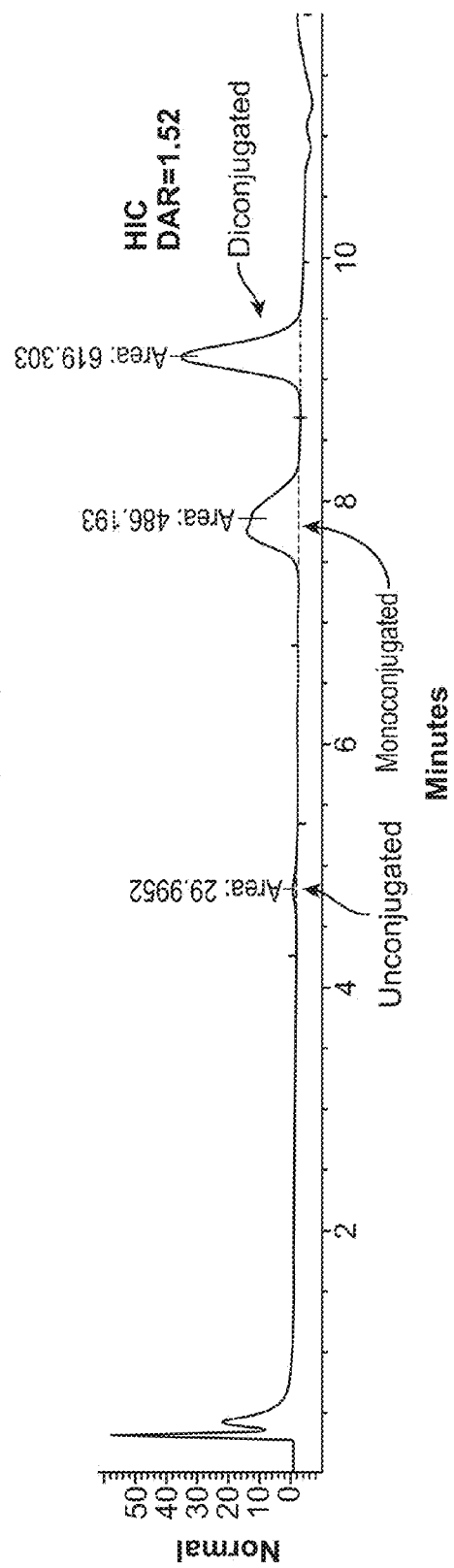

Results are shown in FIGS. 69A-69B, which shows a size exclusion chromatography (SEC) trace (FIG. 69A) and a hydrophobic interaction column (HIC) trace (FIG. 69B) of the aldehyde-tagged antibody conjugated to HIPS-PAPip(PEG2(CO2H))-Valine-Citrulline-PABC-MMAD. The unconjugated, mono-conjugated and di-conjugated protein conjugates were observed.

Conjugation of AzaHIPS-PAPip(PEG2(CO2H))-Valine-Citrulline-PABC-MMAD to an Aldehyde-Tagged Antibody AzaHIPS-PAPip(PEG2(CO2H))-Valine-Citrulline-PABC-MMAD was reacted with an aldehyde-tagged antibody according to the conjugation method described above.

Figures 70A, 70B:
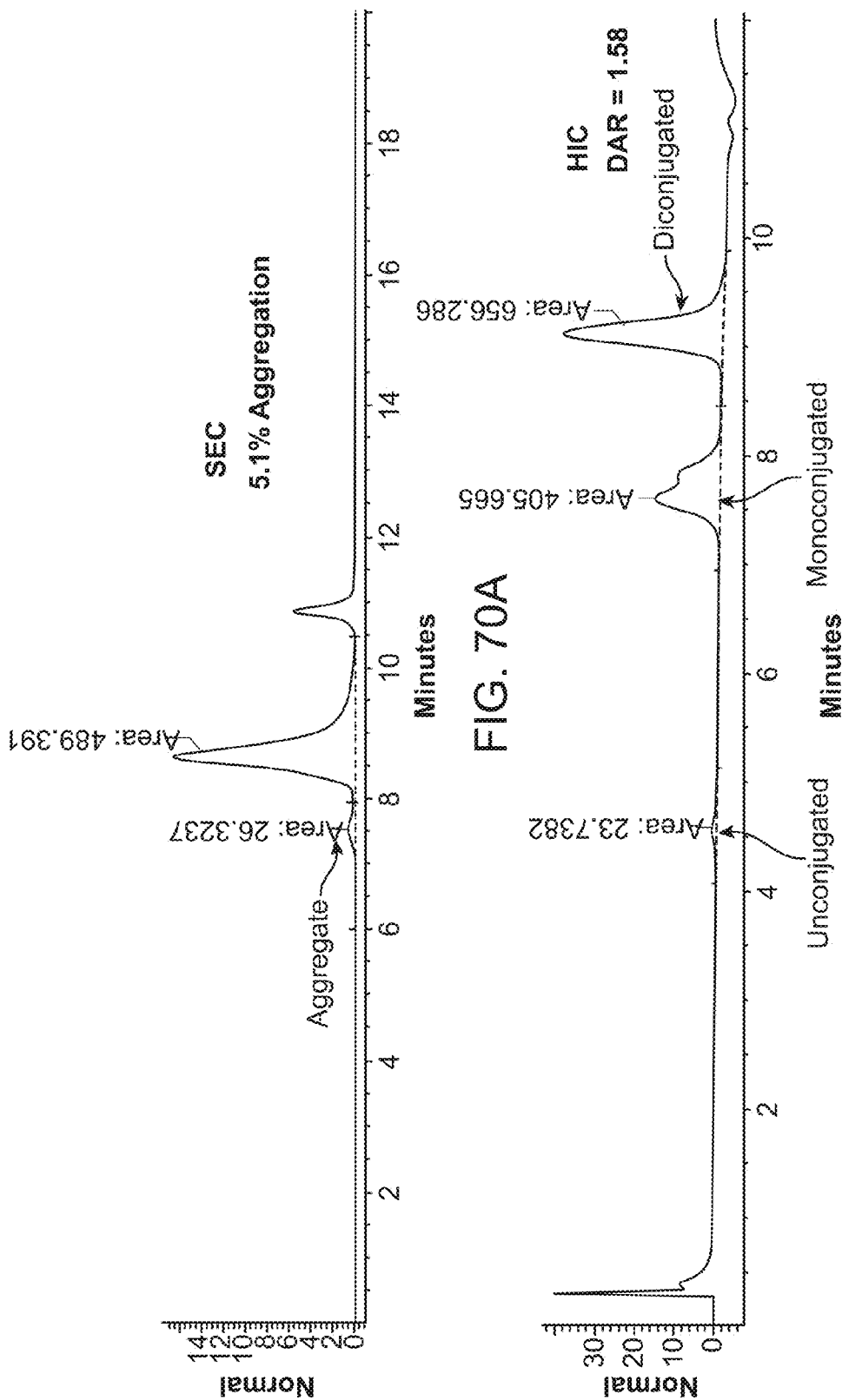
FIGS. 70A-70B show a size exclusion chromatography (SEC) trace (FIG. 70A) and a hydrophobic interaction column (HIC) trace (FIG. 70B) of an aldehyde-tagged antibody conjugated to AzaHIPS-PAPip(PEG2(CO2H))-Valine-Citrulline-PABC-MMAD, according to embodiments of the present disclosure.

Results are shown in FIGS. 70A-70B, which shows a size exclusion chromatography (SEC) trace (FIG. 70A) and a hydrophobic interaction column (HIC) trace (FIG. 70B) of the aldehyde-tagged antibody conjugated to AzaHIPS-PAPip(PEG2(CO2H))-Valine-Citrulline-PABC-MMAD. The unconjugated, mono-conjugated and di-conjugated protein conjugates were observed.

Conjugation of HIPS-Glutamic Acid-PEG2-Valine-Citrulline-PABC-Maytansine to an Aldehyde-Tagged Antibody HIPS-Glutamic Acid-PEG2-Valine-Citrulline-PABC-Maytansine was reacted with an aldehyde-tagged antibody according to the conjugation method described above.

Figures 71A, 71B:
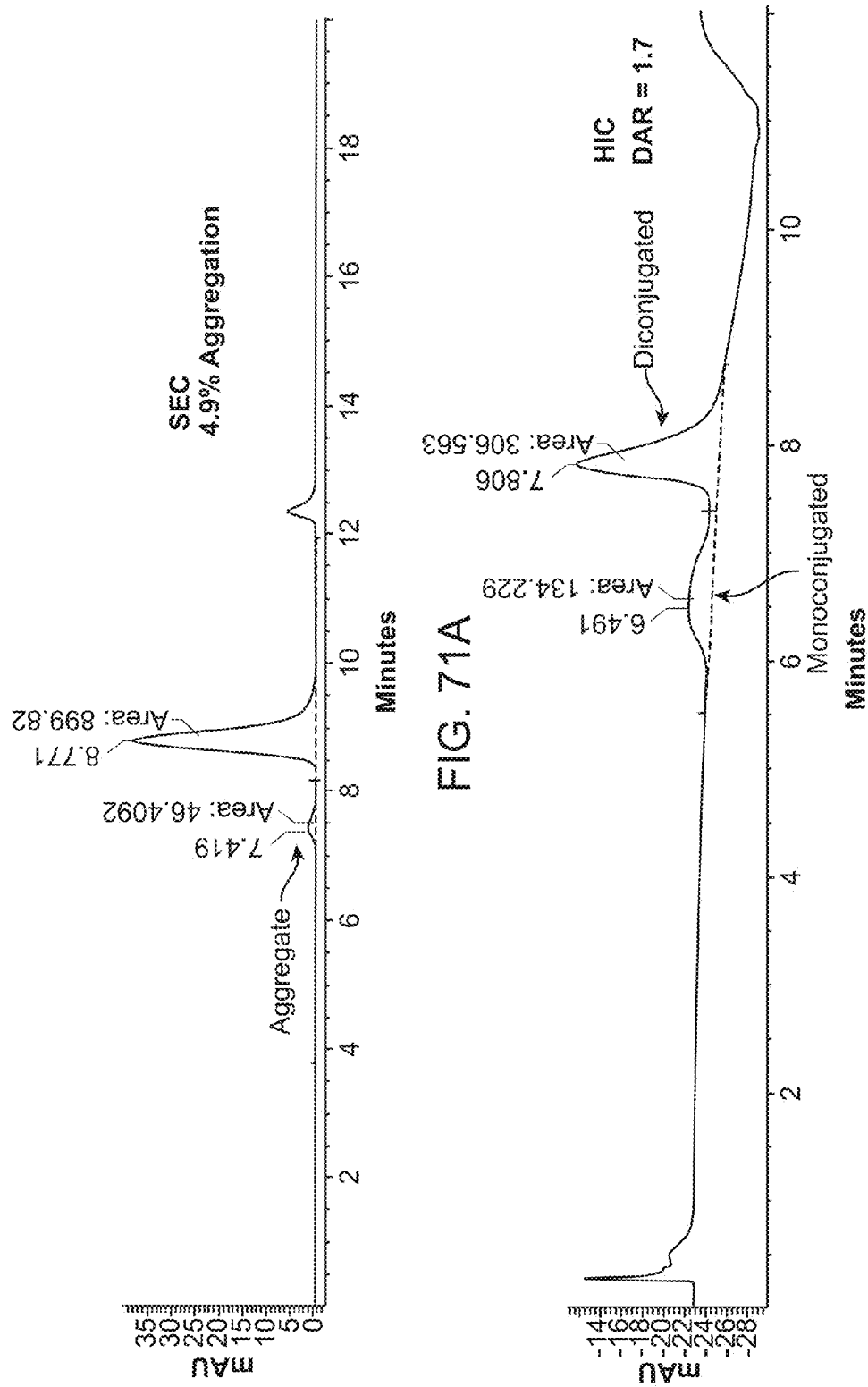
FIGS. 71A-71C show a size exclusion chromatography (SEC) trace (FIG. 71A), a hydrophobic interaction column (HIC) trace (FIG. 71B), and a mass spectrometer (MS) trace (FIG. 71C) of an aldehyde-tagged antibody conjugated to HIPS-Glutamic Acid-PEG2-Valine-Citrulline-PABC-Maytansine, according to embodiments of the present disclosure.
Figure 71C:
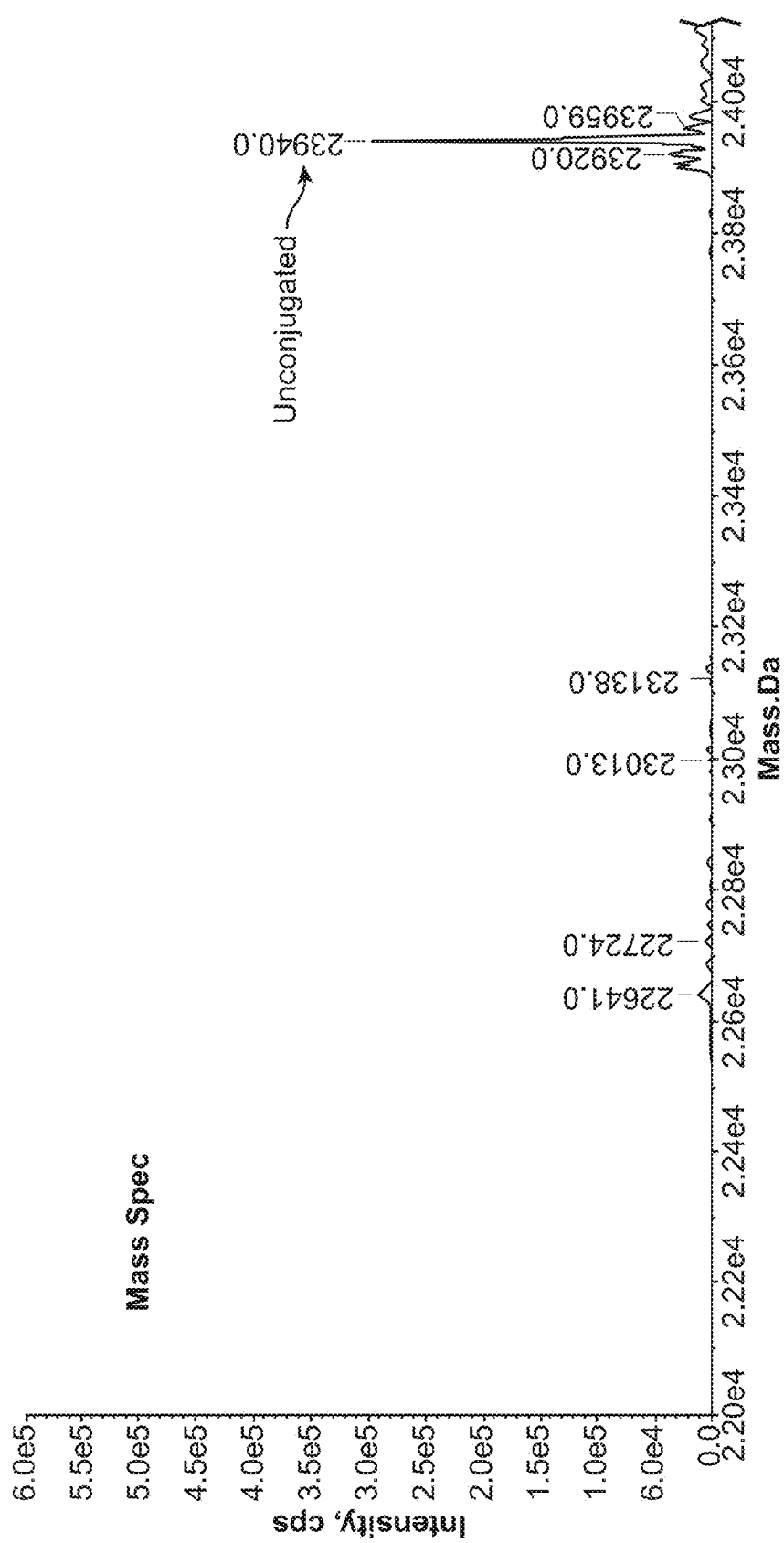

Results are shown in FIGS. 71A-71C, which shows a size exclusion chromatography (SEC) trace (FIG. 71A), a hydrophobic interaction column (HIC) trace (FIG. 71B), and a mass spectrometer (MS) trace (FIG. 71C) of the aldehyde-tagged antibody conjugated to HIPS-Glutamic Acid-PEG2-Valine-Citrulline-PABC-Maytansine. The unconjugated and mono-conjugated protein conjugates were observed.

Conjugation of HIPS-Asparagine-PEG2-Maytansine to an Aldehyde-Tagged Antibody

HIPS-Asparagine-PEG2-Maytansine was reacted with an aldehyde-tagged antibody according to the conjugation method described above.

Figure 72A:
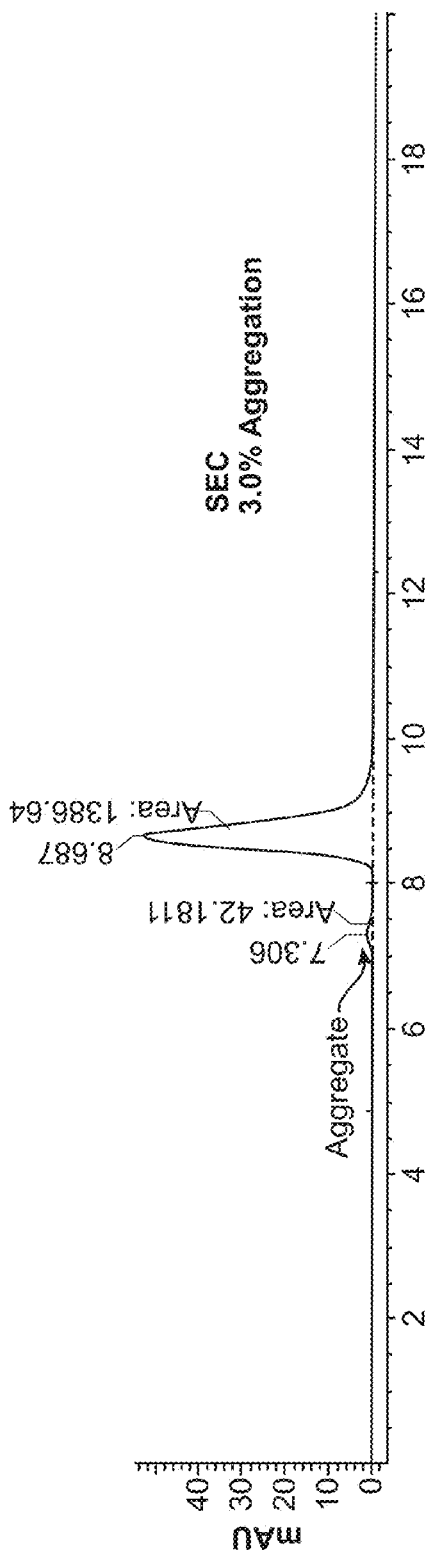
FIGS. 72A-72C show a size exclusion chromatography (SEC) trace (FIG. 72A), a hydrophobic interaction column (HIC) trace (FIG. 72B), and a mass spectrometer (MS) trace (FIG. 72C) of an aldehyde-tagged antibody conjugated to HIPS-Asparagine-PEG2-Maytansine, according to embodiments of the present disclosure.
Figure 72B:
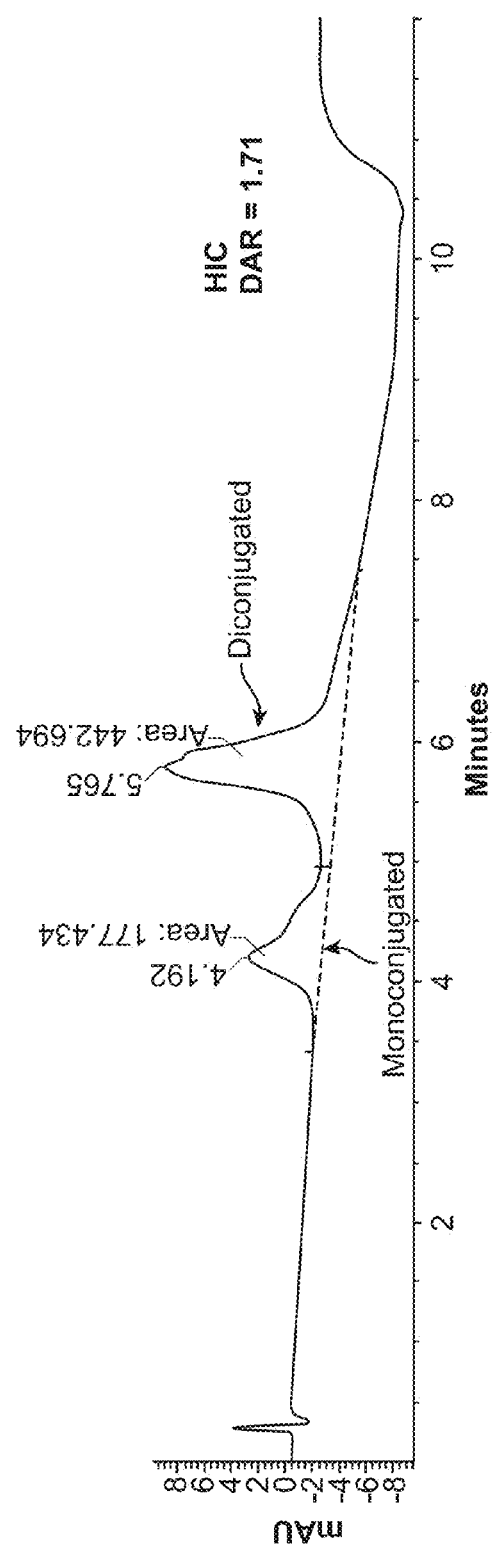
Figure 72C:
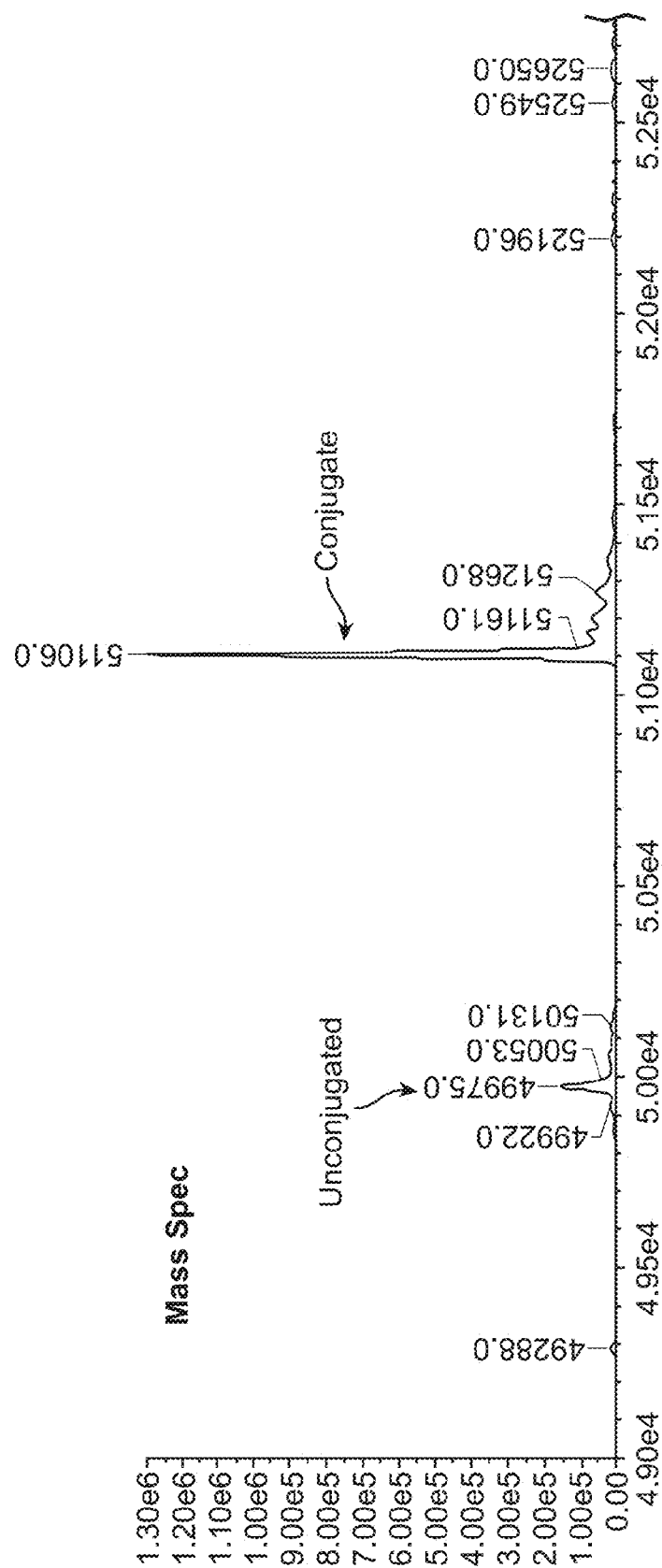
Figure 72C:
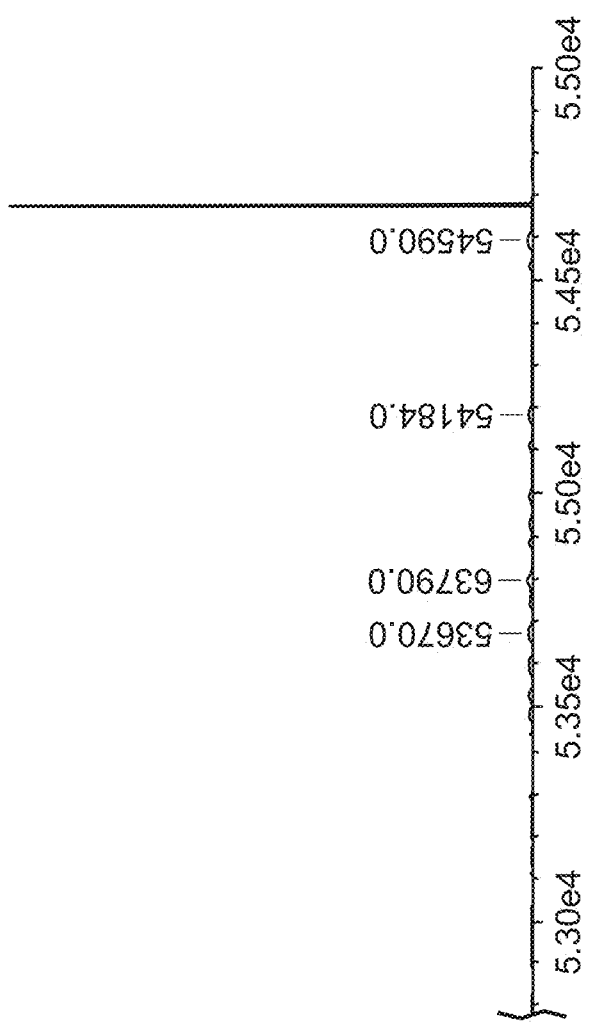

Results are shown in FIGS. 72A-72C, which shows a size exclusion chromatography (SEC) trace (FIG. 72A), a hydrophobic interaction column (HIC) trace (FIG. 72B), and a mass spectrometer (MS) trace (FIG. 72C) of the aldehyde-tagged antibody conjugated to HIPS-Asparagine-PEG2-Maytansine. The unconjugated, mono-conjugated and diconjugated protein conjugates were observed.

Conjugation of HIPS-Alanine-PEG2-Maytansine to an Aldehyde-Tagged Antibody

HIPS-Alanine-PEG2-Maytansine was reacted with an aldehyde-tagged antibody according to the conjugation method described above.

Figures 73A, 73B:
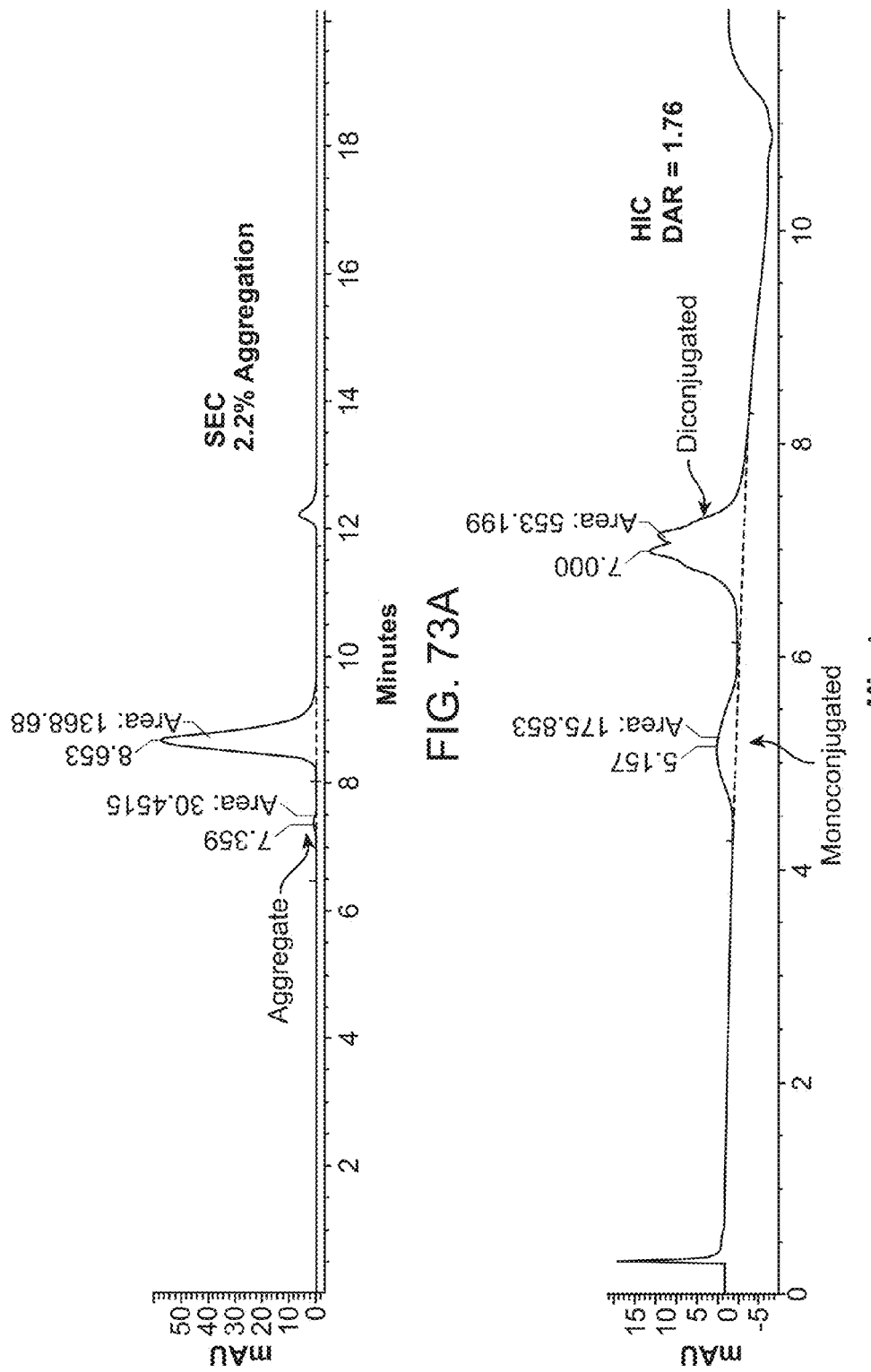
FIGS. 73A-73C show a size exclusion chromatography (SEC) trace (FIG. 73A), a hydrophobic interaction column (HIC) trace (FIG. 73B), and a mass spectrometer (MS) trace (FIG. 73C) of an aldehyde-tagged antibody conjugated to HIPS-Alanine-PEG2-Maytansine, according to embodiments of the present disclosure.
Figure 73C:
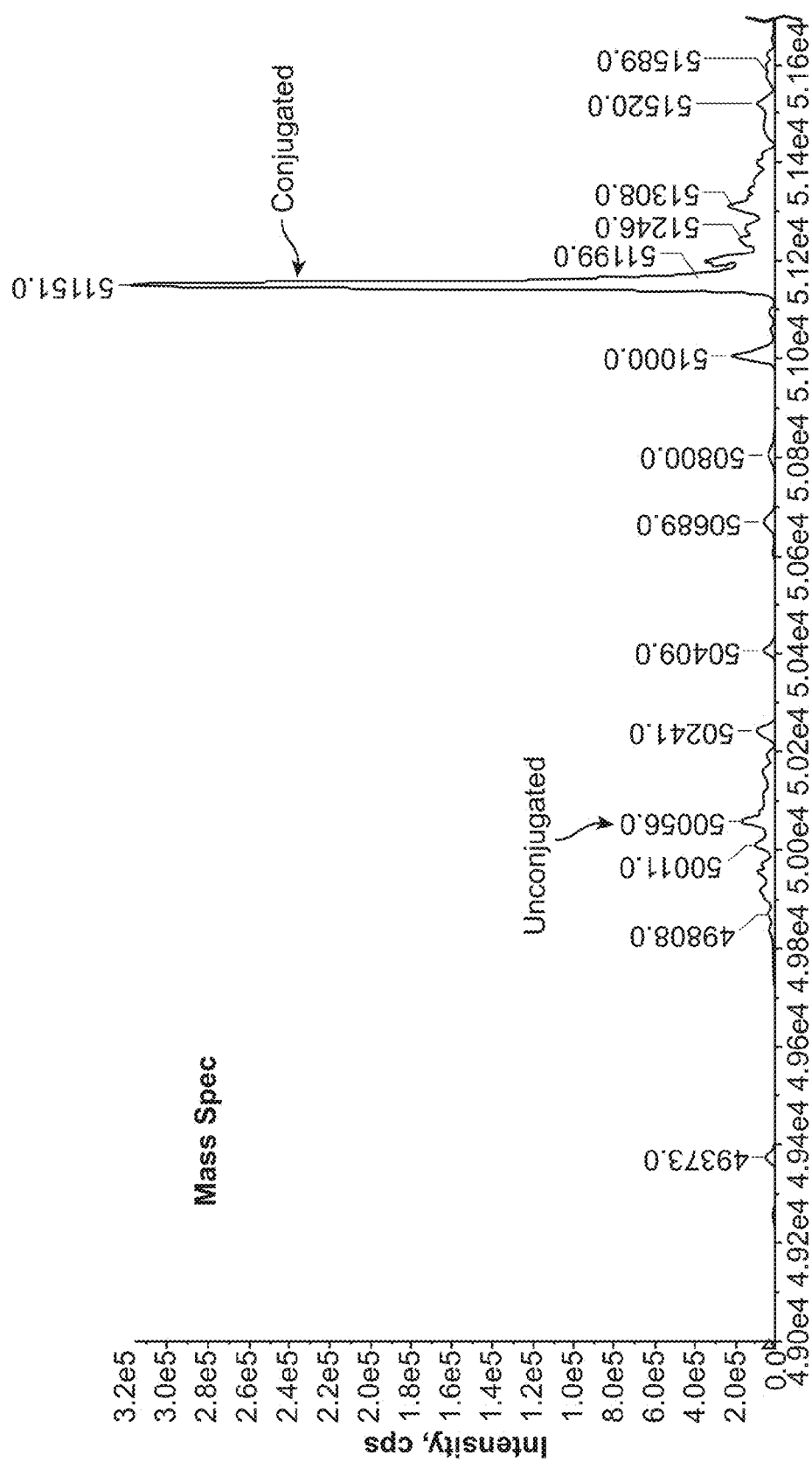
Figure 73C:
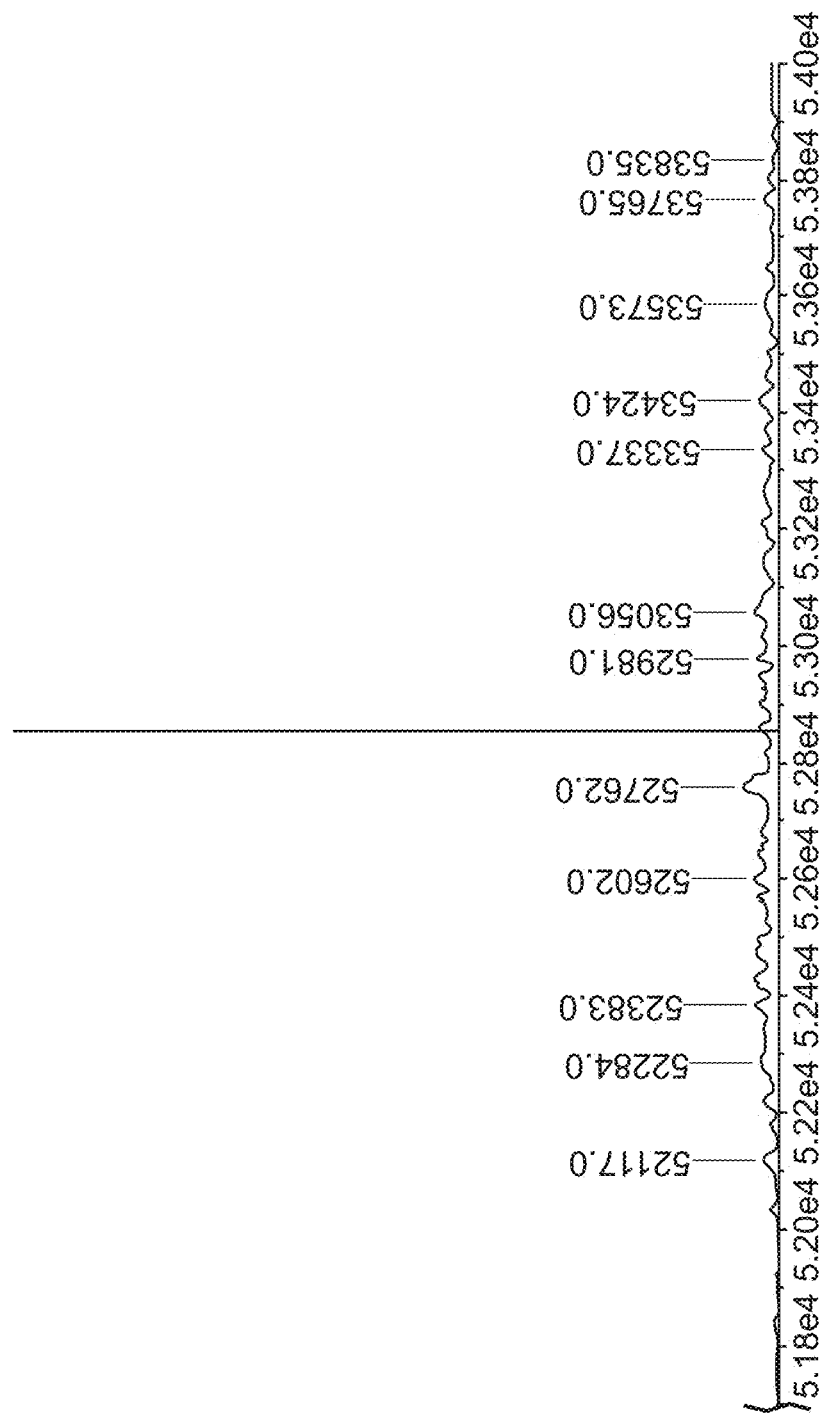

Results are shown in FIGS. 73A-73C, which shows a size exclusion chromatography (SEC) trace (FIG. 73A), a hydrophobic interaction column (HIC) trace (FIG. 73B), and a mass spectrometer (MS) trace (FIG. 73C) of the aldehyde-tagged antibody conjugated to HIPS-Alanine-PEG2-Maytansine. The unconjugated, mono-conjugated and diconjugated protein conjugates were observed.

Example 20

Figure 60:
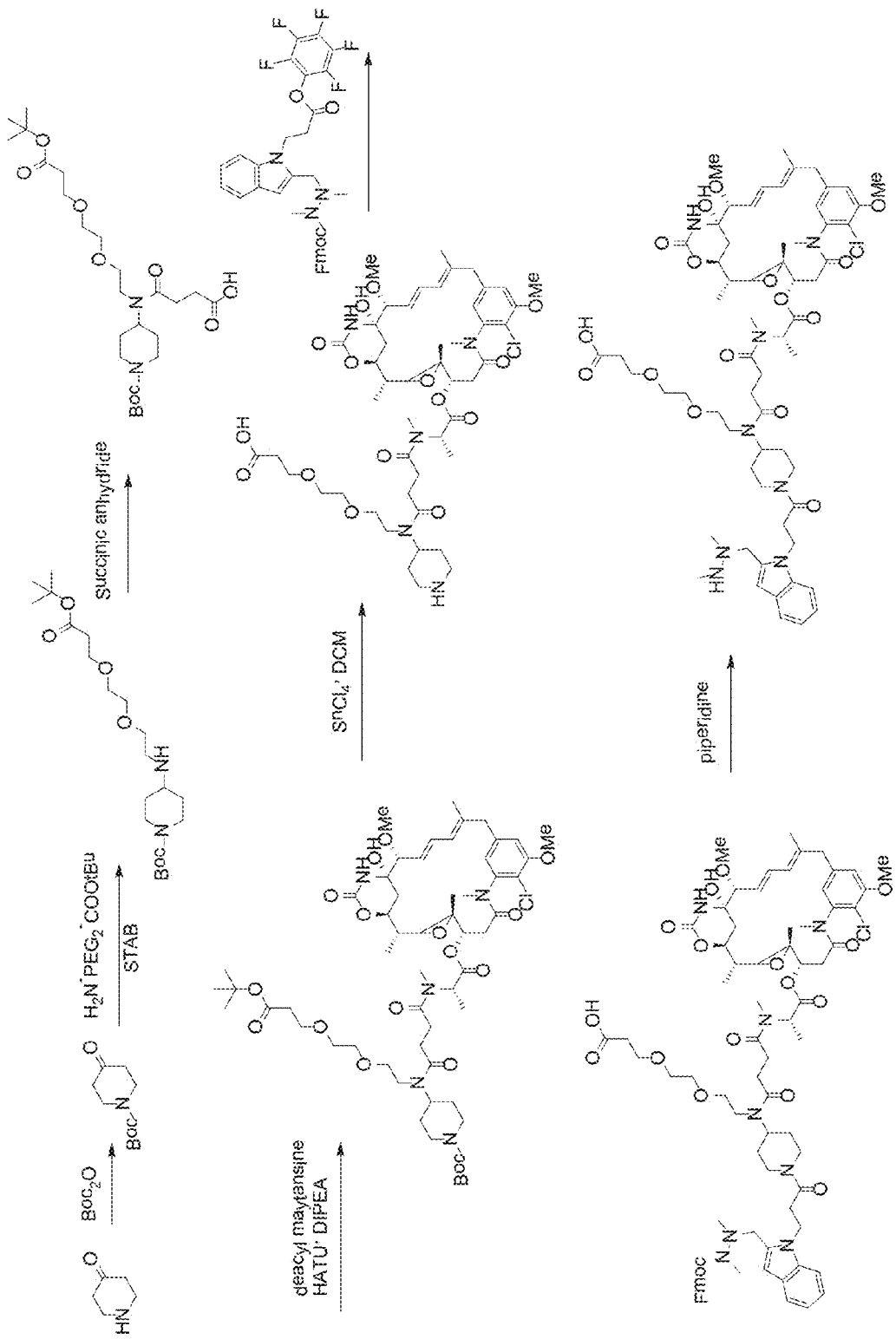
FIG. 60 shows a reaction scheme for the synthesis of (2S)-8-(1-(3-(2-((2-(((9H-fluoren-9-yl)methoxy)carbonyl)-1,2-dimethylhydrazinyl)methyl)-1H-indol-1-yl)propanoyl)piperidin-4-yl)-1-((($1^4$S,$1^6$S,$3^3$S,2R,4S,10E,12E,14R)-$8^6$-chloro-$1^4$-hydroxy-$8^5$,14-dimethoxy-$3^3$,2,7,10-tetramethyl- 12,6-dioxo-7-aza-1(6,4)-oxazinana-3(2,3)-oxirana-8(1,3)-benzenacyclotetradecaphane-10,12-dien-4-yl)oxy)-2,3-dimethyl-1,4,7-trioxo-11,14-dioxa-3,8-diazaheptadecan-17-oic acid (Fmoc-HIPS-PAPip(PEG2(CO2H))-maytansine) according to embodiments of the present disclosure, see e.g., Example 20.

A reaction scheme for the synthesis of (2S)-1-(((1$^4$S,1$^6$S, 3$^3$S,2R,4S,10E,12E,14R)-8$^6$-chloro-1$^4$-hydroxy-8$^5$,14-dimethoxy-3$^3$,2,7,10-tetramethyl-1$^2$,6-dioxo-7-aza-1(6,4)-oxazinana-3(2,3)-oxirana-8(1,3)-benzenacyclotetradecaphane-10,12-dien-4-yl)oxy)-8-(1-(3-(2-((1,2-dimethylhydrazinyl) methyl)-1H-indol-1-yl)propanoyl)piperidin-4-yl)-2,3-dimethyl-1,4,7-trioxo-11,14-dioxa-3,8-diazaheptadecan-17-oic acid is shown in FIG. 60.

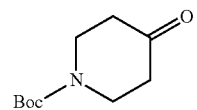

Preparation of tert-butyl 4-oxopiperidine-1-carboxylate (FIG. 60)

To a 100 mL round-bottom flask containing a magnetic stir bar was added piperidinone hydrochloride monohydrate (1.53 g, 10 mmol), Boc anhydride (2.39 g, 11 mmol), sodium carbonate (1.22 g, 11.5 mmol), dioxane (10 mL), and water (1 mL). The reaction mixture was stirred at room temperature for 1 h. The mixture was diluted with water (100 mL) and extracted with EtOAc (3×100 mL). The combined organic layers were washed with brine, dried over Na$_2$SO$_4$, filtered, and concentrated under reduced pressure. The resulting material was dried in vacuo to yield the title compound as a white solid (1.74 g, 87% yield).

$^1$H NMR (CDCl$_3$) δ 3.73 (t, 4H, J=6.0), 2.46 (t, 4H, J=6.0), 1.51 (s, 9H).

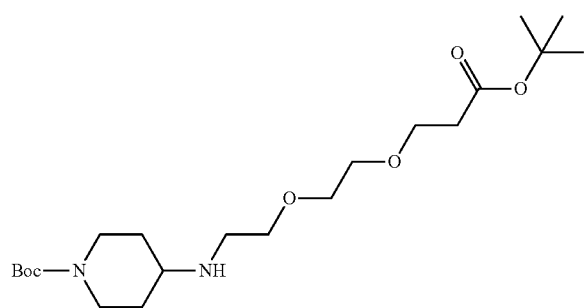 [SMILES: CC(C)(C)OC(=O)CCOCCOCCNC1CCN(C(=O)OC(C)(C)C)CC1]

Preparation of tert-butyl 4-((2-(2-(3-(tert-butoxy)-3-oxopropoxy)ethoxy)ethyl)amino)piperidine-1-carboxylate (FIG. 60)

To a dried scintillation vial containing a magnetic stir bar was added tert-butyl 4-oxopiperidine-1-carboxylate (399 mg, 2 mmol), H$_2$N-PEG$_2$-COOt-Bu (550 mg, 2.4 mmol), 4 Å molecular sieves (activated powder, 200 mg), and 1,2-dichloroethane (5 mL). The mixture was stirred for 1 h at room temperature. To the reaction mixture was added sodium triacetoxyborohydride (845 mg, 4 mmol). The mixture was stirred for 3 days at room temperature. The resulting mixture was partitioned between EtOAc and saturated aqueous NaHCO$_3$. The organic layer was washed with brine, dried over Na$_2$SO$_4$, filtered, and concentrated under reduced pressure to yield the title compound as a viscous oil (850 mg, >100% yield).

ESI-MS calculated [MH]$^+$: 417.3; found 417.2.

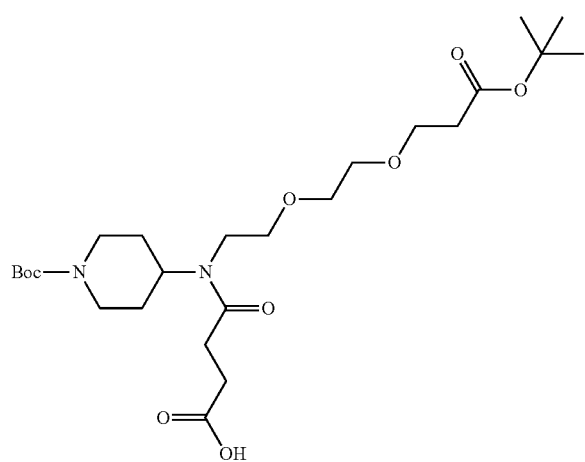 [SMILES: CC(C)(C)OC(=O)CCOCCOCCN(C(=O)CCC(=O)O)C1CCN(C(=O)OC(C)(C)C)CC1]

Preparation of 13-(1-(tert-butoxycarbonyl)piperidin-4-yl)-2,2-dimethyl-4,14-dioxo-3,7,10-trioxa-13-azaheptadecan-17-oic acid (FIG. 60)

To a dried scintillation vial containing a magnetic stir bar was added tert-butyl 4-((2-(2-(3-(tert-butoxy)-3-oxopropoxy)ethoxy)ethyl)amino)piperidine-1-carboxylate (220 mg, 0.5 mmol), succinic anhydride (55 mg, 0.55 mmol), 4-(dimethylamino)pyridine (5 mg, 0.04 mmol), and dichloromethane (3 mL). The mixture was stirred for 24 h at room temperature. The reaction mixture was partially purified by flash chromatography (elute 50-100% EtOAc/Hexanes) to yield the title compound as a clear oil (117 mg), which was carried forward without further characterization.

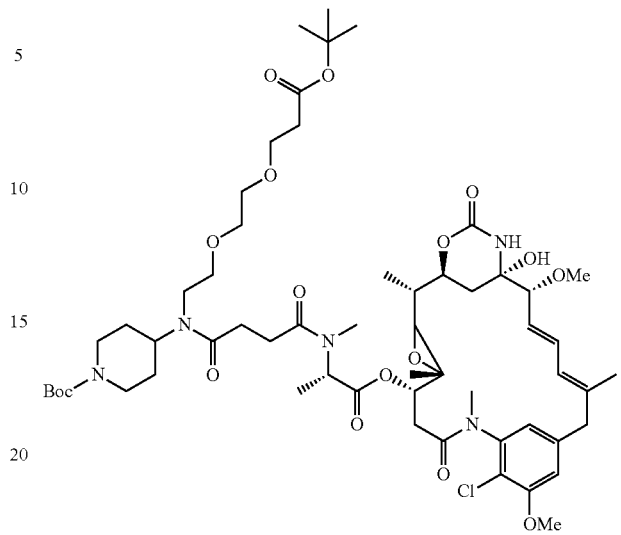

Preparation of 17-(tert-butyl) 1-((1$^4$S,1$^6$S,3$^3$S,2R, 4S,10E,12E,14R)-8$^6$-chloro-1$^4$-hydroxy-8$^5$,14-dimethoxy-3$^3$,2,7,10-tetramethyl-1$^2$,6-dioxo-7-aza-1(6,4)-oxazinana-3(2,3)-oxirana-8(1,3)-benzenacyclotetradecaphane-10,12-dien-4-yl) (2S)-8-(1-(tert-butoxycarbonyl)piperidin-4-yl)-2,3-dimethyl-4,7-dioxo-11,14-dioxa-3,8-diazaheptadecanedioate (Boc-PAPip(PEG2(CO2t-Bu)-maytansine) (FIG. 60)

To a dried scintillation vial containing a magnetic stir bar was added 13-(1-(tert-butoxycarbonyl)piperidin-4-yl)-2,2-dimethyl-4,14-dioxo-3,7,10-trioxa-13-azaheptadecan-17-oic acid (55 mg, 0.1 mmol), deacyl maytansine (65 mg, 0.1 mmol), HATU (43 mg, 0.11 mmol), DMF (1 mL), and dichloromethane (0.5 mL). The mixture was stirred for 8 h at room temperature. The reaction mixture was directly purified by C18 flash chromatography (elute 5-100% MeCN/water) to yield the title compound as a white film (18 mg, 16% yield).

ESI-MS calculated [MH]$^+$: 1148.6; found 1148.7.

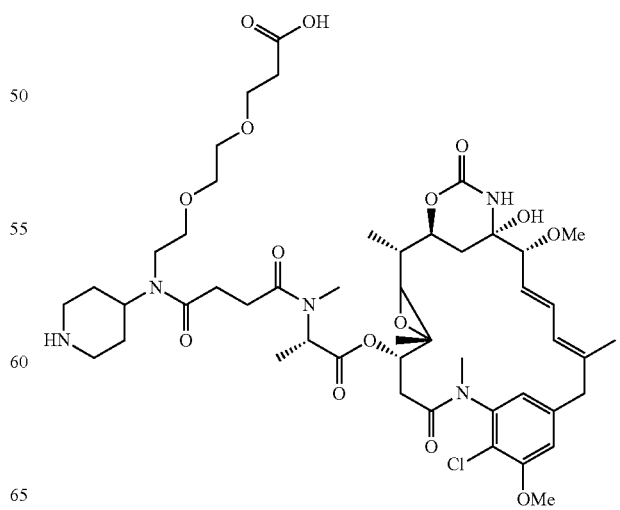

Preparation of (2S)-1-(((1⁴S,1⁶S,3³S,2R,4S,10E, 12E,14R)-8⁶-chloro-1⁴-hydroxy-8⁵,14-dimethoxy-3³,2,7,10-tetramethyl-1²,6-dioxo-7-aza-1 (6,4)-oxazinana-3(2,3)-oxirana-8(1,3)-benzenacyclotetradecaphane-10,12-dien-4-yl)oxy)-2,3-dimethyl-1,4,7-trioxo-8-(piperidin-4-yl)-11,14-dioxa-3,8-diazaheptadecan-17-oic acid (PAPip (PEG2(CO2H))-maytansine) (FIG. 60)

To a dried scintillation vial containing a magnetic stir bar was added Boc-PAPip(PEG2(CO2t-Bu)-maytansine (31 mg, 0.027 mmol) and dichloromethane (1 mL). The solution was cooled to 0° C. and tin(IV) tetrachloride (1.0 M solution in dichloromethane, 0.3 mL, 0.3 mmol) was added. The reaction mixture was stirred for 1 h at 0° C. The reaction mixture was directly purified by C18 flash chromatography (elute 5-100% MeCN/water) to yield the title compound as a white solid (16 mg, 60% yield).

ESI-MS calculated [MH]⁺: 992.5; found 992.6.

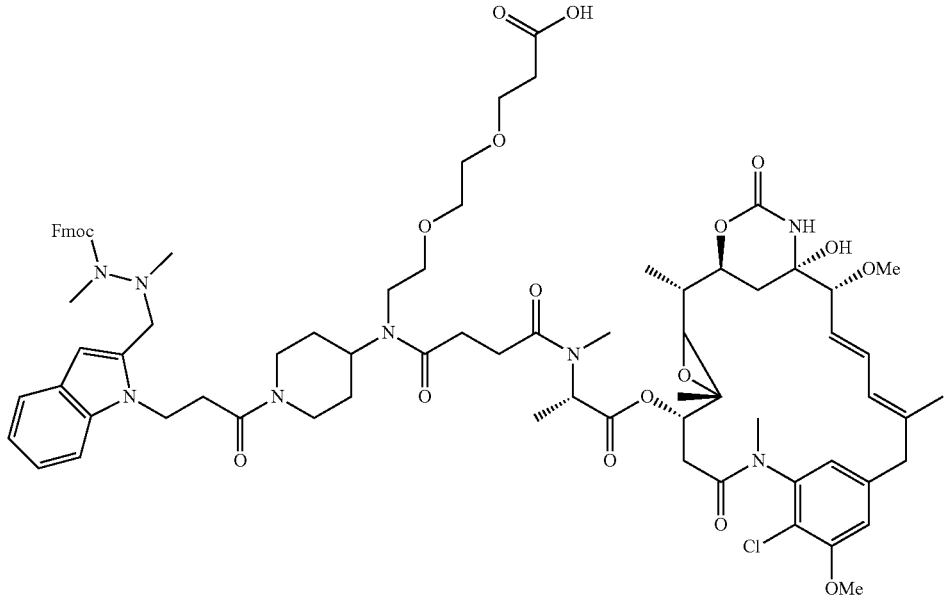

Preparation of (2S)-8-(1-(3-(2-((2-(((9H-fluoren-9-yl)methoxy)carbonyl)-1,2-dimethylhydrazinyl) methyl)-1H-indol-1-yl)propanoyl)piperidin-4-yl)-1-(((1⁴S,1⁶S,3³S,2R,4S,10E,12E,14R)-8⁶-chloro-1⁴-hydroxy-8⁵,14-dimethoxy-3³,2,7,10-tetramethyl-1², 6-dioxo-7-aza-1(6,4)-oxazinana-3(2,3)-oxirana-8(1, 3)-benzenacyclotetradecaphane-10,12-dien-4-yl) oxy)-2,3-dimethyl-1,4,7-trioxo-11,14-dioxa-3,8-diazaheptadecan-17-oic acid (Fmoc-HIPS-PAPip (PEG2(CO2H))-maytansine) (FIG. 60)

To a dried scintillation vial containing a magnetic stir bar was added PAPip(PEG2(CO2H))-maytansine (16 mg, 0.016 mmol), (9H-fluoren-9-yl)methyl 1,2-dimethyl-2-((1-(3-oxo-3-(perfluorophenoxy)propyl)-1H-indol-2-yl)methyl)hydrazine-1-carboxylate (13 mg, 0.02 mmol), DIPEA (8 µL, 0.05 mmol), and DMF (1 mL). The solution was stirred for 18 h at room temperature. The reaction mixture was directly purified by C18 flash chromatography (elute 5-100% MeCN/water) to yield the title compound as a white solid (18 mg, 77% yield).

ESI-MS calculated [MH]⁺: 1457.7; found 1457.9.

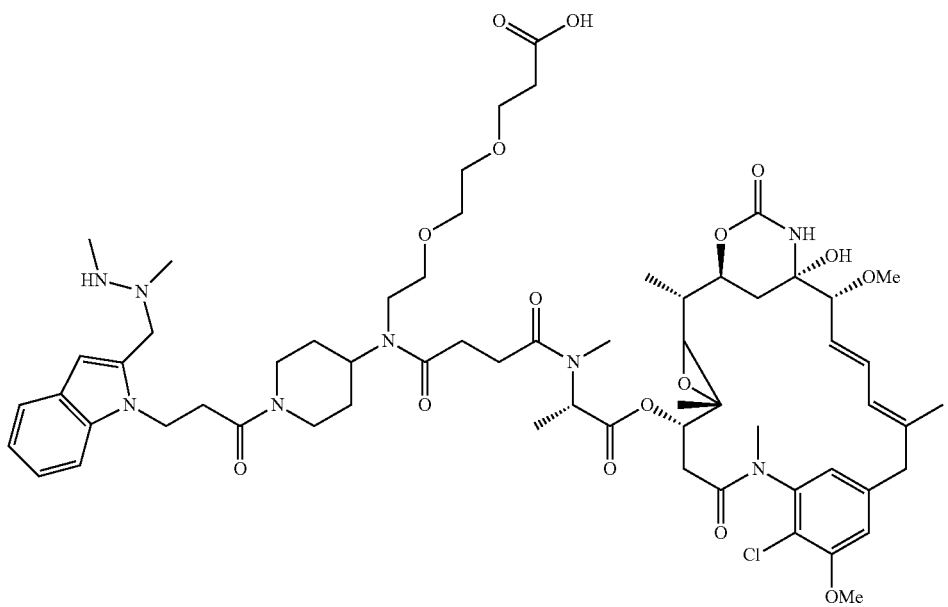 [SMILES: CNN(C)Cc1cc2ccccc2n1CCC(=O)N1CCC(N(CCOCCOCCC(=O)O)C(=O)CCC(=O)N(C)[C@@H](C)C(=O)O[C@H]2CC(=O)N(C)c3cc(cc(OC)c3Cl)C/C(C)=C/C=C/[C@@H](OC)[C@@]3(O)C[C@H](OC(=O)N3)[C@@H](C)C3O[C@]32C)CC1]

Preparation of (2S)-1-(((1⁴S,1⁶S,3³S,2R,4S,10E, 12E,14R)-8⁶-chloro-1⁴-hydroxy-8⁵,14-dimethoxy-3³,2,7,10-tetramethyl-1²,6-dioxo-7-aza-1(6,4)-oxazinana-3(2,3)-oxirana-8(1,3)-benzenacyclotetradecaphane-10,12-dien-4-yl)oxy)-8-(1-(3-(2-((1,2-dimethylhydrazinyl)methyl)-1H-indol-1-yl)propanoyl)piperidin-4-yl)-2,3-dimethyl-1,4,7-trioxo-11,14-dioxa-3,8-diazaheptadecan-17-oic acid (FIG. 60)

To a dried scintillation vial containing a magnetic stir bar was added Fmoc-HIPS-PAPip(PEG2(CO2H))-maytansine (18 mg, 0.012 mmol), piperidine (20 μL, 0.02 mmol), and DMF (1 mL). The solution was stirred for 20 minutes at room temperature. The reaction mixture was directly purified by C18 flash chromatography (elute 1-60% MeCN/water) to yield the title compound as a white solid (15 mg, 98% yield).

ESI-MS calculated [MH]⁺: 1235.6; found 1236.0.

Example 21

Figure 61:
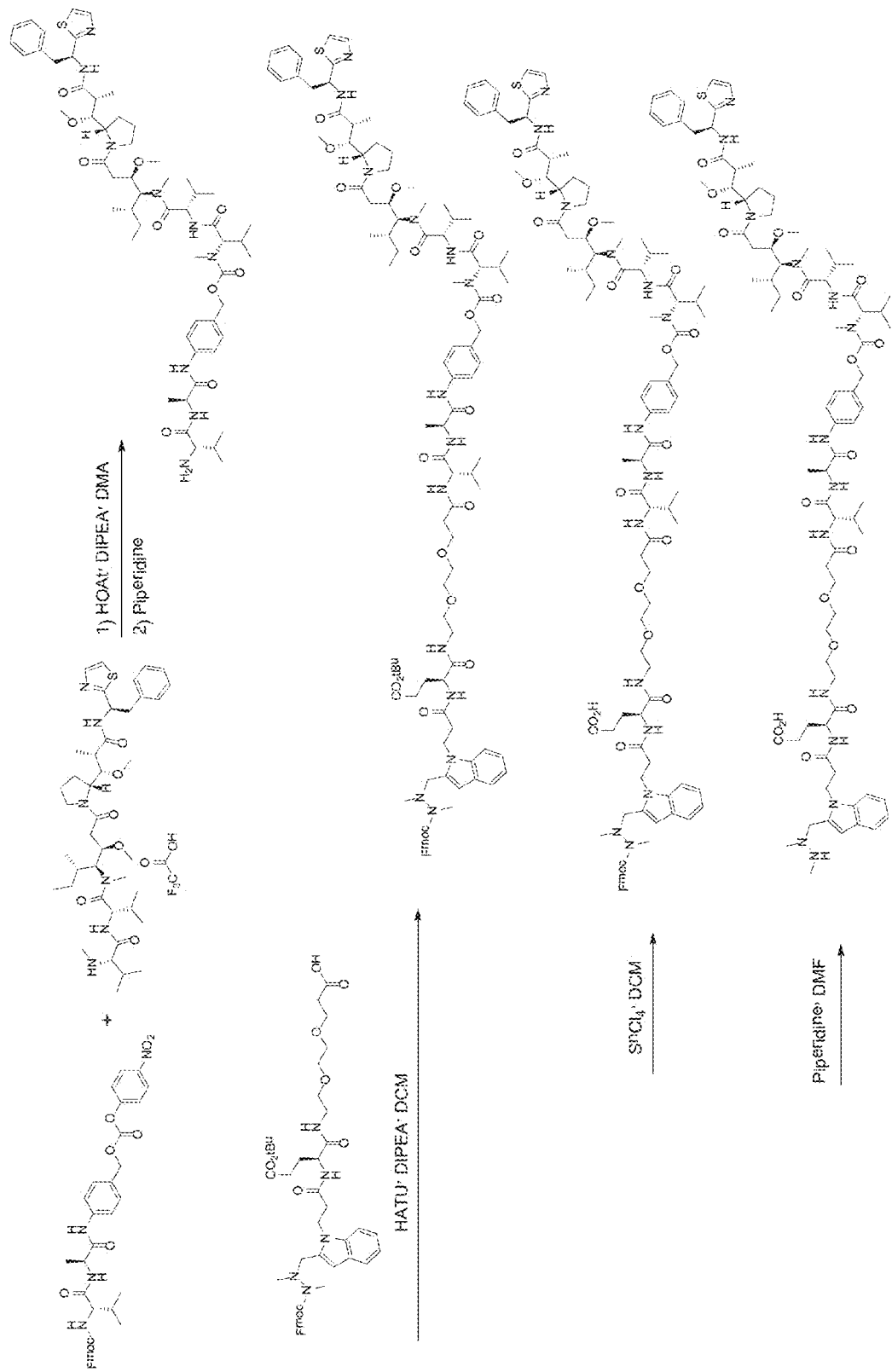
FIG. 61 shows a reaction scheme for the synthesis of (2S,5S,18S)-1-((4-((5S,8S,11S,12R)-11-((S)-sec-butyl)-5,8-diisopropyl-12-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-4,10-dimethyl-3,6,9-trioxo-2,13-dioxa-4,7,10-triazatetradecyl)phenyl)amino)-18-(3-(2-((1,2-dimethylhydrazinyl)methyl)-1H-indol-1-yl)propanamido)-5-isopropyl-2-methyl-1,4,7,17-tetraoxo-10,13-dioxa-3,6,16-triazahenicosan-21-oic acid (HIPS-Glu(OH)-PEG2-Val-Ala-PABC-MMAD) according to embodiments of the present disclosure, see e.g., Example 21.

A reaction scheme for the synthesis of (2S,5S,18S)-1-((4-((5S,8S,11S,12R)-11-((S)-sec-butyl)-5,8-diisopropyl-12-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-4,10-dimethyl-3,6,9-trioxo-2,13-dioxa-4,7,10-triazatetradecyl)phenyl)amino)-18-(3-(2-((1,2-dimethylhydrazinyl)methyl)-1H-indol-1-yl)propanamido)-5-isopropyl-2-methyl-1,4,7,17-tetraoxo-10,13-dioxa-3,6,16-triazahenicosan-21-oic acid (HIPS-Glu(OH)-PEG2-Val-Ala-PABC-MMAD) is shown in FIG. 61.

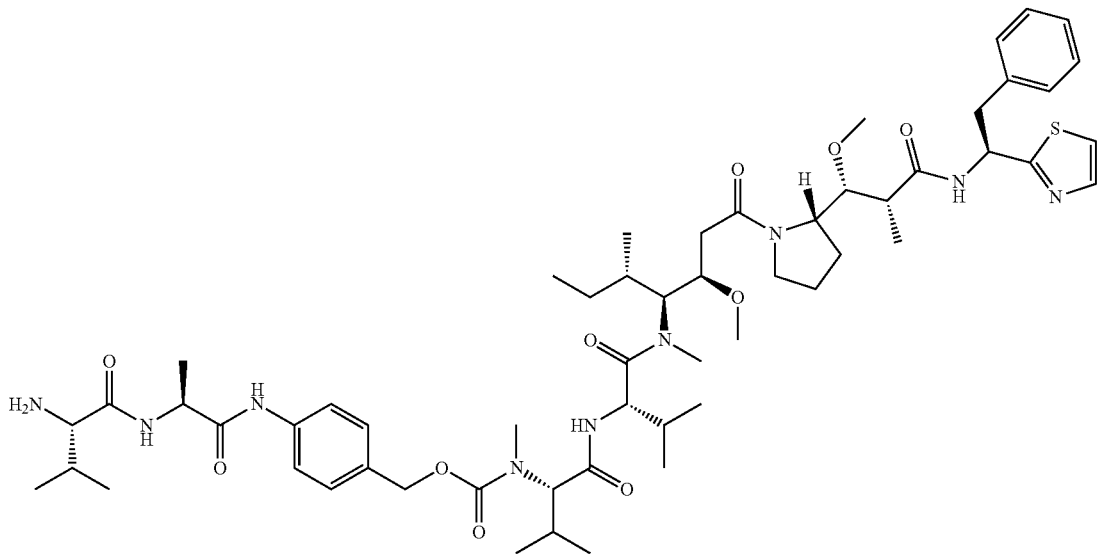 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)C(=O)OCc1ccc(NC(=O)[C@H](C)NC(=O)[C@@H](N)C(C)C)cc1)C(C)C]

Preparation of 4-((S)-2-((S)-2-amino-3-methylbutanamido)propanamido)benzyl ((S)-1-(((S)-1-(((3R,4S,5S)-3-methoxy-1-((S)-2-((1R,2R)-1-methoxy-2-methyl-3-oxo-3-(((S)-2-phenyl-1-(thiazol-2-yl)ethyl)amino)propyl)pyrrolidin-1-yl)-5-methyl-1-oxoheptan-4-yl)(methyl)amino)-3-methyl-1-oxobutan-2-yl)amino)-3-methyl-1-oxobutan-2-yl)(methyl)carbamate ($H_2N$-Val-Ala-PABC-MMAD) (FIG. 61)

To a dried scintillation vial containing a magnetic stir bar was added (9H-fluoren-9-yl)methyl ((S)-3-methyl-1-(((S)-1-((4-(((((4-nitrophenoxy)carbonyl)oxy)methyl)phenyl)amino)-1-oxopropan-2-yl)amino)-1-oxobutan-2-yl)carbamate (102 mg, 0.15 mmol), monomethyl auristatin D (TFA salt, 110 mg, 0.125 mmol), HOAt (14 mg, 0.01 mmol), DIPEA (65 µL, 0.37 mmol), and DMA (1 mL). The solution was stirred for 20 hours at room temperature. The MMAD was consumed as detected by HPLC. Piperidine (100 µL, 1 mmol) was added to the reaction mixture and the resulting solution was stirred for an additional 20 minutes at room temperature. The reaction mixture was directly purified by C18 flash chromatography (elute 5-100% MeCN/water) to yield the title compound as a light yellow solid (101 mg, 75% yield).

ESI-MS calculated [MH]$^+$: 1090.6; found 1090.6.

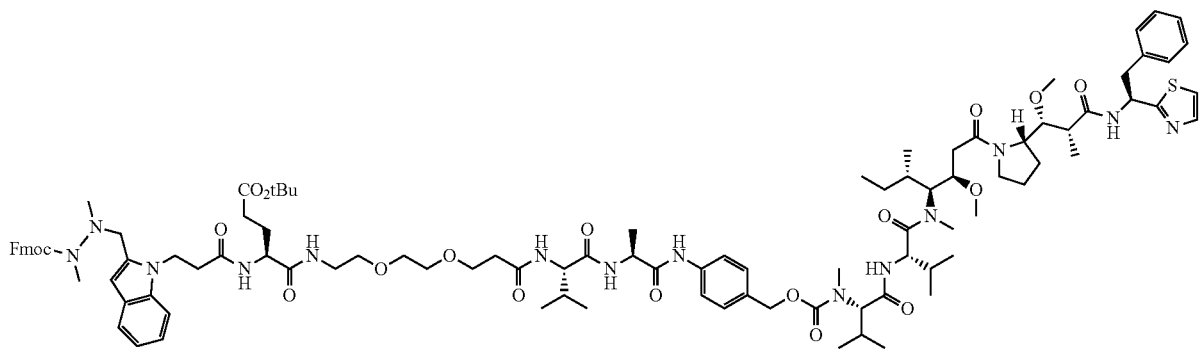

Preparation of tert-butyl (2S,5S,18S)-18-(3-(2-((2-(((9H-fluoren-9-yl)methoxy)carbonyl)-1,2-dimethylhydrazinyl)methyl)-1H-indol-1-yl)propanamido)-1-((4-((5S,8S,11S,12R)-11-((S)-sec-butyl)-5,8-diisopropyl-12-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-4,10-dimethyl-3,6,9-trioxo-2,13-dioxa-4,7,10-triazatetradecyl)phenyl)amino)-5-isopropyl-2-methyl-1,4,7,17-tetraoxo-10,13-dioxa-3,6,16-triazahenicosan-21-oate (Fmoc-HIPS-Glu(OtBu)-PEG2-Val-Ala-PABC-MMAD) (FIG. 61)

To a dried scintillation vial containing a magnetic stir bar was added (S)-7-(3-(2-((2-(((9H-fluoren-9-yl)methoxy)carbonyl)-1,2-dimethylhydrazinyl)methyl)-1H-indol-1-yl)propanamido)-2,2-dimethyl-4,8-dioxo-3,12,15-trioxa-9-azaoctadecan-18-oic acid (42 mg, 0.051 mmol), $H_2N$-Val-Ala-PABC-MMAD (50 mg, 0.046 mmol), HATU (20 mg, 0.053 mmol), DIPEA (16 µL, 0.09 mmol), and DCM (1 mL). The solution was stirred for 18 hours at room temperature. An additional portion of (S)-7-(3-(2-((2-(((9H-fluoren-9-yl)methoxy)carbonyl)-1,2-dimethylhydrazinyl)methyl)-1H-indol-1-yl)propanamido)-2,2-dimethyl-4,8-dioxo-3,12,15-trioxa-9-azaoctadecan-18-oic acid (6 mg, 0.007 mmol), HATU (10 mg, 0.03 mmol), and DIPEA (10 µL, 0.06 mmol) were added and the resulting solution was stirred for an additional 2 hours at room temperature. The reaction mixture was concentrated under reduced pressure and subsequently purified by C18 flash chromatography (elute 25-100% MeCN/water) to yield the title compound as a white solid (82 mg, 94% yield).

ESI-MS calculated [MH]$^+$: 1900.0; found 1900.3.

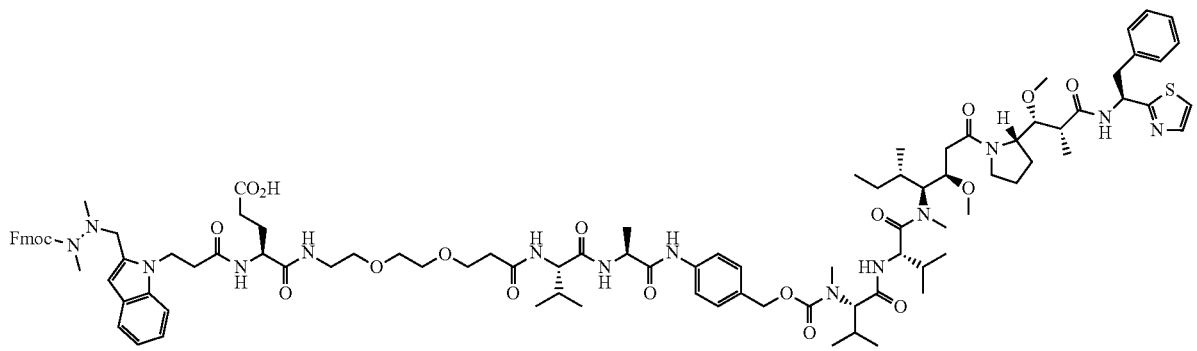

Preparation of (2S,5S,18S)-18-(3-(2-((2-(((9H-fluoren-9-yl)methoxy)carbonyl)-1,2-dimethylhydrazinyl)methyl)-1H-indol-1-yl)propanamido)-1-((4-((5S,8S,11S,12R)-11-((S)-sec-butyl)-5,8-diisopropyl-12-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-4,10-dimethyl-3,6,9-trioxo-2,13-dioxa-4,7,10-triazatetradecyl)phenyl)amino)-5-isopropyl-2-methyl-1,4,7,17-tetraoxo-10,13-dioxa-3,6,16-triazahenicosan-21-oic acid (Fmoc-HIPS-Glu(OH)-PEG2-Val-Ala-PABC-MMAD) (FIG. 61)

To a dried scintillation vial containing a magnetic stir bar was added Fmoc-HIPS-Glu(OtBu)-PEG2-Val-Ala-PABC-MMAD (82 mg, 0.043 mmol) and DCM (0.5 mL). The solution was cooled to 0° C. and tin(IV) tetrachloride was added (0.25 mL, 1.0 M in DCM, 0.25 mmol). The resulting mixture was stirred for 1 hour at 0° C. The reaction mixture was directly purified by C18 flash chromatography (elute 5-100% MeCN/water) to yield the title compound as a white solid (62 mg, 78% yield).

ESI-MS calculated [MH]$^+$: 1844.0; found 1844.2.

Preparation of (2S,5S,18S)-1-((4-((5S,8S,11S,12R)-11-((S)-sec-butyl)-5,8-diisopropyl-12-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-4,10-dimethyl-3,6,9-trioxo-2,13-dioxa-4,7,10-triazatetradecyl)phenyl)amino)-18-(3-(2-((1,2-dimethylhydrazinyl)methyl)-1H-indol-1-yl)propanamido)-5-isopropyl-2-methyl-1,4,7,17-tetraoxo-10,13-dioxa-3,6,16-triazahenicosan-21-oic acid (HIPS-Glu(OH)-PEG2-Val-Ala-PABC-MMAD) (FIG. 61)

To a dried scintillation vial containing a magnetic stir bar was added Fmoc-HIPS-Glu(OH)-PEG2-Val-Ala-PABC-MMAD (62 mg, 0.034 mmol), piperidine (0.1 mL, 1 mmol) and DMF (0.5 mL). The reaction mixture was stirred for 20 minutes at room temperature and then purified by C18 flash chromatography (elute 5-75% MeCN/water) to yield the title compound as a white solid (25 mg, 46% yield).

ESI-MS calculated [MH]$^+$: 1621.9; found 1622.1.

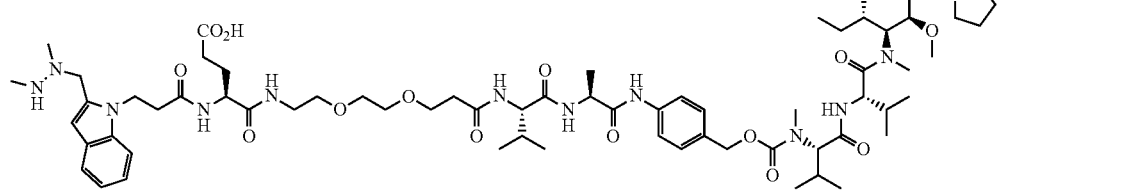

Example 22

Figure 62:
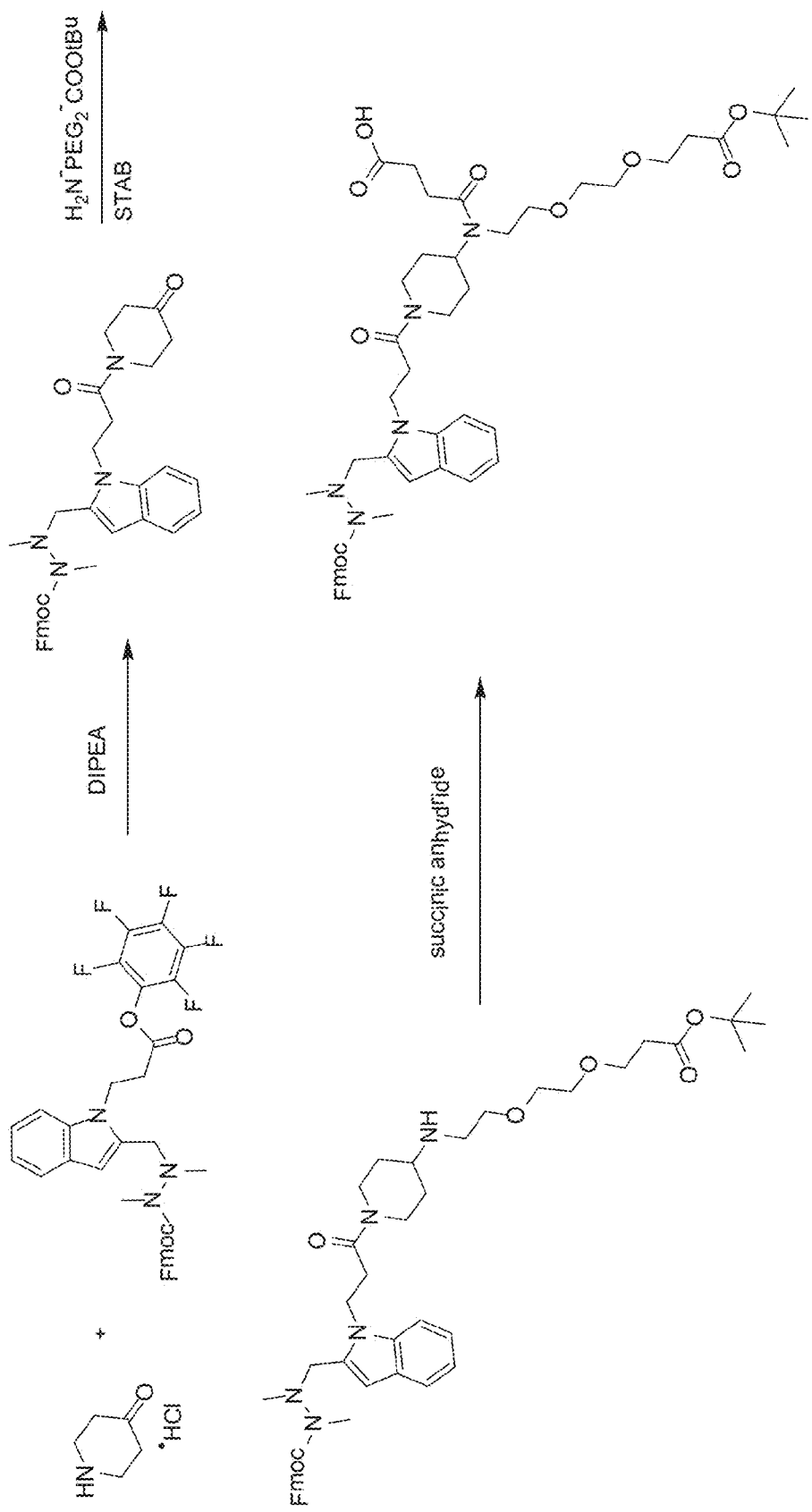
FIG. 62 shows a reaction scheme for the synthesis of 13-(1-(3-(2-((2-(((9H-fluoren-9-yl)methoxy)carbonyl)-1,2-dimethylhydrazinyl)methyl)-1H-indol-1-yl)propanoyl)piperidin-4-yl)-2,2-dimethyl-4,14-dioxo-3,7,10-trioxa-13-azaheptadecan-17-oic acid (Fmoc-HIPS-PAPip(PEG2(CO2t-Bu))CO2H) according to embodiments of the present disclosure, see e.g., Example 22.

A reaction scheme for the synthesis of 13-(1-(3-(2-((2-(((9H-fluoren-9-yl)methoxy)carbonyl)-1,2-dimethylhydrazinyl)methyl)-1H-indol-1-yl)propanoyl)piperidin-4-yl)-2,2-dimethyl-4,14-dioxo-3,7,10-trioxa-13-azaheptadecan-17-oic acid (Fmoc-HIPS-PAPip(PEG2(CO2t-Bu))CO2H) is shown in FIG. 62.

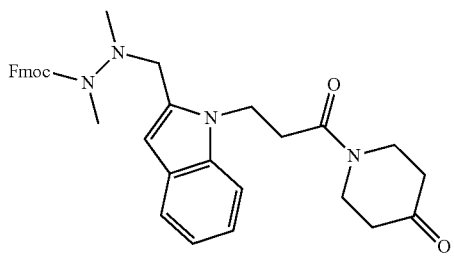

Preparation of (9H-fluoren-9-yl)methyl 1,2-dimethyl-2-((1-(3-oxo-3-(4-oxopiperidin-1-yl)propyl)-1H-indol-2-yl)methyl)hydrazine-1-carboxylate (Fmoc-HIPS-piperidinone) (FIG. 62)

To a dried scintillation vial containing a magnetic stir bar was added (9H-fluoren-9-yl)methyl 1,2-dimethyl-2-((1-(3-oxo-3-(perfluorophenoxy)propyl)-1H-indol-2-yl)methyl)hydrazine-1-carboxylate (700 mg, 1.08 mmol), 4-piperidinone hydrochloride monohydrate (183 mg, 1.2 mmol), DIPEA (400 µL, 2.3 mmol), 1,2-dichloroethane (5 mL), and DMF (0.5 mL). The solution was stirred for 2 hours at room temperature. The reaction mixture was diluted with EtOAc (100 mL) and then washed with HCl (1 M, 3×30 mL), saturated NaHCO$_3$ (3×30 mL), water (2×30 mL), and brine (1×30 mL). The organic layer was dried over Na$_2$SO$_4$, filtered and, concentrated under reduced pressure, and dried in vacuo to yield the title compound as a white solid (355 mg, 58% yield), which was used without further characterization.

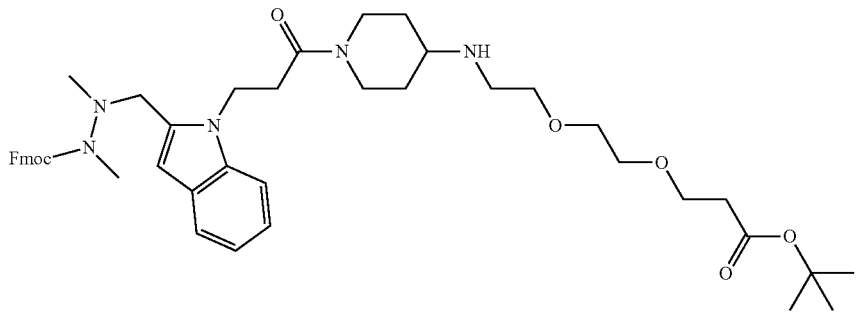

Preparation of (9H-fluoren-9-yl)methyl 2-((1-(3-(4-((2-(2-(3-(tert-butoxy)-3-oxopropoxy)ethoxy)ethyl)amino)piperidin-1-yl)-3-oxopropyl)-1H-indol-2-yl)methyl)-1,2-dimethylhydrazine-1-carboxylate (Fmoc-HIPS-PAPip(PEG2(CO2t-Bu))NH) (FIG. 62)

To a dried scintillation vial containing a magnetic stir bar was added Fmoc-HIPS-piperidinone (355 mg, 0.63 mmol), H$_2$N-PEG2-COOtBu (175 mg, 0.76 mmol), 4 Å molecular sieves (activated powder, 100 mg), and 1,2-dichloroethane (2.5 mL). The mixture was stirred for 1 h at room temperature. To the reaction mixture was added sodium triacetoxyborohydride (314 mg, 1.48 mmol). The mixture was stirred for 18 hours at room temperature. The resulting mixture was partitioned between EtOAc and saturated aqueous NaHCO$_3$. The organic layer was washed with saturated aqueous NaHCO$_3$ (2×5 mL), and brine (1×5 mL), dried over Na$_2$SO$_4$, filtered, and concentrated under reduced pressure to yield the title compound as a yellow oil, which was carried forward without further characterization.

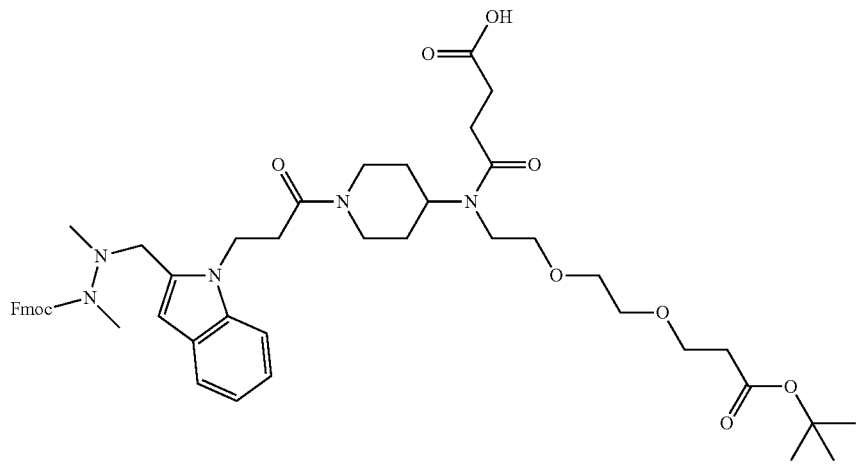

Preparation of 13-(1-(3-(2-((2-(((9H-fluoren-9-yl)methoxy)carbonyl)-1,2-dimethylhydrazinyl)methyl)-1H-indol-1-yl)propanoyl)piperidin-4-yl)-2,2-dimethyl-4,14-dioxo-3,7,10-trioxa-13-azaheptadecan-17-oic acid (Fmoc-HIPS-PAPip(PEG2(CO2t-Bu))CO2H) (FIG. 62)

To a dried scintillation vial containing a magnetic stir bar was added Fmoc-HIPS-PAPip(PEG2(CO2t-Bu))NH from the previous step, succinic anhydride (153 mg, 1.53 mmol), 4-(dimethylamino)pyridine (5 mg, 0.04 mmol), and dichloromethane (2 mL). The mixture was stirred for 1 h at room temperature. Methanol (1 mL) was added and the mixture was stirred for 15 minutes. The reaction mixture was purified by C18 flash chromatography (elute 5-100% MeCN/water with 0.1% acetic acid). Product-containing fractions were concentrated under reduced pressure and then azeotroped with toluene (3×50 mL) to remove residual acetic acid. The title compound was obtained as a foamy white solid (366 mg, 38% yield over 3 steps).

ESI-MS calculated [MH]$^+$: 882.5; found 882.7.

Example 23

Figure 63:
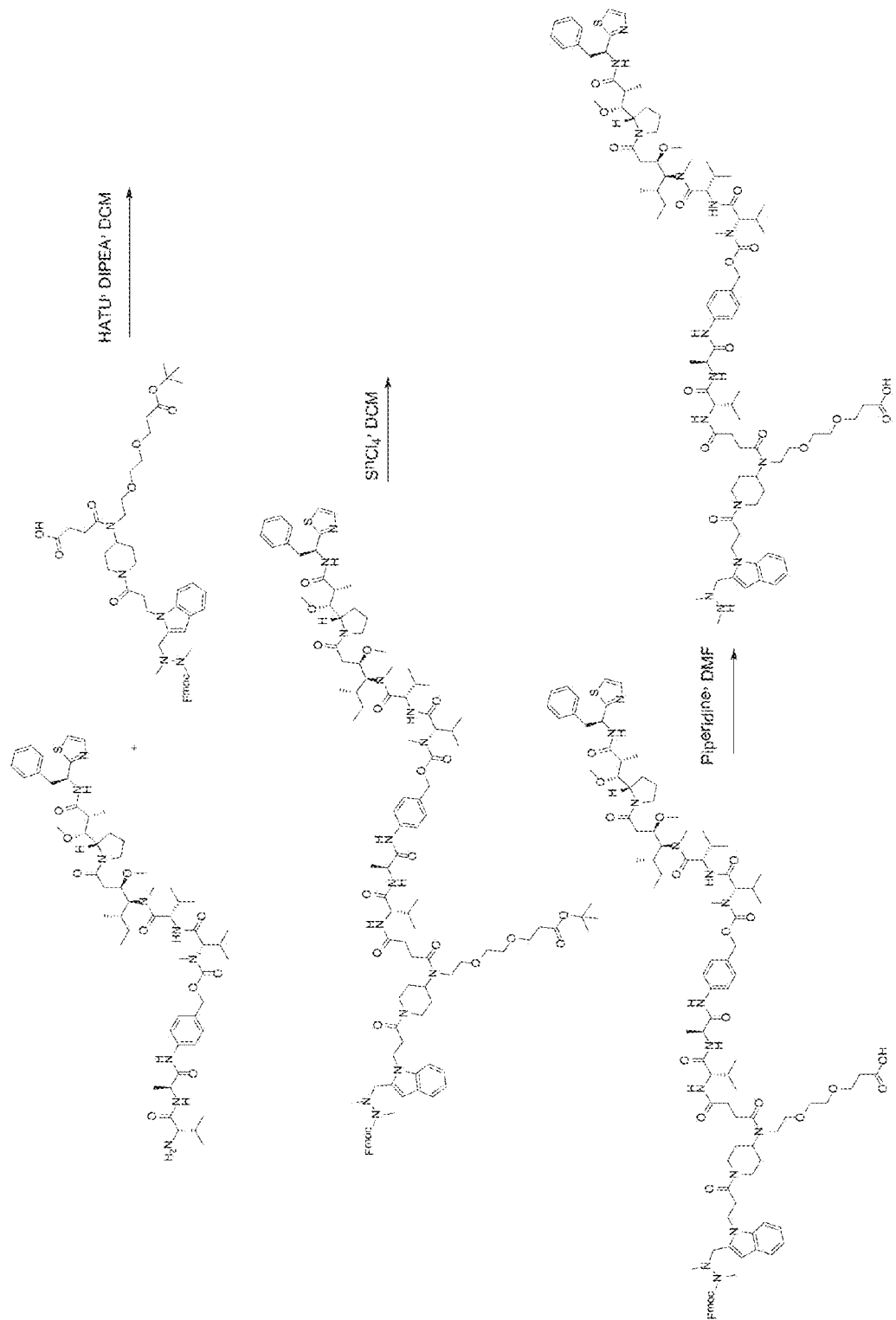
FIG. 63 shows a reaction scheme for the synthesis of (2S,5S)-1-((4-((5S,8S,11S,12R)-11-((S)-sec-butyl)-5,8-diisopropyl-12-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-4,10-dimethyl-3,6,9-trioxo-2,13-dioxa-4,7,10-triazatetradecyl)phenyl)amino)-11-(1-(3-(2-((1,2-dimethylhydrazinyl)methyl)-1H-indol-1-yl)propanoyl)piperidin-4-yl)-5-isopropyl-2-methyl-1,4,7,10-tetraoxo-14,17-dioxa-3,6,11-triazaicosan-20-oic acid according to embodiments of the present disclosure, see e.g., Example 23.

A reaction scheme for the synthesis of (2S,5S)-1-((4-((5S,8S,11S,12R)-11-((S)-sec-butyl)-5,8-diisopropyl-12-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-4,10-dimethyl-3,6,9-trioxo-2,13-dioxa-4,7,10-triazatetradecyl)phenyl)amino)-11-(1-(3-(2-((1,2-dimethylhydrazinyl)methyl)-1H-indol-1-yl)propanoyl)piperidin-4-yl)-5-isopropyl-2-methyl-1,4,7,10-tetraoxo-14,17-dioxa-3,6,11-triazaicosan-20-oic acid is shown in FIG. 63.

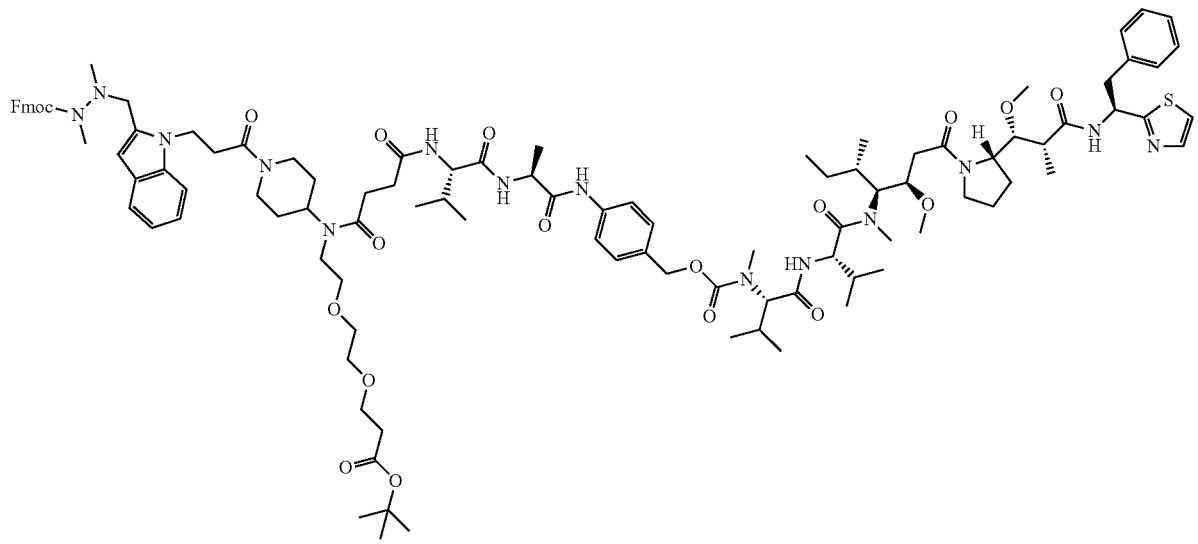

Preparation of tert-butyl (2S,5S)-11-(1-(3-(2-((2-(((9H-fluoren-9-yl)methoxy)carbonyl)-1,2-dimethyl-hydrazinyl)methyl)-1H-indol-1-yl)propanoyl)piperidin-4-yl)-1-((4-((5S,8S,11S,12R)-11-((S)-sec-butyl)-5,8-diisopropyl-12-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-4,10-dimethyl-3,6,9-trioxo-2,13-dioxa-4,7,10-triazatetradecyl)phenyl)amino)-5-isopropyl-2-methyl-1,4,7,10-tetraoxo-14,17-dioxa-3,6,11-triazaicosan-20-oate (Fmoc-HIPS-PAPip(PEG2(CO2t-Bu))-Val-Ala-PABC-MMAD) (FIG. 63)

To a dried scintillation vial containing a magnetic stir bar was added Fmoc-HIPS-PAPip(PEG2(CO2t-Bu))CO2H (45 mg, 0.051 mmol), H$_2$N-Val-Ala-PABC-MMAD (50 mg, 0.046 mmol), HATU (20 mg, 0.053 mmol), DIPEA (16 μL, 0.09 mmol), and DCM (1 mL). The solution was stirred for 18 hours at room temperature. The reaction mixture was concentrated under reduced pressure and subsequently purified by C18 flash chromatography (elute 20-100% MeCN/water) to yield the title compound as a white solid (89 mg, 99% yield).

ESI-MS calculated [MH]$^+$: 1954.1; found 1954.3.

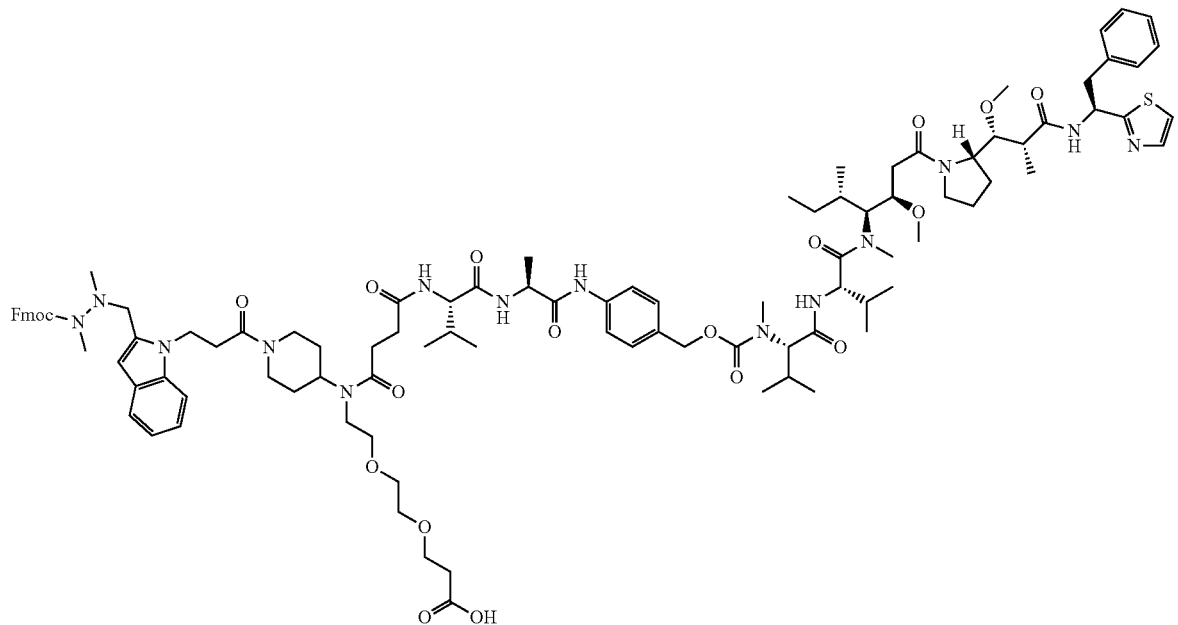

Preparation of (2S,5S)-11-(1-(3-(2-((2-(((9H-fluoren-9-yl)methoxy)carbonyl)-1,2-dimethylhydrazinyl)methyl)-1H-indol-1-yl)propanoyl)piperidin-4-yl)-1-((4-((5S,8S,11S,12R)-11-((S)-sec-butyl)-5,8-diisopropyl-12-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-4,10-dimethyl-3,6,9-trioxo-2,13-dioxa-4,7,10-triazatetradecyl)phenyl)amino)-5-isopropyl-2-methyl-1,4,7,10-tetraoxo-14,17-dioxa-3,6,11-triazaicosan-20-oic acid (Fmoc-HIPS-PAPip(PEG2(CO2H))-Val-Ala-PABC-MMAD) (FIG. 63)

To a dried scintillation vial containing a magnetic stir bar was added Fmoc-HIPS-PAPip(PEG2(CO2t-Bu))-Val-Ala-PABC-MMAD (89 mg, 0.045 mmol) and DCM (0.5 mL). The solution was cooled to 0° C. and tin(IV) tetrachloride was added (0.25 mL, 1.0 M in DCM, 0.25 mmol). The resulting mixture was stirred for 1 hour at 0° C. The reaction mixture was directly purified by C18 flash chromatography (elute 10-100% MeCN/water) to yield the title compound as a white solid (48 mg, 56% yield).

ESI-MS calculated [MH]$^+$: 1898.0; found 1898.2.

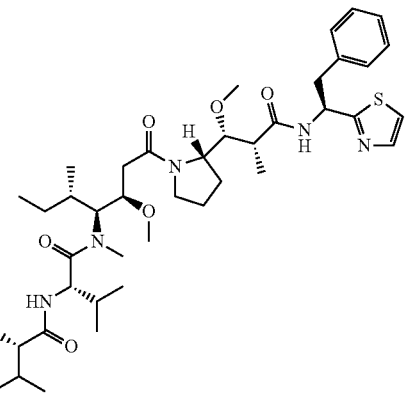
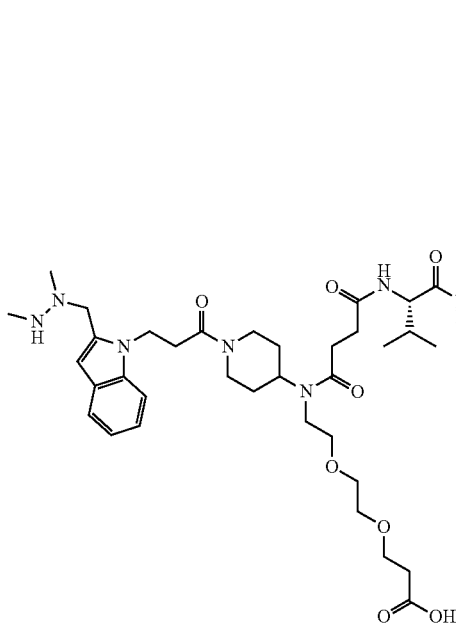

Preparation of (2S,5S)-1-((4-((5S,8S,11S,12R)-11-((S)-sec-butyl)-5,8-diisopropyl-12-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-4,10-dimethyl-3,6,9-trioxo-2,13-dioxa-4,7,10-triazatetradecyl)phenyl)amino)-11-(1-(3-(2-((1,2-dimethylhydrazinyl)methyl)-1H-indol-1-yl)propanoyl)piperidin-4-yl)-5-isopropyl-2-methyl-1,4,7,10-tetraoxo-14,17-dioxa-3,6,11-triazaicosan-20-oic acid (FIG. 63)

To a dried scintillation vial containing a magnetic stir bar was added (Fmoc-HIPS-PAPip(PEG2(CO2H))-Val-Ala-PABC-MMAD (48 mg, 0.025 mmol), piperidine (0.1 mL, 1 mmol) and DMF (0.5 mL). The reaction mixture was stirred for 15 minutes at room temperature and then purified by C18 flash chromatography (elute 5-70% MeCN/water) to yield the title compound as a white solid (43 mg, >99% yield).
ESI-MS calculated [MH]+: 1676.0; found 1676.2.

Example 24

Figure 64:
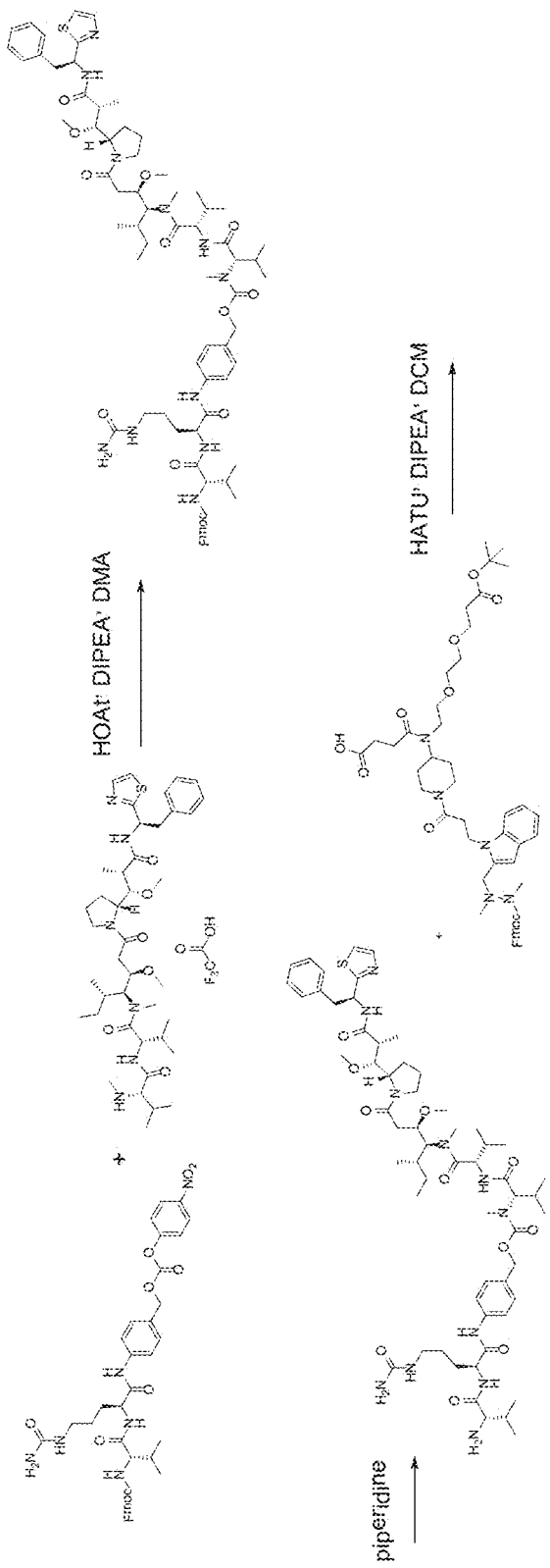
FIG. 64 shows a reaction scheme for the synthesis of (6S,9S)-1-amino-6-((4-((5S,8S,11S,12R)-11-((S)-sec-butyl)-5,8-diisopropyl-12-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-4,10-dimethyl-3,6,9-trioxo-2,13-dioxa-4,7,10-triazatetradecyl)phenyl)carbamoyl)-15-(1-(3-(2-((1,2-dimethylhydrazinyl)methyl)-1H-indol-1-yl)propanoyl)piperidin-4-yl)-9-isopropyl-1,8,11,14-tetraoxo-18,21-dioxa-2,7,10,15-tetraazatetracosan-24-oic acid according to embodiments of the present disclosure, see e.g., Example 24.

A reaction scheme for the synthesis of (6S,9S)-1-amino-6-((4-((5S,8S,11S,12R)-11-((S)-sec-butyl)-5,8-diisopropyl-12-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-4,10-dimethyl-3,6,9-trioxo-2,13-dioxa-4,7,10-triazatetradecyl)phenyl)carbamoyl)-15-(1-(3-(2-((1,2-dimethylhydrazinyl)methyl)-1H-indol-1-yl)propanoyl)piperidin-4-yl)-9-isopropyl-1,8,11,14-tetraoxo-18,21-dioxa-2,7,10,15-tetraazatetracosan-24-oic acid is shown in FIG. 64.

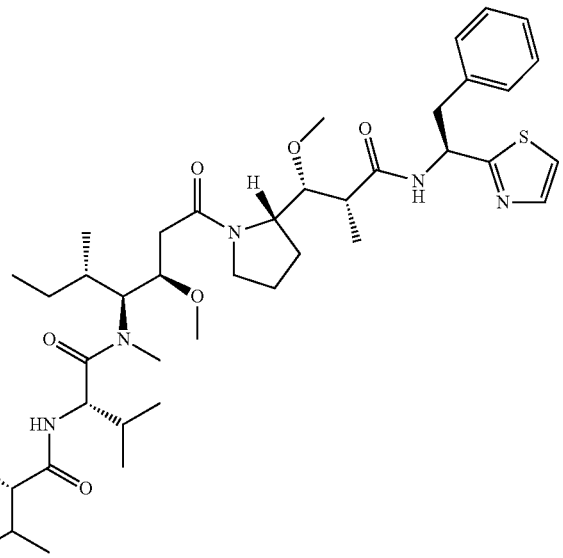
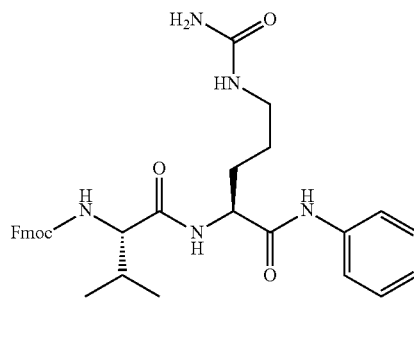

Preparation of 4-((S)-2-((S)-2-((((9H-fluoren-9-yl)
methoxy)carbonyl)amino)-3-methylbutanamido)-5-
ureidopentanamido)benzyl ((S)-1-(((S)-1-(((3R,4S,
5S)-3-methoxy-1-((S)-2-((1R,2R)-1-methoxy-2-
methyl-3-oxo-3-(((S)-2-phenyl-1-(thiazol-2-yl)ethyl)
amino)propyl)pyrrolidin-1-yl)-5-methyl-1-
oxoheptan-4-yl)(methyl)amino)-3-methyl-1-
oxobutan-2-yl)amino)-3-methyl-1-oxobutan-2-yl)
(methyl)carbamate (Fmoc-Val-Cit-PABC-MMAD)
(FIG. 64)

To a dried scintillation vial containing a magnetic stir bar was added (9H-fluoren-9-yl)methyl ((S)-3-methyl-1-(((S)-1-((4-((((4-nitrophenoxy)carbonyl)oxy)methyl)phenyl)amino)-1-oxopropan-2-yl)amino)-1-oxobutan-2-yl)carbamate (84 mg, 0.11 mmol), monomethyl auristatin D (TFA salt, 88 mg, 0.1 mmol), HOAt (5 mg, 0.004 mmol), DIPEA (35 µL, 0.2 mmol), and DMA (0.5 mL). The solution was stirred for 1 hour at room temperature. To the reaction mixture was added lutidine (35 µL, 0.3 mmol), additional (9H-fluoren-9-yl)methyl ((S)-3-methyl-1-(((S)-1-((4-((((4-nitrophenoxy)carbonyl)oxy)methyl)phenyl)amino)-1-oxopropan-2-yl)amino)-1-oxobutan-2-yl)carbamate (17 mg, 0.02 mmol), and DIPEA (35 µL, 0.2 mmol). The reaction mixture was heated to 40° C. and stirred for 24 hours. The reaction mixture was purified by flash chromatography (elute 1-20% MeOH/DCM) to yield the title compound as a white solid (107 mg, 76% yield).

ESI-MS calculated [MH]$^+$: 1398.8; found 1399.1.

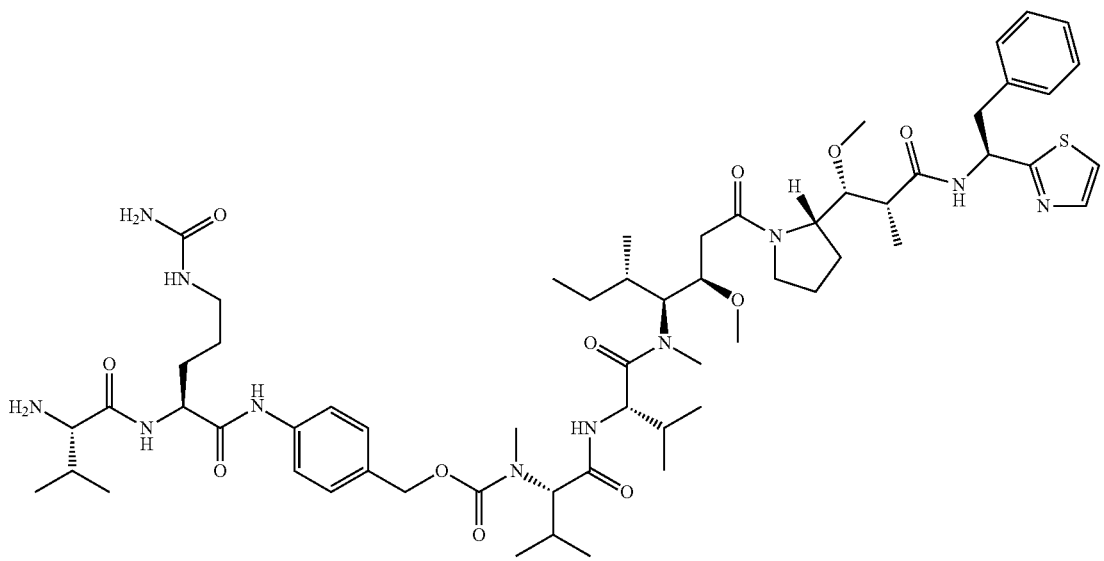 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)C(=O)OCc1ccc(NC(=O)[C@H](CCCNC(N)=O)NC(=O)[C@@H](N)C(C)C)cc1)C(C)C]

Preparation of 4-((S)-2-((S)-2-amino-3-methylbu-
tanamido)-5-ureidopentanamido)benzyl ((S)-1-(((S)-
1-(((3R,4S,5S)-3-methoxy-1-((S)-2-((1R,2R)-1-
methoxy-2-methyl-3-oxo-3-(((S)-2-phenyl-1-
(thiazol-2-yl)ethyl)amino)propyl)pyrrolidin-1-yl)-5-
methyl-1-oxoheptan-4-yl)(methyl)amino)-3-methyl-
1-oxobutan-2-yl)amino)-3-methyl-1-oxobutan-2-yl)
(methyl)carbamate (H$_2$N-Val-Cit-PABC-MMAD)
(FIG. 64)

To a dried scintillation vial containing a magnetic stir bar was added Fmoc-Val-Cit-PABC-MMAD (107 mg, 0.076 mmol), piperidine (0.1 mL, 1 mmol) and DMF (0.5 mL). The reaction mixture was stirred for 20 minutes at room temperature and then purified by C18 flash chromatography (elute 5-100% MeCN/water) to yield the title compound as a white solid (52 mg, 58% yield), which was carried forward without further characterization.

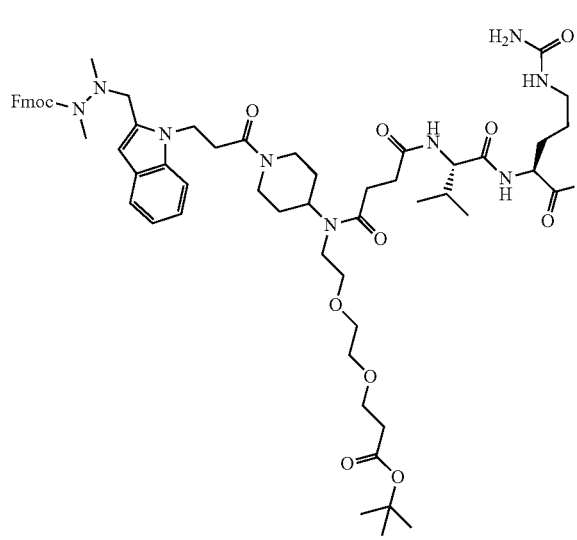
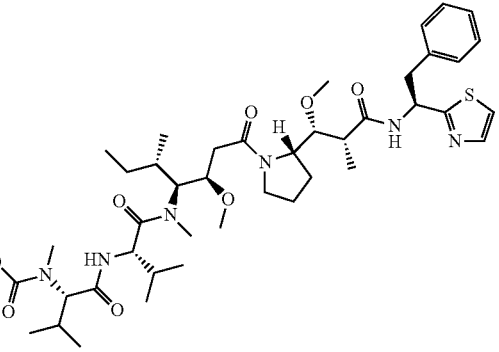

Preparation of tert-butyl (6S,9S)-15-(1-(3-(2-((2-(((9H-fluoren-9-yl)methoxy)carbonyl)-1,2-dimethylhydrazinyl)methyl)-1H-indol-1-yl)propanoyl)piperidin-4-yl)-1-amino-6-((4-((5S,8S,11S,12R)-11-((S)-sec-butyl)-5,8-diisopropyl-12-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-4,10-dimethyl-3,6,9-trioxo-2,13-dioxa-4,7,10-triazatetradecyl)phenyl)carbamoyl)-9-isopropyl-1,8,11,14-tetraoxo-18,21-dioxa-2,7,10,15-tetraazatetracosan-24-oate (Fmoc-HIPS-PAPip(PEG2(CO2t-Bu))-Val-Cit-PABC-MMAD)(FIG. 64)

To a dried scintillation vial containing a magnetic stir bar was added Fmoc-HIPS-PAPip(PEG2(CO2t-Bu))CO2H (28 mg, 0.032 mmol), H$_2$N-Val-Cit-PABC-MMAD (36 mg, 0.031 mmol), HATU (24 mg, 0.063 mmol), DIPEA (20 μL, 0.12 mmol), DMF (0.5 mL), and DCM (0.6 mL). The solution was stirred for 1 hour at room temperature. The reaction mixture was purified by C18 flash chromatography (elute 25-100% MeCN/water) to yield the title compound as a white solid (53 mg, 85% yield).

ESI-MS calculated [MH]$^+$: 2040.1; found 2040.5.

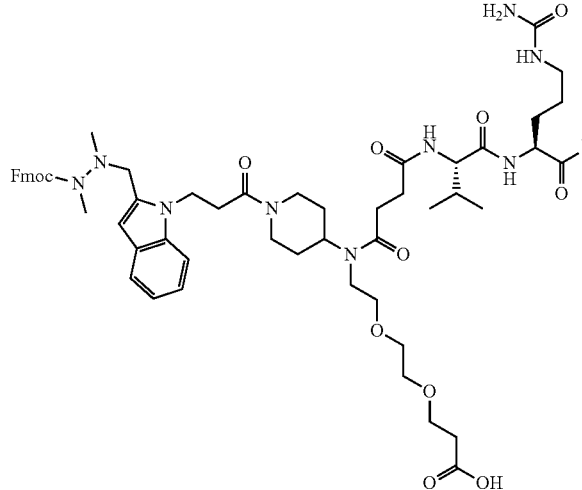
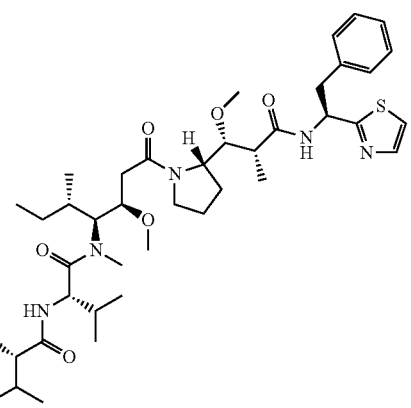

Preparation of (6S,9S)-15-(1-(3-(2-((2-(((9H-fluoren-9-yl)methoxy)carbonyl)-1,2-dimethylhydrazinyl)methyl)-1H-indol-1-yl)propanoyl)piperidin-4-yl)-1-amino-6-((4-((5S,8S,11S,12R)-11-((S)-sec-butyl)-5,8-diisopropyl-12-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-4,10-dimethyl-3,6,9-trioxo-2,13-dioxa-4,7,10-triazatetradecyl)phenyl)carbamoyl)-9-isopropyl-1,8,11,14-tetraoxo-18,21-dioxa-2,7,10,15-tetraazatetracosan-24-oic acid (Fmoc-HIPS-PAPip(PEG2(CO2H))-Val-Cit-PABC-MMAD)(FIG. 64)

To a dried scintillation vial containing a magnetic stir bar was added Fmoc-HIPS-PAPip(PEG2(CO2t-Bu))-Val-Cit-PABC-MMAD (53 mg, 0.026 mmol) and DCM (0.8 mL). The solution was cooled to 0° C. and tin(IV) tetrachloride was added (0.2 mL, 1.0 M in DCM, 0.2 mmol). The resulting mixture was stirred for 1 hour at 0° C. The reaction mixture was directly purified by C18 flash chromatography (elute 5-100% MeCN/water) to yield the title compound as a white solid (24 mg, 47% yield).
ESI-MS calculated [MH]$^+$: 1984.1; found 1984.3.

for 15 minutes at room temperature and then purified by C18-flash chromatography (elute 5-80% MeCN/water) to yield the title compound as a white solid (15 mg, 70% yield).
ESI-MS calculated [MH]$^+$: 1762.0; found 1762.2.

Example 25

Figure 65:
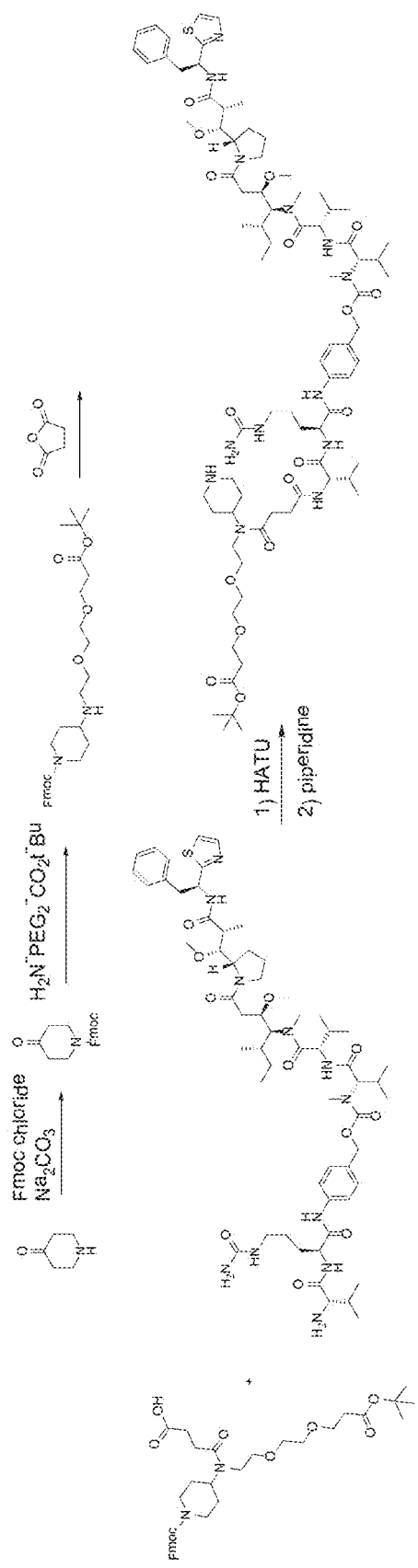
FIG. 65 shows a reaction scheme for the synthesis of (6S,9S)-1-amino-6-((4-((5S,8S,11S,12R)-11-((S)-sec-butyl)-5,8-diisopropyl-12-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-4,10-dimethyl-3,6,9-trioxo-2,13-dioxa-4,7,10-triazatetradecyl)phenyl)carbamoyl)-15-(1-(3-(2-((1,2-dimethylhydrazinyl)methyl)-1H-pyrrolo[2,3-b]pyridin-1-yl)propanoyl)piperidin-4-yl)-9-isopropyl-1,8,11,14-tetraoxo-18,21-dioxa-2,7,10,15-tetraazatetracosan-24-oic acid according to embodiments of the present disclosure, see e.g., Example 25.

A reaction scheme for the synthesis of (6S,9S)-1-amino-6-((4-((5S,8S,11S,12R)-11-((S)-sec-butyl)-5,8-diisopropyl-12-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-4,10-dimethyl-3,6,9-trioxo-2,13-dioxa-4,7,10-triazatetradecyl)phenyl)carbamoyl)-15-(1-(3-(2-((1,2-dimethylhydrazinyl)methyl)-1H-pyrrolo[2,3-b]pyridin-1-yl)propanoyl)piperidin-4-yl)-9-isopropyl-1,8,11,14-tetraoxo-18,21-dioxa-2,7,10,15-tetraazatetracosan-24-oic acid is shown in FIG. 65.

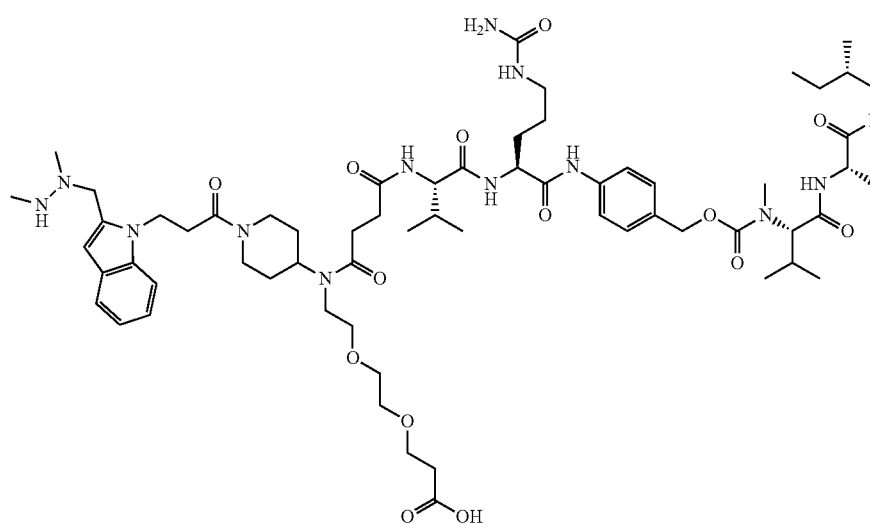

Preparation of (6S,9S)-1-amino-6-((4-((5S,8S,11S,12R)-11-((S)-sec-butyl)-5,8-diisopropyl-12-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-4,10-dimethyl-3,6,9-trioxo-2,13-dioxa-4,7,10-triazatetradecyl)phenyl)carbamoyl)-15-(1-(3-(2-((1,2-dimethylhydrazinyl)methyl)-1H-indol-1-yl)propanoyl)piperidin-4-yl)-9-isopropyl-1,8,11,14-tetraoxo-18,21-dioxa-2,7,10,15-tetraazatetracosan-24-oic acid (FIG. 64)

To a dried scintillation vial containing a magnetic stir bar was added (Fmoc-HIPS-PAPip(PEG2(CO2H))-Val-Cit-PABC-MMAD (24 mg, 0.012 mmol), piperidine (0.1 mL, 1 mmol) and DMF (0.5 mL). The reaction mixture was stirred

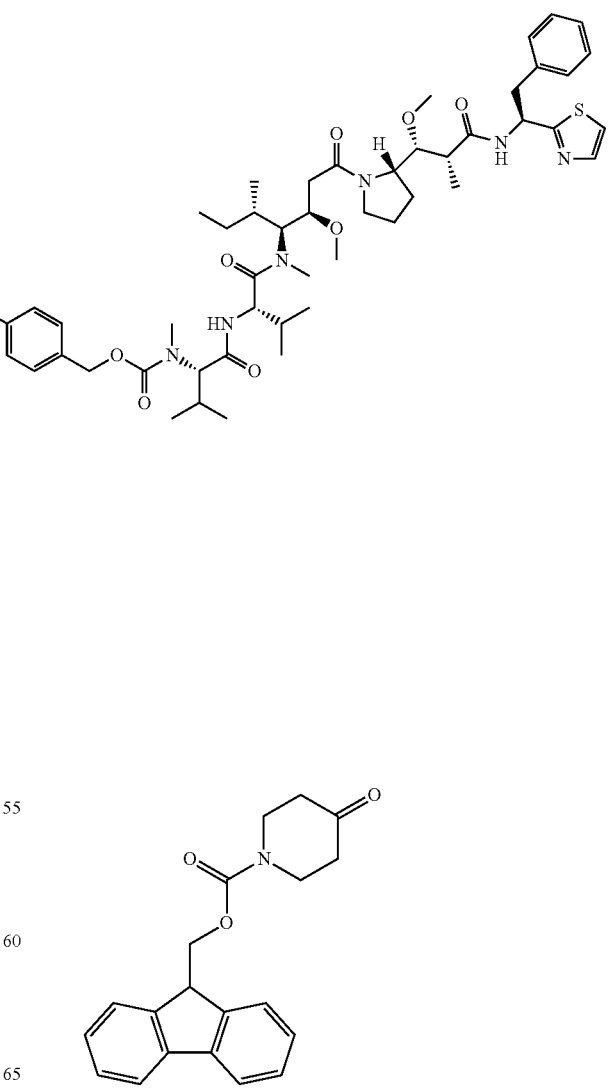

Preparation of (9H-fluoren-9-yl)methyl 4-oxopiperidine-1-carboxylate (N-Fmoc-piperidinone) (FIG. 65)

To a 100 mL round-bottom flask containing a magnetic stir bar was added piperidinone hydrochloride monohydrate (1.53 g, 10 mmol), Fmoc chloride (2.58 g, 10 mmol), sodium carbonate (3.18 g, 30 mmol), dioxane (20 mL), and water (2 mL). The reaction mixture was stirred at room temperature for 1 h. The mixture was diluted with EtOAc (100 mL) and extracted with water (1×100 mL). The organic layer was dried over $Na_2SO_4$, filtered, and concentrated under reduced pressure. The resulting material was dried in vacuo to yield the title compound as a white solid (3.05 g, 95% yield).

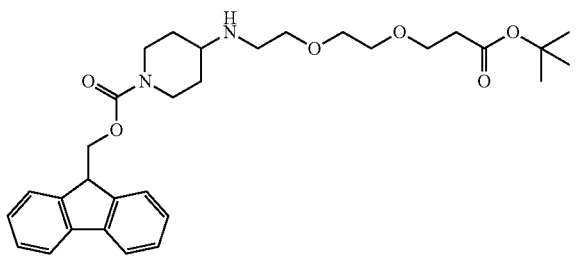 [SMILES: CC(C)(C)OC(=O)CCOCCOCCNC1CCN(C(=O)OCC2c3ccccc3-c3ccccc32)CC1]

Preparation of (9H-fluoren-9-yl)methyl 4-((2-(2-(3-(tert-butoxy)-3-oxopropoxy)ethoxy)ethyl)amino)piperidine-1-carboxylate (N-Fmoc-piperidine-4-amino-PEG2-COOtBu) (FIG. 65)

To a dried scintillation vial containing a magnetic stir bar was added Fmoc-piperidinone (642 mg, 2.0 mmol), H2N-PEG2-COOtBu (560 mg, 2.4 mmol), 4 Å molecular sieves (activated powder, 500 mg), and 1,2-dichloroethane (5 mL). The mixture was stirred for 1 h at room temperature. To the reaction mixture was added sodium triacetoxyborohydride (845 mg, 4.0 mmol). The mixture was stirred for 5 days at room temperature. The resulting mixture was diluted with EtOAc. The organic layer was washed with saturated $NaHCO_3$ (1×50 mL), and brine (1×50 mL), dried over $Na_2SO_4$, filtered, and concentrated under reduced pressure to yield the title compound as an oil, which was carried forward without further purification.

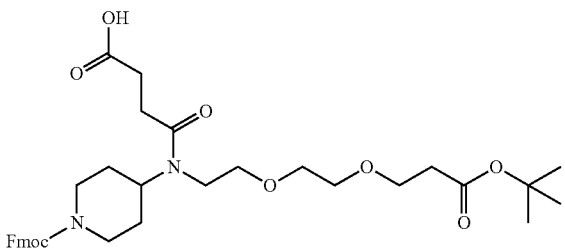

Preparation of 13-(1-(((9H-fluoren-9-yl)methoxy)carbonyl)piperidin-4-yl)-2,2-dimethyl-4,14-dioxo-3,7,10-trioxa-13-azaheptadecan-17-oic acid (Fmoc-PAPip(PEG2(CO2t-Bu))-COOH) (FIG. 65)

To a dried scintillation vial containing a magnetic stir bar was added N-Fmoc-piperidine-4-amino-PEG2-COOt-Bu from the previous step, succinic anhydride (270 mg, 2.7 mmol), and dichloromethane (5 mL). The mixture was stirred for 18 hours at room temperature. The reaction mixture was partitioned between EtOAc and saturated $NaHCO_3$. The aqueous layer was extracted with EtOAc (3×). The aqueous layer was acidified with HCl (1 M) until the pH ~3. The aqueous layer was extracted with DCM (3×). The combined organic layers were dried over $Na_2SO_4$, filtered, and concentrated under reduced pressure. The reaction mixture was purified by C18-flash chromatography (elute 10-100% MeCN/water with 0.1% acetic acid). Product containing fractions were concentrated under reduced pressure and then azeotroped with toluene (3×50 mL) to remove residual acetic acid. The title compound was obtained as a white solid (534 mg, 42% yield over 2 steps).

ESI-MS calculated [MH]$^+$: 639.3; found 639.2.

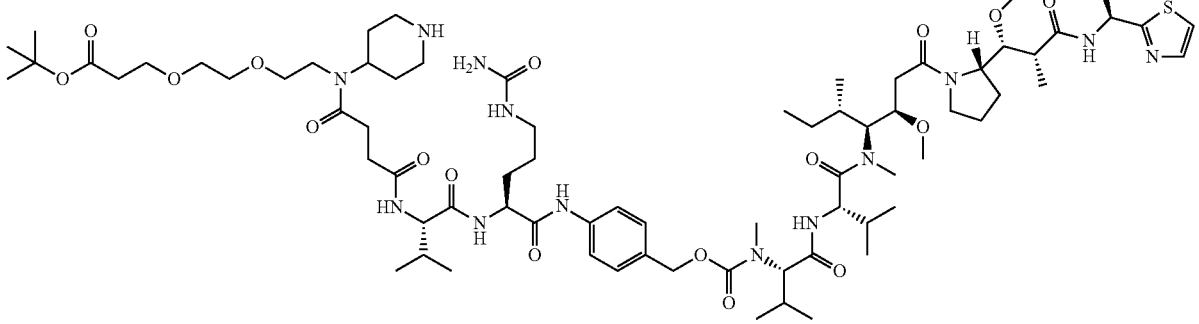

Preparation of tert-butyl (6S,9S)-1-amino-6-((4-((5S,8S,11S,12R)-11-((S)-sec-butyl)-5,8-diisopropyl-12-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-4,10-dimethyl-3,6,9-trioxo-2,13-dioxa-4,7,10-triazatetradecyl)phenyl)carbamoyl)-9-isopropyl-1,8,11,14-tetraoxo-15-(piperidin-4-yl)-18,21-dioxa-2,7,10,15-tetraazatetracosan-24-oate (PAPip(PEG2(CO2t-Bu))-Val-Cit-PABC-MMAD)(FIG. 65)

To a dried scintillation vial containing a magnetic stir bar was added Fmoc-PAPip(PEG2(CO2t-Bu))-COOH (22 mg, 0.034 mmol), H₂N-Val-Cit-PABC-MMAD (36 mg, 0.031 mmol), HATU (24 mg, 0.063 mmol), DIPEA (20 µL, 0.12 mmol), and DMF (1 mL). The solution was stirred for 18 hours at room temperature. Piperidine (0.2 mL, 2 mmol) was added to the reaction mixture and the resulting solution was stirred for 20 minutes at room temperature. The reaction mixture was purified by C18-flash chromatography (elute 5-80% MeCN/water) to yield the title compound as a white solid (20 mg, 85% yield).

ESI-MS calculated [MH]⁺: 1574.9; found 1575.1.

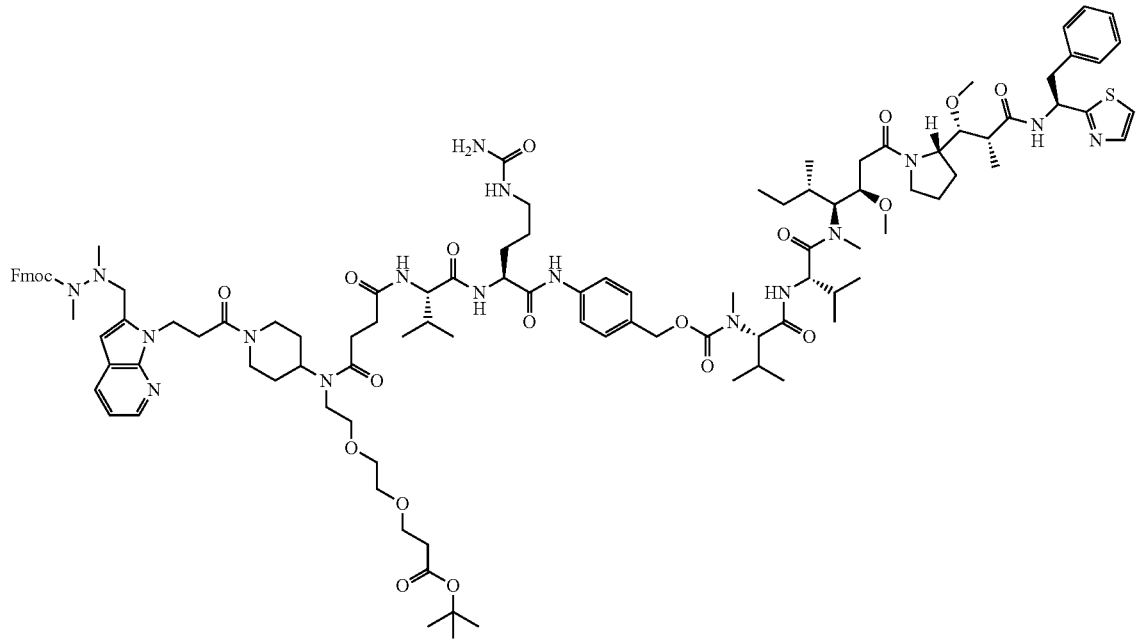

Preparation of tert-butyl (6S,9S)-15-(1-(3-(2-((2-(((9H-fluoren-9-yl)methoxy)carbonyl)-1,2-dimethylhydrazinyl)methyl)-1H-pyrrolo[2,3-b]pyridin-1-yl)propanoyl)piperidin-4-yl)-1-amino-6-((4-((5S,8S,11S,12R)-11-((S)-sec-butyl)-5,8-diisopropyl-12-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-4,10-dimethyl-3,6,9-trioxo-2,13-dioxa-4,7,10-triazatetradecyl)phenyl)carbamoyl)-9-isopropyl-1,8,11,14-tetraoxo-18,21-dioxa-2,7,10,15-tetraazatetracosan-24-oate (Fmoc-AzaHIPS-PAPip(PEG2 (CO2t-Bu))-Val-Cit-PABC-MMAD) (FIG. 65)

To a dried scintillation vial containing a magnetic stir bar was added (PAPip(PEG2(CO2t-Bu))-Val-Cit-PABC-MMAD (20 mg, 0.013 mmol), 3-(2-((2-(((9H-fluoren-9-yl)methoxy)carbonyl)-1,2-dimethylhydrazinyl)methyl)-1H-pyrrolo[2,3-b]pyridin-1-yl)propanoic acid (7 mg, 0.014 mmol), PyAOP (8 mg, 0.015 mmol), DIPEA (3 µL, 0.017 mmol), and DMF (0.5 mL). The solution was stirred for 2 hours at room temperature. The reaction mixture was purified by C18-flash chromatography (elute 5-100% MeCN/water) to yield the title compound as a white solid (20 mg, 77% yield).

ESI-MS calculated [MH]⁺: 2041.1; found 2041.3.

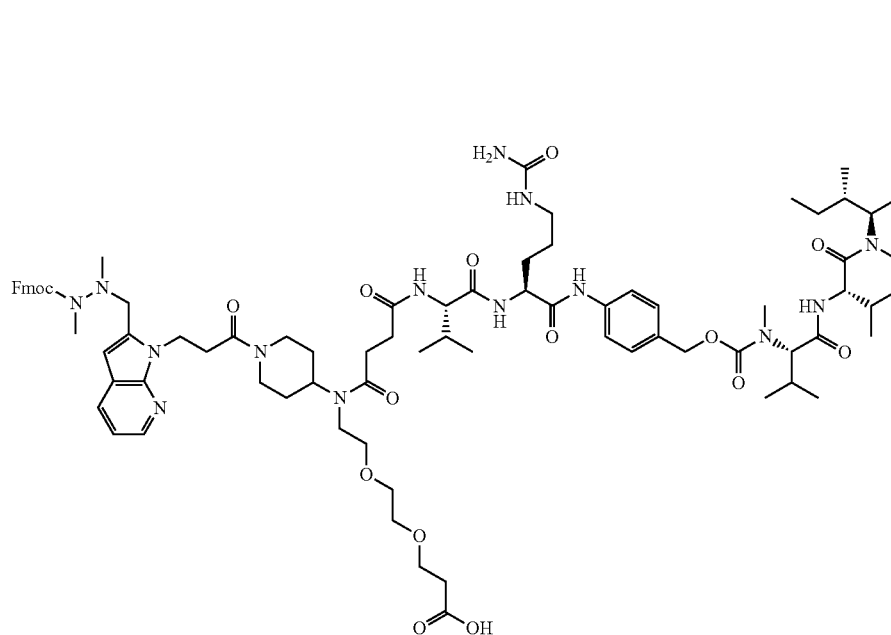
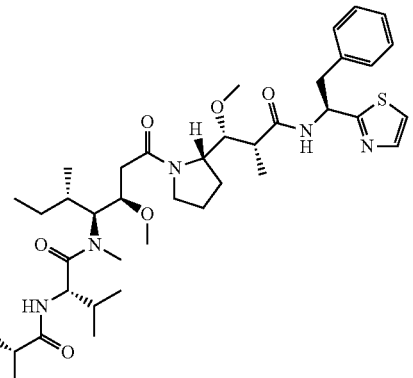

Preparation of (6S,9S)-15-(1-(3-(2-((2-(((9H-fluoren-9-yl)methoxy)carbonyl)-1,2-dimethylhydrazinyl)methyl)-1H-pyrrolo[2,3-b]pyridin-1-yl)propanoyl)piperidin-4-yl)-1-amino-6-((4-((5S,8S,11S,12R)-11-((S)-sec-butyl)-5,8-diisopropyl-12-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-4, 10-dimethyl-3,6,9-trioxo-2,13-dioxa-4,7,10-triazatetradecyl)phenyl)carbamoyl)-9-isopropyl-1,8,11,14-tetraoxo-18,21-dioxa-2,7,10,15-tetraazatetracosan-24-oic acid (Fmoc-AzaHIPS-PAPip(PEG2(CO2H))-Val-Cit-PABC-MMAD) (FIG. 65)

To a dried scintillation vial containing a magnetic stir bar was added Fmoc-AzaHIPS-PAPip(PEG2(CO2t-Bu))-Val-Cit-PABC-MMAD (20 mg, 0.01 mmol) and DCM (0.8 mL). The solution was cooled to 0° C. and tin(IV) tetrachloride was added (0.1 mL, 1.0 M in DCM, 0.1 mmol). The resulting mixture was stirred for 1 hour at 0° C. The reaction mixture was directly purified by C18-flash chromatography (elute 10-100% MeCN/water) to yield the title compound as a white solid (14 mg, 72% yield).

ESI-MS calculated [MH]$^+$: 1985.1; found 1985.3.

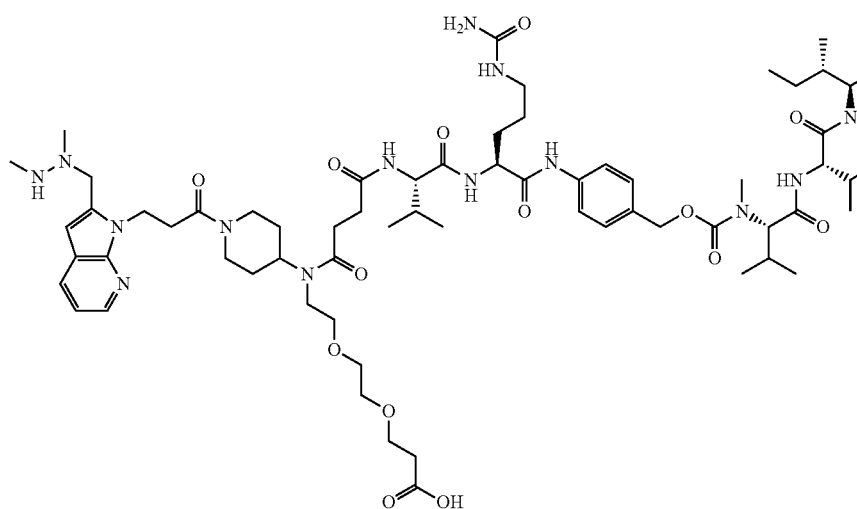
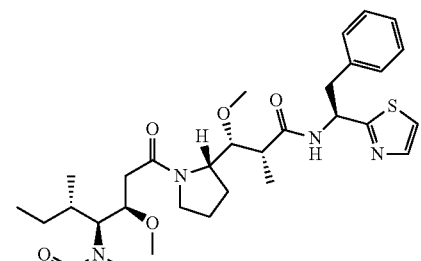

Preparation of (6S,9S)-1-amino-6-((4-((5S,8S,11S,12R)-11-((S)-sec-butyl)-5,8-diisopropyl-12-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-4,10-dimethyl-3,6,9-trioxo-2,13-dioxa-4,7,10-triazatetradecyl)phenyl)carbamoyl)-15-(1-(3-(2(1,2-dimethylhydrazinyl)methyl)-1H-pyrrolo[2,3-b]pyridin-1-yl)propanoyl)piperidin-4-yl)-9-isopropyl-1,8,11,14-tetraoxo-18,21-dioxa-2,7,10,15-tetraazatetracosan-24-oic acid (FIG. 65)

To a dried scintillation vial containing a magnetic stir bar was added Fmoc-AzaHIPS-PAPip(PEG2(CO2H))-Val-Cit-PABC-MMAD (14 mg, 0.007 mmol), piperidine (0.05 mL, 0.5 mmol) and DMF (0.5 mL). The reaction mixture was stirred for 15 minutes at room temperature and then purified by C18-flash chromatography (elute 5-80% MeCN/water) to yield the title compound as a white solid (5 mg, 40% yield).

ESI-MS calculated [MH]$^+$: 1763.0; found 1763.2.

Example 26

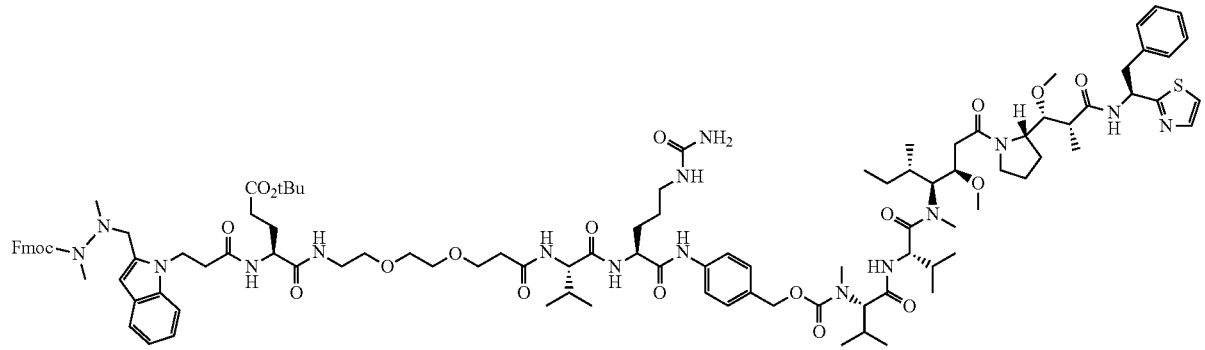

Preparation of tert-butyl (6S,9S,22S)-22-(3-(2-((2-(((9H-fluoren-9-yl)methoxy)carbonyl)-1,2-dimethylhydrazinyl)methyl)-1H-indol-1-yl)propanamido)-1-amino-6-((4-((5S,8S,11S,12R)-11-((S)-sec-butyl)-5,8-diisopropyl-12-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-4,10-dimethyl-3,6,9-trioxo-2,13-dioxa-4,7,10-triazatetradecyl)phenyl)carbamoyl)-9-isopropyl-1,8,11,21-tetraoxo-14,17-dioxa-2,7,10,20-tetraazapentacosan-25-oate (Fmoc-HIPS-Glu(OtBu)-PEG2-Val-Cit-PABC-MMAD)

To a dried scintillation vial containing a magnetic stir bar was added Fmoc-HIPS-Glu(OtBu)-PEG2-COOH (41 mg, 0.042 mmol), H$_2$N-Val-Cit-PABC-MMAD (52 mg, 0.044 mmol), HATU (20 mg, 0.053 mmol), DIPEA (16 µL, 0.1 mmol), and DCM (1 mL). The solution was stirred for 2 hours at room temperature. The reaction mixture was purified by flash chromatography (elute 1-15% MeOH/DCM) to yield the title compound as a white solid (90 mg, >99% yield).

ESI-MS calculated [MH]$^+$: 1986.1; found 1986.4.

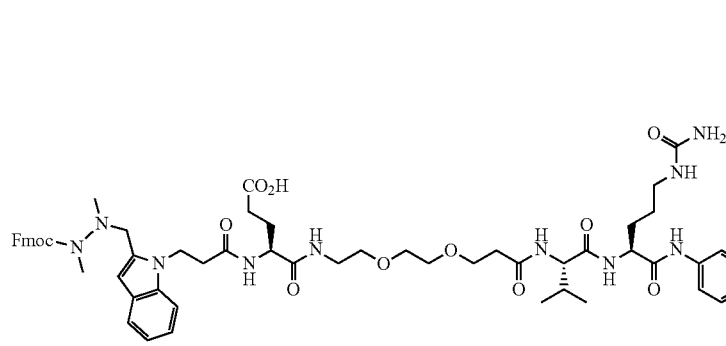
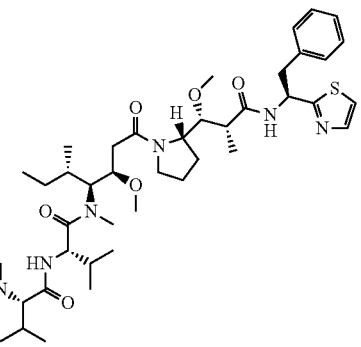

Preparation of (6S,9S,22S)-22-(3-(2-((2-(((9H-fluoren-9-yl)methoxy)carbonyl)-1,2-dimethylhydrazinyl)methyl)-1H-indol-1-yl)propanamido)-1-amino-6-((4-((5S,8S,11S,12R)-11-((S)-sec-butyl)-5,8-diisopropyl-12-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-4,10-dimethyl-3,6,9-trioxo-2,13-dioxa-4,7,10-triazatetradecyl)phenyl)carbamoyl)-9-isopropyl-1,8,11,21-tetraoxo-14,17-dioxa-2,7,10,20-tetraazapentacosan-25-oic acid (Fmoc-HIPS-Glu(OH)-PEG2-Val-Cit-PABC-MMAD)

To a dried scintillation vial containing a magnetic stir bar was added Fmoc-HIPS-Glu(OtBu)-PEG2-Val-Cit-PABC-MMAD (45 mg, 0.023 mmol) and DCM (0.5 mL). The solution was cooled to 0° C. and tin(IV) tetrachloride was added (0.2 mL, 1.0 M in DCM, 0.2 mmol). The resulting mixture was stirred for 1 hour at 0° C. The reaction mixture was directly purified by C18 flash chromatography (elute 10-100% MeCN/water) to yield the title compound as a white solid (35 mg, 71% yield).

ESI-MS calculated [MH]$^+$: 1930.0; found 1930.3.

Preparation of (6S,9S,22S)-1-amino-6-((4-((5S,8S,11S,12R)-11-((S)-sec-butyl)-5,8-diisopropyl-12-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-4,10-dimethyl-3,6,9-trioxo-2,13-dioxa-4,7,10-triazatetradecyl)phenyl)carbamoyl)-22-(3-(2-((1,2-dimethylhydrazinyl)methyl)-1H-indol-1-yl)propanamido)-9-isopropyl-1,8,11,21-tetraoxo-14,17-dioxa-2,7,10,20-tetraazapentacosan-25-oic acid (HIPS-Glu(OH)-2PEG-Val-Cit-PABC-MMAD)

To a dried scintillation vial containing a magnetic stir bar was added Fmoc-HIPS-Glu-PEG2-Val-Cit-PABC-MMAD (35 mg, 0.018 mmol), piperidine (0.1 mL, 1 mmol) and DMF (0.5 mL). The reaction mixture was stirred for 30 minutes at room temperature and then purified by C18 flash chromatography (elute 5-100% MeCN/water) to yield the title compound as a white solid (25 mg, 81% yield).

ESI-MS calculated [MH]$^+$: 1708.0; found 1708.1.

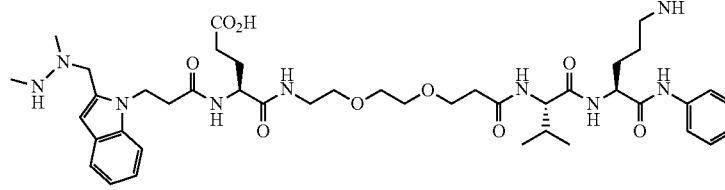
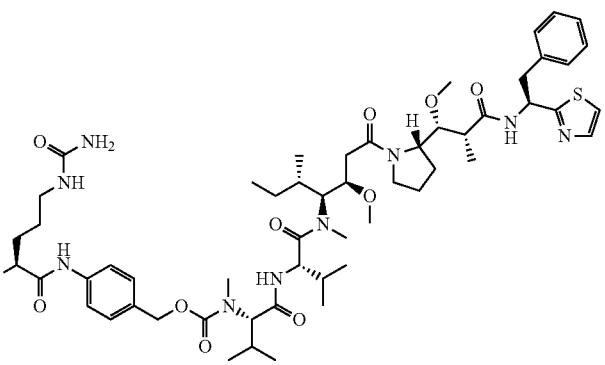

Example 27

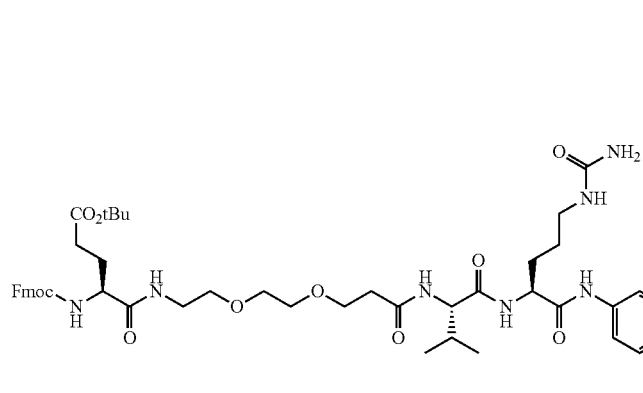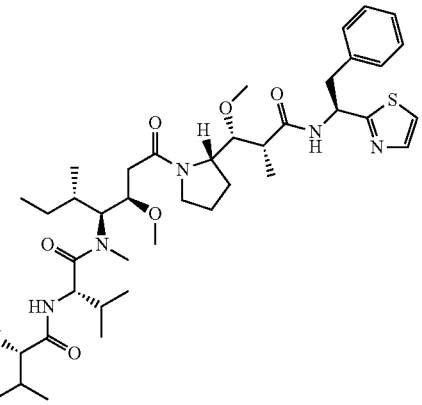

Preparation of tert-butyl (6S,9S,22S)-22-((((9H-fluoren-9-yl)methoxy)carbonyl)amino)-1-amino-6-((4-((5S,8S,11S,12R)-11-((S)-sec-butyl)-5,8-diisopropyl-12-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-4,10-dimethyl-3,6,9-trioxo-2,13-dioxa-4,7,10-triazatetradecyl)phenyl)carbamoyl)-9-isopropyl-1,8,11,21-tetraoxo-14,17-dioxa-2,7,10,20-tetraazapentacosan-25-oate (Fmoc-Glu(OtBu)-PEG2-Val-Cit-PABC-MMAD)

To a dried scintillation vial containing a magnetic stir bar was added Fmoc-Glu(OtBu)-PEG2-COOH (25 mg, 0.042 mmol), H$_2$N-Val-Cit-PABC-MMAD (36 mg, 0.031 mmol), HATU (20 mg, 0.053 mmol), DIPEA (20 μL, 0.12 mmol), DCM (0.6 mL), and DMF (0.5 mL). The solution was stirred for 2 hours at room temperature. The reaction mixture was purified by C18 flash chromatography (elute 10-100% MeCN/water with 0.1% HOAc) to yield the title compound as a white solid (33 mg, 62% yield).
ESI-MS calculated [MH]$^+$: 1743.0; found 1743.2.

Preparation of tert-butyl (6S,9S,22S)-1,22-diamino-6-((4-((5S,8S,11S,12R)-11-((S)-sec-butyl)-5,8-diisopropyl-12-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-4,10-dimethyl-3,6,9-trioxo-2,13-dioxa-4,7,10-triazatetradecyl)phenyl)carbamoyl)-9-isopropyl-1,8,11,21-tetraoxo-14,17-dioxa-2,7,10,20-tetraazapentacosan-25-oate (H2N-Glu(OtBu)-2PEG-Val-Cit-PABC-MMAD)

To a dried scintillation vial containing a magnetic stir bar was added Fmoc-Glu(OtBu)-PEG2-Val-Cit-PABC-MMAD (33 mg, 0.019 mmol), piperidine (0.1 mL, 1 mmol) and DMF (0.8 mL). The reaction mixture was stirred for 15 minutes at room temperature and then purified by C18 flash chromatography (elute 5-100% MeCN/water) to yield the title compound as a white solid (24 mg, 83% yield), which was carried forward without further characterization.

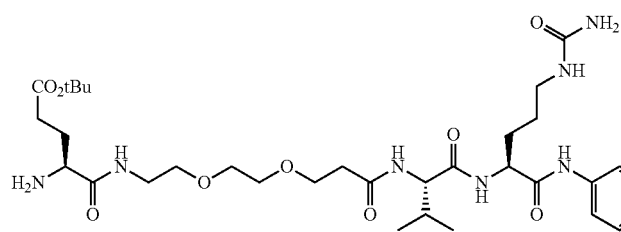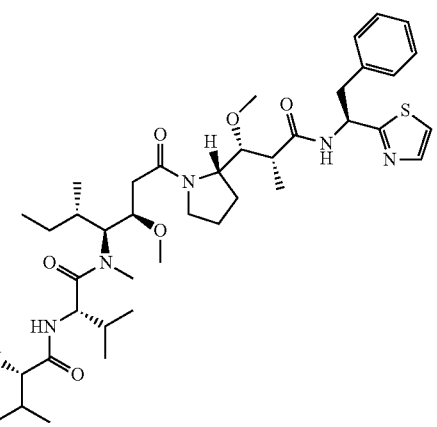

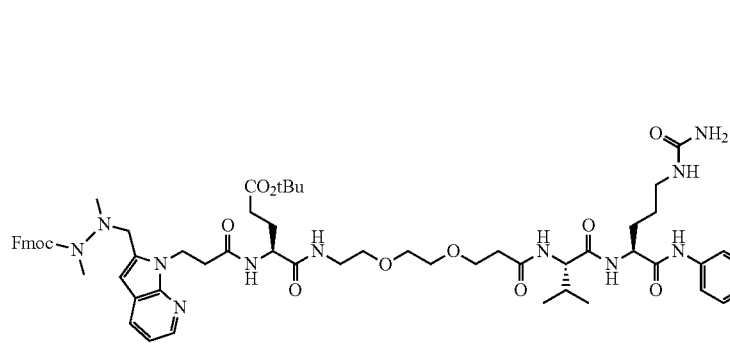
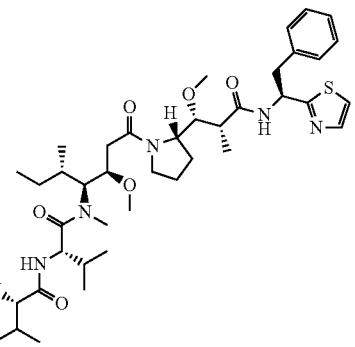

Preparation of tert-butyl (6S,9S,22S)-22-(3-(2-((2-(((9H-fluoren-9-yl)methoxy)carbonyl)-1,2-dimethylhydrazinyl)methyl)-1H-pyrrolo[2,3-b]pyridin-1-yl)propanamido)-1-amino-6-((4-((5S,8S,11S,12R)-11-((S)-sec-butyl)-5,8-diisopropyl-12-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-4,10-dimethyl-3,6,9-trioxo-2,13-dioxa-4,7,10-triazatetradecyl)phenyl)carbamoyl)-9-isopropyl-1,8,11,21-tetraoxo-14,17-dioxa-2,7,10,20-tetraazapentacosan-25-oate (Fmoc-AzaHIPS-Glu(OtBu)-PEG2-Val-Cit-PABC-MMAD)

To a dried scintillation vial containing a magnetic stir bar was added (H2N-Glu(OtBu)-PEG2-Val-Cit-PABC-MMAD (24 mg, 0.016 mmol), 3-(2-((2-(((9H-fluoren-9-yl)methoxy)carbonyl)-1,2-dimethylhydrazinyl)methyl)-1H-pyrrolo[2,3-b]pyridin-1-yl)propanoic acid (9 mg, 0.019 mmol), PyAOP (9 mg, 0.017 mmol), DIPEA (3 µL, 0.017 mmol), and DMF (0.5 mL). The solution was stirred for 2 hours at room temperature. The reaction mixture was purified by C18 flash chromatography (elute 5-100% MeCN/water with 0.1% formic acid) to yield the title compound as a white solid (32 mg, >99% yield).

ESI-MS calculated [MH]⁺: 1987.1; found 1987.3.

Preparation of (6S,9S,22S)-22-(3-(2-((2-(((9H-fluoren-9-yl)methoxy)carbonyl)-1,2-dimethylhydrazinyl)methyl)-1H-pyrrolo[2,3-b]pyridin-1-yl)propanamido)-1-amino-6-((4-((5S,8S,11S,12R)-11-((S)-sec-butyl)-5,8-diisopropyl-12-(2-((S)-2-((1R,2R)-1-methoxy-2-methyl-3-oxo-3-(((S)-2-phenyl-1-(thiazol-2-yl)ethyl)amino)propyl)pyrrolidin-1-yl)-2-oxoethyl)-4,10-dimethyl-3,6,9-trioxo-2,13-dioxa-4,7,10-triazatetradecyl)phenyl)carbamoyl)-9-isopropyl-1,8,11,21-tetraoxo-14,17-dioxa-2,7,10,20-tetraazapentacosan-25-oic acid (Fmoc-AzaHIPS-Glu(OH)-2PEG-Val-Cit-PABC-MMAD)

To a dried scintillation vial containing a magnetic stir bar was added Fmoc-AzaHIPS-Glu(OtBu)-2PEG-Val-Cit-PABC-MMAD (32 mg, 0.016 mmol) and DCM (0.5 mL). The solution was cooled to 0° C. and tin(IV) tetrachloride was added (0.2 mL, 1.0 M in DCM, 0.2 mmol). The resulting mixture was stirred for 1 hour at 0° C. The reaction mixture was directly purified by C18 flash chromatography (elute 10-100% MeCN/water) to yield the title compound as a white solid (22 mg, 71% yield).

ESI-MS calculated [MH]⁺: 1931.0; found 1921.2.

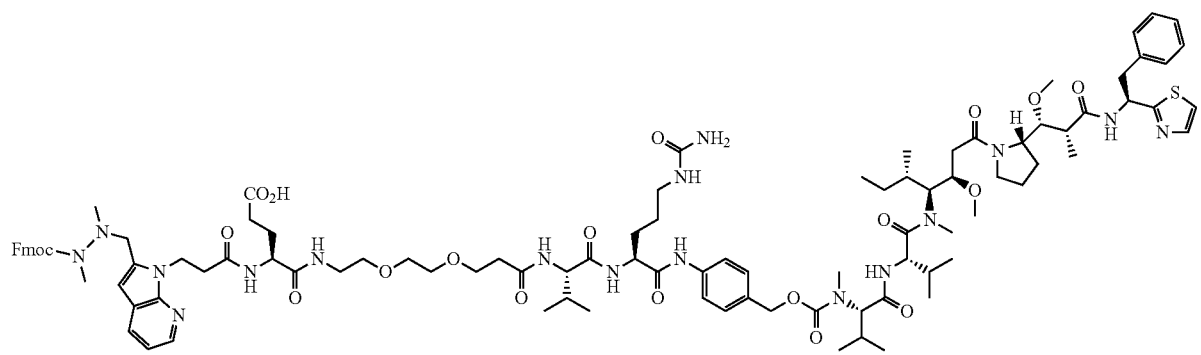

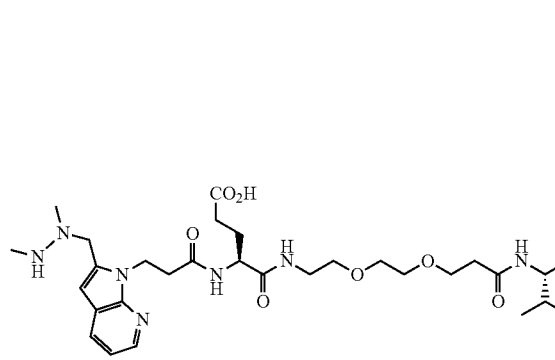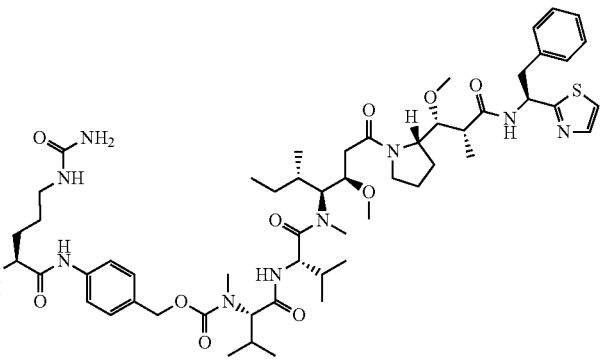

Preparation of (6S,9S,22S)-1-amino-6-((4-((5S,8S,11S,12R)-11-((S)-sec-butyl)-5,8-diisopropyl-12-(2-((S)-2-((1R,2R)-1-methoxy-2-methyl-3-oxo-3-(((S)-2-phenyl-1-thiazol-2-yl)ethyl)amino)propyl)pyrrolidin-1-yl)-2-oxoethyl)-4,10-dimethyl-3,6,9-trioxo-2,13-dioxa-4,7,10-triazatetradecyl)phenyl)carbamoyl)-22-(3-(2-((1,2-dimethylhydrazinyl)methyl)-1H-pyrrolo[2,3-b]pyridin-1-yl)propanamido)-9-isopropyl-1,8,11,21-tetraoxo-14,17-dioxa-2,7,10,20-tetraazapentacosan-25-oic acid (AzaHIPS-Glu(OH)-2PEG-Val-Cit-PABC-MMAD)

To a dried scintillation vial containing a magnetic stir bar was added Fmoc-AzaHIPS-Glu-PEG2-Val-Cit-PABC-MMAD (22 mg, 0.011 mmol), piperidine (0.05 mL, 0.5 mmol) and DMF (0.5 mL). The reaction mixture was stirred for 15 minutes at room temperature and then purified by C18 flash chromatography (elute 5-100% MeCN/water) to yield the title compound as a white solid (15 mg, 77% yield).

ESI-MS calculated [MH]$^+$: 1709.0; found 1709.1.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A conjugate comprising at least one modified amino acid residue of formula (III):

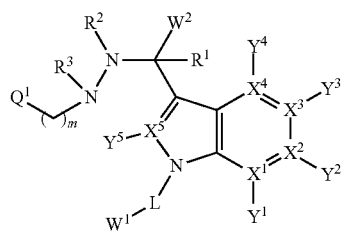

(III)

wherein m is 0 or 1;

$R^1$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;

$R^2$ and $R^3$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, or $R^2$ and $R^3$ are optionally cyclically linked to form a 5 or 6-membered heterocyclyl;

$X^1$ is C or N;

$X^2$, $X^3$ and $X^4$ are each C;

$X^5$ is C;

$Y^1$, $Y^2$, $Y^3$, $Y^4$ and $Y^5$, if present, are each independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, wherein $Y^1$ and $Y^2$, $Y^2$ and $Y^3$, or $Y^3$ and $Y^4$ are optionally cyclically linked;

$Q^1$ is a bond to either $X^4$ or $X^5$, wherein if $Q^1$ is a bond to $X^4$, then $Y^4$ is absent, or if $Q^1$ is a bond to $X^5$, then $Y^5$ is absent;

L is a linker of the formula -$(T^1-V^1)_a$-$(T^2-V^2)_b$-$(T^3-V^3)_c$-$(T^4-V^4)_d$-$(T^5-V^5)_e$—, wherein a, b, c, d and e are each independently 0 or 1, where the sum of a, b, c, d and e is 1 to 5;

$T^1$, $T^2$, and $T^3$ are each independently selected from ($C_1$-$C_{12}$)alkyl, substituted ($C_1$-$C_{12}$)alkyl, (EDA)$_w$, (PEG)$_n$, (AA)$_p$, —(CR$^{13}$OH)$_h$—, piperidin-4-amino (P4A), para-amino-benzyloxycarbonyl (PABC), meta-amino-benzyloxycarbonyl (MABC), para-amino-benzyloxy (PABO), meta-amino-benzyloxy (MABO), para-aminobenzyl, an acetal group, a disulfide, a hydrazine, a carbohydrate, a beta-lactam, an ester, (AA)$_p$-MABC-(AA)$_p$, (AA)$_p$-MABO-(AA)$_p$, (AA)$_p$-PABO-(AA)$_p$ and (AA)$_p$-PABC-(AA)$_p$;

$T^4$ is selected from ($C_1$-$C_{12}$)alkyl, substituted ($C_1$-$C_{12}$)alkyl, (EDA)$_w$, (PEG)$_n$, (AA)$_p$, —(CR$^{13}$OH)$_h$—, piperidin-4-amino (P4A), para-amino-benzyloxycarbonyl (PABC), meta-amino-benzyloxycarbonyl (MABC), para-amino-benzyloxy (PABO), meta-amino-benzyloxy (MABO), para-aminobenzyl, an acetal group, a disulfide, a hydrazine, a carbohydrate, a beta-lactam, an ester, $(AA)_p$-MABC-$(AA)_p$, $(AA)_p$-MABO-$(AA)_p$, $(AA)_p$-PABO)-$(AA)_p$, $(AA)_p$-PABC-$(AA)_p$, PABC-$(AA)_p$, $(AA)_p$-PABO, and MABC-$(AA)_p$;

$T^5$ is selected from $(C_1-C_{12})$alkyl, substituted $(C_1-C_{12})$ alkyl, $(EDA)_w$, $(PEG)_n$, $(AA)_p$, $-(CR^{13}OH)_h-$, piperidin-4-amino (P4A), para-amino-benzyloxycarbonyl (PABC), meta-amino-benzyloxycarbonyl (MABC), para-amino-benzyloxy (PABO), meta-amino-benzyloxy (MABO), para-aminobenzyl, an acetal group, a disulfide, a hydrazine, a carbohydrate, a beta-lactam, an ester, $(AA)_p$-MABC-$(AA)_p$, $(AA)_p$-MABO-$(AA)_p$, $(AA)_p$-PABO-$(AA)_p$, $(AA)_p$-PABC-$(AA)_p$, and PABC-$(AA)_p$;

wherein:

EDA is an ethylene diamine having the following structure:

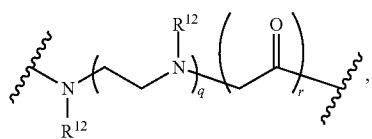

where q is an integer from 1 to 6 and r is 0 or 1;
piperidin-4-amino (P4A) is

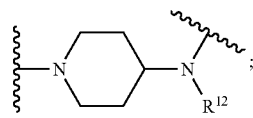

PEG is a polyethylene glycol;
AA is an amino acid residue;
w is an integer from 1 to 20;
n is an integer from 1 to 30;
p is an integer from 1 to 20;
h is an integer from 1 to 12;
$V^1$, $V^2$, $V^3$, $V^4$ and $V^5$ are each independently selected from the group consisting of a covalent bond, —CO—, —CONR$^{11}$—, —NR$^{11}$CO—, —C(O)O—, —OC(O)—, —O—, —S—, —S(O)—, —SO$_2$—, —SO$_2$NR$^{11}$—, —NR$^{11}$SO$_2$— and —P(O)OH—, and each R$^{11}$ and R$^{13}$ are independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;

each R$^{12}$ of the EDA is independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, wherein any two adjacent R$^{12}$ groups may be cyclically linked to form a piperazinyl ring;

each R$^{12}$ of the P4A is independently selected from hydrogen, alkyl, substituted alkyl, polyethylene glycol, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;

wherein one of W$^1$ and W$^2$ is a polypeptide and the other is a chemical entity selected from the group consisting of a drug and a detectable label, and wherein when the sum of a, b, c, d and e is 2 and one of $T^1$-$V^1$, $T^2$-$V^2$, $T^3$-$V^3$, $T^4$-$V^4$ or $T^5$-$V^5$ is (PEG)$_n$—CO, then n is not 6.

2. The conjugate of claim 1, wherein $Y^1$ and $Y^2$, $Y^2$ and $Y^3$, or $Y^3$ and $Y^4$ are cyclically linked to form a fused benzo ring.

3. The conjugate of claim 1, wherein:

$T^1$ is selected from a $(C_1-C_{12})$alkyl and a substituted $(C_1-C_{12})$alkyl;

$T^2$, $T^3$, $T^4$ and $T^5$ are each independently selected from $(EDA)_w$, $(PEG)_n$, $(C_1-C_{12})$alkyl, substituted $(C_1-C_{12})$ alkyl, $(AA)_p$, $-(CR^{13}OH)_h-$, piperidin-4-amino, MABC, MABO, PABO, PABC, para-aminobenzyl, an acetal group, a disulfide, a hydrazine, a carbohydrate, a beta-lactam, an ester, $(AA)_p$-MABC-$(AA)_p$, $(AA)_p$-MABO-$(AA)_p$, $(AA)_p$-PABO-$(AA)_p$ and $(AA)_p$-PABC-$(AA)_p$; and $V^1$, $V^2$, $V^3$, $V^4$ and $V^5$ are each independently selected from the group consisting of: a covalent bond, —CO—, —NR$^{11}$—, —CONR$^{11}$—, —NR$^{11}$CO—, —C(O)O—, —OC(O)—, —O—, —S—, —S(O)—, —SO$_2$—, —SO$_2$NR$^{11}$—, —NR$^{11}$SO$_2$—, and —P(O)OH—;

wherein:

(PEG)$_n$ is

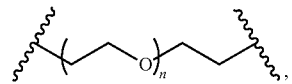

where n is an integer from 1 to 30;
EDA is an ethylene diamine having the following structure:

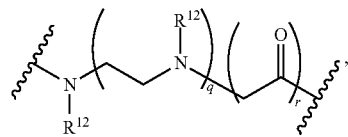

where q is an integer from 1 to 6 and r is 0 or 1;
piperidin-4-amino is

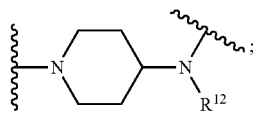

each R$^{11}$ and R$^{12}$ is independently selected from hydrogen, an alkyl, a substituted alkyl, a polyethylene glycol, an aryl and a substituted aryl, wherein any two adjacent $R^{12}$ groups may be cyclically linked to form a piperazinyl ring; and $R^{13}$ is selected from hydrogen, an alkyl, a substituted alkyl, an aryl, and a substituted aryl.

4. The conjugate of claim 1, wherein:
a, b, c and d are each 1, and e is 0; or
a, b and c are each 1, and d and e are each 0; or
a and b are each 1, and c, d and e are each 0.

5. The conjugate of claim 1, wherein $T^1$, $T^2$, $T^3$, $T^4$ and $T^5$ and $V^1$, $V^2$, $V^3$, $V^4$ and $V^5$ are selected from the following table:

| $T^1$ | $V^1$ | $T^2$ | $V^2$ | $T^3$ | $V^3$ | $T^4$ | $V^4$ | $T^5$ | $V^5$ |
|---|---|---|---|---|---|---|---|---|---|
| $(C_1-C_{12})$alkyl | —$CONR^{11}$— | $(PEG)_n$ | —CO— | — | — | — | — | — | — |
| $(C_1-C_{12})$alkyl | —CO— | $(AA)_p$ | —$NR^{11}$— | $(PEG)_n$ | —CO— | — | — | — | — |
| $(C_1-C_{12})$alkyl | —CO— | $(AA)_p$ | — | — | — | — | — | — | — |
| $(C_1-C_{12})$alkyl | —$CONR^{11}$— | $(PEG)_n$ | —$NR^{11}$— | — | — | — | — | — | — |
| $(C_1-C_{12})$alkyl | —CO— | $(AA)_p$ | —$NR^{11}$— | $(PEG)_n$ | —$NR^{11}$— | — | — | — | — |
| $(C_1-C_{12})$alkyl | —CO— | $(EDA)_w$ | —CO— | — | — | — | — | — | — |
| $(C_1-C_{12})$alkyl | —$CONR^{11}$— | $(C_1-C_{12})$alkyl | —$NR^{11}$— | — | — | — | — | — | — |
| $(C_1-C_{12})$alkyl | —$CONR^{11}$— | $(PEG)_n$ | —CO— | $(EDA)_w$ | — | — | — | — | — |
| $(C_1-C_{12})$alkyl | —CO— | $(EDA)_w$ | — | — | — | — | — | — | — |
| $(C_1-C_{12})$alkyl | —CO— | $(EDA)_w$ | —CO— | $(CR^{13}OH)_h$ | —$CONR^{11}$— | $(C_1-C_{12})$alkyl | —CO— | — | — |
| $(C_1-C_{12})$alkyl | —CO— | $(AA)_p$ | —$NR^{11}$— | $(C_1-C_{12})$alkyl | —CO— | — | — | — | — |
| $(C_1-C_{12})$alkyl | —$CONR^{11}$— | $(PEG)_n$ | —CO— | $(AA)_p$ | — | — | — | — | — |
| $(C_1-C_{12})$alkyl | —$CONR^{11}$— | $(PEG)_n$ | —CO— | $(AA)_p$ | — | MABO | — | — | — |
| $(C_1-C_{12})$alkyl | —$CONR^{11}$— | $(PEG)_n$ | —CO— | $(AA)_p$ | — | PABO | — | — | — |
| $(C_1-C_{12})$alkyl | —$CONR^{11}$— | $(PEG)_n$ | —CO— | $(AA)_p$ | — | PABC | — | — | — |
| $(C_1-C_{12})$alkyl | —CO— | $(EDA)_w$ | —CO— | $(CR^{13}OH)_h$ | —CO— | $(AA)_p$ | — | — | — |
| $(C_1-C_{12})$alkyl | —CO— | $(AA)_p$ | —$NR^{11}$— | $(C_1-C_{12})$alkyl | —CO— | $(AA)_p$ | — | — | — |
| $(C_1-C_{12})$alkyl | —CO— | $(AA)_p$ | —$NR^{11}$— | $(PEG)_n$ | —CO— | $(AA)_p$ | — | — | — |
| $(C_1-C_{12})$alkyl | —CO— | $(AA)_p$ | —$NR^{11}$— | $(C_1-C_{12})$alkyl | —CO— | $(AA)_p$ | — | — | — |
| $(C_1-C_{12})$alkyl | —CO— | $(AA)_p$ | —$NR^{11}$— | $(PEG)_n$ | —CO— | $(AA)_p$-PABC-$(AA)_p$ | — | — | — |
| $(C_1-C_{12})$alkyl | —CO— | $(AA)_p$ | —$NR^{11}$— | $(PEG)_n$ | —CO— | $(AA)_p$ | — | PABC-$(AA)_p$ | — |
| $(C_1-C_{12})$alkyl | —CO— | $(AA)_p$ | —$NR^{11}$— | $(PEG)_n$ | —CO— | $(AA)_p$-PABO | — | — | — |
| $(C_1-C_{12})$alkyl | —CO— | $(AA)_p$ | —$NR^{11}$— | $(PEG)_n$ | —CO— | $(AA)_p$ | — | PABO | — |
| $(C_1-C_{12})$alkyl | —CO— | $(AA)_p$ | —$NR^{11}$— | $(PEG)_n$ | —$SO_2$— | $(AA)_p$ | — | — | — |
| $(C_1-C_{12})$alkyl | —$CONR^{11}$— | $(PEG)_n$ | —CO— | $(AA)_p$ | — | PABC-$(AA)_p$ | — | — | — |
| $(C_1-C_{12})$alkyl | —$CONR^{11}$— | $(PEG)_n$ | —CO— | $(AA)_p$ | — | PABC | — | $(AA)_p$ | — |
| $(C_1-C_{12})$alkyl | —CO— | $(EDA)_w$ | —CO— | $(CR^{13}OH)_h$ | —$CONR^{11}$— | $(PEG)_n$ | —CO— | — | — |
| $(C_1-C_{12})$alkyl | —CO— | $(AA)_p$ | —$NR^{11}$— | $(PEG)_n$ | —CO— | MABC-$(AA)_p$- | — | — | — |
| $(C_1-C_{12})$alkyl | —CO— | $(AA)_p$ | —$NR^{11}$— | $(PEG)_n$ | —CO— | MABC | — | $(AA)_p$ | — |
| $(C_1-C_{12})$alkyl | —$CONR^{11}$— | $(PEG)_n$ | —CO— | MABO | — | — | — | — | — |
| $(C_1-C_{12})$alkyl | —CO— | $(AA)_p$ | —$NR^{11}$— | $(PEG)_n$ | —CO— | MABO | — | — | — |
| $(C_1-C_{12})$alkyl | —CO— | $(AA)_p$ | —$NR^{11}$— | $(PEG)_n$ | —CO— | PABO | — | — | — |
| $(C_1-C_{12})$alkyl | —CO— | $(AA)_p$ | —$NR^{11}$— | $(PEG)_n$ | —CO— | PABC | — | — | — |
| $(C_1-C_{12})$alkyl | —$CONR^{11}$— | $(PEG)_n$ | —CO— | MABC | — | $(AA)_p$ | — | — | — |
| $(C_1-C_{12})$alkyl | —CO— | $(CR^{13}OH)_h$ | —CO— | — | — | — | — | — | — |
| $(C_1-C_{12})$alkyl | —$CONR^{11}$— | substituted $(C_1-C_{12})$alkyl | —$NR^{11}$— | $(PEG)_n$ | —CO— | — | — | — | — |
| $(C_1-C_{12})$alkyl | —$SO_2$— | $(C_1-C_{12})$alkyl | —CO— | — | — | — | — | — | — |
| $(C_1-C_{12})$alkyl | —$CONR^{11}$— | $(PEG)_n$ | —CO— | $(AA)_p$ | — | PABC | —$NR^{11}$— | — | — |
| $(C_1-C_{12})$alkyl | —$CONR^{11}$— | $(C_1-C_{12})$alkyl | — | $(CR^{13}OH)_h$ | —$CONR^{11}$— | — | — | — | — |
| $(C_1-C_{12})$alkyl | —CO— | P4A | —CO— | $(C_1-C_{12})$alkyl | —CO— | $(AA)_p$ | — | PABO | —CO— |
| $(C_1-C_{12})$alkyl | —CO— | P4A | —CO— | $(C_1-C_{12})$alkyl | —CO— | $(AA)_p$ | — | PABO | — |
| $(C_1-C_{12})$alkyl | —CO— | P4A | —CO— | $(C_1-C_{12})$alkyl | —CO— | $(AA)_p$ | — | PABC-$(AA)_p$ | — |
| $(C_1-C_{12})$alkyl | —CO— | P4A | —CO— | $(C_1-C_{12})$alkyl | —CO— | $(AA)_p$ | — | — | —. |

6. The conjugate of claim 1, wherein L is selected from the group consisting of the following structures:

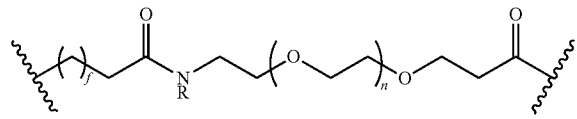

-continued
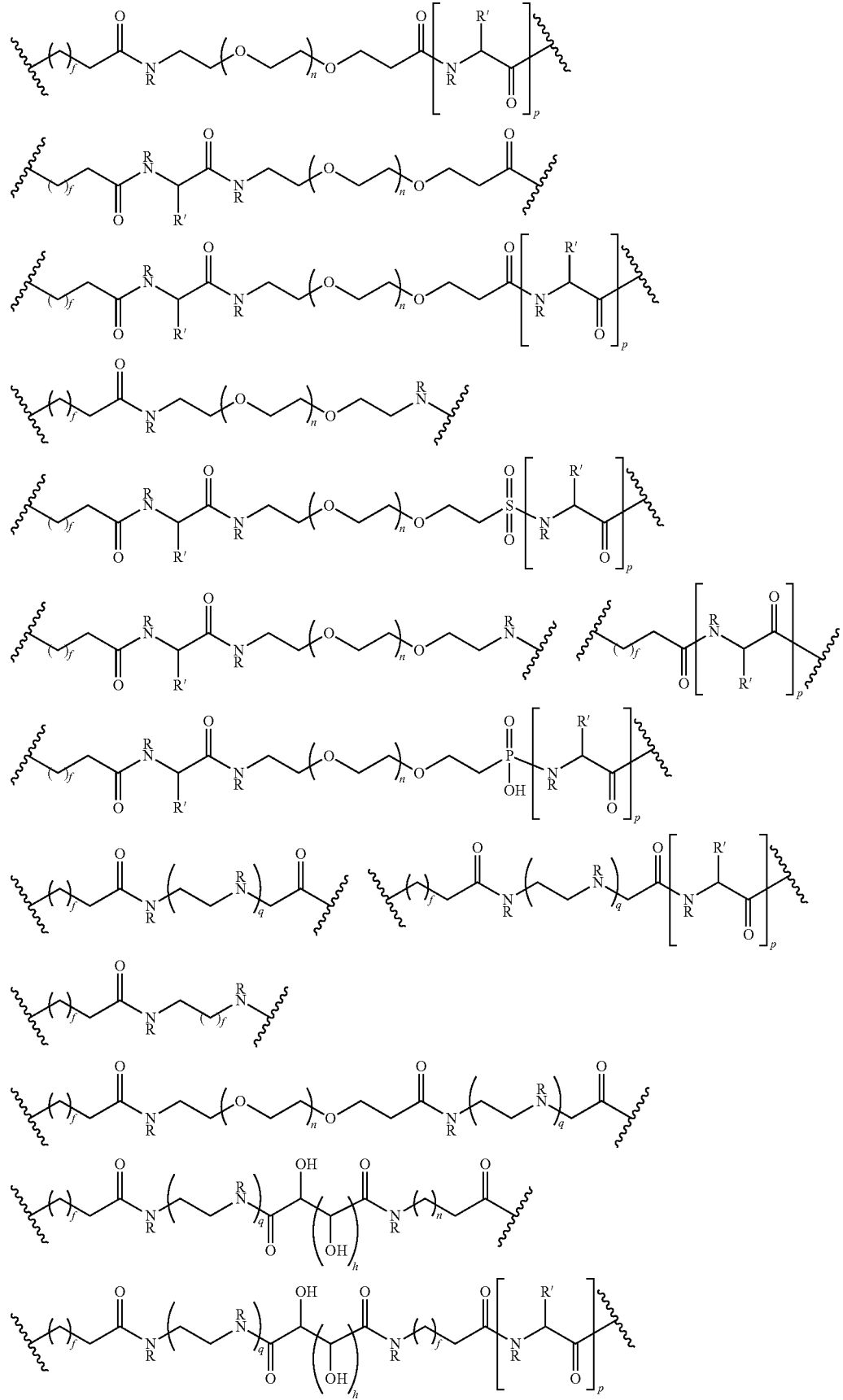

315 316
-continued
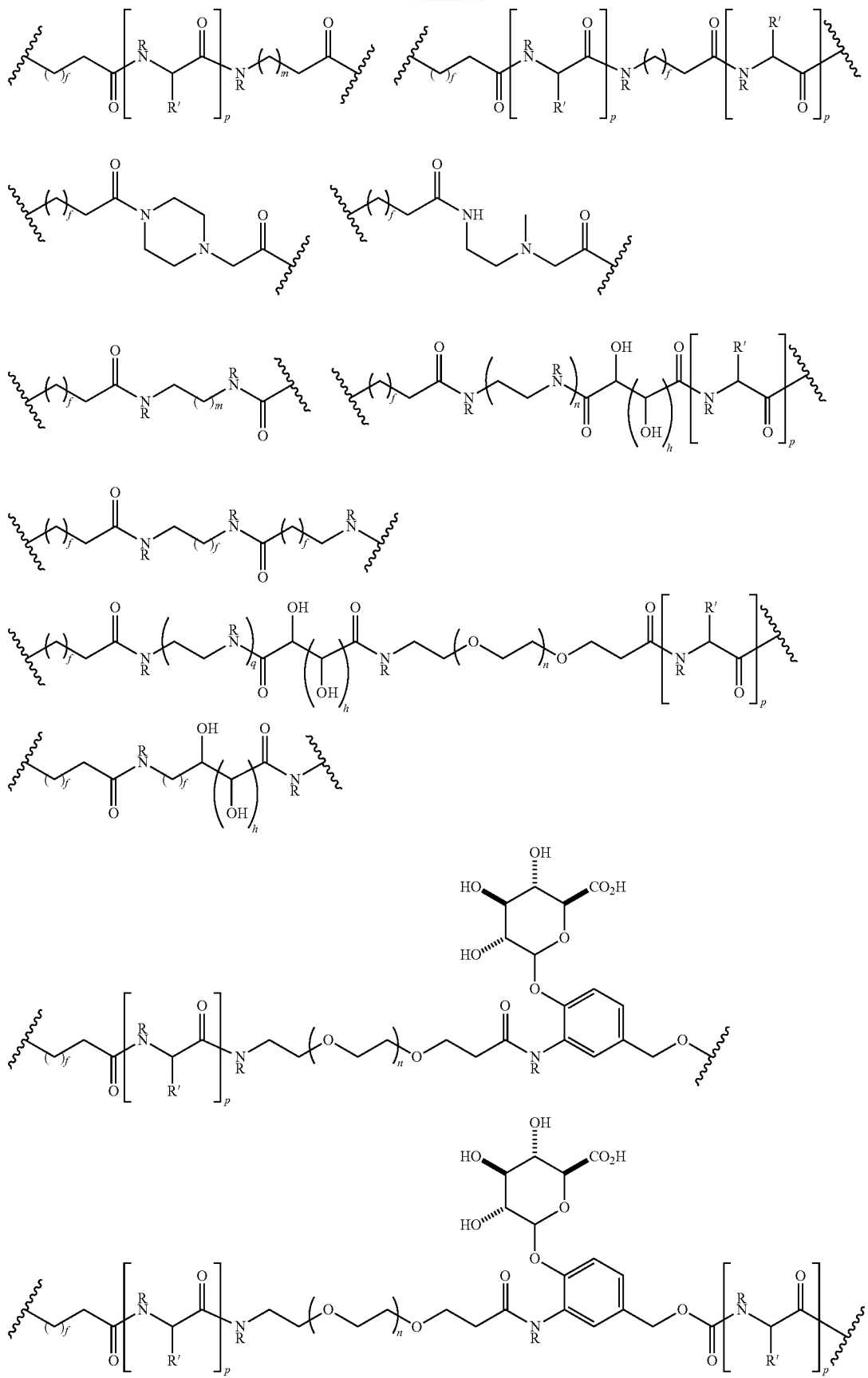

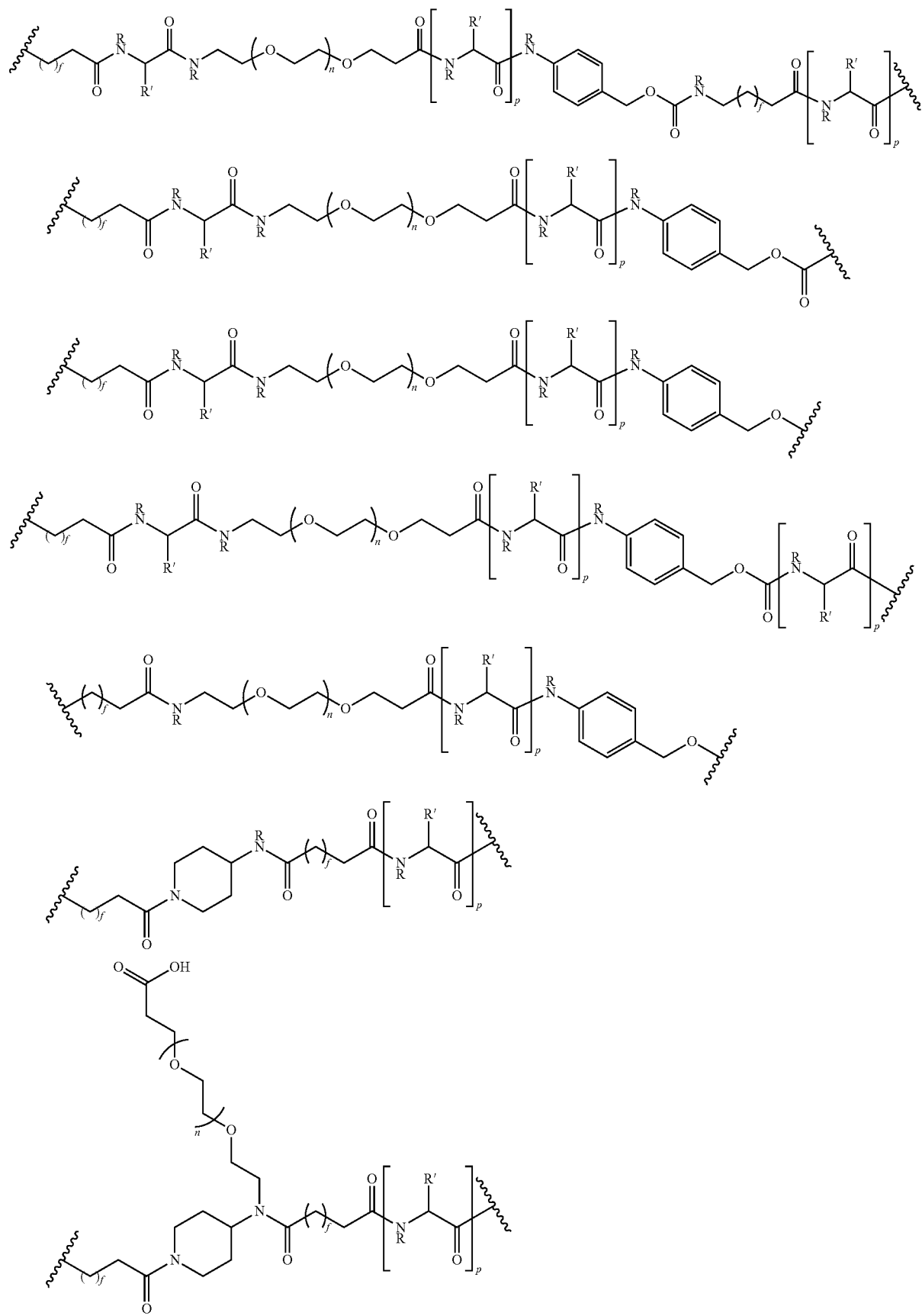

-continued

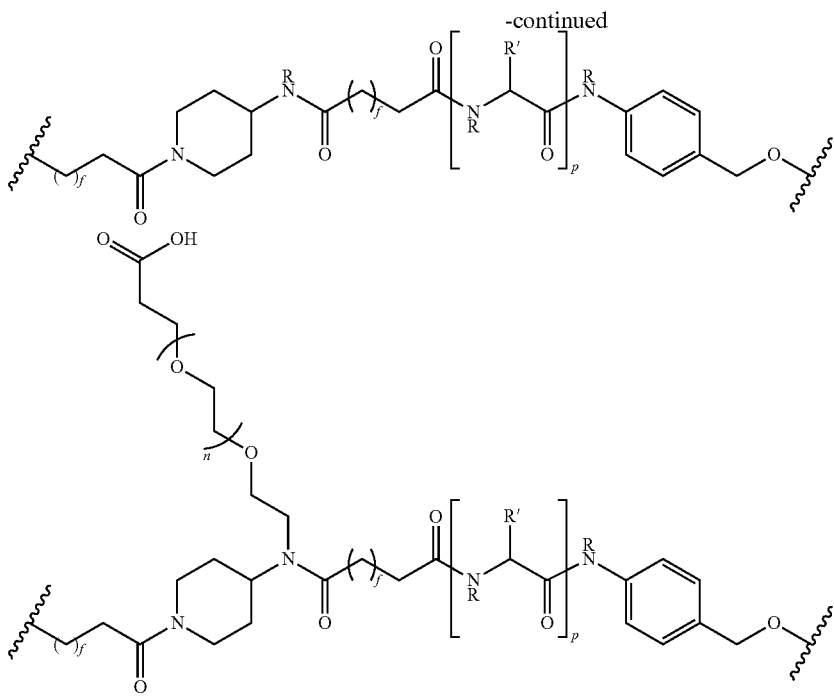

wherein:
each f is independently 0 or an integer from 1 to 12;
each w is independently 0 or an integer from 1 to 20;
each n is independently 0 or an integer from 1 to 30;
each p is independently 0 or an integer from 1 to 20;
each h is independently 0 or an integer from 1 to 12;
each R is independently hydrogen, alkyl, substituted alkyl, a polyethylene glycol, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl; and
each R' is independently H, a sidechain group of an amino acid, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl.

7. The conjugate of claim 1, wherein $Q^1$ is a bond to $X^5$ and $Y^5$ is absent.

8. The conjugate of claim 1, wherein m is 1.

9. The conjugate of claim 1, wherein $R^2$ and $R^3$ are each independently selected from alkyl and substituted alkyl.

10. The conjugate of claim 1, wherein $X^1$, $X^2$, $X^3$ and $X^4$ are each C.

11. The conjugate of claim 1, wherein $Y^1$, $Y^2$ and $Y^3$ are each H, and one of either $Y^4$ or $Y^5$ is H.

12. The conjugate of claim 1, wherein the conjugate comprises at least one modified amino acid residue of formula (IIIa):

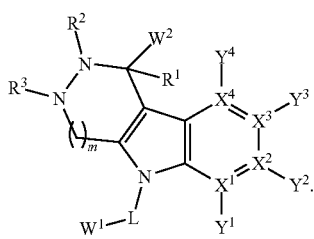

(IIIa)

13. The conjugate of claim 1, wherein the conjugate comprises at least one modified amino acid residue of formula (IIId):

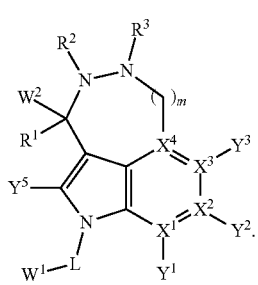

(IIId)

14. The conjugate of claim 1, wherein the chemical entity is a drug.

15. The conjugate of claim 1, wherein $W^1$ is the chemical entity, and $W^2$ is the polypeptide; or wherein $W^1$ is the polypeptide, and $W^2$ is the chemical entity.

16. A pharmaceutical composition comprising:
a conjugate of claim 1; and
a pharmaceutically acceptable excipient.

17. A method of delivering a conjugate to a subject, the method comprising: administering to the subject an effective amount of a conjugate of claim 1.

* * * * *

UNITED STATES PATENT AND TRADEMARK OFFICE
CERTIFICATE OF CORRECTION

PATENT NO. : 9,493,413 B2
APPLICATION NO. : 14/555283
DATED : November 15, 2016
INVENTOR(S) : Rabuka et al.

Page 1 of 1

It is certified that error appears in the above-identified patent and that said Letters Patent is hereby corrected as shown below:

In the Specification

In Column 15, Line 61, "substituted heterocycyl" should read -- substituted heterocyclyl --.

In Column 50, Line 49, "one of $Z^1$, $Z^2$, and $Z^4$" should read -- one of $Z^1$, $Z^2$, $Z^3$ and $Z^4$ --.

In Column 51, Line 29, "one of $Z^1$, $Z^2$, and $Z^4$" should read -- one of $Z^1$, $Z^2$, $Z^3$ and $Z^4$ --.

In Column 95, Line 14, "formula (DO)" should read -- formula (IXb) --.

In Column 140, Line 67, "Groa/IL-8" should read -- Groα/IL-8 --.

In Column 153, Line 40, "F2-a" should read -- F2-α --.

Signed and Sealed this
Fourth Day of April, 2017

Michelle K. Lee
*Director of the United States Patent and Trademark Office*